US009441019B2

(12) United States Patent
Nabel et al.

(10) Patent No.: US 9,441,019 B2
(45) Date of Patent: Sep. 13, 2016

(54) INFLUENZA HEMAGGLUTININ PROTEIN-BASED VACCINES

(71) Applicant: THE UNITED STATES OF AMERICA, as represented by THE SECRETARY, DEPARTMENT OF HEALTH & HUMAN SERVICES, Washington, DC (US)

(72) Inventors: Gary J. Nabel, Washington, DC (US); Masaro Kanekiyo, Silver Spring, MD (US); Chih-Jen Wei, Potomac, MD (US); Patrick M. McTamney, Bethesda, MD (US); Hadi M. Yassine, Rockville, MD (US); Jeffrey C. Boyington, Clarksburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/346,849

(22) PCT Filed: Sep. 24, 2012

(86) PCT No.: PCT/US2012/056822
§ 371 (c)(1),
(2) Date: Mar. 24, 2014

(87) PCT Pub. No.: WO2013/044203
PCT Pub. Date: Mar. 28, 2013

(65) Prior Publication Data
US 2014/0302079 A1 Oct. 9, 2014

Related U.S. Application Data

(60) Provisional application No. 61/538,663, filed on Sep. 23, 2011, provisional application No. 61/661,209, filed on Jun. 18, 2012.

(51) Int. Cl.
C07K 14/205 (2006.01)
A61K 39/12 (2006.01)
A61K 39/145 (2006.01)
A61K 39/00 (2006.01)
G01N 33/569 (2006.01)
C07K 14/005 (2006.01)
A61K 39/02 (2006.01)

(52) U.S. Cl.
CPC ............ *C07K 14/205* (2013.01); *A61K 39/12* (2013.01); *A61K 39/145* (2013.01); *C07K 14/005* (2013.01); *G01N 33/56983* (2013.01); *A61K 39/105* (2013.01); *A61K 2039/55566* (2013.01); *A61K 2039/6031* (2013.01); *A61K 2039/70* (2013.01); *C07K 2319/00* (2013.01); *C12N 2760/16034* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| | | | |
|---|---|---|---|
| 7,094,598 B2 | 8/2006 | Nabel et al. | |
| 7,097,841 B2 | 8/2006 | Carter et al. | |
| 7,608,268 B2 | 10/2009 | Carter et al. | |
| 2002/0054882 A1 | 5/2002 | Okuno et al. | |
| 2005/0042229 A1 | 2/2005 | Yang et al. | |
| 2005/0108791 A1 | 5/2005 | Edgerton | |
| 2006/0251679 A1* | 11/2006 | Carter et al. ............... | 424/204.1 |
| 2007/0082054 A1 | 4/2007 | Van Den Mooter et al. | |
| 2007/0224205 A1 | 9/2007 | Powell et al. | |
| 2008/0299151 A1 | 12/2008 | Fomsgaard | |
| 2009/0233377 A1 | 9/2009 | Iwahori et al. | |
| 2010/0137412 A1 | 6/2010 | Zhou et al. | |
| 2010/0285982 A1 | 11/2010 | Golding et al. | |
| 2010/0297174 A1 | 11/2010 | Garcia-Sastre et al. | |
| 2011/0038025 A1 | 2/2011 | Naitou et al. | |
| 2011/0059130 A1 | 3/2011 | Yusibov | |
| 2011/0177122 A1 | 7/2011 | Nabel et al. | |
| 2011/0212128 A1 | 9/2011 | Galarza et al. | |

FOREIGN PATENT DOCUMENTS

| | | |
|---|---|---|
| EP | 1504037 | 12/2009 |
| WO | WO 03/094849 | 11/2003 |

(Continued)

OTHER PUBLICATIONS

Cohen et al., Neoplasia, Feb. 2005, 7(2):109-117.*
A3KF33, UniProtKB A3KF33_I57A5, Sep. 21, 2011 [online]. [Retrieved on Feb. 26, 2013]. Retrieved from the internet <URL: http://www.uniprot.org/uniprot/A3KF33.txt?version=36>.
Bachmann, M.F., et al., "Neutralizing antiviral B cell responses," Annu Rev Immunol, 1997, 15:235-270.
Caton, A.J., et al., "The antigenic structure of the influenza virus A/PR/8/34 hemagglutinin (H1 subtype)," Cell, 1982, 31:417-427.

(Continued)

*Primary Examiner* — Nicole Kinsey White
(74) *Attorney, Agent, or Firm* — Sheridan Ross P.C.

(57) ABSTRACT

Novel vaccines are provided that elicit broadly neutralizing anti-influenza antibodies. Some vaccines comprise nanoparticles that display hemagglutinin trimers from influenza virus on their surface. The nanoparticles comprise fusion proteins comprising a monomeric subunit of ferritin joined to at least a portion of an influenza hemagglutinin protein. Some portions comprise the ectodomain while some portions are limited to the stem region. The fusion proteins self-assemble to form the hemagglutinin-displaying nanoparticles. Some vaccines comprise only the stem region of an influenza hemagglutinin protein joined to a trimerization domain. Such vaccines can be used to vaccinate an individual against infection by heterologous influenza viruses and influenza virus that are antigenically divergent from the virus from which the nanoparticle hemagglutinin protein was obtained. Also provided are fusion proteins and nucleic acid molecules encoding such proteins.

21 Claims, 87 Drawing Sheets

(56) References Cited

FOREIGN PATENT DOCUMENTS

WO     WO 2011/035422    *   3/2011
WO     WO 2011/044152 A1    4/2011

OTHER PUBLICATIONS

C0LT38, UniProtKB C0LT38_9INFB, Sep. 21, 2011 [online]. [Retrieved on Feb. 26, 2013]. Retrieved from the internet <URL: http://www.uniprot.org/uniprot/C0LT38.txt?version=18>.
Corti, D., et al., "Heterosubtypic neutralizing antibodies are produced by individuals immunized with a seasonal influenza vaccine," J Clin Invest, 2010, 120:1663-1673.
Corti, D., et al., "A neutralizing antibody selected from plasma cells that binds to group 1 and group 2 influenza A hemagglutinins," Science, 2011, 333:850-856.
Dintzis, H.M. et al., "Molecular determinants of immunogenicity: the immunon model of immune response," Proc Natl Acad Sci USA, 1976, 73:3671-3675.
Ekiert, D.C., et al., "A highly conserved neutralizing epitope on group 2 influenza A viruses," Science, 2011,333:843-850.
Ekiert, D.C., et al., "Antibody recognition of a highly conserved influenza virus epitope," Science, 2009, 324:246-251.
Haynes, J.R., "Influenza virus-like particle vaccines," Expert Rev Vaccines, 2009, 8:435-445.
Kashyap, A.K., et al., "Combinatorial antibody libraries from survivors of the Turkish H5N1 avian influenza outbreak reveal virus neutralization strategies," Proc Natl Acad Sci USA, 2008, 105:5986-5991.
Kong, W.P., et al., "Protective immunity to lethal challenge of the 1918 pandemic influenza virus by vaccination," Proc Natl Acad Sci USA, 2006, 103:15987-15991.
Krause, J.C., et al., "A broadly neutralizing human monoclonal antibody that recognizes a conserved, novel epitope on the globular head of the influenza H1N1 virus hemagglutinin," J Virol, 2011, 85:10905-10908.
Lambert, L.C., et al., "Influenza vaccines for the future," N Engl J Med, 2010, 363, 2036-2044.
Li, C.Q. et al., "Ferritin nanoparticle technology: A new platform for antigen presentation and vaccine development," Industrial Biotechnol 2, 143-147 (2006).
Meldrum, F.C., et al., "Magnetoferritin: in vitro synthesis of a novel magnetic protein," Science, 1992, 257:522-523.
Nabel, G.J., et al., "Induction of unnatural immunity: prospects for a broadly protective universal influenza vaccine," Nat Med, 2010, 16:1389-1391.
Okuno, Y., et al., "A common neutralizing epitope conserved between the hemagglutinins of influenza A virus H1 and H2 strains," J Virol, 1993, 67:2552-2558.
Roldao, A., et al., "Virus-like particles in vaccine development," Expert Rev Vaccines, 2010, 9:1149-1176.
Sheridan, C., "Flu vaccine makers upgrade technology—and pray for time," Nat Biotechnol, 2009, 27:489-491.
Steel, J. et al., "Influenza Virus Vaccine Based on the Conserved Hemagglutinin Stalk Domain," MBio 1, e0018 (2010).
Sui, J., et al., "Structural and functional bases for broad-spectrum neutralization of avian and human influenza a viruses," Nat Struct Mol Biol, 2009, 16:265-273.
Treanor, J.J., et al., "Safety and immunogenicity of a recombinant hemagglutinin vaccine for H5 influenza in humans," Vaccine, 2001, 19:1732-1737.
Treanor, J.J., "Safety and immunogenicity of a baculovirus-expressed hemagglutinin influenza vaccine: a randomized controlled trial," JAMA, 2007, 297:1577-1582.
Wang, T.T., et al., "Broadly protective monoclonal antibodies against H3 influenza viruses following sequential immunization with different hemagglutinins," PLoS Pathog, 2010, vol. 6, Issue 2, e1000796.
Wei, C.J., et al., "Induction of broadly neutralizing H1N1 influenza antibodies by vaccination," Science, 2010, 329:1060-1064.
Wei, C.J., et al., "Comparative efficacy of neutralizing antibodies elicited by recombinant hemagglutinin proteins from avian H5N1 influenza virus," J Virol, 2008, 82:6200-6208.
Wei, C.J., et al., Cross-neutralization of 1918 and 2009 influenza viruses: role of glycans in viral evolution and vaccine design. *Sci Transl Med*, 2010, 2, 24ra21.
Whittle, J.R., et al., "Broadly neutralizing human antibody that recognizes the receptor-binding pocket of influenza virus hemagglutinin," Proc Natl Acad Sci USA, 2011, 108:14216-14221.
WHO Reference on Animal Influenza Diagnosis and Surveillance, 2002, Department of Communicable Disease Surveillance and Response, World Health Organization).
Wu, C.Y., et al., "Mammalian expression of virus-like particles for advanced mimicry of authentic influenza virus," PLoS One 5, 2010, e9784.
Xiong, A.S., et al., "PCR-based accurate synthesis of long DNA sequences," Nat Protoc, 2006, 1(2):791-797.
Yamashita, I., et al., "Ferritin in the field of nanodevices," Biochim Biophys Acta, 2010, 1800:846-857.
Yang, Z.Y., et al., "Immunization by avian H5 influenza hemagglutinin mutants with altered receptor binding specificity," *Science*, 2007, 317:825-828.
Zhang, Y., et al., "Self-Assembly in the Ferritin Nano-Cage Protein Superfamily," Int. J. Mol. Sci., 2011, 12:5406-5421.
Invitation to remedy deficiencies pursuant to Rule 30(3) EPC / Rules 163(3) EPC, dated May 23, 2014, in European Patent Application No. 12834398.5.

* cited by examiner

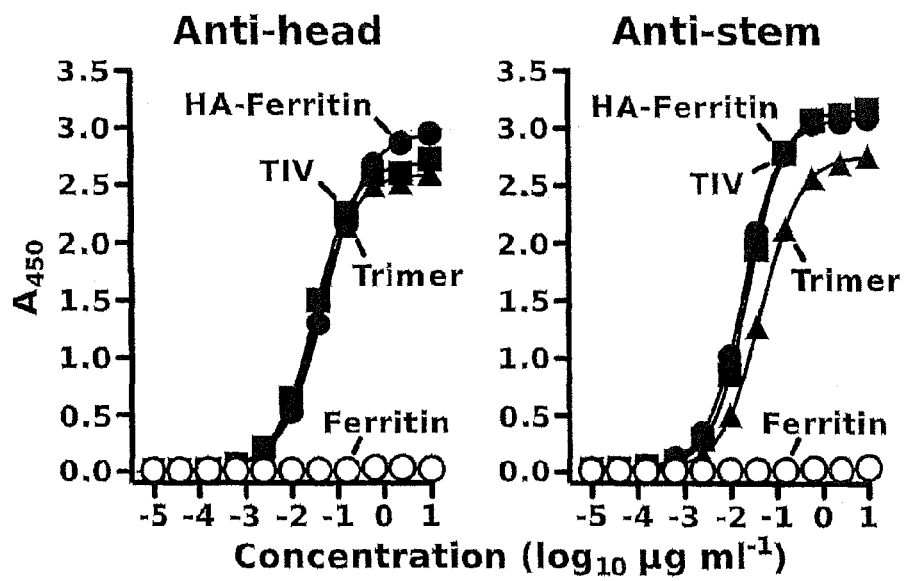
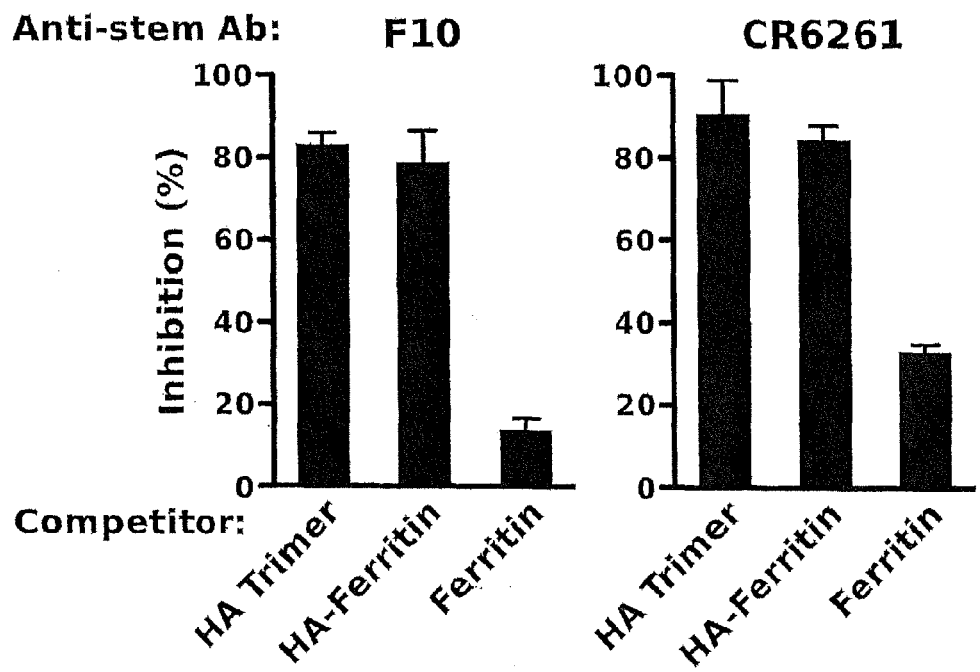
Fig. 3

Immunization of Pan-Group1 HA-Ferritin nanoparticles in Mice and Ferrets

Pan-group1 HA-np vaccine:

H1 A/NC/20/1999
H1 A/CA/04/2009
H2 A/Singapore/1/1957
H5 A/Indonesia/05/2005

Dose:
Mice: 6.8 μg (1.67 μg of each HA-np) + Ribi adjuvant
Ferrets: 10 μg (2.5 μg of each HA-np) + Ribi adjuvant
Injection: Intramuscular, weeks 0 and 3 (mice) or 4 (ferrets)

Fig. 11

Immunogenicity of Pan-Group1 HA-np In Mice

H1

| Virus | 1918 SC | 1934 PR8 | 1947 FM | 1954 MAL | 1986 SG | 1995 BJ | 1999 NC | 2006 SI | 2007 Bris | 2009 CA |
|---|---|---|---|---|---|---|---|---|---|---|
| Animal ID | | | | | | | | | | |
| 5726 | 2978 | <50 | <50 | <50 | <50 | <50 | 8306 | 690 | 423 | 9040 |
| 5727 | >3200 | <50 | <50 | <50 | <50 | 261 | 6208 | <50 | <50 | >12800 |
| 5728 | >3200 | <50 | 76 | <50 | <50 | 221 | >12800 | 1360 | 825 | >12800 |
| 5729 | >3200 | <50 | <50 | <50 | <50 | 989 | >12800 | <50 | 121 | >12800 |
| 5730 | 2521 | <50 | <50 | <50 | <50 | 4390 | 10906 | <50 | <50 | 11137 |

H2

| Virus | 1957 SG | 2006 MO (Swine) | 2007 NED (Avian) |
|---|---|---|---|
| Animal ID | | | |
| 5726 | >12800 | >12800 | >12800 |
| 5727 | >12800 | >12800 | >12800 |
| 5728 | >12800 | >12800 | >12800 |
| 5729 | >12800 | >12800 | >12800 |
| 5730 | >12800 | >12800 | >12800 |

H9

| | 1999 HK |
|---|---|
| Animal ID | |
| 5726 | <50 |
| 5727 | <50 |
| 5728 | <50 |
| 5729 | <50 |
| 5730 | <50 |

H5

| Virus | 2004 VN1203 | 2005 Indo | 2006 Nigeria (Avian) | 2007 Anhui |
|---|---|---|---|---|
| | Clade 1 | Clade 2.1.3 | Clade 2.2 | Clade 2.3.4 |
| Animal ID | | | | |
| 5726 | 488 | 1128 | 1438 | <50 |
| 5727 | 100 | 537 | 1192 | <50 |
| 5728 | 112 | 461 | 1002 | <50 |
| 5729 | 112 | 335 | 2539 | <50 |
| 5730 | 105 | 424 | 1105 | <50 |

IC50 titers are shown

Fig. 12

Immunogenicity of Pan-Group1 HA-np In Ferrets

| Virus | H1 | | | | | | | | |
|---|---|---|---|---|---|---|---|---|---|
| | 1918 SC | 1934 PR8 | 1947 FM | 1954 Mal | 1986 SG | 1999 NC | 2007 Bis | 2009 CA |
| Animal ID | | | | | | | | |
| 456 | <50 | <50 | <50 | <50 | 751 | 5726 | 888 | >6400 |
| 457 | 215 | <50 | 474 | 982 | 1438 | >6400 | >6400 | >6400 |
| 487 | <50 | <50 | <50 | <50 | 393 | 3568 | 402 | 2417 |
| 488 | <50 | <50 | <50 | <50 | 646 | >6400 | 851 | >6400 |
| 492 | 138 | <50 | 401 | <50 | 1342 | >6400 | 1755 | >6400 |
| 493 | <50 | <50 | 331 | 437 | 815 | >6400 | 3193 | >6400 |
| 444 | 140 | <50 | <50 | <50 | 421 | 6400 | 1223 | 5547 |
| 445 | <50 | <50 | <50 | <50 | 596 | 2978 | 741 | 3825 |
| 485 | <50 | <50 | <50 | <50 | 501 | 1962 | 762 | 794 |
| 486 | <50 | <50 | 50 | <50 | 441 | 6400 | 1079 | 1707 |
| 489 | <50 | <50 | <50 | <50 | 501 | 4712 | 455 | 1172 |
| 490 | 258 | <50 | 709 | 885 | >6400 | >6400 | 5569 | >6400 |

| Virus | H2 | |
|---|---|---|
| | 1957 SG | 2006 MO (Swine) | 2007 NED (Avian) |
| Animal ID | | | |
| 456 | 2193 | 247 | 2351 |
| 457 | >6400 | 1035 | >6400 |
| 487 | 2740 | 284 | 1637 |
| 488 | >6400 | 663 | >6400 |
| 492 | >6400 | 682 | >6400 |
| 493 | 3423 | 365 | 3720 |
| 444 | 6400 | 482 | 2628 |
| 445 | 762 | <50 | 751 |
| 485 | 1425 | 127 | 762 |
| 486 | 3329 | 331 | 1638 |
| 489 | 4276 | 365 | 2133 |
| 490 | 4276 | 577 | 1856 |

| Virus | H5 | | | |
|---|---|---|---|---|
| | 2004 VN1203 Clade 1 | 2005 Indo Clade 2.1.3 | 2006 Nigeria (Avian) Clade 2.2 | 2007 Anhui Clade 2.3.4 |
| Animal ID | | | | |
| 456 | TBD | 546 | 1571 | 806 |
| 457 | TBD | 1189 | 4276 | 2384 |
| 487 | TBD | <50 | 365 | <50 |
| 488 | TBD | 258 | 900 | 482 |
| 492 | TBD | 380 | 1780 | 731 |
| 493 | TBD | 335 | 992 | 523 |
| 444 | TBD | 296 | 817 | 585 |
| 445 | TBD | <50 | 272 | <50 |
| 485 | TBD | <50 | <50 | <50 |
| 486 | TBD | <50 | 577 | 112 |
| 489 | TBD | 50 | 828 | 292 |
| 490 | TBD | 370 | 1348 | 449 |

IC50 titers are shown

Fig. 13

HAI Titers from Pan-Group1 HA-np Immunized Ferrets

| | HAI | | | | | |
|---|---|---|---|---|---|---|
| Virus | H1 1986 SG | H1 1999 NC | H1 2007 Bris | H1 2009 CA | H2 1957 SG | H5 2005 Indo |
| Animal ID | | | | | | |
| 456 | 16 | 2560 | 160 | 2560 | 2560 | 2560 |
| 457 | 40 | 5120 | 640 | 5120 | 20480 | 5120 |
| 487 | 40 | 1280 | 40 | 640 | 2560 | 320 |
| 488 | 40 | 2560 | 80 | 1280 | 10240 | 1280 |
| 492 | 20 | 2560 | 40 | 5120 | 10240 | 1280 |
| 493 | 16 | 2560 | 80 | 5120 | 2560 | 640 |
| 444 | 20 | 2560 | 40 | 1280 | 2560 | 1280 |
| 445 | 40 | 1280 | 80 | 1280 | 640 | 20 |
| 485 | 20 | 1280 | 20 | 320 | 1280 | 80 |
| 486 | 20 | 2560 | 80 | 2560 | 2560 | 640 |
| 489 | 16 | 2560 | 80 | 1280 | 5120 | 320 |
| 490 | 40 | 10240 | 160 | 5120 | 2560 | 640 |

HAI assays were performed using the sera obtained from the immunization studies. The assays were performed using H1N1 viruses or H2 and H5 HA-ferritin nanoparticles.

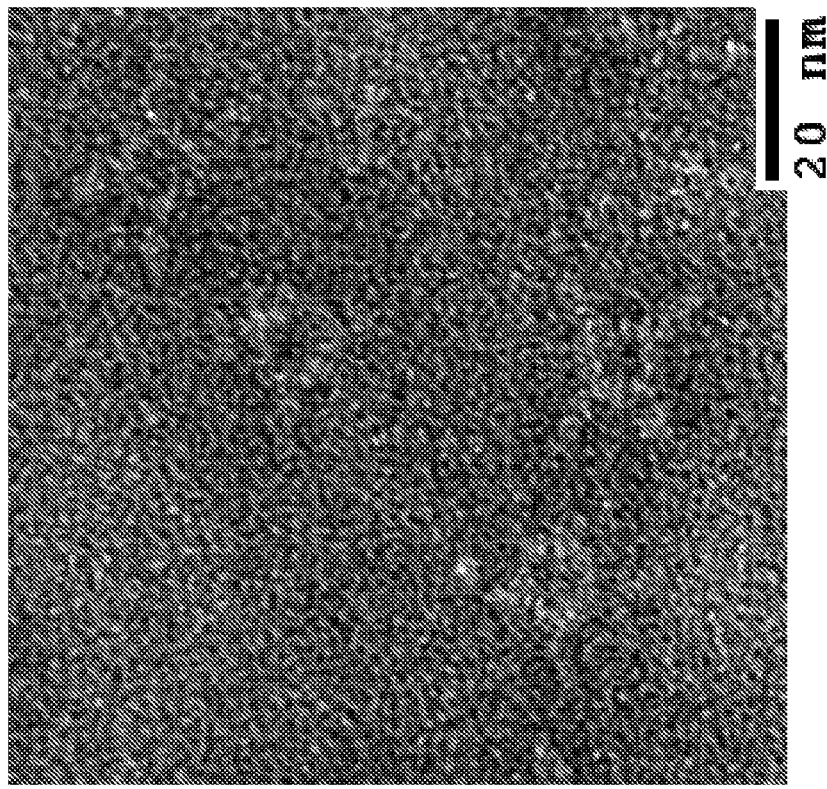
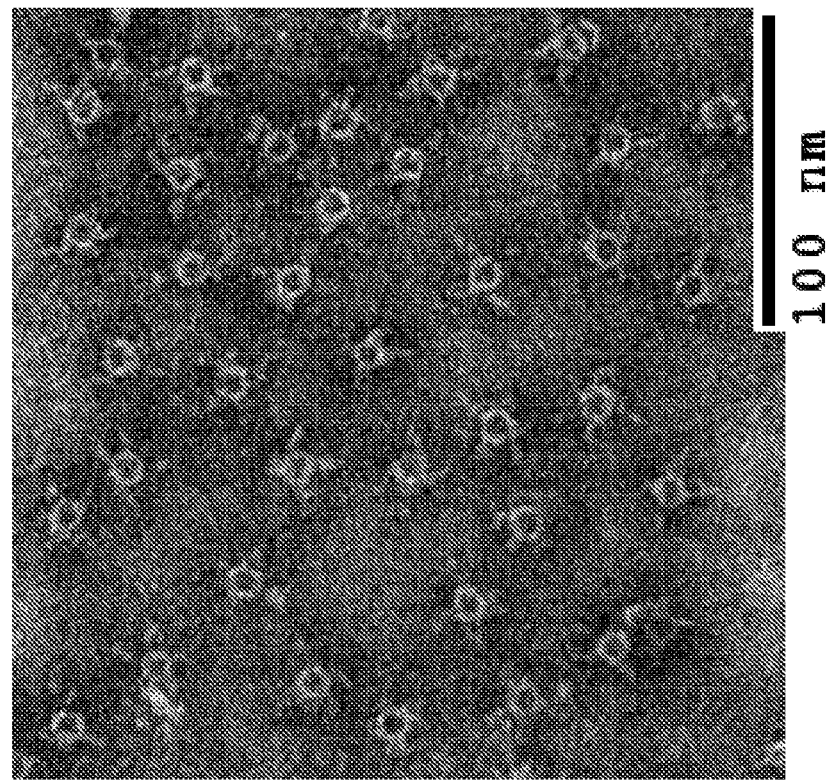
Fig. 20

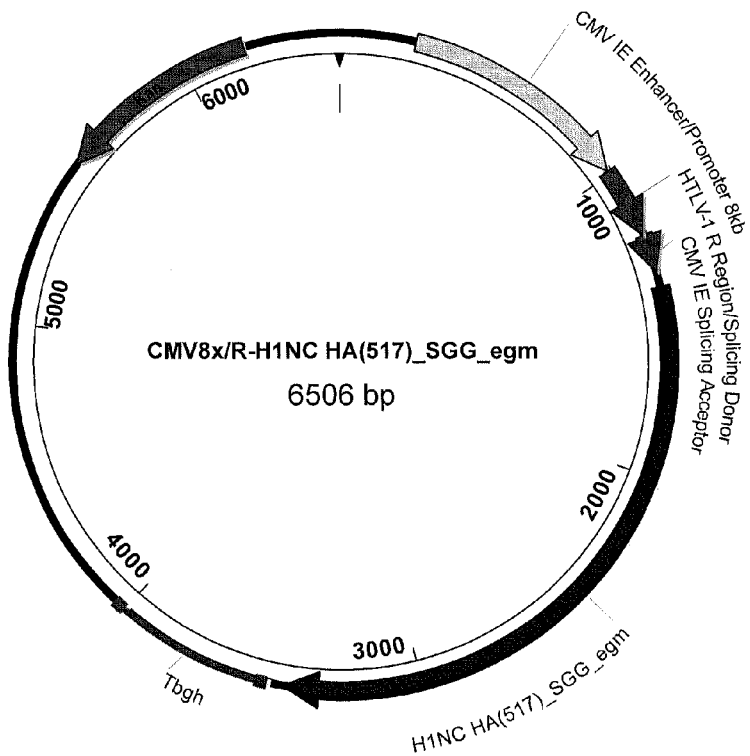
H1NC HA(517)_SGG_egm (H1 1999NC HA-ferritin)

Plasmid DNA sequence (SEQ ID NO:130)
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 25-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCAAACTGCTGGTGCTGCTGTGTA
CCTTTACCGCCACCTACGCCGACACAATCTGTATCGGCTACCACGCCAACAATAGCACCGACACCGTGGAT
ACAGTGCTGGAGAAGAACGTGACCGTGACCCACTCTGTGAACCTGCTGGAGGACAGCCACAATGGCAAGCT
GTGTCTGCTGAAAGGCATTGCCCCTCTGCAGCTGGGCAATTGTTCTGTGGCCGGATGGATTCTGGGCAACC
CCGAGTGTGAGCTGCTGATTTCTAAGGAGAGCTGGAGCTACATCGTGGAGACCCCCAATCCTGAGAATGGC
ACCTGCTACCCTGGCTACTTCGCCGATTACGAGGAGCTGCGCGAGCAGCTGTCTAGCGTGTCCAGCTTCGA
GAGATTCGAGATCTTCCCCAAGGAGTCCAGCTGGCCTAATCACACAGTGACAGGCGTGTCTGCCAGCTGTA
GCCACAACGGCAAAAGCAGCTTCTACCGGAACCTGCTGTGGCTGACAGGCAAGAATGGCCTGTACCCCAAC
CTGAGCAAGAGCTACGTGAACAACAAGGAAAAGGAAGTGCTGGTGCTGTGGGGAGTGCACCACCCTCCCAA
CATCGGAAATCAGCGGGCCCTGTACCACACAGAGAACGCCTATGTGAGCGTGGTGTCCAGCCACTACAGCA
AAGATTCACCCCCGAGATCGCCAAGAGACCCAAAGTGAGAGACCAGGAGGGCCGGATCAATTACTACTGG
ACCCTGCTGGAGCCTGGCGATACCATCATCTTCGAGGCCAACGGCAATCTGATCGCCCCTTGGTATGCCTT
TGCCCTGAGCAGAGGCTTTGGCAGCGGCATCATCACAAGCAACGCCCCCATGGATGAGTGTGATGCCAAGT
GCCAGACACCTCAGGGCGCCATCAATAGCAGCCTGCCCTTCCAGAATGTGCACCCTGTGACCATCGGCGAG
TGCCCCAAGTATGTGAGAAGCGCCAAGCTGAGAATGGTGACCGGCCTGAGAAACATCCCTCAGAGGGAGAC
CAGAGGACTGTTTGGAGCCATCGCCGGATTCATCGAGGGAGGATGGACAGGCATGGTGGATGGCTGGTACG
GCTACCACCACCAGAATGAGCAGGGCTCTGGATATGCCGCCGATCAGAAGTCTACCCAGAACGCCATCAAC
GGCATCACCAACAAGGTGAACAGCGTGATCGAGAAGATGAACACCCAGTTTACCGCTGTGGGCAAGGAGTT
CAACAAGCTGGAGCGGAGGATGGAGAACCTGAACAAGAAGGTGGACGACGGCTTTCTGGACATCTGGACCT
ACAATGCCGAACTCCTGGTCCTCCTCGAGAATGAGAGGACCCTGGACTTCCACGACAGCAACGTGAAGAAC
CTGTATGAGAAGGTGAAGAGCCAGCTGAAGAACAACGCCAAGGAGATCGGCAACGGCTGCTTCGAGTTCTA
CCACAAGTGTAACAACGAGTGTATGGAGAGCGTGAAGAACGGCACCTACGACTACCCTAAGTACAGCGAGG
AGAGCAAGCTGAACCGGGAGAAGATCGATTCCGGAGGCGACATCATCAAGCTGCTGAACGAGCAGGTGAAC
AAGGAGATGCAGAGCAGCAACCTGTACATGAGCATGAGCAGCTGGTGCTACACCCACAGCCTGGACGGCGC
CGGCCTGTTCCTGTTCGACCACGCCGCCGAGGAGTACGAGCACGCCAAGAAGCTGATCATCTTCCTGAACG
AGAACAACGTGCCCGTGCAGCTGACCAGCATCAGCGCCCCCGAGCACAAGTTCGAGGGCCTGACCCAGATC
TTCCAGAAGGCCTACGAGCACGAGCAGCACATCAGCGAGAGCATCAACAACATCGTGGACCACGCCATCAA
GAGCAAGGACCACGCCACCTTCAACTTCCTGCAGTGGTACGTGGCCGAGCAGCACGAGGAGGAGGTGCTGT
TCAAGGACATCCTGGACAAGATCGAGCTGATCGGCAACGAGAACCACGGCCTGTACCTGGCCGACCAGTAC
GTGAAGGGCATCGCCAAGAGCAGGAAGAGCGGATCCTAGCATCATCATCATCATTAGTCTGGAAGGGCGAA
TTGATCCAGATCTGCTGTGCCTTCTAGTTGCCAGCCATCTGTTGTTTGCCCCTCCCCGTGCCTTCCTTGA
CCCTGGAAGGTGCCACTCCCACTGTCCTTTCCTAATAAAATGAGGAAATTGCATCGCATTGTCTGAGTAGG
TGTCATTCTATTCTGGGGGGTGGGGTGGGGCAGGACAGCAAGGGGGAGGATTGGGAAGACAATAGCAGGCA
TGCTGGGGATGCGGTGGGCTCTATGGGTACCCAGGTGCTGAAGAATTGACCCGGTTCCTCCTGGGCCAGAA
AGAAGCAGGCACATCCCCTTCTCTGTGACACACCCTGTCCACGCCCCTGGTTCTTAGTTCCAGCCCCACTC
ATAGGACACTCATAGCTCAGGAGGGCTCCGCCTTCAATCCCACCCGCTAAAGTACTTGGAGCGGTCTCTCC
CTCCCTCATCAGCCCACCAAACCAAACCTAGCCTCCAAGAGTGGGAAGAAATTAAAGCAAGATAGGCTATT
AAGTGCAGAGGGAGAGAAAATGCCTCCAACATGTGAGGAAGTAATGAGAGAAATCATAGAATTTTAAGGCC
ATGATTTAAGGCCATCATGGCCTTAATCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCC
ATAGGCTCCGCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCC
```

Fig. 25-2

```
TTATCCGGTAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATTAAAAATGAAGT
TTTAAATCAATCTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCGGGGGGGGGGGCGCTGAGGTCTGC
CTCGTGAAGAAGGTGTTGCTGACTCATACCAGGCCTGAATCGCCCCATCATCCAGCCAGAAAGTGAGGGAG
CCACGGTTGATGAGAGCTTTGTTGTAGGTGGACCAGTTGGTGATTTTGAACTTTTGCTTTGCCACGGAACG
GTCTGCGTTGTCGGGAAGATGCGTGATCTGATCCTTCAACTCAGCAAAAGTTCGATTTATTCAACAAAGCC
GCCGTCCCGTCAAGTCAGCGTAATGCTCTGCCAGTGTTACAACCAATTAACCAATTCTGATTAGAAAAACT
CATCGAGCATCAAATGAAACTGCAATTTATTCATATCAGGATTATCAATACCATATTTTTGAAAAAGCCGT
TTCTGTAATGAAGGAGAAAACTCACCGAGGCAGTTCCATAGGATGGCAAGATCCTGGTATCGGTCTGCGAT
TCCGACTCGTCCAACATCAATACAACCTATTAATTTCCCCTCGTCAAAAATAAGGTTATCAAGTGAGAAAT
CACCATGAGTGACGACTGAATCCGGTGAGAATGGCAAAAGCTTATGCATTTCTTTCCAGACTTGTTCAACA
GGCCAGCCATTACGCTCGTCATCAAAATCACTCGCATCAACCAAACCGTTATTCATTCGTGATTGCGCCTG
AGCGAGACGAAATACGCGATCGCTGTTAAAAGGACAATTACAAACAGGAATCGAATGCAACCGGCGCAGGA
ACACTGCCAGCGCATCAACAATATTTTCACCTGAATCAGGATATTCTTCTAATACCTGGAATGCTGTTTTC
CCGGGGATCGCAGTGGTGAGTAACCATGCATCATCAGGAGTACGGATAAAATGCTTGATGGTCGGAAGAGG
CATAAATTCCGTCAGCCAGTTTAGTCTGACCATCTCATCTGTAACATCATTGGCAACGCTACCTTTGCCAT
GTTTCAGAAACAACTCTGGCGCATCGGGCTTCCCATACAATCGATAGATTGTCGCACCTGATTGCCCGACA
TTATCGCGAGCCCATTTATACCCATATAAATCAGCATCCATGTTGGAATTTAATCGCGGCCTCGAGCAAGA
CGTTTCCCGTTGAATATGGCTCATAACACCCCTTGTATTACTGTTTATGTAAGCAGACAGTTTTATTGTTC
ATGATGATATATTTTTATCTTGTGCAATGTAACATCAGAGATTTTGAGACACAACGTGGCTTTCCCCCCCC
CCCCATTATTGAAGCATTTATCAGGGTTATTGTCTCATGAGCGGATACATATTTGAATGTATTTAGAAAAA
TAAACAAATAGGGGTTCCGCGCACATTTCCCCGAAAAGTGCCACCTGACGTCTAAGAAACCATTATTATCA
TGACATTAACCTATAAAAATAGGCGTATCACGAGGCCCTTTCGTC
```

Coding sequence (SEQ ID NO:131)
```
ATGAAGGCCAAACTGCTGGTGCTGCTGTGTACCTTTACCGCCACCTACGCCGACACAATCTGTATCGGCTA
CCACGCCAACAATAGCACCGACACCGTGGATACAGTGCTGGAGAAGAACGTGACCGTGACCCACTCTGTGA
ACCTGCTGGAGGACAGCCACAATGGCAAGCTGTGTCTGCTGAAAGGCATTGCCCCTCTGCAGCTGGGCAAT
TGTTCTGTGGCCGGATGGATTCTGGGCAACCCCGAGTGTGAGCTGCTGATTTCTAAGGAGAGCTGGAGCTA
CATCGTGGAGACCCCCAATCCTGAGAATGGCACCTGCTACCCTGGCTACTTCGCCGATTACGAGGAGCTGC
GCGAGCAGCTGTCTAGCGTGTCCAGCTTCGAGAGATTCGAGATCTTCCCCAAGGAGTCCAGCTGGCCTAAT
CACACAGTGACAGGCGTGTCTGCCAGCTGTAGCCACAACGGCAAAGCAGCTTCTACCGGAACCTGCTGTG
GCTGACAGGCAAGAATGGCCTGTACCCCAACCTGAGCAAGAGCTACGTGAACAACAAGGAAAAGGAAGTGC
TGGTGCTGTGGGGAGTGCACCACCCTCCCAACATCGGAAATCAGCGGGCCCTGTACCACACAGAGAACGCC
TATGTGAGCGTGGTGTCCAGCCACTACAGCAGAAGATTCACCCCCGAGATCGCCAAGAGACCCAAAGTGAG
AGACCAGGAGGGCCGGATCAATTACTACTGGACCCTGCTGGAGCCTGGCGATACCATCATCTTCGAGGCCA
ACGGCAATCTGATCGCCCCTTGGTATGCCTTTGCCCTGAGCAGAGGCTTTGGCAGCGGCATCATCACAAGC
AACGCCCCCATGGATGAGTGTGATGCCAAGTGCCAGACACCTCAGGGCGCCATCAATAGCAGCCTGCCCTT
CCAGAATGTGCACCCTGTGACCATCGGCGAGTGCCCCAAGTATGTGAGAAGCGCCAAGCTGAGAATGGTGA
CCGGCCTGAGAAACATCCCTCAGAGGGAGACCAGAGGACTGTTTGGAGCCATCGCCGGATTCATCGAGGGA
GGATGGACAGGCATGGTGGATGGCTGGTACGGCTACCACCACCAGAATGAGCAGGGCTCTGGATATGCCGC
CGATCAGAAGTCTACCCAGAACGCCATCAACGGCATCACCAACAAGGTGAACAGCGTGATCGAGAAGATGA
ACACCCAGTTTACCGCTGTGGGCAAGGAGTTCAACAAGCTGGAGCGGAGGATGGAGAACCTGAACAAGAAG
GTGGACGACGGCTTTCTGGACATCTGGACCTACAATGCCGAACTCCTGGTCCTCCTCGAGAATGAGAGGAC
CCTGGACTTCCACGACAGCAACGTGAAGAACCTGTATGAGAAGGTGAAGAGCCAGCTGAAGAACAACGCCA
AGGAGATCGGCAACGGCTGCTTCGAGTTCTACCACAAGTGTAACAACGAGTGTATGGAGAGCGTGAAGAAC
GGCACCTACGACTACCCTAAGTACAGCGAGGAGAGCAAGCTGAACCGGGAGAAGATCGATTCCGGAGGCGA
CATCATCAAGCTGCTGAACGAGCAGGTGAACAAGGAGATGCAGAGCAGCAACCTGTACATGAGCATGAGCA
GCTGGTGCTACACCCACAGCCTGGACGGCGCCGGCCTGTTCCTGTTCGACCACGCCGCCGAGGAGTACGAG
```

Fig. 25-3

```
CACGCCAAGAAGCTGATCATCTTCCTGAACGAGAACAACGTGCCCGTGCAGCTGACCAGCATCAGCGCCCC
CGAGCACAAGTTCGAGGGCCTGACCCAGATCTTCCAGAAGGCCTACGAGCACGAGCAGCACATCAGCGAGA
GCATCAACAACATCGTGGACCACGCCATCAAGAGCAAGGACCACGCCACCTTCAACTTCCTGCAGTGGTAC
GTGGCCGAGCAGCACGAGGAGGAGGTGCTGTTCAAGGACATCCTGGACAAGATCGAGCTGATCGGCAACGA
GAACCACGGCCTGTACCTGGCCGACCAGTACGTGAAGGGCATCGCCAAGAGCAGGAAGAGCGGATCCTAG
```

Translation (SEQ ID NO:41)
```
MKAKLLVLLCTFTATYADTICIGYHANNSTDTVDTVLEKNVTVTHSVNLLEDSHNGKLCLLKGIAPLQLGN
CSVAGWILGNPECELLISKESWSYIVETPNPENGTCYPGYFADYEELREQLSSVSSFERFEIFPKESSWPN
HTVTGVSASCSHNGKSSFYRNLLWLTGKNGLYPNLSKSYVNNKEKEVLVLWGVHHPPNIGNQRALYHTENA
YVSVVSSHYSRRFTPEIAKRPKVRDQEGRINYYWTLLEPGDTIIFEANGNLIAPWYAFALSRGFGSGIITS
NAPMDECDAKCQTPQGAINSSLPFQNVHPVTIGECPKYVRSAKLRMVTGLRNIPQRETRGLFGAIAGFIEG
GWTGMVDGWYGYHHQNEQGSGYAADQKSTQNAINGITNKVNSVIEKMNTQFTAVGKEFNKLERRMENLNKK
VDDGFLDIWTYNAELLVLLENERTLDFHDSNVKNLYEKVKSQLKNNAKEIGNGCFEFYHKCNNECMESVKN
GTYDYPKYSEESKLNREKIDSGGDIIKLLNEQVNKEMQSSNLYMSMSSWCYTHSLDGAGLFLFDHAAEEYE
HAKKLIIFLNENNVPVQLTSISAPEHKFEGLTQIFQKAYEHEQHISESINNIVDHAIKSKDHATFNFLQWY
VAEQHEEEVLFKDILDKIELIGNENHGLYLADQYVKGIAKSRKSGS
```

Fig. 25-4

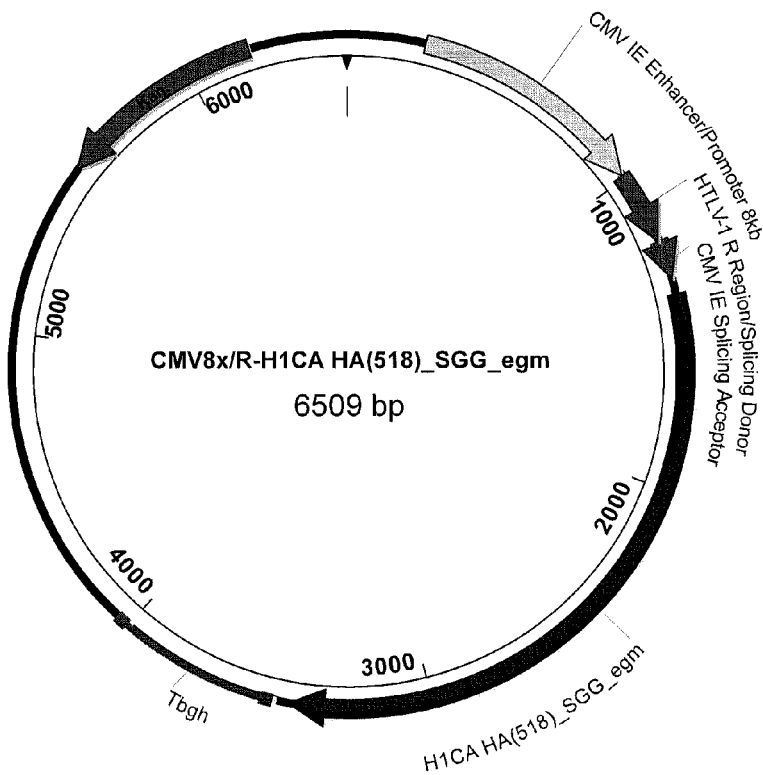
H1CA HA(518)_SGG_egm (H1 2009CA HA-ferritin)

Plasmid DNA sequence (SEQ ID NO:132)
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 26-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCATCCTGGTGGTGCTGCTGTACA
CCTTCGCCACCGCCAACGCCGACACCCTGTGCATCGGCTACCACGCCAACAACAGCACCGACACCGTGGAC
ACCGTGCTGGAGAAGAACGTGACCGTGACCCACAGCGTGAACCTGCTGGAGGACAAGCACAACGGCAAGCT
GTGCAAGCTGCGGGGCGTGGCCCCCCTGCACCTGGGCAAGTGCAACATCGCCGGCTGGATTCTGGGCAACC
CCGAGTGCGAGAGCCTGAGCACCGCCAGCAGCTGGAGCTACATCGTGGAGACCCCCAGCAGCGACAACGGC
ACCTGCTACCCCGGCGACTTCATCGACTACGAGGAGCTGCGGGAGCAGCTGAGCAGCGTGAGCAGCTTCGA
GCGGTTCGAGATCTTCCCCAAGACCAGCAGCTGGCCCAACCACGACAGCAACAAGGGCGTGACCGCCGCCT
GCCCCCACGCCGGCGCCAAGAGCTTCTACAAGAACCTGATCTGGCTGGTGAAGAAGGGCAACAGCTACCCC
AAGCTGAGCAAGAGCTACATCAACGACAAGGGCAAGGAGGTGCTGGTGCTGTGGGGCATCCACCACCCCAG
CACCAGCGCCGACCAGCAGAGCCTGTACCAGAACGCCGACACCTACGTGTTCGTGGGCAGCAGCCGGTACA
GCAAGAAGTTCAAGCCCGAGATCGCCATCCGGCCCAAGGTGCGGGACCAGGAGGGCCGGATGAACTACTAC
TGGACCCTGGTGGAGCCCGGCGACAAGATCACCTTCGAGGCCACCGGCAACCTGGTGGTGCCCCGGTACGC
CTTCGCCATGGAGCGGAACGCCGGCAGCGGCATCATCATCAGCGACACCCCCGTGCACGACTGCAACACCA
CCTGCCAGACCCCCAAGGGCGCCATCAACACCAGCCTGCCCTTCCAGAACATCCACCCCATCACCATCGGC
AAGTGCCCCAAGTACGTGAAGAGCACCAAGCTGCGGCTGGCCACCGGCCTGCGGAACATCCCCAGCATCCA
GAGCCGGGGCCTGTTCGGCGCCATCGCCGGCTTCATCGAGGGCGGCTGGACCGGCATGGTGGACGGCTGGT
ACGGCTACCACCACCAGAACGAGCAGGGCAGCGGCTACGCCGCCGACCTGAAGAGCACCCAGAACGCCATC
GACGAGATCACCAACAAGGTGAACAGCGTGATCGAGAAGATGAACACCCAGTTCACCGCCGTGGGCAAGGA
GTTCAACCACCTGGAGAAGCGGATCGAGAACCTGAACAAGAAGGTGGACGACGGCTTCCTGGACATCTGGA
CCTACAACGCCGAGCTGCTGGTGCTGCTGGAGAACGAGCGGACCCTGGACTACCACGACAGCAACGTGAAG
AACCTGTACGAGAAGGTGCGGAGCCAGCTGAAGAACAACGCCAAGGAGATCGGCAACGGCTGCTTCGAGTT
CTACCACAAGTGCGACAACACCTGCATGGAGAGCGTGAAGAACGGCACCTACGACTACCCCAAGTACAGCG
AGGAGGCCAAGCTGAACCGGGAGGAGATCGACTCCGGAGGCGACATCATCAAGCTGCTGAACGAGCAGGTG
AACAAGGAGATGCAGAGCAGCAACCTGTACATGAGCATGAGCAGCTGGTGCTACACCCACAGCCTGGACGG
CGCCGGCCTGTTCCTGTTCGACCACGCCGCCGAGGAGTACGAGCACGCCAAGAAGCTGATCATCTTCCTGA
ACGAGAACAACGTGCCCGTGCAGCTGACCAGCATCAGCGCCCCCGAGCACAAGTTCGAGGGCCTGACCCAG
ATCTTCCAGAAGGCCTACGAGCACGAGCAGCACATCAGCGAGAGCATCAACAACATCGTGGACCACGCCAT
CAAGAGCAAGGACCACGCCACCTTCAACTTCCTGCAGTGGTACGTGGCCGAGCAGCACGAGGAGGAGGTGC
TGTTCAAGGACATCCTGGACAAGATCGAGCTGATCGGCAACGAGAACCACGGCCTGTACCTGGCCGACCAG
TACGTGAAGGGCATCGCCAAGAGCAGGAAGAGCGGATCCTAGCATCATCATCATCATTAGTCTGGAAGGGC
GAATTGATCCAGATCTGCTGTGCCTTCTAGTTGCCAGCCATCTGTTGTTTGCCCCTCCCCGTGCCTTCCT
TGACCCTGGAAGGTGCCACTCCCACTGTCCTTTCCTAATAAAATGAGGAAATTGCATCGCATTGTCTGAGT
AGGTGTCATTCTATTCTGGGGGGTGGGGTGGGCAGGACAGCAAGGGGGAGGATTGGGAAGACAATAGCAG
GCATGCTGGGGATGCGGTGGGCTCTATGGGTACCCAGGTGCTGAAGAATTGACCCGGTTCCTCCTGGGCCA
GAAAGAAGCAGGCACATCCCCTTCTCTGTGACACACCCTGTCCACGCCCCTGGTTCTTAGTTCCAGCCCCA
CTCATAGGACACTCATAGCTCAGGAGGGCTCCGCCTTCAATCCCACCCGCTAAAGTACTTGGAGCGGTCTC
TCCCTCCCTCATCAGCCCACCAAACCAAACCTAGCCTCCAAGAGTGGGAAGAAATTAAAGCAAGATAGGCT
ATTAAGTGCAGAGGGAGAGAAAATGCCTCCAACATGTGAGGAAGTAATGAGAGAAATCATAGAATTTTAAG
GCCATGATTTAAGGCCATCATGGCCTTAATCTTCCGCTTCCTCGCTCACTGACTCGCTGCGCTCGGTCGTT
CGGCTGCGGCGAGCGGTATCAGCTCACTCAAAGGCGGTAATACGGTTATCCACAGAATCAGGGGATAACGC
AGGAAAGAACATGTGAGCAAAAGGCCAGCAAAAGGCCAGGAACCGTAAAAAGGCCGCGTTGCTGGCGTTTT
TCCATAGGCTCCGCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTAGGTATC
TCAGTTCGGTGTAGGTCGTTCGCTCCAAGCTGGGCTGTGTGCACGAACCCCCCGTTCAGCCCGACCGCTGC
```

Fig. 26-2

GCCTTATCCGGTAACTATCGTCTTGAGTCCAACCCGGTAAGACACGACTTATCGCCACTGGCAGCAGCCAC
TGGTAACAGGATTAGCAGAGCGAGGTATGTAGGCGGTGCTACAGAGTTCTTGAAGTGGTGGCCTAACTACG
GCTACACTAGAAGAACAGTATTTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCAGTGGAACGAAAACT
CACGTTAAGGGATTTTGGTCATGAGATTATCAAAAAGGATCTTCACCTAGATCCTTTTAAATTAAAAATGA
AGTTTTAAATCAATCTAAAGTATATATGAGTAAACTTGGTCTGACAGTTACCAATGCTTAATCAGTGAGGC
ACCTATCTCAGCGATCTGTCTATTTCGTTCATCCATAGTTGCCTGACTCGGGGGGGGGGGCGCTGAGGTC
TGCCTCGTGAAGAAGGTGTTGCTGACTCATACCAGGCCTGAATCGCCCCATCATCCAGCCAGAAAGTGAGG
GAGCCACGGTTGATGAGAGCTTTGTTGTAGGTGGACCAGTTGGTGATTTTGAACTTTTGCTTTGCCACGGA
ACGGTCTGCGTTGTCGGAAGATGCGTGATCTGATCCTTCAACTCAGCAAAAGTTCGATTTATTCAACAAA
GCCGCCGTCCCGTCAAGTCAGCGTAATGCTCTGCCAGTGTTACAACCAATTAACCAATTCTGATTAGAAAA
ACTCATCGAGCATCAAATGAAACTGCAATTTATTCATATCAGGATTATCAATACCATATTTTGAAAAAGC
CGTTTCTGTAATGAAGGAGAAAACTCACCGAGGCAGTTCCATAGGATGGCAAGATCCTGGTATCGGTCTGC
GATTCCGACTCGTCCAACATCAATACAACCTATTAATTTCCCCTCGTCAAAAATAAGGTTATCAAGTGAGA
AATCACCATGAGTGACGACTGAATCCGGTGAGAATGGCAAAAGCTTATGCATTTCTTTCCAGACTTGTTCA
ACAGGCCAGCCATTACGCTCGTCATCAAAATCACTCGCATCAACCAAACCGTTATTCATTCGTGATTGCGC
CTGAGCGAGACGAAATACGCGATCGCTGTTAAAAGGACAATTACAAACAGGAATCGAATGCAACCGGCGCA
GGAACACTGCCAGCGCATCAACAATATTTTCACCTGAATCAGGATATTCTTCTAATACCTGGAATGCTGTT
TTCCCGGGGATCGCAGTGGTGAGTAACCATGCATCATCAGGAGTACGGATAAAATGCTTGATGGTCGGAAG
AGGCATAAATTCCGTCAGCCAGTTTAGTCTGACCATCTCATCTGTAACATCATTGGCAACGCTACCTTTGC
CATGTTTCAGAAACAACTCTGGCGCATCGGGCTTCCCATACAATCGATAGATTGTCGCACCTGATTGCCCG
ACATTATCGCGAGCCCATTTATACCCATATAAATCAGCATCCATGTTGGAATTTAATCGCGGCCTCGAGCA
AGACGTTTCCCGTTGAATATGGCTCATAACACCCCTTGTATTACTGTTTATGTAAGCAGACAGTTTTATTG
TTCATGATGATATATTTTTATCTTGTGCAATGTAACATCAGAGATTTTGAGACACAACGTGGCTTTCCCCC
CCCCCCCATTATTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACGTCTAAGAAACCATTATTA
TCATGACATTAACCTATAAAAATAGGCGTATCACGAGGCCCTTTCGTC

Coding sequence (SEQ ID NO:133)
ATGAAGGCCATCCTGGTGGTGCTGCTGTACACCTTCGCCACCGCCAACGCCGACACCCTGTGCATCGGCTA
CCACGCCAACAACAGCACCGACACCGTGGACACCGTGCTGGAGAAGAACGTGACCGTGACCCACAGCGTGA
ACCTGCTGGAGGACAAGCACAACGGCAAGCTGTGCAAGCTGCGGGGCGTGGCCCCCCTGCACCTGGGCAAG
TGCAACATCGCCGGCTGGATTCTGGGCAACCCCGAGTGCGAGAGCCTGAGCACCGCCAGCAGCTGGAGCTA
CATCGTGGAGACCCCCAGCAGCGACAACGGCACCTGCTACCCCGGCGACTTCATCGACTACGAGGAGCTGC
GGGAGCAGCTGAGCAGCGTGAGCAGCTTCGAGCGGTTCGAGATCTTCCCCAAGACCAGCAGCTGGCCCAAC
CACGACAGCAACAAGGGCGTGACCGCCGCCTGCCCCACGCCGGCGCCAAGAGCTTCTACAAGAACCTGAT
CTGGCTGGTGAAGAAGGGCAACAGCTACCCCAAGCTGAGCAAGAGCTACATCAACGACAAGGGCAAGGAGG
TGCTGGTGCTGTGGGGCATCCACCACCCCAGCACCAGCGCCGACCAGCAGAGCCTGTACCAGAACGCCGAC
ACCTACGTGTTCGTGGGCAGCAGCCGGTACAGCAAGAAGTTCAAGCCCGAGATCGCCATCCGGCCCAAGGT
GCGGGACCAGGAGGGCCGGATGAACTACTACTGGACCCTGGTGGAGCCCGGCGACAAGATCACCTTCGAGG
CCACCGGCAACCTGGTGGTGCCCCGGTACGCCTTCGCCATGGAGCGGAACGCCGGCAGCGGCATCATCATC
AGCGACACCCCCGTGCACGACTGCAACACCACCTGCCAGACCCCCAAGGGCGCCATCAACACCAGCCTGCC
CTTCCAGAACATCCACCCCATCACCATCGGCAAGTGCCCCAAGTACGTGAAGAGCACCAAGCTGCGGCTGG
CCACCGGCCTGCGGAACATCCCCAGCATCCAGAGCCGGGGCCTGTTCGGCGCCATCGCCGGCTTCATCGAG
GGCGGCTGGACCGGCATGGTGGACGGCTGGTACGGCTACCACCACCAGAACGAGCAGGGCAGCGGCTACGC
CGCCGACCTGAAGAGCACCCAGAACGCCATCGACGAGATCACCAACAAGGTGAACAGCGTGATCGAGAAGA
TGAACACCCAGTTCACCGCCGTGGGCAAGGAGTTCAACCACCTGGAGAAGCGGATCGAGAACCTGAACAAG
AAGGTGGACGACGGCTTCCTGGACATCTGGACCTACAACGCCGAGCTGCTGGTGCTGCTGGAGAACGAGCG
GACCCTGGACTACCACGACAGCAACGTGAAGAACCTGTACGAGAAGGTGCGGAGCCAGCTGAAGAACAACG
CCAAGGAGATCGGCAACGGCTGCTTCGAGTTCTACCACAAGTGCGACAACACCTGCATGGAGAGCGTGAAG
AACGGCACCTACGACTACCCCAAGTACAGCGAGGAGGCCAAGCTGAACCGGGAGGAGATCGACTCCGGAGG
CGACATCATCAAGCTGCTGAACGAGCAGGTGAACAAGGAGATGCAGAGCAGCAACCTGTACATGAGCATGA
GCAGCTGGTGCTACACCCACAGCCTGGACGGCGCCGGCCTGTTCCTGTTCGACCACGCCGCCGAGGAGTAC

Fig. 26-3

GAGCACGCCAAGAAGCTGATCATCTTCCTGAACGAGAACAACGTGCCCGTGCAGCTGACCAGCATCAGCGC
CCCCGAGCACAAGTTCGAGGGCCTGACCCAGATCTTCCAGAAGGCCTACGAGCACGAGCAGCACATCAGCG
AGAGCATCAACAACATCGTGGACCACGCCATCAAGAGCAAGGACCACGCCACCTTCAACTTCCTGCAGTGG
TACGTGGCCGAGCAGCACGAGGAGGAGGTGCTGTTCAAGGACATCCTGGACAAGATCGAGCTGATCGGCAA
CGAGAACCACGGCCTGTACCTGGCCGACCAGTACGTGAAGGGCATCGCCAAGAGCAGGAAGAGCGGATCC

Translation (SEQ ID NO:44)
MKAILVVLLYTFATANADTLCIGYHANNSTDTVDTVLEKNVTVTHSVNLLEDKHNGKLCKLRGVAPLHLGK
CNIAGWILGNPECESLSTASSWSYIVETPSSDNGTCYPGDFIDYEELREQLSSVSSFERFEIFPKTSSWPN
HDSNKGVTAACPHAGAKSFYKNLIWLVKKGNSYPKLSKSYINDKGKEVLVLWGIHHPSTSADQQSLYQNAD
TYVFVGSSRYSKKFKPEIAIRPKVRDQEGRMNYYWTLVEPGDKITFEATGNLVVPRYAFAMERNAGSGIII
SDTPVHDCNTTCQTPKGAINTSLPFQNIHPITIGKCPKYVKSTKLRLATGLRNIPSIQSRGLFGAIAGFIE
GGWTGMVDGWYGYHHQNEQGSGYAADLKSTQNAIDEITNKVNSVIEKMNTQFTAVGKEFNHLEKRIENLNK
KVDDGFLDIWTYNAELLVLLENERTLDYHDSNVKNLYEKVRSQLKNNAKEIGNGCFEFYHKCDNTCMESVK
NGTYDYPKYSEEAKLNREEIDSGGDIIKLLNEQVNKEMQSSNLYMSMSSWCYTHSLDGAGLFLFDHAAEEY
EHAKKLIIFLNENNVPVQLTSISAPEHKFEGLTQIFQKAYEHEQHISESINNIVDHAIKSKDHATFNFLQW
YVAEQHEEEVLFKDILDKIELIGNENHGLYLADQYVKGIAKSRKSGS

Fig. 26-4

CMV8x/R-H2Sing HA(514)_SGG_egm
6497 bp

Labels on plasmid map: CMV IE Enhancer/Promoter 8kb; HTLV-1 R Region/Splicing Donor; CMV IE Splicing Acceptor; H2Sing(514)_SGG_egm; Tbgh.

H2 Sing HA(514)_SGG_egm (H2 1957Sing HA-ferritin)

Plasmid DNA sequence   (SEQ ID NO:134)

```
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG
```

Fig. 27-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGGCCATCATCTACCTGATCCTGCTGTTTA
CAGCTGTGCGGGGCGATCAGATCTGTATCGGCTACCACGCCAACAATAGCACCGAGAAGGTGGACACCATC
CTGGAAAGAAATGTGACCGTGACCCACGCCAAGGATATTCTGGAAAAGACCCACAACGGCAAGCTGTGCAA
GCTGAATGGCATTCCTCCTCTGGAACTGGGCGATTGTTCTATTGCTGGCTGGCTGCTGGGAAATCCTGAGT
GCGATAGACTGCTGTCTGTGCCTGAGTGGAGCTACATCATGGAAAAAGAGAACCCTAGGGACGGACTGTGT
TACCCCGGCAGCTTCAACGATTACGAGGAACTGAAGCACCTGCTGTCCAGCGTGAAGCACTTCGAGAAAGT
GAAGATCCTGCCCAAGGATAGATGGACCCAGCATACAACAACAGGCGGAAGCAGAGCTTGTGCTGTGTCCG
GCAACCCCAGCTTCTTCAGAAATATGGTCTGGCTGACCAAGAAGGGCTCTAATTATCCTGTGGCCAAGGGC
AGCTACAATAATACAAGCGGCGAGCAGATGCTGATTATTTGGGGCGTGCACCACCCTAATGATGAGACAGA
GCAGAGAACCCTGTACCAGAATGTGGGCACATACGTGTCTGTGGGCACCAGCACACTGAATAAGAGAAGCA
CCCCCGATATTGCCACCAGACCCAAAGTGAATGGACAGGGCGGCAGAATGGAATTTTCCTGGACCCTGCTG
GATATGTGGGACACCATCAACTTTGAGAGCACCGGGAATCTGATTGCCCCTGAGTACGGCTTCAAGATCAG
CAAGAGAGGCAGCAGCGGCATCATGAAAACAGAGGGCACCCTGGAAAACTGTGAAACCAAGTGTCAGACAC
CTCTGGGCGCCATTAATACCACCCTGCCCTTCCATAATGTGCACCCTCTGACAATCGGCGAGTGCCCTAAG
TACGTGAAGTCTGAGAAACTGGTGCTGGCCACAGGACTGAGAAATGTGCCCCAGATCGAGTCAAGAGGCCT
GTTTGGAGCCATTGCCGGCTTTATTGAAGGCGGATGGCAGGGAATGGTGGATGGGTGGTACGGCTATACC
ACAGCAATGATCAGGGATCTGGCTATGCCGCCGATAAAGAGAGCACCCAGAAGGCCTTTGACGGCATCACC
AACAAAGTGAACAGCGTGATCGAGAAGATGAACACCCAGTTTGAGGCCGTGGGCAAAGAGTTCAGCAATCT
GGAAAGACGGCTGGAAAACCTGAACAAGAAAATGGAAGATGGCTTCCTGGACGTGTGGACATATAATGCCG
AGCTGCTGGTGCTGATGGAAAACGAGAGGACCCTGGACTTTCACGACAGCAACGTGAAGAACCTGTACGAC
AAAGTGCGGATGCAGCTGAGAGACAATGTGAAAGAGCTGGGCAACGGCTGCTTTGAGTTCTACCACAAGTG
CGACGACGAGTGCATGAATAGCGTGAAGAACGGCACCTACGACTACCCTAAGTATGAGGAAGAGAGCAAGC
TGAACAGAAACGAGATCAAGTCCGGAGGCGACATCATCAAGCTGCTGAACGAGCAGGTGAACAAGGAGATG
CAGAGCAGCAACCTGTACATGAGCATGAGCAGCTGGTGCTACACCCACAGCCTGGACGGCGCCGGCCTGTT
CCTGTTCGACCACGCCGCCGAGGAGTACGAGCACGCCAAGAAGCTGATCATCTTCCTGAACGAGAACAACG
TGCCCGTGCAGCTGACCAGCATCAGCGCCCCCGAGCACAAGTTCGAGGGCCTGACCCAGATCTTCCAGAAG
GCCTACGAGCACGAGCAGCACATCAGCGAGAGCATCAACAACATCGTGGACCACGCCATCAAGAGCAAGGA
CCACGCCACCTTCAACTTCCTGCAGTGGTACGTGGCCGAGCAGCACGAGGAGGAGGTGCTGTTCAAGGACA
TCCTGGACAAGATCGAGCTGATCGGCAACGAGAACCACGGCCTGTACCTGGCCGACCAGTACGTGAAGGGC
ATCGCCAAGAGCAGGAAGAGCGGATCCTAGCATCATCATCATCATTAGTCTGGAAGGGCGAATTGATCCAG
ATCTGCTGTGCCTTCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGACAATAGCAGGCATGCTGGGGA
TGCGGTGGGCTCTATGGGTACCCAGGTGCTGAAGAATTGACCCGGTTCCTCCTGGGCCAGAAAGAAGCAGG
CACATCCCCTTCTCTGTGACACACCCTGTCCACGCCCCTGGTTCTTAGTTCCAGCCCCACTCATAGGACAC
TCATAGCTCAGGAGGGCTCCGCCTTCAATCCCACCCGCTAAAGTACTTGGAGCGGTCTCTCCCTCCCTCAT
CAGCCCACCAAACCAAACCTAGCCTCCAAGAGTGGGAAGAAATTAAAGCAAGATAGGCTATTAAGTGCAGA
GGGAGAGAAAATGCCTCCAACATGTGAGGAAGTAATGAGAGAAATCATAGAATTTTAAGGCCATGATTTAA
GGCCATCATGGCCTTAATCTTCCGCTTCCTCGCTCACTGACTCGCTGCGCTCGGTCGTTCGGCTGCGGCGA
GCGGTATCAGCTCACTCAAAGGCGGTAATACGGTTATCCACAGAATCAGGGGATAACGCAGGAAAGAACAT
GTGAGCAAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGACCCTGCCGCTTACCGGATACCT
GTCCGCCTTTCTCCCTTCGGGAAGCGTGGCGCTTTCTCATAGCTCACGCTGTAGGTATCTCAGTTCGGTGT
AGGTCGTTCGCTCCAAGCTGGGCTGTGTGCACGAACCCCCGTTCAGCCCGACCGCTGCGCCTTATCCGGT
```

Fig. 27-2

```
AACTATCGTCTTGAGTCCAACCCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGCCTAACTACGGCTACACTAGAA
GAACAGTATTTGGTATCTGCGCTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCAGATTACGCGCAGAAAAAAGG
ATCTCAAGAAGATCCTTTGATCTTTTCTACGGGGTCTGACGCTCAGTGGAACGAAAACTCACGTTAAGGGA
TTTTGGTCATGAGATTATCAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGAGGCACCTATCTCAGC
GATCTGTCTATTTCGTTCATCCATAGTTGCCTGACTCGGGGGGGGGGGGCGCTGAGGTCTGCCTCGTGAAG
AAGGTGTTGCTGACTCATACCAGGCCTGAATCGCCCCATCATCCAGCCAGAAAGTGAGGGAGCCACGGTTG
ATGAGAGCTTTGTTGTAGGTGGACCAGTTGGTGATTTTGAACTTTTGCTTTGCCACGGAACGGTCTGCGTT
GTCGGGAAGATGCGTGATCTGATCCTTCAACTCAGCAAAAGTTCGATTTATTCAACAAAGCCGCCGTCCCG
TCAAGTCAGCGTAATGCTCTGCCAGTGTTACAACCAATTAACCAATTCTGATTAGAAAAACTCATCGAGCA
TCAAATGAAACTGCAATTTATTCATATCAGGATTATCAATACCATATTTTTGAAAAAGCCGTTTCTGTAAT
GAAGGAGAAAACTCACCGAGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAGTGAGAAATCACCATGAG
TGACGACTGAATCCGGTGAGAATGGCAAAAGCTTATGCATTTCTTTCCAGACTTGTTCAACAGGCCAGCCA
TTACGCTCGTCATCAAAATCACTCGCATCAACCAAACCGTTATTCATTCGTGATTGCGCCTGAGCGAGACG
AAATACGCGATCGCTGTTAAAAGGACAATTACAAACAGGAATCGAATGCAACCGGCGCAGGAACACTGCCA
GCGCATCAACAATATTTTCACCTGAATCAGGATATTCTTCTAATACCTGGAATGCTGTTTTCCCGGGGATC
GCAGTGGTGAGTAACCATGCATCATCAGGAGTACGGATAAAATGCTTGATGGTCGGAAGAGGCATAAATTC
CGTCAGCCAGTTTAGTCTGACCATCTCATCTGTAACATCATTGGCAACGCTACCTTTGCCATGTTTCAGAA
ACAACTCTGGCGCATCGGGCTTCCCATACAATCGATAGATTGTCGCACCTGATTGCCCGACATTATCGCGA
GCCCATTTATACCCATATAAATCAGCATCCATGTTGGAATTTAATCGCGGCCTCGAGCAAGACGTTTCCCG
TTGAATATGGCTCATAACACCCCTTGTATTACTGTTTATGTAAGCAGACAGTTTTATTGTTCATGATGATA
TATTTTTATCTTGTGCAATGTAACATCAGAGATTTTGAGACACAACGTGGCTTTCCCCCCCCCCCCATTAT
TGAAGCATTTATCAGGGTTATTGTCTCATGAGCGGATACATATTTGAATGTATTTAGAAAAATAAACAAAT
AGGGGTTCCGCGCACATTTCCCCGAAAAGTGCCACCTGACGTCTAAGAAACCATTATTATCATGACATTAA
CCTATAAAAATAGGCGTATCACGAGGCCCTTTCGTC

Coding sequence  (SEQ ID NO:135)
ATGGCCATCATCTACCTGATCCTGCTGTTTACAGCTGTGCGGGGCGATCAGATCTGTATCGGCTACCACGC
CAACAATAGCACCGAGAAGGTGGACACCATCCTGGAAAGAAATGTGACCGTGACCCACGCCAAGGATATTC
TGGAAAAGACCCACAACGGCAAGCTGTGCAAGCTGAATGGCATTCCTCCTCTGGAACTGGGCGATTGTTCT
ATTGCTGGCTGGCTGCTGGGAAATCCTGAGTGCGATAGACTGCTGTCTGTGCCTGAGTGGAGCTACATCAT
GGAAAAAGAGAACCCTAGGGACGGACTGTGTTACCCCGGCAGCTTCAACGATTACGAGGAACTGAAGCACC
TGCTGTCCAGCGTGAAGCACTTCGAGAAAGTGAAGATCCTGCCCAAGGATAGATGGACCCAGCATACAACA
ACAGGCGGAAGCAGAGCTTGTGCTGTGTCCGGCAACCCCAGCTTCTTCAGAAATATGGTCTGGCTGACCAA
GAAGGGCTCTAATTATCCTGTGGCCAAGGGCAGCTACAATAATACAAGCGGCGAGCAGATGCTGATTATTT
GGGGCGTGCACCACCCTAATGATGAGACAGAGCAGAGAACCCTGTACCAGAATGTGGGCACATACGTGTCT
GTGGGCACCAGCACACTGAATAAGAGAAGCACCCCGATATTGCCACCAGACCCAAAGTGAATGGACAGGG
CGGCAGAATGGAATTTTCCTGGACCCTGCTGGATATGTGGACACCATCAACTTTGAGAGCACCGGAATC
TGATTGCCCCTGAGTACGGCTTCAAGATCAGCAAGAGAGGCAGCAGCGGCATCATGAAAACAGAGGGCACC
CTGGAAAACTGTGAAACCAAGTGTCAGACACCTCTGGGCGCCATTAATACCACCCTGCCCTTCCATAATGT
GCACCCTCTGACAATCGGCGAGTGCCCTAAGTACGTGAAGTCTGAGAAACTGGTGCTGGCCACAGGACTGA
GAAATGTGCCCCAGATCGAGTCAAGAGGCCTGTTTGGAGCCATTGCCGGCTTTATTGAAGGCGGATGGCAG
GGAATGGTGGATGGTGGTACGGCTATCACCACAGCAATGATCAGGGATCTGGCTATGCCGCCGATAAAGA
GAGCACCCAGAAGGCCTTTGACGGCATCACCAACAAAGTGAACAGCGTGATCGAGAAGATGAACACCCAGT
TTGAGGCCGTGGGCAAAGAGTTCAGCAATCTGGAAAGACGGCTGGAAAACCTGAACAAGAAATGGAAGAT
GGCTTCCTGGACGTGTGGACATATAATGCCGAGCTGCTGGTGCTGATGGAAAACGAGAGGACCCTGGACTT
TCACGACAGCAACGTGAAGAACCTGTACGACAAAGTGCGGATGCAGCTGAGAGACAATGTGAAAGAGCTGG
GCAACGGCTGCTTTGAGTTCTACCACAAGTGCGACGACGAGTGCATGAATAGCGTGAAGAACGGCACCTAC
GACTACCCTAAGTATGAGGAAGAGAGCAAGCTGAACAGAAACGAGATCAAGTCCGGAGGCGACATCATCAA
GCTGCTGAACAGCAGGTGAACAAGGAGATGCAGAGCAGCAACCTGTACATGAGCATGAGCAGCTGGTGCT
ACACCCACAGCCTGGACGGCGCCGGCCTGTTCCTGTTCGACCACGCCGCCGAGGAGTACGAGCACGCCAAG
```

AAGCTGATCATCTTCCTGAACGAGAACAACGTGCCCGTGCAGCTGACCAGCATCAGCGCCCCCGAGCACAA
GTTCGAGGGCCTGACCCAGATCTTCCAGAAGGCCTACGAGCACGAGCAGCACATCAGCGAGAGCATCAACA
ACATCGTGGACCACGCCATCAAGAGCAAGGACCACGCCACCTTCAACTTCCTGCAGTGGTACGTGGCCGAG
CAGCACGAGGAGGAGGTGCTGTTCAAGGACATCCTGGACAAGATCGAGCTGATCGGCAACGAGAACCACGG
CCTGTACCTGGCCGACCAGTACGTGAAGGGCATCGCCAAGAGCAGGAAGAGCGGATCC

Translation (SEQ ID NO:47)
MAIIYLILLFTAVRGDQICIGYHANNSTEKVDTILERNVTVTHAKDILEKTHNGKLCKLNGIPPLELGDCS
IAGWLLGNPECDRLLSVPEWSYIMEKENPRDGLCYPGSFNDYEELKHLLSSVKHFEKVKILPKDRWTQHTT
TGGSRACAVSGNPSFFRNMVWLTKKGSNYPVAKGSYNNTSGEQMLIIWGVHHPNDETEQRTLYQNVGTYVS
VGTSTLNKRSTPDIATRPKVNGQGGRMEFSWTLLDMWDTINFESTGNLIAPEYGFKISKRGSSGIMKTEGT
LENCETKCQTPLGAINTTLPFHNVHPLTIGECPKYVKSEKLVLATGLRNVPQIESRGLFGAIAGFIEGGWQ
GMVDGWYGYHHSNDQGSGYAADKESTQKAFDGITNKVNSVIEKMNTQFEAVGKEFSNLERRLENLNKKMED
GFLDVWTYNAELLVLMENERTLDFHDSNVKNLYDKVRMQLRDNVKELGNGCFEFYHKCDDECMNSVKNGTY
DYPKYEEESKLNRNEIKSGGDIIKLLNEQVNKEMQSSNLYMSMSSWCYTHSLDGAGLFLFDHAAEEYEHAK
KLIIFLNENNVPVQLTSISAPEHKFEGLTQIFQKAYEHEQHISESINNIVDHAIKSKDHATFNFLQWYVAE
QHEEEVLFKDILDKIELIGNENHGLYLADQYVKGIAKSRKSGS

Fig. 27-4

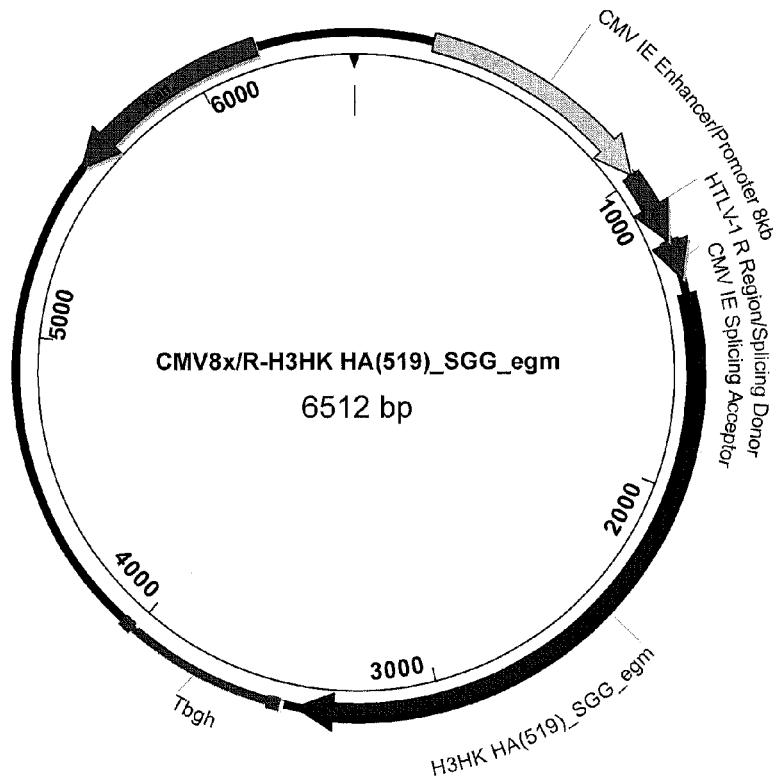
H3 HK HA(519)_SGG_egm (H3 1968HK HA-ferritin)

Plasmid DNA sequence (SEQ ID NO:136)

TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 28-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAAACCATCATTGCCCTGAGCTACATCT
TTTGTCTGGCTCTGGGCCAGGATCTGCCCGGCAATGATAATAGCACCGCCACCCTGTGTCTGGGACACCAC
GCCGTGCCTAATGGCACCCTGGTGAAAACCATTACCGACGACCAGATCGAAGTGACCAATGCCACCGAGCT
GGTGCAGAGCAGCAGCACCGGCAAGATCTGCAACAACCCCACAGAATCCTGGATGGCATCGACTGTACCC
TGATCGATGCCCTGCTGGGCGATCCTCACTGCGACGTGTTCCAGAACGAGACATGGGACCTGTTCGTGGAG
AGAAGCAAGGCCTTCAGCAACTGCTACCCCTACGATGTGCCCGATTACGCCTCTCTGAGAAGCCTGGTGGC
CAGCAGCGGCACACTGGAATTCATCACCGAGGGCTTTACCTGGACAGGCGTGACCCAGAATGGCGGCAGCA
ATGCCTGTAAAAGAGGCCCTGGCAGCGGCTTCTTCAGCAGACTGAACTGGCTGACCAAGTCCGGCAGCACC
TACCCTGTGCTGAACGTGACCATGCCCAACAACGACAACTTCGACAAGCTGTACATCTGGGGCGTGCACCA
CCCTAGCACCAATCAGGAACAGACCAGCCTGTACGTGCAGGCCAGCGGCAGAGTGACCGTGTCTACCAGAC
GGTCCCAGCAGACCATCATCCCCAACATCGAGTCAAGACCTTGGGTGCGCGGCCTGAGCAGCAGAATCAGC
ATCTACTGGACCATCGTGAAACCTGGCGACGTGCTGGTGATCAACAGCAATGGCAACCTGATCGCCCCCAG
AGGCTACTTCAAGATGCGGACCGGCAAGAGCAGCATCATGAGAAGCGACGCCCCCATCGATACCTGTATCA
GCGAGTGCATCACCCCCAACGGCAGCATCCCCAACGACAAGCCCTTCCAGAACGTGAACAAGATCACCTAC
GGCGCCTGCCCTAAGTACGTGAAGCAGAACACCCTGAAGCTGGCCACCGGCATGAGAAATGTGCCCGAGAA
GCAGACAAGAGGCCTGTTTGGCGCCATTGCCGGCTTTATCGAGAACGGCTGGGAGGGCATGATCGATGGGT
GGTACGGCTTCAGACACCAGAATTCTGAGGGCACAGGACAGGCCGCCGATCTGAAGTCTACACAGGCCGCC
ATCGACCAGATCAACGGCAAGCTGAACAGAGTGATCGAGAAAACCAACGAGAAGTTCCACCAGATCGAGAA
AGAATTCAGCGAGGTGGAGGGCAGAATCCAGGACCTGGAAAAATACGTGGAGGACACCAAGATCGACCTGT
GGAGCTACAATGCCGAACTGCTGGTCGCCCTGGAAAACCAGCACACCATCGACCTGACCGACAGCGAGATG
AATAAGCTGTTCGAAAAGACCAGACGGCAGCTGAGAGAAAACGCCGAGGACATGGGCAACGGCTGCTTCAA
GATCTACCACAAGTGCGACAACGCCTGCATCGAGAGCATCAGAAACGGCACCTACGACCACGATGTGTACA
GGGACGAGGCCCTGAACAACAGATTCCAGATCAAGTCCGGAGGCGACATCATCAAGCTGCTGAACGAGCAG
GTGAACAAGGAGATGCAGAGCAGCAACCTGTACATGAGCATGAGCAGCTGGTGCTACACCCACAGCCTGGA
CGGCGCCGGCCTGTTCCTGTTCGACCACGCCGCCGAGGAGTACGAGCACGCCAAGAAGCTGATCATCTTCC
TGAACGAGAACAACGTGCCCGTGCAGCTGACCAGCATCAGCGCCCCCGAGCACAAGTTCGAGGGCCTGACC
CAGATCTTCCAGAAGGCCTACGAGCACGAGCAGCACATCAGCGAGAGCATCAACAACATCGTGGACCACGC
CATCAAGAGCAAGGACCACGCCACCTTCAACTTCCTGCAGTGGTACGTGGCCGAGCAGCACGAGGAGGAGG
TGCTGTTCAAGGACATCCTGGACAAGATCGAGCTGATCGGCAACGAGAACCACGCCCTGTACCTGGCCGAC
CAGTACGTGAAGGGCATCGCCAAGAGCAGGAAGAGCGGATCCTAGCATCATCATCATCATTAGTCTGGAAG
GGCGAATTGATCCAGATCTGCTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCATTGTCTG
AGTAGGTGTCATTCTATTCTGGGGGGTGGGGTGGGCAGGACAGCAAGGGGGAGGATTGGGAAGACAATAG
CAGGCATGCTGGGGATGCGGTGGGCTCTATGGGTACCCAGGTGCTGAAGAATTGACCCGGTTCCTCCTGGG
CCAGAAAGAAGCAGGCACATCCCCTTCTCTGTGACACACCCTGTCCACGCCCTGGTTCTTAGTTCCAGCC
CCACTCATAGGACACTCATAGCTCAGGAGGGCTCCGCCTTCAATCCCACCCGCTAAAGTACTTGGAGCGGT
CTCTCCCTCCCTCATCAGCCCACCAAACCAAACCTAGCCTCCAAGAGTGGGAAGAAATTAAAGCAAGATAG
GCTATTAAGTGCAGAGGGAGAGAAAATGCCTCCAACATGTGAGGAAGTAATGAGAGAAATCATAGAATTTT
AAGGCCATGATTTAAGGCCATCATGGCCTTAATCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGT
TTTTCCATAGGCTCCGCCCCCTGACGAGCATCACAAAAATCGACGCTCAAGTCAGAGGTGGCGAAACCCG
ACAGGACTATAAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCCCGACCGC
```

Fig. 28-2

TGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTAC
GCGCAGAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTTTAAATTAAAAA
TGAAGTTTTAAATCAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCGGGGGGGGGGGCGCTGAG
GTCTGCCTCGTGAAGAAGGTGTTGCTGACTCATACCAGGCCTGAATCGCCCCATCATCCAGCCAGAAAGTG
AGGGAGCCACGGTTGATGAGAGCTTTGTTGTAGGTGGACCAGTTGGTGATTTTGAACTTTTGCTTTGCCAC
GGAACGGTCTGCGTTGTCGGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACCAATTCTGATTAGA
AAAACTCATCGAGCATCAAATGAAACTGCAATTTATTCATATCAGGATTATCAATACCATATTTTTGAAAA
AGCCGTTTCTGTAATGAAGGAGAAAACTCACCGAGGCAGTTCCATAGGATGGCAAGATCCTGGTATCGGTC
TGCGATTCCGACTCGTCCAACATCAATACAACCTATTAATTTCCCCTCGTCAAAAATAAGGTTATCAAGTG
AGAAATCACCATGAGTGACGACTGAATCCGGTGAGAATGGCAAAAGCTTATGCATTTCTTTCCAGACTTGT
TCAACAGGCCAGCCATTACGCTCGTCATCAAAATCACTCGCATCAACCAAACCGTTATTCATTCGTGATTG
CGCCTGAGCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTGGAATGCT
GTTTTCCCGGGGATCGCAGTGGTGAGTAACCATGCATCATCAGGAGTACGGATAAAATGCTTGATGGTCGG
AAGAGGCATAAATTCCGTCAGCCAGTTTAGTCTGACCATCTCATCTGTAACATCATTGGCAACGCTACCTT
TGCCATGTTTCAGAAACAACTCTGGCGCATCGGGCTTCCCATACAATCGATAGATTGTCGCACCTGATTGC
CCGACATTATCGCGAGCCCATTTATACCCATATAAATCAGCATCCATGTTGGAATTTAATCGCGGCCTCGA
GCAAGACGTTTCCCGTTGAATATGGCTCATAACACCCCTTGTATTACTGTTTATGTAAGCAGACAGTTTTA
TTGTTCATGATGATATATTTTTATCTTGTGCAATGTAACATCAGAGATTTTGAGACACAACGTGGCTTTCC
CCCCCCCCCCATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTCGTC

Coding sequence (SEQ ID NO:137)
ATGAAAACCATCATTGCCCTGAGCTACATCTTTTTGTCTGGCTCTGGGCCAGGATCTGCCCGGCAATGATAA
TAGCACCGCCACCCTGTGTCTGGGACACCACGCCGTGCCTAATGGCACCCTGGTGAAAACCATTACCGACG
ACCAGATCGAAGTGACCAATGCCACCGAGCTGGTGCAGAGCAGCAGCACCGGCAAGATCTGCAACAACCCC
CACAGAATCCTGGATGGCATCGACTGTACCCTGATCGATGCCCTGCTGGGCGATCCTCACTGCGACGTGTT
CCAGAACGAGACATGGGACCTGTTCGTGGAGAGAAGCAAGGCCTTCAGCAACTGCTACCCCTACGATGTGC
CCGATTACGCCTCTCTGAGAAGCCTGGTGGCCAGCAGCGGCACACTGGAATTCATCACCGAGGGCTTTACC
TGGACAGGCGTGACCCAGAATGGCGGCAGCAATGCCTGTAAAAGAGGCCCTGGCAGCGGCTTCTTCAGCAG
ACTGAACTGGCTGACCAAGTCCGGCAGCACCTACCCTGTGCTGAACGTGACCATGCCCAACAACGACAACT
TCGACAAGCTGTACATCTGGGCGTGCACCACCCTAGCACCAATCAGGAACAGACCAGCCTGTACGTGCAG
GCCAGCGGCAGAGTGACCGTGTCTACCAGACGGTCCCAGCAGACCATCATCCCCAACATCGAGTCAAGACC
TTGGGTGCGCGGCCTGAGCAGCAGAATCAGCATCTACTGGACCATCGTGAAACCTGGCGACGTGCTGGTGA
TCAACAGCAATGGCAACCTGATCGCCCCCAGAGGCTACTTCAAGATGCGGACCGGCAAGAGCAGCATCATG
AGAAGCGACGCCCCCATCGATACCTGTATCAGCGAGTGCATCACCCCCAACGGCAGCATCCCCAACGACAA
GCCCTTCCAGAACGTGAACAAGATCACCTACGGCGCCTGCCCTAAGTACGTGAAGCAGAACACCCTGAAGC
TGGCCACCGGCATGAGAAATGTGCCCGAGAAGCAGACAAGAGGCCTGTTTGGCGCCATTGCCGGCTTTATC
GAGAACGGCTGGGAGGGCATGATCGATGGGTGGTACGGCTTCAGACACCAGAATTCTGAGGGCACAGGACA
GGCCGCCGATCTGAAGTCTACACAGGCCGCCATCGACCAGATCAACGGCAAGCTGAACAGAGTGATCGAGA
AAACCAACGAGAAGTTCCACCAGATCGAGAAGAATTCAGCGAGGTGGAGGGCAGAATCCAGGACCTGGAA
AAATACGTGGAGGACACCAAGATCGACCTGTGGAGCTACAATGCCGAACTGCTGGTCGCCCTGGAAAACCA
GCACACCATCGACCTGACCGACAGCGAGATGAATAAGCTGTTCGAAAAGACCAGACGGCAGCTGAGAGAAA
ACGCCGAGGACATGGGCAACGGCTGCTTCAAGATCTACCACAAGTGCGACAACGCCTGCATCGAGAGCATC
AGAAACGGCACCTACGACCACGATGTGTACAGGGACGAGGCCCTGAACAACAGATTCCAGATCAAGTCCGG
AGGCGACATCATCAAGCTGCTGAACGAGCAGGTGAACAAGGAGATGCAGAGCAGCAACCTGTACATGAGCA
TGAGCAGCTGGTGCTACACCCACAGCCTGGACGGCGCCGGCCTGTTCCTGTTCGACCACGCCGCCGAGGAG

Fig. 28-3

TACGAGCACGCCAAGAAGCTGATCATCTTCCTGAACGAGAACAACGTGCCCGTGCAGCTGACCAGCATCAG
CGCCCCCGAGCACAAGTTCGAGGGCCTGACCCAGATCTTCCAGAAGGCCTACGAGCACGAGCAGCACATCA
GCGAGAGCATCAACAACATCGTGGACCACGCCATCAAGAGCAAGGACCACGCCACCTTCAACTTCCTGCAG
TGGTACGTGGCCGAGCAGCACGAGGAGGAGGTGCTGTTCAAGGACATCCTGGACAAGATCGAGCTGATCGG
CAACGAGAACCACGGCCTGTACCTGGCCGACCAGTACGTGAAGGGCATCGCCAAGAGCAGGAAGAGCGGAT
CC

Translation (SEQ ID NO:50)
MKTIIALSYIFCLALGQDLPGNDNSTATLCLGHHAVPNGTLVKTITDDQIEVTNATELVQSSSTGKICNNP
HRILDGIDCTLIDALLGDPHCDVFQNETWDLFVERSKAFSNCYPYDVPDYASLRSLVASSGTLEFITEGFT
WTGVTQNGGSNACKRGPGSGFFSRLNWLTKSGSTYPVLNVTMPNNDNFDKLYIWGVHHPSTNQEQTSLYVQ
ASGRVTVSTRRSQQTIIPNIESRPWVRGLSSRISIYWTIVKPGDVLVINSNGNLIAPRGYFKMRTGKSSIM
RSDAPIDTCISECITPNGSIPNDKPFQNVNKITYGACPKYVKQNTLKLATGMRNVPEKQTRGLFGAIAGFI
ENGWEGMIDGWYGFRHQNSEGTGQAADLKSTQAAIDQINGKLNRVIEKTNEKFHQIEKEFSEVEGRIQDLE
KYVEDTKIDLWSYNAELLVALENQHTIDLTDSEMNKLFEKTRRQLRENAEDMGNGCFKIYHKCDNACIESI
RNGTYDHDVYRDEALNNRFQIKSGGDIIKLLNEQVNKEMQSSNLYMSMSSWCYTHSLDGAGLFLFDHAAEE
YEHAKKLIIFLNENNVPVQLTSISAPEHKFEGLTQIFQKAYEHEQHISESINNIVDHAIKSKDHATFNFLQ
WYVAEQHEEEVLFKDILDKIELIGNENHGLYLADQYVKGIAKSRKSGS

Fig. 28-4

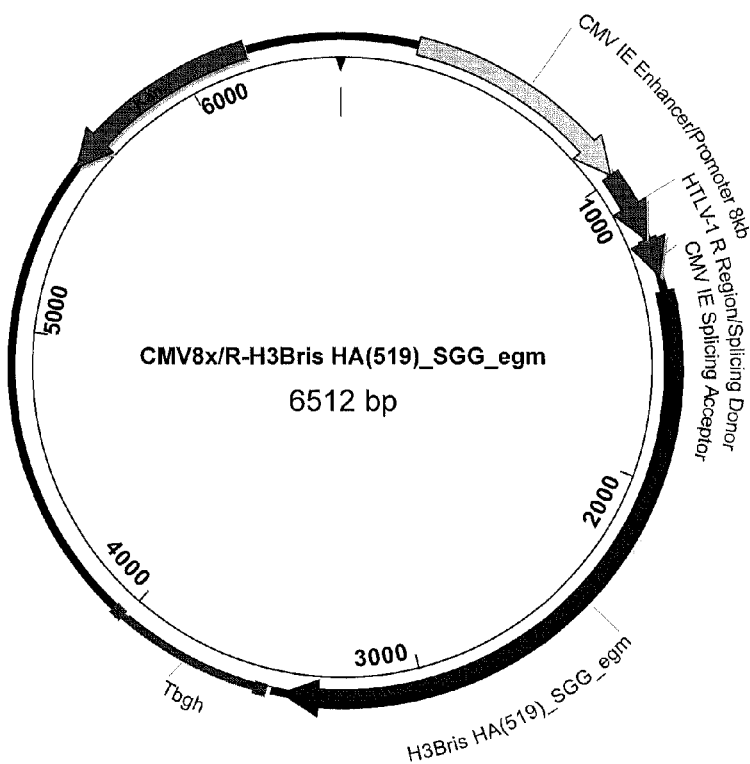
H3 Bris HA(519)_SGG_egm (H3 2007Bris HA-ferritin)

Plasmid DNA sequence (SEQ ID NO:138)

TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 29-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAAACCATCATTGCCCTGAGCTACATCC
TGTGCCTGGTGTTCACACAGAAGCTGCCCGGCAACGATAATAGCACCGCCACACTGTGTCTGGGACACCAC
GCCGTGCCTAATGGCACCATCGTGAAAACAATCACCAACGACCAGATCGAAGTGACCAATGCCACAGAGCT
GGTGCAGAGCAGCAGCACAGGCGAGATCTGTGACAGCCCCACCAGATCCTGGATGGCGAGAACTGTACCC
TGATCGATGCCCTGCTGGGCGATCCTCAGTGCGACGGCTTCCAGAACAAGAAATGGGACCTGTTCGTGGAG
AGAAGCAAGGCCTACAGCAACTGCTACCCCTACGACGTGCCTGATTACGCCAGCCTGAGAAGCCTGGTGGC
CTCTAGCGGCACCCTGGAATTCAACAACGAGAGCTTCAACTGGACCGGCGTGACACAGAATGGCACCAGCA
GCGCCTGCATCAGACGGTCCAACAACAGCTTCTTCAGTAGACTGAATTGGCTGACCCACCTGAAGTTCAAG
TACCCCGCCCTGAACGTGACCATGCCCAACAATGAGAAGTTCGACAAGCTGTACATCTGGGGAGTGCACCA
CCCTGGCACCGACAACGATCAGATCTTCCCTTACGCCCAGGCCAGCGGCAGAATCACCGTGTCCACCAAGA
GAAGCCAGCAGACCGTGATCCCCAATATCGGCAGCAGACCCAGAGTGCGGAACATCCCCAGCAGGATCAGC
ATCTACTGGACAATCGTGAAGCCTGGCGACATCCTGCTGATCAACAGCACCGGCAACCTGATCGCCCCTCG
GGGCTACTTTAAGATCAGAAGCGGCAAGAGCAGCATCATGAGATCCGACGCCCCCATCGGCAAGTGCAACA
GCGAGTGCATCACCCCAAACGGCAGCATCCCCAACGACAAGCCCTTCCAGAACGTGAACAGGATCACCTAC
GGCGCCTGCCCTAGATACGTGAAGCAGAACACCCTGAAGCTGGCCACCGGCATGAGAAATGTGCCCGAGAA
GCAGACCAGAGGCATCTTTGGCGCCATTGCCGGCTTTATCGAGAATGGCTGGGAGGGAATGGTGGATGGGT
GGTACGGCTTCAGACACCAGAATAGCGAGGGAATTGGACAGGCCGCCGATCTGAAATCTACCCAGGCCGCC
ATCGACCAGATCAACGGCAAGCTGAACAGGCTGATCGGCAAGACCAACGAGAAGTTCCACCAGATCGAGAA
AGAATTCAGCGAGGTGGAGGGCAGAATCCAGGACCTGGAAAAATACGTGGAGGACACCAAGATCGACCTGT
GGAGCTACAATGCCGAACTGCTGGTCGCCCTGGAAAACCAGCACACAATTGATCTGACAGACAGTGAGATG
AATAAGCTGTTCGAGAAAACCAAGAAGCAGCTGAGAGAAAACGCCGAGGACATGGGCAACGGCTGCTTCAA
GATCTACCACAAGTGCGACAACGCCTGCATCGGCAGCATCAGAAACGGCACCTACGACCACGACGTGTACA
GAGATGAGGCCCTGAACAACCGGTTTCAGATCAAGTCCGGAGGCGACATCATCAAGCTGCTGAACGAGCAG
GTGAACAAGGAGATGCAGAGCAGCAACCTGTACATGAGCATGAGCAGCTGGTGCTACACCCACAGCCTGGA
CGGCGCCGGCCTGTTCCTGTTCGACCACGCCGCCGAGGAGTACGAGCACGCCAAGAAGCTGATCATCTTCC
TGAACGAGAACAACGTGCCCGTGCAGCTGACCAGCATCAGCGCCCCCGAGCACAAGTTCGAGGGCCTGACC
CAGATCTTCCAGAAGGCCTACGAGCACGAGCAGCACATCAGCGAGAGCATCAACAACATCGTGGACCACGC
CATCAAGAGCAAGGACCACGCCACCTTCAACTTCCTGCAGTGGTACGTGGCCGAGCAGCACGAGGAGGAGG
TGCTGTTCAAGGACATCCTGGACAAGATCGAGCTGATCGGCAACGAGAACCACGGCCTGTACCTGGCCGAC
CAGTACGTGAAGGGCATCGCCAAGAGCAGGAAGAGCGGATCCTAGCATCATCATCATCATTAGTCTGGAAG
GGCGAATTGATCCAGATCTGCTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCATTGTCTG
AGTAGGTGTCATTCTATTCTGGGGGGTGGGGTGGGCAGGACAGCAAGGGGGAGGATTGGGAAGACAATAG
CAGGCATGCTGGGGATGCGGTGGGCTCTATGGGTACCCAGGTGCTGAAGAATTGACCCGGTTCCTCCTGGG
CCAGAAAGAAGCAGGCACATCCCCTTCTCTGTGACACACCCTGTCCACGCCCCTGGTTCTTAGTTCCAGCC
CCACTCATAGGACACTCATAGCTCAGGAGGGCTCCGCCTTCAATCCCACCCGCTAAAGTACTTGGAGCGGT
CTCTCCCTCCCTCATCAGCCCACCAAACCAAACCTAGCCTCCAAGAGTGGGAAGAAATTAAAGCAAGATAG
GCTATTAAGTGCAGAGGGAGAGAAAATGCCTCCAACATGTGAGGAAGTAATGAGAGAAATCATAGAATTTT
AAGGCCATGATTTAAGGCCATCATGGCCTTAATCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCAAGTCAGAGGTGGCGAAACCCG
ACAGGACTATAAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCCCGACCGC
```

Fig. 29-2

```
TGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTAC
GCGCAGAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAGGATCTTCACCTAGATCCTTTTAAATTAAAAA
TGAAGTTTTAAATCAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCGGGGGGGGGGGCGCTGAG
GTCTGCCTCGTGAAGAAGGTGTTGCTGACTCATACCAGGCCTGAATCGCCCCATCATCCAGCCAGAAAGTG
AGGGAGCCACGGTTGATGAGAGCTTTGTTGTAGGTGGACCAGTTGGTGATTTTGAACTTTTGCTTTGCCAC
GGAACGGTCTGCGTTGTCGGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACCAATTCTGATTAGA
AAAACTCATCGAGCATCAAATGAAACTGCAATTTATTCATATCAGGATTATCAATACCATATTTTTGAAAA
AGCCGTTTCTGTAATGAAGGAGAAAACTCACCGAGGCAGTTCCATAGGATGGCAAGATCCTGGTATCGGTC
TGCGATTCCGACTCGTCCAACATCAATACAACCTATTAATTTCCCCTCGTCAAAAATAAGGTTATCAAGTG
AGAAATCACCATGAGTGACGACTGAATCCGGTGAGAATGGCAAAAGCTTATGCATTTCTTTCCAGACTTGT
TCAACAGGCCAGCCATTACGCTCGTCATCAAAATCACTCGCATCAACCAAACCGTTATTCATTCGTGATTG
CGCCTGAGCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTGGAATGCT
GTTTTCCCGGGGATCGCAGTGGTGAGTAACCATGCATCATCAGGAGTACGGATAAAATGCTTGATGGTCGG
AAGAGGCATAAATTCCGTCAGCCAGTTTAGTCTGACCATCTCATCTGTAACATCATTGGCAACGCTACCTT
TGCCATGTTTCAGAAACAACTCTGGCGCATCGGGCTTCCCATACAATCGATAGATTGTCGCACCTGATTGC
CCGACATTATCGCGAGCCCATTTATACCCATATAAATCAGCATCCATGTTGGAATTTAATCGCGGCCTCGA
GCAAGACGTTTCCCGTTGAATATGGCTCATAACACCCCTTGTATTACTGTTTATGTAAGCAGACAGTTTTA
TTGTTCATGATGATATATTTTTATCTTGTGCAATGTAACATCAGAGATTTTGAGACACAACGTGGCTTTCC
CCCCCCCCCATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTC
```

Coding sequence    (SEQ ID NO:139)
```
ATGAAAACCATCATTGCCCTGAGCTACATCCTGTGCCTGGTGTTCACACAGAAGCTGCCCGGCAACGATAA
TAGCACCGCCACACTGTGTCTGGGACACCACGCCGTGCCTAATGGCACCATCGTGAAAACAATCACCAACG
ACCAGATCGAAGTGACCAATGCCACAGAGCTGGTGCAGAGCAGCAGCACAGGCGAGATCTGTGACAGCCCC
CACCAGATCCTGGATGGCGAGAACTGTACCCTGATCGATGCCCTGCTGGGCGATCCTCAGTGCGACGGCTT
CCAGAACAAGAAATGGGACCTGTTCGTGGAGAGAAGCAAGGCCTACAGCAACTGCTACCCCTACGACGTGC
CTGATTACGCCAGCCTGAGAAGCCTGGTGGCCTCTAGCGGCACCCTGGAATTCAACAACGAGAGCTTCAAC
TGGACCGGCGTGACACAGAATGGCACCAGCAGCGCCTGCATCAGACGGTCCAACAACAGCTTCTTCAGTAG
ACTGAATTGGCTGACCCACCTGAAGTTCAAGTACCCCGCCCTGAACGTGACCATGCCCAACAATGAGAAGT
TCGACAAGCTGTACATCTGGGGAGTGCACCACCCTGGCACCGACAACGATCAGATCTTCCCTTACGCCCAG
GCCAGCGGCAGAATCACCGTGTCCACCAAGAGAAGCCAGCAGACCGTGATCCCCAATATCGGCAGCAGACC
CAGAGTGCGGAACATCCCCAGCAGGATCAGCATCTACTGGACAATCGTGAAGCCTGGCGACATCCTGCTGA
TCAACAGCACCGGCAACCTGATCGCCCCTCGGGGCTACTTTAAGATCAGAAGCGGCAAGAGCAGCATCATG
AGATCCGACGCCCCCATCGGCAAGTGCAACAGCGAGTGCATCACCCCAAACGGCAGCATCCCCAACGACAA
GCCCTTCCAGAACGTGAACAGGATCACCTACGGCGCCTGCCCTAGATACGTGAAGCAGAACACCCTGAAGC
TGGCCACCGGCATGAGAAATGTGCCCGAGAAGCAGACCAGAGGCATCTTTGGCGCCATTGCCGGCTTTATC
GAGAATGGCTGGGAGGGAATGGTGGATGGGTGGTACGGCTTCAGACACCAGAATAGCGAGGGAATTGGACA
GGCCGCCGATCTGAAATCTACCCAGGCCGCCATCGACCAGATCAACGGCAAGCTGAACAGGCTGATCGGCA
AGACCAACGAGAAGTTCCACCAGATCGAGAAGAATTCAGCGAGGTGGAGGGCAGAATCCAGGACCTGGAA
AAATACGTGGAGGACACCAAGATCGACCTGTGGAGCTACAATGCCGAACTGCTGGTCGCCCTGGAAAACCA
GCACACAATTGATCTGACAGACAGTGAGATGAATAAGCTGTTCGAGAAAACCAAGAAGCAGCTGAGAGAAA
ACGCCGAGGACATGGGCAACGGCTGCTTCAAGATCTACCACAAGTGCGACAACGCCTGCATCGGCAGCATC
AGAAACGGCACCTACGACCACGACGTGTACAGAGATGAGGCCCTGAACAACCGGTTTCAGATCAAGTCCGG
AGGCGACATCATCAAGCTGCTGAACGAGCAGGTGAACAAGGAGATGCAGAGCAGCAACCTGTACATGAGCA
TGAGCAGCTGGTGCTACACCCACAGCCTGGACGGCGCCGGCCTGTTCCTGTTCGACCACGCCGCCGAGGAG
```

Fig. 29-3

```
TACGAGCACGCCAAGAAGCTGATCATCTTCCTGAACGAGAACAACGTGCCCGTGCAGCTGACCAGCATCAG
CGCCCCCGAGCACAAGTTCGAGGGCCTGACCCAGATCTTCCAGAAGGCCTACGAGCACGAGCAGCACATCA
GCGAGAGCATCAACAACATCGTGGACCACGCCATCAAGAGCAAGGACCACGCCACCTTCAACTTCCTGCAG
TGGTACGTGGCCGAGCAGCACGAGGAGGAGGTGCTGTTCAAGGACATCCTGGACAAGATCGAGCTGATCGG
CAACGAGAACCACGGCCTGTACCTGGCCGACCAGTACGTGAAGGGCATCGCCAAGAGCAGGAAGAGCGGAT
CC
```

Translation (SEQ ID NO:53)
```
MKTIIALSYILCLVFTQKLPGNDNSTATLCLGHHAVPNGTIVKTITNDQIEVTNATELVQSSSTGEICDSP
HQILDGENCTLIDALLGDPQCDGFQNKKWDLFVERSKAYSNCYPYDVPDYASLRSLVASSGTLEFNNESFN
WTGVTQNGTSSACIRRSNNSFFSRLNWLTHLKFKYPALNVTMPNNEKFDKLYIWGVHHPGTDNDQIFPYAQ
ASGRITVSTKRSQQTVIPNIGSRPRVRNIPSRISIYWTIVKPGDILLINSTGNLIAPRGYFKIRSGKSSIM
RSDAPIGKCNSECITPNGSIPNDKPFQNVNRITYGACPRYVKQNTLKLATGMRNVPEKQTRGIFGAIAGFI
ENGWEGMVDGWYGFRHQNSEGIGQAADLKSTQAAIDQINGKLNRLIGKTNEKFHQIEKEFSEVEGRIQDLE
KYVEDTKIDLWSYNAELLVALENQHTIDLTDSEMNKLFEKTKKQLRENAEDMGNGCFKIYHKCDNACIGSI
RNGTYDHDVYRDEALNNRFQIKSGGDIIKLLNEQVNKEMQSSNLYMSMSSWCYTHSLDGAGLFLFDHAAEE
YEHAKKLIIFLNENNVPVQLTSISAPEHKFEGLTQIFQKAYEHEQHISESINNIVDHAIKSKDHATFNFLQ
WYVAEQHEEEVLFKDILDKIELIGNENHGLYLADQYVKGIAKSRKSGS
```

Fig. 29-4

CMV8x/R-H5Indo HA(520)_SGG_egm
6515 bp

Labels on plasmid map: CMV IE Enhancer/Promoter 8kb, HTLV-1 R Region/Splicing Donor, CMV IE Splicing Acceptor, H5Indo HA(520)_SGG_egm, Tbgh H5 Indo HA(520)_SGG_egm (H5 2005Indo HA-ferritin)

Plasmid DNA sequence (SEQ ID NO:140)
```
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGACTTCCATAAGCTTGCATTATGCCCAGTACATGACC
TTATGGGAATTTCCTACTTGGCAGTACATCTACGTATTAGTCATCGCTATTACCATGGTGATGCGGTTTG
```

Fig. 30-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGGAAAAGATCGTGCTGCTGCTGGCCATTG
TGAGCCTGGTGAAGAGCGACCAGATCTGCATTGGCTACCACGCCAACAATAGCACAGAGCAGGTGGACACC
ATCATGGAAAAAAACGTGACCGTGACCCACGCTCAGGACATCCTGGAAAAGACCCACAACGGCAAGCTGTG
TGATCTGGACGGCGTGAAGCCTCTGATCCTGAGAGATTGTAGCGTGGCTGGATGGCTGCTGGGCAACCCTA
TGTGCGACGAGTTCATCAACGTGCCCGAGTGGAGCTATATCGTGGAGAAGGCCAACCCCACCAACGATCTG
TGTTACCCCGGCAGCTTCAACGATTACGAGGAACTGAAGCACCTGCTGTCCCGGATCAACCACTTCGAGAA
GATCCAGATCATCCCCAAGTCCTCTTGGAGCGATCACGAAGCCTCTAGCGGAGTGTCTAGCGCCTGTCCTT
ACCTGGGCAGCCCCAGCTTCTTCAGAAACGTGGTGTGGCTGATCAAGAAGAACAGCACCTACCCCACCATC
AAGAAGAGCTACAACAACACCAACCAGGAAGATCTGCTGGTCCTGTGGGGAATCCACCACCCTAATGATGC
CGCCGAGCAGACCAGACTGTACCAGAACCCCACCACCTATATCAGCATCGGCACCAGCACCCTGAATCAGA
GACTGGTGCCCAAGATCGCCACCAGATCCAAGGTGAACGGCCAGAGCGGCAGGATGGAATTCTTCTGGACC
ATCCTGAAGCCCAACGACGCCATCAACTTCGAGAGCAACGGCAACTTTATCGCCCCTGAGTACGCCTACAA
GATCGTGAAGAAGGGCGACAGCGCCATCATGAAGAGCGAGCTGGAATACGGCAACTGCAACACCAAGTGCC
AGACACCTATGGGCGCCATCAACAGCAGCATGCCCTTCCACAACATCCACCCTCTGACCATCGGCGAGTGC
CCTAAGTACGTGAAGAGCAACAGACTGGTGCTGGCCACAGGCCTGAGAAATAGCCCCCAGCGGGAGAGCAG
AAGAAAGAAGAGGGGCCTGTTTGGAGCCATCGCCGGCTTTATTGAAGGCGGCTGGCAGGGAATGGTGGATG
GCTGGTACGGCTACCACCACAGCAATGAGCAGGGCTCTGGATATGCCGCCGACAAAGAGTCTACCCAGAAG
GCCATCGACGGCGTCACCAACAAGGTGAACAGCATCATCGACAAGATGAACACCCAGTTCGAGGCTGTGGG
CAGAGAGTTCAACAACCTGGAACGGCGGATCGAGAACCTGAACAAGAAAATGGAAGATGGCTTCCTGGATG
TGTGGACCTACAATGCCGAACTGCTGGTGCTGATGGAAAACGAGCGGACCCTGGACTTCCACGACAGCAAC
GTGAAGAACCTGTACGACAAAGTGCGGCTGCAGCTGAGAGACAACGCCAAAGAGCTGGGCAACGGCTGCTT
CGAGTTCTACCACAAGTGCGACAACGAGTGCATGGAAAGCATCAGGAACGGCACCTACAACTACCCTCAGT
ACAGCGAGGAAGCCAGGCTGAAGAGGGAAGAGATCAGCTCCGGAGGCGACATCATCAAGCTGCTGAACGAG
CAGGTGAACAAGGAGATGCAGAGCAGCAACCTGTACATGAGCATGAGCAGCTGGTGCTACACCCACAGCCT
GGACGGCGCCGGCCTGTTCCTGTTCGACCACGCCGCCGAGGAGTACGAGCACGCCAAGAAGCTGATCATCT
TCCTGAACGAGAACAACGTGCCCGTGCAGCTGACCAGCATCAGCGCCCCCGAGCACAAGTTCGAGGGCCTG
ACCCAGATCTTCCAGAAGGCCTACGAGCACGAGCAGCACATCAGCGAGAGCATCAACAACATCGTGGACCA
CGCCATCAAGAGCAAGGACCACGCCACCTTCAACTTCCTGCAGTGGTACGTGGCCGAGCAGCACGAGGAGG
AGGTGCTGTTCAAGGACATCCTGGACAAGATCGAGCTGATCGGCAACGAGAACCACGGCCTGTACCTGGCC
GACCAGTACGTGAAGGGCATCGCCAAGAGCAGGAAGAGCGGATCCTAGCATCATCATCATCATTAGTCTGG
AAGGGCGAATTGATCCAGATCTGCTGTGCCTTCTAGTTGCCAGCCATCTGTTGTTTGCCCCTCCCCCGTGC
CTTCCTTGACCCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGCAGGACAGCAAGGGGGAGGATTGGGAAGACAA
TAGCAGGCATGCTGGGGATGCGGTGGCTCTATGGGTACCCAGGTGCTGAAGAATTGACCCGGTTCCTCCT
GGGCCAGAAAGAAGCAGGCACATCCCCTTCTCTGTGACACACCCTGTCCACGCCCTGGTTCTTAGTTCCA
GCCCCACTCATAGGACACTCATAGCTCAGGAGGGCTCCGCCTTCAATCCCACCCGCTAAAGTACTTGGAGC
GGTCTCTCCCTCCCTCATCAGCCCACCAAACCAAACCTAGCCTCCAAGAGTGGGAAGAAATTAAAGCAACA
TAGGCTATTAAGTGCAGAGGGAGAGAAAATGCCTCCAACATGTGAGGAAGTAATGAGAGAAATCATAGAAT
TTTAAGGCCATGATTTAAGGCCATCATGGCCTTAATCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTTGCTGG
CGTTTTTCCATAGGCTCCGCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACCCCCCGTTCAGCCCGAC
```

Fig. 30-2

CGCTGCGCCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGGTGGCCTA
ACTACGGCTACACTAGAAGAACAGTATTTGGTATCTGCGCTCTGCTGAAGCCAGTTACCTTCGGAAAAAGA
GTTGGTAGCTCTTGATCCGGCAAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGGGTCTGACGCTCAGTGGAACG
AAAACTCACGTTAAGGGATTTTGGTCATGAGATTATCAAAAAGGATCTTCACCTAGATCCTTTTAAATTAA
AAATGAAGTTTTAAATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCGGGGGGGGGGGCGCT
GAGGTCTGCCTCGTGAAGAAGGTGTTGCTGACTCATACCAGGCCTGAATCGCCCCATCATCCAGCCAGAAA
GTGAGGGAGCCACGGTTGATGAGAGCTTTGTTGTAGGTGGACCAGTTGGTGATTTTGAACTTTTGCTTTGC
CACGGAACGGTCTGCGTTGTCGGGAAGATGCGTGATCTGATCCTTCAACTCAGCAAAAGTTCGATTTATTC
AACAAAGCCGCCGTCCCGTCAAGTCAGCGTAATGCTCTGCCAGTGTTACAACCAATTAACCAATTCTGATT
AGAAAAACTCATCGAGCATCAAATGAAACTGCAATTTATTCATATCAGGATTATCAATACCATATTTTTGA
AAAAGCCGTTTCTGTAATGAAGGAGAAAACTCACCGAGGCAGTTCCATAGGATGGCAAGATCCTGGTATCG
GTCTGCGATTCCGACTCGTCCAACATCAATACAACCTATTAATTTCCCCTCGTCAAAAATAAGGTTATCAA
GTGAGAAATCACCATGAGTGACGACTGAATCCGGTGAGAATGGCAAAAGCTTATGCATTTCTTTCCAGACT
TGTTCAACAGGCCAGCCATTACGCTCGTCATCAAAATCACTCGCATCAACCAAACCGTTATTCATTCGTGA
TTGCGCCTGAGCGAGACGAAATACGCGATCGCTGTTAAAAGGACAATTACAAACAGGAATCGAATGCAACC
GGCGCAGGAACACTGCCAGCGCATCAACAATATTTTCACCTGAATCAGGATATTCTTCTAATACCTGGAAT
GCTGTTTTCCCGGGGATCGCAGTGGTGAGTAACCATGCATCATCAGGAGTACGGATAAAATGCTTGATGGT
CGGAAGAGGCATAAATTCCGTCAGCCAGTTTAGTCTGACCATCTCATCTGTAACATCATTGGCAACGCTAC
CTTTGCCATGTTTCAGAAACAACTCTGGCGCATCGGGCTTCCCATACAATCGATAGATTGTCGCACCTGAT
TGCCCGACATTATCGCGAGCCCATTTATACCCATATAAATCAGCATCCATGTTGGAATTTAATCGCGGCCT
CGAGCAAGACGTTTCCCGTTGAATATGGCTCATAACACCCCTTGTATTACTGTTTATGTAAGCAGACAGTT
TTATTGTTCATGATGATATATTTTTATCTTGTGCAATGTAACATCAGAGATTTTGAGACACAACGTGGCTT
TCCCCCCCCCCCCATTATTGAAGCATTTATCAGGGTTATTGTCTCATGAGCGGATACATATTTGAATGTAT
TTAGAAAAATAAACAAATAGGGGTTCCGCGCACATTTCCCCGAAAAGTGCCACCTGACGTCTAAGAAACCA
TTATTATCATGACATTAACCTATAAAAATAGGCGTATCACGAGGCCCTTTCGTC

Coding sequence (SEQ ID NO:141)
ATGGAAAAGATCGTGCTGCTGCTGGCCATTGTGAGCCTGGTGAAGAGCGACCAGATCTGCATTGGCTACCA
CGCCAACAATAGCACAGAGCAGGTGGACACCATCATGGAAAAAAACGTGACCGTGACCCACGCTCAGGACA
TCCTGGAAAAGACCCACAACGGCAAGCTGTGTGATCTGGACGGCGTGAAGCCTCTGATCCTGAGAGATTGT
AGCGTGGCTGGATGGCTGCTGGGCAACCCTATGTGCGACGAGTTCATCAACGTGCCCGAGTGGAGCTATAT
CGTGGAGAAGGCCAACCCCACCAACGATCTGTGTTACCCCGGCAGCTTCAACGATTACGAGGAACTGAAGC
ACCTGCTGTCCCGGATCAACCACTTCGAGAAGATCCAGATCATCCCCAAGTCCTCTTGGAGCGATCACGAA
GCCTCTAGCGGAGTGTCTAGCGCCTGTCCTTACCTGGGCAGCCCCAGCTTCTTCAGAAACGTGGTGTGGCT
GATCAAGAAGAACAGCACCTACCCCACCATCAAGAAGAGCTACAACAACACCAACCAGGAAGATCTGCTGG
TCCTGTGGGGAATCCACCACCCTAATGATGCCGCCGAGCAGACCAGACTGTACCAGAACCCCACCACCTAT
ATCAGCATCGGCACCAGCACCCTGAATCAGAGACTGGTGCCCAAGATCGCCACCAGATCCAAGGTGAACGG
CCAGAGCGGCAGGATGGAATTCTTCTGGACCATCCTGAAGCCCAACGACGCCATCAACTTCGAGAGCAACG
GCAACTTTATCGCCCCTGAGTACGCCTACAAGATCGTGAAGAAGGGCGACAGCGCCATCATGAAGAGCGAG
CTGGAATACGGCAACTGCAACACCAAGTGCCAGACACCTATGGGCGCCATCAACAGCAGCATGCCCTTCCA
CAACATCCACCCTCTGACCATCGGCGAGTGCCCTAAGTACGTGAAGAGCAACAGACTGGTGCTGGCCACAG
GCCTGAGAAATAGCCCCCAGCGGGAGAGCAGAAGAAAGAAGAGGGGCCTGTTTGGAGCCATCGCCGGCTTT
ATTGAAGGCGGCTGGCAGGGAATGGTGGATGGCTGGTACGGCTACCACCACAGCAATGAGCAGGGCTCTGG
ATATGCCGCCGACAAAGAGTCTACCCAGAAGGCCATCGACGGCGTCACCAACAAGGTGAACAGCATCATCG
ACAAGATGAACACCCAGTTCGAGGCTGTGGGCAGAGAGTTCAACAACCTGGAACGGCGGATCGAGAACCTG
AACAAGAAAATGGAAGATGGCTTCCTGGATGTGTGGACCTACAATGCCGAACTGCTGGTGCTGATGGAAAA
CGAGCGGACCCTGGACTTCCACGACAGCAACGTGAAGAACCTGTACGACAAAGTGCGGCTGCAGCTGAGAG
ACAACGCCAAAGAGCTGGGCAACGGCTGCTTCGAGTTCTACCACAAGTGCGACAACGAGTGCATGGAAAGC
ATCAGGAACGGCACCTACAACTACCCTCAGTACAGCGAGGAAGCCAGGCTGAAGAGGGAAGAGATCAGCTC
CGGAGGCGACATCATCAAGCTGCTGAACGAGCAGGTGAACAAGGAGATGCAGAGCAGCAACCTGTACATGA
GCATGAGCAGCTGGTGCTACACCCACAGCCTGGACGGCGCCGGCCTGTTCCTGTTCGACCACGCCGCCGAG

Fig. 30-3

GAGTACGAGCACGCCAAGAAGCTGATCATCTTCCTGAACGAGAACAACGTGCCCGTGCAGCTGACCAGCAT
CAGCGCCCCCGAGCACAAGTTCGAGGGCCTGACCCAGATCTTCCAGAAGGCCTACGAGCACGAGCAGCACA
TCAGCGAGAGCATCAACAACATCGTGGACCACGCCATCAAGAGCAAGGACCACGCCACCTTCAACTTCCTG
CAGTGGTACGTGGCCGAGCAGCACGAGGAGGAGGTGCTGTTCAAGGACATCCTGGACAAGATCGAGCTGAT
CGGCAACGAGAACCACGGCCTGTACCTGGCCGACCAGTACGTGAAGGGCATCGCCAAGAGCAGGAAGAGCG
GATCC

Translation (SEQ ID NO:56)
MEKIVLLLAIVSLVKSDQICIGYHANNSTEQVDTIMEKNVTVTHAQDILEKTHNGKLCDLDGVKPLILRDC
SVAGWLLGNPMCDEFINVPEWSYIVEKANPTNDLCYPGSFNDYEELKHLLSRINHFEKIQIIPKSSWSDHE
ASSGVSSACPYLGSPSFFRNVVWLIKKNSTYPTIKKSYNNTNQEDLLVLWGIHHPNDAAEQTRLYQNPTTY
ISIGTSTLNQRLVPKIATRSKVNGQSGRMEFFWTILKPNDAINFESNGNFIAPEYAYKIVKKGDSAIMKSE
LEYGNCNTKCQTPMGAINSSMPFHNIHPLTIGECPKYVKSNRLVLATGLRNSPQRESRRKKRGLFGAIAGF
IEGGWQGMVDGWYGYHHSNEQGSGYAADKESTQKAIDGVTNKVNSIIDKMNTQFEAVGREFNNLERRIENL
NKKMEDGFLDVWTYNAELLVLMENERTLDFHDSNVKNLYDKVRLQLRDNAKELGNGCFEFYHKCDNECMES
IRNGTYNYPQYSEEARLKREEISSGGDIIKLLNEQVNKEMQSSNLYMSMSSWCYTHSLDGAGLFLFDHAAE
EYEHAKKLIIFLNENNVPVQLTSISAPEHKFEGLTQIFQKAYEHEQHISESINNIVDHAIKSKDHATFNFL
QWYVAEQHEEEVLFKDILDKIELIGNENHGLYLADQYVKGIAKSRKSGS

Fig. 30-4

CMV8x/R-B.Florida HA(534)_SGG_egm
6557 bp

B Florida HA(534)_SGG_egm (B 2006FL HA-ferritin)

Plasmid DNA sequence (SEQ ID NO:142)
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 31-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCATCATCGTGCTGCTGATGGTGG
TGACCAGCAACGCCGATAGAATCTGCACCGGCATCACCAGCAGCAATAGCCCCCATGTGGTGAAAACAGCC
ACCCAGGGCGAAGTGAATGTGACAGGCGTGATCCCTCTGACCACCACCCCCACCAAGAGCTACTTCGCCAA
CCTGAAGGGCACCAGAACCAGAGGCAAGCTGTGCCCCGATTGCCTGAACTGCACCGATCTGGATGTGGCTC
TGGGCAGACCTATGTGTGTGGGCACCACACCATCTGCCAAGGCCAGCATCCTGCACGAAGTGAAGCCTGTG
ACCAGCGGCTGCTTCCCCATCATGCACGACCGGACCAAGATCAGACAGCTGCCCAACCTGCTGAGAGGCTA
CGAGAACATCCGGCTGTCCACCCAGAATGTGATCGATGCCGAGAAAGCCCCTGGCGGACCTTATAGACTGG
GCACCAGCGGCTCTTGTCCCAATGCCACCTCCAAGAGCGGCTTTTTTGCCACAATGGCCTGGGCCGTGCCT
AAGGACAACAACAAGAACGCCACCAACCCTCTGACCGTGGAGGTGCCCTACATCTGTACAGAGGGCGAGGA
TCAGATCACAGTGTGGGGCTTCCACAGCGACGACAAGACCCAGATGAAGAACCTGTACGGCGACAGCAACC
CCCAGAAGTTTACCAGCAGCGCCAATGGCGTGACCACCCACTACGTGTCCCAGATCGGCAGCTTTCCCGAT
CAGACAGAGGATGGCGGACTGCCTCAGTCTGGCAGGATCGTGGTGGACTACATGATGCAGAAGCCTGGCAA
GACCGGCACCATCGTGTATCAGAGAGGCGTGCTGCTGCCTCAGAAAGTGTGGTGTGCCAGCGGCAGGTCTA
AAGTGATCAAGGGCAGCCTGCCTCTGATTGGCGAGGCCGACTGTCTGCACGAAAAGTACGGCGGCCTGAAC
AAGAGCAAGCCCTACTACACAGGCGAGCACGCCAAGGCCATCGGCAATTGCCCCATCTGGGTGAAAACCCC
CCTGAAGCTGGCCAATGGCACCAAGTACAGACCTCCCGCCAAGCTGCTGAAAGAGAGAGGCTTCTTTGGCG
CCATTGCCGGATTTCTGGAAGGCGGCTGGGAGGGAATGATTGCCGGCTGGCACGGCTATACATCTCATGGG
GCCCATGGCGTGGCTGTGGCCGCCGATCTGAAGTCTACCCAGGAAGCCATCAACAAGATCACCAAGAACCT
GAACAGCCTGAGCGAGCTGGAAGTGAAGAATCTGCAGAGACTGAGCGGCGCCATGGATGAGCTGCACAACG
AGATCCTGGAACTGGACGAGAAAGTGGATGATCTCCGCGCCGATACAATTTCCTCCCAGATTGAACTGGCC
GTGCTGCTGTCCAACGAGGGCATCATCAACAGCGAGGATGAACACCTGCTGGCCCTGGAACGGAAGCTGAA
GAAGATGCTGGGCCCTTCTGCCGTGGAGATCGGCAACGGCTGCTTCGAGACAAAGCACAAGTGCAACCAGA
CCTGCCTGGATAGAATCGCCGCTGGCACCTTCAATGCCGGCGAGTTCAGCCTGCCTACCTTCGACAGCCTG
AATATCACCTCCGGAGGCGACATCATCAAGCTGCTGAACGAGCAGGTGAACAAGGAGATGCAGAGCAGCAA
CCTGTACATGAGCATGAGCAGCTGGTGCTACACCCACAGCCTGGACGGCGCCGGCCTGTTCCTGTTCGACC
ACGCCGCCGAGGAGTACGAGCACGCCAAGAAGCTGATCATCTTCCTGAACGAGAACAACGTGCCCGTGCAG
CTGACCAGCATCAGCGCCCCCGAGCACAAGTTCGAGGGCCTGACCCAGATCTTCCAGAAGGCCTACGAGCA
CGAGCAGCACATCAGCGAGAGCATCAACAACATCGTGGACCACGCCATCAAGAGCAAGGACCACGCCACCT
TCAACTTCCTGCAGTGGTACGTGGCCGAGCAGCACGAGGAGGAGGTGCTGTTCAAGGACATCCTGGACAAG
ATCGAGCTGATCGGCAACGAGAACCACGGCCTGTACCTGGCCGACCAGTACGTGAAGGGCATCGCCAAGAG
CAGGAAGAGCGGATCCTAGCATCATCATCATCATTAGTCTGGAAGGGCGAATTGATCCAGATCTGCTGTGC
CTTCTAGTTGCCAGCCATCTGTTGTTTGCCCCTCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTATTCTGGGGGG
TGGGGTGGGGCAGGACAGCAAGGGGGAGGATTGGGAAGACAATAGCAGGCATGCTGGGGATGCGGTGGGCT
CTATGGGTACCCAGGTGCTGAAGAATTGACCCGGTTCCTCCTGGGCCAGAAAGAAGCAGGCACATCCCCTT
CTCTGTGACACACCCTGTCCACGCCCTGGTTCTTAGTTCCAGCCCCACTCATAGGACACTCATAGCTCAG
GAGGGCTCCGCCTTCAATCCCACCCGCTAAAGTACTTGGAGCGGTCTCTCCCTCCCTCATCAGCCCACCAA
ACCAAACCTAGCCTCCAAGAGTGGGAAGAAATTAAAGCAAGATAGGCTATTAAGTGCAGAGGGAGAGAAAA
TGCCTCCAACATGTGAGGAAGTAATGAGAGAAATCATAGAATTTTAAGGCCATGATTTAAGGCCATCATGG
CCTTAATCTTCCGCTTCCTCGCTCACTGACTCGCTGCGCTCGGTCGTTCGGCTGCGGCGAGCGGTATCAGC
TCACTCAAAGGCGGTAATACGGTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAGTTCGGTGTAGGTCGTTCGC
```

Fig. 31-2

```
TCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGA
GGTATGTAGGCGGTGCTACAGAGTTCTTGAAGTGGTGGCCTAACTACGGCTACACTAGAAGAACAGTATTT
GGTATCTGCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCATG
AGATTATCAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATCTGTCTAT
TTCGTTCATCCATAGTTGCCTGACTCGGGGGGGGGGCGCTGAGGTCTGCCTCGTGAAGAAGGTGTTGCT
GACTCATACCAGGCCTGAATCGCCCCATCATCCAGCCAGAAAGTGAGGGAGCCACGGTTGATGAGAGCTTT
GTTGTAGGTGGACCAGTTGGTGATTTTGAACTTTTGCTTTGCCACGGAACGGTCTGCGTTGTCGGAAGAT
GCGTGATCTGATCCTTCAACTCAGCAAAGTTCGATTTATTCAACAAAGCCGCCGTCCCGTCAAGTCAGCG
TAATGCTCTGCCAGTGTTACAACCAATTAACCAATTCTGATTAGAAAAACTCATCGAGCATCAAATGAAAC
TGCAATTTATTCATATCAGGATTATCAATACCATATTTTGAAAAAGCCGTTTCTGTAATGAAGGAGAAAA
CTCACCGAGGCAGTTCCATAGGATGGCAAGATCCTGGTATCGGTCTGCGATTCCGACTCGTCCAACATCAA
TACAACCTATTAATTTCCCCTCGTCAAAAATAAGGTTATCAAGTGAGAAATCACCATGAGTGACGACTGAA
TCCGGTGAGAATGGCAAAAGCTTATGCATTTCTTTCCAGACTTGTTCAACAGGCCAGCCATTACGCTCGTC
ATCAAAATCACTCGCATCAACCAAACCGTTATTCATTCGTGATTGCGCCTGAGCGAGACGAAATACGCGAT
CGCTGTTAAAAGGACAATTACAAACAGGAATCGAATGCAACCGGCGCAGGAACACTGCCAGCGCATCAACA
ATATTTTCACCTGAATCAGGATATTCTTCTAATACCTGGAATGCTGTTTTCCCGGGGATCGCAGTGGTGAG
TAACCATGCATCATCAGGAGTACGGATAAAATGCTTGATGGTCGGAAGAGGCATAAATTCCGTCAGCCAGT
TTAGTCTGACCATCTCATCTGTAACATCATTGGCAACGCTACCTTTGCCATGTTTCAGAAACAACTCTGGC
GCATCGGGCTTCCCATACAATCGATAGATTGTCGCACCTGATTGCCCGACATTATCGCGAGCCCATTTATA
CCCATATAAATCAGCATCCATGTTGGAATTTAATCGCGGCCTCGAGCAAGACGTTTCCCGTTGAATATGGC
TCATAACACCCCTTGTATTACTGTTTATGTAAGCAGACAGTTTTATTGTTCATGATGATATATTTTTATCT
TGTGCAATGTAACATCAGAGATTTTGAGACACAACGTGGCTTTCCCCCCCCCCCATTATTGAAGCATTTA
TCAGGGTTATTGTCTCATGAGCGGATACATATTTGAATGTATTTAGAAAAATAAACAAATAGGGGTTCCGC
GCACATTTCCCCGAAAAGTGCCACCTGACGTCTAAGAAACCATTATTATCATGACATTAACCTATAAAAAT
AGGCGTATCACGAGGCCCTTTCGTC
```

Coding sequence (SEQ ID NO:143)
```
ATGAAGGCCATCATCGTGCTGCTGATGGTGGTGACCAGCAACGCCGATAGAATCTGCACCGGCATCACCAG
CAGCAATAGCCCCCATGTGGTGAAAACAGCCACCCAGGGCGAAGTGAATGTGACAGGCGTGATCCCTCTGA
CCACCACCCCCACCAAGAGCTACTTCGCCAACCTGAAGGGCACCAGAACCAGAGGCAAGCTGTGCCCCGAT
TGCCTGAACTGCACCGATCTGGATGTGGCTCTGGGCAGACCTATGTGTGTGGGCACCACACCATCTGCCAA
GGCCAGCATCCTGCACGAAGTGAAGCCTGTGACCAGCGGCTGCTTCCCCATCATGCACGACCGGACCAAGA
TCAGACAGCTGCCCAACCTGCTGAGAGGCTACGAGAACATCCGGCTGTCCACCCAGAATGTGATCGATGCC
GAGAAAGCCCCTGGCGGACCTTATAGACTGGGCACCAGCGGCTCTTGTCCCAATGCCACCTCCAAGAGCGG
CTTTTTTGCCACAATGGCCTGGGCCGTGCCTAAGGACAACAACAAGAACGCCACCAACCCTCTGACCGTGG
AGGTGCCCTACATCTGTACAGAGGGCGAGGATCAGATCACAGTGTGGGGCTTCCACAGCGACGACAAGACC
CAGATGAAGAACCTGTACGGCGACAGCAACCCCCAGAAGTTTACCAGCAGCGCCAATGGCGTGACCACCCA
CTACGTGTCCCAGATCGGCAGCTTTCCCGATCAGACAGAGGATGGCGGACTGCCTCAGTCTGGCAGGATCG
TGGTGGACTACATGATGCAGAAGCCTGGCAAGACCGGCACCATCGTGTATCAGAGAGGCGTGCTGCTGCCT
CAGAAAGTGTGGTGTGCCAGCGGCAGGTCTAAAGTGATCAAGGGCAGCCTGCCTCTGATTGGCGAGGCCGA
CTGTCTGCACGAAAAGTACGGCGGCCTGAACAAGAGCAAGCCCTACTACACAGGCGAGCACGCCAAGGCCA
TCGGCAATTGCCCCATCTGGGTGAAAACCCCCTGAAGCTGGCCAATGGCACCAAGTACAGACCTCCCGCC
AAGCTGCTGAAAGAGAGAGGCTTCTTTGGCGCCATTGCCGGATTTCTGGAAGGCGGCTGGGAGGGAATGAT
TGCCGGCTGGCACGGCTATACATCTCATGGGCCCATGGCGTGGCTGTGGCCGCCGATCTGAAGTCTACCC
AGGAAGCCATCAACAAGATCACCAAGAACCTGAACAGCCTGAGCGAGCTGGAAGTGAAGAATCTGCAGAGA
CTGAGCGGCGCCATGGATGAGCTGCACAACGAGATCCTGGAACTGGACGAGAAAGTGGATGATCTCCGCGC
CGATACAATTTCCTCCCAGATTGAACTGGCCGTGCTGCTGTCCAACGAGGGCATCATCAACAGCGAGGATG
AACACCTGCTGGCCCTGGAACGGAAGCTGAAGAAGATGCTGGGCCCTTCTGCCGTGGAGATCGGCAACGGC
TGCTTCGAGACAAAGCACAAGTGCAACCAGACCTGCCTGGATAGAATCGCCGCTGGCACCTTCAATGCCGG
CGAGTTCAGCCTGCCTACCTTCGACAGCCTGAATATCACCTCCGGAGGCGACATCATCAAGCTGCTGAACG
```

Fig. 31-3

```
AGCAGGTGAACAAGGAGATGCAGAGCAGCAACCTGTACATGAGCATGAGCAGCTGGTGCTACACCCACAGC
CTGGACGGCGCCGGCCTGTTCCTGTTCGACCACGCCGCCGAGGAGTACGAGCACGCCAAGAAGCTGATCAT
CTTCCTGAACGAGAACAACGTGCCCGTGCAGCTGACCAGCATCAGCGCCCCCGAGCACAAGTTCGAGGGCC
TGACCCAGATCTTCCAGAAGGCCTACGAGCACGAGCAGCACATCAGCGAGAGCATCAACAACATCGTGGAC
CACGCCATCAAGAGCAAGGACCACGCCACCTTCAACTTCCTGCAGTGGTACGTGGCCGAGCAGCACGAGGA
GGAGGTGCTGTTCAAGGACATCCTGGACAAGATCGAGCTGATCGGCAACGAGAACCACGGCCTGTACCTGG
CCGACCAGTACGTGAAGGGCATCGCCAAGAGCAGGAAGAGCGGATCC
```

Translation (SEQ ID NO:59)
```
MKAIIVLLMVVTSNADRICTGITSSNSPHVVKTATQGEVNVTGVIPLTTTPTKSYFANLKGTRTRGKLCPD
CLNCTDLDVALGRPMCVGTTPSAKASILHEVKPVTSGCFPIMHDRTKIRQLPNLLRGYENIRLSTQNVIDA
EKAPGGPYRLGTSGSCPNATSKSGFFATMAWAVPKDNNKNATNPLTVEVPYICTEGEDQITVWGFHSDDKT
QMKNLYGDSNPQKFTSSANGVTTHYVSQIGSFPDQTEDGGLPQSGRIVVDYMMQKPGKTGTIVYQRGVLLP
QKVWCASGRSKVIKGSLPLIGEADCLHEKYGGLNKSKPYYTGEHAKAIGNCPIWVKTPLKLANGTKYRPPA
KLLKERGFFGAIAGFLEGGWEGMIAGWHGYTSHGAHGVAVAADLKSTQEAINKITKNLNSLSELEVKNLQR
LSGAMDELHNEILELDEKVDDLRADTISSQIELAVLLSNEGIINSEDEHLLALERKLKKMLGPSAVEIGNG
CFETKHKCNQTCLDRIAAGTFNAGEFSLPTFDSLNITSGGDIIKLLNEQVNKEMQSSNLYMSMSSWCYTHS
LDGAGLFLFDHAAEEYEHAKKLIIFLNENNVPVQLTSISAPEHKFEGLTQIFQKAYEHEQHISESINNIVD
HAIKSKDHATFNFLQWYVAEQHEEEVLFKDILDKIELIGNENHGLYLADQYVKGIAKSRKSGS
```

Fig. 31-4

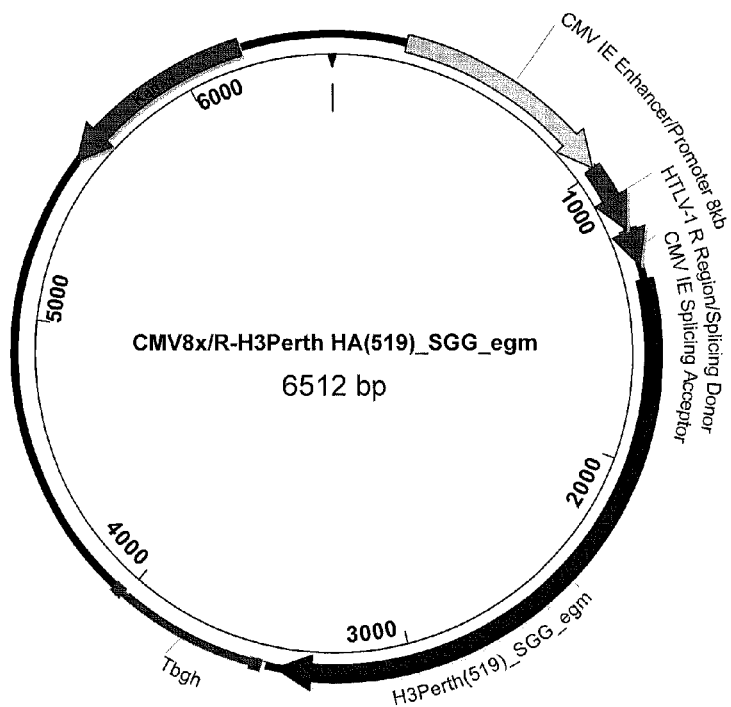
H3 Perth HA(519)_SGG_egm (H3 2009Perth HA-ferritin)

Plasmid DNA sequence (SEQ ID NO:144)
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 32-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAAACCATAATTGCGCTGTCCTACATAC
TGTGTCTGGTGTTTGCCCAGAAACTGCCGGGCAATGACAACTCAACAGCCACGCTCTGCTTGGGGCACCAT
GCCGTCCCTAACGGGACCATTGTGAAAACCATTACTAACGATCAGATAGAGGTGACTAATGCCACCGAGCT
GGTGCAAAGTAGCTCCACAGGAGAGATCTGCGATAGTCCCCACCAGATTCTGGACGGAAAGAATTGTACGC
TGATCGACGCGCTGTTGGGCGACCCTCAGTGTGACGGATTTCAGAATAAGAAGTGGGATCTGTTTGTGGAA
AGGTCAAAGGCTTATTCAAATTGCTACCCTTACGATGTGCCTGATTATGCCAGCCTGCGGTCCTCGTCGC
GTCTAGTGGGACTCTGGAGTTCAACAACGAGTCATTTAACTGGACTGGCGTTACACAGAACGGGACTAGTT
CCGCTTGCATAAGGAGAAGCAAAAATAGTTTCTTCAGCAGACTGAATTGGCTGACACATCTGAACTTCAAG
TACCCTGCACTGAATGTAACCATGCCCAACAACGAGCAGTTCGATAAGCTTTACATTTGGGGAGTTCATCA
TCCTGGCACTGACAAGGATCAGATCTTTCTGTATGCCCAGGCTTCCGGCAGGATTACCGTGTCTACAAAGA
GAAGCCAGCAAACTGTGTCTCCCAATATCGGCAGTAGACCCAGAGTACGGAACATCCCTAGTCGCATCAGT
ATTTACTGGACCATCGTGAAACCAGGCGATATTCTCCTGATTAACAGTACTGGCAACCTGATCGCCCCCCG
GGGATACTTTAAAATCCGCTCTGGAAAGTCCTCCATTATGAGATCAGATGCACCGATCGGAAAATGCAACT
CTGAGTGTATCACACCCAATGGGAGCATTCCCAATGACAAACCTTTCCAGAACGTTAATCGAATAACTTAT
GGGGCCTGTCCACGGTACGTGAAGCAAAATACCTTGAAACTGGCGACCGGTATGCGCAATGTCCCCGAAAA
ACAGACCCGCGGGATATTTGGGCTATCGCAGGCTTATCGAGAATGGCTGGGAAGGGATGGTGGATGGTT
GGTATGGTTTTAGACATCAAAACTCCGAAGGCAGAGGCCAGGCTGCCGATCTCAAGAGCACGCAGGCCGCT
ATAGATCAGATCAATGGAAAGCTCAACGACTGATCGGGAAAACCAACGAAAAATTCCATCAGATCGAGAA
AGAGTTCTCCGAAGTCGAGGGGCGCATACAGGACCTGGAGAAGTATGTTGAGGATACAAAGATTGATCTGT
GGTCCTACAATGCCGAGCTGCTGGTGGCTCTGGAGAATCAGCACACTATTGACCTGACCGATTCAGAGATG
AACAAACTTTTTGAGAAGACGAAGAAGCAGCTTAGAGAAAATGCAGAGGACATGGGGAACGGATGCTTTAA
AATATATCATAAGTGTGATAATGCCTGCATCGGATCAATTAGAAATGGTACCTATGATCACGATGTTTACA
GGGACGAAGCGCTGAATAACAGGTTCCAGATAAAATCCGGAGGCGACATCATCAAGCTGCTGAACGAGCAG
GTGAACAAGGAGATGCAGAGCAGCAACCTGTACATGAGCATGAGCAGCTGGTGCTACACCCACAGCCTGGA
CGGCGCCGGCCTGTTCCTGTTCGACCACGCCGCCGAGGAGTACGAGCACGCCAAGAAGCTGATCATCTTCC
TGAACGAGAACAACGTGCCCGTGCAGCTGACCAGCATCAGCGCCCCCGAGCACAAGTTCGAGGGCCTGACC
CAGATCTTCCAGAAGGCCTACGAGCACGAGCAGCACATCAGCGAGAGCATCAACAACATCGTGGACCACGC
CATCAAGAGCAAGGACCACGCCACCTTCAACTTCCTGCAGTGGTACGTGGCCGAGCAGCACGAGGAGGAGG
TGCTGTTCAAGGACATCCTGGACAAGATCGAGCTGATCGGCAACGAGAACCACGGCCTGTACCTGGCCGAC
CAGTACGTGAAGGGCATCGCCAAGAGCAGGAAGAGCGGATCCTAGCATCATCATCATCATTAGTCTGGAAG
GGCGAATTGATCCAGATCTGCTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCATTGTCTG
AGTAGGTGTCATTCTATTCTGGGGGGTGGGGTGGGGCAGGACAGCAAGGGGGAGGATTGGGAAGACAATAG
CAGGCATGCTGGGGATGCGGTGGGCTCTATGGGTACCCAGGTGCTGAAGAATTGACCCGGTTCCTCCTGGG
CCAGAAAGAAGCAGGCACATCCCCTTCTCTGTGACACACCCTGTCCACGCCCCTGGTTCTTAGTTCCAGCC
CCACTCATAGGACACTCATAGCTCAGGAGGGCTCCGCCTTCAATCCCACCCGCTAAAGTACTTGGAGCGGT
CTCTCCCTCCCTCATCAGCCCACCAAACCAAACCTAGCCTCCAAGAGTGGGAAGAAATTAAAGCAAGATAG
GCTATTAAGTGCAGAGGGAGAGAAAATGCCTCCAACATGTGAGGAAGTAATGAGAGAAATCATAGAATTTT
AAGGCCATGATTTAAGGCCATCATGGCCTTAATCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCAAGTCAGAGGTGGCGAAACCCG
ACAGGACTATAAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCCCGACCGC
```

Fig. 32-2

TGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTAC
GCGCAGAAAAAAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTTTAAATTAAAAA
TGAAGTTTTAAATCAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCGGGGGGGGGGGCGCTGAG
GTCTGCCTCGTGAAGAAGGTGTTGCTGACTCATACCAGGCCTGAATCGCCCCATCATCCAGCCAGAAAGTG
AGGGAGCCACGGTTGATGAGAGCTTTGTTGTAGGTGGACCAGTTGGTGATTTTGAACTTTTGCTTTGCCAC
GGAACGGTCTGCGTTGTCGGGAAGATGCGTGATCTGATCCTTCAACTCAGCAAAAGTTCGATTTATTCAAC
AAAGCCGCCGTCCCGTCAAGTCAGCGTAATGCTCTGCCAGTGTTACAACCAATTAACCAATTCTGATTAGA
AAAACTCATCGAGCATCAAATGAAACTGCAATTTATTCATATCAGGATTATCAATACCATATTTTTGAAAA
AGCCGTTTCTGTAATGAAGGAGAAAACTCACCGAGGCAGTTCCATAGGATGGCAAGATCCTGGTATCGGTC
TGCGATTCCGACTCGTCCAACATCAATACAACCTATTAATTTCCCCTCGTCAAAAATAAGGTTATCAAGTG
AGAAATCACCATGAGTGACGACTGAATCCGGTGAGAATGGCAAAAGCTTATGCATTTCTTTCCAGACTTGT
TCAACAGGCCAGCCATTACGCTCGTCATCAAAATCACTCGCATCAACCAAACCGTTATTCATTCGTGATTG
CGCCTGAGCGAGACGAAATACGCGATCGCTGTTAAAAGGACAATTACAAACAGGAATCGAATGCAACCGGC
GCAGGAACACTGCCAGCGCATCAACAATATTTTCACCTGAATCAGGATATTCTTCTAATACCTGGAATGCT
GTTTTTCCCGGGGATCGCAGTGGTGAGTAACCATGCATCATCAGGAGTACGGATAAAATGCTTGATGGTCGG
AAGAGGCATAAATTCCGTCAGCCAGTTTAGTCTGACCATCTCATCTGTAACATCATTGGCAACGCTACCTT
TGCCATGTTTCAGAAACAACTCTGGCGCATCGGGCTTCCCATACAATCGATAGATTGTCGCACCTGATTGC
CCGACATTATCGCGAGCCCATTTATACCCATATAAATCAGCATCCATGTTGGAATTTAATCGCGGCCTCGA
GCAAGACGTTTCCCGTTGAATATGGCTCATAACACCCCTTGTATTACTGTTTATGTAAGCAGACAGTTTTA
TTGTTCATGATGATATATTTTTATCTTGTGCAATGTAACATCAGAGATTTTGAGACACAACGTGGCTTTCC
CCCCCCCCCCATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTCTAAGAAACCATTA
TTATCATGACATTAACCTATAAAAATAGGCGTATCACGAGGCCCTTTCGTC

Coding sequence (SEQ ID NO:145)
ATGAAAACCATAATTGCGCTGTCCTACATACTGTGTCTGGTGTTTGCCCAGAAACTGCCGGGCAATGACAA
CTCAACAGCCACGCTCTGCTTGGGGCACCATGCCGTCCCTAACGGGACCATTGTGAAAACCATTACTAACG
ATCAGATAGAGGTGACTAATGCCACCGAGCTGGTGCAAAGTAGCTCCACAGGAGAGATCTGCGATAGTCCC
CACCAGATTCTGGACGGAAAGAATTGTACGCTGATCGACGCGCTGTTGGGCGACCCTCAGTGTGACGGATT
TCAGAATAAGAAGTGGGATCTGTTTGTGGAAAGGTCAAAGGCTTATTCAAATTGCTACCCTTACGATGTGC
CTGATTATGCCAGCCTGCGGTCCCTCGTCGCGTCTAGTGGGACTCTGGAGTTCAACAACGAGTCATTTAAC
TGGACTGGCGTTACACAGAACGGGACTAGTTCCGCTTGCATAAGGAGAAGCAAAAATAGTTTCTTCAGCAG
ACTGAATTGGCTGACACATCTGAACTTCAAGTACCCTGCACTGAATGTAACCATGCCCAACAACGAGCAGT
TCGATAAGCTTTACATTTGGGGAGTTCATCATCCTGGCACTGACAAGGATCAGATCTTTCTGTATGCCCAG
GCTTCCGGCAGGATTACCGTGTCTACAAAGAGAAGCCAGCAAACTGTGTCTCCCAATATCGGCAGTAGACC
CAGAGTACGGAACATCCCTAGTCGCATCAGTATTTACTGGACCATCGTGAAACCAGGCGATATTCTCCTGA
TTAACAGTACTGGCAACCTGATCGCCCCCCGGGGATACTTTAAAATCCGCTCTGGAAAGTCCTCCATTATG
AGATCAGATGCACCGATCGGAAAATGCAACTCTGAGTGTATCACACCCAATGGGAGCATTCCCAATGACAA
ACCTTTCCAGAACGTTAATCGAATAACTTATGGGGCCTGTCCACGGTACGTGAAGCAAATACCTTGAAAC
TGGCGACCGGTATGCGCAATGTCCCCGAAAAACAGACCCGCGGGATATTTGGGCTATCGCAGGCTTTATC
GAGAATGGCTGGGAAGGGATGGTGGATGGTTGGTATGGTTTTAGACATCAAAACTCCGAAGGCAGAGGCCA
GGCTGCCGATCTCAAGAGCACGCAGGCCGCTATAGATCAGATCAATGGAAAGCTCAACAGACTGATCGGGA
AAACCAACGAAAATTCCATCGATCGAGAAAGAGTTCTCCGAAGTCGAGGGGCGCATACAGGACCTGGAG
AAGTATGTTGAGGATACAAAGATTGATCTGTGGTCCTACAATGCCGAGCTGCTGGTGGCTCTGGAGAATCA
GCACACTATTGACCTGACCGATTCAGAGATGAACAAACTTTTTGAGAAGACGAAGAAGCAGCTTAGAGAAA
ATGCAGAGGACATGGGGAACGGATGCTTTAAAATATATCATAAGTGTGATAATGCCTGCATCGGATCAATT
AGAAATGGTACCTATGATCACGATGTTTACAGGGACGAAGCGCTGAATAACAGGTTCCAGATAAAATCCGG
AGGCGACATCATCAAGCTGCTGAACGAGCAGGTGAACAAGGAGATGCAGAGCAGCAACCTGTACATGAGCA
TGAGCAGCTGGTGCTACACCCACAGCCTGGACGGCGCCGGCCTGTTCCTGTTCGACCACGCCGCCGAGGAG

Fig. 32-3

```
TACGAGCACGCCAAGAAGCTGATCATCTTCCTGAACGAGAACAACGTGCCCGTGCAGCTGACCAGCATCAG
CGCCCCCGAGCACAAGTTCGAGGGCCTGACCCAGATCTTCCAGAAGGCCTACGAGCACGAGCAGCACATCA
GCGAGAGCATCAACAACATCGTGGACCACGCCATCAAGAGCAAGGACCACGCCACCTTCAACTTCCTGCAG
TGGTACGTGGCCGAGCAGCACGAGGAGGAGGTGCTGTTCAAGGACATCCTGGACAAGATCGAGCTGATCGG
CAACGAGAACCACGGCCTGTACCTGGCCGACCAGTACGTGAAGGGCATCGCCAAGAGCAGGAAGAGCGGAT
CC
```

Translation   (SEQ ID NO:62)
```
MKTIIALSYILCLVFAQKLPGNDNSTATLCLGHHAVPNGTIVKTITNDQIEVTNATELVQSSSTGEICDSP
HQILDGKNCTLIDALLGDPQCDGFQNKKWDLFVERSKAYSNCYPYDVPDYASLRSLVASSGTLEFNNESFN
WTGVTQNGTSSACIRRSKNSFFSRLNWLTHLNFKYPALNVTMPNNEQFDKLYIWGVHHPGTDKDQIFLYAQ
ASGRITVSTKRSQQTVSPNIGSRPRVRNIPSRISIYWTIVKPGDILLINSTGNLIAPRGYFKIRSGKSSIM
RSDAPIGKCNSECITPNGSIPNDKPFQNVNRITYGACPRYVKQNTLKLATGMRNVPEKQTRGIFGAIAGFI
ENGWEGMVDGWYGFRHQNSEGRGQAADLKSTQAAIDQINGKLNRLIGKTNEKFHQIEKEFSEVEGRIQDLE
KYVEDTKIDLWSYNAELLVALENQHTIDLTDSEMNKLFEKTKKQLRENAEDMGNGCFKIYHKCDNACIGSI
RNGTYDHDVYRDEALNNRFQIKSGGDIIKLLNEQVNKEMQSSNLYMSMSSWCYTHSLDGAGLFLFDHAAEE
YEHAKKLIIFLNENNVPVQLTSISAPEHKFEGLTQIFQKAYEHEQHISESINNIVDHAIKSKDHATFNFLQ
WYVAEQHEEEVLFKDILDKIELIGNENHGLYLADQYVKGIAKSRKSGS
```

Fig. 32-4

H1 Bris HA(517)_SGG_egm (H1 2007Bris HA-ferritin)

Plasmid DNA sequence   (SEQ ID NO:146)
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 33-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAAGTGAAGCTGCTGGTGCTGCTGTGTA
CCTTTACCGCCACCTACGCCGATACCATCTGTATCGGCTACCACGCCAACAATAGCACCGACACCGTGGAT
ACCGTGCTGGAAAAGAACGTGACCGTGACCCACAGCGTGAACCTGCTGGAAAACAGCCACAACGGCAAGCT
GTGTCTGCTGAAAGGCATTGCCCCTCTGCAGCTGGGAAATTGTAGCGTGGCCGGCTGGATTCTGGGCAATC
CTGAGTGCGAGCTGCTGATTTCCAAAGAGTCCTGGTCCTACATCGTGGAGAAGCCCAACCCTGAGAATGGC
ACCTGCTACCCTGGCCACTTCGCCGATTACGAGGAACTGAGAGAACAGCTGTCCAGCGTGTCCAGCTTCGA
GAGATTCGAGATCTTCCCCAAAGAGAGCAGCTGGCCCAATCATACAGTGACCGGCGTGAGCGCCTCTTGTA
GCCACAATGGCGAGAGCAGCTTCTACAGAAACCTGCTGTGGCTGACCGGCAAGAACGGCCTGTACCCCAAC
CTGAGCAAGAGCTACGCCAACAACAAAGAAAAAGAAGTGCTGGTCCTCTGGGGAGTGCACCACCCTCCTAA
CATCGGCATCCAGAAGGCCCTGTACCACACCGAGAATGCCTACGTGTCCGTGGTGTCCAGCCACTACAGCA
GAAAGTTCACCCCCGAGATCGCCAAAAGACCCAAAGTGCGGGACCAGGAAGGCAGGATCAACTACTACTGG
ACCCTGCTGGAACCTGGCGACACCATCATCTTCGAGGCCAACGGCAATCTGATCGCCCCTAGATACGCCTT
TGCCCTGAGCAGAGGCTTTGGCAGCGGCATCATCAACAGCAACGCCCCCATGGACAAGTGTGACGCCAAGT
GTCAGACACCACAGGGAGCTATCAATAGCAGCCTGCCCTTCCAGAATGTGCACCCTGTGACCATCGGCGAG
TGTCCTAAATACGTGCGGAGCGCCAAGCTGAGAATGGTGACCGGCCTGAGGAATATCCCCAGCATCCAGAG
CAGAGGCCTGTTTGGCGCCATTGCCGGCTTTATCGAGGCGGATGGACAGGCATGGTGGATGGGTGGTACG
GCTACCACCACCAGAATGAGCAGGGATCTGGCTATGCCGCCGATCAGAAGAGCACCCAGAACGCCATCAAC
GGCATCACCAACAAAGTGAACAGCGTGATCGAGAAGATGAACACCCAGTTCACCGCCGTGGGCAAAGAGTT
CAACAAGCTGGAACGGCGGATGGAAAACCTGAACAAGAAGGTGGACGACGGCTTCATCGACATCTGGACCT
ACAACGCCGAACTCCTGGTCCTCCTGGAAAATGAGAGGACCCTGGACTTCCACGACAGCAACGTGAAGAAC
CTGTACGAGAAAGTGAAGAGCCAGCTGAAGAACAACGCCAAAGAGATCGGCAACGGCTGCTTCGAGTTCTA
CCACAAGTGCAACGACGAGTGCATGGAAAGCGTGAAGAACGGCACCTACGACTACCCCAAGTACAGCGAGG
AAAGCAAGCTGAACCGGGAGAAGATCGATTCCGGAGGCGACATCATCAAGCTGCTGAACGAGCAGGTGAAC
AAGGAGATGCAGAGCAGCAACCTGTACATGAGCATGAGCAGCTGGTGCTACACCCACAGCCTGGACGGCGC
CGGCCTGTTCCTGTTCGACCACGCCGCCGAGGAGTACGAGCACGCCAAGAAGCTGATCATCTTCCTGAACG
AGAACAACGTGCCCGTGCAGCTGACCAGCATCAGCGCCCCCGAGCACAAGTTCGAGGGCCTGACCCAGATC
TTCCAGAAGGCCTACGAGCACGAGCAGCACATCAGCGAGAGCATCAACAACATCGTGGACCACGCCATCAA
GAGCAAGGACCACGCCACCTTCAACTTCCTGCAGTGGTACGTGGCCGAGCAGCACGAGGAGGAGGTGCTGT
TCAAGGACATCCTGGACAAGATCGAGCTGATCGGCAACGAGAACCACGGCCTGTACCTGGCCGACCAGTAC
GTGAAGGGCATCGCCAAGAGCAGGAAGAGCGGATCCTAGCATCATCATCATCATTAGTCTGGAAGGGCGAA
TTGATCCAGATCTGCTGTGCCTTCTAGTTGCCAGCCATCTGTTGTTTGCCCCTCCCCGTGCCTTCCTTGA
CCCTGGAAGGTGCCACTCCCACTGTCCTTTCCTAATAAAATGAGGAAATTGCATCGCATTGTCTGAGTAGG
TGTCATTCTATTCTGGGGGGTGGGTGGGGCAGGACAGCAAGGGGGAGGATTGGGAAGACAATAGCAGGCA
TGCTGGGGATGCGGTGGGCTCTATGGGTACCCAGGTGCTGAAGAATTGACCCGGTTCCTCCTGGGCCAGAA
AGAAGCAGGCACATCCCCTTCTCTGTGACACACCCTGTCCACGCCCCTGGTTCTTAGTTCCAGCCCCACTC
ATAGGACACTCATAGCTCAGGAGGGCTCCGCCTTCAATCCCACCCGCTAAAGTACTTGGAGCGGTCTCTCC
CTCCCTCATCAGCCCACCAAACCAAACCTAGCCTCCAAGAGTGGGAAGAAATTAAAGCAAGATAGGCTATT
AAGTGCAGAGGGAGAGAAAATGCCTCCAACATGTGAGGAAGTAATGAGAGAAATCATAGAATTTTAAGGCC
ATGATTTAAGGCCATCATGGCCTTAATCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCGACCGCTGCGCC
```

Fig. 33-2

```
TTATCCGGTAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGTCTGACGCTCAGTGGAACGAAAACTCAC
GTTAAGGGATTTTGGTCATGAGATTATCAAAAGGATCTTCACCTAGATCCTTTTAAATTAAAAATGAAGT
TTTAAATCAATCTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCGGGGGGGGGGGCGCTGAGGTCTGC
CTCGTGAAGAAGGTGTTGCTGACTCATACCAGGCCTGAATCGCCCCATCATCCAGCCAGAAAGTGAGGGAG
CCACGGTTGATGAGAGCTTTGTTGTAGGTGGACCAGTTGGTGATTTTGAACTTTTGCTTTGCCACGGAACG
GTCTGCGTTGTCGGGAAGATGCGTGATCTGATCCTTCAACTCAGCAAAAGTTCGATTTATTCAACAAAGCC
GCCGTCCCGTCAAGTCAGCGTAATGCTCTGCCAGTGTTACAACCAATTAACCAATTCTGATTAGAAAAACT
CATCGAGCATCAAATGAAACTGCAATTTATTCATATCAGGATTATCAATACCATATTTTTGAAAAAGCCGT
TTCTGTAATGAAGGAGAAAACTCACCGAGGCAGTTCCATAGGATGGCAAGATCCTGGTATCGGTCTGCGAT
TCCGACTCGTCCAACATCAATACAACCTATTAATTTCCCCTCGTCAAAAATAAGGTTATCAAGTGAGAAAT
CACCATGAGTGACGACTGAATCCGGTGAGAATGGCAAAAGCTTATGCATTTCTTTCCAGACTTGTTCAACA
GGCCAGCCATTACGCTCGTCATCAAAATCACTCGCATCAACCAAACCGTTATTCATTCGTGATTGCGCCTG
AGCGAGACGAAATACGCGATCGCTGTTAAAAGGACAATTACAAACAGGAATCGAATGCAACCGGCGCAGGA
ACACTGCCAGCGCATCAACAATATTTTCACCTGAATCAGGATATTCTTCTAATACCTGGAATGCTGTTTTC
CCGGGGATCGCAGTGGTGAGTAACCATGCATCATCAGGAGTACGGATAAAATGCTTGATGGTCGGAAGAGG
CATAAATTCCGTCAGCCAGTTTAGTCTGACCATCTCATCTGTAACATCATTGGCAACGCTACCTTTGCCAT
GTTTCAGAAACAACTCTGGCGCATCGGGCTTCCCATACAATCGATAGATTGTCGCACCTGATTGCCCGACA
TTATCGCGAGCCCATTTATACCCATATAAATCAGCATCCATGTTGGAATTTAATCGCGGCCTCGAGCAAGA
CGTTTCCCGTTGAATATGGCTCATAACACCCCTTGTATTACTGTTTATGTAAGCAGACAGTTTTATTGTTC
ATGATGATATATTTTTATCTTGTGCAATGTAACATCAGAGATTTTGAGACACAACGTGGCTTTCCCCCCCC
CCCCATTATTGAAGCATTTATCAGGGTTATTGTCTCATGAGCGGATACATATTTGAATGTATTTAGAAAAA
TAAACAAATAGGGGTTCCGCGCACATTTCCCCGAAAAGTGCCACCTGACGTCTAAGAAACCATTATTATCA
TGACATTAACCTATAAAAATAGGCGTATCACGAGGCCCTTTCGTC
```

<u>Coding sequence</u>    (SEQ ID NO:147)
```
ATGAAAGTGAAGCTGCTGGTGCTGCTGTGTACCTTTACCGCCACCTACGCCGATACCATCTGTATCGGCTA
CCACGCCAACAATAGCACCGACACCGTGGATACCGTGCTGGAAAAGAACGTGACCGTGACCCACAGCGTGA
ACCTGCTGGAAAACAGCCACAACGGCAAGCTGTGTCTGCTGAAAGGCATTGCCCCTCTGCAGCTGGGAAAT
TGTAGCGTGGCCGGCTGGATTCTGGGCAATCCTGAGTGCGAGCTGCTGATTTCCAAAGAGTCCTGGTCCTA
CATCGTGGAGAAGCCCAACCCTGAGAATGGCACCTGCTACCCTGGCCACTTCGCCGATTACGAGGAACTGA
GAGAACAGCTGTCCAGCGTGTCCAGCTTCGAGAGATTCGAGATCTTCCCCAAAGAGAGCAGCTGGCCCAAT
CATACAGTGACCGGCGTGAGCGCCTCTTGTAGCCACAATGGCGAGAGCAGCTTCTACAGAAACCTGCTGTG
GCTGACCGGCAAGAACGGCCTGTACCCCAACCTGAGCAAGAGCTACGCCAACAACAAAGAAAAAGAAGTGC
TGGTCCTCTGGGGAGTGCACCACCCTCCTAACATCGGCATCCAGAAGGCCCTGTACCACACCGAGAATGCC
TACGTGTCCGTGGTGTCCAGCCACTACAGCAGAAAGTTCACCCCCGAGATCGCCAAAAGACCCAAAGTGCG
GGACCAGGAAGGCAGGATCAACTACTACTGGACCCTGCTGGAACCTGGCGACACCATCATCTTCGAGGCCA
ACGGCAATCTGATCGCCCCTAGATACGCCTTTGCCCTGAGCAGAGGCTTTGGCAGCGGCATCATCAACAGC
AACGCCCCCATGGACAAGTGTGACGCCAAGTGTCAGACACCACAGGGAGCTATCAATAGCAGCCTGCCCTT
CCAGAATGTGCACCCTGTGACCATCGGCGAGTGTCCTAAATACGTGCGGAGCGCCAAGCTGAGAATGGTGA
CCGGCCTGAGGAATATCCCCAGCATCCAGAGCAGAGGCCTGTTTGGCGCCATTGCCGGCTTTATCGAGGGC
GGATGGACAGGCATGGTGGATGGGTGGTACGGCTACCACCAGAATGAGCAGGGATCTGGCTATGCCGC
CGATCAGAAGAGCACCCAGAATGCCATCAACGGCATCACCAACAAAGTGAACAGCGTGATCGAGAAGATGA
ACACCCAGTTCACCGCCGTGGGCAAAGAGTTCAACAAGCTGGAACGGCGGATGGAAAACCTGAACAAGAAG
GTGGACGACGGCTTCATCGACATCTGGACCTACAACGCCGAACTCCTGGTCCTCCTGGAAAATGAGAGGAC
CCTGGACTTCCACGACAGCAACGTGAAGAACCTGTACGAGAAAGTGAAGAGCCAGCTGAAGAACAACGCCA
AAGAGATCGGCAACGGCTGCTTCGAGTTCTACCACAAGTGCAACGACGAGTGCATGGAAAGCGTGAAGAAC
GGCACCTACGACTACCCCAAGTACAGCGAGGAAAGCAAGCTGAACCGGGAGAAGATCGATTCCGGAGGCGA
CATCATCAAGCTGCTGAACGAGCAGGTGAACAAGGAGATGCAGAGCAGCAACCTGTACATGAGCATGAGCA
GCTGGTGCTACACCCACAGCCTGGACGGCGCCGGCCTGTTCCTGTTCGACCACGCCGCCGAGGAGTACGAG
```

Fig. 33-3

CACGCCAAGAAGCTGATCATCTTCCTGAACGAGAACAACGTGCCCGTGCAGCTGACCAGCATCAGCGCCCC
CGAGCACAAGTTCGAGGGCCTGACCCAGATCTTCCAGAAGGCCTACGAGCACGAGCAGCACATCAGCGAGA
GCATCAACAACATCGTGGACCACGCCATCAAGAGCAAGGACCACGCCACCTTCAACTTCCTGCAGTGGTAC
GTGGCCGAGCAGCACGAGGAGGAGGTGCTGTTCAAGGACATCCTGGACAAGATCGAGCTGATCGGCAACGA
GAACCACGGCCTGTACCTGGCCGACCAGTACGTGAAGGGCATCGCCAAGAGCAGGAAGAGCGGATCC

Translation  (SEQ ID NO:65)
MKVKLLVLLCTFTATYADTICIGYHANNSTDTVDTVLEKNVTVTHSVNLLENSHNGKLCLLKGIAPLQLGN
CSVAGWILGNPECELLISKESWSYIVEKPNPENGTCYPGHFADYEELREQLSSVSSFERFEIFPKESSWPN
HTVTGVSASCSHNGESSFYRNLLWLTGKNGLYPNLSKSYANNKEKEVLVLWGVHHPPNIGIQKALYHTENA
YVSVVSSHYSRKFTPEIAKRPKVRDQEGRINYYWTLLEPGDTIIFEANGNLIAPRYAFALSRGFGSGIINS
NAPMDKCDAKCQTPQGAINSSLPFQNVHPVTIGECPKYVRSAKLRMVTGLRNIPSIQSRGLFGAIAGFIEG
GWTGMVDGWYGYHHQNEQGSGYAADQKSTQNAINGITNKVNSVIEKMNTQFTAVGKEFNKLERRMENLNKK
VDDGFIDIWTYNAELLVLLENERTLDFHDSNVKNLYEKVKSQLKNNAKEIGNGCFEFYHKCNDECMESVKN
GTYDYPKYSEESKLNREKIDSGGDIIKLLNEQVNKEMQSSNLYMSMSSWCYTHSLDGAGLFLFDHAAEEYE
HAKKLIIFLNENNVPVQLTSISAPEHKFEGLTQIFQKAYEHEQHISESINNIVDHAIKSKDHATFNFLQWY
VAEQHEEEVLFKDILDKIELIGNENHGLYLADQYVKGIAKSRKSGS

Fig. 33-4

CMV8x/R-B.Bris HA(535)_SGG_egm
6560 bp

Labels: Amp, CMV IE Enhancer/Promoter 8kb, HTLV-1 R Region/Splicing Donor, CMV IE Splicing Acceptor, B.Bris(535)_SGG_egm, Tbgh B Bris HA(535)_SGG_egm (B 2008Bris HA-ferritin)

Plasmid DNA sequence  (SEQ ID NO:148)
TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 34-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCATCATCGTGCTGCTGATGGTGG
TCACAAGCAACGCCGATAGAATCTGTACCGGCATCACCAGCAGCAATAGCCCTCACGTCGTGAAAACAGCT
ACACAGGGCGAAGTGAATGTGACCGGCGTGATCCCTCTGACCACAACACCTACAAAGAGCCACTTCGCCAA
TCTGAAGGGCACAGAGACAAGAGGCAAGCTGTGTCCCAAGTGCCTGAATTGCACAGATCTGGATGTGGCTC
TGGGCAGACCTAAGTGTACAGGCAAAATCCCTAGCGCCAGAGTGTCCATTCTGCATGAAGTGCGACCTGTG
ACCAGCGGCTGTTTTCCTATTATGCACGACCGGACCAAGATCAGACAGCTGCCTAATCTGCTGAGAGGCTA
CGAGCACATCAGACTGAGCACCCACAATGTGATCAACGCCGAAAATGCTCCTGGCGGCCCTTATAAGATCG
GCACATCTGGCAGCTGCCCCAACATTACAAATGGCAATGGCTTCTTTGCCACCATGGCTTGGGCCGTGCCT
AAGAACGATAAGAACAAGACCGCCACCAACCCCCTGACAATCGAGGTGCCATATATCTGTACAGAGGGCGA
GGATCAGATCACCGTGTGGGATTTCACAGCGACAACGAAACACAGATGGCCAAGCTGTACGGCGATAGCA
AGCCTCAGAAGTTTACCAGCTCTGCCAATGGCGTGACCACACACTATGTGTCTCAGATCGGCGGCTTCCCT
AATCAGACAGAAGATGGCGGACTGCCTCAGTCTGGAAGAATCGTGGTGGATTACATGGTGCAGAAGTCTGG
CAAGACCGGCACCATCACATATCAGAGAGGAATCCTGCTGCCCCAGAAAGTGTGGTGCGCTTCTGGAAGAT
CCAAAGTGATCAAGGGCAGCCTGCCTCTGATTGGAGAAGCCGATTGTCTGCACGAGAAATACGGCGGCCTG
AACAAGAGCAAGCCTTACTATACAGGCGAGCACGCCAAGGCCATCGGCAATTGTCCTATTTGGGTCAAGAC
CCCTCTGAAGCTGGCCAATGGCACAAAGTATAGACCTCCAGCCAAGCTGCTGAAAGAGAGAGGCTTTTTTG
GAGCTATCGCCGGCTTTCTGGAAGGCGGATGGGAGGGAATGATTGCTGGATGGCATGGCTACACATCTCAT
GGCGCACATGGCGTGGCAGTGGCTGCTGATCTGAAATCTACACAGGAAGCCATCAACAAGATCACCAAGAA
CCTGAACAGCCTGAGCGAGCTGGAAGTGAAGAATCTGCAGAGACTGTCTGGCGCCATGGACGAACTGCACA
ATGAGATCCTGGAACTGGACGAGAAGGTGGACGATCTGAGAGCCGATACAATCAGCAGCCAGATTGAACTG
GCTGTGCTGCTGTCTAACGAGGGCATCATCAATAGCGAGGACGAACATCTGCTGGCCCTGGAAAGAAAGCT
GAAGAAGATGCTGGGACCTAGCGCCGTGGAAATCGGCAATGGATGCTTTGAGACAAAGCACAAGTGCAACC
AGACCTGCCTGGATAGAATTGCCGCCGGAACATTTGATGCCGGCGAGTTTTCTCTGCCCACCTTCGATAGC
CTGAATATCACATCCGGAGGCGACATCATCAAGCTGCTGAACGAGCAGGTGAACAAGGAGATGCAGAGCAG
CAACCTGTACATGAGCATGAGCAGCTGGTGCTACACCCACAGCCTGGACGGCGCCGGCCTGTTCCTGTTCG
ACCACGCCGCCGAGGAGTACGAGCACGCCAAGAAGCTGATCATCTTCCTGAACGAGAACAACGTGCCCGTG
CAGCTGACCAGCATCAGCGCCCCCGAGCACAAGTTCGAGGGCCTGACCCAGATCTTCCAGAAGGCCTACGA
GCACGAGCAGCACATCAGCGAGAGCATCAACAACATCGTGGACCACGCCATCAAGAGCAAGGACCACGCCA
CCTTCAACTTCCTGCAGTGGTACGTGGCCGAGCAGCACGAGGAGGAGGTGCTGTTCAAGGACATCCTGGAC
AAGATCGAGCTGATCGGCAACGAGAACCACGGCCTGTACCTGGCCGACCAGTACGTGAAGGGCATCGCCAA
GAGCAGGAAGAGCGGATCCTAGCATCATCATCATCATTAGTCTGGAAGGGCGAATTGATCCAGATCTGCTG
TGCCTTCTAGTTGCCAGCCATCTGTTGTTTGCCCCTCCCCGTGCCTTCCTTGACCCTGGAAGGTGCCACT
CCCACTGTCCTTTCCTAATAAAATGAGGAAATTGCATCGCATTGTCTGAGTAGGTGTCATTCTATTCTGGG
GGGTGGGGTGGGCAGGACAGCAAGGGGGAGGATTGGGAAGACAATAGCAGGCATGCTGGGGATGCGGTGG
GCTCTATGGGTACCCAGGTGCTGAAGAATTGACCCGGTTCCTCCTGGGCCAGAAAGAAGCAGGCACATCCC
CTTCTCTGTGACACACCCTGTCCACGCCCTGGTTCTTAGTTCCAGCCCCACTCATAGGACACTCATAGCT
CAGGAGGGCTCCGCCTTCAATCCCACCCGCTAAAGTACTTGGAGCGGTCTCTCCCTCCCTCATCAGCCCAC
CAAACCAAACCTAGCCTCCAAGAGTGGGAAGAAATTAAAGCAAGATAGGCTATTAAGTGCAGAGGGAGAGA
AAATGCCTCCAACATGTGAGGAAGTAATGAGAGAAATCATAGAATTTTAAGGCCATGATTTAAGGCCATCA
TGGCCTTAATCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGCTCCGCCCCCCT
GACGAGCATCACAAAAATCGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTATCTCAGTTCGGTGTAGGTCGTT
```

Fig. 34-2

```
CGCTCCAAGCTGGGCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCTACACTAGAAGAACAGTA
TTTGGTATCTGCGCTCTGCTGAAGCCAGTTACCTTCGGAAAAAGAGTTGGTAGCTCTTGATCCGGCAAACA
AACCACCGCTGGTAGCGGTGGTTTTTTTGTTTGCAAGCAGCAGATTACGCGCAGAAAAAAGGATCTCAAG
AAGATCCTTTGATCTTTTCTACGGGGTCTGACGCTCAGTGGAACGAAAACTCACGTTAAGGGATTTTGGTC
ATGAGATTATCAAAAGGATCTTCACCTAGATCCTTTTAAATTAAAAATGAAGTTTTAAATCAATCTAAAG
TATATATGAGTAAACTTGGTCTGACAGTTACCAATGCTTAATCAGTGAGGCACCTATCTCAGCGATCTGTC
TATTTCGTTCATCCATAGTTGCCTGACTCGGGGGGGGGGCGCTGAGGTCTGCCTCGTGAAGAAGGTGTT
GCTGACTCATACCAGGCCTGAATCGCCCCATCATCCAGCCAGAAAGTGAGGGAGCCACGGTTGATGAGAGC
TTTGTTGTAGGTGGACCAGTTGGTGATTTTGAACTTTTGCTTTGCCACGGAACGGTCTGCGTTGTCGGGAA
GATGCGTGATCTGATCCTTCAACTCAGCAAAAGTTCGATTTATTCAACAAAGCCGCCGTCCCGTCAAGTCA
GCGTAATGCTCTGCCAGTGTTACAACCAATTAACCAATTCTGATTAGAAAAACTCATCGAGCATCAAATGA
AACTGCAATTTATTCATATCAGGATTATCAATACCATATTTTTGAAAAAGCCGTTTCTGTAATGAAGGAGA
AAACTCACCGAGGCAGTTCCATAGGATGGCAAGATCCTGGTATCGGTCTGCGATTCCGACTCGTCCAACAT
CAATACAACCTATTAATTTCCCCTCGTCAAAAATAAGGTTATCAAGTGAGAAATCACCATGAGTGACGACT
GAATCCGGTGAGAATGGCAAAAGCTTATGCATTTCTTTCCAGACTTGTTCAACAGGCCAGCCATTACGCTC
GTCATCAAAATCACTCGCATCAACCAAACCGTTATTCATTCGTGATTGCGCCTGAGCGAGACGAAATACGC
GATCGCTGTTAAAAGGACAATTACAAACAGGAATCGAATGCAACCGGCGCAGGAACACTGCCAGCGCATCA
ACAATATTTTCACCTGAATCAGGATATTCTTCTAATACCTGGAATGCTGTTTTCCCGGGGATCGCAGTGGT
GAGTAACCATGCATCATCAGGAGTACGGATAAAATGCTTGATGGTCGGAAGAGGCATAAATTCCGTCAGCC
AGTTTAGTCTGACCATCTCATCTGTAACATCATTGGCAACGCTACCTTTGCCATGTTTCAGAAACAACTCT
GGCGCATCGGGCTTCCCATACAATCGATAGATTGTCGCACCTGATTGCCCGACATTATCGCGAGCCCATTT
ATACCCATATAAATCAGCATCCATGTTGGAATTTAATCGCGGCCTCGAGCAAGACGTTTCCCGTTGAATAT
GGCTCATAACACCCCTTGTATTACTGTTTATGTAAGCAGACAGTTTTATTGTTCATGATGATATATTTTTA
TCTTGTGCAATGTAACATCAGAGATTTTGAGACACAACGTGGCTTTCCCCCCCCCCCATTATTGAAGCAT
TTATCAGGGTTATTGTCTCATGAGCGGATACATATTTGAATGTATTTAGAAAAATAAACAAATAGGGGTTC
CGCGCACATTTCCCCGAAAAGTGCCACCTGACGTCTAAGAAACCATTATTATCATGACATTAACCTATAAA
AATAGGCGTATCACGAGGCCCTTTCGTC
```

Coding sequence (SEQ ID NO:149)
```
ATGAAGGCCATCATCGTGCTGCTGATGGTGGTCACAAGCAACGCCGATAGAATCTGTACCGGCATCACCAG
CAGCAATAGCCCTCACGTCGTGAAAACAGCTACACAGGGCGAAGTGAATGTGACCGGCGTGATCCCTCTGA
CCACAACACCTACAAAGAGCCACTTCGCCAATCTGAAGGGCACAGAGACAAGAGGCAAGCTGTGTCCCAAG
TGCCTGAATTGCACAGATCTGGATGTGGCTCTGGGCAGACCTAAGTGTACAGGCAAAATCCCTAGCGCCAG
AGTGTCCATTCTGCATGAAGTGCGACCTGTGACCAGCGGCTGTTTTCCTATTATGCACGACCGGACCAAGA
TCAGACAGCTGCCTAATCTGCTGAGAGGCTACGAGCACATCAGACTGAGCACCCACAATGTGATCAACGCC
GAAAATGCTCCTGGCGGCCCTTATAAGATCGGCACATCTGGCAGCTGCCCCAACATTACAAATGGCAATGG
CTTCTTTGCCACCATGGCTTGGGCCGTGCCTAAGAACGATAAGAACAAGACCGCCACCAACCCCCTGACAA
TCGAGGTGCCATATATCTGTACAGAGGGCGAGGATCAGATCACCGTGTGGGATTTCACAGCGACAACGAA
ACACAGATGGCCAAGCTGTACGGCGATAGCAAGCCTCAGAAGTTTACCAGCTCTGCCAATGGCGTGACCAC
ACACTATGTGTCTCAGATCGGCGGCTTCCCTAATCAGACAGAAGATGGCGGACTGCCTCAGTCTGGAAGAA
TCGTGGTGGATTACATGGTGCAGAAGTCTGGCAAGACCGGCACCATCACATATCAGAGAGGAATCCTGCTG
CCCCAGAAAGTGTGGTGCGCTTCTGGAAGATCCAAAGTGATCAAGGGCAGCCTGCCTCTGATTGGAGAAGC
CGATTGTCTGCACGAGAAATACGGCGGCCTGAACAAGAGCAAGCCTTACTATACAGGCGAGCACGCCAAGG
CCATCGGCAATTGTCCTATTTGGGTCAAGACCCCTCTGAAGCTGGCCAATGGCACAAAGTATAGACCTCCA
GCCAAGCTGCTGAAAGAGAGAGGCTTTTTTGGAGCTATCGCCGGCTTTCTGGAAGGCGGATGGGAGGGAAT
GATTGCTGGATGGCATGGCTACACATCTCATGGCGCACATGGCGTGGCAGTGGCTGCTGATCTGAAATCTA
CACAGGAAGCCATCAACAAGATCACCAAGAACCTGAACAGCCTGAGCGAGCTGGAAGTGAAGAATCTGCAG
AGACTGTCTGGCGCCATGGACGAACTGCACAATGAGATCCTGGAACTGGACGAGAAGGTGGACGATCTGAG
AGCCGATACAATCAGCAGCCAGATTGAACTGGCTGTGCTGCTGTCTAACGAGGGCATCATCAATAGCGAGG
ACGAACATCTGCTGGCCCTGGAAAGAAAGCTGAAGAAGATGCTGGGACCTAGCGCCGTGGAAATCGGCAAT
GGATGCTTTGAGACAAAGCACAAGTGCAACCAGACCTGCCTGGATAGAATTGCCGCCGGAACATTTGATGC
CGGCGAGTTTTCTCTGCCCACCTTCGATAGCCTGAATATCACATCCGGAGGCGACATCATCAAGCTGCTGA
```

```
ACGAGCAGGTGAACAAGGAGATGCAGAGCAGCAACCTGTACATGAGCATGAGCAGCTGGTGCTACACCCAC
AGCCTGGACGGCGCCGGCCTGTTCCTGTTCGACCACGCCGCCGAGGAGTACGAGCACGCCAAGAAGCTGAT
CATCTTCCTGAACGAGAACAACGTGCCCGTGCAGCTGACCAGCATCAGCGCCCCCGAGCACAAGTTCGAGG
GCCTGACCCAGATCTTCCAGAAGGCCTACGAGCACGAGCAGCACATCAGCGAGAGCATCAACAACATCGTG
GACCACGCCATCAAGAGCAAGGACCACGCCACCTTCAACTTCCTGCAGTGGTACGTGGCCGAGCAGCACGA
GGAGGAGGTGCTGTTCAAGGACATCCTGGACAAGATCGAGCTGATCGGCAACGAGAACCACGGCCTGTACC
TGGCCGACCAGTACGTGAAGGGCATCGCCAAGAGCAGGAAGAGCGGATCC
```

Translation   (SEQ ID NO:68)

```
MKAIIVLLMVVTSNADRICTGITSSNSPHVVKTATQGEVNVTGVIPLTTTPTKSHFANLKGTETRGKLCPK
CLNCTDLDVALGRPKCTGKIPSARVSILHEVRPVTSGCFPIMHDRTKIRQLPNLLRGYEHIRLSTHNVINA
ENAPGGPYKIGTSGSCPNITNGNGFFATMAWAVPKNDKNKTATNPLTIEVPYICTEGEDQITVWGFHSDNE
TQMAKLYGDSKPQKFTSSANGVTTHYVSQIGGFPNQTEDGGLPQSGRIVVDYMVQKSGKTGTITYQRGILL
PQKVWCASGRSKVIKGSLPLIGEADCLHEKYGGLNKSKPYYTGEHAKAIGNCPIWVKTPLKLANGTKYRPP
AKLLKERGFFGAIAGFLEGGWEGMIAGWHGYTSHGAHGVAVAADLKSTQEAINKITKNLNSLSELEVKNLQ
RLSGAMDELHNEILELDEKVDDLRADTISSQIELAVLLSNEGIINSEDEHLLALERKLKKMLGPSAVEIGN
GCFETKHKCNQTCLDRIAAGTFDAGEFSLPTFDSLNITSGGDIIKLLNEQVNKEMQSSNLYMSMSSWCYTH
SLDGAGLFLFDHAAEEYEHAKKLIIFLNENNVPVQLTSISAPEHKFEGLTQIFQKAYEHEQHISESINNIV
DHAIKSKDHATFNFLQWYVAEQHEEEVLFKDILDKIELIGNENHGLYLADQYVKGIAKSRKSGS
```

Fig. 34-4

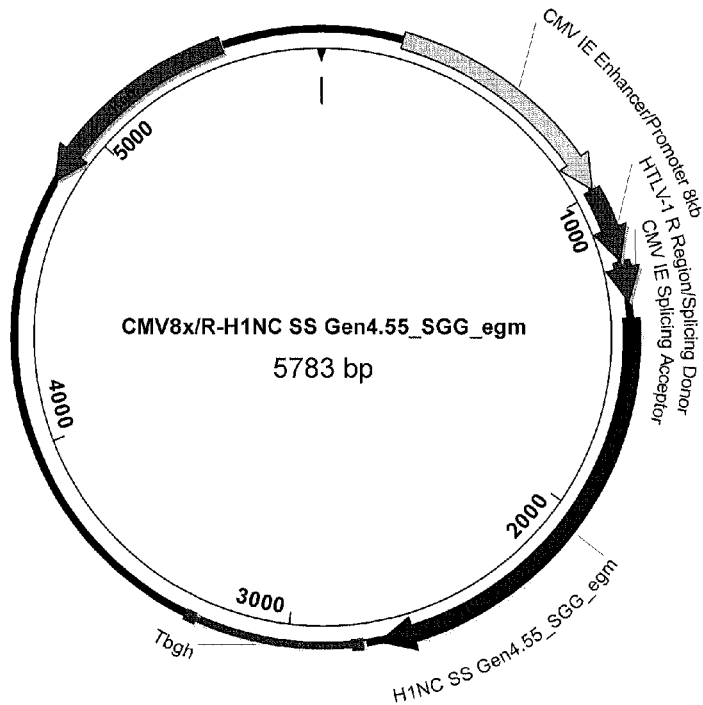
H1 NC Stabilized Stem Gen4.55_SGG_egm (H1 1999NC SS Gen4.55-ferritin)

Plasmid DNA sequence (SEQ ID NO:150)

TCGCGCGTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGTGTGAAATACCGCACAGATGCG
TAAGGAGAAAATACCGCATCAGATTGGCTATTGGCCATTGCATACGTTGTATCCATATCATAATATGTACA
TTTATATTGGCTCATGTCCAACATTACCGCCATGTTGACATTGATTATTGACTAGTTATTAATAGTAATCA
ATTACGGGAACTTCCATAGCCCATATATGGAGTTCCGCGTTACATAACTTACGGGAATTTCCAAACCTGGC
TGACCGCCCAACGACCCCCGCCCATTGACGTCAATAATGACGTATGTTCCCATAGTAACGCCAATAGGGAA
CTTCCATTGACGTCAATGGGTGGAGTATTTACGGTAAACTGCCCACTTGGGAATTTCCAAGTGTATCATAT
GCCAAGTACGCCCCCTATTGACGTCAATGACGGGAACTTCCATAAGCTTGCATTATGCCCAGTACATGACC
TTATGGGAATTTCCTACTTGGCAGTACATCTACGTATTAGTCATCGCTATTACCATGGTGATGCGGTTTTG

Fig. 35-1

```
GCAGTACATCAATGGGCGTGGATAGCGGTTTGACTCACGGGAACTTCCAAGTCTCCACCCCATTGACGTCA
ATGGGAGTTTGTTTTGACTCACCAAAATCAACGGGAATTCCCAAAATGTCGTAACAACTCCGCCCCATTGA
CGCAAATGGGCGGTAGGCGTGTACGGTGGGAGGTCTATATAAGCAGAGCTCGTTTAGTGAACCGTCAGATC
GCCTGGAGACGCCATCCACGCTGTTTTGACCTCCATAGAAGACACCGGGACCGATCCAGCCTCCATCGGCT
CGCATCTCTCCTTCACGCGCCCGCCGCCCTACCTGAGGCCGCCATCCACGCCGGTTGAGTCGCGTTCTGCC
GCCTCCCGCCTGTGGTGCCTCCTGAACTGCGTCCGCCGTCTAGGTAAGTTTAAAGCTCAGGTCGAGACCGG
GCCTTTGTCCGGCGCTCCCTTGGAGCCTACCTAGACTCAGCCGGCTCTCCACGCTTTGCCTGACCCTGCTT
GCTCAACTCTAGTTAACGGTGGAGGGCAGTGTAGTCTGAGCAGTACTCGTTGCTGCCGCGCGCCACCAG
ACATAATAGCTGACAGACTAACAGACTGTTCCTTTCCATGGGTCTTTTCTGCAGTCACCGTCGTCGACACG
TGTGATCAGATATCGCGGCCGCTCTAGAGATATCGCCACCATGAAGGCCAAGCTGCTGGTGCTGCTGTGCA
CCTTTACCGCCACCTACGCCGACACCATCTGCATTGGCTACCACGCCAACAACAGCACCGACACCGTGGAT
ACCGTGCTGGAAAAGAACGTGACCGTGACCCACAGCGTGAACCTGGGATCCGGACTGAGAATGGTCACCGG
CCTGAGAAACATCCCCAGCATCCAGAGCAGAGGCCTGTTTGGAGCCATTGCCGGCTTTATTGAGGGCGGAT
GGACCGGAATGGTGGATGGGTGGTACGGCTACCACCACCAGAATGAGCAGGGCTCTGGCTATGCCGCCGAT
CAGAAGTCTACCCAGAACGCCATCAACGGCATCACCAACAAAGTGAACAGCGTGATCGAGAAGATGGGCGG
CGATCCTGAATGGGACAGAGAGATCAACAACTACACCAGCATCATCTACAGCCTGATCGAGGAAAGCCAGA
ACCAGCAGGAAAACGGCACAGGCGGCGGATCTGGAATTGTGCAGCAGCAGAACAACCTGCTGAGAGCCATT
GAGGCCCAGCAGCATCTGCTGCAGCTGACAGTGTGGGGCATCAAGCAGCTGCAGACCTACAATGCCGAGCT
GCTGGTCCTCCTGGAAAACGAGAGAACCCTGGACTTCCACGACAGCAACGTGAAGAACCTGTACGAGAAAG
TGAAGTCCCAGCTGAAGAACAACGCCAAAGAGATCGGCAACGGCTGCTTCGAGTTCTACCACAAGTGCAAC
AACGAGTGCATGGAAAGCGTGAAGAACGGCACCTACGACTACCCCAAGTACAGCGAGGAAAGCAAGCTGAA
CAGAGAGAAGATCGACTCCGGAGGCGACATCATCAAGCTGCTGAACGAGCAGGTGAACAAGGAGATGCAGA
GCAGCAACCTGTACATGAGCATGAGCAGCTGGTGCTACACCCACAGCCTGGACGGCGCCGGCCTGTTCCTG
TTCGACCACGCCGCCGAGGAGTACGAGCACGCCAAGAAGCTGATCATCTTCCTGAACGAGAACAACGTGCC
CGTGCAGCTGACCAGCATCAGCGCCCCCGAGCACAAGTTCGAGGGCCTGACCCAGATCTTCCAGAAGGCCT
ACGAGCACGAGCAGCACATCAGCGAGAGCATCAACAACATCGTGGACCACGCCATCAAGAGCAAGGACCAC
GCCACCTTCAACTTCCTGCAGTGGTACGTGGCCGAGCAGCACGAGGAGGAGGTGCTGTTCAAGGACATCCT
GGACAAGATCGAGCTGATCGGCAACGAGAACCACGGCCTGTACCTGGCCGACCAGTACGTGAAGGGCATCG
CCAAGAGCAGGAAGAGCGGATCCTAGCATCATCATCATCATTAGTCTGGAAGGGCGAATTGATCCAGATCT
GCTGTGCCTTCTAGTTGCCAGCCATCTGTTGTTTGCCCCTCCCCCGTGCCTTCCTTGACCCTGGAAGGTGC
CACTCCCACTGTCCTTTCCTAATAAAATGAGGAAATTGCATCGCATTGTCTGAGTAGGTGTCATTCTATTC
TGGGGGGTGGGGTGGGGCAGGACAGCAAGGGGGAGGATTGGGAAGACAATAGCAGGCATGCTGGGGATGCG
GTGGGCTCTATGGGTACCCAGGTGCTGAAGAATTGACCCGGTTCCTCCTGGGCCAGAAAGAAGCAGGCACA
TCCCCTTCTCTGTGACACACCCTGTCCACGCCCCTGGTTCTTAGTTCCAGCCCCACTCATAGGACACTCAT
AGCTCAGGAGGGCTCCGCCTTCAATCCCACCCGCTAAAGTACTTGGAGCGGTCTCTCCCTCCCTCATCAGC
CCACCAAACCAAACCTAGCCTCCAAGAGTGGGAAGAAATTAAAGCAAGATAGGCTATTAAGTGCAGAGGGA
GAGAAAATGCCTCCAACATGTGAGGAAGTAATGAGAGAAATCATAGAATTTTAAGGCCATGATTTAAGGCC
ATCATGGCCTTAATCTTCCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGCAGGAAAGAACATGTGA
GCAAAAGGCCAGCAAAAGGCCAGGAACCGTAAAAAGGCCGCGTTGCTGGCGTTTTTCCATAGGCTCCGCCC
CCCTGACGAGCATCACAAAAATCGACGCTCAAGTCAGAGGTGGCGAAACCCGACAGGACTATAAAGATACC
AGGCGTTTCCCCCTGGAAGCTCCCTCGTGCGCTCTCCTGTTCCGACCCTGCCGCTTACCGGATACCTGTCC
GCCTTTCTCCCTTCGGGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCCGGTAACT
ATCGTCTTGAGTCCAACCCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTACGGCTACACTAGAAGAAC
AGTATTTGGTATCTGCGCTCTGCTGAAGCCAGTTACCTTCGGAAAAGAGTTGGTAGCTCTTGATCCGGCA
AACAAACCACCGCTGGTAGCGGTGGTTTTTTGTTTGCAAGCAGCAGATTACGCGCAGAAAAAAGGATCT
CAAGAAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTATCTCAGCGATC
TGTCTATTTCGTTCATCCATAGTTGCCTGACTCGGGGGGGGGGCGCTGAGGTCTGCCTCGTGAAGAAGG
TGTTGCTGACTCATACCAGGCCTGAATCGCCCCATCATCCAGCCAGAAAGTGAGGGAGCCACGGTTGATGA
GAGCTTTGTTGTAGGTGGACCAGTTGGTGATTTTGAACTTTTGCTTTGCCACGGAACGGTCTGCGTTGTCG
```

Fig. 35-2

```
GGAAGATGCGTGATCTGATCCTTCAACTCAGCAAAAGTTCGATTTATTCAACAAAGCCGCCGTCCCGTCAA
GTCAGCGTAATGCTCTGCCAGTGTTACAACCAATTAACCAATTCTGATTAGAAAAACTCATCGAGCATCAA
ATGAAACTGCAATTTATTCATATCAGGATTATCAATACCATATTTTTGAAAAAGCCGTTTCTGTAATGAAG
GAGAAAACTCACCGAGGCAGTTCCATAGGATGGCAAGATCCTGGTATCGGTCTGCGATTCCGACTCGTCCA
ACATCAATACAACCTATTAATTTCCCCTCGTCAAAAATAAGGTTATCAAGTGAGAAATCACCATGAGTGAC
GACTGAATCCGGTGAGAATGGCAAAAGCTTATGCATTTCTTTCCAGACTTGTTCAACAGGCCAGCCATTAC
GCTCGTCATCAAAATCACTCGCATCAACCAAACCGTTATTCATTCGTGATTGCGCCTGAGCGAGACGAAAT
ACGCGATCGCTGTTAAAAGGACAATTACAAACAGGAATCGAATGCAACCGGCGCAGGAACACTGCCAGCGC
ATCAACAATATTTTCACCTGAATCAGGATATTCTTCTAATACCTGGAATGCTGTTTTCCGGGGATCGCAG
TGGTGAGTAACCATGCATCATCAGGAGTACGGATAAATGCTTGATGGTCGGAAGAGGCATAAATTCCGTC
AGCCAGTTTAGTCTGACCATCTCATCTGTAACATCATTGGCAACGCTACCTTTGCCATGTTTCAGAAACAA
CTCTGGCGCATCGGGCTTCCCATACAATCGATAGATTGTCGCACCTGATTGCCCGACATTATCGCGAGCCC
ATTTATACCCATATAAATCAGCATCCATGTTGGAATTTAATCGCGGCCTCGAGCAAGACGTTTCCCGTTGA
ATATGGCTCATAACACCCCTTGTATTACTGTTTATGTAAGCAGACAGTTTTATTGTTCATGATGATATATT
TTTATCTTGTGCAATGTAACATCAGAGATTTTGAGACACAACGTGGCTTTCCCCCCCCCCCATTATTGAA
GCATTTATCAGGGTTATTGTCTCATGAGCGGATACATATTTGAATGTATTTAGAAAAATAAACAAATAGGG
GTTCCGCGCACATTTCCCCGAAAAGTGCCACCTGACGTCTAAGAAACCATTATTATCATGACATTAACCTA
TAAAAATAGGCGTATCACGAGGCCCTTTCGTC
```

Coding sequence (SEQ ID NO:151)
```
ATGAAGGCCAAGCTGCTGGTGCTGCTGTGCACCTTTACCGCCACCTACGCCGACACCATCTGCATTGGCTA
CCACGCCAACAACAGCACCGACACCGTGGATACCGTGCTGGAAAAGAACGTGACCGTGACCCACAGCGTGA
ACCTGGGATCCGGACTGAGAATGGTCACCGGCCTGAGAAACATCCCCAGCATCCAGAGCAGAGGCCTGTTT
GGAGCCATTGCCGGCTTTATTGAGGGCGGATGGACCGGAATGGTGGATGGGTGGTACGGCTACCACCACCA
GAATGAGCAGGGCTCTGGCTATGCCGCCGATCAGAAGTCTACCCAGAACGCCATCAACGGCATCACCAACA
AAGTGAACAGCGTGATCGAGAAGATGGGCGGCGATCCTGAATGGGACAGAGAGATCAACAACTACACCAGC
ATCATCTACAGCCTGATCGAGGAAAGCCAGAACCAGCAGGAAAACGGCACAGGCGGCGGATCTGGAATTGT
GCAGCAGCAGAACAACCTGCTGAGAGCCATTGAGGCCCAGCAGCATCTGCTGCAGCTGACAGTGTGGGGCA
TCAAGCAGCTGCAGACCTACAATGCCGAGCTGCTGGTCCTCCTGGAAAACGAGAGAACCCTGGACTTCCAC
GACAGCAACGTGAAGAACCTGTACGAGAAAGTGAAGTCCCAGCTGAAGAACAACGCCAAAGAGATCGGCAA
CGGCTGCTTCGAGTTCTACCACAAGTGCAACAACGAGTGCATGGAAAGCGTGAAGAACGGCACCTACGACT
ACCCCAAGTACAGCGAGGAAAGCAAGCTGAACAGAGAGAAGATCGACTCCGGAGGCGACATCATCAAGCTG
CTGAACGAGCAGGTGAACAAGGAGATGCAGAGCAGCAACCTGTACATGAGCATGAGCAGCTGGTGCTACAC
CCACAGCCTGGACGGCGCCGGCCTGTTCCTGTTCGACCACGCCGCCGAGGAGTACGAGCACGCCAAGAAGC
TGATCATCTTCCTGAACGAGAACAACGTGCCCGTGCAGCTGACCAGCATCAGCGCCCCCGAGCACAAGTTC
GAGGGCCTGACCCAGATCTTCCAGAAGGCCTACGAGCACGAGCAGCACATCAGCGAGAGCATCAACAACAT
CGTGGACCACGCCATCAAGAGCAAGGACCACGCCACCTTCAACTTCCTGCAGTGGTACGTGGCCGAGCAGC
ACGAGGAGGAGGTGCTGTTCAAGGACATCCTGGACAAGATCGAGCTGATCGGCAACGAGAACCACGGCCTG
TACCTGGCCGACCAGTACGTGAAGGGCATCGCCAAGAGCAGGAAGAGCGGATCC
```

Translation (SEQ ID NO:101)
```
MKAKLLVLLCTFTATYADTICIGYHANNSTDTVDTVLEKNVTVTHSVNLGSGLRMVTGLRNIPSIQSRGLF
GAIAGFIEGGWTGMVDGWYGYHHQNEQGSGYAADQKSTQNAINGITNKVNSVIEKMGGDPEWDREINNYTS
IIYSLIEESQNQQENGTGGGSGIVQQQNNLLRAIEAQQHLLQLTVWGIKQLQTYNAELLVLLENERTLDFH
DSNVKNLYEKVKSQLKNNAKEIGNGCFEFYHKCNNECMESVKNGTYDYPKYSEESKLNREKIDSGGDIIKL
LNEQVNKEMQSSNLYMSMSSWCYTHSLDGAGLFLFDHAAEEYEHAKKLIIFLNENNVPVQLTSISAPEHKF
EGLTQIFQKAYEHEQHISESINNIVDHAIKSKDHATFNFLQWYVAEQHEEEVLFKDILDKIELIGNENHGL
YLADQYVKGIAKSRKSGS
```

Fig. 35-3

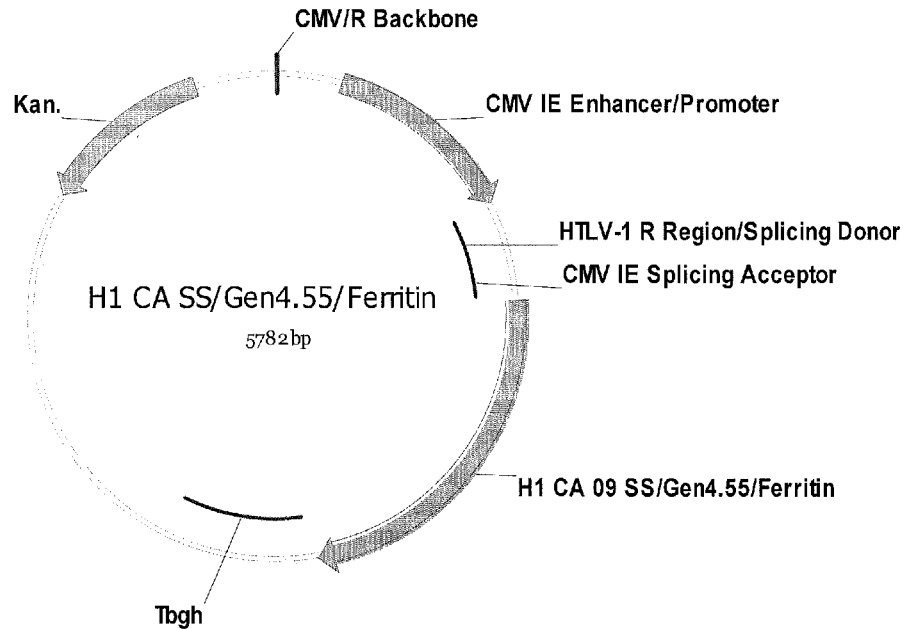

H1 CA SS/Gen4.55/ferritin (SEQ ID NO:152)

tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgacccccgcccattgacgtcaataatgacgtatgt
tcccatagtaacgccaatagggactttccattgacgtcaatgggtggagtatttacggtaaactgcccacttggcagtacatcaagtgtatcatat
gccaagtacgccccctattgacgtcaatgacggtaaatggcccgcctggcattatgcccagtacatgaccttatgggactttcctacttggcagta
catctacgtattagtcatcgctattaccatggtgatgcggttttggcagtacatcaatgggcgtggatagcggtttgactcacggggatttccaagt
ctccaccccattgacgtcaatgggagtttgttttggcaccaaaatcaacgggactttccaaaatgtcgtaacaactccgccccattgacgcaaatg
ggcggtaggcgtgtacggtgggaggtctatataagcagagctcgtttagtgaaccgtcagatcgcctggagacgccatccacgctgttttgacct
ccatagaagacaccgggaccgatccagcctccatcggctcgcatctctccttcacgcgcccgccgccctacctgaggccgccatccacgccggtt
gagtcgcgttctgccgcctcccgcctgtggtgcctcctgaactgcgtccgccgtctaggtaagtttaaagctcaggtcgagaccgggcctttgtccg
gcgctcccttggagcctacctagactcagccggctctccacgctttgcctgaccctgcttgctcaactctagttaacggtggagggcagtgtagtct
gagcagtactcgttgctgccgcgcgcgccaccagacataatagctgacagactaacagactgttcctttccatgggtcttttctgcagtcaccgtc
gtcgacacgtgtgatcagatatcgcggccgctctagagatatcgccaccatgaaggctatcctggtggtgctgctgtacacctttgccaccgccaa
tgccgacaccctgtgtattggctaccacgccaacaacagcaccgacaccgtggataccgtgctggaaaagaacgtgaccgtgacccacagcgt
gaacctgggctccggcctgagactggccaccggcctgagaaacatccccagcattcagagcagaggcctgtttggagccattgccggctttattg
agggcggatggaccggaatggtggatgggtggtacggctaccaccaccagaatgagcagggctctggctatgccgccgacctgaagtctaccc
agaacgccatcgacgagatcaccaacaaagtgaacagcgtgatcgagaagatgggcggctgggacccatgggacagagagatcaacaacta
caccagcatcatctacagcctgatcgaggaaagccagaaccagcaggaaaacggcacaggcggcggatctggaattgtgcagcagcagaaca
acctgctgagagccattgaggcccagcagcatctgctgcagctgacagtgtggggcatcaagcagctgcagacctacaacgccgagctgctggt
gctgctcgagaatgagagaaccctggactaccacgacagcaacgtgaagaacctgtacgagaaagtgcggagccagctgaagaacaacgcc
aaagagatcggcaacggctgcttcgagttctaccacaagtgcgacaatacctgcatggaaagcgtgaagaacggcacctacgactaccccaag
tacagcgaggaagccaagctgaaccgggaagagatcgattccggaggcgacatcatcaagctgctgaacgagcaggtgaacaaggagatgc
agagcagcaacctgtacatgagcatgagcagctggtgctacacccacagcctggacggcgccggcctgttcctgttcgaccacgccgccgagga

Fig. 36-1

```
gtacgagcacgccaagaagctgatcatcttcctgaacgagaacaacgtgcccgtgcagctgaccagcatcagcgcccccgagcacaagttcga
gggcctgacccagatcttccagaaggcctacgagcacgagcagcacatcagcgagagcatcaacaacatcgtggaccacgccatcaagagca
aggaccacgccaccttcaacttcctgcagtggtacgtggccgagcagcacgaggaggaggtgctgttcaaggacatcctggacaagatcgagct
gatcggcaacgagaaccacggcctgtacctggccgaccagtacgtgaagggcatcgccaagagcaggaagagcggatcctagcatcatcatc
atcatcattagtctgaagggcgaattgatccagctgtgccttctagttgccagccatctgttgtttgcccctccccgtgccttccttgaccctggaa
ggtgccactcccactgtcctttcctaataaaatgaggaaattgcatcgcattgtctgagtaggtgtcattctattctgggggtgggtggggcag
gacagcaaggggaggattgggaagacaatagcaggcatgctggggatgcggtgggctctatgggtacccaggtgctgaagaattgacccggt
tcctcctgggccagaaagaagcaggcacatccccttctctgtgacacacctgtccacgccctggttcttagttccagccccactcataggacac
tcatagctcaggagggctccgccttcaatcccaccgctaaagtacttggagcggtctctccctccctcatcagcccaccaaaccaaacctagcct
ccaagagtgggaagaaattaaagcaagataggctattaagtgcagagggagagaaaatgcctccaacatgtgaggaagtaatgagagaaat
catagaattttaaggccatgatttaaggccatcatggccttaatcttccgcttcctcgctcactgactcgctgcgctcggtcgttcggctgcggcga
gcggtatcagctcactcaaaggcggtaatacggttatccacagaatcaggggataacgcaggaaagaacatgtgagcaaaaggccagcaaaa
ggccaggaaccgtaaaaaggccgcgttgctggcgtttttccataggctccgcccccctgacgagcatcacaaaaatcgacgctcaagtcagagg
tggcgaaacccgacaggactataaagataccaggcgtttccccctggaagctccctcgtgcgctctcctgttccgaccctgccgcttaccggatac
ctgtccgcctttctcccttcgggaagcgtggcgctttctcatagctcacgctgtaggtatctcagttcggtgtaggtcgttcgctccaagctgggctg
tgtgcacgaaccccccgttcagcccgaccgctgcgccttatccggtaactatcgtcttgagtccaacccggtaagacacgacttatcgccactggc
agcagccactggtaacaggattagcagagcgaggtatgtaggcggtgctacagagttcttgaagtggtggcctaactacggctacactagaaga
acagtatttggtatctgcgctctgctgaagccagttaccttcggaaaaagagttggtagctcttgatccggcaaacaaaccaccgctggtagcggt
ggttttttttgtttgcaagcagcagattacgcgcagaaaaaaaggatctcaagaagatcctttgatcttttctacggggtctgacgctcagtggaac
gaaaactcacgttaagggattttggtcatgagattatcaaaaaggatcttcacctagatccttttaaattaaaaatgaagttttaaatcaatctaa
agtatatatgagtaaacttggtctgacagttaccaatgcttaatcagtgaggcacctatctcagcgatctgtctatttcgttcatccatagttgcctg
actcggggggggggggcgctgaggtctgcctcgtgaagaaggtgttgctgactcataccaggcctgaatcgccccatcatccagccagaaagtg
agggagccacggttgatgagagctttgttgtaggtggaccagttggtgattttgaacttttgctttgccacggaacggtctgcgttgtcgggaagat
gcgtgatctgatccttcaactcagcaaaagttcgatttattcaacaaagccgccgtcccgtcaagtcagcgtaatgctctgccagtgttacaacca
attaaccaattctgattagaaaaactcatcgagcatcaaatgaaactgcaatttattcatatcaggattatcaataccatattttgaaaaagccg
tttctgtaatgaaggagaaaactcaccgaggcagttccataggatggcaagatcctggtatcggtctgcgattccgactcgtccaacatcaatac
aacctattaatttccctcgtcaaaaataaggttatcaagtgagaaatcaccatgagtgacgactgaatccggtgagaatggcaaaagcttatgc
atttctttccagacttgttcaacaggccagccattacgctcgtcatcaaaatcactcgcatcaaccaaaccgttattcattcgtgattgcgcctgag
cgagacgaaatacgcgatcgctgttaaaaggcaattacaaacaggaatcgaatgcaaccggcgcaggaacactgccagcgcatcaacaata
ttttcacctgaatcaggatattcttctaatacctggaatgctgtttcccggggatcgcagtggtgagtaaccatgcatcatcaggagtacggataa
aatgcttgatggtcggaagaggcataaattccgtcagccagtttagtctgaccatctcatctgtaacatcattggcaacgctacctttgccatgttt
cagaaacaactctggcgcatcgggcttcccatacaatcgatagattgtcgcacctgattgcccgacattatcgcgagcccatttatacccatataa
atcagcatccatgttggaatttaatcgcggcctcgagcaagacgtttcccgttgaatatggctcataacacccccttgtattactgtttatgtaagca
gacagtttattgttcatgatgatatattttatcttgtgcaatgtaacatcagagattttgagacacaacgtggctttcccccccccccccattattga
agcatttatcagggttattgtctcatgagcggatacatatttgaatgtatttagaaaaataaacaaataggggttccgcgcacatttccccgaaaa
gtgccacctgacgtctaagaaaccattattatcatgacattaacctataaaaataggcgtatcacgaggcccttcgtc
```

Fig. 36-2

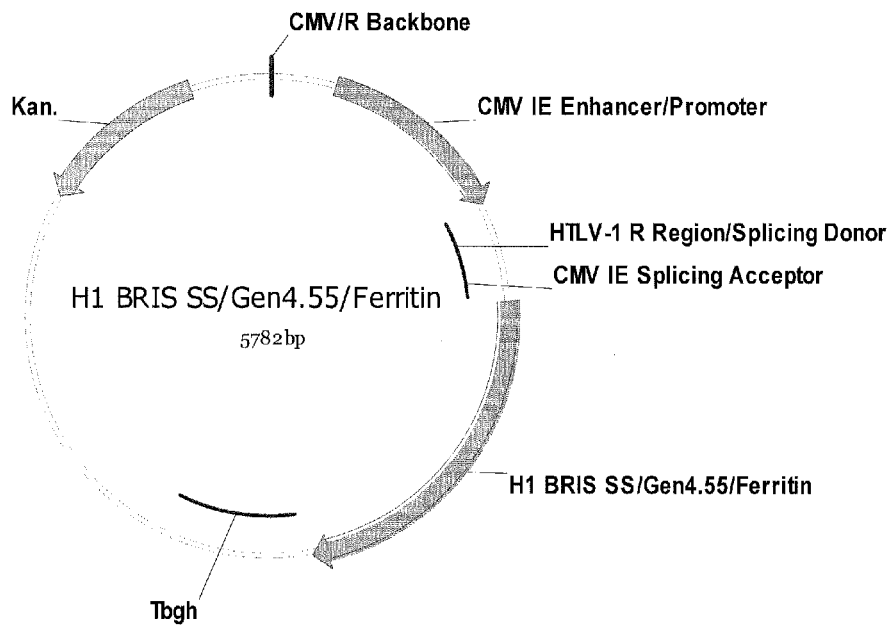
H1 Bris SS/Gen4.55/ferritin (SEQ ID NO:153)
tcgcgcgtttcgg

```
cagagcagcaacctgtacatgagcatgagcagctggtgctacacccacagcctggacggcgccggcctgttcctgttcgaccacgccgccgagg
agtacgagcacgccaagaagctgatcatcttcctgaacgagaacaacgtgcccgtgcagctgaccagcatcagcgcccccgagcacaagttcg
agggcctgacccagatcttccagaaggcctacgagcacgagcagcacatcagcgagagcatcaacaacatcgtggaccacgccatcaagagc
aaggaccacgccaccttcaacttcctgcagtggtacgtggccgagcagcacgaggaggaggtgctgttcaaggacatcctggacaagatcgag
ctgatcggcaacgagaaccacggcctgtacctggccgaccagtacgtgaagggcatcgccaagagcaggaagagcggatcctagcatcatcat
catcatcattagtctgaagggcgaattgatccagctgtgccttctagttgccagccatctgttgtttgccctcccccgtgccttccttgaccctgga
aggtgccactcccactgtcctttcctaataaaatgaggaaattgcatcgcattgtctgagtaggtgtcattctattctgggggggtggggtggggca
ggacagcaaggggggaggattgggaagacaatagcaggcatgctggggatgcggtgggctctatgggtacccaggtgctgaagaattgaccccg
gttcctcctgggccagaaagaagcaggcacatcccctctctgtgacacacccctgtccacgccccctggttcttagttccagccccactcataggac
actcatagctcaggagggctccgccttcaatcccacccgctaaagtacttggagcggtctctccctccctcatcagcccaccaaaccaaacctag
cctccaagagtgggaagaaattaaagcaagataggctattaagtgcagagggagagaaaatgcctccaacatgtgaggaagtaatgagagaa
atcatagaattttaaggccatgatttaaggccatcatggccttaatcttccgcttcctcgctcactgactcgctgcgctcggtcgttcggctgcggcg
agcggtatcagctcactcaaaggcggtaatacggttatccacagaatcaggggataacgcaggaaagaacatgtgagcaaaaggccagcaaa
aggccaggaaccgtaaaaaggccgcgttgctggcgtttttccataggctccgcccccctgacgagcatcacaaaaatcgacgctcaagtcagag
gtggcgaaacccgacaggactataaagataccaggcgtttccccctggaagctccctcgtgcgctctcctgttccgaccctgccgcttaccggata
cctgtccgcctttctcccttcgggaagcgtggcgctttctcatagctcacgctgtaggtatctcagttcggtgtaggtcgttcgctccaagctgggct
gtgtgcacgaaccccccgttcagcccgaccgctgcgccttatccggtaactatcgtcttgagtccaacccggtaagacacgacttatcgccactgg
cagcagccactggtaacaggattagcagagcgaggtatgtaggcggtgctacagagttcttgaagtggtggcctaactacggctacactagaag
aacagtatttggtatctgcgctctgctgaagccagttaccttcggaaaaagagttggtagctcttgatccggcaaacaaaccaccgctggtagcg
gtggtttttttgtttgcaagcagcagattacgcgcagaaaaaaaggatctcaagaagatcctttgatcttttctacggggtctgacgctcagtgga
acgaaaactcacgttaagggattttggtcatgagattatcaaaaaggatcttcacctagatccttttaaattaaaaatgaagttttaaatcaatct
aaagtatatatgagtaaacttggtctgacagttaccaatgcttaatcagtgaggcacctatctcagcgatctgtctatttcgttcatccatagttgcc
tgactcgggggggggggggcgctgaggtctgcctcgtgaagaaggtgttgctgactcataccaggcctgaatcgccccatcatccagccagaaag
tgagggagccacggttgatgagagctttgttgtaggtggaccagttggtgattttgaacttttgctttgccacggaacggtctgcgttgtcgggaag
atgcgtgatctgatccttcaactcagcaaaagttcgatttattcaacaaagccgcgtcccgtcaagtcagcgtaatgctctgccagtgttacaac
caattaaccaattctgattagaaaaactcatcgagcatcaaatgaaactgcaatttattcatatcaggattatcaataccatatttttgaaaaagc
cgtttctgtaatgaaggagaaaactcaccgaggcagttccataggatggcaagatcctggtatcggtctgcgattccgactcgtccaacatcaat
acaacctattaatttcccctcgtcaaaaataaggttatcaagtgagaaatcaccatgagtgacgactgaatccggtgagaatggcaaaagcttat
gcatttctttccagacttgttcaacaggccagccattacgctcgtcatcaaaatcactcgcatcaaccaaaccgttattcattcgtgattgcgcctg
agcgagacgaaatacgcgatcgctgttaaaaggacaattacaaacaggaatcgaatgcaaccggcgcaggaacactgccagcgcatcaacaa
tattttcacctgaatcaggatattcttctaatacctggaatgctgttttcccggggatcgcagtggtgagtaaccatgcatcatcaggagtacggat
aaaatgcttgatggtcggaagaggcataaattccgtcagccagtttagtctgaccatctcatctgtaacatcattggcaacgctacctttgccatgt
ttcagaaacaactctggcgcatcgggcttcccatacaatcgatagattgtcgcacctgattgcccgacattatcgcgagcccatttatacccatat
aaatcagcatccatgttggaatttaatcgcggcctcgagcaagacgtttcccgttgaatatggctcataacaccccttgtattactgtttatgtaag
cagacagttttattgttcatgatgatatatttttatcttgtgcaatgtaacatcagagattttgagacacaacgtggctttcccccccccccccattatt
gaagcatttatcagggttattgtctcatgagcggatacatatttgaatgtatttagaaaaataaacaaataggggttccgcgcacatttcccccgaa
aagtgccacctgacgtctaagaaaccattattatcatgacattaacctataaaaataggcgtatcacgaggccctttcgtc
```

Fig. 37-2

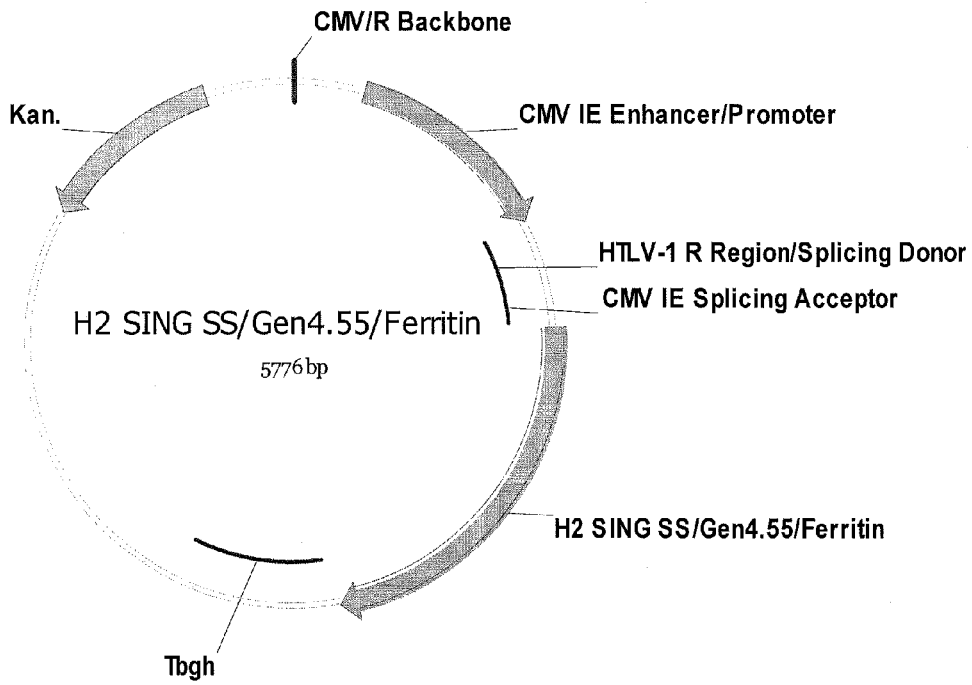

H2 Sing SS/Gen4.55/ferritin    (SEQ ID NO:154)
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgaccccccgcccattgacgtcaataatgacgtatgt
tcccatagtaacgccaatagggactttccattgacgtcaatgggtggagtatttacggtaaactgcccacttggcagtacatcaagtgtatcatat
gccaagtacgccccctattgacgtcaatgacggtaaatggcccgcctggcattatgcccagtacatgaccttatgggactttcctacttggcagta
catctacgtattagtcatcgctattaccatggtgatgcggttttggcagtacatcaatgggcgtggatagcggtttgactcacggggatttccaagt
ctccacccattgacgtcaatgggagtttgttttggcaccaaaatcaacgggactttccaaaatgtcgtaacaactccgccccattgacgcaaatg
ggcggtaggcgtgtacggtgggaggtctatataagcagagctcgtttagtgaaccgtcagatcgcctggagacgccatccacgctgttttgacct
ccatagaagacaccgggaccgatccagcctccatcggctcgcatctctccttcacgcgcccgccgccctacctgaggccgccatccacgccggtt
gagtcgcgttctgccgcctcccgcctgtggtgcctcctgaactgcgtccgccgtctaggtaagtttaaagctcaggtcgagaccgggcctttgtccg
gcgctcccttggagcctacctagactcagccggctctccacgctttgcctgaccctgcttgctcaactctagttaacggtggagggcagtgtagtct
gagcagtactcgttgctgccgcgcgcgccaccagacataatagctgacagactaacagactgttcctttccatgggtctttctgcagtcaccgtc
gtcgacacgtgtgatcagatatcgcggccgctctagagatatcgccaccatggccatcatctacctgattctgctgtttacagccgtcagaggcga
tcagatctgtattggctaccacgccaacaatagcaccgagaaagtggataccatcctggaaagaaatgtgacagtgacacacgccaaggatatt
ggatcaggactggtgctggctacaggactgagaaatgtgcctcagattgagagcagaggcctgtttggagccattgctggctttattgaaggcgg
atggcagggaatgattgatgggtggtacggctaccaccactctaatgatcagggatctggatatgccgccgacaaagaatctacacagaaagc
cttcgacggcatcaccaacaaagtgaatagcgtgatcgagaagatgggcggagatcccgaatgggacagagagatcaacaactacaccagca
tcatctacagcctgatcgaggaaagccagaatcagcaggaaaatggaacaggcggaggatctggaattgtgcagcagcagaacaatctgctg
agagctattgaagctcagcagcatctgctgaatctgacagtgtggggaatcaaacagctgcagacatacaatgctgagctgctggtgctgatgg
aaaatgagagaaccctggacttccacgacagcaatgtgaagaacctgtacgacaaagtgcggatgcagctgagagacaatgtgaaagaactg
ggcaatggctgcttcgagttctaccacaagtgcgacgatgagtgtatgaacagcgtgaagaacggcacctacgactaccctaagtacgaggaa
gagagcaagctgaacagaaatgagatcaagtccggaggcgacatcatcaagctgctgaacgagcaggtgaacaaggagatgcagagcagca

Fig. 38-1

```
acctgtacatgagcatgagcagctggtgctacacccacagcctggacggcgccggcctgttcctgttcgaccacgccgccgaggagtacgagca
cgccaagaagctgatcatcttcctgaacgagaacaacgtgcccgtgcagctgaccagcatcagcgcccccgagcacaagttcgagggcctgac
ccagatcttccagaaggcctacgagcacgagcagcacatcagcgagagcatcaacaacatcgtggaccacgccatcaagagcaaggaccacg
ccaccttcaacttcctgcagtggtacgtggccgagcagcacgaggaggaggtgctgttcaaggacatcctggacaagatcgagctgatcggcaa
cgagaaccacggcctgtacctggccgaccagtacgtgaagggcatcgccaagagcaggaagagcggatcctagcatcatcatcatcatcatta
gtctgaagggcgaattgatccagctgtgcctcctagttgccagccatctgttgtttgcccctcccccgtgccttccttgaccctggaaggtgccactc
ccactgtcctttcctaataaaatgaggaaattgcatcgcattgtctgagtaggtgtcattctattctgggggggtggggtggggcaggacagcaagg
gggaggattgggaagacaatagcaggcatgctggggatgcggtgggctctatgggtacccaggtgctgaagaattgacccggttcctcctgggc
cagaaagaagcaggcacatccccttctctgtgacacaccctgtccacgcccctggttcttagttccagccccactcataggacactcatagctcag
gagggctccgccttcaatcccacccgctaaagtacttggagcggtctctccctccctcatcagcccaccaaaccaaacctagcctccaagagtgg
gaagaaattaaagcaagataggctattaagtgcagagggagagaaatgcctccaacatgtgaggaagtaatgagagaaatcatagaatttt
aaggccatgatttaaggccatcatggccttaatcttccgcttcctcgctcactgactcgctgcgctcggtcgttcggctgcggcagcggtatcagc
tcactcaaaggcggtaatacggttatccacagaatcaggggataacgcaggaaagaacatgtgagcaaaaggccagcaaaaggccaggaac
cgtaaaaaggccgcgttgctggcgtttttccataggctccgcccccctgacgagcatcacaaaaatcgacgctcaagtcagaggtggcgaaacc
cgacaggactataaagataccaggcgtttccccctggaagctccctcgtgcgctctcctgttccgaccctgccgcttaccggatacctgtccgcctt
tctcccttcgggaagcgtggcgctttctcatagctcacgctgtaggtatctcagttcggtgtaggtcgttcgctccaagctgggctgtgtgcacgaa
ccccccgttcagcccgaccgctgcgccttatccggtaactatcgtcttgagtccaacccggtaagacacgacttatcgccactggcagcagccact
ggtaacaggattagcagagcgaggtatgtaggcggtgctacagagttcttgaagtggtggcctaactacggctacactagaagaacagtatttg
gtatctgcgctctgctgaagccagttaccttcggaaaaagagttggtagctcttgatccggcaaacaaaccaccgctggtagcggtggtttttttgt
ttgcaagcagcagattacgcgcagaaaaaaaggatctcaagaagatcctttgatcttttctacggggtctgacgctcagtggaacgaaaactca
cgttaagggattttggtcatgagattatcaaaaaggatcttcacctagatccttttaaattaaaaatgaagtttaaatcaatctaaagtatatatg
agtaaacttggtctgacagttaccaatgcttaatcagtgaggcacctatctcagcgatctgtctatttcgttcatccatagttgcctgactcggggg
ggggggcgctgaggtctgcctcgtgaagaaggtgttgctgactcataccaggcctgaatcgccccatcatccagccagaaagtgagggagcc
acggttgatgagagctttgttgtaggtggaccagttggtgattttgaacttttgctttgccacggaacggtctgcgttgtcgggaagatgcgtgatc
tgatccttcaactcagcaaaagttcgatttattcaacaaagccgccgtcccgtcaagtcagcgtaatgctctgccagtgttacaaccaattaacca
attctgattagaaaaactcatcgagcatcaaatgaaactgcaatttattcatatcaggattatcaataccatattttgaaaaagccgtttctgtaa
tgaaggagaaaactcaccgaggcagttccataggatggcaagatcctggtatcggtctgcgattccgactcgtccaacatcaatacaacctatta
atttccctcgtcaaaaataaggttatcaagtgagaaatcaccatgagtgacgactgaatccggtgagaatggcaaaagcttatgcatttctttcc
agacttgttcaacaggccagccattacgctcgtcatcaaaatcactcgcatcaaccaaaccgttattcattcgtgattgcgcctgagcgagacga
aatacgcgatcgctgttaaaaggacaattacaaacaggaatcgaatgcaaccggcgcaggaacactgccagcgcatcaacaatattttcacct
gaatcaggatattcttctaatacctggaatgctgttttcccggggatcgcagtggtgagtaaccatgcatcatcaggagtacggataaaatgcttg
atggtcggaagaggcataaaattccgtcagccagtttagtctgaccatctcatctgtaacatcattggcaacgctaccttcgccatgtttcagaaac
aactctggcgcatcgggcttcccatacaatcgatagattgtcgcacctgattgcccgacattatcgcgagcccatttatacccatataaatcagca
tccatgttggaatttaatcgcggcctcgagcaagacgtttcccgttgaatatggctcataacaccccttgtattactgtttatgtaagcagacagttt
tattgttcatgatgatatattttatcttgtgcaatgtaacatcagagattttgagacacaacgtggctttccccccccccccattattgaagcattta
tcaggttattgtctcatgagcggatacatatttgaatgtatttagaaaaataaacaaataggggttccgcgcacatttccccgaaaagtgccacc
tgacgtctaagaaaccattattatcatgacattaacctataaaaataggcgtatcacgaggccctttcgtc
```

Fig. 38-2

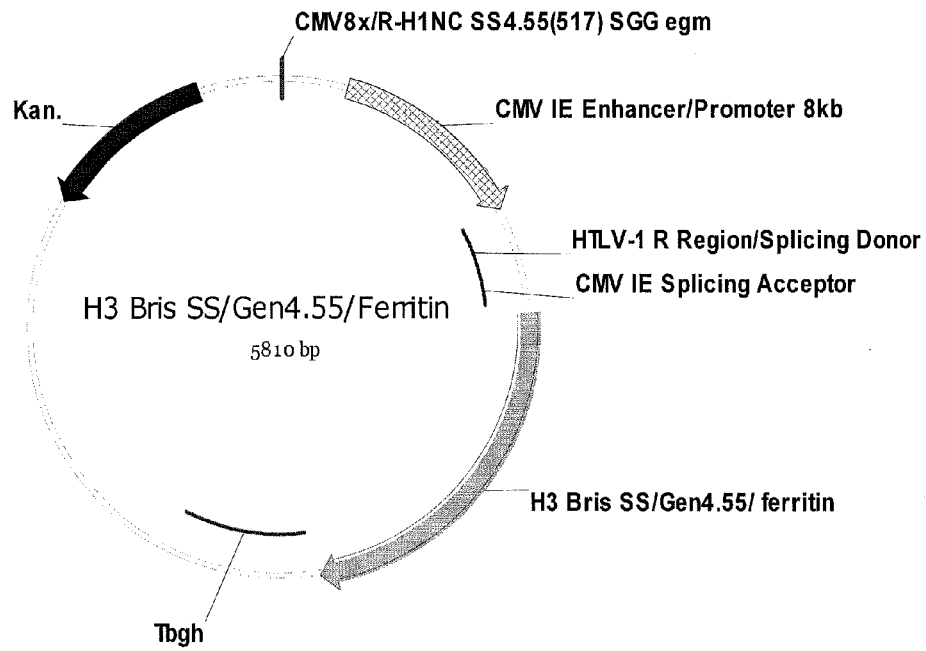

H3 Bris SS/Gen4.55/ferritin  (SEQ ID NO:155)
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgccccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
accccattgacgtcaatgggagtttgttttgactcaccaaaatcaacgggaattcccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgcgccaccagacataatagctgacagactaacagactgttcctttccatgggtcttttctgcagtcaccgtcgt
cgacacgtgtgatcagatatcgcggccgctctagagatatcgccaccatgaaaaccatcattgccctgagctacatcctgtgcctggtgttcacac
agaagctgcccggcaacgataatagcaccgccacactgtgtctgggacaccacgccgtgcctaatggcaccatcgtgaaaacaatcaccaacg
accagatcgaagtgaccaatgccacagagctgggctccggcctgaagctggccaccggcatgagaaatgtgcccgagaagcagaccagaggc
atctttggcgccattgccggctttatcgagaatggctgggagggaatggtggatgggtggtacggcttcagacaccagaatagcgagggaattg
gacaggccgccgatctgaaatctacccaggccgccatcgaccagatcaacggcaagctgaacaggctgatcggcaagaccggcggcgatccc
gagtgggaccgggagatcaacaactacaccagcatcatctacagcctgatcgaggagagccagaaccagcaggagaacggcaccggcggcg
gcagcggcatcgtgcagcagcagaacaacctgctgcgggccatcgaggcccagcagcacctgctgcagctgaccgtgtggggcatcaagcagc
tgcagagctacaatgccgaactgctggtcgccctggaaaaccagcacacaattgatctgacagacagtgagatgaataagctgttcgagaaaa
ccaagaagcagctgagagaaaacgccgaggacatgggcaacggctgcttcaagatctaccacaagtgcgacaacgcctgcatcggcagcatc
agaaacggcacctacgaccacgacgtgtacagagatgaggccctgaacaaccggtttcagatcaagggctccggaggcgacatcatcaagctg
ctgaacgagcaggtgaacaaggagatgcagagcagcaacctgtacatgagcatgagcagctggtgctacacccacagcctggacggcgccgg
cctgttcctgttcgaccacgccgccgaggagtacgagcacgccaagaagctgatcatcttcctgaacgagaacaacgtgcccgtgcagctgacc

Fig. 39-1 agcatcagcgcccccgagcacaagttcgagggcctgacccagatcttccagaaggcctacgagcacgagcagcacatcagcgagagcatcaa
caacatcgtggaccacgccatcaagagcaaggaccacgccaccttcaacttcctgcagtggtacgtggccgagcagcacgaggaggaggtgct
gttcaaggacatcctggacaagatcgagctgatcggcaacgagaaccacgcctgtacctggccgaccagtacgtgaagggcatcgccaagag
caggaagagcggatcctagcatcatcatcatcatcattagtctgaagggcgaattgatccagctgtgccttctagttgccagccatctgttgtttgc
ccctcccccgtgccttccttgaccctggaaggtgccactcccactgtcctttcctaataaaatgaggaaattgcatcgcattgtctgagtaggtgtc
attctattctgggggtgggtggggcaggacagcaaggggaggattgggaagacaatagcaggcatgctggggatgcggtgggctctatgg
gtacccaggtgctgaagaattgacccggttcctcctgggccagaaagaagcaggcacatccccttctctgtgacacaccctgtccacgcccctgg
ttcttagttccagccccactcataggacactcatagctcaggagggctccgccttcaatcccacccgctaaagtacttggagcggtctctccctccc
tcatcagcccaccaaaccaaacctagcctccaagagtgggaagaaattaaagcaagataggctattaagtgcagagggagagaaaatgcctc
caacatgtgaggaagtaatgagagaaatcatagaattttaaggccatgatttaaggccatcatggccttaatcttccgcttcctcgctcactgact
cgctgcgctcggtcgttcggctgcggcgagcggtatcagctcactcaaaggcggtaatacggttatccacagaatcagggataacgcaggaaa
gaacatgtgagcaaaaggccagcaaaaggccaggaaccgtaaaaaggccgcgttgctggcgtttttccataggctccgcccccctgacgagca
tcacaaaaatcgacgctcaagtcagaggtggcgaaacccgacaggactataaagataccaggcgtttccccctggaagctccctcgtgcgctct
cctgttccgaccctgccgcttaccggatacctgtccgcctttctcccttcgggaagcgtggcgctttctcatagctcacgctgtaggtatctcagttc
ggtgtaggtcgttcgctccaagctgggctgtgtgcacgaaccccccgttcagcccgaccgctgcgccttatccggtaactatcgtcttgagtccaa
cccggtaagacacgacttatcgccactggcagcagccactggtaacaggattagcagagcgaggtatgtaggcggtgctacagagttcttgaag
tggtggcctaactacggctacactagaagaacagtatttggtatctgcgctctgctgaagccagttaccttcggaaaaagagttggtagctcttga
tccggcaaacaaaccaccgctggtagcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaaaaaggatcttcacctagatccttta
aattaaaaatgaagttttaaatcaatctaaagtatatatgagtaaacttggtctgacagttaccaatgcttaatcagtgaggcacctatctcagcg
atctgtctatttcgttcatccatagttgcctgactcgggggggggggcgctgaggtctgcctcgtgaagaaggtgttgctgactcataccaggcct
gaatcgccccatcatccagccagaaagtgagggagccacggttgatgagagctttgttgtaggtggaccagttggtgattttgaacttttgctttg
ccacggaacggtctgcgttgtcgggaagatgcgtgatctgatccttcaactcagcaaaagttcgatttattcaacaaagccgccgtcccgtcaagt
cagcgtaatgctctgccagtgttacaaccaattaaccaattctgattagaaaaactcatcgagcatcaaatgaaactgcaatttattcatatcagg
attatcaataccatatttttgaaaaagccgtttctgtaatgaaggagaaaactcaccgaggcagttccataggatggcaagatcctggtatcggt
ctgcgattccgactcgtccaacatcaatacaacctattaatttcccctcgtcaaaaataaggttatcaagtgagaaatcaccatgagtgacgactg
aatccggtgagaatggcaaaagcttatgcatttctttccagacttgttcaacaggccagccattacgctcgtcatcaaaatcactcgcatcaacca
aaccgttattcattcgtgattgcgcctgagcgagacgaaatacgcgatcgctgttaaaaggacaattacaaacaggaatcgaatgcaaccggcg
caggaacactgccagcgcatcaacaatattttcacctgaatcaggatattcttctaatacctggaatgctgttttcccggggatcgcagtggtgag
taaccatgcatcatcaggagtacggataaaatgcttgatggtcggaagaggcataaattccgtcagccagtttagtctgaccatctcatctgtaac
atcattggcaacgctacctttgccatgtttcagaaacaactctggcgcatcgggcttcccatacaatcgatagattgtcgcacctgattgcccgac
attatcgcgagcccatttatacccatataaatcagcatccatgttggaatttaatcgcggcctcgagcaagacgtttcccgttgaatatggctcata
acacccccttgtattactgtttatgtaagcagacagttttattgttcatgatgatatatttttatcttgtgcaatgtaacatcagagattttgagacaca
acgtggctttcccccccccccattattgaagcatttatcagggttattgtctcatgagcggatacatatttgaatgtatttagaaaaataaacaaa
taggggttccgcgcacatttccccgaaaagtgccacctgacgtctaagaaaccattattatcatgacattaacctataaaaataggcgtatcacg
aggccctttcgtc

Fig. 39-2

H3 Perth SS/Gen4.55/ferritin (SEQ ID NO:156)
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgccccctattgacgtcaatgacggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
accccattgacgtcaatgggagtttgttttgactcaccaaaatcaacgggaattcccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgccaccagacataatagctgacagactaacagactgttcctttccatgggtcttttctgcagtcaccgtcgt
cgacacgtgtgatcagatatcgcggccgctctagagatatcgccaccatgaaaaccataattgcgctgtcctacatactgtgtctggtgtttgccc
agaaactgccgggcaatgacaactcaacagccacgctctgcttggggcaccatgccgtccctaacgggaccattgtgaaaaccattactaacga
tcagatagaggtgactaatgccaccgagctgggctccggcttgaaactggcgaccggtatgcgcaatgtccccgaaaaacagacccgcgggat
atttggggctatcgcaggcttatcgagaatggctgggaagggatggtggatggttggtatggttttagacatcaaaactccgaaggcagaggcc
aggctgccgatctcaagagcacgcaggccgctatagatcagatcaatggaaagctcaacagactgatcgggaaaaccggcggcgatcccgag
tgggaccgggagatcaacaactacaccagcatcatctacagcctgatcgaggagagccagaaccagcaggagaacggcaccggcggcggca
gcggcatcgtcagcagcagaacaacctgctgcggggccatcgaggcccagcagcacctgctgcagctgaccgtgtggggcatcaagcagctgc
agtcctacaatgccgagctgctggtggctctggagaatcagcacactattgacctgaccgattcagagatgaacaaacttttgagaagacgaa
gaagcagcttagagaaaatgcagaggacatggggaacggatgctttaaaatatatcataagtgtgataatgcctgcatcggatcaattagaaat
ggtacctatgatcacgatgtttacagggacgaagcgctgaataacaggttccagataaaaggctccggaggcgacatcatcaagctgctgaac
gagcaggtgaacaaggagatgcagagcagcaacctgtacatgagcatgagcagctggtgctacacccacagcctggacggcgccggcctgttc

Fig. 40-1 ctgttcgaccacgccgccgaggagtacgagcacgccaagaagctgatcatcttcctgaacgagaacaacgtgcccgtgcagctgaccagcatc
agcgcccccgagcacaagttcgagggcctgacccagatcttccagaaggcctacgagcacgagcagcacatcagcgagagcatcaacaacat
cgtggaccacgccatcaagagcaaggaccacgccaccttcaacttcctgcagtggtacgtggccgagcagcacgaggaggaggtgctgttcaa
ggacatcctggacaagatcgagctgatcggcaacgagaaccacgccctgtacctggccgaccagtacgtgaagggcatcgccaagagcagga
agagcggatcctagcatcatcatcatcatcattagtctgaagggcgaattgatccagctgtgccttctagttgccagccatctgttgtttgcccctcc
cccgtgccttccttgacccctggaaggtgccactcccactgtcctttcctaataaaatgaggaaattgcatcgcattgtctgagtaggtgtcattctat
tctggggggtggggtggggcaggacagcaaggggggaggattgggaagacaatagcaggcatgctggggatgcggtgggctctatgggtaccc
aggtgctgaagaattgacccggttcctcctgggccagaaagaagcaggcacatcccttctctgtgacacaccctgtccacgccoctggttcttag
ttccagccccactcataggacactcatagctcaggagggctccgccttcaatcccacccgctaaagtacttggagcggtctctccctccctcatca
gcccaccaaaccaaacctagcctccaagagtgggaagaaattaaagcaagataggctattaagtgcagagggagagaaaatgcctccaacat
gtgaggaagtaatgagagaaatcatagaattttaaggccatgatttaaggccatcatggccttaatcttccgcttcctcgctcactgactcgctgc
gctcggtcgttcggctgcggcgagcggtatcagctcactcaaaggcggtaatacggttatccacagaatcaggggataacgcaggaaagaaca
tgtgagcaaaaggccagcaaaaggccaggaaccgtaaaaaggccgcgttgctggcgtttttccataggctccgcccccctgacgagcatcaca
aaaatcgacgctcaagtcagaggtggcgaaacccgacaggactataaagataccaggcgtttccccctggaagctccctcgtgcgctctcctgtt
ccgaccctgccgcttaccggatacctgtccgcctttctcccttcgggaagcgtggcgctttctcatagctcacgctgtaggtatctcagttcggtgta
ggtcgttcgctccaagctgggctgtgtgcacgaaccccccgttcagcccgaccgctgcgccttatccggtaactatcgtcttgagtccaacccggt
aagacacgacttatcgccactggcagcagccactggtaacaggattagcagagcgaggtatgtaggcggtgctacagagttcttgaagtggtgg
cctaactacggctacactagaagaacagtatttggtatctgcgctctgctgaagccagttaccttcggaaaaagagttggtagctcttgatccggc
aaacaaaccaccgctggtagcggtggtttttttgtttgcaagcagcagattacgcgcagaaaaaaaggatctcaagaagatcctttgatcttttct
acggggtctgacgctcagtggaacgaaaactcacgttaagggattttggtcatgagattatcaaaaaggatcttcacctagatcctttaaattaa
aaatgaagttttaaatcaatctaaagtatatatgagtaaacttggtctgacagttaccaatgcttaatcagtgaggcacctatctcagcgatctgt
ctatttcgttcatccatagttgcctgactcgggggggggggggcgctgaggtctgcctcgtgaagaaggtgttgctgactcataccaggcctgaatc
gccccatcatccagccagaaagtgagggagccacggttgatgagagctttgttgtaggtggaccagttggtgattttgaacttttgctttgccacg
gaacggtctgcgttgtcgggaagatgcgtgatctgatccttcaactcagcaaaagttcgatttattcaacaaagccgccgtcccgtcaagtcagc
gtaatgctctgccagtgttacaaccaattaaccaattctgattagaaaaactcatcgagcatcaaatgaaactgcaatttattcatatcaggatta
tcaataccatattttgaaaaagccgtttctgtaatgaaggagaaaactcaccgaggcagttccataggatggcaagatcctggtatcggtctgc
gattccgactcgtccaacatcaatacaacctattaatttcccctcgtcaaaaataaggttatcaagtgagaaatcaccatgagtgacgactgaat
ccggtgagaatggcaaaagcttatgcatttctttccagacttgttcaacaggccagccattacgctcgtcatcaaaatcactcgcatcaaccaaac
cgttattcattcgtgattgcgcctgagcgagacgaaatacgcgatcgctgttaaaaggacaattacaaacaggaatcgaatgcaaccggcgcag
gaacactgccagcgcatcaacaatatttcacctgaatcaggatattcttaatacctggaatgctgtttccggggatcgcagtggtgagtaa
ccatgcatcatcaggagtacggataaaatgcttgatggtcggaagaggcataaattccgtcagccagtttagtctgaccatctcatctgtaacatc
attggcaacgctacctttgccatgtttcagaaacaactctggcgcatcgggcttcccatacaatcgatagattgtcgcacctgattgcccgacatta
tcgcgagcccatttatacccatataaatcagcatccatgttggaatttaatcgcggcctcgagcaagacgtttcccgttgaatatggctcataaca
ccccttgtattactgtttatgtaagcagacagttttattgttcatgatgatatattttatcttgtgcaatgtaacatcagagattttgagacacaacg
tggctttccccccccccccattattgaagcatttatcagggttattgtctcatgagcggatacatatttgaatgtatttagaaaaataaacaaatag
gggttccgcgcacatttccccgaaaagtgccacctgacgtctaagaaaccattattatcatgacattaacctataaaaataggcgtatcacgagg
ccctttcgtc
```

Fig. 40-2

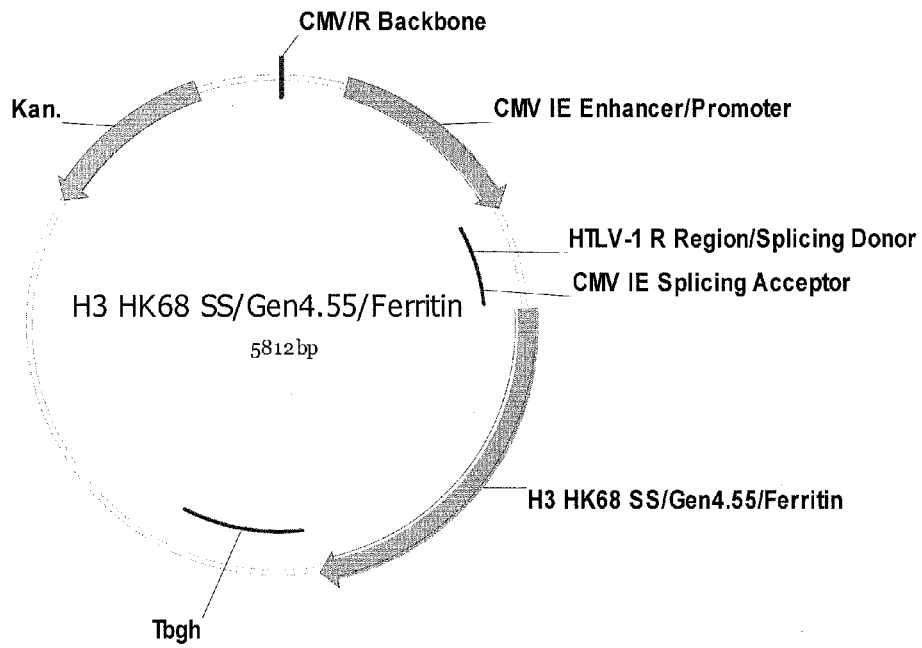

H3 HK SS/Gen4.55/ferritin (SEQ ID NO:157)
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgaccccgcccattgacgtcaataatgacgtatgt
tcccatagtaacgccaatagggactttccattgacgtcaatgggtggagtatttacggtaaactgcccacttggcagtacatcaagtgtatcatat
gccaagtacgccccctattgacgtcaatgacggtaaatggcccgcctggcattatgcccagtacatgaccttatgggactttcctacttggcagta
catctacgtattagtcatcgctattaccatggtgatgcggttttggcagtacatcaatgggcgtggatagcggtttgactcacggggatttccaagt
ctccacccccattgacgtcaatgggagtttgttttggcaccaaaatcaacgggactttccaaaatgtcgtaacaactccgccccattgacgcaaatg
ggcggtaggcgtgtacggtgggaggtctatataagcagagctcgtttagtgaaccgtcagatcgcctggagacgccatccacgctgttttgacct
ccatagaagacaccgggaccgatccagcctccatcggctcgcatctctccttcacgcgcccgccgccctacctgaggccgccatccacgccggtt
gagtcgcgttctgccgcctcccgcctgtggtgcctcctgaactgcgtccgccgtctaggtaagtttaaagctcaggtcgagaccgggcctttgtccg
gcgctcccttggagcctacctagactcagccggctctccacgctttgcctgaccctgcttgctcaactcagttaacggtggagggcagtgtagtct
gagcagtactcgttgctgccgcgcgccaccagacataatagctgacagactaacagactgttcctttccatgggtcttttctgcagtcaccgtc
gtcgacacgtgtgatcagatatcgcggccgctctagagatatcgccaccatgaagaccatcatcgccctgagctacatcttctgcctggccctggg
ccaggacctgcccggcaacgacaacagcaccgccaccctgtgcctgggccaccacgccgtgcccaacggcacccctggtgaagaccatcaccga
cgaccagatcgaggtgaccaacgccaccgagctgggctccggcctgaagctggccaccggcatgcggaacgtgcccgagaagcagacccggg
gcctgttcggcgccatcgccggcttcatcgagaacggctgggagggcatgatcgacggctggtacggcttccggcaccagaacagcgagggca
ccggccaggccgccgacctgaagagcacccaggccgccatcgaccagatcaacggcaagctgaaccggtgatcgagaagaccggcggcgat
cccgagtgggaccgggagatcaacaactacaccagcatcatctacagcctgatcgaggagagccagaaccagcaggagaacggcaccggcg
gcggcagcggcatcgtgcagcagcagaacaacctgctgcgggccatcgaggcccagcagcacctgctgcagctgaccgtgtggggcatcaagc
agctgcagagctacaacgccgagctgctggtggccctggagaaccagcacaccatcgacctgaccgacagcgagatgaacaagctgttcgaga
gacccggcggcagctgcgggagaacgccgaggacatgggcaacggctgcttcaagatctaccacaagtgcgacaacgcctgcatcgagagc
atccggaacggcacctacgaccacgacgtgtaccgggacgaggccctgaacaaccggttccagatcaagggctccggaggcgacatcatcaa
gctgctgaacgagcaggtgaacaaggagatgcagagcagcaacctgtacatgagcatgagcagctggtgctacacccacagcctggacggcg
ccggcctgttcctgttcgaccacgccgccgaggagtacgagcacgccaagaagctgatcatcttcctgaacgagaacaacgtgcccgtgcagct

Fig. 41-1

```
gaccagcatcagcgcccccgagcacaagttcgagggcctgacccagatcttccagaaggcctacgagcacgagcagcacatcagcgagagca
tcaacaacatcgtggaccacgccatcaagagcaaggaccacgccaccttcaacttcctgcagtggtacgtggccgagcagcacgaggaggagg
tgctgttcaaggacatcctggacaagatcgagctgatcggcaacgagaaccacggcctgtacctggccgaccagtacgtgaagggcatcgcca
agagcaggaagagcggatcctagcatcatcatcatcatcattagtctgaagggcgaattgatccagctgtgccttctagttgccagccatctgttg
tttgcccctcccccgtgccttccttgaccctggaaggtgccactcccactgtcctttcctaataaaatgaggaaattgcatcgcattgtctgagtagg
tgtcattctattctgggggggtggggtggggcaggacagcaaggggggaggattgggaagacaatagcaggcatgctgggggatgcggtgggctct
atgggtacccaggtgctgaagaattgacccggttcctcctgggccagaaagaagcaggcacatcccttctctgtgacacaccctgtccacgccc
ctggttcttagttccagccccactcataggacactcatagctcaggagggctccgccttcaatcccacccgctaaagtacttggagcggtctctccc
tccctcatcagcccaccaaaccaaacctagcctccaagagtgggaagaaattaaagcaagataggctattaagtgcagagggagagaaaatg
cctccaacatgtgaggaagtaatgagagaaatcatagaattttaaggccatgatttaaggccatcatggccttaatcttccgcttcctcgctcact
gactcgctgcgctcggtcgttcggctgcggcagcggtatcagctcactcaaaggcggtaatacggttatccacagaatcagggqataacgcag
gaaagaacatgtgagcaaaaggccagcaaaaggccaggaaccgtaaaaaggccgcgttgctggcgtttttccataggctccgcccccctgacg
agcatcacaaaaatcgacgctcaagtcagaggtggcgaaacccgacaggactataaagataccaggcgtttccccctggaagctccctcgtgc
gctctcctgttccgaccctgccgcttaccggatacctgtccgcctttctcccttcgggaagcgtggcgctttctcatagctcacgctgtaggtatctc
agttcggtgtaggtcgttcgctccaagctgggctgtgtgcacgaaccccccgttcagcccgaccgctgcgccttatccggtaactatcgtcttgagt
ccaacccggtaagacacgacttatcgccactggcagcagccactggtaacaggattagcagagcgaggtatgtaggcggtgctacagagttctt
gaagtggtggcctaactacggctacactagaagaacagtatttggtatctgcgctctgctgaagccagttaccttcggaaaaagagttggtagct
cttgatccggcaaacaaaccaccgctggtagcggtggtttttttgtttgcaagcagcagattacgcgcagaaaaaaaggatctcaagaagatcct
ttgatcttttctacggggtctgacgctcagtggaacgaaaactcacgttaagggattttggtcatgagattatcaaaaaggatcttcacctagatc
cttttaaattaaaaatgaagttttaaatcaatctaaagtatatatgagtaaacttggtctgacagttaccaatgcttaatcagtgaggcacctatct
cagcgatctgtctatttcgttcatccatagttgcctgactcgggggggggggggcgctgaggtctgcctcgtgaagaaggtgttgctgactcatacc
aggcctgaatcgccccatcatccagccagaaagtgagggagccacggttgatgagagctttgttgtaggtggaccagttggtgattttgaacttt
gctttgccacggaacggtctgcgttgtcggaagatgcgtgatctgatccttcaactcagcaaaagttcgatttattcaacaaagccgccgtcccg
tcaagtcagcgtaatgctctgccagtgttacaaccaattaaccaattctgattagaaaaactcatcgagcatcaaatgaaactgcaatttattcat
atcaggattatcaataccatattttgaaaaagccgtttctgtaatgaaggagaaaactcaccgaggcagttccataggatggcaagatcctggt
atcggtctgcgattccgactcgtccaacatcaatcaacctattaatttcccctcgtcaaaaataaggttatcaagtgagaaatcaccatgagtga
cgactgaatccggtgagaatggcaaaagcttatgcatttctttccagacttgttcaacaggccagccattacgctcgtcatcaaaatcactcgcat
caaccaaaccgttattcattcgtgattgcgcctgagcgagacgaaatacgcgatcgctgttaaaaggacaattacaaacaggaatcgaatgcaa
ccggcgcaggaacactgccagcgcatcaacaatattttcacctgaatcaggatattcttctaatacctggaatgctgttttcccggggatcgcagt
ggtgagtaaccatgcatcatcaggagtacggataaaatgcttgatggtcggaagaggcataaattccgtcagccagtttagtctgaccatctcat
ctgtaacatcattggcaacgctaccttgccatgtttcagaaacaactctggcgcatcgggcttcccatacaatcgatagattgtcgcacctgattg
cccgacattatcgcgagcccatttatacccatataaatcagcatccatgttggaatttaatcgcggcctcgagcaagacgtttcccgttgaatatg
gctcataacacccccttgtattactgtttatgtaagcagacagtttttattgttcatgatgatatatttttatcttgtgcaatgtaacatcagagattttga
gacacaacgtggctttccccccccccccattattgaagcatttatcagggttattgtctcatgagcggatacatatttgaatgtatttagaaaaata
aacaaatagggggttccgcgcacatttccccgaaaagtgccacctgacgtctaagaaaccattattatcatgacattaacctataaaaataggcgt
atcacgaggcccttttcgtc
```

Fig. 41-2

CMV/R 8kb Influenza A/New Caledonia/20/99 foldon-his AY289929

Kan.

CMV IE Enhancer/Promoter 8kb

HTLV-1 R Region/Splicing Donor
CMV IE Splicing Acceptor

H5 INDO SS/Gen4.55/Ferr
5789 bp

H5 INDO SS/Gen4.55/Ferritin

Tbgh

H5 Indo SS/Gen4.55/ferritin   (SEQ ID NO:158)
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgcccccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
acccccattgacgtcaatgggagtttgttttgactcaccaaaatcaacgggaattcccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgcgccaccagacataatagctgacagactaacagactgttcctttccatgggtcttttctgcagtcaccgtcgt
cgacacgtgtgatcagatatcgcggccgctctagagatatcgccaccatggagaagatcgtgctgctgctggccatcgtgagcctggtgaagag
cgaccagatctgcatcggctaccacgccaacaacagcaccgagcaggtggacaccatcatggagaagaacgtgaccgtgacccacgcccagg
acatcggctccggcctggtgctggccaccggcctgcggaacagcccccagcggagagccggcggaagaagcggggcctgttcggcgccatcg
ccggcttcatcgagggcggctggcagggcatggtggacggctggtacggctaccaccacagcaacgagcagggcagcggctacgccgccgac
aaggagagcacccagaaggccatcgacggcgtgaccaacaaggtgaacagcatcatcgacaagatgggcggcgatcccgagtgggaccggg
agatcaacaactacaccagcatcatctacagcctgatcgaggagagccagaaccagcaggagaacggcaccggcggcggcagcggcatcgtg
cagcagcagaacaacctgctgcgggccatcgaggcccagcagcacctgctgcagctgaccgtgtggggcatcaagcagctgcagacctacaac
gccgagctgctggtgctgatggagaacgagcggacccctggacttccacgacagcaacgtgaagaacctgtacgacaaggtgcggctgcagctg
cgggacaacgccaaggagctgggcaacggctgcttcgagttctaccacaagtgcgacaacgagtgcatggagagcatccggaacggcaccta
caactaccccagtacagcgaggagcccggctgaagcgggaggagatcagctccggaggcgacatcatcaagctgctgaacgagcaggtga
acaaggagatgcagagcagcaacctgtacatgagcatgagcagctggtgctacacccacagcctggacggcgccggcctgttcctgttcgacca
cgccgccgaggagtacgagcacgccaagaagctgatcatcttcctgaacgagaacaacgtgcccgtgcagctgaccagcatcagcgcccccga
gcacaagttcgagggcctgacccagatcttccagaaggcctacgagcacgagcagcacatcagcgagagcatcaacaacatcgtggaccacg
ccatcaagagcaaggaccacgccaccttcaacttcctgcagtggtacgtggccgagcagcacgaggaggaggtgctgttcaaggacatcctgg

Fig. 42-1

```
acaagatcgagctgatcggcaacgagaaccacggcctgtacctggccgaccagtacgtgaagggcatcgccaagagcaggaagagcggatcc
tagcatcatcatcatcatcattagtctgaagggcgaattgatccagctgtgccttctagttgccagccatctgttgtttgcccctcccccgtgccttcc
ttgaccctggaaggtgccactcccactgtcctttcctaataaaatgaggaaattgcatcgcattgtctgagtaggtgtcattctattctgggggtg
gggtggggcaggacagcaagggggaggattgggaagacaatagcaggcatgctgggatgcggtgggctctatgggtacccaggtgctgaag
aattgacccggttcctcctgggccagaaagaagcaggcacatccccttctctgtgacacaccctgtccacgcccctggttcttagttccagcccca
ctcataggacactcatagctcaggagggctccgccttcaatcccacccgctaaagtacttggagcggtctctccctccctcatcagcccaccaaac
caaacctagcctccaagagtgggaagaaattaaagcaagataggctattaagtgcagagggagagaaaatgcctccaacatgtgaggaagta
atgagagaaatcatagaattttaaggccatgatttaaggccatcatggccttaatcttccgcttcctcgctcactgactcgctgcgctcggtcgttc
ggctgcggcgagcggtatcagctcactcaaaggcggtaatacggttatccacagaatcaggggataacgcaggaaagaacatgtgagcaaaa
ggccagcaaaaggccaggaaccgtaaaaaggccgcgttgctggcgtttttccataggctccgcccccctgacgagcatcacaaaaatcgacgct
caagtcagaggtggcgaaacccgacaggactataaagataccaggcgtttccccctggaagctccctcgtgcgctctcctgttccgaccctgccg
cttaccggatacctgtccgcctttctcccttcgggaagcgtggcgctttctcatagctcacgctgtaggtatctcagttcggtgtaggtcgttcgctcc
aagctgggctgtgtgcacgaaccccccgttcagcccgaccgctgcgccttatccggtaactatcgtcttgagtccaacccggtaagacacgactt
atcgccactggcagcagccactggtaacaggattagcagagcgaggtatgtaggcggtgctacagagttcttgaagtggtggcctaactacggc
tacactagaagaacagtatttggtatctgcgctctgctgaagccagttaccttcggaaaaagagttggtagctcttgatccggcaaacaaaccac
cgctggtagcggtggtttttttgtttgcaagcagcagattacgcgcagaaaaaaaggatctcaagaagatcctttgatcttttctacggggtctga
cgctcagtggaacgaaaactcacgttaagggattttggtcatgagattatcaaaaaggatcttcacctagatccttttaaattaaaaatgaagttt
taaatcaatctaaagtatatatgagtaaacttggtctgacagttaccaatgcttaatcagtgaggcacctatctcagcgatctgtctatttcgttcat
ccatagttgcctgactcggggggggggggcgctgaggtctgcctcgtgaagaaggtgttgctgactcataccaggcctgaatcgccccatcatcc
agccagaaagtgagggagccacggttgatgagagctttgttgtaggtggaccagttggtgattttgaacttttgctttgccacggaacggtctgcg
ttgtcgggaagatgcgtgatctgatccttcaactcagcaaaagttcgatttattcaacaaagccgccgtcccgtcaagtcagcgtaatgctctgcc
agtgttacaaccaattaaccaattctgattagaaaaactcatcgagcatcaaatgaaactgcaatttattcatatcaggattatcaataccatatt
tttgaaaaagccgtttctgtaatgaaggagaaaactcaccgaggcagttccataggatggcaagatcctggtatcggtctgcgattccgactcgt
ccaacatcaatacaacctattaatttcccctcgtcaaaaataaggttatcaagtgagaaatcaccatgagtgacgactgaatccggtgagaatgg
caaaagcttatgcatttctttccagacttgttcaacaggccagccattacgctcgtcatcaaaatcactcgcatcaaccaaaccgttattcattcgt
gattgcgcctgagcgagacgaaatacgcgatcgctgttaaaaggacaattacaaacaggaatcgaatgcaaccggcgcaggaacactgccag
cgcatcaacaatattttcacctgaatcaggatattcttctaatacctggaatgctgttttcccggggatcgcagtggtgagtaaccatgcatcatca
ggagtacggataaaatgcttgatggtcggaagaggcataaattccgtcagccagtttagtctgaccatctcatctgtaacatcattggcaacgct
acctttgccatgtttcagaaacaactctggcgcatcgggcttcccatacaatcgatagattgtcgcacctgattgcccgacattatcgcgagcccat
ttatacccatataaatcagcatccatgttggaatttaatcgcggcctcgagcaagacgtttcccgttgaatatggctcataacaccccttgtattac
tgtttatgtaagcagacagttttattgttcatgatgatatatttttatcttgtgcaatgtaacatcagagattttgagacacaacgtggctttccccc
cccccattattgaagcatttatcagggttattgtctcatgagcggatacatatttgaatgtatttagaaaaataaacaatagggggttccgcgca
catttccccgaaaagtgccacctgacgtctaagaaaccattattatcatgacattaacctataaaaataggcgtatcacgaggccctttcgtc
```

Fig. 42-2

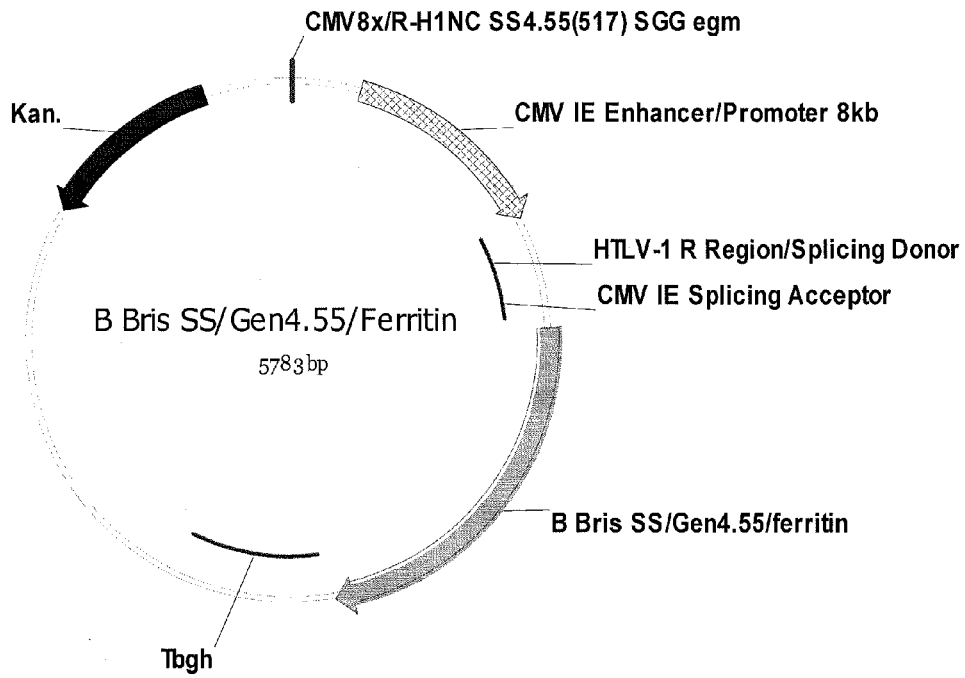

B Bris SS/Gen4.55/ferritin    (SEQ ID NO:159)
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgcccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
accccattgacgtcaatgggagtttgttttgactcaccaaaatcaacgggaattcccaaaatgtcgtaacaactccgccccattgacgcaaatgg
gcggtaggcgtgtacggtgggaggtctatataagcagagctcgtttagtgaaccgtcagatcgcctggagacgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgcgccaccagacataatagctgacagactaacagactgttccttttccatgggtcttttctgcagtcaccgtcgt
cgacacgtgtgatcagatatcgcggccgctctagagatatcgccaccatgaaggccatcatcgtgctgctgatggtggtcacaagcaacgccga
tagaatctgtaccggcatcaccagcagcaatagccctcacgtcgtgaaaacagctacacagggcgaagtgaatgtgaccggcgtgatccctctg
ggatcaggactgaagctggccaatggcacaaagtatagacctccagccaagctgctgaaagagagaggcttttttggagctatcgccggctttct
ggaaggcggatgggagggaatgattgctggatggcatggctacacatctcatggcgcacatggcgtggcagtggctgctgatctgaaatctaca
caggaagccatcaacaagatcaccaagaacctgaacagcctgagcgagctggaaggaggcgaccccgagtgggatcgcgaaatcaacaact
acacatctatcatctacagtctgattgaggaaagccagaaccagcaggagaatgggactggggaggctccggaatcgtgcagcagcagaac
aatctgctgcgagccattgaagctcagcagcacctgctgcagctgacagtgtggggcatcaagcagctgcaggggagccagattgaactggctg
tgctgctgtctaacgagggcatcatcaatagcgaggacgaacatctgctggccctggaaagaaagctgaagaagatgctgggacctagcgccg
tggaaatcggcaatggatgctttgagacaaagcacaagtgcaaccagacctgcctggatagaattgccgccggaacatttgatgccggcgagtt
ttctctgcccaccttcgatagcctgaatatcacatccggaggcgacatcatcaagctgctgaacgagcaggtgaacaaggagatgcagagcagc
aacctgtacatgagcatgagcagctggtgctacacccacagcctggacggcgccggcctgttcctgttcgaccacgccgccgaggagtacgagc

Fig. 43-1 acgccaagaagctgatcatcttcctgaacgagaacaacgtgcccgtgcagctgaccagcatcagcgcccccgagcacaagttcgagggcctga
cccagatcttccagaaggcctacgagcacgagcagcacatcagcgagagcatcaacaacatcgtggaccacgccatcaagagcaaggaccac
gccaccttcaacttcctgcagtggtacgtggccgagcagcacgaggaggaggtgctgttcaaggacatcctggacaagatcgagctgatcggca
acgagaaccacgacctgtacctggccgaccagtacgtgaagggcatcgccaagagcaggaagagcggatcctagtagcatcatcatcatcatc
attagtctgaagggcgaattgatccagctgtgccttctagttgccagccatctgttgtttgcccctccccgtgccttccttgaccctggaaggtgcc
actcccactgtcctttcctaataaaatgaggaaattgcatcgcattgtctgagtaggtgtcattctattctgggggtggggtggggcaggacagc
aaggggggaggattgggaagacaatagcaggcatgctggggatgcggtgggctctatgggtacccaggtgctgaagaattgacccggttcctcct
gggccagaaagaagcaggcacatcccttctctgtgacacaccctgtccacgccccctggttcttagttccagccccactcataggacactcatag
ctcaggagggctccgccttcaatcccacccgctaaagtacttggagcggtctctccctccctcatcagcccaccaaaccaaacctagcctccaag
agtgggaagaaattaaagcaagataggctattaagtgcagagggagagaaaatgcctccaacatgtgaggaagtaatgagagaaatcatag
aattttaaggccatgatttaaggccatcatggccttaatcttccgcttcctcgctcactgactcgctgcgctcggtcgttcggctgcggcgagcggt
atcagctcactcaaaggcggtaatacggttatccacagaatcaggggataacgcaggaaagaacatgtgagcaaaaggccagcaaaaggcca
ggaaccgtaaaaaggccgcgttgctggcgtttttccataggctccgccccctgacgagcatcacaaaaatcgacgctcaagtcagaggtggcg
aaacccgacaggactataaagataccaggcgtttccccctggaagctccctcgtgcgctctcctgttccgaccctgccgcttaccggatacctgtc
cgccttctcccttcgggaagcgtggcgctttctcatagctcacgctgtaggtatctcagttcggtgtaggtcgttcgctccaagctgggctgtgtgc
acgaacccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactagaagaacag
tatttggtatctgcgctctgctgaagccagttaccttcggaaaaagagttggtagctcttgatccggcaaacaaaccaccgctggtagcggtggtt
tttttgtttgcaagcagcagattacgcgcagaaaaaaaggatctcaagaagatcctttgatcttttctacggggtctgacgctcagtggaacgaa
aactcacgttaagggattttggtcatgagattatcaaaaaggatcttcacctagatccttttaaattaaaaatgaagttttaaatcaatctaaagta
tatatgagtaaacttggtctgacagttaccaatgcttaatcagtgaggcacctatctcagcgatctgtctatttcgttcatccatagttgcctgactc
ggggggggggggcgctgaggtctgcctcgtgaagaaggtgttgctgactcataccaggcctgaatcgccccatcatccagccagaaagtgagg
gagccacggttgatgagagctttgttgtaggtggaccagttggtgattttgaacttttgctttgccacggaacggtctgcgttgtcgggaagatgcg
tgatctgatccttcaactcagcaaaagttcgatttattcaacaaagccgccgtcccgtcaagtcagcgtaatgctctgccagtgttacaaccaatt
aaccaattctgattagaaaaactcatcgagcatcaaatgaaactgcaatttattcatatcaggattatcaataccatatttttgaaaaagccgttt
ctgtaatgaaggagaaaactcaccgaggcagttccataggatggcaagatcctggtatcggtctgcgattccgactcgtccaacatcaatacaa
cctattaatttccctcgtcaaaaataaggttatcaagtgagaaatcaccatgagtgacgactgaatccggtgagaatggcaaaagcttatgcat
ttctttccagacttgttcaacaggccagccattacgctcgtcatcaaaatcactcgcatcaaccaaaccgttattcattcgtgattgcgcctgagcg
agacgaaatacgcgatcgctgttaaaaggacaattacaaacaggaatcgaatgcaaccggcgcaggaacactgccagcgcatcaacaatattt
tcacctgaatcaggatattcttctaatacctggaatgctgttttcccggggatcgcagtggtgagtaaccatgcatcatcaggagtacggataaaa
tgcttgatggtcggaagaggcataaattccgtcagccagtttagtctgaccatctcatctgtaacatcattggcaacgctacctttgccatgtttca
gaaacaactctggcgcatcgggcttcccatacaatcgatagattgtcgcacctgattgcccgacattatcgcgagcccatttatacccatataaat
cagcatccatgttgaatttaatcgcggcctcgagcaagacgtttcccgttgaatatggctcataacaccccttgtattactgtttatgtaagcaga
cagttttattgttcatgatgatatattttttatcttgtgcaatgtaacatcagagattttgagacacaacgtggctttcccccccccccccattattgaag
catttatcagggttattgtctcatgagcggatacatatttgaatgtatttagaaaaataaacaaatagggggttccgcgcacatttccccgaaaagt
gccacctgacgtctaagaaaccattattatcatgacattaacctataaaaataggcgtatcacgaggccctttcgtc

Fig. 43-2

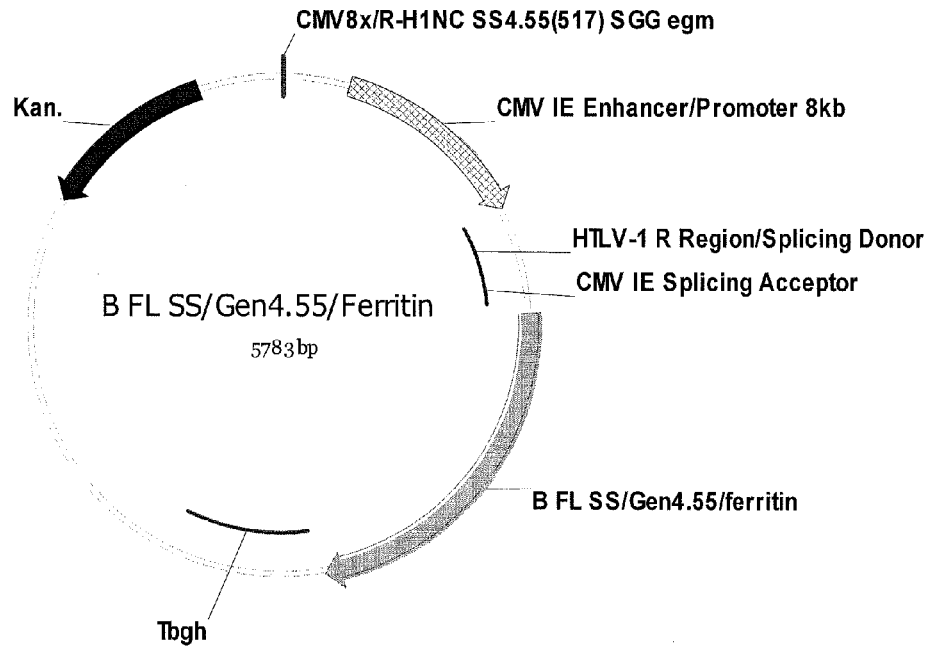

B FL SS/Gen4.55/ferritin (SEQ ID NO:160)
tcgcgcgtttcggtgatgacggtgaaaacctctgacacatgcagctcccggagacggtcacagcttgtctgtaagcggatgccgggagcagaca
agcccgtcagggcgcgtcagcgggtgttggcgggtgtcggggctggcttaactatgcggcatcagagcagattgtactgagagtgcaccatatg
cggtgtgaaataccgcacagatgcgtaaggagaaaataccgcatcagattggctattggccattgcatacgttgtatccatatcataatatgtac
atttatattggctcatgtccaacattaccgccatgttgacattgattattgactagttattaatagtaatcaattacgggaacttccatagcccatat
atggagttccgcgttacataacttacgggaatttccaaacctggctgaccgcccaacgaccccgcccattgacgtcaataatgacgtatgttccc
atagtaacgccaatagggaacttccattgacgtcaatgggtggagtatttacggtaaactgcccacttgggaatttccaagtgtatcatatgccaa
gtacgccccctattgacgtcaatgacgggaacttccataagcttgcattatgcccagtacatgaccttatgggaatttcctacttggcagtacatct
acgtattagtcatcgctattaccatggtgatgcggttttggcagtacatcaatgggcgtggatagcggtttgactcacgggaacttccaagtctcc
accccattgacgtcaatgggagtttgttttgactcaccaaaatcaacgggaattcccaaaatgtcgtaacaactccgccccattgacgcaaatgg
gcggtaggcgtgtacggtgggaggtctatataagcagagctcgtttagtgaaccgtcagatcgcctggagagcgccatccacgctgttttgacctc
catagaagacaccgggaccgatccagcctccatcggctcgcatctctccttcacgcgcccgccgccctacctgaggccgccatccacgccggttg
agtcgcgttctgccgcctcccgcctgtggtgcctcctgaactgcgtccgccgtctaggtaagtttaaagctcaggtcgagaccgggcctttgtccgg
cgctcccttggagcctacctagactcagccggctctccacgctttgcctgaccctgcttgctcaactctagttaacggtggagggcagtgtagtctg
agcagtactcgttgctgccgcgcgccaccagacataatagctgacagactaacagactgttcctttccatgggtcttttctgcagtcaccgtcgt
cgacacgtgtgatcagatatcgcggccgctctagagatatcgccaccatgaaggccatcatcgtgctgctgatggtggtgaccagcaacgccgat
agaatctgcaccggcatcaccagcagcaatagcccccatgtggtgaaaacagccacccagggcgaagtgaatgtgacaggcgtgatccctctg
ggatcaggactgaagctggccaatggcaccaagtacgacctcccgccaagctgctgaaagagagaggcttctttggcgccattgccggatttc
tggaaggcggctgggagggaatgattgccggctggcacggctatacatctcatggggcccatggcgtggctgtggccgccgatctgaagtctac
ccaggaagccatcaacaagatcaccaagaacctgaacagcctgagcgagctggaaggaggcgaccccgagtgggatcgcgaaatcaacaac
tacacatctatcatctacagtctgattgaggaaagccagaaccagcaggagaatgggactgggggaggctccggaatcgtgcagcagcagaac
aatctgctgcgagccattgaagctcagcagcacctgctgcagctgacagtgtggggcatcaagcagctgcaggggtcccagattgaactggccg
tgctgctgtccaacgagggcatcatcaacagcgaggatgaacacctgctggccctggaacggaagctgaagaagatgctgggccccttctgccgt
ggagatcggcaacggctgcttcgagacaaagcacaagtgcaaccagacctgcctggatagaatcgccgctggccaccttcaatgccggcgagtt
cagcctgcctaccttcgacagcctgaatatcacctccggaggcgacatcatcaagctgctgaacgagcaggtgaacaaggagatgcagagcag
caacctgtacatgagcatgagcagctggtgctacacccacagcctggacggcgccggcctgttcctgttcgaccacgccgccgaggagtacgag
cacgccaagaagctgatcatcttcctgaacgagaacaacgtgcccgtgcagctgaccagcatcagcgcccccgagcacaagttcgagggcctg

Fig. 44-1

```
acccagatcttccagaaggcctacgagcacgagcagcacatcagcgagagcatcaacaacatcgtggaccacgccatcaagagcaaggacca
cgccaccttcaacttcctgcagtggtacgtggccgagcagcacgaggaggaggtgctgttcaaggacatcctggacaagatcgagctgatcggc
aacgagaaccacggcctgtacctggccgaccagtacgtgaagggcatcgccaagagcaggaagagcggatcctagtagcatcatcatcatcat
cattagtctgaagggcgaattgatccagctgtgccttcagttgccagccatctgttgtttgcccctcccccgtgccttccttgaccctggaaggtgc
cactcccactgtcctttcctaataaaatgaggaaattgcatcgcattgtctgagtaggtgtcattctattctggggggtggggtggggcaggacag
caaggggaggattgggaagacaatagcaggcatgctggggatgcggtgggctctatgggtacccaggtgctgaagaattgacccggttcctc
ctgggccagaaagaagcaggcacatcccccttctctgtgacacaccctgtccacgccccctggttcttagttccagccccactcataggacactcata
gctcaggagggctccgccttcaatcccacccgctaaagtacttggagcggtctctccctccctcatcagcccaccaaaccaaacctagcctccaa
gagtgggaagaaattaaagcaagataggctattaagtgcagagggagagaaaatgcctccaacatgtgaggaagtaatgagagaaatcatag
aattttaaggccatgatttaaggccatcatggccttaatcttccgcttcctcgctcactgactcgctgcgctcggtcgttcggctgcggcgagcggt
atcagctcactcaaaggcggtaatacggttatccacagaatcaggggataacgcaggaaagaacatgtgagcaaaaggccagcaaaaggcca
ggaaccgtaaaaaggccgcgttgctggcgtttttccataggctccgcccccctgacgagcatcacaaaaatcgacgctcaagtcagaggtggcg
aaacccgacaggactataaagataccaggcgtttccccctggaagctccctcgtgcgctctcctgttccgaccctgccgcttaccggatacctgtc
cgcctttctcccttcgggaagcgtggcgctttctcatagctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactagaagaacag
tatttggtatctgcgctctgctgaagccagttaccttcggaaaaagagttggtagctcttgatccggcaaacaaaccaccgctggtagcggtggtt
tttttgtttgcaagcagcagattacgcgcagaaaaaaaggatctcaagaagatcctttgatcttttctacggggtctgacgctcagtggaacgaa
aactcacgttaagggattttggtcatgagattatcaaaaaggatcttcacctagatccttttaaattaaaaatgaagttttaaatcaatctaaagta
tatatgagtaaacttggtctgacagttaccaatgcttaatcagtgaggcacctatctcagcgatctgtctatttcgttcatccatagttgcctgactc
ggggggggggggcgctgaggtctgcctcgtgaagaaggtgttgctgactcataccaggcctgaatcgccccatcatccagccagaaagtgagg
gagccacggttgatgagagctttgttgtaggtggaccagttggtgattttgaacttttgctttgccacggaacggtctgcgttgtcgggaagatgcg
tgatctgatccttcaactcagcaaaagttcgatttattcaacaaagccgccgtcccgtcaagtcagcgtaatgctctgccagtgttacaaccaatt
aaccaattctgattagaaaaactcatcgagcatcaaatgaaactgcaatttattcatatcaggattatcaataccatatttttgaaaaagccgttt
ctgtaatgaaggagaaaactcaccgaggcagttccataggatggcaagatcctggtatcggtctgcgattccgactcgtccaacatcaatacaa
cctattaatttcccctcgtcaaaaataaggttatcaagtgagaaatcaccatgagtgacgactgaatccggtgagaatggcaaaagcttatgcat
ttctttccagacttgttcaacaggccagccattacgctcgtcatcaaaatcactcgcatcaaccaaaccgttattcattcgtgattgcgcctgagcg
agacgaaatacgcgatcgctgttaaaaggacaattacaaacaggaatcgaatgcaaccggcgcaggaacactgccagcgcatcaacaatattt
tcacctgaatcaggatattcttctaatacctggaatgctgtttcccggggatcgcagtggtgagtaaccatgcatcatcaggagtacggataaaa
tgcttgatggtcggaagaggcataaattccgtcagccagtttagtctgaccatctcatctgtaacatcattggcaacgctacctttgccatgtttca
gaaacaactctggcgcatcgggcttcccatacaatcgatagattgtcgcacctgattgcccgacattatcgcgagcccatttataccatataaat
cagcatccatgttggaatttaatcgcggcctcgagcaagacgtttcccgttgaatatggctcataacacccttgtattactgtttatgtaagcaga
cagttttattgttcatgatgatatattttatcttgtgcaatgtaacatcagagattttgagacacaacgtggctttcccccccccccccattattgaag
catttatcagggttattgtctcatgagcggatacatatttgaatgtatttagaaaaataaacaatagggggttccgcgcacatttccccgaaaagt
gccacctgacgtctaagaaaccattattcatgacattaacctataaaaataggcgtatcacgaggccctttcgtc
```

Fig. 44-2

INFLUENZA HEMAGGLUTININ PROTEIN-BASED VACCINES

CROSS REFERENCE TO RELATED APPLICATIONS

This application is a national stage application under 35 U.S.C. 371 and claims the benefit of PCT Application No. PCT/US2012/056822 having an international filing date of Sep. 24, 2012, which designated the United States, which PCT application claimed the benefit of U.S. Provisional Application No. 61/538,663 filed Sep. 23, 2011, and U.S. Provisional Application No. 61/661,209 filed Jun. 18, 2012, the disclosure of each of which are incorporated herein by reference.

REFERENCE TO SEQUENCE LISTING

This application contains a Sequence Listing submitted as an electronic text file named "6137NIAID-26-C1-PCT_sequence_listing_ST25.txt", having a size in bytes of 338 KB, and created on Sep. 21, 2012. The information contained in this electronic file is hereby incorporated by reference in its entirety pursuant to 37 CFR §1.52(e)(5).

SUMMARY OF THE INVENTION

The present invention provides novel hemagglutinin protein-based influenza vaccines that are easily manufactured, potent, and which elicit broadly neutralizing influenza antibodies. In particular, the present invention provides influenza hemagglutinin proteins, and portions thereof, that are useful in inducing the production of neutralizing antibodies. It also provides novel HA-ferritin nanoparticle (np) vaccines. Such nanoparticles comprise fusion proteins, each of which comprises a monomeric subunit of ferritin joined to an immunogenic portion of an influenza hemagglutinin protein. Because such nanoparticles display influenza hemagglutinin protein on their surface, they can be used to vaccinate an individual against influenza virus.

In one embodiment, the invention is a nanoparticle that comprises a fusion protein, and in this embodiment the fusion protein comprises at least 25 contiguous amino acids from a monomeric ferritin subunit protein joined to a first influenza hemagglutinin (HA) protein, such that the nanoparticle comprises influenza virus HA protein trimers on its surface. The nanoparticle can form an octahedron, which can consist of 24 subunits having 432 symmetry. Further, the monomeric ferritin subunit protein can be selected from a bacterial ferritin, a plant ferritin, an algal ferritin, an insect ferritin, a fungal ferritin and a mammalian ferritin, and in a preferred embodiment, is a *Helicobacter pylori* ferritin protein.

In this embodiment, the monomeric ferritin subunit protein can comprise at least 25 contiguous amino acids of an amino acid sequence selected from SEQ ID NO:2 and SEQ ID NO:5 or can comprise an amino acid at least about 80% identical, at least about 85% identical, at least about 90% identical, at least about 95% identical, at least about 97% identical, at least about 99% identical to those sequences or can comprise those sequences. In another embodiment, the monomeric subunit comprises a region corresponding to amino acids 5-167 of SEQ ID NO:2.

In this embodiment, the hemagglutinin protein can comprise at least 25 contiguous amino acids from the hemagglutinin protein of an influenza virus selected from A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). Also, the hemagglutinin protein can comprise an amino acid sequence that is selected from the amino acid sequences of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 or one that is at least 80% identical, at least about 85% identical, at least about 90% identical, at least about 95% identical, at least about 97% identical, at least about 99% identical thereto. Alternatively, the hemagglutinin protein can comprise an amino acid sequence that is selected from the amino acid sequences of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98 or one that is at least 80% identical, at least about 85% identical, at least about 90% identical, at least about 95% identical, at least about 97% identical, at least about 99% identical thereto.

In this embodiment, the hemagglutinin protein can be capable of eliciting an immune response to a protein comprising an amino acid sequence selected from SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 or it can comprise a region selected from a region capable of allowing formation of a hemagglutinin trimer, a stem region, an ectodomain, and a region comprising the amino acid sequence from the amino acid residue immediately distal to the last amino acid of the second helical coiled coil to the amino acid residue proximal to the first amino acid of the transmembrane domain.

The hemagglutinin protein can also comprise a hemagglutinin spike domain, a region corresponding to amino acids 1-519 of SEQ ID NO:8 or an amino acid sequence selected from the group consisting of amino acids 1-519 of SEQ ID NO:8 and SEQ ID NO:11.

In this embodiment, the fusion protein can comprise a linker sequence.

In this embodiment, the nanoparticle can elicit an immune response against a stem region of influenza hemagglutinin, a spike of influenza hemagglutinin, an influenza virus strain that is heterologous to the strain influenza virus from which the hemagglutinin protein was obtained or an influenza virus that is antigenically divergent from the influenza virus from which the hemagglutinin protein was obtained.

In this embodiment, the fusion protein can comprise an amino acid sequence at least about 80% identical, at least about 85% identical, at least about 90% identical, at least about 95% identical, at least about 97% identical, at least about 99% identical to a sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68, wherein the nanoparticle elicits an immune response against an influenza virus or can comprise an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. The fusion protein can also comprise an amino acid sequence at least 80% identical, at least about 85% identical, at least about 90% identical, at least about 95% identical, at least about 97% identical, at least about 99% identical to a sequence selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128, wherein the nanoparticle elicits an immune response against an influenza virus.

In this embodiment, the nanoparticle can comprise a second fusion protein comprising a second influenza hemagglutinin protein, wherein the first and second influenza hemagglutinin proteins are from different Types, from different sub-types or different strains of influenza viruses.

Another embodiment of the present invention is a vaccine composition comprising any of the foregoing nanoparticle. The vaccine composition can further comprise at least one additional nanoparticle that comprises at least one hemagglutinin protein from a different strain of influenza than the first hemagglutinin protein and the second hemagglutinin protein.

A further embodiment of the invention is a method to produce a vaccine against influenza virus. The method includes expressing a fusion protein comprising a monomeric ferritin protein joined to an influenza hemagglutinin protein under conditions such that the fusion proteins form a nanoparticle displaying hemagglutinin trimers on its surface and recovering the nanoparticle.

The invention also includes a method to vaccinate an individual against influenza that includes administering a nanoparticle to an individual such that the nanoparticle elicits an immune response against influenza virus. In this embodiment, the nanoparticle comprises a monomeric subunit of ferritin joined to an influenza hemagglutinin protein and the nanoparticle displays influenza hemagglutinin trimers on its surface. In this embodiment, the nanoparticle can elicit an immune response to an influenza virus strain that is heterologous to the sub-type or strain of or that is antigenically divergent from the influenza virus from which the hemagglutinin protein was obtained.

This method can further include administering to the individual a first vaccine composition and then at a later time, administering a second vaccine composition comprising a nanoparticle that comprises an HA-SS-ferritin fusion protein. The HA SS-ferritin fusion protein can comprise an amino acid sequence selected from SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98 or one that is at least 80% identical, at least 85% identical, at least 90% identical, at least 95% identical, at least 97% identical or at least 99% identical thereto, wherein the HA SS-ferritin fusion protein elicits an immune response to an influenza virus. The HA SS-ferritin fusion protein can comprise an amino acid sequence selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128, or one at least 80% identical, at least 85% identical, at least 90% identical, at least 95% identical, at least 97% identical or at least 99% identical thereto, wherein the HA SS-ferritin fusion protein elicits an immune response to an influenza virus.

In this method, the first vaccine composition can comprise a nanoparticle comprising an ectodomain from the hemagglutinin protein of an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). Alternatively, the hemagglutinin of the first vaccine composition protein can comprise an amino acid sequence selected from SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 or one that is at least about 80% identical, at least about 85% identical, at least about 90% identical, at least about 95% identical, at least about 97% identical, at least about 99% identical thereto. Further, the first vaccine composition can comprise an HA-ferritin fusion protein comprising an amino acid sequence selected from SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68 or an amino acid sequence that is at least 80% identical, at least about 85% identical, at least about 90% identical, at least about 95% identical, at least about 97% identical, at least about 99% identical thereto, wherein the nanoparticle elicits an immune response against an influenza virus.

Administration of the boosting composition is generally weeks or months after administration of the priming composition.

A further embodiment of the present invention is a fusion protein comprising a monomeric ferritin subunit protein joined to an influenza hemagglutinin protein. The monomeric ferritin subunit protein can be selected from a bacterial ferritin, a plant ferritin, an algal ferritin, an insect ferritin, a fungal ferritin and a mammalian ferritin or can be a monomeric subunit of a *Helicobacter pylori* ferritin protein. The monomeric ferritin subunit protein can comprise a domain that allows the fusion protein to self-assemble into nanoparticles. In this embodiment, the monomeric ferritin subunit protein can comprise SEQ ID NO:2 or SEQ ID NO:5 or comprise at least 25 contiguous amino acids from or be at least about 80% identical, at least about 85% identical, at least about 90% identical, at least about 95% identical, at least about 97% identical, at least about 99% to a sequence selected from SEQ ID NO:2 and SEQ ID NO:5 and the fusion protein can be capable of self-assembling into nanoparticles. Additionally, the monomeric subunit can comprise a region corresponding to amino acids 5-167 of SEQ ID NO:2.

In this embodiment, the hemagglutinin protein can comprise at least 25 amino acids from an influenza virus selected from A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and B/Brisbane/60/2008 (2008 Bris, B). Alternatively, the hemagglutinin protein can be capable of eliciting an immune response to a protein comprising an amino acid sequence selected from SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 or one that is at least about 80% identical, at least about 85% identical, at least about 90% identical, at least about 95% identical, at least about 97% identical, at least about 99% thereto. In this embodiment, the fusion protein can comprise an amino acid sequence selected from SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68 or one that is at least about 80% identical, at least about 85% identical, at least about 90% identical, at least about 95% identical, at least about 97% identical, at least about 99% identical thereto.

Further in this embodiment, the hemagglutinin protein can comprise a region selected from a region capable of allowing trimerization of the hemagglutinin protein, a stem region, an ectodomain, and a region comprising the amino acid sequence from the amino acid residue immediately distal to the last amino acid of the second helical coiled coil to the amino acid residue proximal to the first amino acid of the transmembrane domain. The hemagglutinin protein alternatively can comprise a region corresponding to amino acids 1-519 of SEQ ID NO:8, an amino acid sequence selected from the group consisting of amino acids 1-519 of SEQ ID NO:8 and SEQ ID NO:11, or a hemagglutinin spike domain. Further, the hemagglutinin protein can comprise the stem region from an influenza virus selected from A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), or κ/Brisbane/60/2008 (2008 Bris, B). The hemagglutinin protein can also comprise an amino acid sequence at least about 80% identical, at least about 85% identical, at least about 90% identical, at least about 95% identical, at least about 97% identical, at least about 99% to SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

In this embodiment, the fusion protein can comprise one or more linker sequences or an amino acid sequence of selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128 or a sequence that is at least about 80% identical, at least about 85% identical, at least about 90% identical, at least about 95% identical, at least about 97% identical, at least about 99% thereto.

A further embodiment of the present invention is a nucleic acid molecule encoding any of the fusion proteins described above. In this embodiment, the nucleic acid molecule can be functionally linked to a promoter. Other embodiments of the invention include recombinant cells and viruses that comprise such nucleic acid molecules.

Another embodiment of the invention is a protein comprising an amino acid sequence at least 80% identical, at least about 85% identical, at least about 90% identical, at least about 95% identical, at least about 97% identical, at least about 99% to an amino acid selected from SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98, wherein the protein is joined to one or more trimerization domains. In this embodiment, the protein can be joined to at least a portion of the head region of an influenza hemagglutinin protein, comprise one or more linker regions or elicit an immune response against an influenza virus. A further embodiment is a nucleic acid molecule encoding such a protein.

BACKGROUND

Protective immune responses induced by vaccination against influenza virus are primarily directed to the viral hemagglutinin (HA) protein, which is a glycoprotein on the surface of the virus responsible for interaction of the virus with host cell receptors. HA proteins on the virus surface are trimers of hemagglutinin protein monomers that are enzymatically cleaved to yield amino-terminal HA1 and carboxy-terminal HA2 polypeptides. The globular head consists exclusively of the major portion of the HA1 polypeptide, whereas the stem that anchors the hemagglutinin protein into the viral lipid envelope is comprised of HA2 and part of HA1. The globular head of a hemagglutinin protein includes two domains: the receptor binding domain (RBD), an ~148-amino acid residue domain that includes the sialic acid-binding site, and the vestigial esterase domain, a smaller ~75-amino acid residue region just below the RBD. The top part of the RBD adjacent to the 2,6-sialic acid recognition sites includes a large region (amino acids 131-143, 170-182, 205-215 and 257-262, 1918 numbering) (referred to herein as the RBD-A region) of over 6000 Å$^2$ per trimer that is 95% conserved between A/South Carolina/1/1918 (1918 SC) and A/California/04/2009 (2009 CA) pandemic strains. The globular head includes several antigenic sites that include immunodominant epitopes. Examples include the Sa, Sb, $Ca_1$, $Ca_2$ and Cb antigenic sites (see, for example, Caton A J et al, 1982, Cell 31, 417-427). The RBD-A region includes the Sa antigenic site and part of the Sb antigenic site.

Antibodies against influenza often target variable antigenic sites in the globular head of HA, which surround a conserved sialic acid binding site, and thus, neutralize only antigenically closely related viruses. The variability of the HA head is due to the constant antigenic drift of influenza viruses and is responsible for seasonal endemics of influenza. In contrast, gene segments of the viral genome can undergo reassortment (antigenic shift) in host species, creating new viruses with altered antigenicity that are capable of becoming pandemics [Salomon, R. et al. Cell 136, 402-410 (2009)]. Until now, each year, influenza vaccine is updated to reflect the predicted HA and neuraminidase (NA) for upcoming circulating viruses.

Current vaccine strategies for influenza use either a chemically inactivated or a live attenuated influenza virus. Both vaccines are generally produced in embryonated eggs which present major manufacturing limitations due to the time consuming process and limited production capacity. Another more critical limitation of current vaccines is its highly strain-specific efficacy. These challenges became glaring obvious during emergence of the 2009 H1N1 pandemic, thus validating the necessity for new vaccine platforms capable of overcoming these limitations. Virus-like particles represent one of such alternative approaches and are currently being evaluated in clinical trials [Roldao, A. et al. Expert Rev Vaccines 9, 1149-1176 (2010); Sheridan, C. Nat Biotechnol 27, 489-491 (2009)]. Instead of embryonated eggs, VLPs that often comprise HA, NA and matrix protein 1 (M1) can be mass-produced in mammalian or insect cell expression systems [Haynes, J. R. Expert Rev Vaccines 8, 435-445 (2009)]. The advantages of this approach are its particulate, multivalent nature and the authentic display of properly folded, trimeric HA spikes that faithfully mimic the infectious virion. In contrast, by the nature of its assembly, the enveloped VLPs contain a small but finite host cell component that may present potential safety, immunogenicity challenges following repeated use of this platform [Wu, C. Y. et al. PLoS One 5, e9784 (2010)]. Moreover, the immunity induced by the VLPs is essentially the same as current vaccines do, and thus, does not likely improve both potency and breadth of vaccine-induced protective immunity. In addition to VLPs, a recombinant HA protein has also been evaluated in humans [Treanor, J. J. et al. *Vaccine* 19, 1732-1737 (2001); Treanor, J. J. *JAMA* 297, 1577-1582 (2007)], though the ability to induce protective neutralizing antibody titers are limited. The recombinant HA proteins used in those trials were produced in insect cells and might not form native trimer preferentially [Stevens, J. *Science* 303, 1866-1870 (2004)].

Recently, entirely new classes of broadly neutralizing antibodies against influenza viruses were isolated. One class of antibodies recognizes the highly conserved HA stem [Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. *J Virol* 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)], and another class of antibodies precisely recognizes the sialic acid binding site of the RBD on the variable HA head [Whittle, J. R. et al. *Proc Natl Acad Sci USA* 108, 14216-14221 (2011); Krause, J. C. et al. *J Virol* 85, 10905-10908 (2011)]. Unlike strain-specific antibodies, those antibodies are capable of neutralizing multiple antigenically distinct viruses, and hence inducing such antibodies has been a focus of next generation universal vaccine [Nabel, G. J. et al. *Nat Med* 16, 1389-1391 (2010)]. However, robustly eliciting these antibodies with such heterologous neutralizing profile by vaccination has been difficult [Steel, J. et al. *MBio* 1, e0018 (2010); Wang, T. T. et al. *PLoS Pathog* 6, e1000796 (2010); Wei, C. J. et al. *Science* 329, 1060-1064 (2010)].

Despite several alternatives to conventional influenza vaccines, advances in biotechnology in past decades have allowed engineering of biological materials to be exploited for the generation of novel vaccine platforms. Ferritin, an iron storage protein found in almost all living organisms, is an example which has been extensively studied and engineered for a number of potential biochemical/biomedical purposes [Iwahori, K. U.S. Patent 2009/0233377 (2009); Meldrum, F. C. et al. *Science* 257, 522-523 (1992); Naitou, M. et al. U.S. Patent 2011/0038025 (2011); Yamashita, I. *Biochim Biophys Acta* 1800, 846-857 (2010)], including a potential vaccine platform for displaying exogenous epitope peptides [Carter, D. C. et al. U.S. Patent 2006/0251679 (2006); Li, C. Q. et al. *Industrial Biotechnol* 2, 143-147 (2006)]. Its use as a vaccine platform is particularly interesting because of its self-assembly and multivalent presentation of antigen which induces stronger B cell responses than monovalent form as well as induce T-cell independent antibody responses [Bachmann, M. F. et al. *Annu Rev Immunol* 15, 235-270 (1997); Dintzis, H. M. et al. *Proc Natl Acad Sci USA* 73, 3671-3675 (1976)]. Further, the molecular architecture of ferritin, which consists of 24 subunits assembling into an octahedral cage with 432 symmetry has the potential to display multimeric antigens on its surface.

There remains a need for an efficacious influenza vaccine that provides robust protection against influenza virus. There particularly remains a need for an influenza vaccine that protects individuals from heterologous strains of influenza virus, including evolving seasonal and pandemic influenza virus strains of the future. The present invention meets this need by providing a novel HA-ferritin nanoparticle (HA-ferritin np) influenza vaccine that is easily manufactured, potent, and elicits broadly neutralizing influenza antibodies

BRIEF DESCRIPTION OF THE FIGURES

FIG. 3. Antigenic characterization of HA-ferritin np. (a) Binding of mAbs directed to globular head and stem of HA was measured by ELISA. Equal amount (200 ng of HA per well) of HA trimer (▲), TIV (■), HA-ferritin (●) or Ferr (equimolar amount as HA-Ferr) (○) were coated on the plates and wells were probed with anti-head mAb (3u-u) and anti-stem mAb CR6261. The half maximal effective concentrations ($EC_{50}$) of binding were calculated for each antibody and showed as ng ml$^{-1}$ (b) Inhibition of antibody-mediated neutralization of 1999 NC pseudotyped virus by using HA trimer, HA-Ferr or Ferr as a competitor. Inhibition of neutralization was plotted as percent inhibition respect to no competitor control. The anti-stem neutralizing mAbs, F10 (left) and CR6261 (right) were used at 3.125 and 25 μg ml$^{-1}$, respectively. Competitor proteins were added to the reactions at a final concentration of 20 μg ml$^{-1}$.

Beijing) or 1:3,200 (1999 NC) were plotted. Each symbol represents the individual ferret serum and mean is indicated as a red line with s.d. (n=6 for 1986 Sing, 1995 Beijing and 1999 NC; n=3 for 2007 Bris). The relative contribution of the stem- and RBS-directed neutralization was determined by the inhibition of neutralization for each competitor protein (right). Mean percent contributions in neutralizing each virus were plotted as pile-up bars (n=6).

Figure 9:
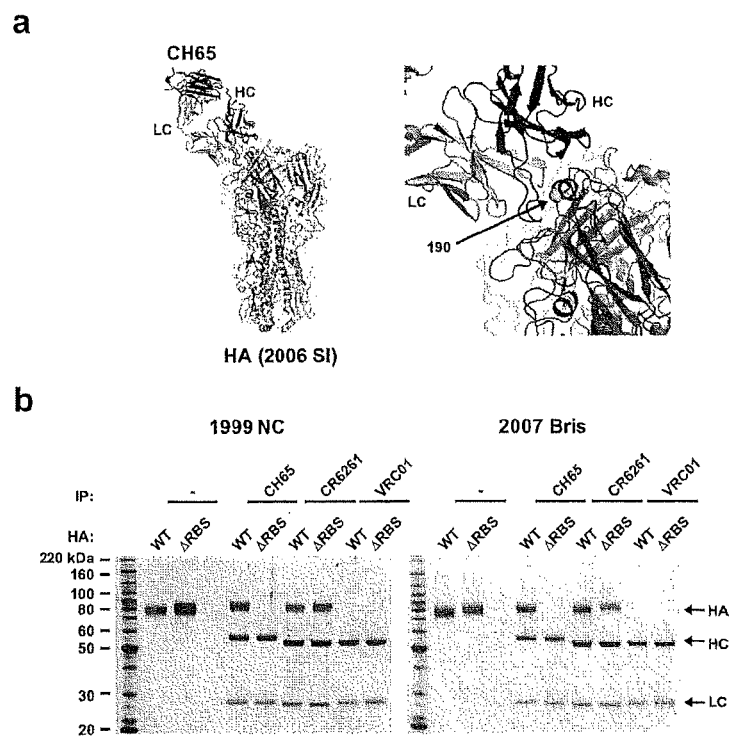

FIG. 9. Characterization of ΔRBS HA probe. (a) Crystal structure of HA (A/Solomon Islands/3/2006) complex with an anti-RBS mAb CH65 Fab (PDB: 3sm5) (J. R. Whittle et al., Broadly neutralizing human antibody that recognizes the receptor-binding pocket of influenza virus hemagglutinin. *Proc Natl Acad Sci USA* 108, 14216-14221 (2011)) (left). Close up view of CH65 contact area (right). The residue HA1 190 which has been mutated to be glycosylated in ΔRBS mutant is highlighted. The CH65 Fab-bound HA1 protomer is darkened. (b) Characterization of the soluble trimer of WT and ΔRBS HAs from 1999 NC and 2007 Bris. The WT and ΔRBS HA proteins were immunoprecipitated with anti-RBS (CH65), stem (CR6261) and control (anti-HIV, VRC01) mAbs. Immune complexes were then dissolved in Lamini buffer and analyzed by SDS-PAGE. Antibody heavy and light chains are labeled as HC and LC, respectively.

Figure 10:
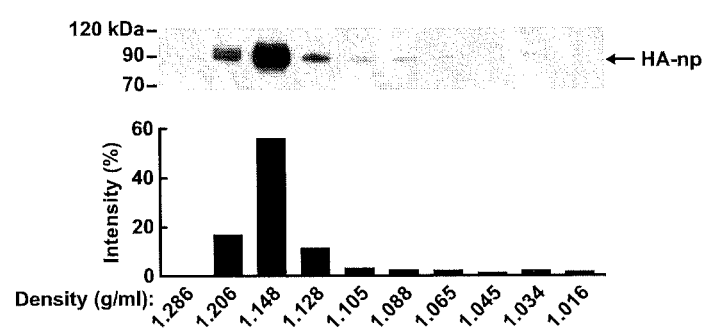

FIG. 10. Purification of HA-np. HA-np were purified by routine iodixanol gradient ultracentrifugation routinely. Fractions containing HA-np were confirmed by SDS-PAGE and Western blotting using a mAb against 1999 NC HA. The HA-np were enriched in the fraction with density of ~1.15 g/ml.

FIG. 11. Protocol for immunization of mice and ferrets using pan-group 1 HA-ferritin np. Mice were injected intramuscularly twice (Week 0 and week 4) with PBS (control) or 6.8 ug (1.7 ug of each HA-ferritin np) pan-group 1 vaccine in Ribi. Ferrets were injected intramuscularly twice (Week 0 and week 4) with PBS (control) or 10 ug (2.5 ug of each HA-ferritin np) pan-group 1 vaccine in Ribi.

FIG. 12. Neutralization activity of mouse antisera against Group 1 HA pseudotyped viruses. Neutralization activity of murine antisera from control or pan Group1 HA-np immunized mice against the indicated HA pseudotyped viruses. IC50 titers are shown for all panels.

FIG. 13. Neutralization activity of ferret antisera against Group1 HA pseudotyped viruses. Neutralization activity of ferret antisera from control or pan Group1 HA np immunized ferrets against the indicated HA pseudotyped viruses. IC50 titers are shown for all panels.

FIG. 14. H1 HAI assays were performed using the sera obtained from the ferritin immunization studies. These studies were performed using actual H1 virus, and H2 and H5 HAI were performed using HA-ferritin np FIG. 15. Protection of ferrets from viral challenge with Influenza A/Brisbane/59/2007 Brisbane (H1N1) (2007 Bris). Two groups of ferrets (n=6 for control and n=5 for pan-group1 immune) were immunized with pan Group1 HA np vaccine or PBS (control) and challenged with heterologous 2007 Bris virus ($10^{6.5}$ $EID_{50}$). Virus titers were measured in nasal swabs collected on day 3 and day 5 post challenge. Titers were determined using end-point titration in MDCK cells.

Figure 16:
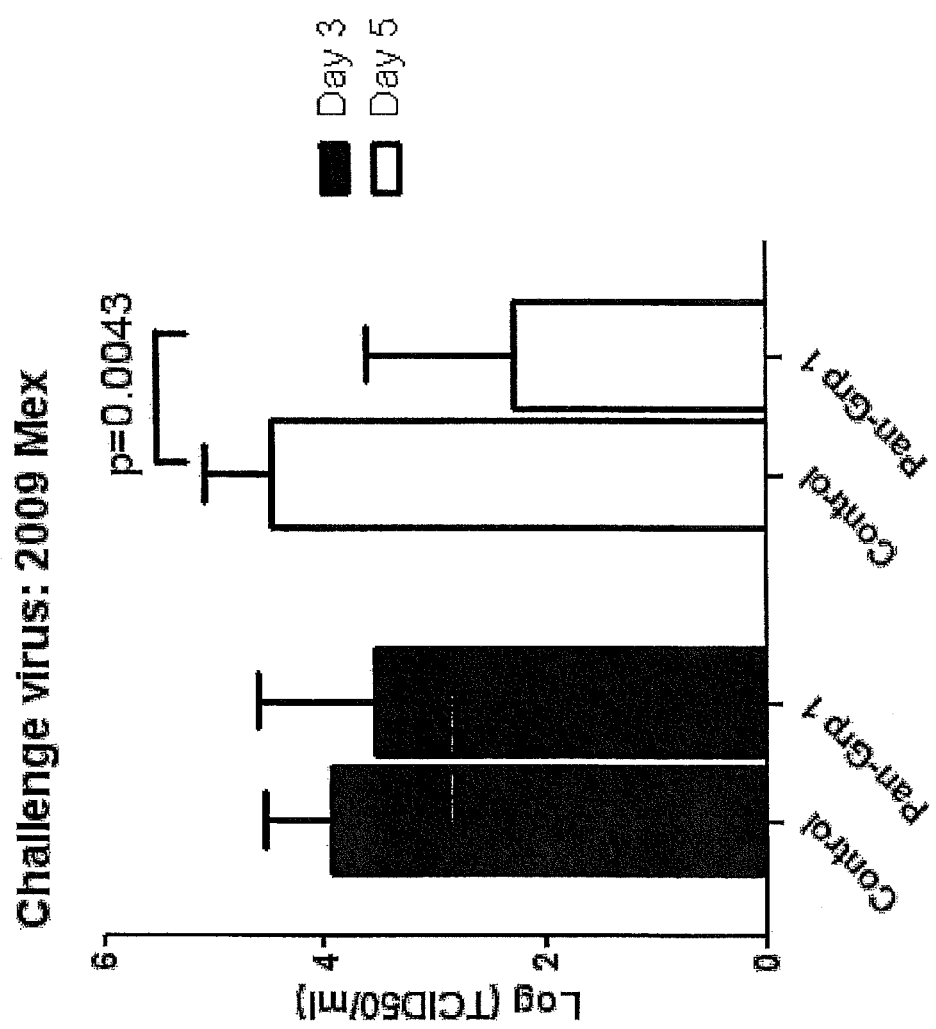

FIG. 16. Protection of ferrets from viral challenge with Influenza A/Mexico/2009 (H1N1) (2009 Mex). Two groups of ferrets (n=6) were immunized with pan Group1 HA np vaccine or PBS (control) and challenged with heterologous 2009 Mex virus ($10^{6.5}$ $EID_{50}$). Virus titers were measured in nasal swabs collected on day 3 and day 5 post challenge. Titers were determined using end-point titration in MDCK cells.

FIG. 17. Conservation of the influenza HA stem region. (left, right) Neutralizing antibodies that react with both Group 1 and Group 2 viruses act at the sites of vulnerability shown in the Figure. (Right) Space filling model of influenza HA protein illustrating amino acid sequence conservation in over 800 human H1N1 strains. Light residues indicate residues that are 100% conserved. Dark residues as indicate sites of variation.

Figure 18:
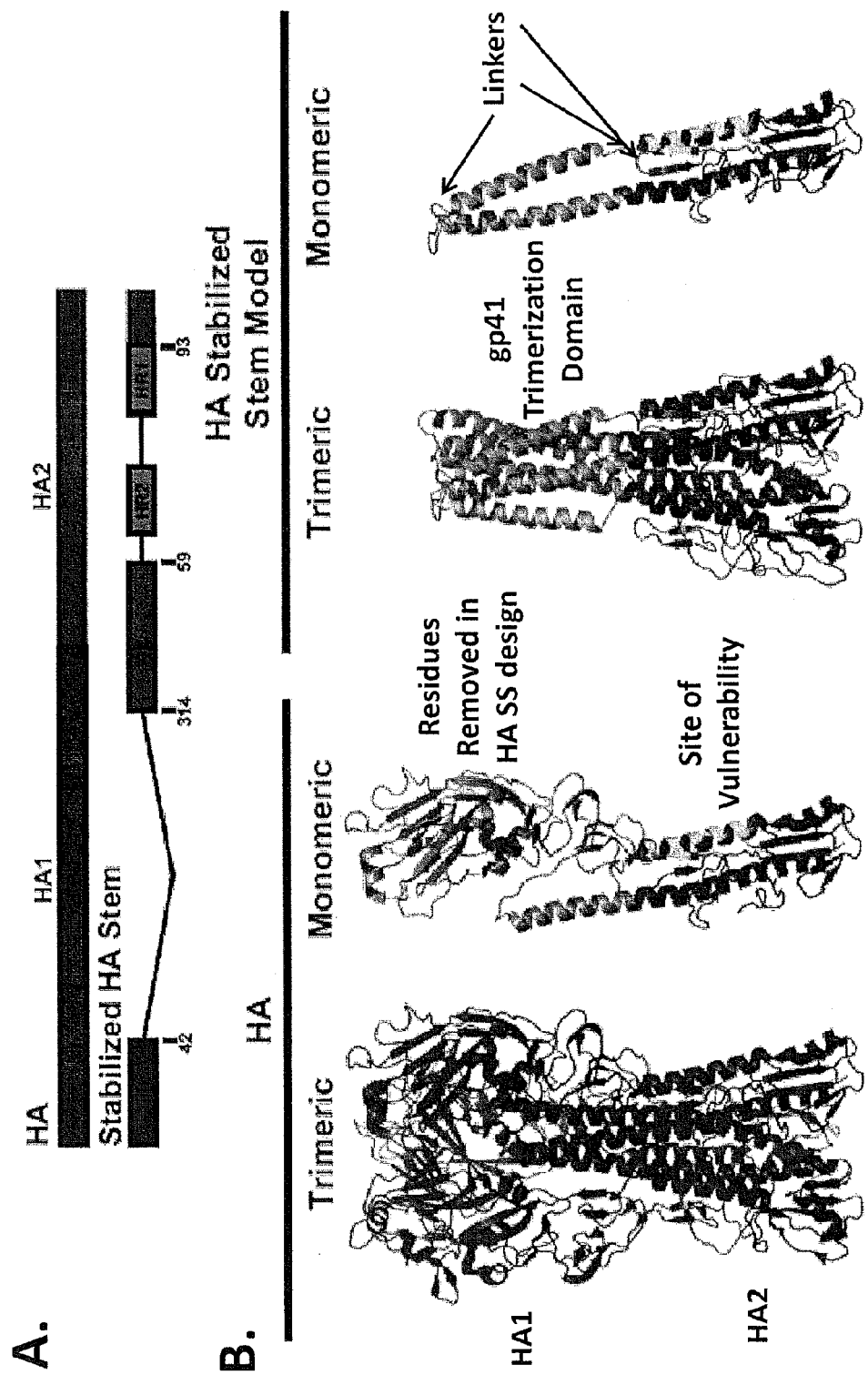

FIG. 18. Design of HA Stabilized Stem protein. (A) Schematic of the HA SS (bottom) in comparison to HA (top). HA SS was constructed by inserting a GWG linker between residues 42 and 314 of HA1 RBD head, a gp41 post-fusion trimerization motif inserted in place of residues 59 through 93 of HA2, a GG linker between HA2 and the gp41 HR2 helix and an NGTGGGSG linker between the two gp41 helices. The gene sequence of H1 NC 99 SS is provided in the supplemental materials. (B) Trimeric and monomeric representation of HA (PDB entry 1RU7) in comparison to the HA SS model. Coloring is respective to above panel, with the monomeric representation also illustrating the CR6261 epitope as yellow and HA residues which are omitted in the stabilized HA stem as grey. (C) CR6261, FI6v3, and the germline of the VH1-69 Ab 70-5B03 have similar affinity to HA and SS by ELISA. HA SS competes with CR6261 (D) binding to HA and (E) neutralization of H1N1 pseudovirus similar to soluble HA trimer.

Figure 19:
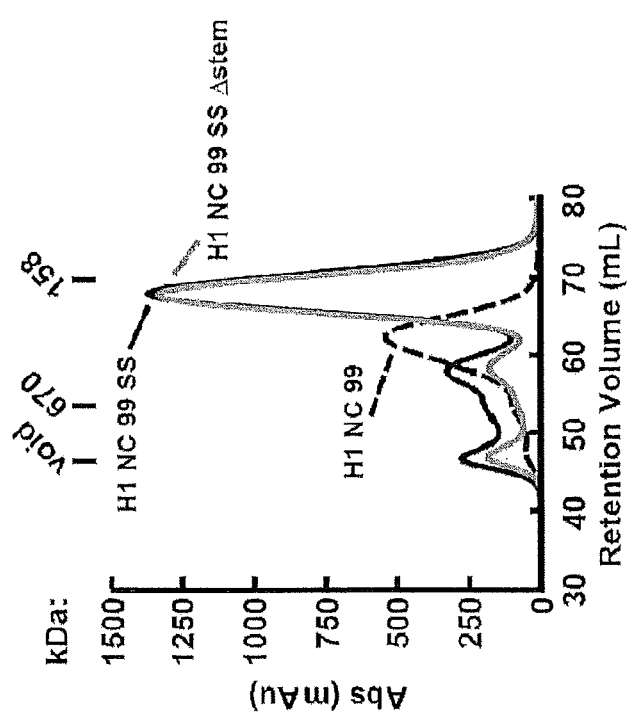

FIG. 19. Size exclusion chromatogram of HA and HA SS probes. Calibration standards are shown above the curves as vertical lines.

FIG. 20. Electron microscopic analysis of nanoparticles. Purified SS-np were subjected to transmission electron microscopic analysis. The samples were negatively stained with ammonium molybdate and images were recorded on a Tecnai T12 microscope (FEI) at 80 kV with a CCD camera (AMT Corp.). Images of lower (left) and higher (right) magnifications are shown. The SS spikes were protruding perpendicularly from the particle core and clearly visible.

Figure 21:
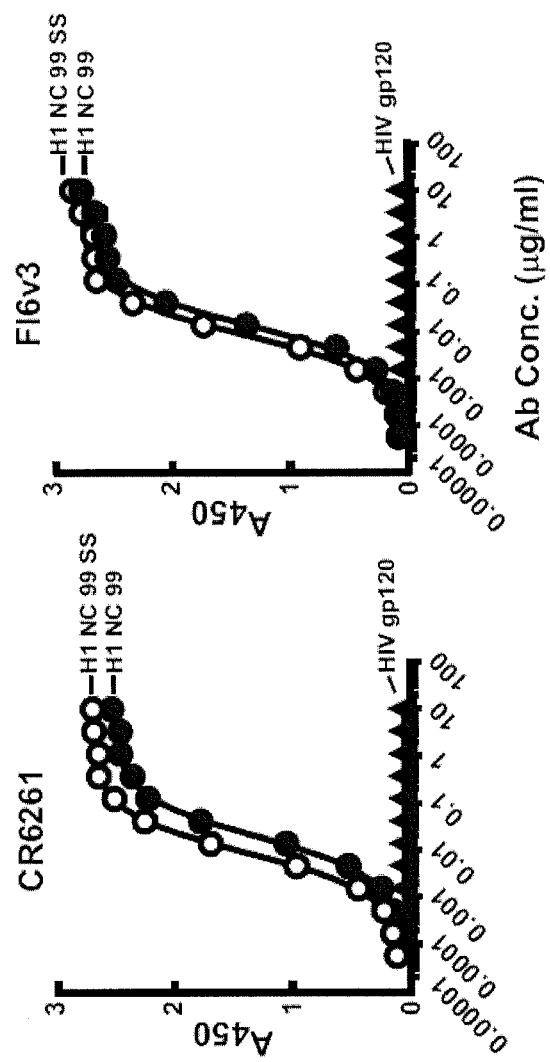

FIG. 21. Antigenic characterization of HA SS-ferritin np. The ability of purified HA SS and HA SS-np to bind to monoclonal Abs CR6261 (left) and FI6v3 (right) was characterized by ELISA. HA and HIV gp120 proteins served as controls.

Figure 22:
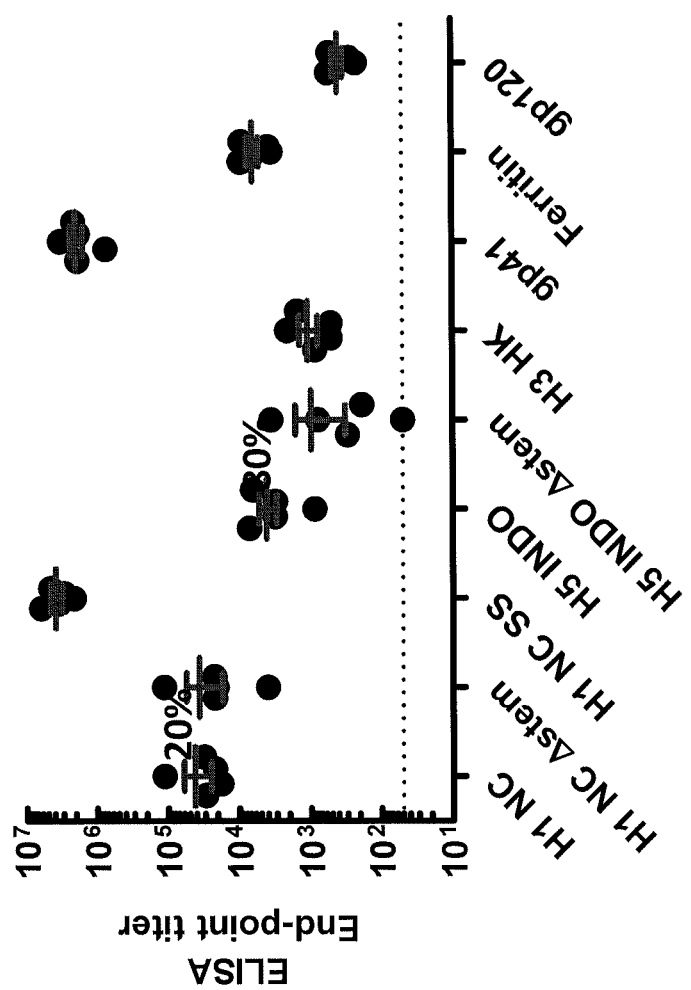

FIG. 22. Immune sera of mice immunized heterologously with HA-np prime and HA SS-np boost are reactive to the conserved HA stem epitope. Antibodies elicited by vaccination target the conserved HA stem epitope as individual mice possess differential binding (a minimum of 2-fold difference in endpoint dilution) between wt and Δstem HA variants. The percentage of mice displaying differential binding is given above matched wt and Δstem constructs. Error bars represent standard error.

Figure 23:
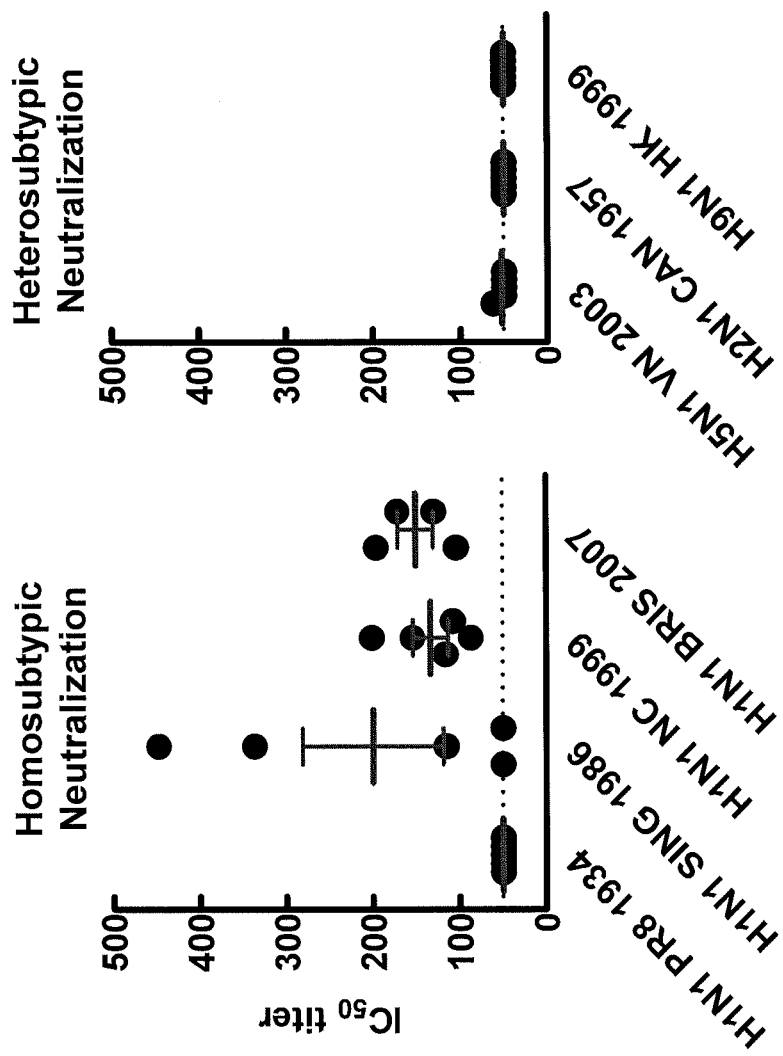

FIG. 23. Immune sera of mice immunized with HA SS neutralizes diverse pseudovirus stains. IC50 values are shown for individual mice against H1 homosubtypic strains and H2, H5 and H9 group-1 heterosubtypic strains. Dashed lines represents the lowest dilution assayed (50). Error bars represent standard error.

Figure 24:
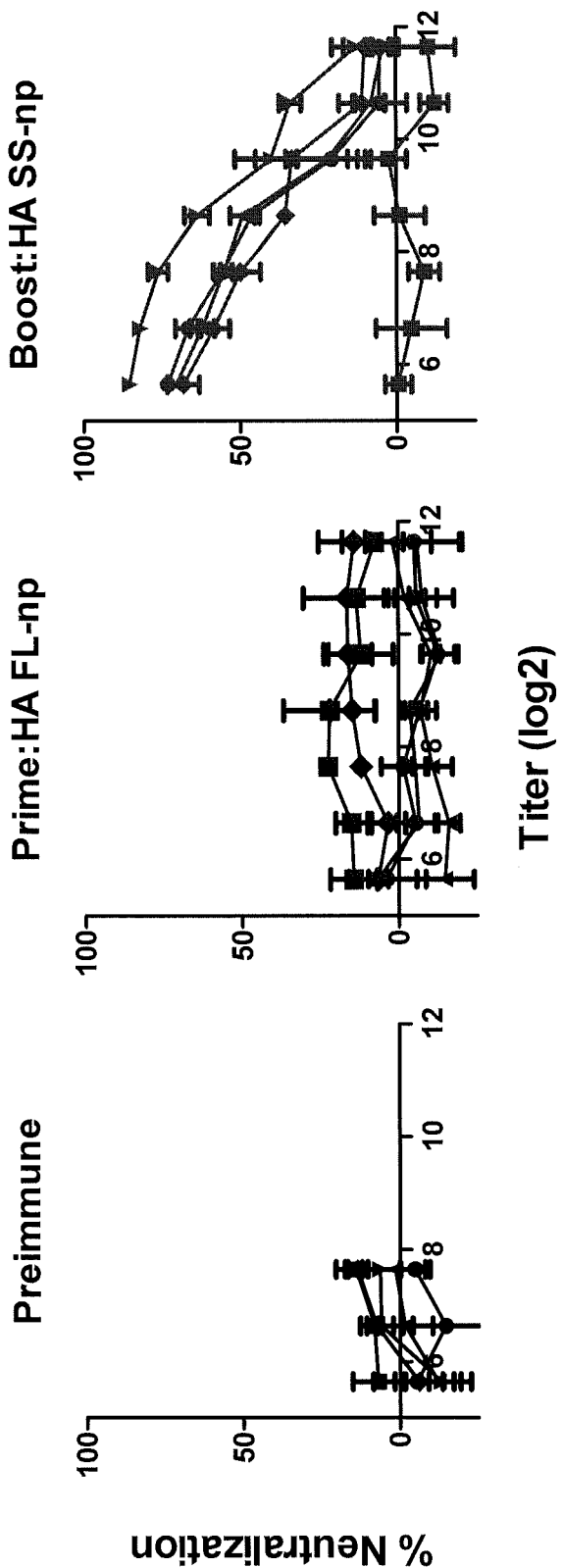

FIG. 24. Boosting with HA SS-np increases neutralizing titers in ferrets against H1N1 New Calendonia. Pseudovirus neutralizing titers were calculated for preimmune, HA FL-np primed, and HA SS-np boosted sera from individual mice. Error bars represent standard deviation of values.

FIG. 25. Map and sequence of CMV8x/R-H1NC HA(517)_SGG-egm (SEQ ID NO:130), the nucleic acid sequence encoding the related HA-ferritin fusion protein (SEQ ID NO:131) and the amino acid sequence of the encoded HA-ferritin fusion protein.

FIG. 26. Map and sequence of CMV8x/R-H1CA HA (518)_SGG-egm (SEQ ID NO:132), the nucleic acid sequence encoding the related HA-ferritin fusion protein (SEQ ID NO:133) and the amino acid sequence of the encoded HA-ferritin fusion protein.

FIG. 27. Map and sequence of CMV8x/R-H2Sing HA(514)_SGG-egm (SEQ ID NO:134), the nucleic acid sequence encoding the related HA-ferritin fusion protein (SEQ ID NO:135) and the amino acid sequence of the encoded HA-ferritin fusion protein.

FIG. 28. Map and sequence of CMV8x/R-H3HK HA(519)_SGG-egm (SEQ ID NO:136), the nucleic acid sequence encoding the related HA-ferritin fusion protein (SEQ ID NO:137) and the amino acid sequence of the encoded HA-ferritin fusion protein.

FIG. 29. Map and sequence of CMV8x/R-H3Bris HA(519)_SGG-egm (SEQ ID NO:138), the nucleic acid sequence encoding the related HA-ferritin fusion protein (SEQ ID NO:139) and the amino acid sequence of the encoded HA-ferritin fusion protein.

FIG. 30. Map and sequence of CMV8x/R-H5Indo HA(520)_SGG-egm (SEQ ID NO:140), the nucleic acid sequence encoding the related HA-ferritin fusion protein (SEQ ID NO:141) and the amino acid sequence of the encoded HA-ferritin fusion protein.

FIG. 31. Map and sequence of CMV8x/R-B.Florida HA(534)_SGG-egm (SEQ ID NO:142), the nucleic acid sequence encoding the related HA-ferritin fusion protein (SEQ ID NO:143) and the amino acid sequence of the encoded HA-ferritin fusion protein.

FIG. 32. Map and sequence of CMV8x/R-H3Perth HA(519)_SGG-egm (SEQ ID NO:144), the nucleic acid sequence encoding the related HA-ferritin fusion protein (SEQ ID NO:145) and the amino acid sequence of the encoded HA-ferritin fusion protein.

FIG. 33. Map and sequence of CMV8x/R-H1Bris HA(517)_SGG-egm (SEQ ID NO:146) and the nucleic acid sequence encoding the related HA-ferritin fusion protein (SEQ ID NO:147) and the amino acid sequence of the encoded HA-ferritin fusion protein.

FIG. 34. Map and sequence of CMV8x/R-B.Bris HA(535)_SG G-egm (SEQ ID NO:148), the nucleic acid sequence encoding the related HA-ferritin fusion protein (SEQ ID NO:149) and the amino acid sequence of the encoded HA-ferritin fusion protein.

FIG. 35. Map and sequence of CMV8x/R-H1NC SS Gen4.55_SGG-egm (SEQ ID NO:150), the nucleic acid sequence encoding the related HA-ferritin fusion protein (SEQ ID NO:151) and the amino acid sequence of the encoded HA-ferritin fusion protein.

FIG. 36. Map and sequence of CMV/R H1 CA SS/Gen4.55/ferritin (SEQ ID NO:152).

FIG. 37. Map and sequence of CMV/R H1 Bris SS/Gen4.55/ferritin (SEQ ID NO:152).

FIG. 38. Map and sequence of CMV/R H2 Sing SS/Gen4.55/ferritin (SEQ ID NO:152).

FIG. 39. Map and sequence of CMV/R H3 Bris SS/Gen4.55/ferritin (SEQ ID NO:152).

FIG. 40. Map and sequence of CMV/R H3 Perth SS/Gen4.55/ferritin (SEQ ID NO:152).

FIG. 41. Map and sequence of CMV/R H3 HK68 SS/Gen4.55/ferritin (SEQ ID NO:152).

FIG. 42. Map and sequence of CMV/R H5 Indo SS/Gen4.55/ferritin (SEQ ID NO:152).

FIG. 43. Map and sequence of CMV/R B Bris SS/Gen4.55/ferritin (SEQ ID NO:152).

FIG. 44. Map and sequence of CMV/R B FL SS/Gen4.55/ferritin (SEQ ID NO:152).

DETAILED DESCRIPTION OF THE INVENTION

The present invention relates to a novel vaccine for influenza virus. More specifically, the present invention relates to novel, influenza hemagglutinin protein-based vaccines that elicit an immune response against a broad range of influenza viruses. It also relates to self-assembling ferritin-based, nanoparticles that display immunogenic portions of influenza hemagglutinin protein on their surface. Such nanoparticles are useful for vaccinating individuals against influenza virus. Accordingly, the present invention also relates to fusion proteins for producing such nanoparticles and nucleic acid molecules encoding such proteins. Additionally, the present invention relates to, methods of producing nanoparticles of the present invention, and methods of using such nanoparticles to vaccinate individuals.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In addition to the above, unless specifically defined otherwise, the following terms and phrases, which are common to the various embodiments disclosed herein, are defined as follows:

As used herein, the term immunogenic refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 94% identical, at least 96% identical, at least 98% identical or at least 99% identical.

As used herein, an immune response to a vaccine, or nanoparticle, of the present invention is the development in a subject of a humoral and/or a cellular immune response to a hemagglutinin protein present in the vaccine. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+ T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a hemagglutinin protein present in the vaccine. These responses may serve to neutralize infectivity, and/or mediate antibody-complement, or antibody dependent cell cytotoxicity (ADCC) to provide protection to an immunized individual. Such responses can be determined using standard immunoassays and neutralization assays, well known in the art.

According to the present invention all nomenclature used to classify influenza virus is that commonly used by those skilled in the art. Thus, a Type, or Group, of influenza virus refers to influenza Type A, influenza Type B or influenza type C. It is understood by those skilled in the art that the designation of a virus as s specific Type relates to sequence difference in the respective M1 (matrix) protein or NP (nucleoprotein). Type A influenza viruses are further divided into Group1 and Group 2. These Groups are further divided into subtypes, which refers to classification of a virus based on the sequence of its HA protein. Examples of current commonly recognized subtypes are H1, H2, H3, H4, H5, H6, H7, H8, H8, H10, H11, H12, H13, H14, H15 or H16. Group 1 influenza subtypes are H1, H2, H5, H7 and H9. Group 2 influenza subtypes are H4, H4, H6, H8, H10, H11, H12, H13, H14, H15 and H16. Finally, the term strain refers to viruses within a subtype that differ from one another in that they have small, genetic variations in their genome.

As used herein, neutralizing antibodies are antibodies that prevent influenza virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles and budding of viral particles from the host cell membrane.

As used herein, broadly neutralizing antibodies are antibodies that neutralize more than one type, subtype and/or strain of influenza virus. For example, broadly neutralizing antibodies elicited against an HA protein from a Type A influenza virus may neutralize a Type B or Type C virus. As a further example, broadly neutralizing antibodies elicited against an HA protein from Group I influenza virus may neutralize a Group 2 viru. AS an additional example, broadly neutralizing antibodies elicited against an HA protein from one sub-type or strain of virus, may neutralize another sub-type or strain of virus. For example, broadly neutralizing antibodies elicited against an HA protein from an H1 influenza virus may neutralize viruses from one or more sub-types selected from the group consisting of H2, H3, H4, H5, H6, H7, H8, H8, H10, H11, H12, H13, H14, H15 or H16.

As used herein, an influenza hemagglutinin protein, or HA protein, refers to a full-length influenza hemagglutinin protein or any portion thereof, that is capable of eliciting an immune response. Preferred HA proteins are those that are capable of forming a trimer. An epitope of a full-length influenza hemagglutinin protein refers to a portion of such protein that can elicit a neutralizing antibody response against the homologous influenza strain, i.e., a strain from which the HA is derived. In some embodiments, such an epitope can also elicit a neutralizing antibody response against a heterologous influenza strain, i.e., a strain having an HA that is not identical to that of the HA of the immunogen.

With regard to hemagglutinin proteins, it is understood by those skilled in the art that hemagglutinin proteins from different influenza viruses may have different lengths due to mutations (insertions, deletions) in the protein. Thus, reference to a corresponding region refers to a region of another proteins that is identical, or nearly so (e.g., at least 95%, identical, at least 98% identical or at least 99% identical), in sequence, structure and/or function to the region being compared. For example, with regard to the stem region of a hemagglutinin protein, the corresponding region in another hemagglutinin protein may not have the same residue numbers, but will have a nearly identical sequence and will perform the same function. To better clarify sequences comparisons between viruses, numbering systems are used by those in the field, which relate amino acid positions to a reference sequence. Thus, corresponding amino acid residues in hemagglutinin proteins from different strains of influenza may not have the same residue number with respect to their distance from the n-terminal amino acid of the protein. For example, using the H3 numbering system, reference to residue 100 in A/New Caledonia/20/1999 (1999 NC, H1) does not mean it is the $100^{th}$ residue from the N-terminal amino acid. Instead, residue 100 of A/New Caledonia/20/1999 (1999 NC, H1) aligns with residue 100 of influenza H3N2 strain. The use of such numbering systems is understood by those skilled in the art. Unless otherwise noted, reference to amino acids in hemagglutinin proteins herein is made using the H3 numbering system.

According to the present invention, a trimerization domain is a series of amino acids that when joined (also referred to as fused) to a protein or peptide, allow the fusion protein to interact with other fusion proteins containing the trimerization domain, such that a trimeric structure is formed. Any known trimerization domain can be used in the present invention. Examples of trimerization domains include, but are not limited to, the HIV-1 gp41 trimerization domain, the SIV gp41 trimerization domain, the Ebola virus gp-2 trimerization domain, the HTLV-1 gp-21 trimerization domain, the T4 fibritin trimerization domain (i.e., foldon), the yeast heat shock transcription factor trimerization domain, and the human collagen trimerization domain.

As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique know to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing antibodies against an influenza virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, variant proteins of the present invention can contain amino acid substitutions relative to the influenza HA proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:
1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 1.

TABLE 1

Amino Acid Substitutions

| Original Amino Acid | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30%, at least 40% or at least 50%. With regard to the present invention, such an activity may be measured, for example, as the ability of a protein to elicit neutralizing antibodies against an influenza virus. Such activity may be measured by measuring the titer of such antibodies against influenza virus, or by measuring the number of types, subtypes or strains neutralized by the elicited antibodies. Methods of determining antibody titers and methods of performing virus neutralization assays are known to those skilled in the art. In addition to the activities described above, other activities that may be measured include the ability to agglutinate red blood cells and the binding affinity of the protein for a cell. Methods of measuring such activities are known to those skilled in the art.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of monomeric subunits that make up ferritin, and the amino acid sequences of influenza hemagglutinin proteins are not normally found joined together via a peptide bond.

The terms individual, subject, and patient are well-recognized in the art, and are herein used interchangeably to refer to any human or other animal susceptible to influenza infection. Examples include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have influenza virus in their body.

As used herein, a vaccinated subject is a subject that has been administered a vaccine that is intended to provide a protective effect against an influenza virus.

As used herein, the terms exposed, exposure, and the like, indicate the subject has come in contact with a person of animal that is known to be infected with an influenza virus.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

According to the present invention, vaccines are provided that elicit a broad immune response against influenza viruses. Some vaccines disclosed herein may elicit an immune response against the entire HA protein, while others may elicit an immune response against a specific region or portion of an influenza HA protein. Moreover, the inventors have discovered that specific fusion proteins comprising portions of hemagglutinin protein are useful for eliciting a broad immune response against influenza viruses. Each of these embodiments will now be disclosed in detail below.

Vaccines Against the Stem Region of Influenza HA Protein

As stated previously, the amino acid sequence of the stem region of the hemagglutinin protein is highly conserved across types, sub-types and strains of influenza viruses and contains a site of vulnerability for group 1 viruses. Thus, an immune response directed this region of the HA protein may protect individuals against influenza viruses from several types, sub-types and/or strains.

Consequently, one embodiment of the present invention is a protein that elicits an immune response against the stem region of an influenza HA protein. In one embodiment, the immune response can be directed against the stem region of an HA protein from a virus selected from the group consisting of influenza A viruses, influenza B viruses and influenza C viruses. In one embodiment, the immune response can be directed against the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. In one embodiment, the immune response can be directed against the stem region of an HA protein from a strain of virus selected from the group of viruses listed in Table 2.

TABLE 2

| SEQ ID NO | Comments |
|---|---|
| FERRITIN | |
| 1 | Coding sequence for ferritin monomeric subunit protein from *H. pylori* |
| 2 | Amino acid sequence encoded by SEQ ID NO: 1 |
| 3 | Complement of SEQ ID NO 1 |
| 4 | Nucleic acid sequence encoding amino acids 5-167 from SEQ ID NO: 2; Asn19 has been replaced with Gln |
| 5 | Amino acid sequence encoded by SEQ ID NO: 3 |
| 6 | Complement of SEQ ID NO 3 |

TABLE 2-continued

| SEQ ID NO | Comments |
|---|---|
| | FULL LENGTH HA |
| 7 | Nucleic acid sequence encoding full length hemagglutinin protein from A/New Caledonia/20/1999 (1999 NC, H1)(GenBank: AY289929) |
| 8 | Amino acid sequence encoded by SEQ ID NO: 7 (full length hemagglutinin protein from A/New Caledonia/20/1999 (1999 NC, H1)(GenBank: AY289929)) |
| 9 | Complement of SEQ ID NO: 7 |
| | ECTODOMAINS |
| 10 | Nucleic acid sequence encoding ectodomain from hemagglutinin protein from A/New Caledonia/20/1999 (1999 NC, H1). |
| 11 | Amino acid sequence encoded by SEQ ID NO: 10 (ectodomain from hemagglutinin protein from A/New Caledonia/20/1999 (1999 NC, H1). Amino acids 1-517 from SEQ ID NO: 8. |
| 12 | Complement of SEQ ID NO: 10 |
| 13 | Nucleic acid sequence encoding ectodomain from hemagglutinin protein from A/California/04/2009 (2009 CA, H1). |
| 14 | Amino acid sequence encoded by SEQ ID NO: 13 (ectodomain from hemagglutinin protein from A/California/04/2009 (2009 CA, H1)) |
| 15 | Complement of SEQ ID NO: 13 |
| 16 | Nucleic acid sequence encoding ectodomain from hemagglutinin protein from A/Singapore/1/1957 (1957 Sing, H2). |
| 17 | Amino acid sequence encoded by SEQ ID NO: 16 (ectodomain from hemagglutinin protein from A/Singapore/1/1957 (1957 Sing, H2)) |
| 18 | Complement of SEQ ID NO: 16 |
| 19 | Nucleic acid sequence encoding ectodomain from hemagglutinin protein from A/Hong Kong/1/1968 (1968 HK, H3). |
| 20 | Amino acid sequence encoded by SEQ ID NO: 19) ectodomain from hemagglutinin protein from A/Hong Kong/1/1968 (1968 HK, H3)) |
| 21 | Complement of SEQ ID NO: 19 |
| 22 | Nucleic acid sequence encoding ectodomain from hemagglutinin protein from A/Brisbane/10/2007 (2007 Bris, H3). |
| 23 | Amino acid sequence encoded by SEQ ID NO: 22 (ectodomain from hemagglutinin protein from A/Brisbane/10/2007 (2007 Bris, H3)) |
| 24 | Complement of SEQ ID NO: 22. |
| 25 | Nucleic acid sequence encoding ectodomain from hemagglutinin protein from A/Indonesia/05/2005 (2005 Indo, H5) |
| 26 | Amino acid sequence encoded by SEQ ID NO: 25 (ectodomain from hemagglutinin protein from A/Indonesia/05/2005 (2005 Indo, H5)) |
| 27 | Complement of SEQ ID NO: 25 |
| 28 | Nucleic acid sequence encoding ectodomain from hemagglutinin protein from B/Florida/4/2006 (2006 Flo, B) |
| 29 | Amino acid sequence encoded by SEQ ID NO: 28 (ectodomain from hemagglutinin protein from B/Florida/4/2006 (2006 Flo, B)) |
| 30 | Complement of SEQ ID NO: 28 |
| 31 | Nucleic acid sequence encoding ectodomain from hemagglutinin protein from A/Perth/16/2009 (2009 Per, H3) |
| 32 | Amino acid sequence encoded by SEQ ID NO: 31 (ectodomain from hemagglutinin protein from A/Perth/16/2009 (2009 Per, H3)) |
| 33 | Complement of SEQ ID NO: 31 |
| 34 | Nucleic acid sequence encoding ectodomain from hemagglutinin protein from A/Brisbane/59/2007 (2007 Bris, H1) |
| 35 | Amino acid sequence encoded by SEQ ID NO: 34 (ectodomain from hemagglutinin protein from A/Brisbane/59/2007 (2007 Bris, H1)) |
| 36 | Complement of SEQ ID NO: 34 |
| 37 | Nucleic acid sequence encoding ectodomain from hemagglutinin protein from B/Brisbane/60/2008 (2008 Bris, B) |
| 38 | Amino acid sequence encoded by SEQ ID NO: 37 (ectodomain from hemagglutinin protein from B/Brisbane/60/2008 (2008 Bris, B)) |
| 39 | Complement of SEQ ID NO: 37 |
| | FERRITIN-HA ECTODOMAIN FUSION |
| 40 | Nucleic acid sequence encoding SEQ ID NO: 41 |
| 41 | Amino acid sequence of ferritin-HA fusion (ectodomain from hemagglutinin protein from A/New Caledonia/20/1999 (1999 NC, H1)) |
| 42 | Complement of SEQ ID NO: 40 |
| 43 | Nucleic acid sequence encoding SEQ ID NO: 44 |
| 44 | Amino acid sequence of ferritin-HA fusion (ectodomain from hemagglutinin protein from A/California/04/2009 (2009 CA, H1)) |
| 45 | Complement of SEQ ID NO: 43 |
| 46 | Nucleic acid sequence encoding SEQ ID NO: 47 |
| 47 | Amino acid sequence of ferritin-HA fusion (ectodomain from hemagglutinin protein from A/Singapore/1/1957 (1957 Sing, H2)) |
| 48 | Complement of SEQ ID NO: 46 |
| 49 | Nucleic acid sequence encoding SEQ ID NO: 50 |
| 50 | Amino acid sequence of ferritin-HA fusion (ectodomain from hemagglutinin protein from A/Hong Kong/1/1968 (1968 HK, H3)) |
| 51 | Complement of SEQ ID NO: 49 |
| 52 | Nucleic acid sequence encoding SEQ ID NO: 53 |
| 53 | Amino acid sequence of ferritin-HA fusion (ectodomain from hemagglutinin protein from A/Brisbane/10/2007 (2007 Bris, H3)) |
| 54 | Complement of SEQ ID NO: 52 |
| 55 | Nucleic acid sequence encoding SEQ ID NO: 56 |
| 56 | Amino acid sequence of ferritin-HA fusion (ectodomain from hemagglutinin protein from A/Indonesia/05/2005 (2005 Indo, H5)) |
| 57 | Compliment of SEQ ID NO: 55 |
| 58 | Nucleic acid sequence encoding SEQ ID NO: 59 |
| 59 | Amino acid sequence of ferritin-HA fusion protein (ectodomain from hemagglutinin protein from B/Florida/4/2006 (2006 Flo, B)) |
| 60 | Complement of SEQ ID NO: 58 |
| 61 | Nucleic acid sequence encoding SEQ ID NO: 62 |
| 62 | Amino acid sequence of ferritin-HA fusion protein (ectodomain from hemagglutinin protein from A/Perth/16/2009 (2009 Per, H3)) |
| 63 | Complement of SEQ ID NO: 61 |
| 64 | Nucleic acid sequence encoding SEQ ID NO: 65 |
| 65 | Amino acid sequence of ferritin-HA fusion protein (ectodomain from hemagglutinin protein from A/Brisbane/59/2007 (2007 Bris, H1)) |
| 66 | Complement of SEQ ID NO: 64 |
| 67 | Nucleic acid sequence encoding SEQ ID NO: 68 |
| 68 | Amino acid sequence of ferritin-HA fusion protein (ectodomain from hemagglutinin protein from B/Brisbane/60/2008 (2008 Bris, B)) |
| 69 | Complement of SEQ ID NO: 67 |
| | STEM REGION |
| 70 | Nucleic acid molecule encoding SEQ ID NO: 71 |
| 71 | Amino acid sequence of stem region from A/New Caledonia/20/1999 (1999 NC, H1)(GenBank: AY289929) |
| 72 | Complement of SEQ ID NO: 70 |
| 73 | Nucleic acid sequence encoding SEQ ID NO: 74 |
| 74 | Amino acid sequence of stem region from A/California/04/2009 (2009 CA, H1) |
| 75 | Complement of SEQ ID NO: 73 |
| 76 | Nucleic acid sequence encoding SEQ ID NO: 77 |
| 77 | Amino acid sequence of stem region from A/Singapore/1/1957 (1957 Sing, H2) |
| 78 | Complement of SEQ ID NO: 76 |
| 79 | Nucleic acid sequence encoding SEQ ID NO: 80 |
| 80 | Amino acid sequence of stem region from A/Hong Kong/1/1968 (1968 HK, H3) |
| 81 | Complement of SEQ ID NO: 79 |
| 82 | Nucleic acid sequence encoding SEQ ID NO: 83 |
| 83 | Amino acid sequence of stem region from A/Brisbane/10/2007 (2007 Bris, H3) |

TABLE 2-continued

| SEQ ID NO | Comments |
|---|---|
| 84 | Complement of SEQ ID NO: 82 |
| 85 | Nucleic acid sequence encoding SEQ ID NO: 86 |
| 86 | Amino acid sequence of stem region from A/Indonesia/05/2005 (2005 Indo, H5) |
| 87 | Complement of SEQ ID NO: 85 |
| 88 | Nucleic acid sequence encoding SEQ ID NO: 89 |
| 89 | Amino acid sequence of stem region from B/Florida/4/2006 (2006 Flo, B) |
| 90 | Complement of SEQ ID NO: 88 |
| 91 | Nucleic acid sequence encoding SEQ ID NO: 92 |
| 92 | Amino acid sequence of stem region from A/Perth/16/2009 (2009 Per, H3) |
| 93 | Complement of SEQ ID NO: 91 |
| 94 | Nucleic acid sequence encoding SEQ ID NO: 95 |
| 95 | Amino acid sequence of stem region from A/Brisbane/59/2007 (2007 Bris, H1) |
| 96 | Complement of SEQ ID NO: 94 |
| 97 | Nucleic acid sequence encoding SEQ ID NO: 98 |
| 98 | Amino acid sequence of stem region from B/Brisbane/60/2008 (2008 Bris, B) |
| 99 | Complement of SEQ ID NO: 97 |
| | FERRITIN- HA STEM REGION FUSION |
| 100 | Nucleic acid sequence encoding SEQ ID NO: 101 |
| 101 | Amino acid sequence of ferritin-HA stem region fusion protein A/New Caledonia/20/1999 (1999 NC, H1) |
| 102 | Complement of SEQ ID NO: 100 |
| 103 | Nucleic acid sequence encoding SEQ ID NO: 104 |
| 104 | Amino acid sequence of ferritin-HA stem region fusion protein (H1 CA) |
| 105 | Complement of SEQ ID NO: 103 |
| 106 | Nucleic acid sequence encoding SEQ ID NO: 107 |
| 107 | Amino acid sequence of ferritin-HA stem region fusion protein (H2 Sing) |
| 108 | Complement of SEQ ID NO: 106 |
| 109 | Nucleic acid sequence encoding SEQ ID NO: 110 |
| 110 | Amino acid sequence of ferritin-HA stem region fusion protein (H3 Hong Kong) |
| 111 | Complement of SEQ ID NO: 109 |
| 112 | Nucleic acid sequence encoding SEQ ID NO: 113 |
| 113 | Amino acid sequence of ferritin-HA stem region fusion protein (H5 Indonesia) |
| 114 | Complement of SEQ ID NO: 112 |
| 115 | Nucleic acid sequence encoding SEQ ID NO: 116 |
| 116 | Amino acid sequence of ferritin-HA stem region fusion protein (A/Brisbane/59/2007 (2007 Bris, H1)) |
| 117 | Complement of SEQ ID NO: 115 |
| 118 | Nucleic acid sequence encoding SEQ ID NO: 119 |
| 119 | Amino acid sequence of ferritin-HA stem region fusion protein (A/Brisbane/10/2007 (2007 Bris, H3)) |
| 120 | Complement of SEQ ID NO: 118 |
| 121 | Nucleic acid sequence encoding SEQ ID NO: 122 |
| 122 | Amino acid sequence of ferritin-HA stem region fusion protein (A/Perth/16/2009 (2009 Per, H3)) |
| 123 | Complement of SEQ ID NO: 121 |
| 124 | Nucleic acid sequence encoding SEQ ID NO: 125 |
| 125 | Amino acid sequence of ferritin-HA stem region fusion protein (B/Brisbane/60/2008 (2008 Bris, B) |
| 126 | Complement of SEQ ID NO: 124 |
| 127 | Nucleic acid sequence encoding SEQ ID NO: 128 |
| 128 | Amino acid sequence of ferritin-HA stem region fusion protein (B/Florida/4/2006 (2006 Flo, B)) |
| 129 | Complement of SEQ ID NO: 127 |
| 130 | Sequence of plasmid CMV8x/R-H1NC HA(517)_SGG_egm Synthetic sequence (FIG. 25) |
| 131 | Nucleic acid sequence encoding SEQ ID NO: 41. Contains stop codon. Identical to SEQ ID NO: 40, Synthetic (FIG. 25) |
| 132 | Sequence of plasmid CMV8x/R-H1CA HA(518)_SGG_egm Synthetic sequence (FIG. 26) |
| 133 | Nucleic acid sequence encoding SEQ ID NO: 44. Nearly identical to SEQ ID NO: 43 but lacks stop codon. (FIG. 26) |
| 134 | Sequence of plasmid CMV8x/R-H2SINGHA(514)_SGG_egm, Synthetic sequence (FIG. 27) |
| 135 | Nucleic acid sequence encoding SEQ ID NO: 47. Nearly identical to SEQ ID NO: 46 but lacks stop codon, Synthetic (FIG. 27) |
| 136 | Sequence of plasmid CMV8x/R-H3HK HA(519)_SGG_egm Synthetic sequence (FIG. 28) |
| 137 | Nucleic acid sequence encoding SEQ ID NO: 50. Nearly identical to SEQ ID NO: 49 but lacks stop codon. Synthetic (FIG. 28) |
| 138 | Sequence of plasmid CMV8x/R-H3Bris HA(519)_SGG_egm Synthetic sequence (FIG. 29) |
| 139 | Nucleic acid sequence encoding SEQ ID NO: 53. Nearly identical to SEQ ID NO: 52 but lacks stop codon. Synthetic (FIG. 29) |
| 140 | Sequence of plasmid CMV8x/R-H5Indo HA/(520)_SGG_egm, Synthetic sequences (FIG. 30) |
| 141 | Nucleic acid sequence encoding SEQ ID NO: 56. Neaarly identical to SEQ ID NO: 55 but lacks stop codon. Synthetic (FIG. 30) |
| 142 | Sequence of plasmid CMV8x/R-B.Florida HA(534)_SGG_egm, Synthetic sequence (FIG. 31) |
| 143 | Nucleic acid sequence encoding SEQ ID NO: 59. Nearly identical to SEQ ID NO: 58 but lacks stop codon. Synthetic (FIG. 31) |
| 144 | Sequence of plasmid CMV8x/R-H3-Perth HA(519)_SGG_egm, Synthetic sequence (FIG. 32) |
| 145 | Nucleic acid sequence encoding SEQ ID NO: 62. Nearly identical to SEQ ID NO: 61 but lacks stop codon. Synthetic (FIG. 32) |
| 146 | Sequence of plasmid CMV8x/R-H1Bris HA(517)_SGG_egm Synthetic sequence (FIG. 33) |
| 147 | Nucleic acid sequence encoding SEQ ID NO: 65. Nearly identical to SEQ ID NO: 64 but lacks stop codon. Synthetic (FIG. 33) |
| 148 | Sequence of plasmid CMV8x/R-B.Bris HA(535)_SGG_egm Synthetic sequence (FIG. 34) |
| 149 | Nucleic acid sequence encoding SEQ ID NO: 68. Nearly identical to SEQ ID NO: 67 but lacks stop codon. Synthetic (FIG. 34) |
| 150 | Sequence of plasmid CMV8x/R-H1NC SS Gen4.55_SGG_egm, Synthetic sequence (Fig. 35) |
| 151 | Nucleic acid sequence encoding SEQ ID NO: 101. Identical to SEQ ID NO: 100. Both lack stop codon. (FIG. 35) |
| 152 | Sequence of plasmid H1CA SS/Gen4.55/Ferritin Synthetic sequence (FIG. 36) |
| 153 | Sequence of plasmid H1Bris SS/Gen4.55/Ferritin Synthetic sequence (FIG. 37) |
| 154 | Sequence of plasmid H1Sing SS/Gen4.55/Ferritin Synthtic sequence (FIG. 38) |
| 155 | Sequence of plasmid H3Bris SS/Gen4.55/Ferritin Synthetic sequence (FIG. 39) |
| 156 | Sequence of plasmid H1Perth SS/Gen4.55/Ferritin Synthetic sequence (FIG. 40) |
| 157 | Sequence of plasmid H3 HK68 SS/Gen4.55/Ferritin Synthetic sequence (FIG. 41) |
| 158 | Sequence of plasmid H5Indo SS/Gen4.55/Ferritin Synthetic sequence (FIG. 42) |
| 159 | Sequence of plasmid B Bris SS/Gen4.55/Ferritin Synthetic sequence (FIG. 43) |
| 160 | Sequence of plasmid B FL SS/Gen4.55/Ferritin Synthetic sequence Synthetic sequence (FIG. 44) |

One type of immune response is a B-cell response, which results in the production of antibodies against the antigen that elicited the immune response. Thus, one embodiment of the present invention is a protein that elicits antibodies that bind to the stem region of influenza HA protein from a virus selected from the group consisting of influenza A viruses, influenza B viruses and influenza C viruses. One embodiment of the present invention is a protein that elicits antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein HA protein, an H12 influenza virus HA protein, an H13 influenza virus HA protein, an H14 influenza virus HA protein, an H15 influenza virus HA protein and an H16 influenza virus HA protein. One embodiment of the present invention is a protein that elicits antibodies that bind to the stem region of influenza HA protein from a strain of virus selected from the viruses listed in Table 2.

While all antibodies are capable of binding to the antigen which elicited the immune response that resulted in antibody production, preferred antibodies are those that neutralize an influenza virus. Thus, one embodiment of the present invention is a protein that elicits neutralizing antibodies that bind to the stem region of influenza HA protein from a virus selected from the group consisting of influenza A viruses, influenza B viruses and influenza C viruses. One embodiment of the present invention is a protein that elicits neutralizing antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein and an H16 influenza virus HA protein. One embodiment of the present invention is a protein that elicits neutralizing antibodies that bind to the stem region of influenza HA protein from a strain of virus selected from the viruses listed in Table 2. One embodiment of the present invention is a protein that elicits neutralizing antibodies that bind to a protein comprising an amino acid sequence at least 80% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. One embodiment of the present invention is a protein that elicits neutralizing antibodies that bind to a protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

Neutralizing antibodies elicited by proteins of the present invention can neutralize viral infections by affecting any step in the life cycle of the virus. For example, neutralizing antibodies may prevent an influenza virus from attaching to a cell, entering a cell, releasing viral ribonucleoproteins into the cytoplasm, forming new viral particles in the infected cell and budding new viral particles from the infected host cell membrane. In one embodiment, neutralizing antibodies elicited by proteins of the present invention prevent influenza virus from attaching to the host cell. In one embodiment, neutralizing antibodies elicited by proteins of the present invention prevent influenza virus from entering the host cell. In one embodiment, neutralizing antibodies elicited by proteins of the present invention prevent fusion of viral membranes with endosomal membranes. In one embodiment, neutralizing antibodies elicited by proteins of the present invention prevent release of ribonucleoproteins into the cytoplasm of the host cell. In one embodiment, neutralizing antibodies elicited by proteins of the present invention prevent assembly of new virus in the infected host cell. In one embodiment, neutralizing antibodies elicited by proteins of the present invention prevent release of newly formed virus from the infected host cell.

Because the amino acid sequence of the stem region of influenza virus is highly conserved, neutralizing antibodies elicited by proteins of the present invention may be broadly neutralizing. That is, neutralizing antibodies elicited by proteins of the present invention may neutralize influenza viruses of more than one type, subtype and/or strain, Thus, one embodiment of the present invention is a protein that elicits broadly neutralizing antibodies that bind the stem region of influenza HA protein. One embodiment is a protein that elicits antibodies that bind the stem region of an HA protein from more than one type of influenza virus selected from the group consisting of influenza type A viruses, influenza type B viruses and influenza type C viruses. One embodiment is a protein that elicits antibodies that bind the stem region of an HA protein from more than one sub-type of influenza virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. One embodiment is a protein that elicits antibodies that bind the stem region of an HA protein from more than strain of influenza virus. One embodiment is a protein that elicits antibodies that bind the stem region of an HA protein from more than one strain of influenza virus selected from the viruses listed in Table 2. One embodiment of the present invention is a protein that elicits antibodies that bind more than one protein comprising an amino acid sequence at least 80% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. One embodiment of the present invention is a protein that elicits neutralizing antibodies that bind to more than one protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

Particularly useful proteins of the present invention are those comprising an immunogenic portion of an influenza HA protein. Thus, one embodiment of the present invention is a protein comprising at least one immunogenic portion from the stem region of influenza HA protein, wherein the protein elicits neutralizing antibodies against an influenza virus. Such a protein is referred to as a stem-region protein (or a stem-region immunogen). One embodiment of the present invention is a protein comprising at least one immunogenic portion from the stem region of an HA protein from a virus selected from the group consisting of influenza type A viruses, influenza type B viruses and influenza type C viruses, wherein the protein elicits neutralizing antibodies against an influenza virus. One embodiment of the present invention is a protein comprising at least one immunogenic portion from the stem region of an HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein and an H16 influenza virus HA protein. One embodiment of the present invention is a protein comprising at least one immunogenic portion from the stem region of an HA protein from the viruses listed in Table 2. One embodiment of the present invention is a protein comprising at least one immunogenic portion from a protein comprising an amino acid sequence at least 80% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. One embodiment of the present invention is a protein comprising at least one immunogenic portion from a protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. In one embodiment, such proteins comprising immunogenic portions of the HA protein elicit the production of broadly neutralizing antibodies against influenza virus.

Immunogenic portions of proteins comprise epitopes, which are clusters of amino acid residues that are recognized by the immune system, thereby eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that epitopes require a minimum of six amino acid residues in order to be recognized by the immune system. Thus, in one embodiment the immunogenic portion from the influenza HA protein comprises at least one epitope. One embodiment of the present invention is a protein comprising at least 6 amino acids, at least 10 amino acids, at least 25 amino acids, at least 50 amino acids, at least 75 amino acids or at least 100 amino acids from the stem region of influenza HA protein. One embodiment of the present invention is a protein comprising at least 6 amino acids, at least 10 amino acids, at least 25 amino acids, at least 50 amino acids, at least 75 amino acids or at least 100 amino acids from the stem region of an HA protein from a virus selected from the group consisting of influenza type A viruses, influenza type B viruses and influenza type C viruses. One embodiment of the present invention is a protein comprising at least 6 amino acids, at least 10 amino acids, at least 25 amino acids, at least 50 amino acids, at least 75 amino acids or at least 100 amino acids from the stem region of an HA protein selected from the group consisting an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein and an H16 influenza virus HA protein. One embodiment of the present invention is a protein comprising at least 6 amino acids, at least 10 amino acids, at least 25 amino acids, at least 50 amino acids, at least 75 amino acids or at least 100 amino acids from the stem region of an HA protein from a strain of virus selected from the viruses listed in Table 2. In one embodiment, the amino acids are contiguous amino acids from the stem region of the HA protein. In one embodiment, such proteins comprising at least 6 amino acids, at least 10 amino acids, at least 25 amino acids, at least 50 amino acids, at least 75 amino acids or at least 100 amino acids from the stem region of an HA protein elicit the production of broadly neutralizing antibodies against influenza virus. One embodiment of the present invention is a protein comprising at least 6 amino acids, at least 10 amino acids, at least 25 amino acids, at least 50 amino acids, at least 75 amino acids or at least 100 amino acids from the stem region of an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the amino acids are contiguous amino acids from the stem region of the HA protein. In one embodiment, the amino acids are non-contiguous, but are in close spatial proximity in the final protein.

While the present application discloses the use of stem regions from several exemplary HA proteins having specific sequences, the invention may also be practiced using stem regions from proteins comprising variations of the disclosed HA sequences. Thus, one embodiment of the present invention is a stem-region protein comprising an amino acid sequence at least 80%, at least 85%, at least 90%, at least 92%, at least 94%, at least 96%, at least 98% or at least 99% identical the stem region of an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. One embodiment of the present invention is a stem-region protein comprising an amino acid sequence at least 80%, at least 85%, at least 90%, at least 92%, at least 94%, at least 96%, at least 98% or at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. One embodiment of the present invention is a stem-region protein comprising the stem region of an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. One embodiment of the present invention is a stem-region protein comprising an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

While the proteins disclosed thus far may elicit broadly neutralizing antibodies against an influenza virus, the inventors have discovered that such proteins are more stable and easier to purify when they exist in a trimeric form. Thus, one embodiment is a protein comprising the stem-region protein of the present invention joined to a trimerization domain. In one embodiment, the stem region is from an HA protein comprising an amino acid sequence at least 80% identical, at least 85% identical, at least 90% identical, at least 92% identical, at least 94% identical, at least 96% identical, at least 98% identical or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region is from an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein comprises an amino acid sequence at least 80% identical, at least 85% identical, at least 90% identical, at least 92% identical, at least 94% identical, at least 96% identical, at least 98% identical or at least 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the stem region protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the trimerization domain is selected from the group consisting of the HIV-1 gp41 trimerization domain, the SIV gp41 trimerization domain, the Ebola virus gp-2 trimerization domain, the HTLV-1 gp-21 trimerization domain, the T4 fibritin trimerization domain (i.e., foldon), the yeast heat shock transcription factor trimerization domain, and the human collagen trimerization domain. In one embodiment, the trimerization domain is an HIV gp41 trimerization domain.

The inventors have also found that, in some instances, stem region proteins of the present invention may be more stable when joined to at least part of the head region of the HA protein. Thus, one embodiment of the present invention is a protein comprising a stem region protein joined to the head region of an HA protein and a trimerization domain. In one embodiment, the stem region protein is from an HA protein comprising an amino acid sequence at least 80% identical, at least 85% identical, at least 90% identical, at least 92% identical, at least 94% identical, at least 96% identical, at least 98% identical or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein is from an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein comprises an amino acid sequence at least 80% identical, at least 85% identical, at least 90% identical, at least 92% identical, at least 94% identical, at least 96% identical, at least 98% identical or at least 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the stem region protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

In some embodiments of the present invention, the various protein domains (e.g., stem region protein, trimerization domain, head region, etc.) may be joined directly to one another. In other embodiments, it may be necessary to employ linkers (also referred to as a spacer sequences) so that the various domains are in the proper special orientation. The linker sequence is designed to position the hemagglutinin protein in such a way to that it maintains the ability to elicit an immune response to the influenza virus. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine Examples of such linker sequences include, but are not limited to, SGG, GSG, GG and NGTGGSG. Amino acids can be added or subtracted as needed. Those skilled in the art are capable of determining appropriate linker sequences for proteins of the present invention.

One embodiment of the present invention is a fusion protein comprising a stem region protein joined to at least a portion of the head region of an HA protein and a trimerization domain, wherein the fusion protein comprises one or more linker sequences. In one embodiment, the stem region protein is from an HA protein comprising an amino acid sequence at least 80% identical, at least 85% identical, at least 90% identical, at least 92% identical, at least 94% identical, at least 96% identical, at least 98% identical or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein is from an HA protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the stem region protein comprises an amino acid sequence at least 80% identical, at least 85% identical, at least 90% identical, at least 92% identical, at least 94% identical, at least 96% identical, at least 98% identical or at least 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the stem region protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the linker is selected from the group consisting of GG, GSG and NGTGGSG. In one embodiment, the protein elicits antibodies that neutralize at least one virus that is a different Type, sub-type or strain than the Type, sub-type or strain of the virus from which the HA protein was obtained.

Vaccines Comprising HA-Ferritin Fusion Proteins

The inventors have also discovered that fusion of influenza HA protein with ferritin protein (HA-ferritin fusion protein) results in a vaccine that elicits a robust immune response to influenza virus. Such HA-ferritin fusion proteins self-assemble into nanoparticles that display immunogenic portions of influenza hemagglutinin protein on their surface. These nanoparticles are useful for vaccinating individuals against a broad range of influenza viruses. Thus, one embodiment of the present invention is an HA-ferritin fusion protein comprising a monomeric ferritin subunit disclosed herein joined to an influenza hemagglutinin protein disclosed herein, wherein the HA-ferritin fusion protein is capable of self-assembling into nanoparticles.

Ferritin is a globular protein found in all animals, bacteria, and plants, that acts primarily to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa. An example of the sequence of one such monomeric ferritin subunit is represented by SEQ ID NO:2. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, and D & E' from the N-terminus respectively. The N-terminal sequence lies adjacent to the capsid three-fold axis and extends to the surface, while the E helices pack together at the four-fold axis with the C-terminus extending into the particle core. The consequence of this packing creates two pores on the capsid surface. It is expected that one or both of these pores represent the point by which the hydrated iron diffuses into and out of the capsid. Following production, these monomeric ferritin subunit proteins self-assemble into the globular ferritin protein. Thus, the globular form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the globular form of the protein. Amino acid sequences from monomeric ferritin subunits of any known ferritin protein can be used to produce fusion proteins of the present invention, so long as the monomeric ferritin subunit is capable of self-assembling into a nanoparticle displaying hemagglutinin on its surface. In one embodiment, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In one embodiment, the ferritin protein is from *Helicobacter pylori*.

HA-ferritin fusion proteins of the present invention need not comprise the full-length sequence of a monomeric subunit polypeptide of a ferritin protein. Portions, or regions, of the monomeric ferritin subunit protein can be utilized so long as the portion comprises an amino acid sequence that directs self-assembly of monomeric ferritin subunits into the globular form of the protein. One example of such a region is located between amino acids 5 and 167 of the *Helicobacter pylori* ferritin protein. More specific regions are described in Zhang, Y. Self-Assembly in the Ferritin Nano-Cage Protein Super Family. 2011, Int. J. Mol. Sci., 12, 5406-5421, which is incorporated herein by reference in its entirety.

One embodiment of the present invention is an HA-ferritin fusion protein comprising an HA protein of the present invention joined to at least 25 contiguous amino acids, at least 50 contiguous amino acids, at least 75 contiguous amino acids, at least 100 contiguous amino acids, or at least 150 contiguous amino acids from a monomeric ferritin subunit, wherein the HA-ferritin fusion protein is capable of self-assembling into nanoparticles. One embodiment of the present invention is an HA-ferritin fusion protein comprising an HA protein of the present invention joined to at least 25 contiguous amino acids, at least 50 contiguous amino acids, at least 75 contiguous amino acids, at least 100 contiguous amino acids, or at least 150 contiguous amino acids from the region of a ferritin protein corresponding to the amino acid sequences of the *Helicobacter pylori* ferritin monomeric subunit that direct self-assembly of the monomeric subunits into the globular form of the ferritin protein, wherein the HA-ferritin fusion protein is capable of self-assembling into nanoparticles. One embodiment of the present invention is an HA-ferritin fusion protein comprising an HA protein of the present invention joined to at least 25 contiguous amino acids, at least 50 contiguous amino acids, at least 75 contiguous amino acids, at least 100 contiguous amino acids, or at least 150 contiguous amino acids from SEQ ID NO:2 that are capable of directing self-assembly of the monomeric subunits into the globular ferritin protein, wherein the HA-ferritin fusion protein is capable of self-assembling into nanoparticles. One embodiment of the present invention is an HA-ferritin fusion protein comprising an HA-protein of the present invention joined to at least 25 contiguous amino acids, at least 50 contiguous amino acids, at least 75 contiguous amino acids, at least 100 contiguous amino acids, or at least 150 contiguous amino acids from amino acid residues 5-167 of SEQ ID NO:2, wherein the HA-ferritin fusion protein is capable of self-assembling into nanoparticles. One embodiment of the present invention is an HA-ferritin fusion protein comprising an HA protein of the present invention joined to at least 25 contiguous amino acids, at least 50 contiguous amino acids, at least 75 contiguous amino acids, at least 100 contiguous amino acids, or at least 150 contiguous amino acids from SEQ ID NO:5, wherein the HA-ferritin fusion protein is capable of self-assembling into nanoparticles. One embodiment of the present invention is an HA-ferritin fusion protein comprising an HA protein of the present invention joined to amino acid residues 5-167 from SEQ ID NO:2, or SEQ ID NO:5, wherein the HA-ferritin fusion protein is capable of self-assembling into nanoparticles. As has been previously discussed, it is well-known in the art that some variations can be made in the amino acid sequence of a protein without affecting the activity of the protein. Such variations include insertion of amino acid residues, deletions of amino acid residues, and substitutions of amino acid residues. Thus, in one embodiment, the sequence of the monomeric ferritin subunit is divergent enough from the sequence of a ferritin subunit naturally found in a mammal, such that when the variant monomeric ferritin subunit is introduced into the mammal, it does not result in the production of antibodies that react with the mammal's natural ferritin protein. According to the present invention, such a monomeric subunit is referred to as immunogenically neutral. One embodiment of the present invention is an HA-ferritin fusion protein comprising an HA protein of the present invention joined to an amino acid sequence at least 80%, at least 85%, at least 90%, at least 95%, and at least 97% identical to the amino acid sequence of a monomeric ferritin subunit that is responsible for directing self-assembly of the monomeric ferritin subunits into the globular form of the protein, wherein the HA-ferritin fusion protein is capable of self-assembling into nanoparticles. In one embodiment, the HA-ferritin fusion protein comprises a polypeptide sequence identical in sequence to a monomeric ferritin subunit. One embodiment of the present invention is an HA-ferritin fusion protein comprising an HA protein of the present invention joined to an amino acid sequence at least 80%, at least 85%, at least 90%, at least 95%, and at least 97% identical to the amino acid sequence of a monomeric ferritin subunit from *Helicobacter pylori*, wherein the HA-ferritin fusion protein is capable of self-assembling into nanoparticles. One embodiment of the present invention is an HA-ferritin fusion protein comprising an HA protein of the present invention joined to an amino acid sequence at least 80%, at least 85%, at least 90%, at least 95%, and at least 97% identical to a sequence selected from amino acid residues 5-167 from SEQ ID NO:2 and SEQ ID NO:5, wherein the HA-ferritin fusion protein is capable of self-assembling into nanoparticles. One embodiment of the present invention is an HA-ferritin fusion protein comprising an HA protein of the present invention joined to a sequence selected from amino acid residues 5-167 from SEQ ID NO:2 and SEQ ID NO:5.

In some embodiments, it may be useful to engineer mutations into the amino acid sequences of proteins of the present invention. For example, it may be useful to alter sites such as enzyme recognition sites or glycosylation sites in the monomeric ferritin subunit, the trimerization domain, or linker sequences, in order to give the fusion protein beneficial properties (e.g., solubility, half-life, mask portions of the protein from immune surveillance). In this regard, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site. One such sequence of a mutated monomeric ferritin subunit is represented by SEQ ID NO:5.

According to the present invention, the hemagglutinin protein portion of HA-ferritin fusion proteins of the present invention can be from any influenza virus, so long as the HA-ferritin fusion protein elicits an immune response against an influenza virus. Thus, one embodiment of the preset invention is an HA-ferritin fusion protein comprising a ferritin protein of the present invention joined to an amino acid sequence from an HA protein from an influenza A virus, an influenza B virus or an influenza C virus. One embodiment of the preset invention is an HA-ferritin fusion protein comprising a ferritin protein of the present invention joined to an amino acid sequence from an influenza A Group 1 virus HA protein. One embodiment of the preset invention is an HA-ferritin fusion protein comprising a ferritin protein of the present invention joined to an amino acid sequence from an influenza A Group 2 virus HA protein. One embodiment of the preset invention is an HA-ferritin fusion protein comprising a ferritin protein of the present invention joined to an amino acid sequence from an HA protein selected from the group consisting of an H1 influenza virus HA protein, an H2 influenza virus HA protein, an H5 influenza virus HA protein, an H7 virus influenza HA protein and an H9 influenza virus HA protein. One embodiment of the preset invention is an HA-ferritin fusion protein comprising a ferritin protein of the present invention joined to an amino acid sequence from an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H15 influenza virus HA protein. One embodiment of the preset invention is an HA-ferritin fusion protein comprising a ferritin protein of the present invention joined to an amino acid sequence of an HA protein from a virus listed in Table 2.

Preferred hemagglutinin proteins to use in constructing HA-ferritin fusion proteins of the present invention are those that elicit an immune response against an influenza virus. Even more preferred hemagglutinin proteins are those that are capable of eliciting antibodies to an influenza virus. One embodiment of the present invention is an HA-ferritin fusion protein that elicits antibodies to a virus selected from the group consisting of influenza A viruses, influenza B viruses and influenza C viruses. One embodiment of the present invention is a HA-ferritin fusion protein that elicits antibodies to a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. One embodiment of the present invention is an HA-ferritin fusion protein that elicits antibodies to a virus listed in Table 2. Preferred antibodies elicited by HA-ferritin fusion proteins of the present invention are those that neutralize an influenza virus. Thus, one embodiment of the present invention is an HA-ferritin fusion protein that elicits neutralizing antibodies to a virus selected from the group consisting of influenza A viruses, influenza B viruses and influenza C viruses. One embodiment of the present invention is an HA-ferritin fusion protein that elicits neutralizing antibodies to a virus having a subtype selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. One embodiment of the present invention is an HA-ferritin fusion protein that elicits neutralizing antibodies to a virus listed in Table 2.

As has been discussed, neutralizing antibodies elicited by a HA-ferritin fusion protein of the present invention can neutralize viral infections by affecting any step in the life cycle of the virus. Thus, in one embodiment of the present invention, an HA-ferritin fusion protein elicits neutralizing antibodies that prevent influenza virus from attaching to the host cell. In one embodiment of the present invention, an HA-ferritin fusion protein may elicit neutralizing antibodies that prevent influenza virus from entering the host cell. In one embodiment of the present invention, an HA-ferritin fusion protein may elicit neutralizing antibodies that prevent fusion of viral membranes with endosomal membranes. In one embodiment of the present invention, an HA-ferritin fusion protein may elicit neutralizing antibodies that prevent influenza virus from releasing ribonucleoproteins into the cytoplasm of the host cell. In one embodiment of the present invention, an HA-ferritin fusion protein may elicit neutralizing antibodies that prevent assembly of new virus in the infected host cell. In one embodiment of the present invention, an HA-ferritin fusion protein may elicit neutralizing antibodies that prevent release of newly formed virus from the infected host cell.

Preferred HA-ferritin fusion proteins of the present invention are those that elicit broadly neutralizing antibodies. Thus, one embodiment is an HA-ferritin fusion protein that elicits antibodies that neutralizes more than one type of influenza virus selected from the group consisting of influenza type A viruses, influenza type B viruses and influenza type C viruses. One embodiment is an HA-ferritin fusion protein that elicits antibodies that neutralize more than one sub-type of influenza virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus and an H16 influenza virus. One embodiment is an HA-ferritin protein that elicits antibodies that neutralize from more than one strain of influenza virus selected from the viruses listed in Table 2.

It will be understood by those skilled in the art that particularly useful HA-ferritin useful proteins of the present invention are those comprising an immunogenic portion of influenza HA protein. Thus, one embodiment of the present invention is an HA-ferritin fusion protein comprising a ferritin protein of the present invention joined to at least one immunogenic portion of an influenza HA protein. One embodiment of the present invention is an HA-ferritin protein comprising a ferritin protein of the present invention joined to at least one immunogenic portion of an HA protein from a virus selected from the group consisting of influenza type A viruses, influenza type B viruses and influenza type C viruses. One embodiment of the present invention is an HA-ferritin protein comprising a ferritin protein of the present invention joined to at least one immunogenic portion of an HA protein selected from the group consisting of an H1 influenza virus HA protein, an H2 influenza virus HA protein, an H5 influenza virus HA protein, an H7 virus influenza HA protein and an H9 influenza virus HA protein. One embodiment of the preset invention is an HA-ferritin fusion protein comprising a ferritin protein of the present invention joined to at least one immunogenic portion of an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, joined to a ferritin protein of the present invention. One embodiment of the present invention is an HA-ferritin protein comprising a ferritin protein of the present invention joined to at least one immunogenic portion of an HA protein from virus listed in Table 2. In one embodiment, an HA-ferritin fusion protein comprising an immunogenic portion of an HA protein elicits the production of broadly neutralizing antibodies against influenza virus.

Immunogenic portions of proteins comprise epitopes, which are clusters of amino acid residues that are recognized by the immune system, thus eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that such epitopes require a minimum of six amino acid residues in order to be recognized by the immune system. Thus, one embodiment of the present invention is an HA-ferritin fusion comprising an immunogenic portion from the influenza HA protein, wherein the immunogenic portion comprises at least one epitope.

It is known in the art that some variation in a protein sequence can be tolerated without significantly affecting the activity of the protein. Thus, one embodiment of the present invention is an HA-ferritin fusion protein comprising a ferritin protein of the present invention joined to an amino acid sequence that is a variant of an HA protein from a virus selected from the group consisting of influenza Type A viruses influenza Type B viruses and influenza type C viruses. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of a HA protein from a virus selected from the group consisting of influenza Type A viruses influenza Type B viruses and influenza type C viruses, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of a HA protein selected from the group consisting an H1 influenza virus HA protein, an H2 influenza virus HA protein, an H5 influenza virus HA protein, an H7 virus influenza HA protein and an H9 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of a HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, joined to a ferritin protein of the present invention, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of a HA protein from a virus listed in Table 2, wherein the HA-ferritin fusion protein elicits the production of neutralizing antibodies against an influenza protein. One embodiment of the present invention is an HA-ferritin fusion protein comprising a ferritin protein of the present invention joined to amino acid sequence at least about 80%, at least about 85%, at least about 90%, at least about 95%, at least about 97% or at least about 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38, wherein the HA-ferritin fusion protein elicits the production of neutralizing antibodies against an influenza protein. One embodiment of the present invention is an HA-ferritin fusion protein comprising a ferritin protein of the present invention joined to amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

One embodiment of the present invention is an HA-ferritin fusion protein comprising an amino acid sequence at least 80%, at least about 85%, at least about 90%, at least about 95%, at least about 97% or at least about 99% identical to a sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. One embodiment of the present invention is an HA-ferritin fusion protein comprising an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68.

It is known in the art that influenza hemagglutinin proteins have various regions, or domains, each possessing specific activities. For example, the globular head extends out from the lipid membrane and comprises two domains: the receptor binding domain (RBD) and the vestigial esterase domain. The RB domain is involved in binding of the HA protein to receptors. The globular head also includes several antigenic sites that include immunodominant epitopes. The stem region is responsible for anchoring the HA protein into the viral lipid envelope. Thus, it will be understood by those skilled in the art that HA-ferritin fusion proteins of the present invention need not comprise the entire sequence of the HA protein. Instead, an HA-ferritin fusion protein can comprise only those portions, regions, domains, and the like, that contain the necessary activities for practicing the present invention. For example, an HA-ferritin fusion protein may contain only those amino acid sequences from the HA protein that contain antigenic sites, epitopes, immunodominant epitopes, and the like.

One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an HA protein from a virus selected from the group consisting of influenza Type A viruses influenza Type B viruses and influenza type C viruses, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an HA protein selected from the group consisting an H1 influenza virus HA protein, an H2 influenza virus HA protein, an H5 influenza virus HA protein, an H7 virus influenza HA protein and an H9 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from and HA protein from a virus listed in Table 2, wherein the HA-ferritin fusion protein elicits the production of neutralizing antibodies against in influenza virus. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

One embodiment of the present invention is an HA-ferritin fusion protein comprising a ferritin protein of the present invention joined to at least one domain from a HA protein from a virus listed in Table 2, wherein the domain is selected from the group consisting of an ectodomain, an RDB domain, a stem domain, and a domain comprising the region stretching from the amino acid residue immediately distal to the last amino acid of second helical coil to the amino acid residue proximal to the first amino acid of the transmembrane domain. According to the present invention, an ectodomain of an influenza hemagglutinin protein refers to the portion of the hemagglutinin protein that lies outside its transmembrane domain. In one embodiment, the HA-ferritin fusion protein comprises a ferritin protein of the present invention joined to a region of a HA protein from a virus listed in Table 2, wherein the region consists of the amino acid immediately distal to the last amino acid of the second helical coiled coil and proximal to the first amino acid of the transmembrane domain. In one embodiment, the HA-ferritin fusion protein comprises a ferritin protein of the present invention joined to a region of a HA protein from a virus listed in Table 2, wherein the region comprises an amino acid sequence distal to the second helical coiled coil and proximal to the transmembrane domain. In one embodiment, the HA-ferritin fusion protein comprises a ferritin protein of the present invention joined to the ectodomain of a HA protein from a virus listed in Table 2. One embodiment of the present invention is an HA-ferritin fusion protein comprising a ferritin protein of the present invention joined a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

The stem region of an influenza HA protein is a particularly useful domain for constructing fusion proteins of the present invention. Thus, one embodiment of the present invention is a ferritin protein of the present invention joined to at least one immunogenic portion from the stem region of influenza HA protein. According to the preset invention, such a protein is referred to an HA SS-ferritin fusion protein. As used herein, the HA stem region of the hemagglutinin protein consists of the amino acids from the membrane up to the head region of the protein. More specifically, the stem region consists of the amino terminal amino acid up to the cysteine at position 52, and all residues after the cysteine residue at position 277 (using standard H3 numbering). Sequences of exemplary stem regions are represented by SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein from a virus selected from the group consisting of influenza Type A viruses influenza Type B viruses and influenza type C viruses, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein selected from the group consisting an H1 influenza virus HA protein, an H2 influenza virus HA protein, an H5 influenza virus HA protein, an H7 virus influenza HA protein and an H9 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, wherein the HA-ferritin fusion protein elicits the production of neutralizing antibodies against an influenza protein. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein from a virus listed in Table 2, wherein the HA-ferritin fusion protein elicits the production of neutralizing antibodies against in influenza virus. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region of an HA protein comprising a sequence selected from the group consisting of SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. One embodiment of the present invention is an HA-ferritin fusion protein comprising a ferritin protein of the present invention joined to at least 25 amino acids, at least 50 amino acids, at least 75 amino acids, at least 100 amino acids, at least 150 amino acids, or at least 200 amino acids from the stem region comprising a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of the stem region of an HA protein from a virus selected from the group consisting of influenza Type A viruses influenza Type B viruses and influenza type C viruses, wherein the Ha-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of the stem region of an HA protein selected from the group consisting an H1 influenza virus HA protein, an H2 influenza virus HA protein, an H5 influenza virus HA protein, an H7 virus influenza HA protein and an H9 influenza virus HA protein, wherein the Ha-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of the stem region of an HA protein selected from the group consisting of an H3 influenza virus HA protein, an H4 influenza virus HA protein, an H6 influenza virus HA protein, an H8 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, and an H16 influenza virus HA protein, joined to a ferritin protein of the present invention, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the sequence of the stem region of an HA protein from a virus listed in Table 2, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to the stem region of an HA protein comprising an amino acid sequence selected from the group consisting of SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence at least about 80%, at least about 85%, at least about 90%, at least about 95%, at least about 97% or at least about 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98, wherein the HA-ferritin fusion protein elicits the production of neutralizing antibodies against an influenza protein. One embodiment of the present invention is an HA-ferritin fusion protein comprising a ferritin protein of the present invention joined to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

As has been described for stem region proteins of the present invention, the inventors have found that HA-ferritin fusion proteins are more stable and easier to purify when they exist in a trimeric form. Thus, in one embodiment of the present invention the HA portion of the HA-ferritin fusion protein is joined to one or more trimerization domains. In one embodiment, the HA protein comprises an amino acid sequence at least 80% identical, at least 85% identical, at least 90% identical, at least 92% identical, at least 94% identical, at least 96% identical, at least 98% identical or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38, joined to one or more trimerization domains. In one embodiment, the HA protein comprises an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38 joined to one or more trimerization domains. In one embodiment, the HA protein comprises an amino acid sequence at least 80% identical, at least 85% identical, at least 90% identical, at least 92% identical, at least 94% identical, at least 96% identical, at least 98% identical or at least 99% identical to an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98 joined to one or more trimerization domains. In one embodiment, the HA protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98 joined to one or more trimerization domains. In one embodiment, the trimerization domain is selected from the group consisting of the HIV-1 gp41 trimerization domain, the SIV gp41 trimerization domain, the Ebola virus gp-2 trimerization domain, the HTLV-1 gp-21 trimerization domain, the T4 fibritin trimerization domain (i.e., foldon), the yeast heat shock transcription factor trimerization domain, and the human collagen trimerization domain. In one embodiment, the trimerization domain is an HIV gp41 trimerization domain.

Additionally, the inventors have found that, in some instances, HA-ferritin fusion proteins in which the HA portion is limited to HA stem region sequences may be more stable when joined to at least part of the head region of the HA protein. Thus, one embodiment of the present invention is an HA SS-ferritin fusion protein, wherein, the HA portion of the fusion protein is joined to an amino acid sequence from at least a portion of an HA protein head region.

HA-ferritin proteins of the present invention are constructed by joining ferritin proteins of the present invention with HA proteins of the present invention. In addition, HA-ferritin fusion proteins may contain other domains (e.g., stem region protein, trimerization domain, head region, etc.) that improve the functionality of the final HA-ferritin fusion protein. In some embodiments, joining of the various proteins and/or domains can be done such that the sequences are directly linked. In other embodiments, it may be necessary to employ linkers (also referred to as a spacer sequences) between the various proteins and/or domains so that the so that they are in the proper special orientation. More specifically, linker sequence can be inserted so that the hemagglutinin protein is positioned in such a way to maintain the ability to elicit an immune response to the influenza virus. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine Examples of such linker sequences include, but are not limited to, SGG, GSG, GG and NGTGGSG. Amino acids can be added or subtracted as needed. Those skilled in the art are capable of determining appropriate linker sequences for proteins of the present invention.

In accordance with the invention, suitable portions of the hemagglutinin protein can be joined to the ferritin protein either as an exocapsid product by fusion with the N-terminal sequence lying adjacent to the capsid three-fold axis, as an endocapsid product by fusion with the C-terminus extending inside the capsid core, or a combination thereof. In one embodiment, the hemagglutinin portion of the fusion protein is joined to the N-terminal sequence of the ferritin portion of the fusion protein.

One embodiment of the present invention is an HA-ferritin fusion protein comprising an amino acid sequence at least about 80%, at least about 85%, at least about 90%, at least about 95%, at least about 97% or at least about 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128, wherein the HA-ferritin fusion protein elicits the production of neutralizing antibodies against an influenza protein. One embodiment of the present invention is an HA-ferritin fusion protein comprising SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

Proteins of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, *Molecular Cloning: a Laboratory Manual*, 3$^{rd}$ edition, Sambrook et al. 2001 Cold Spring Harbor Laboratory Press, and *Current Protocols in Molecular Biology*, Ausubel et al. eds., John Wiley & Sons, 1994. In one embodiment, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes a stem region immunogen, a ferritin monomeric subunit, a hemagglutinin protein, and/or an HA-ferritin fusion protein of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is know. It is to be appreciated that a nucleic acid construct can comprise one nucleic acid molecule or more than one nucleic acid molecule. It is also to be appreciated that a nucleic acid molecule can encode one protein or more than one protein.

Preferred nucleic acid molecules are those that encode a stem-region protein, a ferritin monomeric subunit, a hemagglutinin protein, and/or an HA-ferritin fusion protein comprising a monomeric subunit of a ferritin protein joined to an influenza hemagglutinin protein. Thus, one embodiment of the present invention is a nucleic acid molecule comprising a nucleic acid sequence encoding a protein that comprises a monomeric subunit of a ferritin protein joined to an influenza hemagglutinin protein. In one embodiment, the monomeric subunit of ferritin is from the ferritin protein of *Helicobacter pylori*. In one embodiment, the monomeric subunit comprises an amino acid sequence at least 80%, at least 85%, at least 90%, at least 92%, at least 94%, at least 96%, at least 98% or at least 99% identical to a sequence selected from the group consisting of SEQ ID NO:2 and SEQ ID NO:5. In one embodiment, the monomeric subunit comprises an amino acid sequence selected from the group consisting of SEQ ID NO:2 and SEQ ID NO:5. In one embodiment the influenza hemagglutinin protein comprises an amino acid sequence at least 80%, at least 85%, at least 90%, at least 92%, at least 94%, at least 96%, at least 98% or at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment the influenza hemagglutinin protein comprises a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment the influenza hemagglutinin protein comprises an amino acid sequence at least 80%, at least 85%, at least 90%, at least 92%, at least 94%, at least 96%, at least 98% or at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment the influenza hemagglutinin protein comprises a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment the influenza hemagglutinin protein comprises at least 25 amino acids, at least 50 amino acids, at least 75 amino acids, at least 100 amino acids, at least 150 amino acids, or at least 200 amino acids from a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment the influenza hemagglutinin protein comprises at least 25 amino acids, at least 50 amino acids, at least 75 amino acids, at least 100 amino acids, at least 150 amino acids, or at least 200 amino acids from a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

One embodiment of the present invention is a nucleic acid molecule comprising a nucleic sequence encoding a protein comprising an amino acid sequence at least 80%, at least 85%, at least 90%, at least 92%, at least 94%, at least 96%, at least 98% or at least 99% identical to a sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. One embodiment of the present invention is a nucleic acid molecule comprising a nucleic sequence encoding an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68.

One embodiment of the present invention is a nucleic acid molecule comprising a nucleic sequence encoding a protein comprising an amino acid sequence at least 80%, at least 85%, at least 90%, at least 92%, at least 94%, at least 96%, at least 98% or at least 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128. One embodiment of the present invention is a nucleic acid molecule comprising a nucleic sequence encoding an amino acid sequence selected from the group consisting of SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

Also embodied in the present invention are nucleic acid sequences that are variants of nucleic acid sequence encoding protein of the present invention. Such variants include nucleotide insertions, deletions, and substitutions, so long as they do not affect the ability of fusion proteins of the present invention to self-assemble into nanoparticles, or significantly affect the ability of the hemagglutinin portion of fusion proteins to elicit an immune response to an influenza virus. Thus, one embodiment of the present invention is a nucleic acid molecule encoding a fusion protein of the present invention, wherein the monomeric subunit is encoded by a nucleotide sequence at least 85%, at least 90%, at least 95%, or at least 97% identical to a nucleotide sequence selected from the group consisting of SEQ ID NO:1 and SEQ ID NO:4. One embodiment of the present invention is a nucleic acid molecule encoding an HA-ferritin fusion protein of the present invention, wherein the HA protein is encoded by a nucleotide sequence at least 85%, at least 90%, at least 95%, at least 97% identical or at least 99% identical to a nucleic acid sequence encoding an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. One embodiment of the present invention is a nucleic acid molecule encoding an HA-ferritin fusion protein of the present invention, wherein the HA protein is encoded by a nucleotide sequence at least 85%, at least 90%, at least 95%, at least 97% identical or at least 99% identical to a nucleic acid sequence encoding an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, and SEQ ID NO:37. One embodiment of the present invention is a nucleic acid molecule comprising a nucleic acid sequence selected from the group consisting of SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, and SEQ ID NO:37.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:40, SEQ ID NO:43, SEQ ID NO:46, SEQ ID NO:49, SEQ ID NO:52, SEQ ID NO:55, SEQ ID NO:58, SEQ ID NO:61, SEQ ID NO:64, and SEQ ID NO:67. One embodiment of the present invention is a nucleic acid molecule comprising a nucleic acid sequence selected from the group consisting of SEQ ID NO:40, SEQ ID NO:43, SEQ ID NO:46, SEQ ID NO:49, SEQ ID NO:52, SEQ ID NO:55, SEQ ID NO:58, SEQ ID NO:61, SEQ ID NO:64, and SEQ ID NO:67.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, and SEQ ID NO:97. One embodiment of the present invention is a nucleic acid molecule comprising a nucleic acid sequence selected from the group consisting of SEQ ID NO:70, SEQ ID NO:73, SEQ ID NO:76, SEQ ID NO:79, SEQ ID NO:82, SEQ ID NO:85, SEQ ID NO:88, SEQ ID NO:91, SEQ ID NO:94, and SEQ ID NO:97.

One embodiment of the present invention is a nucleic acid molecule comprising a nucleic acid sequence at least about 80%, at least about 85%, at least about 90%, at least about 95%, at least about 97% or at least about 99% identical to a nucleic acid sequence selected from the group consisting of SEQ ID NO:100, SEQ ID NO:103, SEQ ID NO:106, SEQ ID NO:109, SEQ ID NO:112, SEQ ID NO:115, SEQ ID NO:121, SEQ ID NO:124, and SEQ ID NO:127. One embodiment of the present invention is a nucleic acid molecule comprising a nucleic acid sequence selected from the group consisting of SEQ ID NO:100, SEQ ID NO:103, SEQ ID NO:106, SEQ ID NO:109, SEQ ID NO:112, SEQ ID NO:115, SEQ ID NO:121, SEQ ID NO:124, and SEQ ID NO:127.

Also encompassed by the present invention are expression systems for producing fusion proteins of the present invention. In one embodiment, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a recombinant cell comprising a nucleic acid molecule of the present invention. One embodiment of the present invention is a recombinant virus comprising a nucleic acid molecule of the present invention.

As indicated above, the recombinant production of the ferritin fusion proteins of the present invention can take place using any suitable conventional recombinant technology currently known in the field. For example, molecular cloning a fusion protein, such as ferritin with a suitable protein such as the recombinant influenza hemagglutinin protein, can be carried out via expression in *E. coli* with the suitable monomeric subunit protein, such as the *helicobacter pylori* ferritin monomeric subunit. The construct may then be transformed into protein expression cells, grown to suitable size, and induced to produce the fusion protein.

As has been described, because HA-ferritin fusion proteins of the present invention comprise a monomeric subunit of ferritin, they can self-assemble. According to the present invention, the supramolecule resulting from such self-assembly is referred to as a hemagglutinin expressing ferritin based nanoparticle. For ease of discussion, the hemagglutinin expressing ferritin based nanoparticle will simply be referred to as a, or the, nanoparticle (np). Nanoparticles of the present invention have the same structural characteristics as the ferritin proteins described earlier. That is, they contain 24 subunits and have 432 symmetry. In the case of nanoparticles of the present invention, the subunits are the fusion proteins comprising a ferritin monomeric subunit joined to an influenza hemagglutinin protein. Such nanoparticles display at least a portion of the hemagglutinin protein on their surface as hemagglutinin trimers. In such a construction, the hemagglutinin trimer is accessible to the immune system and thus can elicit an immune response. Thus, one embodiment of the present invention is a nanoparticle comprising an HA-ferritin fusion protein, wherein the fusion protein comprises a monomeric ferritin subunit joined to an influenza hemagglutinin protein. In one embodiment, the nanoparticle is an octahedron. In one embodiment, the nanoparticle displays the hemagglutinin protein on its surface as a hemagglutinin trimer. In one embodiment, the influenza hemagglutinin protein is capable of eliciting neutralizing antibodies to an influenza virus. In one embodiment, the monomeric ferritin subunit comprises at least 50 amino acids, at least 100 amino acids, or at least 150 amino acids from an amino acid sequence selected from the group consisting of SEQ ID NO:2 and SEQ ID NO:5, and/or comprises an amino acid sequence at least 85%, at least 90%, at least 95%, at least 97% at least 99% identical to an amino acid sequence selected from the group consisting of SEQ ID NO:2 and SEQ ID NO:5. In one embodiment, the monomeric ferritin subunit comprises SEQ ID NO:2 or SEQ ID NO:5.

In one embodiment, the influenza hemagglutinin protein comprises at least one epitope from an influenza hemagglutinin protein listed in Table 2. In one embodiment, the influenza hemagglutinin protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a hemagglutinin protein of a virus listed in Table 2. In one embodiment, the hemagglutinin protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the hemagglutinin protein comprises a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

In one embodiment, the influenza hemagglutinin protein comprises an amino acid sequence at least 80%, at least 85%, at least 90%, at least 95%, at least 97%, at least 99% identical to the sequence of an hemagglutinin protein from a virus listed in Table 2. In one embodiment, the influenza hemagglutinin protein comprises an amino acid sequence at least 80%, at least 85%, at least 90%, at least 95%, at least 97%, at least 99% identical to a protein sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38.

In one embodiment, the hemagglutinin protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the influenza hemagglutinin protein comprises an amino acid sequence at least 80%, at least 85%, at least 90%, at least 95%, at least 97%, at least 99% identical to a protein sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the hemagglutinin protein comprises a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98.

In one embodiment, the HA-ferritin fusion protein comprises an amino acid sequence at least 80%, at least 85%, at least 90%, at least 95%, at least 97%, at least 99% identical to a protein sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, the HA-ferritin fusion protein comprises an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, the HA-ferritin fusion protein comprises an amino acid sequence at least 80%, at least 85%, at least 90%, at least 95%, at least 97%, at least 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128. In one embodiment, the HA-ferritin fusion protein comprises SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

Because stem region immunogens, HA-ferritin fusion proteins and nanoparticles of the present invention can elicit an immune response to an influenza virus, they can be used as vaccines to protect individuals against infection by influenza virus. According to the present invention a vaccine can be a stem region immunogen, an HA-ferritin fusion protein, or a nanoparticle of the present invention. Thus, one embodiment of the present invention is a vaccine comprising a stem region immunogen, an HA-ferritin fusion protein, or a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C—C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C—C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the disclosure is a ferritin-based nanoparticle vaccine that includes more than one influenza hemagglutinin protein. Such a vaccine can include a combination of different influenza hemagglutinin proteins, either on a single nanoparticle or as a mixture of nanoparticles, at least two of which have a unique influenza hemagglutinin proteins. A multivalent vaccine can comprise as many influenza hemagglutinin proteins as necessary in order to result in production of the immune response necessary to protect against a desired breadth of virus strains. In one embodiment, the vaccine comprises a hemagglutinin protein from at least two different influenza strains (bi-valent). In one embodiment, the vaccine comprises a hemagglutinin protein from at least three different influenza strains (tri-valent). In one embodiment, the vaccine comprises a hemagglutinin protein from at least four different influenza strains (tetra-valent). In one embodiment, the vaccine comprises a hemagglutinin protein from at least five different influenza strains (penta-valent). In one embodiment, the vaccine comprises a hemagglutinin protein from at least six different influenza strains (hexa-valent). In various embodiments, a vaccine comprises a hemagglutinin protein from each of 7, 8, 9, or 10 different strains of influenza virus. An example of such a combination is a ferritin-based nanoparticle vaccine that comprises influenza A group 1 hemagglutinin protein, an influenza A group 2 hemagglutinin protein, and an influenza B hemagglutinin protein. In one embodiment, the influenza hemagglutinin proteins are H1 HA, H3 HA, and B HA. In one embodiment, the influenza hemagglutinin proteins are those included in the 2011-2012 influenza vaccine. Another example of a multivalent vaccine is a ferritin based nanoparticle vaccine that comprises hemagglutinin proteins from four different influenza viruses. In one embodiment, the multivalent vaccine comprises hemagglutinin proteins from H1 A/NC/20/1999, H1 A/CA/04/2009, H2 A/Singapore/1/1957 and H5 A/Indonesia/05/2005. Such a vaccine is described in Example 2.

One embodiment of the present invention is a method to vaccinate an individual against influenza virus, the method comprising administering a nanoparticle to an individual such that an immune response against influenza virus is produced in the individual, wherein the nanoparticle comprises a monomeric subunit from ferritin joined to an influenza hemagglutinin protein, and wherein the nanoparticle displays the influenza hemagglutinin on its surface. In one embodiment, the nanoparticle is a monovalent nanoparticle. In one embodiment, the nanoparticle is multivalent nanoparticle. Another embodiment of the present invention is a method to vaccinate an individual against infection with influenza virus, the method comprising:

a) obtaining a nanoparticle comprising monomeric subunits, wherein the monomeric subunits comprise a ferritin protein joined to an influenza hemagglutinin protein, and wherein the nanoparticle displays the influenza hemagglutinin on its surface; and, b) administering the nanoparticle to an individual such that an immune response against an influenza virus is produced.

One embodiment of the present invention is a method to vaccinate an individual against influenza virus, the method comprising administering a vaccine of the embodiments to an individual such that an immune response against influenza virus is produced in the individual, wherein the vaccine comprises at least one nanoparticle comprising a monomeric subunit from ferritin joined to an influenza hemagglutinin protein, and wherein the nanoparticle displays the influenza hemagglutinin on its surface. In one embodiment, the vaccine is a stem region immunogen. In one embodiment, the vaccine is a nanoparticle. In one embodiment, the vaccine is a monovalent vaccine. In one embodiment, the vaccine is multivalent vaccine. Another embodiment of the present invention is a method to vaccinate an individual against infection with influenza virus, the method comprising:

a) obtaining a vaccine comprising at least one nanoparticle comprising an HA-ferritin fusion protein, wherein the fusion protein comprises a ferritin protein joined to an influenza HA protein, and wherein the nanoparticle displays the influenza HA on its surface; and, b) administering the vaccine to an individual such that an immune response against an influenza virus is produced.

In one embodiment, the nanoparticle is a monovalent nanoparticle. In one embodiment, the nanoparticle is multivalent nanoparticle.

In one embodiment, the nanoparticle is an octahedron. In one embodiment, the influenza hemagglutinin protein is capable of eliciting neutralizing antibodies to an influenza virus. In one embodiment, the influenza HA protein is capable of eliciting broadly neutralizing antibodies to an influenza virus. In one embodiment, the ferritin portion of the fusion protein comprise at least 50 amino acids, at least 100 amino acids, or at least 150 amino acids from an amino acid sequence selected from the group consisting of SEQ ID NO:2 and SEQ ID NO:5, and/or comprises an amino acid sequence at least 85%, at least 90%, at least 95%, at least 97% at least 99% identical to an amino acid sequence selected from the group consisting of SEQ ID NO:2 and SEQ ID NO:5. In one embodiment, the HA portion of the fusion protein comprises at least one epitope from an influenza hemagglutinin protein listed in Table 2. In one embodiment, the HA portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a hemagglutinin protein of a virus listed in Table 2. In one embodiment, the HA portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a protein consisting of a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the HA portion of the fusion protein comprises an amino acid sequence at least 80%, at least 85%, at least 90%, at least 95%, at least 97%, at least 99% identical to the sequence of an HA protein from a virus listed in Table 2. In one embodiment, the HA portion of the fusion protein comprises an amino acid sequence at least 80%, at least 85%, at least 90%, at least 95%, at least 97%, at least 99% identical to a sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the HA portion of the fusion protein comprises at least 25 amino acids, at least 50 amino acids, at least 75 amino acids, at least 100 amino acids, at least 150 amino acids, at least 200 amino acids, at least 300 amino acids, at least 400 amino acids, or at least 500 amino acids from a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the HA portion of the fusion protein comprises an amino acid sequence at least 80%, at least 85%, at least 90%, at least 95%, at least 97%, at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95, and SEQ ID NO:98. In one embodiment, the HA-ferritin fusion protein comprises an amino acid sequence at least 80%, at least 85%, at least 90%, at least 95%, at least 97%, at least 99% identical to a protein sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, the HA-ferritin fusion protein comprises an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, the HA-ferritin fusion protein comprises an amino acid sequence at least 80%, at least 85%, at least 90%, at least 95%, at least 97%, at least 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128. In one embodiment, the HA-ferritin fusion protein comprises SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition The first and second vaccine compositions can be, but need not be, the same composition. Thus, in one embodiment of the present invention, the step of administering the vaccine comprises administering a first vaccine composition, and then at a later time, administering a second vaccine composition. In one embodiment, the first vaccine composition comprises a nanoparticle comprising an HA-ferritin fusion protein of the present invention. In one embodiment, the first vaccine composition comprises a nanoparticle comprising an ectodomain from the hemagglutinin protein of an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the hemagglutinin of the first vaccine composition comprises an amino acid sequence at least about 80% identical to an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, and SEQ ID NO:38. In one embodiment, the first vaccine composition comprises an HA-ferritin fusion protein comprising an amino acid sequence at least 80% identical, at least 85% identical, at least 90% identical, at least 95% identical, at least 97% identical or at least 99% identical to a sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68, wherein the nanoparticle elicits an immune response against an influenza virus. In one embodiment, the first vaccine composition comprises an HA-ferritin fusion protein comprising an amino acid sequence selected from the group consisting of SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, and SEQ ID NO:68. In one embodiment, second vaccine composition comprises a nanoparticle comprising an HA SS-ferritin fusion protein of the present invention. In one embodiment, the HA SS-ferritin fusion protein comprises an amino acid sequence at least 80% identical, at least 85% identical, at least 90% identical, at least 95% identical, at least 97% identical or at least 99% identical to a sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. In one embodiment, the HA SS-ferritin fusion protein comprises an amino acid sequence selected from the group consisting of SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98. In one embodiment, the HA SS-ferritin fusion protein comprises an amino acid sequence at least 80% identical, at least 85% identical, at least 90% identical, at least 95% identical, at least 97% identical or at least 99% identical to SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128, wherein the HA SS-ferritin fusion protein elicits an immune response to an influenza virus. In one embodiment, the HA SS-ferritin fusion protein comprises SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128. In one embodiment, the individual is at risk for infection with influenza virus. In one embodiment, the individual has been exposed to influenza virus. As used herein, the terms exposed, exposure, and the like, indicate the subject has come in contact with a person of animal that is known to be infected with an influenza virus. Vaccines of the present invention may be administered using techniques well known to those in the art. Techniques for formulation and administration may be found, for example, in "Remington's Pharmaceutical Sciences", 18$^{th}$ ed., 1990, Mack Publishing Co., Easton, Pa. Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

In one embodiment, vaccines, or nanoparticles, of the present invention can be used to protect an individual against infection by heterologous influenza virus. That is, a vaccine made using hemagglutinin protein from one strain of influenza virus is capable of protecting an individual against infection by different strains of influenza. For example, a vaccine made using hemagglutinin protein from influenza A/New Caledonia/20/1999 (1999 NC, H1), can be used to protect an individual against infection by an influenza virus including, but not limited to A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 indo, H5), A/Perth/16/2009 (2009 Per, H3), and/or A/Brisbane/59/2007 (2007 Bris, H1).

In one embodiment, vaccines, or nanoparticles, of the present invention can be used to protect an individual against infection by an antigenically divergent influenza virus. Antigenically divergent refers to the tendency of a strain of influenza virus to mutate over time, thereby changing the amino acids that are displayed to the immune system. Such mutation over time is also referred to as antigenic drift. Thus, for example, a vaccine made using hemagglutinin protein from a A/New Caledonia/20/1999 (1999 NC, H1) strain of influenza virus is capable of protecting an individual against infection by earlier, antigenically divergent New Caledonia strains of influenza, and by evolving (or diverging) influenza strains of the future.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1

Figure 1:
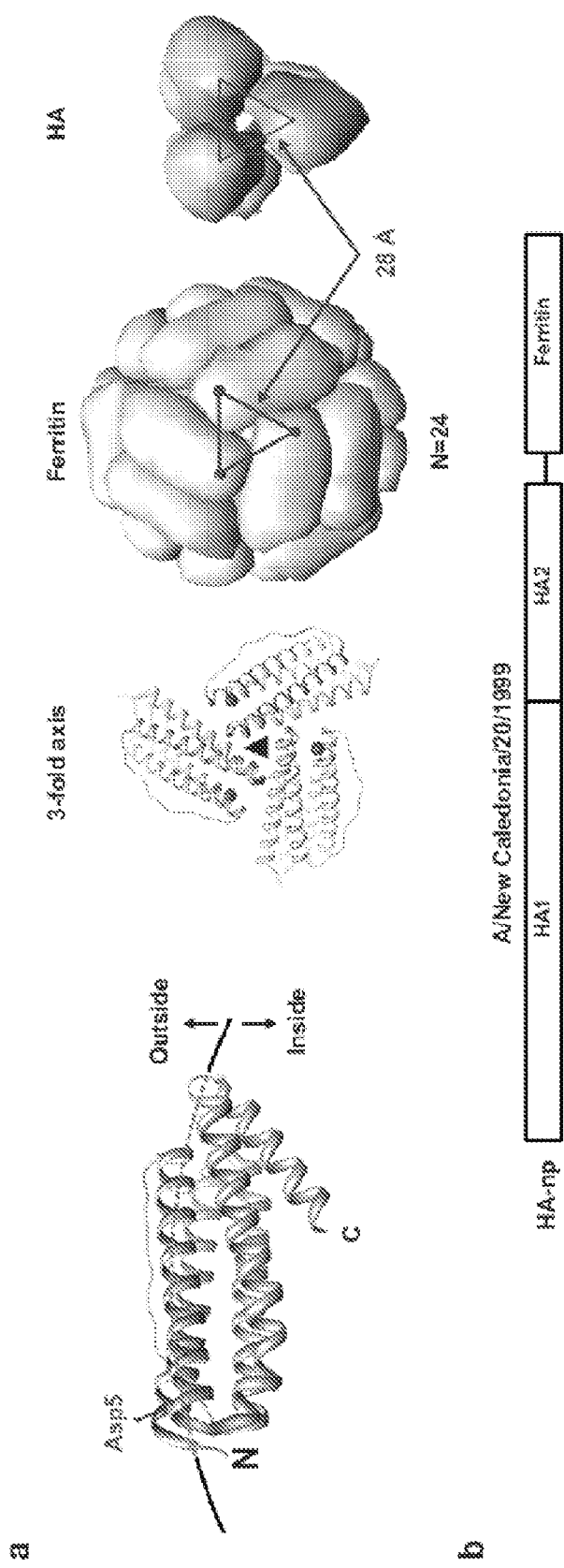
FIG. 1. Molecular design and construction of ferritin particles displaying influenza virus hemagglutinin. (a) Ribbon diagram of a subunit of *H. pylori* nonheme ferritin (PDB: 3bve) (left). Amino- and carboxyl-termini are labeled as N and C, respectively. Three ferritin subunits surrounding an octahedral three-fold axis are shown as a ribbon diagram (middle). Residue Asp5 is indicated. The octahedral assembly of the ferritin particle (viewed at 8 Å resolution along an octahedral three-fold axis) and A/Solomon Islands/3/2006 (H1N1) HA trimer (PDB: 3sm5) (viewed down from membrane proximal side) (right). The measured average distance between the Asp5 residues in each ferritin subunit surrounding an octahedral three-fold axis is shown as a triangle. The same equilateral triangle (a=b=c=28 Å) is also drawn on the HA trimer (right). (b) Schematic representation of the HA-ferritin expression vector used for protein production. (c) Chromatogram of the size exclusion chromatography of ferritin nanoparticles (np) and HA-np (left). Molecular weights (kDa) of calibration standards are indicated above the curves with vertical lines. Calculated molecular weights for ferritin nanoparticles and HA-np were 419 and 2,165 kDa, respectively, and were within 10% of the predicted molecular weights (408 and 2,040 kDa, respectively). Particle size distribution (radius) of purified ferritin nanoparticles and HA-np was determined by dynamic light scattering (middle). Measured mean diameters (d) are indicated. The polydispersity indices of purified ferritin np and HA-np were 0.035 and 0.011, respectively. Purified HA trimer (thrombin uncleaved), HA-np and ferritin nanoparticles were analyzed by SDS-PAGE (right). (d) Negatively stained transmission electron microscopy images of ferritin nanoparticles (left) and HA-np (right). Images were originally recorded at 67,000× magnification. (e) Models representing octahedral four-, three- and two-fold symmetries of HA-ferritin np (top panels) and actual TEM image (bottom panels) are shown. Visible HA spikes are numbered in the images.
Figure 1:
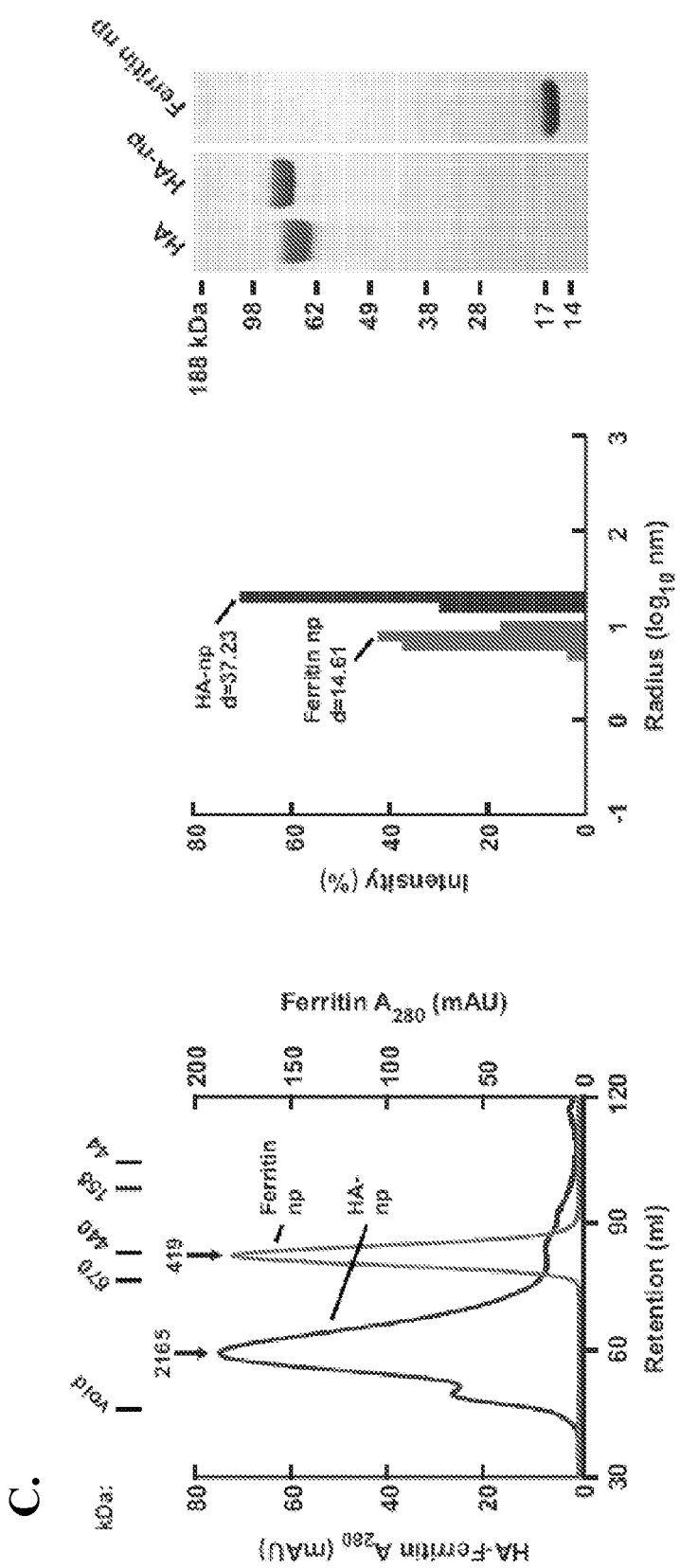
Figure 1:
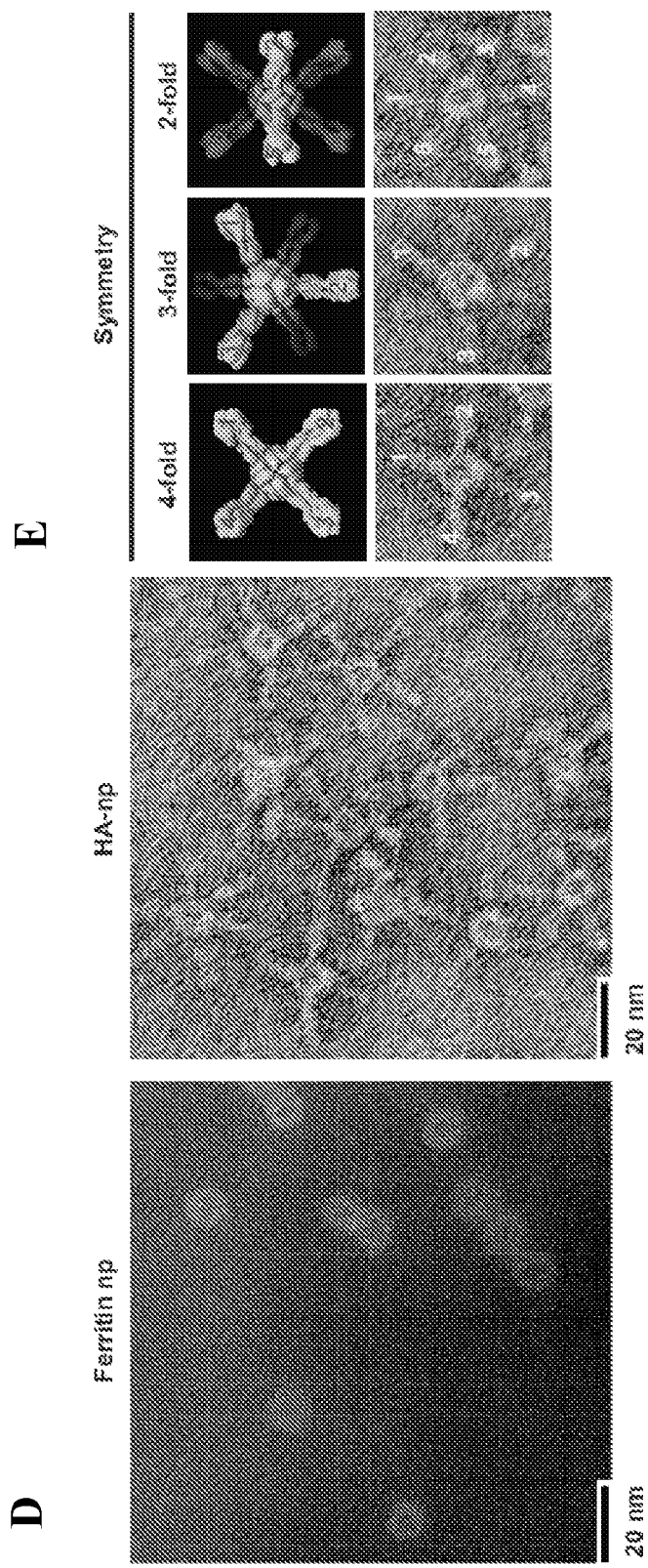

Design and Production of Ferritin-Based Nanoparticles Expressing Influenza Virus HA This Example demonstrates the ability of HA-ferritin fusion proteins to form nanoparticles. Analysis of ferritin structure suggested that it was possible to insert a heterologous protein, specifically influenza virus HA, so that it mimics a physiologically relevant trimeric viral spike (FIG. 1A). Ferritin forms a nearly spherical particle consisting of 24 subunits arranged with octahedral symmetry around a hollow interior. The symmetry of the ferritin nanoparticles includes eight three-fold axes on the surface. The aspartic acid (Asp) at residue 5 near the $NH_2$ terminus is readily accessible, and the distance (28 Å) between each Asp5 on the three-fold axis is almost identical to the distance between the central axes of each HA2 subunit of trimeric HA (FIG. 1A, right).

Vector Construction.

The HA-ferritin fusion proteins were constructed by joining the ectodomain of A/New Caledonia/20/1999 (1999 NC) HA to ferritin (FIG. 1B). Specifically, the gene encoding *H. pylori* nonheme iron-containing ferritin (GenBank NP_223316) with a point mutation (N19Q) to abolish a potential N-linked glycosylation site was synthesized by PCR-based accurate synthesis (M. F. Bachmann, R. M. Zinkernagel, Neutralizing antiviral B cell responses. *Annu Rev Immunol* 15, 235-270 (1997)) using human-preferred codons. The human CD5 leader sequence and a serine-glycine-glycine (SGG) spacer were joined to the gene fragment encoding ferritin (residues 5-167) to generate a secreted protein. The plasmids encoding various influenza virus HAs, including A/South Carolina/1/1918 (1918 SC), GenBank AF117241; A/Puerto Rico/8/1934 (1934 PR8), UniProt P03452; A/Singapore/6/1986 (1986 Sing), GenBank ABO38395; A/Beijing/262/1995 (1995 Beijing), GenBank AAP34323; A/New Caledonia/20/1999 (1999 NC), GenBank AY289929; A/Solomon Islands/3/2006 (2006 SI), GenBank ABU99109; A/Brisbane/59/2007 (2007 Bris), GenBank ACA28844; A/California/04/2009 (2009 CA), GenBank ACP41105; A/Perth/16/2009 (H3 2009 Perth), GenBank ACS71642; B/Florida/04/2006 (B 2006 Florida), GenBank ACA33493 and their corresponding NAs with human preferred codons were synthesized as previously reported (C. J. Wei et al., Induction of broadly neutralizing H1N1 influenza antibodies by vaccination. *Science* 329, 1060-1064 (2010)). The gene fragments encoding HAs (residues HA1 1-HA2 174, H3 numbering) from 1999 NC HA, 2009 CA HA, 2009 Perth H3 and 2006 Florida B were amplified and joined to the ferritin gene fragment (residues 5-167) with an SGG linker to give rise to the HA-ferritin fusion gene. To produce soluble trimeric HA, the 1999 NC HA gene fragment (residues HA1 1-HA2 174, H3 numbering) was joined to a thrombin cleavage site followed by a foldon trimerization motif and a poly-histidine tag as described previously (A. S. Xiong et al., PCR-based accurate synthesis of long DNA sequences. *Nat Protoc* 1, 791-797 (2006)). Both full length and soluble forms of 1999 NC ΔStem (C. J. Wei et al., Induction of broadly neutralizing H1N1 influenza antibodies by vaccination. *Science* 329, 1060-1064 (2010)) and ΔRBS HA mutants were generated by introducing an N-linked glycosylation site at residues HA2 45 (I45N/G47T) and HA1 190 (Q192T), respectively. The soluble form of 2007 Bris ΔRBS HA mutant was generated by introducing an N-linked glycosylation site at the same site. All genes were then cloned into mammalian expression vectors for efficient expression (C. J. Wei et al., Comparative efficacy of neutralizing antibodies elicited by recombinant hemagglutinin proteins from avian H5N1 influenza virus. *J Virol* 82, 6200-6208 (2008)). Plasmids encoding the mAbs, CR6261 (D. C. Ekiert et al., Antibody recognition of a highly conserved influenza virus epitope. *Science* 324, 246-251 (2009)), CH65 (J. R. Whittle et al., Broadly neutralizing human antibody that recognizes the receptor-binding pocket of influenza virus hemagglutinin. *Proc Natl Acad Sci USA* 108, 14216-14221 (2011)) and a single-chain variable fragment F10 (J. Sui et al., Structural and functional bases for broad-spectrum neutralization of avian and human influenza A viruses. *Nat Struct Mol Biol* 16, 265-273 (2009)) were also synthesized as described by C. J. Wei et al., (*Science* 329, 1060-1064 (2010).

Protein Biosyntheses and Purifications.

To produce ferritin nanoparticles, HA-np and trimeric HA, the expression vectors were transfected into 293F cells (Invitrogen), a human embryonic kidney cell line using 293fectin (Invitrogen) according to the manufacturer's instructions. Matched NAs were co-transfected at 20:1 HA:NA (wt:wt). The cells were grown in Freestyle 293 expression medium (Invitrogen) and the culture supernatants were collected 4 days post-transfection by centrifugation and filtered through a 0.22 μm pore filter unit (Nalgene) to remove cell debris. The supernatants were concentrated with a 30 kDa molecular weight cut-off filter unit (Pall Corp.) and then buffer exchanged to a Tris buffer (20 mM Tris, 50 mM NaCl, pH 7.5 for ferritin nanoparticles; 20 mM Tris, 500 mM NaCl, pH 7.5 for HA-np). The ferritin nanoparticles were purified by ion-exchange chromatography using a HiLoad 16/10 Q Sepharose HP column (GE Healthcare). The HA-np were purified by affinity column chromatography using *Erythrina cristagalli* agglutinin (ECA, coral tree lectin; EY Laboratories, Inc.) specific for galactose β(1,4)N-acetylglucosamine. The ferritin nanoparticles and HA-np were further purified by size exclusion chromatography with a Superose 6 PG XK 16/70 column (GE Healthcare) in PBS. The peak fraction was collected and used for further studies. The molecular weights of the ferritin nanoparticle and HA-np were calculated based on two equations generated by least squares linear regression on a semi-log plot using gel filtration low and high molecular weight standards (Bio-Rad), respectively. The yield of 1999 NC HA-np is ~4 mg liter$^{-1}$ and appears stable at 4° C. or frozen at −80° C. The trimeric HA proteins were purified as described by A. S. Xiong et at (*Nat Protoc* 1, 791-797 (2006)) with slight modifications. Briefly, HA proteins were first purified by affinity chromatography using Ni Sepharose HP resin (GE Healthcare), and then were separated by size exclusion chromatography with a HiLoad 16/60 Superdex 200 PG column (GE Healthcare). To remove the foldon trimerization motif and poly-histidine tag, HA proteins were digested with thrombin (EMD Chemicals, Inc.) (3 U mg ml$^{-1}$) overnight at 4° C. Undigested proteins were removed by passing over Ni Sepharose HP resin and the digested HAs were purified on a HiLoad 16/60 Superdex 200 PG column. All purified proteins were verified by SDS-PAGE. Protein purity and size distribution were examined by dynamic light scattering using a DynaPro system (Wyatt Technology). All human mAbs and a single-chain variable fragment were also produced in 293F cells and purified as described previously (C. J. Wei et al., Induction of broadly neutralizing H1N1 influenza antibodies by vaccination. *Science* 329, 1060-1064 (2010); W. P. Kong et al., Protective immunity to lethal challenge of the 1918 pandemic influenza virus by vaccination. *Proc Natl Acad Sci USA* 103, 15987-15991 (2006)). MAbs against 1999 NC HA were purified from hybridoma supernatants as previously described (C. J. Wei et al., Induction of broadly neutralizing H1N1 influenza antibodies by vaccination. *Science* 329, 1060-1064 (2010)).

Iodixanol-Based Gradient Centrifugation.

Alternatively, HA-np were purified by iodixanol gradient ultracentrifugation (FIG. 10) routinely used for virus and VLP purifications (C. J. Wei et al., Cross-neutralization of 1918 and 2009 influenza viruses: role of glycans in viral evolution and vaccine design. *Sci Transl Med* 2, 24ra21 (2010)). Fractions containing HA np were confirmed by SDS-PAGE and Western blotting using a mAb against 1999 NC HA.

Electron Microscopic Analysis.

Purified ferritin nanoparticles and HA-np were subjected to transmission electron microscopic analysis. The samples were negatively stained with phosphotungstic acid (ferritin nanoparticles) or ammonium molybdate (HA-np) and images were recorded on a Tecnai T12 microscope (FEI) at 80 kV with a CCD camera (AMT Corp.).

Analysis of HA-Ferritin Np.

Figure 2:
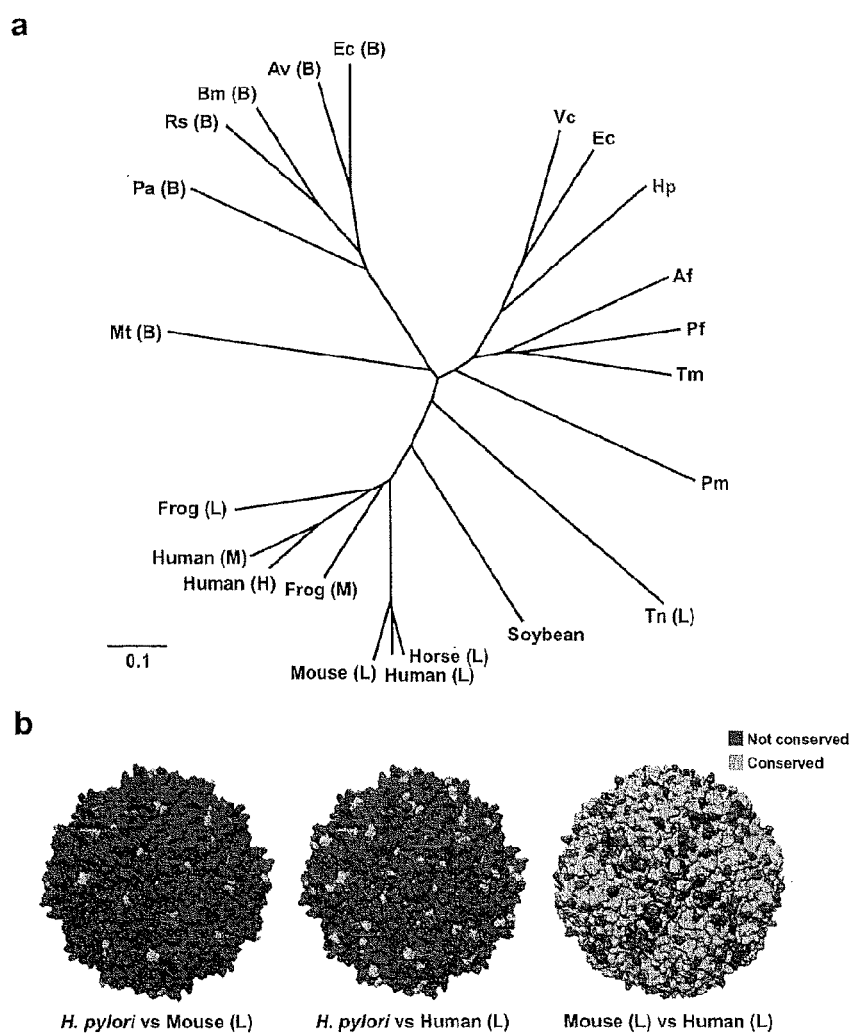
FIG. 2. Genetic and structural comparison of ferritins. (a) Phylogenetic tree analysis of ferritins found in RSCB PDB. Twenty-two sequences contain 16 ferritins including Vc (*Vibrio cholerae*), Ec (*E. coli*), Hp (*H. pylori*), Af (*Archaeoglobus fulgidus*), Pf (*Pyrococcus furiosus*), Tm (*Thermatoga maritime*), Pm (*Pseudo-nitzschia multiseries*), Tn (L) (*Trichoplusia ni* light chain), Soybean (chloroplastic), Horse (L) (light chain), Human (L), (H) and (M) (light, heavy chains and mitochondrial, respectively), Mouse (L) (light chain), and Frog (M) and (L) (middle and lower subunits, respectively), and 6 bacterioferritins (B) including Mt (B) (*Mycobacterium tuberculosis*), Pa (B) (*Pseudomonas aeruginosa*), Rs (B) (*Rhodabacter sphaeroides*), Bm (B) (*Brucella melitensis*), Av (B) (*Azobacter vinelandii*), and Ec (B). Protein sequences were aligned using Clustal W2 (www.ebi.ac.uk/Tools/msa/clustalw2) with Gonnet matrix and a phylogenetic tree was generated with the Phylodendron program (http://iubio.bio.indiana.edu/treeapp/treeprint-form.html) using the neighbor-joining method. (b) Comparison of surface exposed residues between *H. pylori* and mouse (light chain) (left) or human (light chain) (middle), and mouse and human (light chains) (right). Conservation of surface exposed residues was rendered by UCSF Chimera using a protein sequence alignment generated by Clustal W2. Conserved and varied residues between the two ferritins are shown as light and dark residues, respectively. PDB files 3bve (*H. pylori*) (left and middle) and 1 h96 (mouse light chain) (right) were used for surface rendering.

Among the various ferritins, *Helicobacter* (*H.*) *pylori* nonheme ferritin (K. J. Cho et al., The crystal structure of ferritin from *Helicobacter pylori* reveals unusual conformational changes for iron uptake. *J Mol Biol* 390, 83-98 (2009)) was selected as a prototype because of its highly divergent sequence compared to mammalian ferritins (FIG. 2), thus minimizing the likelihood of inducing autoimmunity after vaccination. The final purification step for recombinant HA-ferritin was size exclusion chromatography (FIG. 1C, left) and dynamic light scattering was used to confirm that both ferritin and HA-ferritin self-assembled into supramolecules with diameters of 14.61 and 37.23 nm, respectively (FIG. 1C, middle). HA-ferritin and ferritin subunits from these nanoparticles migrated at the expected respective molecular weights of 85 and 17 kDa by SDS-PAGE compared to 68 kDa for purified HA (FIG. 1C, right). While the morphology of the ferritin nanoparticles was smooth, as visualized by transmission electron microscopy (TEM), HA-ferritin formed np that exhibited clearly visible spikes around the spherical core (FIG. 1D, Ferritin np vs. HA-np). Remarkably, the placement of these spikes clearly illustrated the octahedral symmetry of the HA-np design. Octahedral two-, three- and four-fold axes were distinctly observed in the TEM image (FIG. 1E, right). These data demonstrated the formation of HA spikes on self-assembling HA-ferritin nanoparticles. More importantly, this design enabled HAs from different subtypes or influenza B viruses to be readily joined to a ferritin core without substantial modification.

Example 2

Antigenicity and Immunogenicity of HA-Np in Mice

To verify the antigenicity of the HA spikes on the np, HA-ferritin np were analyzed for their ability to react with anti-HA head ab and a conformation-dependent monoclonal ab (mAb), CR6261, that recognizes a highly conserved structure in the trimeric HA stem and neutralizes diverse influenza A group 1 viruses D. C. Ekiert et al., Antibody recognition of a highly conserved influenza virus epitope. *Science* 324, 246-251 (2009)), using ELISA and a virus neutralization assay.

Analysis by ELISA.

Purified trimeric HA, HA-np, and TIV (2 μg of H1 HA ml$^{-1}$), ferritin nanoparticles (0.68 μg ml$^{-1}$ for FIG. 3 or 2 μg ml$^{-1}$ for the rest), mouse liver ferritin (2 μg ml$^{-1}$, Alpha Diagnostic International, Inc.), ΔStem and ΔRBS HA trimer (2 μg ml$^{-1}$) were coated (100 μl/well) onto MaxiSorp™ plates (Nunc) and the wells were probed with the anti-HA mAbs, anti-mouse liver ferritin IgG (Alpha Diagnostic International, Inc.) or immune sera followed by peroxidase-conjugated secondary antibodies (anti-mouse IgG and anti-human IgG, SouthernBiotech; anti-ferret IgG, Rockland Immunochemicals, Inc.). The wells were developed using a SureBlue chromogen (KPL) and the reaction was stopped by adding 0.5 M sulfuric acid. For the ELISA-based competition assay, HA trimer (2 μg ml$^{-1}$) was coated onto the plates. Plates were incubated with an anti-stem mAb, CR6261 (8 μg ml$^{-1}$) or an isotype control Ab, VRC01 (8 μg ml$^{-1}$) (Z. Y. Yang et al., Immunization by avian H5 influenza hemagglutinin mutants with altered receptor binding specificity. *Science* 317, 825-828 (2007); X. Wu et al., Rational design of envelope identifies broadly neutralizing human monoclonal antibodies to HIV-1. *Science* 329, 856-861 (2010)) before adding serially diluted pre-absorbed ferret immune sera. The wells were probed with anti-ferret IgG and developed as described above. Absorbance at 450 nm was measured by SpectraMax M2e (Molecular Devices). The endpoint titers were determined by calculating the intersection of the observed binding curve and the absorbance threshold (four times background).

Neutralization Assays.

HA/NA-pseudotyped lentiviral vectors encoding luciferase were used. Immune sera used for the assay were pretreated with RDE as described above. Pre-titrated pseudotyped viruses (Gag p24≈6.25 ng ml$^{-1}$) were incubated with serially diluted sera for 20 minutes at room temperature and added to 293A cells (10,000 cells/well in a 96-well plate; 50 µl/well; in triplicate). Plates were then washed and replaced with fresh media 2 hours later, and luciferase activity was measured after 24 hours. For the protein competition assay, neutralizing activity of the mAbs F10, CR6261 or immune sera was measured in the presence of competitor proteins, trimeric HA (WT, ΔStem or ΔRBS), HA-np, ferritin nanoparticles or irrelevant protein (HIV-1 gp120) at final concentration of 20 and 25 µg ml$^{-1}$ for mAbs and immune sera, respectively. The HA-np was able to bind to anti-head or anti-stem mAbs with affinities similar to trimeric HA or trivalent inactivated vaccine (TIV) containing the same 1999 NC HA at equimolar concentrations of HA, in contrast to a ferritin nanoparticle control (FIG. 3A). Analogous to trimeric HA, the HA-np also blocked neutralization by CR6261 and another stem-directed mAb, F10 (4 J. Sui et al., Structural and functional bases for broad-spectrum neutralization of avian and human influenza A viruses. *Nat Struct Mol Biol* 16, 265-273 (2009)) (FIG. 3B). These results indicated that HA molecules on the HA-np antigenically resembled the physiological trimeric viral spike.

Example 3

Immunogenicity of HA-Ferritin Np In Vivo

This Example demonstrates the ability of HA-ferritin np of the present invention to elicit neutralizing antibodies.

To assess the immunogenicity of the HA-ferritin np in vivo, mice were immunized twice with HA-np or TIV's from the 2006-2007 season, with HAs from A/New Caledonia/20/1999 (H1N1), A/Wisconsin/67/2005 (H3N2) and B/Malaysia/2504/04 (type B), or from the 2011-2012 season, with HAs from A/California/07/09-like (H1N1), A/Perth/16/09 (H3N2) and B/Brisbane/60/08 (type B). Briefly, female BALB/c mice (6-8 weeks old; Charles River Laboratories) were immunized (5 mice/group) intramuscularly with 5 or 0.5 µg (1.67 or 0.17 µg of H1 HA) of TIV, 2.24 or 0.22 µg (1.67 or 0.17 µg of HA) of HA-np or 0.57 µg of ferritin nanoparticles (equimolar to 2.24 µg of HA-np) in 100 µl of PBS or in 100 µl of 50% (v/v) mixture of Ribi adjuvant (Sigma) in PBS at weeks 0 and 3. A group of BALB/c mice (n=4) was immunized with 20 µg of trimeric HA (thrombin cleaved) in 100 µl of 50% (v/v) mixture of Ribi adjuvant in PBS at weeks 0 and 4. For the experiment using trivalent HA-np, mice were immunized (n=5) with 6.72 µg (1.67 µg of each HA component) of trivalent HA-np in 100 µl of 50% (v/v) mixture of Ribi adjuvant in PBS at weeks 0 and 3. Blood samples were collected prior to the first dose, and at 2 weeks after each immunization.

Figure 4:
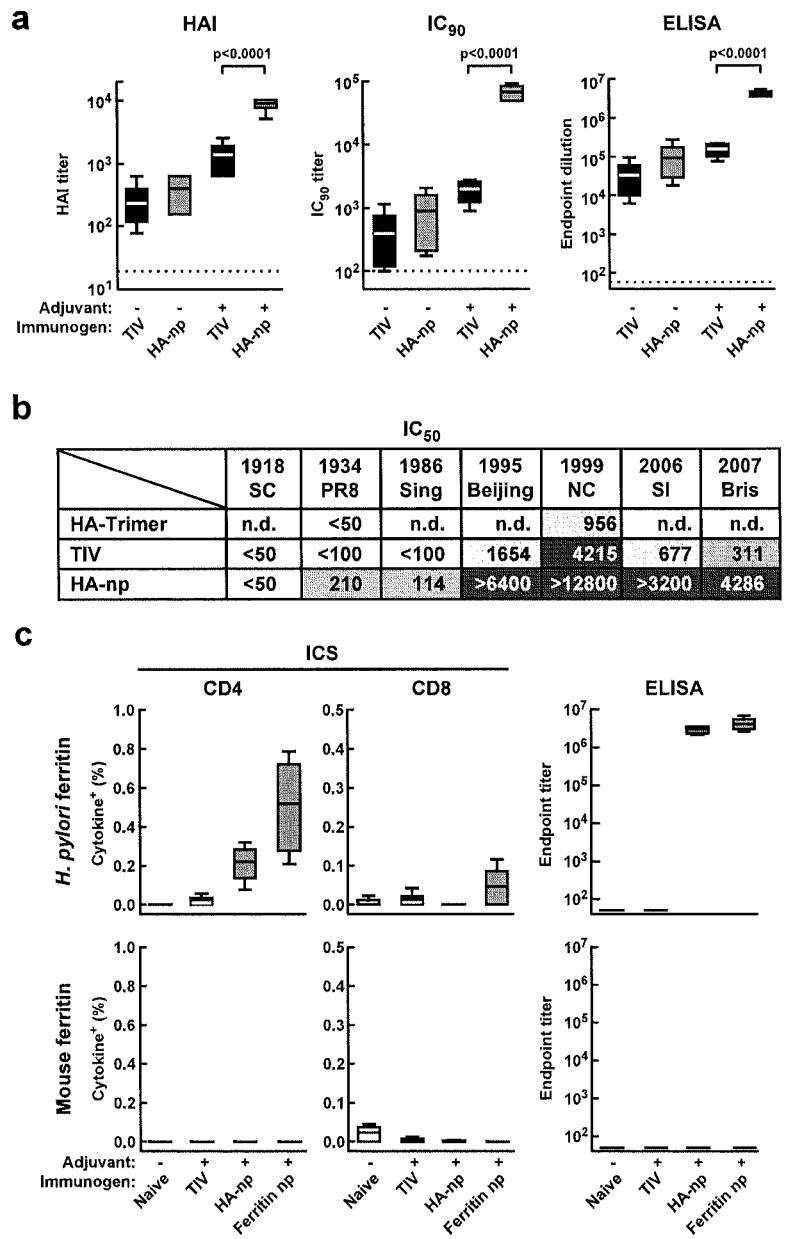
FIG. 4. Immune responses in HA-np-immunized mice. (a) HAI (left), $IC_{90}$ neutralization (middle), and anti-HA ab endpoint titers (right) against 1999 NC HA after two immunizations with 0.17 μg (amount of H1 HA) of TIV or HA-np with or without Ribi adjuvant and a 3-week interval. The immune sera were collected 2 weeks after the second immunization. The data are presented as box-and-whiskers plots (boxed from lower to upper quartile with whiskers from minimum to maximum) with lines at the mean (n=5). (b) Neutralization breadth of the immune sera elicited by HA-trimer, TIV, or HA-np. An additional group of mice (n=4) was immunized twice with 20 μg of trimeric HA protein using Ribi adjuvant and a 4-week interval. The immune sera were collected 2 weeks after the second immunization. $IC_{50}$ neutralization titers against a panel of H1N1 pseudotyped viruses were determined. (c) Cellular and humoral immune responses against *H. pylori* (top) and mouse (bottom) ferritins. Mice were immunized twice with 1.67 μg (amount of H1 HA) of TIV or HA-np, or 0.57 μg of ferritin nanoparticles (equimolar to HA-np) using Ribi adjuvant and a 3-week interval. The splenocytes and immune sera were harvested 11 days after the second immunization. Cytokine-producing CD4$^+$ and CD8$^+$ T cells were measured by ICS (left), and ab response was detected by ELISA (right). All cells expressing IFN-γ, TNFα, or IL-2 were identified as cytokine$^+$ cells. The percentage of cytokine$^+$ cells in CD4$^+$ and CD8$^+$ T cells that were activated in response to stimulation with specific peptides covering the entire *H. pylori* or mouse ferritins (heavy and light chains combined) were plotted. Recombinant *H. pylori* and purified mouse (liver) ferritins were used for detecting anti-ferritin ab responses. The data are presented as box-and-whiskers plots with lines at the mean (n=5).

The resulting antibody titers were determined as described in Example 2. The HA-np induced significantly higher HAI titers than TIV (FIG. 4A, left; p<0.0001), and a similar effect was observed in the neutralization assay and ELISA (FIG. 4A, middle and right; p<0.0001). For example, neutralization titers elicited by HA-np as assessed by the concentration of ab needed to inhibit viral entry by 90% (IC$_{90}$) were ~34 times higher than TIV (FIG. 4A, middle). Because higher titers were observed in groups with the adjuvant Ribi, further comparisons were performed with this adjuvant. Neutralization against a panel of H1N1 strains revealed not only increased potency but also enhanced breadth stimulated by HA-np compared with TIV or trimeric HA (FIG. 4B). Neutralization against two highly divergent H1N1 viruses, A/Puerto Rico/8/1934 (1934 PR8) and A/Singapore/6/1986 (1986 Sing) were only observed in mice immunized with the HA-np, and the titer against the contemporary virus A/Brisbane/59/2007 (2007 Bris) was more than one log higher in mice immunized with HA-np than with TIV (FIG. 4B).

Figure 5:
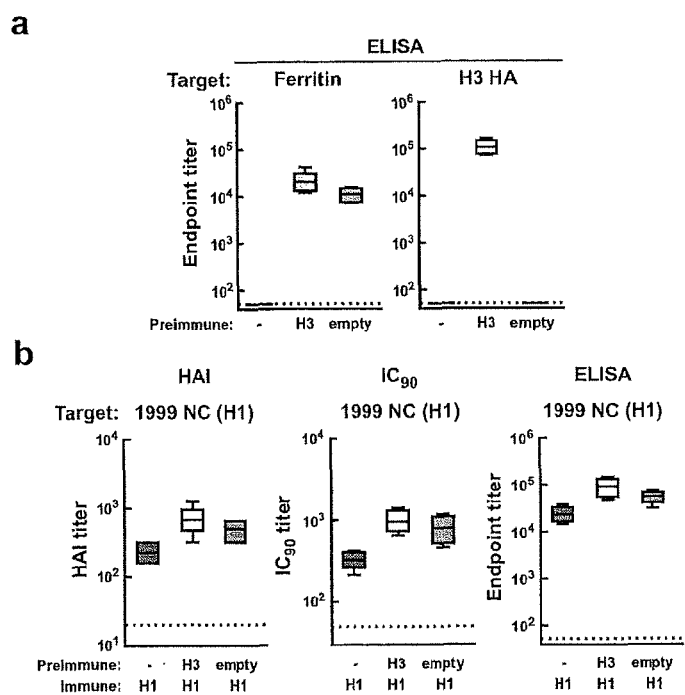
FIG. 5. Successive immunization of HA-nanoparticles in mice. Mice were pre-immunized with 1.67 μg (amount of HA) of 2009 Perth (H3) HA-nanoparticles or 0.57 μg (equimolar to HA-nanoparticle) of empty ferritin nanoparticles at week 0 and then immunized with 1.67 μg (amount of HA) of 1999 NC (H1) HA-nanoparticles at week 3. Ribi was used as an adjuvant. Another group of mice was immunized with 1999 NC (H1) HA-nanoparticles without pre-immunization of empty ferritin nanoparticles or H3 HA-nanoparticles. (a) Ab responses to *H. pylori* ferritin (left) and 2009 Perth H3 HA (right). Immune sera collected 2 weeks after the immunization with H3 HA-nanoparticles or empty ferritin nanoparticles were analyzed by ELISA. (b) Immune responses to 1999 NC (H1) after 1999 NC (H1) HA-nanoparticle immunization. Naïve mice or mice with pre-immunity to ferritin or H3 HA were immunized with H1 HA-nanoparticles at week 3 and HAI (left), $IC_{90}$ neutralization (middle) and ELISA (right) Ab titers were measured 2 weeks after the immunization. The data are presented as box-and-whiskers plots with lines at the mean (n=5).

To assess whether the preexisting immune responses to ferritin nanoparticles or to other HA subtypes would attenuate the immunogenicity of the subsequent immunization of HA-np, mice were pre-immunized with either H3 (A/Perth/16/09, 2009 Perth) HA-np or empty ferritin nanoparticles to elicit anti-H3 HA and/or anti-*H. pylori* ferritin immune responses (FIG. 5A). These animals were then immunized with H1 (1999 NC) HA-np. Comparable HAI, IC$_{90}$ neutralization and ELISA titers against 1999 NC HA were observed in naïve animals as well as in groups pre-immunized with H3 HA-np or empty ferritin nanoparticles (FIG. 5B). These results indicated that preexisting anti-*H. pylori* ferritin immunity did not diminish the HA-specific ab response.

Example 4

Lack of Autoreactivity of *H. pylori* Ferritin Nanoparticles

This Example demonstrates analyzes the ability of HA-ferritin np of the present invention to elicit an auto-immune response against autologous ferritin in mice.

Although the overall structural architecture and physiological functions of ferritin are conserved across organisms, murine ferritin has only 27% amino acid sequence identity to *H. pylori* ferritin. This homology nonetheless raised the possibility that immunization with *H. pylori* ferritin in mice might abrogate immune tolerance and induce autoimmunity. To address this concern, CD4, CD8 T-cell and ab responses against both murine and *H. pylori* ferritins were analyzed by intracellular cytokine staining (ICS) and ELISA in mice immunized with HA-np. ELISAs were performed according to the procedure in Example 2. For intracellular cytokine analysis, CD4$^+$ and CD8$^+$ T-cell responses were evaluated for interferon-γ (IFN-γ), tumor necrosis factor α (TNFα), and interleukin-2 (IL-2) as described by T. Zhou et al. (*Science* 329, 811-817 (2010)). Individual peptide pools (15-mer overlapping by 11 residues, 2.5 µg ml$^{-1}$ for each peptide) covering *H. pylori* ferritin or mouse ferritin light and heavy chains were used to stimulate cells. After stimulation, cells were fixed, permeabilized and stained using anti-mouse CD3, CD4, CD8, IFN-γ, TNFα and IL-2 mAbs (BD Pharmingen) together with aqua blue dye for live/dead stain (Invitrogen). The data were collected by LSR II Flow Cytometer (BD Biosciences) and IFN-γ-, TNFα- and IL-2-positive cells in the CD4$^+$ and CD8$^+$ cell populations were analyzed with FlowJo software (Tree Star).

Although an increase in the ICS staining of CD4$^+$ T cells stimulated with *H. pylori* ferritin peptides (FIG. 4C, top left) was observed, no increases in the CD4$^+$ and CD8$^+$ ICS responses were seen with murine ferritin peptide stimulation (FIG. 4C, bottom left and middle). In addition, while high titers (>10$^6$) of anti-*H. pylori* ferritin abs were detected in ferritin nanoparticle- and HA-np-immune sera, abs to mouse ferritin were undetectable (FIG. 4C, right). These results demonstrate that HA-ferritin np of the present invention do not elicit autoreactivity to autologous ferritin in mice.

Example 5

Generation of Trivalent HA-Np and Immunogenicity in Mice

The Example analyzes whether multivalent HA-np were similar in immunogenicity to monovalent np.

Figure 6:
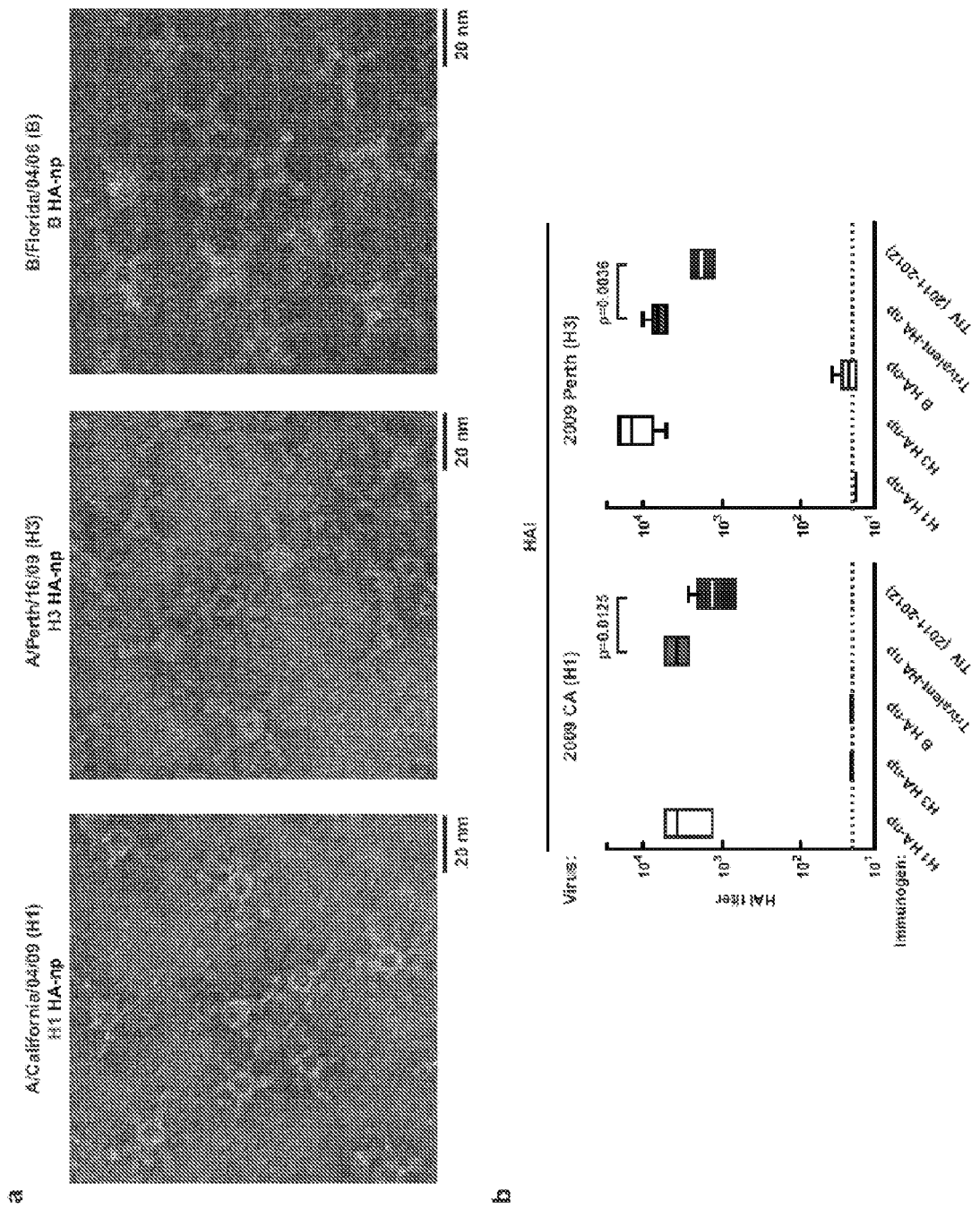
FIG. 6. Development of trivalent HA-np. (a) HA-np consisting of HAs from 2009 CA (H1), 2009 Perth (H3) or 2006 FL (type B) were purified and visualized by TEM. (b) HAI titers against 2009 CA (H1N1) and 2009 Perth (H3N2) viruses in immunized mice. Mice were immunized twice with 1.67 μg (amount of HA) of monovalent H1, monovalent H3, monovalent type B, or 5.0 μg (total amount of HA) of trivalent HA-np or TIV (2011-2012 season) using Ribi adjuvant with a 3-week interval. Immune sera were collected 2 weeks after the second immunization. The data are presented as box-and-whiskers plots with lines at the mean (n=5).

HA-np expressing HAs from H1 (A/California/04/09, 2009 CA), H3 (2009 Perth) or influenza B (B/Florida/04/06, 2006 FL) were generated. The 2009 CA (H1)-, 2009 Perth (H3)- and 2006 FL (type B)-HA-np self-assembled and displayed the same morphology observed for 1999 NC HA-np (FIG. 6A). Trivalent HA-np were generated by combining three monovalent HA-np, and their immunogenicity was compared to a seasonal TIV containing the same H1 and H3 strains and a mismatched type B (B/Brisbane/60/08). HAI titers against homologous H1N1 and H3N2 viruses were significantly increased in animals immunized with trivalent HA-np relative to TIV-immunized animals (FIG. 6B; p=0.0125 and 0.0036, respectively). When compared to animals immunized with the corresponding monovalent HA-np, HAI titers against 2009 CA (H1) and 2009 Perth (H3) induced by trivalent HA-np were comparable (FIG. 6B). These results demonstrate that no substantial antigenic competition between H1 and H3 HA-np was observed with a trivalent HA-np vaccine.

Example 6

Cross-Protective Immunity Elicited by HA-Np in Ferrets

This Example demonstrates that vaccination of ferrets with 1999 NC HA-np elicits a protective immunity similar to that observed in human disease.

Male Fitch ferrets (6 months old; Triple F Farms), seronegative for exposure to H1N1, H3N2 and type B influenza viruses, were housed and cared for at BIOQUAL, Inc. (Rockville, Md.). Prior to study start, a temperature transponder (Biomedic Data Systems, Inc.) was implanted into the neck of each ferret. Ferrets were immunized (6 ferrets/group) intramuscularly with 500 µl of PBS, 7.5 µg (2.5 µg of H1 HA) of TIV or 3.35 µg (2.5 µg of HA) of HA-np in 500 µl of 50% (v/v) mixture of Ribi adjuvant in PBS at weeks 0 and 4. Blood was collected 3 and 2 weeks after the first and the second immunization, respectively.

Figure 7:
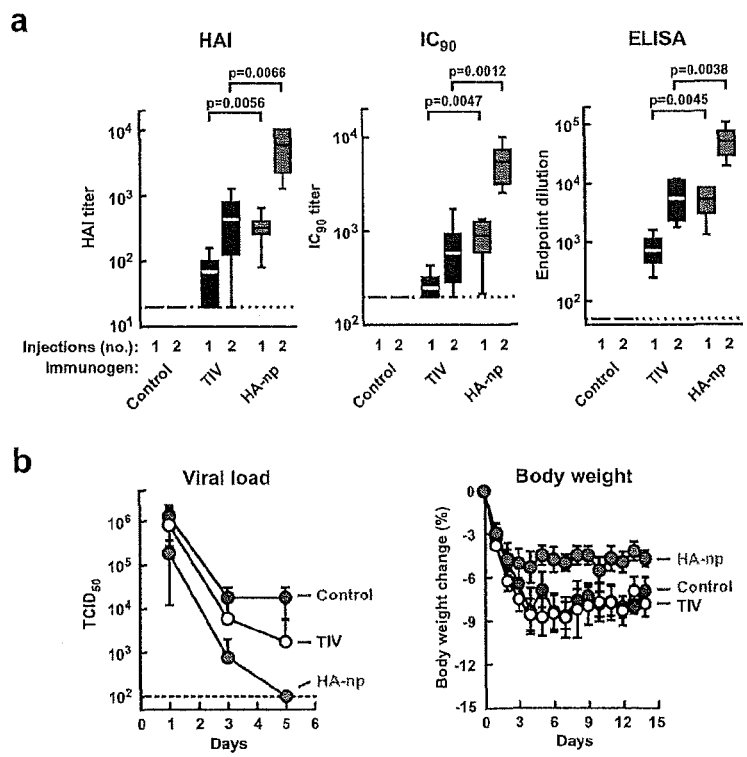
FIG. 7. Protective immunity induced in ferrets immunized with the HA-np. Ferrets were immunized twice with PBS (control), 7.5 ug (2.5 ug of H1 HA) of TIV or 2.5 ug (amount of HA) 1999 NC HA-np using Ribi adjuvant and a 4-week interval. Control animals received PBS. (a) HA1 (left), IC90 neutralization (middle), and anti-HA ab endpoint titers (right) in immunized ferrets against homologous 1999 NC HA were determined. Immune sera were collected 3 and 2 weeks after the first (R. Salomon, R. G. Webster, The influenza virus enigma. *Cell* 136, 402-410 (2009)) and second (L. C. Lambert, A. S. Fauci, Influenza vaccines for the future. *N Engl J Med* 363, 2036-2044 (2010)) immunizations, respectively. The data are presented as box and whisker plots with lines at the mean (n=6). (b) Protection of immunized ferrets from an unmatched 2007 Bris virus challenge. Ferrets were challenged with $10^{6.5}$ 50% egg infectious dose (EID50) of 2007 Bris virus 5 weeks after the second immunization. Virus titers in the nasal washes from 1, 3 and 5 days post challenge were determined by a 50% tissue culture infectious dose ($TCID_{50}$) assay (left). One of six ferrets in the TIV-immunized group showed measurable virus on day 5. Virus titers in 4 out of 6 ferrets on day 3 and 6 out of 6 ferrets on day 5 in the HA-np-immunized group were under the detection limit (<102). The mean viral loads with standard deviation (s.d.) at each time point were plotted (n=6). Change in the body weight after the virus challenge was also monitored (right). Each data point represents the mean percent change in body weight from the pre-challenge (day 0). The mean body weight changes with standard error (s.e.) at each time point were plotted (n=6).

Three weeks after the first immunization, all ferrets receiving HA-np generated protective HAI titers against homologous H1 1999 NC virus (>1:40), while only 50% (3/6) of TIV-immunized ferrets induced HAI titers greater than 1:40 (FIG. 7A, left; p=0.0056). The same trend was also observed for both neutralization and anti-HA ab titers (FIG. 7A, middle and right; p=0.0047 and p=0.0045, respectively), documenting the superior potency of HA-np in a second species. After boosting, the HAI and IC$_{90}$ neutralization titers of the HA-np-immune sera were ~10-fold higher than those of TIV-immunized ferrets (FIG. 7A, left and middle; 457±185 vs. 5760±1541, p=0.0066, and 598±229 vs. 5515±1074, p=0.0012, respectively). A similar enhancement in HA-np vs. TIV immunization was also observed by ELISA titers (FIG. 7A, right; p=0.0038). Remarkably, a single immunization with HA-np induced immune responses comparable to two immunizations with TIV (FIG. 7A).

To determine whether HA-np could confer protection against an unmatched H1N1 virus, five weeks after the last immunization ferrets immunized with 1999 NC HA-np or TIV containing the same H1 HA were challenged with 10$^{6.5}$ EID$_{50}$ of 2007 Bris virus. (1999 NC and 2007 Bris viruses are 8 years apart and their antigenic characteristics are sufficiently different to require the production of two different vaccines to confer protection in humans.) The virus was expanded in embryonated chicken eggs from a seed stock obtained from CDC (Atlanta, Ga.) and has a titer of 10$^{6.5}$ EID$_{50}$ ml$^{-1}$. The virus stock was inoculated intranasally into ferrets, which had been anesthetized with ketamine/xylazine, in a volume of 500 µl per nostril. The ferrets were observed for clinical signs twice daily and weight and temperature measurements recorded daily by technicians blind to the treatment groups. Nasal washes were obtained on days 1, 3 and 5 and infectious viral titers were determined by TCID$_{50}$ assay using MDCK cells as described previously (C. J. Wei et al., Induction of broadly neutralizing H1N1 influenza antibodies by vaccination. *Science* 329, 1060-1064 (2010)).

Ferrets immunized with HA-np showed a significant reduction in viral shedding beginning 1 day after challenge compared to the sham control group (FIG. 7B, left; p=0.0259). At the same time point, no reduction in viral shedding was seen in the TIV-immunized group. Four of six animals immunized with HA-np had no detectable viral load after 3 days and by day 5, all animals in this group cleared the virus, while all animals in the sham control group still had detectable virus (FIG. 7B). In addition, HA-np-immunized ferrets suffered less body weight loss compared to the TIV-immunized and sham control groups (FIG. 7B, right). These results demonstrate faster virus clearance in ferrets immunized with HA-np than with TIV and further demonstrate that HA-np effectively induced cross-protective immunity in vaccinated ferrets.

Example 7

Induction of Two Types of Neutralizing Abs (nAbs) in Ferrets

This Example demonstrates the breadth and specificity of nAbs in ferret immune sera.

Figure 8:
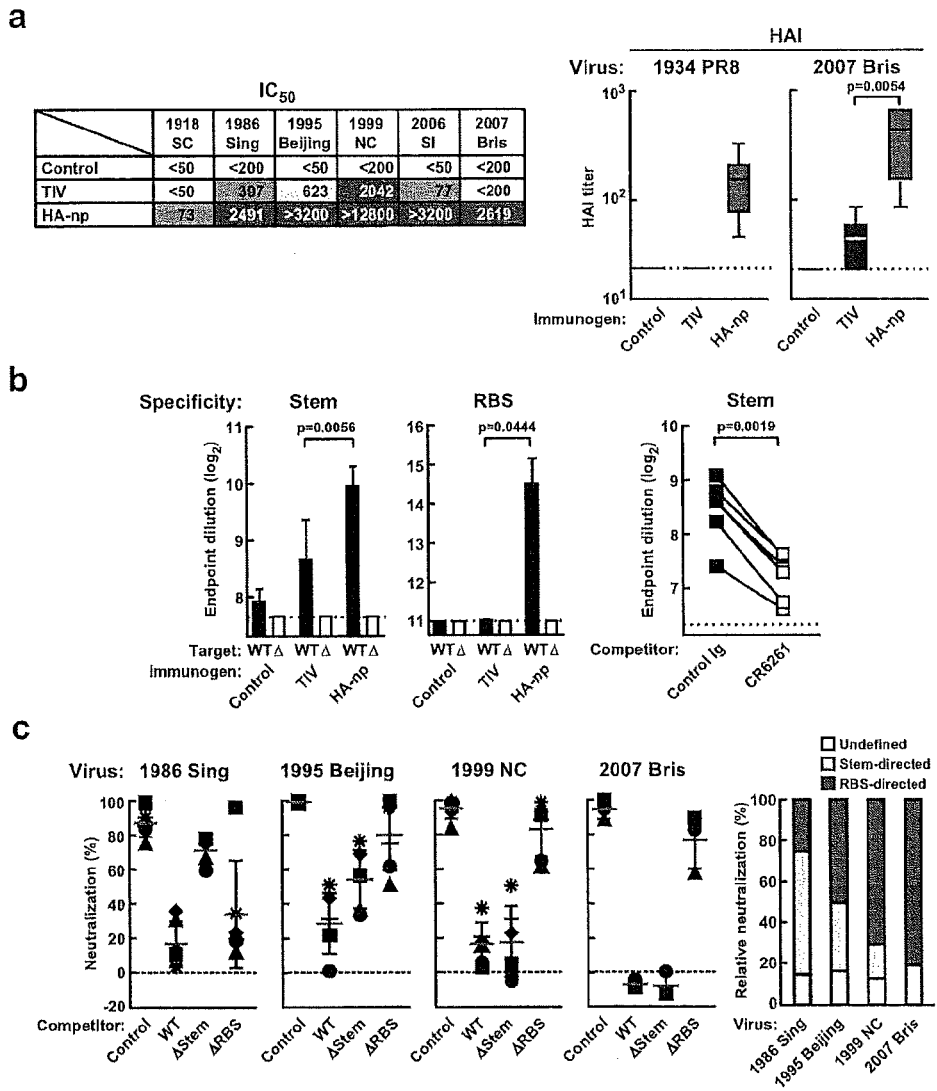
FIG. 8. Improved neutralization breadth and detection of stem- and RBS-directed abs. (a) Neutralization breadth of immune sera in ferrets. $IC_{50}$ neutralization titers against a panel of H1N1 pseudotyped viruses (left) and HAI titers against 1934 PR8 and 2007 Bris H1N1 viruses (right) were determined. The HAI titers are presented as box-and-whiskers plots with lines at the mean (n=6). (b) Stem- and RBS-directed abs elicited by HA-np immunization. Ferret immune sera (diluted 1:100) were pre-absorbed with ΔStem HA-expressing cells and their binding to WT or ΔStem HA were analyzed by ELISA (left). The immune sera (diluted 1:1,000) were pre-absorbed with ΔRBS HA-expressing cells and their binding to WT or ΔRBS HA were analyzed by ELISA (middle). The mean endpoint dilution titers were plotted with s.d. (n=6). Competition ELISA with stem-directed mAb CR6261 (right). The immune sera pre-absorbed with ΔStem were tested for binding to HA in the presence of an isotype control IgG or CR6261. Each symbol represents the titer of an individual ferret (n=6). (c) Neutralization competition with WT, ΔStem or ΔRBS HA protein (left). The neutralization of HA-np immune sera against 1986 Sing, 1995 Beijing, 1999 NC and 2007 Bris was measured in the presence of irrelevant protein (control), WT, ΔStem or ΔRBS HA as a competitor. Percent neutralizations at serum dilution 1:200 (1986 Sing, 2007 Bris), 1:800 (1995

IC$_{50}$ neutralization titers against 1986 Sing, A/Beijing/262/1995 (1995 Beijing), A/Solomon Islands/3/2006 (2006 SI) and 2007 Bris were significantly higher in animals immunized with HA-np compared to immunization with TIV (FIG. 8A, left). This enhanced breadth was due not only to a quantitative increase in overall ab titer (~9-fold against matched virus) but also reflected a qualitative difference in the types of abs elicited (>40-fold enhancement against an unmatched strain). To determine whether the cross-reactivity induced by HA-np was due to nAbs to the conserved HA stem epitope, ferret immune sera were pre-absorbed with cells expressing a stem mutant (ΔStem) HA to remove non-stem directed antibodies. Briefly, ferret immune sera taken 2 weeks after the second immunization were subjected to the assay. The plasmids encoding for ΔStem and ΔRBS HAs were transfected into 293F cells. Three days after transfection, the cells were analyzed by flow cytometry to confirm expression of HA on the cell surface and used for serum absorption. One ml of the immune sera diluted at 1:100 and 1:1,000 was incubated with 100 μl of pre-washed ΔStem and ΔRBS HA-expressing 293F cell pellets, respectively. After incubating for 1 hour at 4° C., supernatants were harvested by centrifugation and binding to WT and mutant HAs was examined by ELISA previously described (C. J. Wei et al., Induction of broadly neutralizing H1N1 influenza antibodies by vaccination. *Science* 329, 1060-1064 (2010)). The ΔStem HA-pre-absorbed sera were also used for competition ELISA.

Stem-specific abs were detected in HA-np-immunized ferrets (6/6) in greater frequency and magnitude than TIV-immune ferrets (2/6) (FIG. 8B, left; p=0.0056). Moreover, binding of these pre-absorbed sera to HA was inhibited by CR6261 mAb (FIG. 8B, right; p=0.0019), further documenting the specificity of HA-np immune sera to the stem epitope. The HAI titers against heterologous 2007 Bris virus were also significantly higher in ferrets immunized with HA-np (6/6, 1:80-1:640) than with TIV (3/6, 1:40-1:80) (FIG. 8A, right; p=0.0054). Interestingly, in contrast to a previous study in which DNA prime/TIV boost was used to elicit anti-stem broadly neutralizing abs (bnAbs) (C. J. Wei et al., Induction of broadly neutralizing H1N1 influenza antibodies by vaccination. *Science* 329, 1060-1064 (2010)), sera from animals immunized with HA-np showed HAI ab titers against a highly divergent 1934 PR8 strain, with titers ≥1:40 in all ferrets. However, no HAI titers against 1934 PR8 were detected in TIV-immunized ferrets (FIG. 8A, right). These data suggested that the HA-np vaccine might elicit another class of nAb directed towards the conserved RBS in the HA head.

To determine whether HA-np elicited abs against RBS, an RBS mutant HA (ΔRBS) was generated by introducing a glycosylation site in the sialic acid binding pocket at residue 190 (FIG. 9) (D. Lingwood et al., Structural and genetic basis for development of broadly neutralizing influenza antibodies. *Nature*, in press). Ferret immune sera were absorbed with ΔRBS HA-expressing cells to remove abs to HA outside of this region and tested for binding against WT or ΔRBS HA. RBS-directed abs were detected with titers of >1:2,000 in all HA-np-immunized ferrets, but only 1 out of 6 ferrets that received TIV (FIG. 8B, middle).

To define the relative contributions of these stem and RBS abs to the breadth of neutralization, neutralization assays were performed in the presence of competitor proteins: WT, ΔStem or ΔRBS HA. In the presence of excess ΔStem HA, only stem-directed abs can neutralize viruses; similarly, ΔRBS HA interferes with all antibodies in the serum except those proximal to the RBS. The relative contribution of stem- and RBS-directed neutralization was measured as activity remaining in the presence of the respective competitor HA. For example, with 2007 Bris, ΔRBS HA only partially inhibited neutralization, while either WT or ΔStem HA almost completely abolished the neutralization activity of the sera; hence, the neutralization against 2007 Bris was due almost entirely to RBS-directed abs (FIG. 8C). Four H1N1 strains were tested in this assay. The pattern of neutralization inhibition varied by strain. Neutralization of 1999 NC or 2007 Bris was mediated predominantly by RBS-directed abs. However, neutralization of 1986 Sing was due mainly to stem-directed abs. Interestingly, the neutralization of 1995 Beijing was more complex. Both stem- and RBS-directed abs contributed to neutralization of this virus (FIG. 8C).

These results demonstrate that HA-np induce both known types of bnAbs—stem-directed and RBS-directed. Together, these abs contribute to the breadth and potency of the immune sera elicited by HA-np. The synergy between them explains mechanistically the observed superior efficacy of the HA-np vaccine and decreases the likelihood of viral escape mutations from either antibody alone.

Taken together the above-disclosed Examples demonstrate that a ferritin-based nanoparticle is able to present trimeric HA in its native fold, rigidly and symmetrically, with sufficient spacing to ensure optimal access to potential bnAbs directed to the stem. They also demonstrate that the nanoparticles have enhanced immunogenicity and an expanded neutralization breadth to both stem and RBD antibodies.

Example 8

Immunization of Mice and Ferrets Using a Tetravalent Vaccine

This Example demonstrates the ability of a multivalent vaccine to elicit an immune response against several strains and sub-types of influenza virus.

The ability of a pan-group 1 vaccine to stimulate neutralizing antibodies against a variety of influenza viruses was tested in mice and ferrets using a protocol similar to that described in Example 1, and outlined in FIG. 11. Briefly, a pan-group 1 HA-ferritin np vaccine was produced by combining four different monovalent HA-ferritin np vaccines. Specifically, HA-ferritin np, each expressing either H1 A/NC/20/1999, H1 A/CA/04/2009, H2 A/Singapore/1/1957 or H5 A/Indonesia/05/2005, were combined to produce a single vaccine containing all four HA proteins. Mice were immunized twice in a four week interval using 6.8 ug total of the pan-group 1 vaccine (1.7 ug of each HA-ferritin np) in Ribi. Ferrets were immunized twice in a four week interval using 10 ug total of the pan-group 1 vaccine (2.5 ug of each HA-ferritin np) in Ribi. Blood was obtained from the immunized animals and the titer of neutralizing antibodies against various influenza viruses measured. The results of this analysis are shown in FIGS. 12-14. Immunized ferrets were also challenged with either influenza A/Brisbane/59/2007 Brisbane (H1N1) (2207 Bris) (FIG. 15) or influenza A/Mexico/2009 (H1N1) (2009 Mex) (FIG. 16) and the resulting virus titers measured on day 3 and 5 post-challenge.

Example 9

Design and Construction HA-Ferritin Stem-Region Fusion Proteins

This Example demonstrates the construction of HA-ferritin proteins and nanoparticles that present the stem region of the influenza HA protein.

As illustrated in FIG. 17, the stem region of the influenza HA protein is highly conserved among different influenza strains, and possesses a site of vulnerability for Group 1 viruses. Thus, a vaccine that elicits neutralizing antibodies against the stem region of the influenza HA protein should be broadly neutralizing. A nanoparticle displaying the stem region of the influenza stem region was constructed as a vaccine.

Design of an HA-Stabilized Stem Fusion Protein.

An HA-stabilized stem fusion protein (HA SS) was constructed as follows: residues 43-313 of the head domain of HA1 were replace with a Gly-Trp-Gly linker. The membrane distal end of HA2 (residues 59 to 93) was replaced by an HIV-1 Bal gp41 HR2 helix followed by a six residue glycine-rich linker (Asn-Gly-Thr-Gly-Gly-Gly-Ser-Gly) and the gp41 HR1 helix. The HR1 helix of gp41 was added in frame with helix C of HA2 so as to generate a long central chimeric helix. The resulting six helix bundle sitting atop the modified hemagglutinin stem provides stability to the SS trimer in lieu of the missing head residues. A schematic of the resulting protein is shown in FIG. 18A, while a ribbon diagram is shown in FIG. 18B. A second trimerization domain consisting of a 28 residue T4 foldon domain was joined to the membrane proximal C-terminus of HA2. The HA SS-ferritin nanoparticle (HA SS-np) protein was generated by joining residue 174 (H3 numbering) of HA SS to *H. pylori* ferritin (residues 5-167) with a Ser-Gly-Gly linker.

In constructing HA-SS fusion proteins, genes encoding wild-type HA proteins (A/Puerto Rico/8/1934 (H1 1934 PR8), A/Singapore/6/1986 (H1 1986 Sing), A/New Caledonia/20/1999 (H1 1999 NC), A/Brisbane/59/2007 (H1 2007 Bris), A/Vietnam/1203/2004 (H5 2004 VN), A/Canada/720/05 (H2 2005 CAN), A/Hong Kong/I/1968 (H3 1968 HK), A/Hong Kong/1073/1999 (H9 1999 HK) and their corresponding NAs, H1 NC 99 SS, RSC3 HIV gp120 control protein, and all Abs (CR6261, F16v3, and VRC01) were synthesized with human preferred codons as previously described (Wei et al. Science 2010, 329(5995):1060-4). *Helicobacter pylori* nonheme iron-containing ferritin (GenBank NP 223316) with a point mutation (N19Q) to abolish a potential N-linked glycosylation site was synthesized by PCR-based accurate synthesis (Xiong et al. *Nat Protoc* 2006, 1(2):791-797) using human-preferred codons. Coding sequences for the human CD5 leader sequence and a serine-glycine-glycine (SGG) spacer were joined to the gene fragment encoding ferritin (residues 5-167) to generate a secreted protein. HA and HA SS-np fusion proteins were generated by overlap PCR by joining the HA ectodomains at residue HA2 174 (H3 numbering) to *H. pylori* ferritin (residues 5-167) with a Ser-Gly-Gly linker. Stem mutant probes Δstem (glycosylation insertion into the CR6261 binding epitope at position 45 in HA2; H3 numbering) which prevent binding at the conserved H1 stem epitope were generated using site directed mutagenesis. Genes encoding these proteins were cloned into a CMVR plasmid backbone for efficient mammalian cell expression.

Protein Expression and Purification

Plasmids encoding soluble proteins were transfected (HA ectodomain genes were cotransfected with the corresponding NA encoding plasmids) into the human embryonic kidney cell line 293F and isolated from expression supernatants 72-96 hrs post-transfection. All HA and HA SS trimeric proteins were purified first by metal chelation affinity chromatography and then by size exclusion chromatography as previously described (Wei et al. J Virol. 2008, 82(13):6200-8). IgG Abs were purified using a Protein G affinity column (GE Healthcare). The HA- and HA SS-np were purified by affinity column chromatography using *Erythrina cnistagalli* agglutinin (ECA, coral tree lectin; EY Laboratories, Inc.) specific for galactose β(1,4)N-acetylglucosamine and *Galanthus nivalis* agglutinin (GNA, snowdrop lectin; EY Laboratories, Inc.) specific for α(1,3) and α(1,6) linked high mannose structures, respectively. HA- and HA SS-np were further purified by size exclusion chromatography with a Superose 6 PG XK 16/70 column (GE Healthcare) in PBS (FIG. 19).

HA SS-Ferritin Characterization.

HA SS-ferritin np were visualized by electron microscopy. Briefly, purified HA SS-np were negatively stained with phosphotungstic acid and ammonium molybdate, respectively, and images were recorded on a Tecnai T12 microscope (FEI) at 80 kV with a CCD camera (AMT Corp.). The results of this analysis are shown in FIG. 20. IN addition, the ability of purified HA SS and HA SS-np to bind to monoclonal Abs CR6261 and FI6v3 ($1.7 \times 10^{-4}$ to 10 μg/mL) was characterized by ELISA. HA and HIV gp120 proteins served as controls. Ab binding was detected by peroxidase-conjugated goat anti-human IgG. The results of this analysis, which are shown in FIG. 21, demonstrate that HASS-ferritin is antigenically similar to HA protein.

Example 10

Immune Response to HA SS-Ferritin Nanoparticles

This Example demonstrates the immune response generated in animals following immunization with HA SS-ferritin np.

BALB/c mice were immunized twice intramuscularly with protein (2 or 10 μg each) formulated with Ribi adjuvant system (Sigma) at a 3 week interval. Mice received either homologous (HA SS-np prime and boost) or heterologous (HA-np prime and HA SS-np boost) immunizations. Ferrets were immunized three times intramuscularly with HA SS-np (10 μg each) formulated with Ribi adjuvant system (Sigma) at weeks 0, 4 and 14. Serum was collected from animals 2 weeks after each immunization and 1 week prior to the first immunization and heat inactivated (30 min at 56° C.).

Pre- and post-immune sera from immunized mice and ferrets were assayed for binding to HA and HA SS by ELISA. Briefly, sera were serially diluted (diluted 50 to $2.3 \times 10^6$) and assayed for reactivity to soluble trimeric HA and HA SS proteins, as well as control proteins (200 ng/well with molar equivalents plated according to HA SS). Binding was detected by peroxidase conjugated anti-mouse or anti-ferret IgG, respectively. Endpoint dilutions were determined from nonlinear fit dose-response curves using a detection limit of 2× background absorbance. The result from this analysis are shown in FIG. 22 and demonstrate that stem specific cross-reactive antibodies which recognize the conserved stem-epitope are elicited by HA SS-np vaccination.

Sera were also analyzed for neutralization of pseudotyped recombinant lentiviruses expressing wild-type HA with the corresponding NA with a luciferase reporter gene as previously described (Wei et al. Science 2010, 329(5995):1060-4) following pretreatment with receptor-destroying enzyme (RDE II; Denka Seiken Co., Ltd.). Psuedotype neutralization competition of ferret serum was performed by incubating serially diluted serum in the presence of either H1 1999 NC SS, H1 1999 NC SS Δstem probe or gp120 control (10 μg/mL) for 1 hr (RT) before addition to pseudotyped recombinant lentiviruses and assaying for neutralization. The results from this analysis are shown in FIG. 23 and demonstrate that vaccination with HA SS-np elicits neutralizing antibodies against various group-1 strains.

Example 11

Immune Response to HA SS-Ferritin Heterologous Immunization Boost

This example demonstrates that HA SS-np can be utilized to boost antibodies directed to the conserved stem epitope.

BALB/c mice were immunized twice intramuscularly with heterologous ferritin proteins (HA-np prime and HA SS-np boost; 2 μg each) formulated with Ribi adjuvant system (Sigma) at a 3 week interval. Serum was collected from animals 2 weeks after each immunization and 1 week prior to the first immunization and heat inactivated (30 min at 56° C.).

Pre- and post-immune sera from immunized mice were assayed for binding to HA and HA SS by ELISA. Briefly, sera were serially diluted (diluted 50 to $2.3 \times 10^6$) and assayed for reactivity to soluble trimeric HA and HA SS proteins, as well as control proteins (200 ng/well with molar equivalents plated according to HA SS). Binding was detected by peroxidase conjugated anti-mouse or anti-ferret IgG, respectively. Endpoint dilutions were determined from nonlinear fit dose-response curves using a detection limit of 2× background absorbance. The results from this analysis are shown in FIG. 22 and demonstrate that cross-reactive stem-epitope specific antibodies are being elicited.

Sera were also analyzed for neutralization of pseudotyped recombinant lentiviruses expressing wild-type HA with the corresponding NA with a luciferase reporter gene as previously described (Wei et al. Science 2010, 329(5995):1060-4) following pretreatment with receptor-destroying enzyme (RDE II; Denka Seiken Co., Ltd.). The results from this analysis are shown in FIG. 24 and demonstrate that mice which have preexisting stem antibodies titers can be boosted with HA SS-np.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

```
                    SEQUENCE LISTING

<160> NUMBER OF SEQ ID NOS: 129

<210> SEQ ID NO 1
<211> LENGTH: 504
<212> TYPE: DNA
<213> ORGANISM: Helicobacter pylori

<400> SEQUENCE: 1
atgttatcaa aagacatcat taagttgcta aacgaacaag tgaataagga aatgaactct      60
tccaacttgt atatgagcat gagttcatgg tgctataccc atagcttaga tggcgcgggg     120
cttttcttgt ttgaccatgc ggctgaagaa tacgagcatg ctaaaaagct tattatcttc     180
ttgaatgaaa acaatgtgcc tgtgcaattg accagcatca gcgcgcctga gcataagttt     240
gaaggtttga ctcaaatttt ccaaaaagcc tatgaacatg agcaacacat cagcgagtct     300
attaacaata tcgtagatca cgccataaaa agcaaagatc atgcgacttt caatttcttg     360
caatggtatg tggctgaaca gcatgaagaa gaagtgcttt tcaaggatat tttggataaa     420
attgagttga ttggtaatga aaaccatggc ttgtatttag ccgatcagta tgtcaaaggg     480
atcgctaaaa gcaggaaatc ttaa                                            504

<210> SEQ ID NO 2
<211> LENGTH: 167
<212> TYPE: PRT
<213> ORGANISM: Helicobacter pylori

<400> SEQUENCE: 2

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Ser Lys
            100                 105                 110
```

Asp His Ala Thr Phe Asn Phe Leu Gln Trp Tyr Val Ala Glu Gln His
            115                 120                 125

Glu Glu Glu Val Leu Phe Lys Asp Ile Leu Asp Lys Ile Glu Leu Ile
    130                 135                 140

Gly Asn Glu Asn His Gly Leu Tyr Leu Ala Asp Gln Tyr Val Lys Gly
145                 150                 155                 160

Ile Ala Lys Ser Arg Lys Ser
                165

<210> SEQ ID NO 3
<211> LENGTH: 504
<212> TYPE: DNA
<213> ORGANISM: Helicobacter pylori

<400> SEQUENCE: 3
ttaagatttc ctgcttttag cgatcccttt gacatactga tcggctaaat acaagccatg      60
gttttcatta ccaatcaact caattttatc caaaatatcc ttgaaaagca cttcttcttc     120
atgctgttca gccacatacc attgcaagaa attgaaagtc gcatgatctt tgcttttat     180 ggcgtgatct acgatattgt taatagactc gctgatgtgt tgctcatgtt cataggcttt     240
ttggaaaatt tgagtcaaac cttcaaactt atgctcaggc gcgctgatgc tggtcaattg     300
cacaggcaca ttgttttcat tcaagaagat aataagcttt ttagcatgct cgtattcttc     360
agccgcatgg tcaaacaaga aaagccccgc gccatctaag ctatgggtat agcaccatga     420
actcatgctc atatacaagt tggaagagtt catttcctta ttcacttgtt cgtttagcaa     480
cttaatgatg tcttttgata acat                                            504

<210> SEQ ID NO 4
<211> LENGTH: 489
<212> TYPE: DNA
<213> ORGANISM: Helicobacter pylori

<400> SEQUENCE: 4
gacatcatca agctgctgaa cgagcaggtg aacaaggaga tgcagagcag caacctgtac      60
atgagcatga gcagctggtg ctacacccac agcctggacg gcgccggcct gttcctgttc     120
gaccacgccg ccgaggagta cgagcacgcc aagaagctga tcatcttcct gaacgagaac     180
aacgtgcccg tgcagctgac cagcatcagc gcccccgagc acaagttcga gggcctgacc     240
cagatcttcc agaaggccta cgagcacgag cagcacatca gcgagagcat caacaacatc     300
gtggaccacg ccatcaagag caaggaccac gccaccttca acttcctgca gtggtacgtg     360
gccgagcagc acgaggagga ggtgctgttc aaggacatcc tggacaagat cgagctgatc     420
ggcaacgaga accacggcct gtacctggcc gaccagtacg tgaagggcat cgccaagagc     480
aggaagagc                                                             489

<210> SEQ ID NO 5
<211> LENGTH: 163
<212> TYPE: PRT
<213> ORGANISM: Helicobacter pylori

<400> SEQUENCE: 5

Asp Ile Ile Lys Leu Leu Asn Glu Gln Val Asn Lys Glu Met Gln Ser
1               5                   10                  15

Ser Asn Leu Tyr Met Ser Met Ser Ser Trp Cys Tyr Thr His Ser Leu
                20                  25                  30

Asp Gly Ala Gly Leu Phe Leu Phe Asp His Ala Ala Glu Glu Tyr Glu

```
                35                  40                  45
His Ala Lys Lys Leu Ile Ile Phe Leu Asn Glu Asn Asn Val Pro Val
 50                  55                  60

Gln Leu Thr Ser Ile Ser Ala Pro Glu His Lys Phe Glu Gly Leu Thr
 65                  70                  75                  80

Gln Ile Phe Gln Lys Ala Tyr Glu His Glu His Ile Ser Glu Ser
                 85                  90                  95

Ile Asn Asn Ile Val Asp His Ala Ile Lys Ser Lys Asp His Ala Thr
            100                 105                 110

Phe Asn Phe Leu Gln Trp Tyr Val Ala Glu Gln His Glu Glu Val
        115                 120                 125

Leu Phe Lys Asp Ile Leu Asp Lys Ile Glu Leu Ile Gly Asn Glu Asn
130                 135                 140

His Gly Leu Tyr Leu Ala Asp Gln Tyr Val Lys Gly Ile Ala Lys Ser
145                 150                 155                 160

Arg Lys Ser

<210> SEQ ID NO 6
<211> LENGTH: 489
<212> TYPE: DNA
<213> ORGANISM: Helicobacter pylori

<400> SEQUENCE: 6
gctcttcctg ctcttggcga tgcccttcac gtactggtcg ccaggtaca ggccgtggtt      60 ctcgttgccg atcagctcga tcttgtccag gatgtccttg aacagcacct cctcctcgtg    120
ctgctcggcc acgtaccact gcaggaagtt gaaggtggcg tggtccttgc tcttgatggc    180
gtggtccacg atgttgttga tgctctcgct gatgtgctgc tcgtgctcgt aggccttctg    240
gaagatctgg gtcaggccct cgaacttgtg ctcggggcg ctgatgctgg tcagctgcac     300
gggcacgttg ttctcgttca ggaagatgat cagcttcttg gcgtgctcgt actcctcggc    360
ggcgtggtcg aacaggaaca ggccggcgcc gtccaggctg tgggtgtagc accagctgct    420
catgctcatg tacaggttgc tgctctgcat ctccttgttc acctgctcgt tcagcagctt    480
gatgatgtc                                                             489

<210> SEQ ID NO 7
<211> LENGTH: 1695
<212> TYPE: DNA
<213> ORGANISM: Influenza virus

<400> SEQUENCE: 7
atgaaggcca aactgctggt gctgctgtgt acctttaccg ccacctacgc cgacacaatc      60
tgtatcggct accacgccaa caatagcacc gacaccgtgg atacagtgct ggagaagaac    120
gtgaccgtga cccactctgt gaacctgctg gaggacagcc acaatggcaa gctgtgtctg    180
ctgaaaggca ttgcccctct gcagctgggc aattgttctg tggccggatg gattctgggc    240
aaccccgagt gtgagctgct gatttctaag agagctggag gctacatcgt ggagaccccc    300
aatcctgaga tggcacctg ctaccctggc tacttcgccg attacgagga gctgcgcgag     360
cagctgtcta gcgtgtccag cttcgagaga ttcgagatct tccccaagga gtccagctgg    420
cctaatcaca cagtgacagg cgtgtctgcc agctgtagcc acaacggcaa agcagcttc     480 taccggaacc tgctgtggct gacaggcaag aatggcctgt accccaacct gagcaagagc    540
tacgtgaaca acaaggaaaa ggaagtgctg gtgctgtggg gagtgcacca ccctcccaac    600
```

```
atcggaaatc agcgggccct gtaccacaca gagaacgcct atgtgagcgt ggtgtccagc    660
cactacagca gaagattcac ccccgagatc gccaagagac ccaaagtgag agaccaggag    720
ggccggatca attactactg gaccctgctg gagcctggcg ataccatcat cttcgaggcc    780
aacggcaatc tgatcgcccc ttggtatgcc tttgccctga gcagaggctt tggcagcggc    840
atcatcacaa gcaacgcccc catggatgag tgtgatgcca agtgccagac acctcagggc    900
gccatcaata gcagcctgcc cttccagaat gtgcaccctg tgaccatcgg cgagtgcccc    960
aagtatgtga gaagcgccaa gctgagaatg gtgaccggcc tgagaaacat ccctagcatc   1020
cagagcagag gactgtttgg agccatcgcc ggattcatcg agggaggatg gacaggcatg   1080
gtggatggct ggtacggcta ccaccaccag aatgagcagg gctctggata tgccgccgat   1140
cagaagtcta cccagaacgc catcaacggc atcaccaaca aggtgaacag cgtgatcgag   1200
aagatgaaca cccagtttac cgctgtgggc aaggagttca acaagctgga gcggaggatg   1260
gagaacctga acaagaaggt ggacgacggc tttctggaca tctggaccta caatgccgaa   1320
ctcctggtcc tcctcgagaa tgagaggacc ctggacttcc acgacagcaa cgtgaagaac   1380
ctgtatgaga aggtgaagag ccagctgaag aacaacgcca aggagatcgg caacggctgc   1440
ttcgagttct accacaagtg taacaacgag tgtatggaga gcgtgaagaa cggcacctac   1500
gactacccta agtacagcga ggagagcaag ctgaaccggg agaagatcga tggcgtgaag   1560
ctggagagca tgggcgtgta tcagatcctg gccatctaca gcacagtggc ctcttctctg   1620
gtgctgctgg tgtctctggg cgccatctcc ttttggatgt gctccaacgg cagcctgcag   1680
tgcaggatct gtatc                                                    1695

<210> SEQ ID NO 8
<211> LENGTH: 565
<212> TYPE: PRT
<213> ORGANISM: Influenza virus

<400> SEQUENCE: 8

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175
```

```
Leu Ser Lys Ser Tyr Val Asn Asn Lys Glu Lys Glu Val Leu Val Leu
            180                 185                 190

Trp Gly Val His His Pro Asn Ile Gly Asn Gln Arg Ala Leu Tyr
        195                 200                 205

His Thr Glu Asn Ala Tyr Val Ser Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 9
<211> LENGTH: 1695
<212> TYPE: DNA
```

<213> ORGANISM: Influenza virus

<400> SEQUENCE: 9

| | |
|---|---|
| gatacagatc ctgcactgca ggctgccgtt ggagcacatc caaaaggaga tggcgcccag | 60 |
| agacaccagc agcaccagag aagaggccac tgtgctgtag atggccagga tctgatacac | 120 |
| gcccatgctc tccagcttca cgccatcgat cttctcccgg ttcagcttgc tctcctcgct | 180 |
| gtacttaggg tagtcgtagg tgccgttctt cacgctctcc atacactcgt tgttacactt | 240 |
| gtggtagaac tcgaagcagc cgttgccgat ctccttggcg ttgttcttca gctggctctt | 300 |
| caccttctca tacaggttct tcacgttgct gtcgtggaag tccagggtcc tctcattctc | 360 |
| gaggaggacc aggagttcgg cattgtaggt ccagatgtcc agaaagccgt cgtccacctt | 420 |
| cttgttcagg ttctccatcc tccgctccag cttgttgaac tccttgccca cagcggtaaa | 480 |
| ctgggtgttc atcttctcga tcacgctgtt caccttgttg gtgatgccgt tgatggcgtt | 540 |
| ctgggtagac ttctgatcgg cggcatatcc agagccctgc tcattctggt ggtggtagcc | 600 |
| gtaccagcca tccaccatgc ctgtccatcc tccctcgatg aatccggcga tggctccaaa | 660 |
| cagtcctctg ctctggatgc tagggatgtt tctcaggccg tcaccattc tcagcttggc | 720 |
| gcttctcaca tacttggggc actcgccgat ggtcacaggg tgcacattct ggaagggcag | 780 |
| gctgctattg atggcgccct gaggtgtctg gcacttggca tcacactcat ccatggggc | 840 |
| gttgcttgtg atgatgccgc tgccaaagcc tctgctcagg gcaaaggcat accaaggggc | 900 |
| gatcagattg ccgttggcct cgaagatgat ggtatcgcca ggctccagca gggtccagta | 960 |
| gtaattgatc cggccctcct ggtctctcac tttgggtctc ttggcgatct cgggggtgaa | 1020 |
| tcttctgctg tagtggctgg acaccacgct cacataggcg ttctctgtgt ggtacagggc | 1080 |
| ccgctgattt ccgatgttgg gagggtggtg cactccccac agcaccagca cttccttttc | 1140 |
| cttgttgttc acgtagctct tgctcaggtt ggggtacagg ccattcttgc ctgtcagcca | 1200 |
| cagcaggttc cggtagaagc tgcttttgcc gttgtggcta cagctggcag acacgcctgt | 1260 |
| cactgtgtga ttaggccagc tggactcctt ggggaagatc tcgaatctct cgaagctgga | 1320 |
| cacgctagac agctgctcgc gcagctcctc gtaatcggcg aagtagccag ggtagcaggt | 1380 |
| gccattctca ggattggggg tctccacgat gtagctccag ctctccttag aaatcagcag | 1440 |
| ctcacactcg gggttgccca gaatccatcc ggccacagaa caattgccca gctgcagagg | 1500 |
| ggcaatgcct ttcagcagac acagcttgcc attgtggctg tcctccagca ggttcacaga | 1560 |
| gtgggtcacg gtcacgttct tctccagcac tgtatccacg gtgtcggtgc tattgttggc | 1620 |
| gtggtagccg atacagattg tgtcggcgta ggtggcggta aggtacaca gcagcaccag | 1680 |
| cagtttggcc ttcat | 1695 |

<210> SEQ ID NO 10
<211> LENGTH: 1551
<212> TYPE: DNA
<213> ORGANISM: Influenza virus

<400> SEQUENCE: 10

| | |
|---|---|
| atgaaggcca aactgctggt gctgctgtgt acctttaccg ccacctacgc cgacacaatc | 60 |
| tgtatcggct accacgccaa caatagcacc gacaccgtgg atacagtgct ggagaagaac | 120 |
| gtgaccgtga cccactctgt gaacctgctg gaggacagcc acaatggcaa gctgtgtctg | 180 |
| ctgaaaggca ttgcccctct gcagctgggc aattgttctg tggccggatg gattctgggc | 240 |
| aaccccgagt gtgagctgct gatttctaag gagagctgga gctacatcgt ggagaccccc | 300 |

-continued

```
aatcctgaga atggcacctg ctaccctggc tacttcgccg attacgagga gctgcgcgag    360
cagctgtcta gcgtgtccag cttcgagaga ttcgagatct tccccaagga gtccagctgg    420
cctaatcaca cagtgacagg cgtgtctgcc agctgtagcc acaacggcaa agcagcttc     480
taccggaacc tgctgtggct gacaggcaag aatggcctgt accccaacct gagcaagagc    540
tacgtgaaca caaggaaaa ggaagtgctg gtgctgtggg gagtgcacca ccctcccaac     600
atcggaaatc agcgggccct gtaccacaca gagaacgcct atgtgagcgt ggtgtccagc    660
cactacagca gaagattcac ccccgagatc gccaagagac ccaaagtgag agaccaggag    720
ggccggatca attactactg gaccctgctg gagcctggcg ataccatcat cttcgaggcc    780
aacggcaatc tgatcgcccc ttggtatgcc tttgccctga gcagaggctt ggcagcggc     840
atcatcacaa gcaacgcccc catggatgag tgtgatgcca agtgccagac acctcagggc    900
gccatcaata gcagcctgcc cttccagaat gtgcaccctg tgaccatcgg cgagtgcccc    960
aagtatgtga aagcgccaa gctgagaatg gtgaccggcc tgagaaacat ccctagcatc    1020
cagagcagag gactgttttgg agccatcgcc ggattcatcg agggaggatg gacaggcatg   1080
gtggatggct ggtacggcta ccaccaccag aatgagcagg gctctggata tgccgccgat   1140
cagaagtcta cccagaacgc catcaacggc atcaccaaca aggtgaacag cgtgatcgag   1200
aagatgaaca cccagtttac cgctgtgggc aaggagttca acaagctgga gcggaggatg   1260
gagaacctga caagaaggt ggacgacggc tttctggaca tctggaccta caatgccgaa   1320
ctcctggtcc tctcgagaa tgagaggacc ctggacttcc acgacagcaa cgtgaagaac   1380
ctgtatgaga aggtgaagag ccagctgaag aacaacgcca aggagatcgg caacggctgc   1440
ttcgagttct accacaagtg taacaacgag tgtatggaga gcgtgaagaa cggcacctac   1500
gactacccta agtacagcga ggagagcaag ctgaaccggg agaagatcga t            1551
```

<210> SEQ ID NO 11
<211> LENGTH: 517
<212> TYPE: PRT
<213> ORGANISM: Influenza virus

<400> SEQUENCE: 11

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
```

```
                        145                 150                 155                 160

Tyr Arg Asn Leu Leu Trp Leu Thr Gly Lys Asn Gly Leu Tyr Pro Asn
                                    165                 170                 175

Leu Ser Lys Ser Tyr Val Asn Asn Lys Glu Lys Glu Val Leu Val Leu
                                    180                 185                 190

Trp Gly Val His His Pro Pro Asn Ile Gly Asn Gln Arg Ala Leu Tyr
                                    195                 200                 205

His Thr Glu Asn Ala Tyr Val Ser Val Val Ser Ser His Tyr Ser Arg
                210                 215                 220

Arg Phe Thr Pro Glu Ile Ala Lys Arg Pro Lys Val Arg Asp Gln Glu
                225                 230                 235                 240

Gly Arg Ile Asn Tyr Tyr Trp Thr Leu Leu Glu Pro Gly Asp Thr Ile
                                    245                 250                 255

Ile Phe Glu Ala Asn Gly Asn Leu Ile Ala Pro Trp Tyr Ala Phe Ala
                                    260                 265                 270

Leu Ser Arg Gly Phe Gly Ser Gly Ile Ile Thr Ser Asn Ala Pro Met
                                    275                 280                 285

Asp Glu Cys Asp Ala Lys Cys Gln Thr Pro Gln Gly Ala Ile Asn Ser
                290                 295                 300

Ser Leu Pro Phe Gln Asn Val His Pro Val Thr Ile Gly Glu Cys Pro
                305                 310                 315                 320

Lys Tyr Val Arg Ser Ala Lys Leu Arg Met Val Thr Gly Leu Arg Asn
                                    325                 330                 335

Ile Pro Ser Ile Gln Ser Arg Gly Leu Phe Gly Ala Ile Ala Gly Phe
                                    340                 345                 350

Ile Glu Gly Gly Trp Thr Gly Met Val Asp Gly Trp Tyr Gly Tyr His
                                    355                 360                 365

His Gln Asn Glu Gln Gly Ser Gly Tyr Ala Ala Asp Gln Lys Ser Thr
                                    370                 375                 380

Gln Asn Ala Ile Asn Gly Ile Thr Asn Lys Val Asn Ser Val Ile Glu
                385                 390                 395                 400

Lys Met Asn Thr Gln Phe Thr Ala Val Gly Lys Glu Phe Asn Lys Leu
                                    405                 410                 415

Glu Arg Arg Met Glu Asn Leu Asn Lys Lys Val Asp Asp Gly Phe Leu
                                    420                 425                 430

Asp Ile Trp Thr Tyr Asn Ala Glu Leu Leu Val Leu Leu Glu Asn Glu
                                    435                 440                 445

Arg Thr Leu Asp Phe His Asp Ser Asn Val Lys Asn Leu Tyr Glu Lys
                                    450                 455                 460

Val Lys Ser Gln Leu Lys Asn Asn Ala Lys Glu Ile Gly Asn Gly Cys
                465                 470                 475                 480

Phe Glu Phe Tyr His Lys Cys Asn Asn Glu Cys Met Glu Ser Val Lys
                                    485                 490                 495

Asn Gly Thr Tyr Asp Tyr Pro Lys Tyr Ser Glu Glu Ser Lys Leu Asn
                                    500                 505                 510

Arg Glu Lys Ile Asp
                            515

<210> SEQ ID NO 12
<211> LENGTH: 1551
<212> TYPE: DNA
<213> ORGANISM: Influenza virus

<400> SEQUENCE: 12
```

```
atcgatcttc tcccggttca gcttgctctc ctcgctgtac ttagggtagt cgtaggtgcc    60
gttcttcacg ctctccatac actcgttgtt acacttgtgg tagaactcga agcagccgtt   120
gccgatctcc ttggcgttgt tcttcagctg gctcttcacc ttctcataca ggttcttcac   180
gttgctgtcg tggaagtcca gggtcctctc attctcgagg aggaccagga gttcggcatt   240
gtaggtccag atgtccagaa agccgtcgtc caccttcttg ttcaggttct ccatcctccg   300
ctccagcttg ttgaactcct tgcccacagc ggtaaactgg tgttcatct tctcgatcac    360 gctgttcacc ttgttggtga tgccgttgat ggcgttctgg gtagacttct gatcggcggc   420
atatccagag ccctgctcat tctggtggtg gtagccgtac cagccatcca ccatgcctgt   480
ccatcctccc tcgatgaatc cggcgatggc tccaaacagt cctctgctct ggatgctagg   540
gatgtttctc aggccggtca ccattctcag cttggcgctt ctcacatact ggggcactc    600 gccgatggtc acagggtgca cattctggaa gggcaggctg ctattgatgg cgccctgagg   660
tgtctggcac ttggcatcac actcatccat ggggcgttg cttgtgatga tgccgctgcc    720
aaagcctctg ctcagggcaa aggcatacca aggggcgatc agattgccgt tggcctcgaa   780
gatgatggta cgccaggct ccagcaggggt ccagtagtaa ttgatccggc cctcctggtc   840
tctcactttg ggtctcttgg cgatctcggg ggtgaatctt ctgctgtagt ggctggacac   900
cacgctcaca taggcgttct ctgtgtggta cagggcccgc tgatttccga tgttgggagg   960
gtggtgcact ccccacagca ccagcacttc cttttccttg ttgttcacgt agctcttgct  1020
caggttgggg tacaggccat tcttgcctgt cagccacagc aggttccggt agaagctgct  1080
tttgccgttg tggctacagc tggcagacac gcctgtcact gtgtgattag gccagctgga  1140
ctccttgggg aagatctcga atctctcgaa gctggacacg ctagacagct gctcgcgcag  1200
ctcctcgtaa tcgcgaagt agccaggggta gcaggtgcca ttctcaggat tgggggtctc  1260
cacgatgtag ctccagctct ccttagaaat cagcagctca cactcggggt tgcccagaat  1320
ccatccggcc acagaacaat tgcccagctg cagaggggca atgccttcca gcagacacag  1380
cttgccattg tggctgtcct ccagcaggtt cacagagtgg gtcacggtca cgttcttctc  1440
cagcactgta tccacggtgt cggtgctatt gttggcgtgg tagccgatac agattgtgtc  1500
ggcgtaggtg gcggtaaagg tacacagcag caccagcagt ttggccttca t           1551
```

<210> SEQ ID NO 13
<211> LENGTH: 1554
<212> TYPE: DNA
<213> ORGANISM: Influenza virus

<400> SEQUENCE: 13

```
atgaaggcca tcctggtggt gctgctgtac accttcgcca ccgccaacgc cgacaccctg    60
tgcatcggct accacgccaa caacagcacc gacaccgtgg acaccgtgct ggagaagaac   120
gtgaccgtga cccacagcgt gaacctgctg gaggacaagc acaacggcaa gctgtgcaag   180
ctgcggggcg tggcccccct gcacctgggc aagtgcaaca tcgccggctg gattctgggc   240
aaccccgagt gcgagagcct gagcaccgcc agcagctgga gctacatcgt ggagaccccc   300
agcagcgaca cggcacctg ctaccccggc gacttcatcg actacgagga gctgcgggag   360
cagctgagca gcgtgagcag cttcgagcgg ttcgagatct ccccaagac cagcagctgg   420 cccaaccacg acagcaacaa gggcgtgacc gccgctgcc ccacgccgg cgccaagagc   480 ttctacaaga acctgatctg gctggtgaag aagggcaaca gctaccccaa gctgagcaag   540
agctacatca acgacaaggg caaggaggtg ctggtgctgt ggggcatcca ccaccccagc   600
```

```
accagcgccg accagcagag cctgtaccag aacgccgaca cctacgtgtt cgtgggcagc      660
agccggtaca gcaagaagtt caagcccgag atcgccatcc ggcccaaggt gcgggaccag      720
gagggccgga tgaactacta ctggaccctg gtggagcccg gcgacaagat caccttcgag      780
gccaccggca acctggtggt gccccggtac gccttcgcca tggagcggaa cgccggcagc      840
ggcatcatca tcagcgacac ccccgtgcac gactgcaaca ccacctgcca gacccccaag      900
ggcgccatca acaccagcct gcccttccag aacatccacc ccatcaccat cggcaagtgc      960
cccaagtacg tgaagagcac caagctgcgg ctggccaccg gcctgcggaa catccccagc     1020
atccagagcc ggggcctgtt cggcgccatc gccggcttca tcgagggcgg ctggaccggc     1080
atggtggacg gctggtacgg ctaccaccac cagaacgagc agggcagcgg ctacgccgcc     1140
gacctgaaga gcacccagaa cgccatcgac gagatcacca caaggtgaa cagcgtgatc     1200 gagaagatga acacccagtt caccgccgtg ggcaaggagt caaccacct ggagaagcgg     1260 atcgagaacc tgaacaagaa ggtggacgac ggcttcctgg acatctggac ctacaacgcc     1320
gagctgctgg tgctgctgga aacgagcgg accctggact accacgacag caacgtgaag     1380
aacctgtacg agaaggtgcg gagccagctg aagaacaacg ccaaggagat cggcaacggc     1440
tgcttcgagt tctaccacaa gtgcgacaac acctgcatgg agagcgtgaa gaacggcacc     1500
tacgactacc ccaagtacag cgaggaggcc aagctgaacc gggaggagat cgac          1554

<210> SEQ ID NO 14
<211> LENGTH: 518
<212> TYPE: PRT
<213> ORGANISM: Influenza virus

<400> SEQUENCE: 14

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205
```

```
Tyr Gln Asn Ala Asp Thr Tyr Val Phe Val Gly Ser Ser Arg Tyr Ser
    210                 215                 220
Lys Lys Phe Lys Pro Glu Ile Ala Ile Arg Pro Lys Val Arg Asp Gln
225                 230                 235                 240
Glu Gly Arg Met Asn Tyr Tyr Trp Thr Leu Val Glu Pro Gly Asp Lys
                245                 250                 255
Ile Thr Phe Glu Ala Thr Gly Asn Leu Val Val Pro Arg Tyr Ala Phe
            260                 265                 270
Ala Met Glu Arg Asn Ala Gly Ser Gly Ile Ile Ile Ser Asp Thr Pro
        275                 280                 285
Val His Asp Cys Asn Thr Thr Cys Gln Thr Pro Lys Gly Ala Ile Asn
    290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Ala Thr Gly Leu Arg
                325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
        355                 360                 365
His His Gln Asn Glu Gln Gly Ser Gly Tyr Ala Ala Asp Leu Lys Ser
    370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
        435                 440                 445
Glu Arg Thr Leu Asp Tyr His Asp Ser Asn Val Lys Asn Leu Tyr Glu
    450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
            500                 505                 510
Asn Arg Glu Glu Ile Asp
        515

<210> SEQ ID NO 15
<211> LENGTH: 1554
<212> TYPE: DNA
<213> ORGANISM: Influenza virus

<400> SEQUENCE: 15
gtcgatctcc tcccggttca gcttggcctc ctcgctgtac ttggggtagt cgtaggtgcc      60
gttcttcacg ctctccatgc aggtgttgtc gcacttgtgg tagaactcga agcagccgtt     120
gccgatctcc ttggcgttgt tcttcagctg gctccgcacc ttctcgtaca ggttcttcac     180
gttgctgtcg tggtagtcca gggtccgctc gttctccagc agcaccagca gctcggcgtt     240
gtaggtccag atgtccagga agccgtcgtc caccttcttg ttcaggttct cgatccgctt     300
```

```
ctccaggtgg ttgaactcct tgcccacggc ggtgaactgg gtgttcatct tctcgatcac    360
gctgttcacc ttgttggtga tctcgtcgat ggcgttctgg gtgctcttca ggtcggcggc    420
gtagccgctg ccctgctcgt tctggtggtg gtagccgtac cagccgtcca ccatgccggt    480
ccagccgccc tcgatgaagc cggcgatggc gccgaacagg ccccggctct ggatgctggg    540
gatgttccgc aggccggtgg ccagccgcag cttggtgctc ttcacgtact tggggcactt    600
gccgatggtg atggggtgga tgttctggaa gggcaggctg gtgttgatgg cgcccttggg    660
ggtctggcag gtggtgttgc agtcgtgcac gggggtgtcg ctgatgatga tgccgctgcc    720
ggcgttccgc tccatggcga aggcgtaccg gggcaccacc aggttgccgg tggcctcgaa    780
ggtgatcttg tcgccgggct ccaccagggt ccagtagtag ttcatccggc cctcctggtc    840
ccgcaccttg ggccggatgg cgatctcggg cttgaacttc ttgctgtacc ggctgctgcc    900
cacgaacacg taggtgtcgg cgttctggta caggctctgc tggtcggcgc tggtgctggg    960
gtggtggatg ccccacagca ccagcacctc cttgcccttg tcgttgatgt agctcttgct   1020
cagcttgggg tagctgttgc ccttcttcac cagccagatc aggttcttgt agaagctctt   1080
ggcgccggcg tgggggcagg cggcggtcac gcccttgttg ctgtcgtggt tgggccagct   1140
gctggtcttg ggaagatct cgaaccgctc gaagctgctc acgctgctca gctgctcccg    1200
cagctcctcg tagtcgatga agtcgccggg gtagcaggtg ccgttgtcgc tgctgggggt   1260
ctccacgatg tagctccagc tgctggcggt gctcaggctc tcgcactcgg ggttgcccag   1320
aatccagccg gcgatgttgc acttgcccag gtgcaggggg gccacgcccc gcagcttgca   1380
cagcttgccg ttgtgcttgt cctccagcag gttcacgctg tgggtcacgg tcacgttctt   1440
ctccagcacg gtgtccacgg tgtcggtgct gttgttggcg tggtagccga tgcacagggt   1500
gtcggcgttg gcggtggcga aggtgtacag cagcaccacc aggatggcct tcat         1554
```
<210> SEQ ID NO 16
<211> LENGTH: 1542
<212> TYPE: DNA
<213> ORGANISM: Influenza virus

<400> SEQUENCE: 16
```
atggccatca tctacctgat cctgctgttt acagctgtgc ggggcgatca gatctgtatc     60
ggctaccacg ccaacaatag caccgagaag gtggacacca tcctggaaag aaatgtgacc    120
gtgacccacg ccaaggatat tctggaaaag acccacaacg gcaagctgtg caagctgaat    180
ggcattcctc ctctggaact gggcgattgt tctattgctg gctggctgct gggaaatcct    240
gagtgcgata gactgctgtc tgtgcctgag tggagctaca tcatggaaaa agagaaccct    300
agggacggac tgtgttaccc cggcagcttc aacgattacg aggaactgaa gcacctgctg    360
tccagcgtga agcacttcga gaaagtgaag atcctgccca aggatagatg gacccagcat    420
acaacaacag gcggaagcag agcttgtgct gtgtccggca accccagctt cttcagaaat    480
atggtctggc tgaccaagaa gggctctaat tatcctgtgg ccaagggcag ctacaataat    540
acaagcggcg agcagatgct gattatttgg ggcgtgcacc accctaatga tgagacagag    600
cagagaaccc tgtaccagaa tgtgggcaca tacgtgtctg tgggcaccag cacactgaat    660
aagagaagca cccccgatat tgccaccaga cccaaagtga atggacaggg cggcagaatg    720
gaattttcct ggaccctgct ggatatgtgg gacaccatca actttgagag caccgggaat    780
ctgattgccc ctgagtacgg cttcaagatc agcaagagag gcagcagcgg catcatgaaa    840
acagagggca ccctggaaaa ctgtgaaacc aagtgtcaga cacctctggg cgccattaat    900
```

```
accaccctgc ccttccataa tgtgcaccct ctgacaatcg gcgagtgccc taagtacgtg      960
aagtctgaga aactggtgct ggccacagga ctgagaaatg tgccccagat cgagtcaaga     1020
ggcctgtttg agccattgc cggctttatt gaaggcggat ggcagggaat ggtggatggg     1080
tggtacggct atcaccacag caatgatcag ggatctggct atgccgccga taaagagagc     1140
acccagaagg cctttgacgg catcaccaac aaagtgaaca gcgtgatcga aagatgaac      1200 acccagtttg aggccgtggg caaagagttc agcaatctgg aaagacggct ggaaaacctg     1260
aacaagaaaa tggaagatgg cttcctggac gtgtggacat ataatgccga gctgctggtg     1320
ctgatggaaa acgagaggac cctggacttt cacgacagca acgtgaagaa cctgtacgac     1380
aaagtgcgga tgcagctgag agacaatgtg aaagagctgg gcaacggctg ctttgagttc     1440
taccacaagt gcgacgacga gtgcatgaat agcgtgaaga acggcaccta cgactaccct     1500
aagtatgagg aagagagcaa gctgaacaga aacgagatca ag                       1542
```

<210> SEQ ID NO 17
<211> LENGTH: 514
<212> TYPE: PRT
<213> ORGANISM: Influenza virus

<400> SEQUENCE: 17

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255
```

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys

<210> SEQ ID NO 18
<211> LENGTH: 1542
<212> TYPE: DNA
<213> ORGANISM: Influenza virus

<400> SEQUENCE: 18
cttgatctcg tttctgttca gcttgctctc ttcctcatac ttagggtagt cgtaggtgcc      60
gttcttcacg ctattcatgc actcgtcgtc gcacttgtgg tagaactcaa agcagccgtt     120
gcccagctct ttcacattgt ctctcagctg catccgcact tgtcgtaca ggttcttcac     180 gttgctgtcg tgaaagtcca gggtcctctc gttttccatc agcaccagca gctcggcatt     240
atatgtccac acgtccagga agccatcttc cattttcttg ttcaggtttt ccagccgtct     300
ttccagattg ctgaactctt tgcccacggc ctcaaactgg gtgttcatct tctcgatcac     360
gctgttcact tgttggtga tgccgtcaaa ggccttctgg gtgctctctt tatcggcggc     420
atagccagat ccctgatcat tgctgtggtg atagccgtac acccatccca ccattccctg     480
ccatccgcct tcaataaagc cggcaatggc tccaaacagg cctcttgact cgatctgggg     540
cacatttctc agtcctgtgg ccagcaccag tttctcagac ttcacgtact tagggcactc     600
gccgattgtc agagggtgca cattatggaa gggcagggtg gtattaatgg cgcccagagg     660

```
tgtctgacac ttggtttcac agttttccag ggtgccctct gtttcatga tgccgctgct    720 gcctctcttg ctgatcttga agccgtactc aggggcaatc agattcccgg tgctctcaaa    780
gttgatggtg tcccacatat ccagcagggt ccaggaaaat tccattctgc cgccctgtcc    840
attcactttg ggtctggtgg caatatcggg ggtgcttctc ttattcagtg tgctggtgcc    900
cacagacacg tatgtgccca cattctggta cagggttctc tgctctgtct catcattagg    960
gtggtgcacg ccccaaataa tcagcatctg ctcgccgctt gtattattgt agctgccctt   1020
ggccacagga taattagagc ccttcttggt cagccagacc atatttctga gaagctggg    1080 gttgccggac acagcacaag ctctgcttcc gcctgttgtt gtatgctggg tccatctatc   1140
cttgggcagg atcttcactt tctcgaagtg cttcacgctg acagcaggt gcttcagttc    1200 ctcgtaatcg ttgaagctgc cggggtaaca cagtccgtcc ctagggttct cttttccat   1260 gatgtagctc cactcaggca cagacagcag tctatcgcac tcaggatttc ccagcagcca   1320
gccagcaata gaacaatcgc ccagttccag aggaggaatg ccattcagct tgcacagctt   1380
gccgttgtgg gtcttttcca gaatatcctt ggcgtgggtc acggtcacat ttcttccag    1440 gatggtgtcc accttctcgg tgctattgtt ggcgtggtag ccgatacaga tctgatcgcc   1500
ccgcacagct gtaaacagca ggatcaggta gatgatggcc at                      1542

<210> SEQ ID NO 19
<211> LENGTH: 1557
<212> TYPE: DNA
<213> ORGANISM: Influenza virus

<400> SEQUENCE: 19
atgaaaacca tcattgccct gagctacatc ttttgtctgg ctctgggcca ggatctgccc     60
ggcaatgata atagcaccgc caccctgtgt ctgggacacc acgccgtgcc taatggcacc    120
ctggtgaaaa ccattaccga cgaccagatc gaagtgacca atgccaccga gctggtgcag    180
agcagcagca ccggcaagat ctgcaacaac ccccacagaa tcctggatgg catcgactgt    240
accctgatcg atgccctgct gggcgatcct cactgcgacg tgttccagaa cgagacatgg    300
gacctgttcg tggagagaag caaggccttc agcaactgct accctacga tgtgcccgat    360 tacgcctctc tgagaagcct ggtggccagc agcggcacac tggaattcat caccgagggc    420
tttacctgga caggcgtgac ccagaatggc ggcagcaatg cctgtaaaag aggccctggc    480
agcggcttct tcagcagact gaactggctg accaagtccg gcagcaccta ccctgtgctg    540
aacgtgacca tgcccaacaa cgacaacttc gacaagctgt acatctgggg cgtgcaccac    600
cctagcacca tcaggaaca gaccagcctg tacgtgcagg ccagcggcag agtgaccgtg    660
tctaccagac ggtcccagca gaccatcatc cccaacatcg agtcaagacc ttgggtgcgc    720
ggcctgagca gcagaatcag catctactgg accatcgtga aacctggcga cgtgctggtg    780
atcaacagca atggcaaccct gatcgccccc agaggctact tcaagatgcg gaccggcaag    840
agcagcatca tgagaagcga cgccccccatc gatacctgta tcagcgagtg catcaccccc    900
aacggcagca tccccaacga caagcccttc cagaacgtga acaagatcac ctacggcgcc    960
tgccctaagt acgtgaagca gaacacccctg aagctggcca ccggcatgag aaatgtgccc   1020
gagaagcaga caagaggcct gtttggcgcc attgccggct ttatcgagaa cggctgggag   1080
ggcatgatcg atgggtggta cggcttcaga caccagaatt ctgagggcac aggacaggcc   1140
gccgatctga agtctacaca ggccgccatc gaccagatca acggcaagct gaacagagtg   1200
```

-continued

```
atcgagaaaa ccaacgagaa gttccaccag atcgagaaag aattcagcga ggtggagggc      1260
agaatccagg acctgaaaaa atacgtggag gacaccaaga tcgacctgtg gagctacaat      1320
gccgaactgc tggtcgccct ggaaaaccag cacaccatcg acctgaccga cagcgagatg      1380
aataagctgt tcgaaaagac cagacggcag ctgagagaaa acgccgagga catgggcaac      1440
ggctgcttca agatctacca caagtgcgac aacgcctgca tcgagagcat cagaaacggc      1500
acctacgacc acgatgtgta cagggacgag gccctgaaca acagattcca gatcaag        1557
```

<210> SEQ ID NO 20
<211> LENGTH: 519
<212> TYPE: PRT
<213> ORGANISM: Influenza virus

<400> SEQUENCE: 20

```
Met Lys Thr Ile Ile Ala Leu Ser Tyr Ile Phe Cys Leu Ala Leu Gly
 1               5                  10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Glu Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320
```

```
Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys
        515

<210> SEQ ID NO 21
<211> LENGTH: 1557
<212> TYPE: DNA
<213> ORGANISM: Influenza virus

<400> SEQUENCE: 21
cttgatctgg aatctgttgt tcagggcctc gtccctgtac acatcgtggt cgtaggtgcc      60
gtttctgatg ctctcgatgc aggcgttgtc gcacttgtgg tagatcttga agcagccgtt     120
gcccatgtcc tcggcgtttt ctctcagctg ccgtctggtc ttttcgaaca gcttattcat     180
ctcgctgtcg gtcaggtcga tggtgtgctg gttttccagg gcgaccagca gttcggcatt     240
gtagctccac aggtcgatct ggtgtcctc acgtattttt ccaggtcct ggattctgcc      300 ctccacctcg ctgaattctt tctcgatctg gtggaacttc tcgttggttt tctcgatcac     360
tctgttcagc ttgccgttga tctggtcgat ggcggcctgt gtagacttca gatcggcggc     420
ctgtcctgtg ccctcagaat tctggtgtct gaagccgtac acccatcga tcatgccctc     480 ccagccgttc tcgataaagc cggcaatggc gccaaacagg cctcttgtct gcttctcggg     540
cacatttctc atgccggtgg ccagcttcag ggtgttctgc ttcacgtact tagggcaggc     600
gccgtaggtg atcttgttca cgttctggaa gggcttgtcg ttggggatgc tgccgttggg     660
ggtgatgcac tcgctgatac aggtatcgat ggggcgtcg cttctcatga tgctgctctt     720
gccggtccgc atcttgaagt agcctctggg ggcgatcagg ttgccattgc tgttgatcac     780
cagcacgtcg ccaggtttca cgatggtcca gtagatgctg attctgctgc tcaggccgcg     840
cacccaaggt cttgactcga tgttggggat gatggtctgc tgggaccgtc tggtagacac     900
ggtcactctg ccgctggcct gcacgtacag gctggtctgt tcctgattgg tgctagggtg     960
```

```
gtgcacgccc cagatgtaca gcttgtcgaa gttgtcgttg ttgggcatgg tcacgttcag    1020
cacagggtag gtgctgccgg acttggtcag ccagttcagt ctgctgaaga agccgctgcc    1080
agggcctctt ttacaggcat tgctgccgcc attctgggtc acgcctgtcc aggtaaagcc    1140
ctcggtgatg aattccagtg tgccgctgct ggccaccagg cttctcagag aggcgtaatc    1200
gggcacatcg tagggggtagc agttgctgaa ggccttgctt ctctccacga acaggtccca    1260
tgtctcgttc tggaacacgt cgcagtgagg atcgcccagc agggcatcga tcagggtaca    1320
gtcgatgcca tccaggattc tgtggggggtt gttgcagatc ttgccggtgc tgctgctctg    1380
caccagctcg gtggcattgg tcacttcgat ctggtcgtcg gtaatggttt tcaccagggt    1440
gccattaggc acggcgtggt gtcccagaca cagggtggcg gtgctattat cattgccggg    1500
cagatcctgg cccagagcca gacaaaagat gtagctcagg gcaatgatgg ttttcat     1557
```

<210> SEQ ID NO 22
<211> LENGTH: 1557
<212> TYPE: DNA
<213> ORGANISM: Influenza virus

<400> SEQUENCE: 22

```
atgaaaacca tcattgccct gagctacatc ctgtgcctgg tgttcacaca gaagctgccc      60
ggcaacgata atagcaccgc cacactgtgt ctgggacacc acgccgtgcc taatggcacc     120
atcgtgaaaa caatcaccaa cgaccagatc gaagtgacca atgccacaga gctggtgcag     180
agcagcagca caggcgagat ctgtgacagc ccccaccaga tcctggatgg cgagaactgt     240
accctgatcg atgccctgct gggcgatcct cagtgcgacg gcttccagaa caagaaatgg     300
gacctgttcg tggagagaag caaggcctac agcaactgct accctacga cgtgcctgat     360 tacgccagcc tgagaagcct ggtggcctct agcggcaccc tggaattcaa caacgagagc     420
ttcaactgga ccggcgtgac acagaatggc accagcagcg cctgcatcag acggtccaac     480
aacagcttct tcagtagact gaattggctg acccacctga gttcaagta ccccgccctg     540 aacgtgacca tgcccaacaa tgagaagttc gacaagctgt acatctgggg agtgcaccac     600
cctggcaccg acaacgatca gatcttccct tacgcccagg ccagcggcag aatcaccgtg     660
tccaccaaga aagccagca gaccgtgatc cccaatatcg gcagcagacc cagagtgcgg     720
aacatcccca gcaggatcag catctactgg acaatcgtga agcctggcga catcctgctg     780
atcaacagca ccggcaacct gatcgccccc tgggggctact ttaagatcag aagcggcaag     840
agcagcatca tgagatccga cgccccccatc ggcaagtgca acagcgagtg catcacccca     900
aacggcagca tccccaacga caagcccttc cagaacgtga acaggatcac ctacggcgcc     960
tgccctagat acgtgaagca gaacaccctg aagctggcca ccggcatgag aaatgtgccc     1020
gagaagcaga ccagaggcat ctttggcgcc attgccggct ttatcgagaa tggctgggag     1080
ggaatggtgg atgggtggta cggcttcaga caccagaata tcgagggaat ggacaggcc     1140 gccgatctga atctaccca ggccgccatc gaccagatca cggcaagct gaacaggctg     1200 atcggcaaga ccaacgagaa gttccaccag atcgagaaag aattcagcga ggtggagggc     1260
agaatccagg acctggaaaa atacgtggag gacaccaaga tcgacctgtg gagctacaat     1320
gccgaactgc tggtcgccct ggaaaaccag cacacaattg atctgacaga cagtgagatg     1380
aataagctgt tcgagaaaac caagaagcag ctgagagaaa acgccgagga catgggcaac     1440
ggctgcttca agatctacca caagtgcgac aacgcctgca tcggcagcat cagaaacggc     1500
```

```
acctacgacc acgacgtgta cagagatgag gccctgaaca accggtttca gatcaag        1557
```

<210> SEQ ID NO 23
<211> LENGTH: 519
<212> TYPE: PRT
<213> ORGANISM: Influenza virus

<400> SEQUENCE: 23

```
Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Pro Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365
```

```
Phe Arg His Gln Asn Ser Glu Gly Ile Gly Gln Ala Ala Asp Leu Lys
    370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
    450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys
        515

<210> SEQ ID NO 24
<211> LENGTH: 1557
<212> TYPE: DNA
<213> ORGANISM: Influenza virus

<400> SEQUENCE: 24
cttgatctga aaccggttgt tcagggcctc atctctgtac acgtcgtggt cgtaggtgcc      60
gtttctgatg ctgccgatgc aggcgttgtc gcacttgtgg tagatcttga agcagccgtt     120
gcccatgtcc tcggcgtttt ctctcagctg cttcttggtt ttctcgaaca gcttattcat     180
ctcactgtct gtcagatcaa ttgtgtgctg gttttccagg cgaccagca gttcggcatt      240
gtagctccac aggtcgatct ggtgtcctc acgtattttt ccaggtcct ggattctgcc       300
ctccacctcg ctgaattctt tctcgatctg gtggaacttc tcgttggtct tgccgatcag     360
cctgttcagc ttgccgttga tctggtcgat ggcggcctgg gtagatttca gatcggcggc     420
ctgtccaatt ccctcgctat tctggtgtct gaagccgtac cacccatcca ccattccctc     480
ccagccattc tcgataaagc cggcaatggc gccaaagatg cctctggtct gcttctcggg     540
cacatttctc atgccggtgg ccagcttcag ggtgttctgc ttcacgtatc tagggcaggc     600
gccgtaggtg atcctgttca cgttctggaa gggcttgtcg ttgggatgc tgccgtttgg     660
ggtgatgcac tcgctgttgc acttgccgat ggggcgtcg atctcatga tgctgctctt      720
gccgcttctg atcttaaagt agccccgagg ggcgatcagg ttgccggtgc tgttgatcag    780
caggatgtcg ccaggcttca cgattgtcca gtagatgctg atcctgctgg ggatgttccg    840
cactctgggt ctgctgccga tattgggat acggtctgc tggcttctct tggtggacac      900
ggtgattctg ccgctggcct gggcgtaagg gaagatctga tcgttgtcgg tgccagggtg    960
gtgcactccc cagatgtaca gcttgtcgaa cttctcattg ttgggcatgg tcacgttcag   1020
ggcggggtac ttgaacttca ggtgggtcag ccaattcagt ctactgaaga agctgttgtt   1080
ggaccgtctg atgcaggcgc tgctggtgcc attctgtgtc acgccggtcc agttgaagct   1140
ctcgttgttg aattccaggg tgccgctaga ggccaccagg cttctcaggc tggcgtaatc   1200
aggcacgtcg taggggtagc agttgctgta ggccttgctt ctctccacga acaggtccca   1260
```

```
tttcttgttc tggaagccgt cgcactgagg atcgcccagc agggcatcga tcagggtaca    1320
gttctcgcca tccaggatct ggtgggggct gtcacagatc tcgcctgtgc tgctgctctg    1380
caccagctct gtggcattgg tcacttcgat ctggtcgttg gtgattgttt tcacgatggt    1440
gccattaggc acggcgtggt gtcccagaca cagtgtggcg gtgctattat cgttgccggg    1500
cagcttctgt gtgaacacca ggcacaggat gtagctcagg gcaatgatgg tttttcat     1557
```

<210> SEQ ID NO 25
<211> LENGTH: 1560
<212> TYPE: DNA
<213> ORGANISM: Influenza virus

<400> SEQUENCE: 25

```
atggaaaaga tcgtgctgct gctggccatt gtgagcctgg tgaagagcga ccagatctgc     60
attggctacc acgccaacaa tagcacagag caggtggaca ccatcatgga aaaaaacgtg    120
accgtgaccc acgctcagga catcctggaa aagacccaca acggcaagct gtgtgatctg    180
gacggcgtga agcctctgat cctgagagat tgtagcgtgg ctggatggct gctgggcaac    240
cctatgtgcg acgagttcat caacgtgccc gagtggagct atatcgtgga aaggccaac    300 cccaccaacg atctgtgtta ccccggcagc ttcaacgatt acgaggaact gaagcacctg    360
ctgtcccgga tcaaccactt cgagaagatc cagatcatcc ccaagtcctc ttggagcgat    420
cacgaagcct ctagcggagt gtctagcgcc tgtccttacc tgggcagccc cagcttcttc    480
agaaacgtgg tgtggctgat caagaagaac agcacctacc ccaccatcaa gaagagctac    540
aacaacacca accaggaaga tctgctggtc ctgtggggaa tccaccaccc taatgatgcc    600
gccgagcaga ccagactgta ccagaacccc accacctata tcagcatcgg caccagcacc    660
ctgaatcaga gactggtgcc caagatcgcc accagatcca aggtgaacgg ccagagcggc    720
aggatggaat tcttctggac catcctgaag cccaacgacg ccatcaactt cgagagcaac    780
ggcaacttta tcgcccctga gtacgcctac aagatcgtga agaagggcga cagcgccatc    840
atgaagagcg agctggaata cggcaactgc aacaccaagt gccagacacc tatgggcgcc    900
atcaacagca gcatgccctt ccacaacatc acccctctga ccatcggcga gtgccctaag    960
tacgtgaaga gcaacagact ggtgctggcc acaggcctga gaaatagccc cagcgggag   1020 agcagaagaa agaagagggg cctgtttgga gccatcgccg gctttattga aggcggctgg   1080
cagggaatgg tggatggctg gtacggctac caccacagca tgagcaggg ctctggatat   1140 gccgccgaca aagagtctac ccagaaggcc atcgacggcg tcaccaacaa ggtgaacagc   1200
atcatcgaca gatgaacac ccagttcgag gctgtgggca gagagttcaa caacctggaa   1260
cggcggatcg agaacctgaa caagaaaatg gaagatggct tcctggatgt gtggacctac   1320
aatgccgaac tgctggtgct gatggaaaac gagcggaccc tggacttcca cgacagcaac   1380
gtgaagaacc tgtacgacaa agtgcggctg cagctgagag acaacgccaa agagctgggc   1440
aacggctgct tcgagttcta ccacaagtgc gacaacgagt gcatggaaag catcaggaac   1500
ggcacctaca actaccctca gtacagcgag gaagccaggc tgaagaggga agagatcagc   1560
```

<210> SEQ ID NO 26
<211> LENGTH: 520
<212> TYPE: PRT
<213> ORGANISM: Influenza virus

<400> SEQUENCE: 26

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
    275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
```

```
                420           425           430
Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
                500                 505                 510

Arg Leu Lys Arg Glu Glu Ile Ser
            515                 520

<210> SEQ ID NO 27
<211> LENGTH: 1560
<212> TYPE: DNA
<213> ORGANISM: Influenza virus

<400> SEQUENCE: 27
gctgatctct ccctcttca gcctggcttc ctcgctgtac tgagggtagt tgtaggtgcc      60
gttcctgatg ctttccatgc actcgttgtc gcacttgtgg tagaactcga agcagccgtt     120
gcccagctct ttggcgttgt ctctcagctg cagccgcact tgtcgtaca ggttcttcac      180 gttgctgtcg tggaagtcca gggtccgctc gttttccatc agcaccagca gttcggcatt     240
gtaggtccac acatccagga agccatcttc cattttcttg ttcaggttct cgatccgccg     300
ttccaggttg ttgaactctc tgcccacagc ctcgaactgg gtgttcatct tgtcgatgat     360
gctgttcacc ttgttggtga cgccgtcgat ggccttctgg gtagactctt gtcggcggc      420 atatccagag ccctgctcat gctgtggtg gtagccgtac cagccatcca ccattccctg      480
ccagccgcct caataaagc cggcgatggc tccaaacagg cccctcttct ttcttctgct      540
ctcccgctgg gggctatttc tcaggcctgt ggccagcacc agtctgttgc tcttcacgta     600
cttagggcac tcgccgatgg tcagagggtg atgttgtgg aagggcatgc tgctgttgat      660
ggcgcccata ggtgtctggc acttggtgtt gcagttgccg tattccagct cgctcttcat     720
gatgcgctgt cgcccttct tcacgatctt gtaggcgtac tcagggcga taaagttgcc      780 gttgctctcg aagttgatgg cgtcgttggg cttcaggatg gtccagaaga attccatcct     840
gccgctctgg ccgttcacct ggatctggt ggcgatcttg gcaccagtc tctgattcag      900 ggtgctggtg ccgatgctga tataggtggt ggggttctgg tacagtctgg tctgctcggc     960
ggcatcatta gggtggtgga ttccccacag gaccagcaga tcttcctggt tggtgttgtt     1020
gtagctcttc ttgatggtgg ggtaggtgct gttcttcttg atcagccaca ccacgtttct    1080
gaagaagctg gggctgccca ggtaaggaca ggcgctagac actccgctag aggcttcgtg    1140
atcgctccaa gaggacttgg ggatgatctg gatcttctcg aagtggttga tccgggacag    1200
caggtgcttc agttcctcgt aatcgttgaa gctgccgggg taacacagat cgttggtggg    1260
gttggccttc tccacgatat agctccactc gggcacgttg atgaactcgt cgcacatagg    1320
gttgcccagc agccatccag ccacgctaca atctctcagg atcagaggct tcacgccgtc    1380
cagatcacac agcttgccgt tgtgggtctt ttccaggatg tcctgagcgt gggtcacggt    1440
cacgtttttt tccatgatgg tgtccacctg ctctgtgcta ttgttggcgt ggtagccaat    1500
gcagatctgg tcgctcttca ccaggctcac aatggccagc agcagcacga tcttttccat    1560
```

<210> SEQ ID NO 28
<211> LENGTH: 1602
<212> TYPE: DNA
<213> ORGANISM: Influenza virus

<400> SEQUENCE: 28

```
atgaaggcca tcatcgtgct gctgatggtg gtgaccagca acgccgatag aatctgcacc     60
ggcatcacca gcagcaatag cccccatgtg gtgaaaacag ccacccaggg cgaagtgaat    120
gtgacaggcg tgatccctct gaccaccacc cccaccaaga gctacttcgc caacctgaag    180
ggcaccagaa ccagaggcaa gctgtgcccc gattgcctga actgcaccga tctggatgtg    240
gctctgggca gacctatgtg tgtgggcacc acaccatctg ccaaggccag catcctgcac    300
gaagtgaagc ctgtgaccag cggctgcttc cccatcatgc acgaccggac caagatcaga    360
cagctgccca acctgctgag aggctacgag aacatccggc tgtccaccca gaatgtgatc    420
gatgccgaga aagcccctgg cggaccttat agactgggca ccagcggctc ttgtcccaat    480
gccacctcca agagcggctt ttttgccaca atggcctggg ccgtgcctaa ggacaacaac    540
aagaacgcca ccaaccctct gaccgtggag gtgccctaca tctgtacaga gggcgaggat    600
cagatcacag tgtggggctt ccacagcgac gacaagaccc agatgaagaa cctgtacggc    660
gacagcaacc cccagaagtt taccagcagc gccaatggcg tgaccaccca ctacgtgtcc    720
cagatcggca gctttcccga tcagacagag gatggcggac tgcctcagtc tggcaggatc    780
gtggtggact acatgatgca gaagcctggc aagaccggca ccatcgtgta tcagagaggc    840
gtgctgctgc ctcagaaagt gtggtgtgcc agcggcaggt ctaaagtgat caagggcagc    900
ctgcctctga ttggcgaggc cgactgtctg cacgaaaagt acggcggcct gaacaagagc    960
aagccctact acacaggcga gcacgccaag gccatcggca attgccccat ctgggtgaaa   1020 accccccctga agctggccaa tggcaccaag tacagacctc ccgccaagct gctgaaagag   1080
agaggcttct ttggcgccat tgccggattt ctggaaggcg gctgggaggg aatgattgcc   1140
ggctggcacg gctatacatc tcatggggcc catggcgtgg ctgtggccgc cgatctgaag   1200
tctacccagg aagccatcaa caagatcacc aagaacctga acagcctgag cgagctggaa   1260
gtgaagaatc tgcagagact gagcggcgcc atggatgagc tgcacaacga gatcctggaa   1320
ctggacgaga aagtggatga tctccgcgcc gatacaattt cctcccagat tgaactggcc   1380
gtgctgctgt ccaacgaggg catcatcaac agcgaggatg aacacctgct ggccctggaa   1440
cggaagctga agaagatgct gggcccttct gccgtggaga tcggcaacgg ctgcttcgag   1500
acaaagcaca agtgcaacca gacctgcctg gatagaatcg ccgctggcac cttcaatgcc   1560
ggcgagttca gcctgcctac cttcgacagc ctgaatatca cc                       1602
```

<210> SEQ ID NO 29
<211> LENGTH: 534
<212> TYPE: PRT
<213> ORGANISM: Influenza virus

<400> SEQUENCE: 29

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45
```

-continued

```
Thr Thr Pro Thr Lys Ser Tyr Phe Ala Asn Leu Lys Gly Thr Arg Thr
     50              55                  60

Arg Gly Lys Leu Cys Pro Asp Cys Leu Asn Cys Thr Asp Leu Asp Val
 65              70                  75                  80

Ala Leu Gly Arg Pro Met Cys Val Gly Thr Thr Pro Ser Ala Lys Ala
                 85                  90                  95

Ser Ile Leu His Glu Val Lys Pro Val Thr Ser Gly Cys Phe Pro Ile
             100                 105                 110

Met His Asp Arg Thr Lys Ile Arg Gln Leu Pro Asn Leu Leu Arg Gly
             115                 120                 125

Tyr Glu Asn Ile Arg Leu Ser Thr Gln Asn Val Ile Asp Ala Glu Lys
            130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
            195                 200                 205

Ser Asp Asp Lys Thr Gln Met Lys Asn Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
            275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
            355                 360                 365

Gly Phe Leu Glu Gly Gly Trp Glu Gly Met Ile Ala Gly Trp His Gly
            370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
            435                 440                 445

Arg Ala Asp Thr Ile Ser Ser Gln Ile Glu Leu Ala Val Leu Leu Ser
450                 455                 460
```

```
Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr
    530

```
<210> SEQ ID NO 30
<211> LENGTH: 1602
<212> TYPE: DNA
<213> ORGANISM: Influenza virus

<400> SEQUENCE: 30

```
ggtgatattc aggctgtcga aggtaggcag gctgaactcg ccggcattga aggtgccagc     60
ggcgattcta tccaggcagg tctggttgca cttgtgcttt gtctcgaagc agccgttgcc    120
gatctccacg gcagaagggc ccagcatctt cttcagcttc cgttccaggg ccagcaggtg    180
ttcatcctcg ctgttgatga tgccctcgtt ggacagcagc acggccagtt caatctggga    240
ggaaattgta tcggcgcgga gatcatccac tttctcgtcc agttccagga tctcgttgtg    300
cagctcatcc atggcgccgc tcagtctctg cagattcttc acttccagct cgctcaggct    360
gttcaggttc ttggtgatct tgttgatggc ttcctgggta gacttcagat cggcggccac    420
agccacgcca tgggccccat gagatgtata gccgtgccag ccggcaatca ttccctccca    480
gccgccttcc agaaatccgg caatggcgcc aaagaagcct ctctctttca gcagcttggc    540
gggaggtctg tacttggtgc cattggccag cttcaggggg gttttcaccc agatggggca    600
attgccgatg gccttggcgt gctcgcctgt gtagtagggc ttgctcttgt tcaggccgcc    660
gtacttttcg tgcagacagt cggcctcgcc aatcagaggc aggctgccct tgatcacttt    720
agacctgccg ctggcacacc acactttctg aggcagcagc acgcctctct gatacacgat    780
ggtgccggtc ttgccaggct tctgcatcat gtagtccacc acgatcctgc cagactgagg    840
cagtccgcca tcctctgtct gatcgggaaa gctgccgatc tgggacacgt agtgggtggt    900
cacgccattg gcgctgctgg taaacttctg gggggttgctg tcgccgtaca ggttcttcat    960
ctgggtcttg tcgtcgctgt ggaagcccca cactgtgatc tgatcctcgc cctctgtaca   1020
gatgtagggc acctccacgg tcagagggtt ggtggcgttc ttgttgttgt ccttaggcac   1080
ggcccaggcc attgtggcaa aaaagccgct cttggaggtg gcattgggac aagagccgct   1140
ggtgcccagt ctataaggtc cgccaggggc tttctcggca tcgatcacat tctgggtgga   1200
cagccggatg ttctcgtagc ctctcagcag gttgggcagc tgtctgatct tggtccggtc   1260
gtgcatgatg gggaagcagc cgctggtcac aggcttcact tcgtgcagga tgctggcctt   1320
ggcagatggt gtggtgccca cacacatagg tctgcccaga gccacatcca gatcggtgca   1380
gttcaggcaa tcggggcaca gcttgcctct ggttctggtg cccttcaggt tggcgaagta   1440
gctcttggtg gggtggtggg tcagagggat cacgcctgtc acattcactt cgccctgggt   1500
ggctgttttc accacatggg ggctattgct gctggtgatg ccggtgcaga ttctatcggc   1560
gttgctggtc accaccatca gcagcacgat gatggccttc at                      1602
```

<210> SEQ ID NO 31

<211> LENGTH: 1493
<212> TYPE: DNA
<213> ORGANISM: Influenza virus

<400> SEQUENCE: 31

```
atgacaactc aacagccacg ctctgcttgg ggcaccatgc cgtccctaac gggaccattg 60
tgaaaaccat tactaacgat cagatagagg tgactaatgc caccgagctg gtgcaaagta 120
gctccacagg agagatctgc gatagtcccc accagattct ggacggaaag aattgtacgc 180
tgatcgacgc gctgttgggc gaccctcagt gtgacggatt tcagaataag aagtgggatc 240
tgtttgtgga aaggtcaaag gcttattcaa attgctaccc ttacgatgtg cctgattatg 300
ccagcctgcg gtccctcgtc gcgtctagtg ggactctgga gttcaacaac gagtcattta 360
actggactgg cgttacacag aacgggacta gttccgcttg cataaggaga agcaaaaata 420
gtttcttcag cagactgaat tggctgacac atctgaactt caagtaccct gcactgaatg 480
taaccatgcc caacaacgag cagttcgata agctttacat ttggggagtt catcatcctg 540
gcactgacaa ggatcagatc tttctgtatg cccaggcttc cggcaggatt accgtgtcta 600
caaagagaag ccagcaaact gtgtctccca atatcggcag tagacccaga gtacggaaca 660
tccctagtcg catcagtatt tactggacca tcgtgaaacc aggcgatatt ctcctgatta 720
acagtactgg caacctgatc gcccccccggg gatactttaa aatccgctct ggaaagtcct 780
ccattatgag atcagatgca ccgatcggaa aatgcaactc tgagtgtatc acacccaatg 840
ggagcattcc caatgacaaa cctttccaga acgttaatcg aataacttat ggggcctgtc 900
cacggtacgt gaagcaaaat accttgaaac tggcgaccgg tatgcgcaat gtccccgaaa 960
aacagacccg cgggatattt ggggctatcg caggctttat cgagaatggc tgggaaggga 1020
tggtggatgg ttggtatggt tttagacatc aaaactccga aggcagaggc caggctgccg 1080
atctcaagag cacgcaggcc gctatagatc agatcaatgg aaagctcaac agactgatcg 1140
ggaaaaccaa cgaaaaattc catcagatcg agaaagagtt ctccgaagtc gaggggcgca 1200
tacaggacct ggagaagtat gttgaggata caaagattga tctgtggtcc tacaatgccg 1260
agctgctggt ggctctggag aatcagcaca ctattgacct gaccgattca gagatgaaca 1320
aactttttga gaagacgaag aagcagctta gagaaaatgc agaggacatg ggaacggat 1380
gctttaaaat atatcataag tgtgataatg cctgcatcgg atcaattaga aatggtacct 1440
atgatcacga tgtttacagg gacgaagcgc tgaataacag gttccagata aaa 1493

<210> SEQ ID NO 32
<211> LENGTH: 519
<212> TYPE: PRT
<213> ORGANISM: Influenza virus

<400> SEQUENCE: 32

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Gln Ile Glu Val Thr Asn Ala Thr Glu Leu Val Gln Ser Ser Ser Thr
50 55 60

Gly Glu Ile Cys Asp Ser Pro His Gln Ile Leu Asp Gly Lys Asn Cys
65 70 75 80
```

Thr Leu Ile Asp Ala Leu Leu Gly Asp Pro Gln Cys Asp Gly Phe Gln
            85                  90                  95

Asn Lys Lys Trp Asp Leu Phe Val Glu Arg Ser Lys Ala Tyr Ser Asn
        100                 105                 110

Cys Tyr Pro Tyr Asp Val Pro Asp Tyr Ala Ser Leu Arg Ser Leu Val
    115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Lys
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ser Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu

```
500 505 510

Asn Asn Arg Phe Gln Ile Lys
515

<210> SEQ ID NO 33
<211> LENGTH: 1493
<212> TYPE: DNA
<213> ORGANISM: Influenza virus
<400> SEQUENCE: 33
ttttatctgg aacctgttat tcagcgcttc gtccctgtaa acatcgtgat cataggtacc 60
atttctaatt gatccgatgc aggcattatc acacttatga tatattttaa agcatccgtt 120
ccccatgtcc tctgcatttt ctctaagctg cttcttcgtc ttctcaaaaa gtttgttcat 180
ctctgaatcg gtcaggtcaa tagtgtgctg attctccaga gccaccagca gctcggcatt 240
gtaggaccac agatcaatct ttgtatcctc aacatacttc tccaggtcct gtatgcgccc 300
ctcgacttcg gagaactctt tctcgatctg atggaatttt tcgttggttt tcccgatcag 360
tctgttgagc tttccattga tctgatctat agcggcctgc gtgctcttga gatcggcagc 420
ctggcctctg ccttcggagt tttgatgtct aaaaccatac caaccatcca ccatcccttc 480
ccagccattc tcgataaagc ctgcgatagc cccaaatatc ccgcgggtct gtttttcggg 540
gacattgcgc ataccggtcg ccagtttcaa ggtattttgc ttcacgtacc gtggacaggc 600
cccataagtt attcgattaa cgttctggaa aggtttgtca ttgggaatgc tcccattggg 660
tgtgatacac tcagagttgc attttccgat cggtgcatct gatctcataa tggaggactt 720
tccagagcgg attttaaagt atccccgggg ggcgatcagg ttgccagtac tgttaatcag 780
gagaatatcg cctggtttca cgatggtcca gtaaatactg atgcgactag ggatgttccg 840
tactctgggt ctactgccga tattgggaga cacagtttgc tggcttctct ttgtagacac 900
ggtaatcctg ccggaagcct gggcatacag aaagatctga tccttgtcag tgccaggatg 960
atgaactccc caaatgtaaa gcttatcgaa ctgctcgttg ttgggcatgg ttacattcag 1020
tgcagggtac ttgaagttca gatgtgtcag ccaattcagt ctgctgaaga aactattttt 1080
gcttctcctt atgcaagcgg aactagtccc gttctgtgta acgccagtcc agttaaatga 1140
ctcgttgttg aactccagag tcccactaga cgcgacgagg gaccgcaggc tggcataatc 1200
aggcacatcg taagggtagc aatttgaata agcctttgac ctttccacaa acagatccca 1260
cttcttattc tgaaatccgt cacactgagg gtcgcccaac agcgcgtcga tcagcgtaca 1320
attctttccg tccagaatct ggtggggact atcgcagatc tctcctgtgg agctactttg 1380
caccagctcg gtggcattag tcacctctat ctgatcgtta gtaatggttt tcacaatggt 1440
cccgttaggg acggcatggt gccccaagca gagcgtggct gttgagttgt cat 1493

<210> SEQ ID NO 34
<211> LENGTH: 1551
<212> TYPE: DNA
<213> ORGANISM: Influenza virus
<400> SEQUENCE: 34
atgaaagtga agctgctggt gctgctgtgt acctttaccg ccacctacgc cgataccatc 60
tgtatcggct accacgccaa caatagcacc gacaccgtgg ataccgtgct ggaaaagaac 120
gtgaccgtga cccacagcgt gaacctgctg gaaaacagcc acaacggcaa gctgtgtctg 180
ctgaaaggca ttgcccctct gcagctggga aattgtagcg tggccggctg gattctgggc 240
```

```
aatcctgagt gcgagctgct gatttccaaa gagtcctggt cctacatcgt ggagaagccc      300
aaccctgaga atggcacctg ctaccctggc cacttcgccg attacgagga actgagagaa      360
cagctgtcca gcgtgtccag cttcgagaga ttcgagatct cccccaaaga gagcagctgg      420
cccaatcata cagtgaccgg cgtgagcgcc tcttgtagcc acaatggcga gagcagcttc      480
tacagaaacc tgctgtggct gaccggcaag aacggcctgt accccaacct gagcaagagc      540
tacgccaaca caaagaaaaa agaagtgctg gtcctctggg gagtgcacca ccctcctaac      600
atcggcatcc agaaggccct gtaccacacc gagaatgcct acgtgtccgt ggtgtccagc      660
cactacagca gaaagttcac ccccgagatc gccaaaagac ccaaagtgcg ggaccaggaa      720
ggcaggatca actactactg gaccctgctg gaacctggcg acaccatcat cttcgaggcc      780
aacggcaatc tgatcgcccc tagatacgcc tttgccctga gcagaggctt tggcagcggc      840
atcatcaaca gcaacgcccc catggacaag tgtgacgcca gtgtcagac accacaggga      900 gctatcaata gcagcctgcc cttccagaat gtgcaccctg tgaccatcgg cgagtgtcct      960
aaatacgtgc ggagcgccaa gctgagaatg gtgaccggcc tgaggaatat ccccagcatc     1020
cagagcagag gcctgtttgg cgccattgcc ggctttatcg agggcggatg gacaggcatg     1080
gtggatgggt ggtacggcta ccaccaccag aatgagcagg gatctggcta tgccgccgat     1140
cagaagagca cccagaacgc catcaacggc atcaccaaca agtgaacag cgtgatcgag     1200 aagatgaaca cccagttcac cgccgtgggc aaagagttca acaagctgga acggcggatg     1260
gaaaacctga caagaaggt ggacgacggc ttcatcgaca tctggaccta caacgccgaa     1320
ctcctggtcc tcctggaaaa tgagaggacc ctggacttcc acgacagcaa cgtgaagaac     1380
ctgtacgaga aagtgaagag ccagctgaag aacaacgcca agagatcgg caacggctgc     1440 ttcgagttct accacaagtg caacgacgag tgcatggaaa gcgtgaagaa cggcacctac     1500
gactacccca gtacagcga ggaaagcaag ctgaaccggg agaagatcga t             1551
```

<210> SEQ ID NO 35
<211> LENGTH: 517
<212> TYPE: PRT
<213> ORGANISM: Influenza virus

<400> SEQUENCE: 35

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140
```

```
Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Ile Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
                260                 265                 270

Leu Ser Arg Gly Phe Gly Ser Gly Ile Ile Asn Ser Asn Ala Pro Met
            275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp
        515

<210> SEQ ID NO 36
<211> LENGTH: 1551
<212> TYPE: DNA
<213> ORGANISM: Influenza virus

<400> SEQUENCE: 36
```

```
atcgatcttc tcccggttca gcttgctttc ctcgctgtac ttggggtagt cgtaggtgcc      60
gttcttcacg ctttccatgc actcgtcgtt gcacttgtgg tagaactcga agcagccgtt     120
gccgatctct ttggcgttgt tcttcagctg gctcttcact ttctcgtaca ggttcttcac     180
gttgctgtcg tggaagtcca gggtcctctc attttccagg aggaccagga gttcggcgtt     240
gtaggtccag atgtcgatga agccgtcgtc caccttcttg ttcaggtttt ccatccgccg     300
ttccagcttg ttgaactctt tgcccacggc ggtgaactgg gtgttcatct tctcgatcac     360
gctgttcact tgttggtga tgccgttgat ggcgttctgg gtgctcttct gatcggcggc      420
atagccagat ccctgctcat tctggtggtg gtagccgtac cacccatcca ccatgcctgt     480
ccatccgccc tcgataaagc cggcaatggc gccaaacagg cctctgctct ggatgctggg     540
gatattcctc aggccggtca ccattctcag cttggcgctc cgcacgtatt taggacactc     600
gccgatggtc acagggtgca cattctggaa gggcaggctg ctattgatag ctccctgtgg     660
tgtctgacac ttggcgtcac acttgtccat ggggcgttg ctgttgatga tgccgctgcc      720
aaagcctctg ctcagggcaa aggcgtatct agggcgatc agattgccgt tggcctcgaa      780
gatgatggtg tcgccaggtt ccagcagggt ccagtagtag ttgatcctgc cttcctggtc     840
ccgcactttg ggtcttttgg cgatctcggg ggtgaacttt ctgctgtagt ggctggacac     900
cacggacacg taggcattct cggtgtggta cagggccttc tggatgccga tgttaggagg     960
gtggtgcact ccccagagga ccagcacttc tttttctttg ttgttggcgt agctcttgct    1020
caggttgggg tacaggccgt tcttgccggt cagccacagc aggtttctgt agaagctgct    1080
ctcgccattg tggctacaag aggcgctcac gccggtcact gtatgattgg ccagctgct    1140 ctctttgggg aagatctcga atctctcgaa gctggacacg ctggacagct gttctctcag    1200
ttcctcgtaa tcggcgaagt ggccagggta gcaggtgcca ttctcagggt gggcttctc    1260 cacgatgtag gaccaggact cttttggaaat cagcagctcg cactcaggat tgcccagaat    1320
ccagccggcc acgctacaat ttcccagctg cagaggggca atgcctttca gcagacacag    1380
cttgccgttg tggctgtttt ccagcaggtt cacgctgtgg gtcacggtca cgttcttttc    1440
cagcacggta tccacggtgt cggtgctatt gttggcgtgg tagccgatac agatgggtatc    1500 ggcgtaggtg gcggtaaagg tacacagcag caccagcagc ttcactttca t             1551
```

<210> SEQ ID NO 37
<211> LENGTH: 1605
<212> TYPE: DNA
<213> ORGANISM: Influenza virus

<400> SEQUENCE: 37

```
atgaaggcca tcatcgtgct gctgatggtg gtcacaagca acgccgatag aatctgtacc      60
ggcatcacca gcagcaatag ccctcacgtc gtgaaaacag ctacacaggg cgaagtgaat     120
gtgaccggcg tgatccctct gaccacaaca cctacaaaga gccacttcgc caatctgaag     180
ggcacagaga caagaggcaa gctgtgtccc aagtgcctga attgcacaga tctggatgtg     240
gctctgggca gacctaagtg tacaggcaaa atccctagcg ccagagtgtc cattctgcat     300
gaagtgcgac ctgtgaccag cggctgtttt cctattatgc acgaccggac caagatcaga     360
cagctgccta atctgctgag aggctacgag cacatcagac tgagcaccca aatgtgatc      420 aacgccgaaa atgctcctgg cggcccttat aagatcggca catctggcag ctgccccaac     480
attacaaatg gcaatggctt ctttgccacc atggcttggg ccgtgcctaa gaacgataag     540
```

```
aacaagaccg ccaccaaccc cctgacaatc gaggtgccat atatctgtac agagggcgag    600
gatcagatca ccgtgtgggg atttcacagc gacaacgaaa cacagatggc caagctgtac    660
ggcgatagca agcctcagaa gtttaccagc tctgccaatg cgtgaccac acactatgtg     720
tctcagatcg gcggcttccc taatcagaca gaagatggcg gactgcctca gtctggaaga    780
atcgtggtgg attacatggt gcagaagtct ggcaagaccg gcaccatcac atatcagaga    840
ggaatcctgc tgccccagaa agtgtggtgc gcttctggaa gatccaaagt gatcaagggc    900
agcctgcctc tgattggaga agccgattgt ctgcacgaga atacggcgg cctgaacaag     960
agcaagcctt actatacagg cgagcacgcc aaggccatcg gcaattgtcc tatttgggtc    1020
aagacccctc tgaagctggc caatggcaca agtatagac ctccagccaa gctgctgaaa     1080
gagagaggct tttttggagc tatcgccggc tttctggaag gcggatggga gggaatgatt    1140
gctggatggc atggctacac atctcatggc gcacatggcg tggcagtggc tgctgatctg    1200
aaatctacac aggaagccat caacaagatc accaagaacc tgaacagcct gagcgagctg    1260
gaagtgaaga atctgcagag actgtctggc gccatggacg aactgcacaa tgagatcctg    1320
gaactggacg agaaggtgga cgatctgaga gccgatacaa tcagcagcca gattgaactg    1380
gctgtgctgc tgtctaacga gggcatcatc aatagcgagg acgaacatct gctggccctg    1440
gaaagaaagc tgaagaagat gctgggacct agcgccgtgg aaatcggcaa tggatgcttt    1500
gagacaaagc acaagtgcaa ccagacctgc ctggatagaa ttgccgccgg aacatttgat    1560
gccggcgagt tttctctgcc caccttcgat agcctgaata tcaca                    1605
```

<210> SEQ ID NO 38
<211> LENGTH: 535
<212> TYPE: PRT
<213> ORGANISM: Influenza virus

<400> SEQUENCE: 38

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
    195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
            245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr
530                 535

<210> SEQ ID NO 39
<211> LENGTH: 1605
<212> TYPE: DNA
<213> ORGANISM: Influenza virus

<400> SEQUENCE: 39
tgtgatattc aggctatcga aggtgggcag agaaaactcg ccggcatcaa atgttccggc      60
ggcaattcta tccaggcagg tctggttgca cttgtgcttt gtctcaaagc atccattgcc     120

-continued

| | |
|---|---|
| gatttccacg cgctaggtc ccagcatctt cttcagcttt ctttccaggg ccagcagatg | 180 |
| ttcgtcctcg ctattgatga tgccctcgtt agacagcagc acagccagtt caatctggct | 240 |
| gctgattgta tcggctctca gatcgtccac cttctcgtcc agttccagga tctcattgtg | 300 |
| cagttcgtcc atggcgccag acagtctctg cagattcttc acttccagct cgctcaggct | 360 |
| gttcaggttc ttggtgatct tgttgatggc ttcctgtgta gatttcagat cagcagccac | 420 |
| tgccacgcca tgtgcgccat gagatgtgta gccatgccat ccagcaatca ttccctccca | 480 |
| tccgccttcc agaaagccgg cgatagctcc aaaaaagcct ctctctttca gcagcttggc | 540 |
| tggaggtcta tactttgtgc cattggccag cttcagaggg gtcttgaccc aaataggaca | 600 |
| attgccgatg gccttggcgt gctcgcctgt atagtaaggc ttgctcttgt tcaggccgcc | 660 |
| gtatttctcg tgcagacaat cggcttctcc aatcagaggc aggctgccct tgatcacttt | 720 |
| ggatcttcca gaagcgcacc acactttctg gggcagcagg attcctctct gatatgtgat | 780 |
| ggtgccggtc ttgccagact tctgcaccat gtaatccacc acgattcttc cagactgagg | 840 |
| cagtccgcca tcttctgtct gattagggaa gccgccgatc tgagacacat agtgtgtggt | 900 |
| cacgccattg gcagagctgg taaacttctg aggcttgcta tcgccgtaca gcttggccat | 960 |
| ctgtgtttcg ttgtcgctgt gaaatcccca cacggtgatc tgatcctcgc cctctgtaca | 1020 |
| gatatatggc acctcgattg tcaggggtt ggtggcggtc ttgttcttat cgttcttagg | 1080 |
| cacggcccaa gccatggtgg caaagaagcc attgccattt gtaatgttgg ggcagctgcc | 1140 |
| agatgtgccg atcttataag ggccgccagg agcattttcg gcgttgatca cattgtgggt | 1200 |
| gctcagtctg atgtgctcgt agcctctcag cagattaggc agctgtctga tcttggtccg | 1260 |
| gtcgtgcata ataggaaaac agccgctggt cacaggtcgc acttcatgca gaatggacac | 1320 |
| tctggcgcta gggattttgc ctgtacactt aggtctgccc agagccacat ccagatctgt | 1380 |
| gcaattcagg cacttgggac acagcttgcc tcttgtctct gtgcccttca gattggcgaa | 1440 |
| gtggctcttt gtaggtgttg tggtcagagg gatcacgccg tcacattca cttcgccctg | 1500 |
| tgtagctgtt ttcacgacgt gagggctatt gctgctggtg atgccggtac agattctatc | 1560 |
| ggcgttgctt gtgaccacca tcagcagcac gatgatggcc ttcat | 1605 |

<210> SEQ ID NO 40
<211> LENGTH: 2058
<212> TYPE: DNA
<213> ORGANISM: Artificial Sequence
<220> FEATURE:
<223> OTHER INFORMATION: Synthetic

<400> SEQUENCE: 40

| | |
|---|---|
| atgaaggcca aactgctggt gctgctgtgt acctttaccg ccacctacgc cgacacaatc | 60 |
| tgtatcggct accacgccaa caatagcacc gacaccgtgg atacagtgct ggagaagaac | 120 |
| gtgaccgtga cccactctgt gaacctgctg gaggacagcc acaatggcaa gctgtgtctg | 180 |
| ctgaaaggca ttgcccctct gcagctgggc aattgttctg tggccggatg gattctgggc | 240 |
| aaccccgagt gtgagctgct gatttctaag gagagctgga gctacatcgt ggagaccccc | 300 |
| aatcctgaga tggcacctg ctaccctggc tacttcgccg attacgagga gctgcgcgag | 360 |
| cagctgtcta gcgtgtccag cttcgagaga ttcgagatct cccccaagga gtccagctgg | 420 |
| cctaatcaca cagtgacagg cgtgtctgcc agctgtagcc acaacggcaa aagcagcttc | 480 |
| taccggaacc tgctgtggct gacaggcaag aatggcctgt accccaacct gagcaagagc | 540 |
| tacgtgaaca acaaggaaaa ggaagtgctg gtgctgtggg gagtgcacca ccctcccaac | 600 |

```
atcggaaatc agcgggccct gtaccacaca gagaacgcct atgtgagcgt ggtgtccagc    660
cactacagca gaagattcac ccccgagatc gccaagagac ccaaagtgag agaccaggag    720
ggccggatca attactactg gaccctgctg gagcctggcg ataccatcat cttcgaggcc    780
aacggcaatc tgatcgcccc ttggtatgcc tttgccctga gcagaggctt tggcagcggc    840
atcatcacaa gcaacgcccc catggatgag tgtgatgcca agtgccagac cctcagggc    900 gccatcaata gcagcctgcc cttccagaat gtgcaccctg tgaccatcgg cgagtgcccc    960
aagtatgtga aagcgccaa gctgagaatg gtgaccggcc tgagaaacat ccctcagagg   1020
gagaccagag gactgtttgg agccatcgcc ggattcatcg aggaggatg acaggcatg    1080 gtggatggct ggtacggcta ccaccaccag aatgagcagg gctctggata tgccgccgat   1140
cagaagtcta cccagaacgc catcaacgg atcaccaaca aggtgaacag cgtgatcgag   1200
aagatgaaca cccagtttac cgctgtgggc aaggagttca caagctgga gcggaggatg   1260 gagaacctga caagaaggt ggacgacggc tttctggaca tctggaccta caatgccgaa   1320
ctcctggtcc tcctcgagaa tgagaggacc ctggacttcc acgacagcaa cgtgaagaac   1380
ctgtatgaga aggtgaagag ccagctgaag aacaacgcca aggagatcgg caacggctgc   1440
ttcgagttct accacaagtg taacaacgag tgtatggaga gcgtgaagaa cggcacctac   1500 gactaccctα gtacagcga ggagagcaag ctgaaccggg agaagatcga ttccggaggc   1560
gacatcatca gctgctgaa cgagcaggtg aacaaggaga tgcagagcag caacctgtac   1620
atgagcatga gcagctggtg ctacacccac agcctggacg cgccggcct gttcctgttc   1680 gaccacgccg ccgaggagta cgagcacgcc aagaagctga tcatcttcct gaacgagaac   1740
aacgtgcccg tgcagctgac cagcatcagc gcccccgagc acaagttcga gggcctgacc   1800
cagatcttcc agaaggccta cgagcacgag cagcacatca gcgagagcat caacaacatc   1860
gtggaccacg ccatcaagag caaggaccac gccaccttca acttcctgca gtggtacgtg   1920
gccgagcagc acgaggagga ggtgctgttc aaggacatcc tggacaagat cgagctgatc   1980
ggcaacgaga accacggcct gtacctggcc gaccagtacg tgaagggcat cgccaagagc   2040
aggaagagcg gatcctag                                                 2058
```

<210> SEQ ID NO 41
<211> LENGTH: 685
<212> TYPE: PRT
<213> ORGANISM: Artificial Sequence
<220> FEATURE:
<223> OTHER INFORMATION: Synthetic

<400> SEQUENCE: 41

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95
```

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
        130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
                275                 280                 285

Asp Glu Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Gln Arg Glu Thr Arg Gly Leu Phe Gly Ala Ile Ala Gly Phe
            340                 345                 350

Ile Glu Gly Gly Trp Thr Gly Met Val Asp Gly Trp Tyr Gly Tyr His
                355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Ser Gly Gly Asp Ile Ile Lys Leu Leu Asn Glu

```
        515                 520                 525
Gln Val Asn Lys Glu Met Gln Ser Ser Asn Leu Tyr Met Ser Met Ser
        530                 535                 540

Ser Trp Cys Tyr Thr His Ser Leu Asp Gly Ala Gly Leu Phe Leu Phe
545                 550                 555                 560

Asp His Ala Ala Glu Tyr Glu His Ala Lys Lys Leu Ile Ile Phe
                565                 570                 575

Leu Asn Glu Asn Asn Val Pro Val Gln Leu Thr Ser Ile Ser Ala Pro
            580                 585                 590

Glu His Lys Phe Glu Gly Leu Thr Gln Ile Phe Gln Lys Ala Tyr Glu
        595                 600                 605

His Glu Gln His Ile Ser Glu Ser Ile Asn Asn Ile Val Asp His Ala
        610                 615                 620

Ile Lys Ser Lys Asp His Ala Thr Phe Asn Phe Leu Gln Trp Tyr Val
625                 630                 635                 640

Ala Glu Gln His Glu Glu Val Leu Phe Lys Asp Ile Leu Asp Lys
                645                 650                 655

Ile Glu Leu Ile Gly Asn Glu Asn His Gly Leu Tyr Leu Ala Asp Gln
            660                 665                 670

Tyr Val Lys Gly Ile Ala Lys Ser Arg Lys Ser Gly Ser
        675                 680                 685

<210> SEQ ID NO 42
<211> LENGTH: 2058
<212> TYPE: DNA
<213> ORGANISM: Artificial Sequence
<220> FEATURE:
<223> OTHER INFORMATION: Synthetic

<400> SEQUENCE: 42
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt     300 cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttg atgatgtcgc ctccggaatc gatcttctcc cggttcagct tgctctcctc     540
gctgtactta gggtagtcgt aggtgccgtt cttcacgctc tccatacact cgttgttaca     600
cttgtggtag aactcgaagc agccgttgcc gatctccttg gcgttgttct tcagctggct     660
cttcaccttc tcatacaggt tcttcacgtt gctgtcgtgg aagtccaggg tcctctcatt     720
ctcgaggagg accaggagtt cggcattgta ggtccagatg tccagaaagc cgtcgtccac     780
cttcttgttc aggttctcca tcctccgctc cagcttgttg aactccttgc ccacagcggt     840
aaactgggtg ttcatcttct cgatcacgct gttcaccttg ttggtgatgc cgttgatggc     900
gttctgggta gacttctgat cggcggcata tccagagccc tgctcattct ggtggtggta     960
gccgtaccag ccatccacca tgcctgtcca tcctccctcg atgaatccgg cgatggctcc    1020
aaacagtcct ctggtctccc tctgagggat gtttctcagg ccggtcacca ttctcagctt    1080
ggcgcttctc acatacttgg ggcactcgcc gatggtcaca gggtgcacat tctggaaggg    1140
```

```
caggctgcta ttgatggcgc cctgaggtgt ctggcacttg gcatcacact catccatggg   1200
ggcgttgctt gtgatgatgc cgctgccaaa gcctctgctc agggcaaagg cataccaagg   1260
ggcgatcaga ttgccgttgg cctcgaagat gatggtatcg ccaggctcca gcagggtcca   1320
gtagtaattg atccggccct cctggtctct cactttgggt ctcttggcga ctcgggggt    1380 gaatcttctg ctgtagtggc tggacaccac gctcacatag gcgttctctg tgtggtacag   1440
ggcccgctga tttccgatgt tgggagggtg gtgcactccc cacagcacca gcacttcctt   1500
ttccttgttg ttcacgtagc tcttgctcag gttggggtac aggccattct tgcctgtcag   1560 cccacagcagg ttccggtaga agctgctttt gccgttgtgg ctacagctgg cagacacgcc  1620
tgtcactgtg tgattaggcc agctggactc cttggggaag atctcgaatc tctcgaagct   1680
ggacacgcta gacagctgct cgcgcagctc ctcgtaatcg gcgaagtagc cagggtagca   1740
ggtgccattc tcaggattgg gggtctccac gatgtagctc cagctctcct tagaaatcag   1800
cagctcacac tcggggttgc ccagaatcca tccggccaca gaacaattgc ccagctgcag   1860 agggggcaatg cctttcagca gacacagctt gccattgtgg ctgtcctcca gcaggttcac  1920
agagtgggtc acggtcacgt tcttctccag cactgtatcc acggtgtcgg tgctattgtt   1980
ggcgtggtag ccgatacaga ttgtgtcggc gtaggtggcg gtaaaggtac acagcagcac   2040
cagcagtttg gccttcat                                                 2058

<210> SEQ ID NO 43
<211> LENGTH: 2061
<212> TYPE: DNA
<213> ORGANISM: Artificial Sequence
<220> FEATURE:
<223> OTHER INFORMATION: Synthetic

<400> SEQUENCE: 43
atgaaggcca tcctggtggt gctgctgtac accttcgcca ccgccaacgc cgacaccctg    60
tgcatcggct accacgccaa caacagcacc gacaccgtgg acaccgtgct ggagaagaac   120
gtgaccgtga cccacagcgt gaacctgctg gaggacaagc acaacggcaa gctgtgcaag   180
ctgcggggcg tggccccccct gcacctgggc aagtgcaaca tcgccggctg gattctgggc   240
aaccccgagt gcgagagcct gagcaccgcc agcagctgga gctacatcgt ggagaccccc   300
agcagcgaca acggcacctg ctaccccggc gacttcatcg actacgagga gctgcgggag   360
cagctgagca gcgtgagcag cttcgagcgg ttcgagatct cccccaagac cagcagctgg   420
cccaaccacg acagcaacaa gggcgtgacc gccgcctgcc ccacgccgg cgccaagagc    480 ttctacaaga acctgatctg gctggtgaag aagggcaaca gctaccccaa gctgagcaag   540
agctacatca cgacaagggc aaggaggtg ctggtgctgt ggggcatcca ccaccccagc    600
accagcgccg accagcagag cctgtaccag aacgccgaca cctacgtgtt cgtgggcagc   660
agccggtaca gcaagaagtt caagcccgag atcgccatcc ggcccaaggt gcgggaccag   720
gagggccgga tgaactacta ctggaccctg gtggagcccg gcgacaagat caccttcgag   780
gccaccggca acctggtggt gccccggtac gccttcgcca tggagcggaa cgccggcagc   840
ggcatcatca tcagcgacac ccccgtgcac gactgcaaca ccacctgcca gacccccaag   900
ggcgccatca acaccagcct gcccttccag aacatccacc ccatcaccat cggcaagtgc   960
cccaagtacg tgaagagcac caagctgcgg ctggccaccg gctgcggaa catcccagc    1020 atccagagcc ggggcctgtt cggcgccatc gccggcttca tcgagggcgg ctggaccggc   1080
```

```
atggtggacg gctggtacgg ctaccaccac cagaacgagc agggcagcgg ctacgccgcc     1140
gacctgaaga gcacccagaa cgccatcgac gagatcacca acaaggtgaa cagcgtgatc     1200
gagaagatga acacccagtt caccgccgtg ggcaaggagt tcaaccacct ggagaagcgg     1260
atcgagaacc tgaacaagaa ggtggacgac ggcttcctgg acatctggac ctacaacgcc     1320
gagctgctgg tgctgctgga gaacgagcgg accctggact accacgacag caacgtgaag     1380
aacctgtacg agaaggtgcg gagccagctg aagaacaacg ccaaggagat cggcaacggc     1440
tgcttcgagt tctaccacaa gtgcgacaac acctgcatgg agagcgtgaa gaacggcacc     1500
tacgactacc ccaagtacag cgaggaggcc aagctgaacc gggaggagat cgactccgga     1560
ggcgacatca tcaagctgct gaacgagcag gtgaacaagg agatgcagag cagcaacctg     1620
tacatgagca tgagcagctg gtgctacacc cacagcctgg acggcgccgg cctgttcctg     1680
ttcgaccacg ccgccgagga gtacgagcac gccaagaagc tgatcatctt cctgaacgag     1740
aacaacgtgc ccgtgcagct gaccagcatc agcgcccccg agcacaagtt cgagggcctg     1800
acccagatct tccagaaggc ctacgagcac gagcagcaca tcgcgagag catcaacaac     1860 atcgtggacc acgccatcaa gagcaaggac cacgccacct tcaacttcct gcagtggtac     1920
gtggccgagc agcacgagga ggaggtgctg ttcaaggaca tcctggacaa gatcgagctg     1980
atcggcaacg agaaccacgg cctgtacctg gccgaccagt acgtgaaggg catcgccaag     2040
agcaggaaga gcggatccta g                                              2061
```

<210> SEQ ID NO 44
<211> LENGTH: 686
<212> TYPE: PRT
<213> ORGANISM: Artificial Sequence
<220> FEATURE:
<223> OTHER INFORMATION: Synthetic

<400> SEQUENCE: 44

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190
```

```
Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
                275                 280                 285

Val His Asp Cys Asn Thr Thr Cys Gln Thr Pro Lys Gly Ala Ile Asn
        290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His His Gln Asn Glu Gln Gly Ser Gly Tyr Ala Ala Asp Leu Lys Ser
        370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Tyr His Asp Ser Asn Val Lys Asn Leu Tyr Glu
        450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Ser Gly Gly Asp Ile Ile Lys Leu Leu Asn
                515                 520                 525

Glu Gln Val Asn Lys Glu Met Gln Ser Ser Asn Leu Tyr Met Ser Met
        530                 535                 540

Ser Ser Trp Cys Tyr Thr His Ser Leu Asp Gly Ala Gly Leu Phe Leu
545                 550                 555                 560

Phe Asp His Ala Ala Glu Glu Tyr Glu His Ala Lys Lys Leu Ile Ile
                565                 570                 575

Phe Leu Asn Glu Asn Asn Val Pro Val Gln Leu Thr Ser Ile Ser Ala
                580                 585                 590

Pro Glu His Lys Phe Glu Gly Leu Thr Gln Ile Phe Gln Lys Ala Tyr
                595                 600                 605
```

```
Glu His Glu Gln His Ile Ser Glu Ser Ile Asn Asn Ile Val Asp His
    610                 615                 620

Ala Ile Lys Ser Lys Asp His Ala Thr Phe Asn Phe Leu Gln Trp Tyr
625                 630                 635                 640

Val Ala Glu Gln His Glu Glu Val Leu Phe Lys Asp Ile Leu Asp
                    645                 650                 655

Lys Ile Glu Leu Ile Gly Asn Glu Asn His Gly Leu Tyr Leu Ala Asp
                660                 665                 670

Gln Tyr Val Lys Gly Ile Ala Lys Ser Arg Lys Ser Gly Ser
            675                 680                 685

<210> SEQ ID NO 45
<211> LENGTH: 2061
<212> TYPE: DNA
<213> ORGANISM: Artificial Sequence
<220> FEATURE:
<223> OTHER INFORMATION: Synthetic

<400> SEQUENCE: 45
```

| | | | | | |
|---|---|---|---|---|---|
| ctaggatccg | ctcttcctgc | tcttggcgat | gcccttcacg | tactggtcgg | ccaggtacag | 60 |
| gccgtggttc | tcgttgccga | tcagctcgat | cttgtccagg | atgtccttga | acagcacctc | 120 |
| ctcctcgtgc | tgctcggcca | cgtaccactg | caggaagttg | aaggtggcgt | ggtccttgct | 180 |
| cttgatggcg | tggtccacga | tgttgttgat | gctctcgctg | atgtgctgct | cgtgctcgta | 240 |
| ggccttctgg | aagatctggg | tcaggccctc | gaacttgtgc | tcggggcgc | tgatgctggt | 300 |
| cagctgcacg | gcacgttgt | tctcgttcag | gaagatgatc | agcttcttgg | cgtgctcgta | 360 |
| ctcctcggcg | gcgtggtcga | acaggaacag | gccggcgccg | tccaggctgt | gggtgtagca | 420 |
| ccagctgctc | atgctcatgt | acaggttgct | gctctgcatc | tccttgttca | cctgctcgtt | 480 |
| cagcagcttg | atgatgtcgc | ctccggagtc | gatctcctcc | cggttcagct | tggcctcctc | 540 |
| gctgtacttg | gggtagtcgt | aggtgccgtt | cttcacgctc | tccatgcagg | tgttgtcgca | 600 |
| cttgtggtag | aactcgaagc | agccgttgcc | gatctccttg | gcgttgttct | tcagctggct | 660 |
| ccgcaccttc | tcgtacaggt | tcttcacgtt | gctgtcgtgg | tagtccaggg | tccgctcgtt | 720 |
| ctccagcagc | accagcagct | cggcgttgta | ggtccagatg | tccaggaagc | cgtcgtccac | 780 |
| cttcttgttc | aggttctcga | tccgcttctc | caggtggttg | aactccttgc | ccacggcgt | 840 |
| gaactgggtg | ttcatcttct | cgatcacgct | gttcaccttg | ttggtgatct | cgtcgatggc | 900 |
| gttctgggtg | ctcttcaggt | cggcggcgta | gccgctgccc | tgctcgttct | ggtggtggta | 960 |
| gccgtaccag | ccgtccacca | tgccggtcca | ccgccctcg | atgaagccgg | cgatggcgcc | 1020 |
| gaacaggccc | cggctctgga | tgctgggat | gttccgcagg | ccggtggcca | gccgcagctt | 1080 |
| ggtgctcttc | acgtacttgg | ggcacttgcc | gatggtgatg | ggtggatgt | ctggaaggg | 1140 |
| caggctggtg | ttgatggcgc | ccttgggggt | ctggcaggtg | gtgttgcagt | cgtgcacggg | 1200 |
| ggtgtcgctg | atgatgatgc | cgctgccggc | gttccgctcc | atggcgaagg | cgtaccgggg | 1260 |
| caccaccagg | ttgccggtgg | cctcgaaggt | gatcttgtcg | ccgggctcca | ccagggtcca | 1320 |
| gtagtagttc | atccggccct | cctggtcccg | caccttgggc | cggatggcga | tctcgggctt | 1380 |
| gaacttcttg | ctgtaccggc | tgctgcccac | gaacacgtag | gtgtcggcgt | tctggtacag | 1440 |
| gctctgctgg | tcggcgctgg | tgctgggtg | gtggatgccc | cacagcacca | gcacctcctt | 1500 |
| gcccttgtcg | ttgatgtagc | tcttgctcag | cttggggtag | ctgttgccct | tcttcaccag | 1560 |
| ccagatcagg | ttcttgtaga | agctcttggc | gccggcgtgg | gggcaggcgg | cggtcacgcc | 1620 |

```
cttgttgctg tcgtggttgg gccagctgct ggtcttgggg aagatctcga accgctcgaa    1680
gctgctcacg ctgctcagct gctcccgcag ctcctcgtag tcgatgaagt cgccggggta    1740
gcaggtgccg ttgtcgctgc tgggggtctc cacgatgtag ctccagctgc tggcggtgct    1800
caggctctcg cactcggggt tgcccagaat ccagccggcg atgttgcact tgcccaggtg    1860 cagggggggcc acgccccgca gcttgcacag cttgccgttg tgcttgtcct ccagcaggtt    1920
cacgctgtgg gtcacggtca cgttcttctc cagcacggtg tccacggtgt cggtgctgtt    1980
gttggcgtgg tagccgatgc acagggtgtc ggcgttggcg gtggcgaagg tgtacagcag    2040
caccaccagg atggccttca t                                              2061
```

<210> SEQ ID NO 46
<211> LENGTH: 2049
<212> TYPE: DNA
<213> ORGANISM: Artificial Sequence
<220> FEATURE:
<223> OTHER INFORMATION: Synthetic

<400> SEQUENCE: 46

```
atggccatca tctacctgat cctgctgttt acagctgtgc ggggcgatca gatctgtatc      60
ggctaccacg ccaacaatag caccgagaag gtggacacca tcctggaaag aaatgtgacc     120
gtgacccacg ccaaggatat tctggaaaag acccacaacg gcaagctgtg caagctgaat     180
ggcattcctc tctgctgaact gggcgattgt tctattgctg ctggctgct gggaaatcct     240 gagtgcgata gactgctgtc tgtgcctgag tggagctaca tcatggaaaa agagaaccct     300
agggacggac tgtgttaccc cggcagcttc aacgattacg aggaactgaa gcacctgctg     360
tccagcgtga agcacttcga gaaagtgaag atcctgccca aggatagatg acccagcat      420 acaacaacag gcggaagcag agcttgtgct gtgtccggca accccagctt cttcagaaat     480
atggtctggc tgaccaagaa gggctctaat tatcctgtgg ccaagggcag ctacaataat     540
acaagcggcg agcagatgct gattatttgg ggcgtgcacc accctaatga tgagacagag     600
cagagaaccc tgtaccagaa tgtgggcaca tacgtgtctg tgggcaccag cacactgaat     660
aagagaagca ccccccgatat tgccaccaga cccaaagtga atggacaggg cggcagaatg     720
gaattttcct ggaccctgct ggatatgtgg gacaccatca ctttgagag caccgggaat     780 ctgattgccc tgagtacggg cttcaagatc agcaagagag gcagcagcgg catcatgaaa     840
acagagggca ccctggaaaa ctgtgaaacc aagtgtcaga cacctctggg cgccattaat     900
accacccctg ccttccataa tgtgcaccct ctgacaatcg cgagtgccc taagtacgtg     960 aagtctgaga aactggtgct ggccacagga ctgagaaatg tgccccagat cgagtcaaga    1020
ggcctgtttg gagccattgc cggctttatt gaaggcggat ggcagggaat ggtggatggg    1080
tggtacggct atcaccacag caatgatcag ggatctggct atgccgccga taaagagagc    1140
acccagaagg cctttgacgg catcaccaac aaagtgaaca gcgtgatcga aaagatgaac    1200 acccagttg aggccgtggg caaagagttc agcaatctgg aaagacggct ggaaaacctg    1260
aacaagaaaa tggaagatgg cttcctggac gtgtggacat ataatgccga gctgctggtg    1320
ctgatggaaa acgagaggac cctggacttt cacgacagca cgtgaagaa cctgtacgac    1380 aaagtgcgga tgcagctgag agacaatgtg aaagagctgg gcaacggctg ctttgagttc    1440
taccacaagt cgacgacga gtgcatgaat agcgtgaaga acggcaccta cgactaccct    1500
aagtatgagg aagagagcaa gctgaacaga aacgagatca gtccggagg cgacatcatc    1560 aagctgctga cgagcaggt gaacaaggag atgcagagca gcaacctgta catgagcatg    1620
```

-continued

```
agcagctggt gctacaccca cagcctggac ggcgccggcc tgttcctgtt cgaccacgcc  1680
gccgaggagt acgagcacgc caagaagctg atcatcttcc tgaacgagaa caacgtgccc  1740
gtgcagctga ccagcatcag cgcccccgag cacaagttcg agggcctgac ccagatcttc  1800
cagaaggcct acgagcacga gcagcacatc agcgagagca tcaacaacat cgtggaccac  1860
gccatcaaga gcaaggacca cgccaccttc aacttcctgc agtggtacgt ggccgagcag  1920
cacgaggagg aggtgctgtt caaggacatc ctggacaaga tcgagctgat cggcaacgag  1980
aaccacggcc tgtacctggc cgaccagtac gtgaagggca tcgccaagag caggaagagc  2040
ggatcctag                                                            2049
```

<210> SEQ ID NO 47
<211> LENGTH: 682
<212> TYPE: PRT
<213> ORGANISM: Artificial Sequence
<220> FEATURE:
<223> OTHER INFORMATION: Synthetic

<400> SEQUENCE: 47

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
```

```
            275                 280                 285
Glu Thr Lys Cys Gln Thr Pro Leu Gly Ala Ile Asn Thr Thr Leu Pro
290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
                340                 345                 350

Gly Trp Gln Gly Met Val Asp Gly Trp Tyr Gly Tyr His His Ser Asn
            355                 360                 365

Asp Gln Gly Ser Gly Tyr Ala Ala Asp Lys Glu Ser Thr Gln Lys Ala
        370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Ser Gly Gly Asp Ile Ile Lys Leu Leu Asn Glu Gln Val Asn
        515                 520                 525

Lys Glu Met Gln Ser Ser Asn Leu Tyr Met Ser Met Ser Ser Trp Cys
530                 535                 540

Tyr Thr His Ser Leu Asp Gly Ala Gly Leu Phe Leu Phe Asp His Ala
545                 550                 555                 560

Ala Glu Glu Tyr Glu His Ala Lys Lys Leu Ile Ile Phe Leu Asn Glu
                565                 570                 575

Asn Asn Val Pro Val Gln Leu Thr Ser Ile Ser Ala Pro Glu His Lys
            580                 585                 590

Phe Glu Gly Leu Thr Gln Ile Phe Gln Lys Ala Tyr Glu His Glu Gln
        595                 600                 605

His Ile Ser Glu Ser Ile Asn Asn Ile Val Asp His Ala Ile Lys Ser
610                 615                 620

Lys Asp His Ala Thr Phe Asn Phe Leu Gln Trp Tyr Val Ala Glu Gln
625                 630                 635                 640

His Glu Glu Glu Val Leu Phe Lys Asp Ile Leu Asp Lys Ile Glu Leu
                645                 650                 655

Ile Gly Asn Glu Asn His Gly Leu Tyr Leu Ala Asp Gln Tyr Val Lys
            660                 665                 670

Gly Ile Ala Lys Ser Arg Lys Ser Gly Ser
        675                 680

<210> SEQ ID NO 48
```

<211> LENGTH: 2049
<212> TYPE: DNA
<213> ORGANISM: Artificial Sequence
<220> FEATURE:
<223> OTHER INFORMATION: Synthetic

<400> SEQUENCE: 48

```
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt      300
cagctgcacg gcacgttgt tctcgttcag gaagatgatc agcttcttgg cgtgctcgta      360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttg atgatgtcgc ctccggactt gatctcgttt ctgttcagct tgctctcttc     540
ctcatactta gggtagtcgt aggtgccgtt cttcacgcta ttcatgcact cgtcgtcgca     600
cttgtggtag aactcaaagc agccgttgcc cagctctttc acattgtctc tcagctgcat     660
ccgcactttg tcgtacaggt tcttcacgtt gctgtcgtga agtccaggg tcctctcgtt      720
ttccatcagc accagcagct cggcattata tgtccacacg tccaggaagc catcttccat     780
tttcttgttc aggttttcca gccgtctttc cagattgctg aactctttgc ccacggcctc    840
aaactgggtg ttcatcttct cgatcacgct gttcactttg ttggtgatgc cgtcaaaggc    900
cttctgggtg ctctctttat cggcggcata gccagatccc tgatcattgc tgtggtgata    960
gccgtaccac ccatccacca ttccctgcca tccgccttca ataaagccgg caatggctcc   1020
aaacaggcct cttgactcga tctggggcac atttctcagt cctgtggcca gcaccagttt   1080
ctcagacttc acgtacttag ggcactcgcc gattgtcaga gggtgcacat tatggaaggg   1140
cagggtggta ttaatggcgc ccagaggtgt ctgacacttg gtttcacagt tttccagggt   1200
gccctctgtt ttcatgatgc cgctgctgcc tctcttgctg atcttgaagc cgtactcagg   1260
ggcaatcaga ttcccggtgc tctcaaagtt gatggtgtcc cacatatcca gcagggtcca   1320
ggaaaattcc attctgccgc cctgtccatt cactttgggt ctggtggcaa atcgggggt    1380
gcttctctta ttcagtgtgc tggtgcccac agacacgtat gtgcccacat tctggtacag   1440
ggttctctgc tctgtctcat cattagggtg gtgcacgccc caaataatca gcatctgctc   1500
gccgcttgta ttattgtagc tgcccttggc cacaggataa ttagagccct tcttggtcag   1560
ccagaccata tttctgaaga gctgggggtt gccggacaca gcacaagctc tgcttccgcc   1620
tgttgttgta tgctgggtcc atctatcctt gggcaggatc ttcactttct cgaagtgctt   1680
cacgctggac agcaggtgct tcagttcctc gtaatcgttg aagctgccgg ggtaacacag   1740
tccgtcccta gggttctctt tttccatgat gtagctccac tcaggcacag acagcagtct   1800
atcgcactca ggatttccca gcagccagcc agcaatagaa caatcgccca gttccagagg   1860
aggaatgcca ttcagcttgc acagcttgcc gttgtgggtc ttttccagaa tatccttggc   1920
gtgggtcacg gtcacatttc tttccaggat ggtgtccacc ttctcggtgc tattgttggc   1980
gtggtagccg atacagatct gatcgccccg cacagctgta aacagcagga tcaggtagat   2040
gatggccat                                                          2049
```

```
<210> SEQ ID NO 49
<211> LENGTH: 2064
<212> TYPE: DNA
<213> ORGANISM: Artificial Sequence
<220> FEATURE:
<223> OTHER INFORMATION: Synthetic

<400> SEQUENCE: 49
atgaaaacca tcattgccct gagctacatc ttttgtctgg ctctgggcca ggatctgccc      60
ggcaatgata tagcaccgc caccctgtgt ctgggacacc acgccgtgcc taatggcacc     120
ctggtgaaaa ccattaccga cgaccagatc gaagtgacca atgccaccga gctggtgcag     180
agcagcagca ccggcaagat ctgcaacaac ccccacagaa tcctggatgg catcgactgt     240
accctgatcg atgccctgct gggcgatcct cactgcgacg tgttccagaa cgagacatgg     300
gacctgttcg tggagagaag caaggccttc agcaactgct accccacga tgtgcccgat     360 tacgcctctc tgagaagcct ggtggccagc agcggcacac tggaattcat caccgagggc     420
tttacctgga caggcgtgac ccagaatggc ggcagcaatg cctgtaaaag ggccctggc      480 agcggcttct tcagcagact gaactggctg accaagtccg gcagcaccta ccctgtgctg     540
aacgtgacca tgcccaacaa cgacaacttc gacaagctgt acatctgggg cgtgcaccac     600
cctagcacca tcaggaaca gaccagcctg tacgtgcagg ccagcggcag agtgaccgtg     660
tctaccagac ggtcccagca gaccatcatc cccaacatcg agtcaagacc ttgggtgcgc     720
ggcctgagca gcagaatcag catctactgg accatcgtga acctggcga cgtgctggtg     780 atcaacagca tggcaacct gatcgccccc agaggctact tcaagatgcg gaccggcaag     840
agcagcatca tgagaagcga cgcccccatc gatacctgta tcagcgagtg catcacccc      900 aacggcagca tccccaacga caagcccttc agaacgtga acaagatcac ctacggcgcc     960
tgccctaagt acgtgaagca gaacaccctg aagctggcca ccggcatgag aaatgtgccc    1020
gagaagcaga caagaggcct gtttggcgcc attgccggct ttatcgagaa cggctgggag    1080
ggcatgatcg atgggtggta cggcttcaga caccagaatt ctgagggcac aggacaggcc    1140
gccgatctga gtctacaca ggccgccatc gaccagatca cggcaagct gaacagagtg    1200 atcgagaaaa ccaacgagaa gttccaccag atcgagaaag aattcagcga ggtggagggc    1260
agaatccagg acctgaaaaa atacgtggag gacaccaaga tcgacctgtg gagctacaat    1320
gccgaactgc tggtcgccct ggaaaaccag cacaccatcg acctgaccga cagcgagatg    1380
aataagctgt tcgaaaagac cagacggcag ctgagagaaa acgccgagga catgggcaac    1440
ggctgcttca gatctacca caagtgcgac aacgcctgca tcgagagcat cagaaacggc    1500
acctacgacc acgatgtgta cagggacgag gccctgaaca acagattcca gatcaagtcc    1560
ggaggcgaca tcatcaagct gctgaacgag caggtgaaca aggagatgca gagcagcaac    1620
ctgtacatga gcatgagcag ctggtgctac acccacagcc tggacggcgc cggcctgttc    1680
ctgttcgacc acgccgccga ggagtacgag cacgccaaga gctgatcat cttcctgaac    1740 gagaacaacg tgcccgtgca gctgaccagc atcagcgccc ccgagcacaa gttcgagggc    1800
ctgacccaga tcttccagaa ggcctacgag cacgagcagc acatcagcga gagcatcaac    1860
aacatcgtgg accacgccat caagagcaag gaccacgcca ccttcaactt cctgcagtgg    1920
tacgtggccg agcagcacga ggaggagtg ctgttcaagg acatcctgga caagatcgag    1980
ctgatcggca cgagaacca cggcctgtac ctggccgacc agtacgtgaa gggcatcgcc    2040
aagagcagga gagcggatc ctag                                            2064
```

<210> SEQ ID NO 50
<211> LENGTH: 687
<212> TYPE: PRT
<213> ORGANISM: Artificial Sequence
<220> FEATURE:
<223> OTHER INFORMATION: Synthetic

<400> SEQUENCE: 50

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Glu Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365
```

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
        450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Ser Gly Gly Asp Ile Ile Lys Leu Leu
        515                 520                 525

Asn Glu Gln Val Asn Lys Glu Met Gln Ser Ser Asn Leu Tyr Met Ser
530                 535                 540

Met Ser Ser Trp Cys Tyr Thr His Ser Leu Asp Gly Ala Gly Leu Phe
545                 550                 555                 560

Leu Phe Asp His Ala Ala Glu Glu Tyr Glu His Ala Lys Lys Leu Ile
                565                 570                 575

Ile Phe Leu Asn Glu Asn Asn Val Pro Val Gln Leu Thr Ser Ile Ser
            580                 585                 590

Ala Pro Glu His Lys Phe Glu Gly Leu Thr Gln Ile Phe Gln Lys Ala
        595                 600                 605

Tyr Glu His Glu Gln His Ile Ser Glu Ser Ile Asn Asn Ile Val Asp
610                 615                 620

His Ala Ile Lys Ser Lys Asp His Ala Thr Phe Asn Phe Leu Gln Trp
625                 630                 635                 640

Tyr Val Ala Glu Gln His Glu Glu Val Leu Phe Lys Asp Ile Leu
                645                 650                 655

Asp Lys Ile Glu Leu Ile Gly Asn Glu Asn His Gly Leu Tyr Leu Ala
            660                 665                 670

Asp Gln Tyr Val Lys Gly Ile Ala Lys Ser Arg Lys Ser Gly Ser
        675                 680                 685

<210> SEQ ID NO 51
<211> LENGTH: 2064
<212> TYPE: DNA
<213> ORGANISM: Artificial Sequence
<220> FEATURE:
<223> OTHER INFORMATION: Synthetic

<400> SEQUENCE: 51
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcgggggcgc tgatgctggt   300

```
cagctgcacg ggcacgttgt tctcgttcag gaagatgatc agcttcttgg cgtgctcgta        360
ctcctcggcg gcgtggtcga acaggaacag gccggcgccg tccaggctgt gggtgtagca        420
ccagctgctc atgctcatgt acaggttgct gctctgcatc tccttgttca cctgctcgtt        480
cagcagcttg atgatgtcgc ctccggactt gatctggaat ctgttgttca gggcctcgtc        540
cctgtacaca tcgtggtcgt aggtgccgtt tctgatgctc tcgatgcagg cgttgtcgca        600
cttgtggtag atcttgaagc agccgttgcc catgtcctcg gcgttttctc tcagctgccg        660
tctggtcttt tcgaacagct tattcatctc gctgtcggtc aggtcgatgg tgtgctggtt        720
ttccagggcg accagcagtt cggcattgta gctccacagg tcgatcttgg tgtcctccac        780 gtattttttcc aggtcctgga ttctgccctc cacctcgctg aattctttct cgatctggtg        840
gaacttctcg ttggttttct cgatcactct gttcagcttg ccgttgatct ggtcgatggc        900
ggcctgtgta gacttcagat cggcggcctg tcctgtgccc tcagaattct ggtgtctgaa        960
gccgtaccac ccatcgatca tgccctccca gccgttctcg ataaagccgg caatggcgcc       1020
aaacaggcct cttgtctgct tctcgggcac atttctcatg ccggtggcca gcttcagggt       1080
gttctgcttc acgtacttag ggcaggcgcc gtaggtgatc ttgttcacgt tctggaaggg       1140
cttgtcgttg gggatgctgc cgttgggggt gatgcactcg ctgatacagg tatcgatggg       1200
ggcgtcgctt tcatgatgc tgctcttgcc ggtccgcatc ttgaagtagc ctctggggggc       1260 gatcaggttg ccattgctgt tgatcaccag cacgtcgcca ggtttcacga tggtccagta       1320
gatgctgatt ctgctgctca ggccgcgcac ccaaggtctt gactcgatgt tggggatgat       1380
ggtctgctgg gaccgtctgg tagacacggt cactctgccg ctggcctgca cgtacaggct       1440
ggtctgttcc tgattggtgc tagggtggtg cacgccccag atgtacagct tgtcgaagtt       1500
gtcgttgttg ggcatggtca cgttcagcac agggtaggtg ctgccggact tggtcagcca       1560
gttcagtctg ctgaagaagc cgctgccagg gcctctttta caggcattgc tgccgccatt       1620
ctgggtcacg cctgtccagg taaagccctc ggtgatgaat tccagtgtgc cgctgctggc       1680
caccaggctt tcagagagg cgtaatcggg cacatcgtag gggtagcagt tgctgaaggc       1740
cttgcttctc tccacgaaca ggtcccatgt ctcgttctgg aacacgtcgc agtgaggatc       1800
gcccagcagg gcatcgatca gggtacagtc gatgccatcc aggattctgt ggggggttgtt       1860 gcagatcttg ccggtgctgc tgctctgcac cagctcggtg cattggtca cttcgatctg       1920 gtcgtcggta atggttttca ccagggtgcc attaggcacg gcgtggtgtc ccagacacag       1980
ggtggcggtg ctattatcat tgccgggcag atcctggccc agagccagac aaaagatgta       2040
gctcagggca atgatggttt tcat                                               2064
```

<210> SEQ ID NO 52
<211> LENGTH: 2064
<212> TYPE: DNA
<213> ORGANISM: Artificial Sequence
<220> FEATURE:
<223> OTHER INFORMATION: Synthetic

<400> SEQUENCE: 52

```
atgaaaacca tcattgccct gagctacatc ctgtgcctgg tgttcacaca gaagctgccc         60
ggcaacgata atagcaccgc cacactgtgt ctgggacacc acgccgtgcc taatggcacc        120
atcgtgaaaa caatcaccaa cgaccagatc gaagtgacca atgccacaga gctggtgcag        180
agcagcagca caggcgagat ctgtgacagc ccccaccaga tcctggatgg cgagaactgt        240
```

```
accctgatcg atgccctgct gggcgatcct cagtgcgacg gcttccagaa caagaaatgg    300
gacctgttcg tggagagaag caaggcctac agcaactgct accctacga cgtgcctgat    360
tacgccagcc tgagaagcct ggtggcctct agcggcaccc tggaattcaa caacgagagc   420
ttcaactgga ccggcgtgac acagaatggc accagcagcg cctgcatcag acggtccaac    480
aacagcttct tcagtagact gaattggctg acccacctga agttcaagta ccccgccctg    540
aacgtgacca tgcccaacaa tgagaagttc gacaagctgt acatctgggg agtgcaccac    600
cctggcaccg acaacgatca gatcttccct tacgcccagg ccagcggcag aatcaccgtg    660
tccaccaaga gaagccagca gaccgtgatc cccaatatcg gcagcagacc cagagtgcgg    720
aacatcccca gcaggatcag catctactgg acaatcgtga agcctggcga catcctgctg    780
atcaacagca ccggcaacct gatcgcccct cggggctact ttaagatcag aagcggcaag    840
agcagcatca tgagatccga cgcccccatc ggcaagtgca acagcgagtg catcaccca    900
aacggcagca tccccaacga caagcccttc agaacgtga acaggatcac ctacggcgcc    960
tgccctagat acgtgaagca gaacaccctg aagctggcca ccggcatgag aaatgtgccc    1020
gagaagcaga ccagaggcat ctttggcgcc attgccggct ttatcgagaa tggctgggag    1080
ggaatggtgg atgggtggta cggcttcaga caccagaata gcgagggaat tggacaggcc    1140
gccgatctga aatctaccca ggccgccatc gaccagatca cggcaagct gaacaggctg    1200
atcggcaaga ccaacgagaa gttccaccag atcgagaaag aattcagcga ggtggagggc    1260
agaatccagg acctggaaaa atacgtggag gacaccaaga tcgacctgtg gagctacaat    1320
gccgaactgc tggtcgccct ggaaaaccag cacacaattg atctgacaga cagtgagatg    1380
aataagctgt tcgagaaaac caagaagcag ctgagagaaa acgccgagga catgggcaac    1440
ggctgcttca gatctaccaa agtgcgac aacgcctgca tcggcagcat cagaaacggc    1500
acctacgacc acgacgtgta cagagatgag gccctgaaca accggtttca gatcaagtcc    1560
ggaggcgaca tcatcaagct gctgaacgag caggtgaaca aggagatgca gagcagcaac    1620
ctgtacatga gcatgagcag ctggtgctac acccacagcc tggacggcgc cggcctgttc    1680
ctgttcgacc acgccgccga ggagtacgag acgccaagaa gctgatcat cttcctgaac    1740
gagaacaacg tgcccgtgca gctgaccagc atcagcgccc ccgagcacaa gttcgagggc    1800
ctgacccaga tcttccagaa ggcctacgag cacgagcagc acatcagcga gagcatcaac    1860
aacatcgtgg accacgccat caagagcaag gaccacgcca ccttcaactt cctgcagtgg    1920
tacgtggccg agcagcacga ggaggagtg ctgttcaagg acatcctgga caagatcgag    1980
ctgatcggca cgagaacca cggcctgtac ctggccgacc agtacgtgaa gggcatcgcc    2040
aagagcagga gagcggatc ctag                                           2064
```

<210> SEQ ID NO 53
<211> LENGTH: 687
<212> TYPE: PRT
<213> ORGANISM: Artificial Sequence
<220> FEATURE:
<223> OTHER INFORMATION: Synthetic

<400> SEQUENCE: 53

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp

-continued

```
                35                  40                  45
Gln Ile Glu Val Thr Asn Ala Thr Glu Leu Val Gln Ser Ser Ser Thr
 50                  55                  60
Gly Glu Ile Cys Asp Ser Pro His Gln Ile Leu Asp Gly Glu Asn Cys
 65                  70                  75                  80
Thr Leu Ile Asp Ala Leu Leu Gly Asp Pro Gln Cys Asp Gly Phe Gln
                 85                  90                  95
Asn Lys Lys Trp Asp Leu Phe Val Glu Arg Ser Lys Ala Tyr Ser Asn
                100                 105                 110
Cys Tyr Pro Tyr Asp Val Pro Asp Tyr Ala Ser Leu Arg Ser Leu Val
                115                 120                 125
Ala Ser Ser Gly Thr Leu Glu Phe Asn Asn Glu Ser Phe Asn Trp Thr
            130                 135                 140
Gly Val Thr Gln Asn Gly Thr Ser Ser Ala Cys Ile Arg Arg Ser Asn
145                 150                 155                 160
Asn Ser Phe Phe Ser Arg Leu Asn Trp Leu Thr His Leu Lys Phe Lys
                165                 170                 175
Tyr Pro Ala Leu Asn Val Thr Met Pro Asn Asn Glu Lys Phe Asp Lys
                180                 185                 190
Leu Tyr Ile Trp Gly Val His His Pro Gly Thr Asp Asn Asp Gln Ile
                195                 200                 205
Phe Pro Tyr Ala Gln Ala Ser Gly Arg Ile Thr Val Ser Thr Lys Arg
210                 215                 220
Ser Gln Gln Thr Val Ile Pro Asn Ile Gly Ser Arg Pro Arg Val Arg
225                 230                 235                 240
Asn Ile Pro Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
                260                 265                 270
Tyr Phe Lys Ile Arg Ser Gly Lys Ser Ser Ile Met Arg Ser Asp Ala
                275                 280                 285
Pro Ile Gly Lys Cys Asn Ser Glu Cys Ile Thr Pro Asn Gly Ser Ile
            290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
                340                 345                 350
Gly Phe Ile Glu Asn Gly Trp Glu Gly Met Val Asp Gly Trp Tyr Gly
                355                 360                 365
Phe Arg His Gln Asn Ser Glu Gly Ile Gly Gln Ala Ala Asp Leu Lys
            370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
                420                 425                 430
Lys Ile Asp Leu Trp Ser Tyr Asn Ala Glu Leu Leu Val Ala Leu Glu
                435                 440                 445
Asn Gln His Thr Ile Asp Leu Thr Asp Ser Glu Met Asn Lys Leu Phe
            450                 455                 460
```

```
Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Ser Gly Gly Asp Ile Ile Lys Leu Leu
            515                 520                 525

Asn Glu Gln Val Asn Lys Glu Met Gln Ser Ser Asn Leu Tyr Met Ser
530                 535                 540

Met Ser Ser Trp Cys Tyr Thr His Ser Leu Asp Gly Ala Gly Leu Phe
545                 550                 555                 560

Leu Phe Asp His Ala Ala Glu Glu Tyr Glu His Ala Lys Lys Leu Ile
                565                 570                 575

Ile Phe Leu Asn Glu Asn Asn Val Pro Val Gln Leu Thr Ser Ile Ser
            580                 585                 590

Ala Pro Glu His Lys Phe Glu Gly Leu Thr Gln Ile Phe Gln Lys Ala
            595                 600                 605

Tyr Glu His Glu Gln His Ile Ser Glu Ser Ile Asn Asn Ile Val Asp
610                 615                 620

His Ala Ile Lys Ser Lys Asp His Ala Thr Phe Asn Phe Leu Gln Trp
625                 630                 635                 640

Tyr Val Ala Glu Gln His Glu Glu Val Leu Phe Lys Asp Ile Leu
                645                 650                 655

Asp Lys Ile Glu Leu Ile Gly Asn Glu Asn His Gly Leu Tyr Leu Ala
            660                 665                 670

Asp Gln Tyr Val Lys Gly Ile Ala Lys Ser Arg Lys Ser Gly Ser
            675                 680                 685

<210> SEQ ID NO 54
<211> LENGTH: 2064
<212> TYPE: DNA
<213> ORGANISM: Artificial Sequence
<220> FEATURE:
<223> OTHER INFORMATION: Synthetic

<400> SEQUENCE: 54
ctaggatccg ctcttcctgc tcttggcgat gcccttcacg tactggtcgg ccaggtacag      60
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcggggcgc tgatgctggt    300 cagctgcacg ggcacgttgt tctcgttcag gaagatgatc agcttcttgg cgtgctcgta    360
ctcctcggcg gcgtggtcga acaggaacag gccggcgccg tccaggctgt gggtgtagca    420
ccagctgctc atgctcatgt acaggttgct gctctgcatc tccttgttca cctgctcgtt    480
cagcagcttg atgatgtcgc ctccggactt gatctgaaac cggttgttca gggcctcatc    540
tctgtacacg tcgtggtcgt aggtgccgtt tctgatgctg ccgatgcagg cgttgtcgca    600
cttgtggtag atcttgaagc agccgttgcc catgtcctcg gcgttttctc tcagctgctt    660
cttggttttc tcgaacagct tattcatctc actgtctgtc agatcaattg tgtgctggtt    720
ttccagggcg accagcagtt cggcattgta gctccacagg tcgatcttgg tgtcctccac    780
```

```
gtatttttcc aggtcctgga ttctgccctc cacctcgctg aattctttct cgatctggtg    840
gaacttctcg ttggtcttgc cgatcagcct gttcagcttg ccgttgatct ggtcgatggc    900
ggcctgggta gatttcagat cggcggcctg tccaattccc tcgctattct ggtgtctgaa    960
gccgtaccac ccatccacca ttccctccca gccattctcg ataaagccgg caatggcgcc   1020
aaagatgcct ctggtctgct tctcgggcac atttctcatg ccggtggcca gcttcagggt   1080
gttctgcttc acgtatctag gcaggcgcc gtaggtgatc ctgttcacgt tctggaaggg   1140
cttgtcgttg gggatgctgc cgtttggggt gatgcactcg ctgttgcact tgccgatggg   1200
ggcgtcggat ctcatgatgc tgctcttgcc gcttctgatc ttaaagtagc cccgaggggc   1260
gatcaggttg ccggtgctgt tgatcagcag gatgtcgcca ggcttcacga ttgtccagta   1320
gatgctgatc ctgctgggga tgttccgcac tctgggtctg ctgccgatat tggggatcac   1380
ggtctgctgg cttctcttgg tggacacggt gattctgccg ctggcctggg cgtaagggaa   1440
gatctgatcg ttgtcggtgc cagggtggtg cactccccag atgtacagct tgtcgaactt   1500
ctcattgttg ggcatggtca cgttcaggc ggggtacttg aacttcaggt gggtcagcca   1560
attcagtcta ctgaagaagc tgttgttgga ccgtctgatg caggcgctgc tggtgccatt   1620
ctgtgtcacg ccggtccagt tgaagctctc gttgttgaat tccagggtgc cgctagaggc   1680
caccaggctt tcaggctggg cgtaatcagg cacgtcgtag gggtagcagt tgctgtaggc   1740
cttgcttctc tccacgaaca ggtcccattt cttgttctgg aagccgtcgc actgaggatc   1800
gcccagcagg gcatcgatca gggtacagtt ctcgccatcc aggatctggt ggggggctgtc   1860
acagatctcg cctgtgctgc tgctctgcac cagctctgtg gcattggtca cttcgatctg   1920
gtcgttggtg attgttttca cgatggtgcc attaggcacg gcgtggtgtc ccagacacag   1980
tgtggcggtg ctattatcgt tgccgggcag cttctgtgtg aacaccaggc acaggatgta   2040
gctcagggca atgatggttt tcat                                         2064
```

<210> SEQ ID NO 55
<211> LENGTH: 2067
<212> TYPE: DNA
<213> ORGANISM: Artificial Sequence
<220> FEATURE:
<223> OTHER INFORMATION: Synthetic

<400> SEQUENCE: 55

```
atggaaaaga tcgtgctgct gctggccatt gtgagcctgg tgaagagcga ccagatctgc     60
attggctacc acgccaacaa tagcacagag caggtggaca ccatcatgga aaaaaacgtg    120
accgtgaccc acgctcagga catcctggaa aagacccaca cggcaagct gtgtgatctg    180
gacggcgtga agcctctgat cctgagagat tgtagcgtgg ctggatggct gctgggcaac    240
cctatgtgcg acgagttcat caacgtgccc gagtggagct atatcgtgga aaggccaac    300
cccaccaacg atctgtgtta ccccggcagc ttcaacgatt acgaggaact gaagcacctg    360
ctgtcccgga tcaaccactt cgagaagatc cagatcatcc caagtcctc ttggagcgat    420
cacgaagcct ctagcggagt gtctagcgcc tgtccttacc tgggcagccc cagcttcttc    480
agaaacgtgg tgtggctgat caagaagaac agcacctacc ccaccatcaa gagagctac    540
aacaacacca accaggaaga tctgctggtc ctgtggggaa tccaccaccc taatgatgcc    600
gccgagcaga ccagactgta ccagaacccc accacctata tcagcatcgg caccagcacc    660
ctgaatcaga gactggtgcc caagatcgcc accagatcca aggtgaacgg ccagagcggc    720
aggatggaat tcttctggac catcctgaag cccaacgacg ccatcaactt cgagagcaac    780
```

-continued

```
ggcaacttta tcgcccctga gtacgcctac aagatcgtga agaagggcga cagcgccatc    840
atgaagagcg agctggaata cggcaactgc aacaccaagt gccagacacc tatgggcgcc    900
atcaacagca gcatgccctt ccacaacatc caccctctga ccatcggcga gtgccctaag    960
tacgtgaaga gcaacagact ggtgctggcc acaggcctga aaatagccc ccagcgggag    1020 agcagaagaa agaagagggg cctgtttgga gccatcgccg gctttattga aggcggctgg    1080
cagggaatgg tggatggctg gtacggctac caccacagca tgagcaggg ctctggatat     1140 gccgccgaca aagagtctac ccagaaggcc atcgacggcg tcaccaacaa ggtgaacagc    1200
atcatcgaca gatgaacac ccagttcgag gctgtgggca gagagttcaa caacctggaa     1260
cggcggatcg agaacctgaa caagaaaatg aagatggct tcctggatgt gtggacctac     1320
aatgccgaac tgctggtgct gatggaaaac gagcggaccc tggacttcca cgacagcaac    1380
gtgaagaacc tgtacgacaa agtgcggctg cagctgagag acaacgccaa agagctgggc    1440
aacggctgct tcgagttcta ccacaagtgc gacaacgagt gcatggaaag catcaggaac    1500
ggcacctaca actaccctca gtacagcgag gaagccaggc tgaagaggga agagatcagc    1560
tccggaggcg acatcatcaa gctgctgaac gagcaggtga acaaggagat gcagagcagc    1620
aacctgtaca tgagcatgag cagctggtgc tacacccaca gcctggacgg cgccggcctg    1680
ttcctgttcg accacgccgc cgaggagtac gagcacgcca agaagctgat catcttcctg    1740
aacgagaaca acgtgcccgt gcagctgacc agcatcagcg cccccgagca aagttcgag     1800 ggcctgaccc agatcttcca gaaggcctac gagcacgagc agcacatcag cgagagcatc    1860
aacaacatcg tggaccacgc catcaagagc aaggaccacg ccaccttcaa cttcctgcag    1920
tggtacgtgg ccgagcagca cgaggaggag gtgctgttca aggacatcct ggacaagatc    1980
gagctgatcg gcaacgagaa ccacggcctg tacctggccg accagtacgt gaagggcatc    2040
gccaagagca ggaagagcgg atcctag                                        2067
```

<210> SEQ ID NO 56
<211> LENGTH: 688
<212> TYPE: PRT
<213> ORGANISM: Artificial Sequence
<220> FEATURE:
<223> OTHER INFORMATION: Synthetic

<400> SEQUENCE: 56

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125
```

-continued

```
Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Ser Gly Gly Asp Ile Ile Lys Leu
        515                 520                 525

Leu Asn Glu Gln Val Asn Lys Glu Met Gln Ser Ser Asn Leu Tyr Met
    530                 535                 540

Ser Met Ser Ser Trp Cys Tyr Thr His Ser Leu Asp Gly Ala Gly Leu
```

```
                545                 550                 555                 560
            Phe Leu Phe Asp His Ala Ala Glu Glu Tyr Glu His Ala Lys Lys Leu
                            565                 570                 575

Ile Ile Phe Leu Asn Glu Asn Val Pro Val Gln Leu Thr Ser Ile
                        580                 585                 590

Ser Ala Pro Glu His Lys Phe Glu Gly Leu Thr Gln Ile Phe Gln Lys
                        595                 600                 605

Ala Tyr Glu His Glu Gln His Ile Ser Glu Ser Ile Asn Asn Ile Val
                    610                 615                 620

Asp His Ala Ile Lys Ser Lys Asp His Ala Thr Phe Asn Phe Leu Gln
            625                 630                 635                 640

Trp Tyr Val Ala Glu Gln His Glu Glu Val Leu Phe Lys Asp Ile
                            645                 650                 655

Leu Asp Lys Ile Glu Leu Ile Gly Asn Glu Asn His Gly Leu Tyr Leu
                        660                 665                 670

Ala Asp Gln Tyr Val Lys Gly Ile Ala Lys Ser Arg Lys Ser Gly Ser
                        675                 680                 685

<210> SEQ ID NO 57
<211> LENGTH: 2067
<212> TYPE: DNA
<213> ORGANISM: Artificial Sequence
<220> FEATURE:
<223> OTHER INFORMATION: Synthetic

<400> SEQUENCE: 57
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgcg tgatgctggt     300
cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttg atgatgtcgc ctccggagct gatctcttcc ctcttcagcc tggcttcctc     540
gctgtactga gggtagttgt aggtgccgtt cctgatgctt ccatgcact cgttgtcgca     600 cttgtggtag aactcgaagc agccgttgcc cagctctttg gcgttgtctc tcagctgcag     660
ccgcactttg tcgtacaggt tcttcacgtt gctgtcgtgg aagtccaggg tccgctcgtt     720
ttccatcagc accagcagtt cggcattgta ggtccacaca tccaggaagc catcttccat     780
tttcttgttc aggttctcga tccgccgttc caggttgttg aactctctgc ccacagcctc     840
gaactgggtg ttcatcttgt cgatgatgct gttcacctg ttggtgacgc cgtcgatggc     900
cttctgggta gactctttgt cggcggcata tccagagccc tgctcattgc tgtggtggta     960
gccgtaccag ccatccacca ttccctgcca gccgccttca ataaagccgg cgatggctcc    1020
aaacaggccc ctcttctttc ttctgctctc ccgctggggg ctatttctca ggcctgtggc    1080
cagcaccagt ctgttgctct tcacgtactt agggcactcg ccgatggtca gagggtggat    1140
gttgtggaag gcatgctgc tgttgatggc gcccataggt gtctggcact tggtgttgca    1200
gttgccgtat tccagctcgc tcttcatgat ggcgctgtcg cccttcttca cgatcttgta    1260
ggcgtactca ggggcgataa agttgccgtt gctctcgaag ttgatggcgt cgttgggctt    1320
```

```
caggatggtc cagaagaatt ccatcctgcc gctctggccg ttcaccttgg atctggtggc   1380
gatcttgggc accagtctct gattcagggt gctggtgccg atgctgatat aggtggtggg   1440
gttctggtac agtctggtct gctcggcggc atcattaggg tggtggattc cccacaggac   1500
cagcagatct tcctggttgg tgttgttgta gctcttcttg atggtggggt aggtgctgtt   1560
cttcttgatc agccacacca cgtttctgaa gaagctgggg ctgcccaggt aaggacaggc   1620
gctagacact ccgctagagg cttcgtgatc gctccaagag acttgggga tgatctggat   1680 cttctcgaag tggttgatcc gggacagcag gtgcttcagt tcctcgtaat cgttgaagct   1740 gccgggtaa cacagatcgt tggtggggtt ggccttctcc acgatatagc tccactcggg   1800
cacgttgatg aactcgtcgc atagggtt gcccagcagc catccagcca cgctacaatc   1860
tctcaggatc agaggcttca cgccgtccag atcacacagc ttgccgttgt gggtcttttc   1920
caggatgtcc tgagcgtggg tcacggtcac gttttttttcc atgatggtgt ccacctgctc   1980
tgtgctattg ttggcgtggt agccaatgca gatctggtcg ctcttcacca ggctcacaat   2040
ggccagcagc agcacgatct tttccat                                      2067
```

<210> SEQ ID NO 58
<211> LENGTH: 2109
<212> TYPE: DNA
<213> ORGANISM: Artificial Sequence
<220> FEATURE:
<223> OTHER INFORMATION: Synthetic

<400> SEQUENCE: 58

```
atgaaggcca tcatcgtgct gctgatggtg gtgaccagca acgccgatag aatctgcacc     60
ggcatcacca gcagcaatag ccccccatgtg gtgaaaacag ccacccaggg cgaagtgaat    120
gtgacaggcg tgatccctct gaccaccacc cccaccaaga gctacttcgc caacctgaag    180
ggcaccagaa ccagaggcaa gctgtgcccc gattgcctga actgcaccga tctggatgtg    240
gctctgggca gacctatgtg tgtgggcacc acaccatctg ccaaggccag catcctgcac    300
gaagtgaagc tgtgaccag cggctgcttc cccatcatgc acgaccggac caagatcaga    360
cagctgccca acctgctgag aggctacgag aacatccggc tgtccaccca gaatgtgatc    420
gatgccgaga agcccctggc ggacccttat agactgggca ccagcggctc ttgtcccaat    480
gccacctcca gagcggcttt ttttgccaca atggcctggg ccgtgcctaa ggacaacaac    540
aagaacgcca ccaaccctct gaccgtggag gtgccctaca tctgtacaga gggcgaggat    600 cagatccacag tgtggggctt ccacagcgac gacaagaccc agatgaagaa cctgtacggc    660
gacagcaacc cccagaagtt taccagcagc gccaatggcg tgaccaccca ctacgtgtcc    720
cagatcggca gctttcccga tcagacagag gatggcggac tgcctcagtc tggcaggatc    780
gtggtggact acatgatgca gaagcctggc aagaccggca ccatcgtgta tcagagaggc    840
gtgctgctgc ctcagaaagt gtggtgtgcc agcggcaggt ctaaagtgat caagggcagc    900
ctgcctctga ttggcgaggc cgactgtctg cacgaaaagt acggcggcct gaacaagagc    960
aagccctact acacaggcga gcacgccaag gccatcggca attgccccat ctgggtgaaa   1020 accccctga agctggccaa tggcaccaag tacagacctc ccgccaagct gctgaaagag   1080
agaggcttct ttggcgccat tgccggattt ctggaaggcg gctgggaggg aatgattgcc   1140
ggctggcacg gctatacatc tcatgggggcc catggcgtgg ctgtgccgc cgatctgaag   1200 tctacccagg aagccatcaa caagatcacc aagaacctga acagcctgag cgagctggaa   1260
```

-continued

```
gtgaagaatc tgcagagact gagcggcgcc atggatgagc tgcacaacga gatcctggaa    1320
ctggacgaga aagtggatga tctccgcgcc gatacaattt cctcccagat tgaactggcc    1380
gtgctgctgt ccaacgaggg catcatcaac agcgaggatg aacacctgct ggccctggaa    1440
cggaagctga agaagatgct gggcccttct gccgtggaga tcggcaacgg ctgcttcgag    1500
acaaagcaca agtgcaacca gacctgcctg gatagaatcg ccgctggcac cttcaatgcc    1560
ggcgagttca gcctgcctac cttcgacagc ctgaatatca cctccggagg cgacatcatc    1620
aagctgctga acgagcaggt gaacaaggag atgcagagca gcaacctgta catgagcatg    1680
agcagctggt gctacaccca cagcctggac ggcgccggcc tgttcctgtt cgaccacgcc    1740
gccgaggagt acgagcacgc caagaagctg atcatcttcc tgaacgagaa caacgtgccc    1800
gtgcagctga ccagcatcag cgcccccgag cacaagttcg agggcctgac ccagatcttc    1860
cagaaggcct acgagcacga gcagcacatc agcgagagca tcaacaacat cgtggaccac    1920
gccatcaaga gcaaggacca cgccaccttc aacttcctgc agtggtacgt ggccgagcag    1980
cacgaggagg aggtgctgtt caaggacatc ctggacaaga tcgagctgat cggcaacgag    2040
aaccacggcc tgtacctggc cgaccagtac gtgaagggca tcgccaagag caggaagagc    2100
ggatcctag                                                            2109
```

<210> SEQ ID NO 59
<211> LENGTH: 702
<212> TYPE: PRT
<213> ORGANISM: Artificial Sequence
<220> FEATURE:
<223> OTHER INFORMATION: Synthetic

<400> SEQUENCE: 59

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

-continued

Ser Asp Asp Lys Thr Gln Met Lys Asn Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
            245                 250                 255

Ser Gly Arg Ile Val Val Asp Tyr Met Met Gln Lys Pro Gly Lys Thr
                260                 265                 270

Gly Thr Ile Val Tyr Gln Arg Gly Val Leu Leu Pro Gln Lys Val Trp
            275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
            435                 440                 445

Arg Ala Asp Thr Ile Ser Ser Gln Ile Glu Leu Ala Val Leu Leu Ser
450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
            515                 520                 525

Asp Ser Leu Asn Ile Thr Ser Gly Gly Asp Ile Ile Lys Leu Leu Asn
530                 535                 540

Glu Gln Val Asn Lys Glu Met Gln Ser Ser Asn Leu Tyr Met Ser Met
545                 550                 555                 560

Ser Ser Trp Cys Tyr Thr His Ser Leu Asp Gly Ala Gly Leu Phe Leu
            565                 570                 575

Phe Asp His Ala Ala Glu Glu Tyr Glu His Ala Lys Lys Leu Ile Ile
            580                 585                 590

Phe Leu Asn Glu Asn Asn Val Pro Val Gln Leu Thr Ser Ile Ser Ala
            595                 600                 605

Pro Glu His Lys Phe Glu Gly Leu Thr Gln Ile Phe Gln Lys Ala Tyr
            610                 615                 620

Glu His Glu Gln His Ile Ser Glu Ser Ile Asn Asn Ile Val Asp His 625                 630                 635                 640
Ala Ile Lys Ser Lys Asp His Ala Thr Phe Asn Phe Leu Gln Trp Tyr
                    645                 650                 655

Val Ala Glu Gln His Glu Glu Glu Val Leu Phe Lys Asp Ile Leu Asp
            660                 665                 670

Lys Ile Glu Leu Ile Gly Asn Glu Asn His Gly Leu Tyr Leu Ala Asp
        675                 680                 685

Gln Tyr Val Lys Gly Ile Ala Lys Ser Arg Lys Ser Gly Ser
    690                 695                 700

<210> SEQ ID NO 60
<211> LENGTH: 2109
<212> TYPE: DNA
<213> ORGANISM: Artificial Sequence
<220> FEATURE:
<223> OTHER INFORMATION: Synthetic

<400> SEQUENCE: 60
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt     300
cagctgcacg ggcacgttgt tctcgttcag gaagatgatc agcttcttgg cgtgctcgta     360
ctcctcggcg cgtggtcga acaggaacag gccggcgccg tccaggctgt gggtgtagca     420
ccagctgctc atgctcatgt acaggttgct gctctgcatc tccttgttca cctgctcgtt     480
cagcagcttg atgatgtcgc ctccggaggt gatattcagg ctgtcgaagg taggcaggct     540
gaactcgccg gcattgaagg tgccagcggc gattctatcc aggcaggtct ggttgcactt     600
gtgctttgtc tcgaagcagc cgttgccgat ctccacggca aagggccca gcatcttctt     660
cagcttccgt tccagggcca gcaggtgttc atcctcgctg ttgatgatgc cctcgttgga     720
cagcagcacg gccagttcaa tctgggagga aattgtatcg gcgcggagat catccacttt     780
ctcgtccagt tccaggatct cgttgtgcag ctcatccatg gcgccgctca gtctctgcag     840
attcttcact tccagctcgc tcaggctgtt caggttcttg gtgatcttgt tgatggcttc     900
ctgggtagac ttcagatcgg cggccacagc cacgccatgg gccccatgag atgtatagcc     960
gtgccagccg gcaatcattc cctcccagcc gccttccaga aatccggcaa tggcgccaaa    1020
gaagcctctc tctttcagca gcttggcggg aggtctgtac ttggtgccat ggccagcttt    1080
cagggggtt ttcacccaga tggggcaatt gccgatggcc ttggcgtgct cgcctgtgta    1140
gtagggcttg ctcttgttca ggccgccgta cttttcgtgc agacagtcgg cctcgccaat    1200
cagaggcagg ctgcccttga tcactttaga cctgccgctg gcacaccaca ctttctgagg    1260
cagcagcacg cctctctgat acacgatggt gccggtcttg ccaggcttct gcatcatgta    1320
gtccaccacg atcctgccag actgaggcag tccgccatcc tctgtctgat cgggaaagct    1380
gccgatctgg acacgtagt gggtggtcac gccattggcg ctgctggtaa acttctgggg    1440
gttgctgtcg ccgtacaggt tcttcatctg ggtcttgtcg tcgctgtgga agccccacac    1500
tgtgatctga tcctcgccct ctgtacagat gtagggcacc tccacggtca gagggttggt    1560
ggcgttcttg ttgttgtcct taggcacggc ccaggccatt gtggcaaaaa agccgctctt    1620
ggaggtggca ttgggacaag agccgctggt gcccagtcta taaggtccgc caggggcttt    1680

-continued

| | |
|---|---|
| ctcggcatcg atcacattct gggtggacag ccggatgttc tcgtagcctc tcagcaggtt | 1740 |
| gggcagctgt ctgatcttgg tccggtcgtg catgatgggg aagcagccgc tggtcacagg | 1800 |
| cttcacttcg tgcaggatgc tggccttggc agatggtgtg gtgcccacac acataggtct | 1860 |
| gcccagagcc acatccagat cggtgcagtt caggcaatcg gggcacagct tgcctctggt | 1920 |
| tctggtgccc ttcaggttgg cgaagtagct cttggtgggg gtggtggtca gagggatcac | 1980 |
| gcctgtcaca ttcacttcgc cctgggtggc tgttttcacc acatggggc tattgctgct | 2040 |
| ggtgatgccg gtgcagattc tatcggcgtt gctggtcacc accatcagca gcacgatgat | 2100 |
| ggccttcat | 2109 |

<210> SEQ ID NO 61
<211> LENGTH: 2064
<212> TYPE: DNA
<213> ORGANISM: Artificial Sequence
<220> FEATURE:
<223> OTHER INFORMATION: Synthetic

<400> SEQUENCE: 61

| | |
|---|---|
| atgaaaacca taattgcgct gtcctacata ctgtgtctgg tgtttgccca gaaactgccg | 60 |
| ggcaatgaca actcaacagc cacgctctgc ttggggcacc atgccgtccc taacgggacc | 120 |
| attgtgaaaa ccattactaa cgatcagata gaggtgacta atgccaccga gctggtgcaa | 180 |
| agtagctcca caggagagat ctgcgatagt ccccaccaga ttctggacgg aaagaattgt | 240 |
| acgctgatcg acgcgctgtt gggcgaccct cagtgtgacg gatttcagaa taagaagtgg | 300 |
| gatctgtttg tggaaaggtc aaaggcttat tcaaattgct acccttacga tgtgcctgat | 360 |
| tatgccagcc tgcggtccct cgtcgcgtct agtgggactc tggagttcaa caacgagtca | 420 |
| tttaactgga ctggcgttac acagaacggg actagttccg cttgcataag gagaagcaaa | 480 |
| aatagtttct tcagcagact gaattggctg cacatctga acttcaagta ccctgcactg | 540 |
| aatgtaacca tgcccaacaa cgagcagttc gataagcttt acatttgggg agttcatcat | 600 |
| cctggcactg acaaggatca gatctttctg tatgcccagg cttccggcag gattaccgtg | 660 |
| tctacaaaga gaagccagca aactgtgtct cccaatatcg gcagtagacc cagagtacgg | 720 |
| aacatcccta gtcgcatcag tatttactgg accatcgtga aaccaggcga tattctcctg | 780 |
| attaacagta ctggcaaccct gatcgccccc cggggatact ttaaaatccg ctctggaaag | 840 |
| tcctccatta tgagatcaga tgcaccgatc ggaaaatgca actctgagtg tatcacaccc | 900 |
| aatgggagca ttcccaatga caaacctttc cagaacgtta atcgaataac ttatggggcc | 960 |
| tgtccacggt acgtgaagca aaataccttg aaactggcga ccggtatgcg caatgtcccc | 1020 |
| gaaaaacaga cccgcgggat atttggggct atcgcaggct ttatcgagaa tggctgggaa | 1080 |
| gggatggtgg atggttggta tggttttaga catcaaaact ccgaaggcag aggccaggct | 1140 |
| gccgatctca agagcacgca ggccgctata atcagatca atggaaagct caacagactg | 1200 |
| atcgggaaaa ccaacgaaaa attccatcag atcgagaaag agttctccga agtcgagggg | 1260 |
| cgcatacagg acctggagaa gtatgttgag gatacaaaga ttgatctgtg gtcctacaat | 1320 |
| gccgagctgc tggtggctct ggagaatcag cacactattg acctgaccga ttcagagatg | 1380 |
| aacaaacttt ttgagaagac gaagaagcag cttagaaaaa tgcagaggga catggggaac | 1440 |
| ggatgcttta aaatatatca taagtgtgat aatgcctgca tcggatcaat tagaaatggt | 1500 |
| acctatgatc acgatgttta cagggacgaa gcgctgaata caggttcca gataaaatcc | 1560 |

```
ggaggcgaca tcatcaagct gctgaacgag caggtgaaca aggagatgca gagcagcaac    1620
ctgtacatga gcatgagcag ctggtgctac acccacagcc tggacggcgc cggcctgttc    1680
ctgttcgacc acgccgccga ggagtacgag cacgccaaga agctgatcat cttcctgaac    1740
gagaacaacg tgcccgtgca gctgaccagc atcagcgccc ccgagcacaa gttcgagggc    1800
ctgacccaga tcttccagaa ggcctacgag cacgagcagc acatcagcga gagcatcaac    1860
aacatcgtgg accacgccat caagagcaag gaccacgcca ccttcaactt cctgcagtgg    1920
tacgtggccg agcagcacga ggaggaggtg ctgttcaagg acatcctgga caagatcgag    1980
ctgatcggca cgagaaacca cggcctgtac ctggccgacc agtacgtgaa gggcatcgcc    2040
aagagcagga gagcggatc ctag                                            2064
```

<210> SEQ ID NO 62
<211> LENGTH: 687
<212> TYPE: PRT
<213> ORGANISM: Artificial Sequence
<220> FEATURE:
<223> OTHER INFORMATION: Synthetic

<400> SEQUENCE: 62

```
Met Lys Thr Ile Ile Ala Leu Ser Tyr Ile Leu Cys Leu Val Phe Ala
 1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Lys Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Lys
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ser Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270
```

```
Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Arg Gly Gln Ala Ala Asp Leu Lys
            370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Ser Gly Gly Asp Ile Ile Lys Leu Leu
            515                 520                 525

Asn Glu Gln Val Asn Lys Glu Met Gln Ser Ser Asn Leu Tyr Met Ser
530                 535                 540

Met Ser Ser Trp Cys Tyr Thr His Ser Leu Asp Gly Ala Gly Leu Phe
545                 550                 555                 560

Leu Phe Asp His Ala Ala Glu Glu Tyr Glu His Ala Lys Lys Leu Ile
            565                 570                 575

Ile Phe Leu Asn Glu Asn Asn Val Pro Val Gln Leu Thr Ser Ile Ser
            580                 585                 590

Ala Pro Glu His Lys Phe Glu Gly Leu Thr Gln Ile Phe Gln Lys Ala
            595                 600                 605

Tyr Glu His Glu Gln His Ile Ser Glu Ser Ile Asn Asn Ile Val Asp
            610                 615                 620

His Ala Ile Lys Ser Lys Asp His Ala Thr Phe Asn Phe Leu Gln Trp
625                 630                 635                 640

Tyr Val Ala Glu Gln His Glu Glu Val Leu Phe Lys Asp Ile Leu
                645                 650                 655

Asp Lys Ile Glu Leu Ile Gly Asn Glu Asn His Gly Leu Tyr Leu Ala
            660                 665                 670

Asp Gln Tyr Val Lys Gly Ile Ala Lys Ser Arg Lys Ser Gly Ser
            675                 680                 685
```

<210> SEQ ID NO 63
<211> LENGTH: 2064
<212> TYPE: DNA
<213> ORGANISM: Artificial Sequence
<220> FEATURE:
<223> OTHER INFORMATION: Synthetic

<400> SEQUENCE: 63

```
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt      300
cagctgcacg ggcacgttgt tctcgttcag gaagatgatc agcttcttgg cgtgctcgta     360
ctcctcggcg cgtggtcga acaggaacag gccggcgccg tccaggctgt gggtgtagca      420
ccagctgctc atgctcatgt acaggttgct gctctgcatc tccttgttca cctgctcgtt     480
cagcagcttg atgatgtcgc ctccggattt tatctggaac ctgttattca gcgcttcgtc     540
cctgtaaaca tcgtgatcat aggtaccatt tctaattgat ccgatgcagg cattatcaca     600
cttatgatat attttaaagc atccgttccc catgtcctct gcattttctc taagctgctt     660
cttcgtcttc tcaaaaagtt tgttcatctc tgaatcggtc aggtcaatag tgtgctgatt     720
ctccagagcc accagcagct cggcattgta ggaccacaga tcaatctttg tatcctcaac     780
atacttctcc aggtcctgta tgcgcccctc gacttcggag aactcttcct cgatctgatg     840
gaatttttcg ttggttttcc cgatcagtct gttgagcttt ccattgatct gatctatagc     900
ggcctgcgtg ctcttgagat cggcagcctg gcctctgcct tcggagtttt gatgtctaaa     960
accataccaa ccatccacca tcccttccca gccattctcg ataaagcctg cgatagcccc    1020
aaatatcccg cgggtctgtt tttcggggac attgcgcata ccggtcgcca gtttcaaggt    1080
attttgcttc acgtaccgtg gacaggcccc ataagttatt cgattaacgt tctggaaagg    1140
tttgtcattg ggaatgctcc cattgggtgt gatacactca gagttgcatt ttccgatcgg    1200
tgcatctgat ctcataatgg aggactttcc agagcggatt ttaaagtatc ccgggggggc    1260
gatcaggttg ccagtactgt taatcaggag aatatcgcct ggtttcacga tggtccagta    1320
aatactgatg cgactaggga tgttccgtac tctgggtcta ctgccgatat gggagacac     1380
agtttgctgg cttctctttg tagacacggt aatcctgccg gaagcctggg catacagaaa    1440
gatctgatcc ttgtcagtgc caggatgatg aactccccaa atgtaaagct tatcgaactg    1500
ctcgttgttg ggcatggtta cattcagtgc agggtacttg aagttcagat gtgtcagcca    1560
attcagtctg ctgaagaaac tatttttgct tctccttatg caagcggaac tagtcccgtt    1620
ctgtgtaacg ccagtccagt taaatgactc gttgttgaac tccagagtcc cactagacgc    1680
gacgagggac cgcaggctgg cataatcagg cacatcgtaa gggtagcaat ttgaataagc    1740
ctttgacctt tccacaaaca gatcccactt cttattctga aatccgtcac actgagggtc    1800
gcccaacagc gcgtcgatca gcgtacaatt ctttccgtcc agaatctggt ggggactatc    1860
gcagatctct cctgtggagc tactttgcac cagctcggtg gcattagtca cctctatctg    1920
atcgttagta atggttttca caatggtccc gttagggacg gcatggtgcc ccaagcagag    1980
cgtggctgtt gagttgtcat tgcccggcag tttctgggca aacaccagac acagtatgta    2040
ggacagcgca attatggttt tcat                                           2064
```

<210> SEQ ID NO 64
<211> LENGTH: 2058
<212> TYPE: DNA
<213> ORGANISM: Artificial Sequence
<220> FEATURE:
<223> OTHER INFORMATION: Synthetic

<400> SEQUENCE: 64

```
atgaaagtga agctgctggt gctgctgtgt acctttaccg ccacctacgc cgataccatc      60
tgtatcggct accacgccaa caatagcacc gacaccgtgg ataccgtgct ggaaaagaac     120
gtgaccgtga cccacagcgt gaacctgctg aaaacagcc acaacggcaa gctgtgtctg      180
ctgaaaggca ttgcccctct gcagctggga aattgtagcg tggccggctg gattctgggc     240
aatcctgagt gcgagctgct gatttccaaa gagtcctggt cctacatcgt ggagaagccc     300
aaccctgaga atggcacctg ctaccctggc cacttcgccg attacgagga actgagagaa     360
cagctgtcca gcgtgtccag cttcgagaga ttcgagatct ccccaaaga gagcagctgg      420
cccaatcata cagtgaccgg cgtgagcgcc tcttgtagcc acaatggcga gagcagcttc     480
tacagaaacc tgctgtggct gaccggcaag aacggcctgt accccaacct gagcaagagc     540
tacgccaaca acaaagaaaa agaagtgctg gtcctctggg gagtgcacca ccctcctaac     600
atcggcatcc agaaggccct gtaccacacc gagaatgcct acgtgtccgt ggtgtccagc     660
cactacagca gaaagttcac ccccgagatc gccaaaagac ccaaagtgcg ggaccaggaa     720
ggcaggatca actactactg gaccctgctg gaacctggcg acaccatcat cttcgaggcc     780
aacggcaatc tgatcgcccc tagatacgcc tttgccctga gcagaggctt tggcagcggc     840
atcatcaaca gcaacgcccc catggacaag tgtgacgcca agtgtcagac accacaggga     900
gctatcaata gcagcctgcc cttccagaat gtgcaccctg tgaccatcgg cgagtgtcct     960
aaatacgtgc ggagcgccaa gctgagaatg gtgaccggcc tgaggaatat ccccagcatc    1020
cagagcagag gcctgtttgg cgccattgcc ggctttatcg agggcggatg gacaggcatg    1080
gtggatgggt ggtacggcta ccaccaccag aatgagcagg gatctggcta tgccgccgat    1140
cagaagagca cccagaacgc catcaacggc atcaccaaca agtgaacag cgtgatcgag    1200
aagatgaaca cccagttcac cgccgtgggc aaagagttca acaagctgga acggcggatg    1260
gaaaacctga acaagaaggt ggacgacggc ttcatcgaca tctggaccta caacgccgaa    1320
ctcctggtcc tcctggaaaa tgagaggacc ctggacttcc acgacagcaa cgtgaagaac    1380
ctgtacgaga aagtgaagag ccagctgaag aacaacgcca agagatcgg caacggctgc    1440
ttcgagttct accacaagtg caacgacgag tgcatggaaa gcgtgaagaa cggcacctac    1500
gactacccca gtacagcga ggaaagcaag ctgaaccggg agaagatcga ttccggaggc    1560
gacatcatca gctgctgaa cgagcaggtg aacaaggaga tgcagagcag caacctgtac    1620
atgagcatga gcagctggtg ctacacccac agcctggacg cgccggcct gttcctgttc    1680
gaccacgccg ccgaggagta cgagcacgcc aagaagctga tcatcttcct gaacgagaac    1740
aacgtgcccg tgcagctgac cagcatcagc gcccccgagc acaagttcga gggcctgacc    1800
cagatcttcc agaaggccta cgagcacgag cagcacatca gcgagagcat caacaacatc    1860
gtggaccacg ccatcaagag caaggaccac gccaccttca acttcctgca gtggtacgtg    1920
gccgagcagc acgaggagga ggtgctgttc aaggacatct ggacaagat cgagctgatc    1980
ggcaacgaga accacggcct gtacctggcc gaccagtacg tgaagggcat cgccaagagc    2040
aggaagagcg gatcctag                                                  2058
```

```
<210> SEQ ID NO 65
<211> LENGTH: 685
<212> TYPE: PRT
<213> ORGANISM: Artificial Sequence
<220> FEATURE:
<223> OTHER INFORMATION: Synthetic

<400> SEQUENCE: 65
```

| | | | | | | | | | | | | | | |
|---|---|---|---|---|---|---|---|---|---|---|---|---|---|---|
| Met | Lys | Val | Lys | Leu | Leu | Val | Leu | Leu | Cys | Thr | Phe | Thr | Ala | Thr | Tyr |
| 1 | | | | 5 | | | | | 10 | | | | | 15 |
| Ala | Asp | Thr | Ile | Cys | Ile | Gly | Tyr | His | Ala | Asn | Asn | Ser | Thr | Asp | Thr |
| | | | 20 | | | | | 25 | | | | | 30 | | |
| Val | Asp | Thr | Val | Leu | Glu | Lys | Asn | Val | Thr | Val | Thr | His | Ser | Val | Asn |
| | | 35 | | | | | 40 | | | | | 45 | | | |
| Leu | Leu | Glu | Asn | Ser | His | Asn | Gly | Lys | Leu | Cys | Leu | Leu | Lys | Gly | Ile |
| | 50 | | | | | 55 | | | | | 60 | | | | |
| Ala | Pro | Leu | Gln | Leu | Gly | Asn | Cys | Ser | Val | Ala | Gly | Trp | Ile | Leu | Gly |
| 65 | | | | | 70 | | | | | 75 | | | | | 80 |
| Asn | Pro | Glu | Cys | Glu | Leu | Leu | Ile | Ser | Lys | Glu | Ser | Trp | Ser | Tyr | Ile |
| | | | 85 | | | | | 90 | | | | | 95 | | |
| Val | Glu | Lys | Pro | Asn | Pro | Glu | Asn | Gly | Thr | Cys | Tyr | Pro | Gly | His | Phe |
| | | | 100 | | | | | 105 | | | | | 110 | | |
| Ala | Asp | Tyr | Glu | Glu | Leu | Arg | Glu | Gln | Leu | Ser | Ser | Val | Ser | Ser | Phe |
| | | | 115 | | | | | 120 | | | | | 125 | | |
| Glu | Arg | Phe | Glu | Ile | Phe | Pro | Lys | Glu | Ser | Ser | Trp | Pro | Asn | His | Thr |
| | 130 | | | | | 135 | | | | | 140 | | | | |
| Val | Thr | Gly | Val | Ser | Ala | Ser | Cys | Ser | His | Asn | Gly | Glu | Ser | Ser | Phe |
| 145 | | | | | 150 | | | | | 155 | | | | | 160 |
| Tyr | Arg | Asn | Leu | Leu | Trp | Leu | Thr | Gly | Lys | Asn | Gly | Leu | Tyr | Pro | Asn |
| | | | | 165 | | | | | 170 | | | | | 175 | |
| Leu | Ser | Lys | Ser | Tyr | Ala | Asn | Asn | Lys | Glu | Lys | Glu | Val | Leu | Val | Leu |
| | | | 180 | | | | | 185 | | | | | 190 | | |
| Trp | Gly | Val | His | His | Pro | Pro | Asn | Ile | Gly | Ile | Gln | Lys | Ala | Leu | Tyr |
| | | | | 195 | | | | | 200 | | | | | 205 | |
| His | Thr | Glu | Asn | Ala | Tyr | Val | Ser | Val | Val | Ser | Ser | His | Tyr | Ser | Arg |
| | 210 | | | | | 215 | | | | | 220 | | | | |
| Lys | Phe | Thr | Pro | Glu | Ile | Ala | Lys | Arg | Pro | Lys | Val | Arg | Asp | Gln | Glu |
| 225 | | | | | 230 | | | | | 235 | | | | | 240 |
| Gly | Arg | Ile | Asn | Tyr | Tyr | Trp | Thr | Leu | Leu | Glu | Pro | Gly | Asp | Thr | Ile |
| | | | | 245 | | | | | 250 | | | | | 255 | |
| Ile | Phe | Glu | Ala | Asn | Gly | Asn | Leu | Ile | Ala | Pro | Arg | Tyr | Ala | Phe | Ala |
| | | | | 260 | | | | | 265 | | | | | 270 | |
| Leu | Ser | Arg | Gly | Phe | Gly | Ser | Gly | Ile | Ile | Asn | Ser | Asn | Ala | Pro | Met |
| | | | 275 | | | | | 280 | | | | | 285 | | |
| Asp | Lys | Cys | Asp | Ala | Lys | Cys | Gln | Thr | Pro | Gln | Gly | Ala | Ile | Asn | Ser |
| | | 290 | | | | | 295 | | | | | 300 | | | |
| Ser | Leu | Pro | Phe | Gln | Asn | Val | His | Pro | Val | Thr | Ile | Gly | Glu | Cys | Pro |
| 305 | | | | | 310 | | | | | 315 | | | | | 320 |
| Lys | Tyr | Val | Arg | Ser | Ala | Lys | Leu | Arg | Met | Val | Thr | Gly | Leu | Arg | Asn |
| | | | | 325 | | | | | 330 | | | | | 335 | |
| Ile | Pro | Ser | Ile | Gln | Ser | Arg | Gly | Leu | Phe | Gly | Ala | Ile | Ala | Gly | Phe |
| | | | 340 | | | | | 345 | | | | | 350 | | |
| Ile | Glu | Gly | Gly | Trp | Thr | Gly | Met | Val | Asp | Gly | Trp | Tyr | Gly | Tyr | His |
| | | | | 355 | | | | | 360 | | | | | 365 | |

| | | | | | | | | | | | |
|---|---|---|---|---|---|---|---|---|---|---|---|
|His|Gln|Asn|Glu|Gln|Gly|Ser|Gly|Tyr|Ala|Ala|Asp|Gln|Lys|Ser|Thr|
| |370| | | |375| | | |380| | |

His Gln Asn Glu Gln Gly Ser Gly Tyr Ala Ala Asp Gln Lys Ser Thr
     370                       375                       380

Gln Asn Ala Ile Asn Gly Ile Thr Asn Lys Val Asn Ser Val Ile Glu
385                       390                       395                     400

Lys Met Asn Thr Gln Phe Thr Ala Val Gly Lys Glu Phe Asn Lys Leu
                 405                       410                       415

Glu Arg Arg Met Glu Asn Leu Asn Lys Lys Val Asp Asp Gly Phe Ile
         420                       425                       430

Asp Ile Trp Thr Tyr Asn Ala Glu Leu Leu Val Leu Leu Glu Asn Glu
        435                     440                     445

Arg Thr Leu Asp Phe His Asp Ser Asn Val Lys Asn Leu Tyr Glu Lys
     450                     455                    460

Val Lys Ser Gln Leu Lys Asn Asn Ala Lys Glu Ile Gly Asn Gly Cys
465                       470                       475                     480

Phe Glu Phe Tyr His Lys Cys Asn Asp Glu Cys Met Glu Ser Val Lys
                 485                       490                       495

Asn Gly Thr Tyr Asp Tyr Pro Lys Tyr Ser Glu Ser Lys Leu Asn
             500                     505                     510

Arg Glu Lys Ile Asp Ser Gly Gly Asp Ile Ile Lys Leu Leu Asn Glu
        515                      520                     525

Gln Val Asn Lys Glu Met Gln Ser Ser Asn Leu Tyr Met Ser Met Ser
     530                     535                    540

Ser Trp Cys Tyr Thr His Ser Leu Asp Gly Ala Gly Leu Phe Leu Phe
545                       550                       555                     560

Asp His Ala Ala Glu Glu Tyr Glu His Ala Lys Lys Leu Ile Ile Phe
                 565                       570                       575

Leu Asn Glu Asn Asn Val Pro Val Gln Leu Thr Ser Ile Ser Ala Pro
        580                      585                    590

Glu His Lys Phe Glu Gly Leu Thr Gln Ile Phe Gln Lys Ala Tyr Glu
     595                     600                    605

His Glu Gln His Ile Ser Glu Ser Ile Asn Asn Ile Val Asp His Ala
        610                      615                    620

Ile Lys Ser Lys Asp His Ala Thr Phe Asn Phe Leu Gln Trp Tyr Val
625                       630                       635                     640

Ala Glu Gln His Glu Glu Val Leu Phe Lys Asp Ile Leu Asp Lys
                 645                       650                       655

Ile Glu Leu Ile Gly Asn Glu Asn His Gly Leu Tyr Leu Ala Asp Gln
                 660                       665                    670

Tyr Val Lys Gly Ile Ala Lys Ser Arg Lys Ser Gly Ser
     675                     680                    685

<210> SEQ ID NO 66
<211> LENGTH: 2058
<212> TYPE: DNA
<213> ORGANISM: Artificial Sequence
<220> FEATURE:
<223> OTHER INFORMATION: Synthetic

<400> SEQUENCE: 66
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240

```
ggccttctgg aagatctggg tcaggccctc gaacttgtgc tcgggggcgc tgatgctggt      300
cagctgcacg ggcacgttgt tctcgttcag gaagatgatc agcttcttgg cgtgctcgta      360
ctcctcggcg gcgtggtcga acaggaacag gccggcgccg tccaggctgt gggtgtagca      420
ccagctgctc atgctcatgt acaggttgct gctctgcatc tccttgttca cctgctcgtt      480
cagcagcttg atgatgtcgc ctccggaatc gatcttctcc cggttcagct tgctttcctc      540
gctgtacttg gggtagtcgt aggtgccgtt cttcacgctt ccatgcact cgtcgttgca       600 cttgtggtag aactcgaagc agccgttgcc gatctctttg gcgttgttct tcagctggct      660
cttcactttc tcgtacaggt tcttcacgtt gctgtcgtgg aagtccaggg tcctctcatt      720
ttccaggagg accaggagtt cggcgttgta ggtccagatg tcgatgaagc cgtcgtccac      780
cttcttgttc aggttttcca tccgccgttc agcttgttg aactctttgc ccacggcgt       840 gaactgggtg ttcatcttct cgatcacgct gttcactttg ttggtgatgc cgttgatggc      900
gttctgggtg ctcttctgat cggcggcata gccagatccc tgctcattct ggtggtggta      960
gccgtaccac ccatccacca tgcctgtcca tccgccctcg ataaagccgg caatggcgcc     1020
aaacaggcct ctgctctgga tgctggggat attcctcagg ccggtcacca ttctcagctt     1080
ggcgctccgc acgtatttag acactcgccg gatggtcaca gggtgcacat tctggaaggg     1140
caggctgcta ttgatagctc cctggtggt ctgacacttg gcgtcacact tgtccatggg      1200
ggcgttgctg ttgatgatgc cgctgccaaa gcctctgctc agggcaaagg cgtatctagg     1260
ggcgatcaga ttgccgttgg cctcgaagat gatggtgtcg ccaggttcca gcagggtcca     1320
gtagtagtta atcctgcctt cctggtcccg cactttgggt cttttggcga ctcgggggt      1380 gaactttctg ctgtagtggc tggacaccac ggacacgtag gcattctcgg tgtggtacag     1440
ggccttctgg atgccgatgt taggaggtg gtgcactccc cagaggacca gcacttcttt      1500
ttctttgttg ttggcgtagc tcttgctcag gttggggtac aggccgttct gccggtcag     1560 ccacagcagg tttctgtaga agctgctctc gccattgtgg ctacaagagg cgctcacgcc     1620
ggtcactgta tgattgggcc agctgctctc tttggggaag atctcgaatc tctcgaagct     1680
ggacacgctg acagctgtt ctctcagttc ctcgtaatcg gcgaagtggc cagggtagca     1740
ggtgccattc tcaggttgg gcttctccac gatgtaggac caggactctt tggaaatcag     1800
cagctcgcac tcaggattgc ccagaatcca gccggccacg ctacaatttc ccagctgcag     1860
aggggcaatg cctttcagca gacacagctt gccgttgtgg ctgttttcca gcaggttcac     1920
gctgtgggtc acggtcacgt tcttttccag cacggtatcc acggtgtcgg tgctattgtt     1980
ggcgtggtag ccgatacaga tggtatcggc gtaggtggcg gtaaaggtac acagcagcac     2040
cagcagcttc actttcat                                                   2058

<210> SEQ ID NO 67
<211> LENGTH: 2112
<212> TYPE: DNA
<213> ORGANISM: Artificial Sequence
<220> FEATURE:
<223> OTHER INFORMATION: Synthetic

<400> SEQUENCE: 67
atgaaggcca tcatcgtgct gctgatggtg gtcacaagca acgccgatag aatctgtacc       60
ggcatcacca gcagcaatag ccctcacgtc gtgaaaacag ctacacaggg cgaagtgaat      120
gtgaccggcg tgatccctct gaccacaaca cctacaaaga gccacttcgc caatctgaag      180
ggcacagaga caagaggcaa gctgtgtccc aagtgcctga attgcacaga tctggatgtg      240
```

```
gctctgggca gacctaagtg tacaggcaaa atccctagcg ccagagtgtc cattctgcat    300
gaagtgcgac ctgtgaccag cggctgtttt cctattatgc acgaccggac caagatcaga    360
cagctgccta atctgctgag aggctacgag cacatcagac tgagcaccca caatgtgatc    420
aacgccgaaa atgctcctgg cggcccttat aagatcggca catctggcag ctgccccaac    480
attacaaatg caatggctt ctttgccacc atggcttggg ccgtgcctaa gaacgataag    540
aacaagaccg ccaccaaccc cctgacaatc gaggtgccat atatctgtac agagggcgag    600
gatcagatca ccgtgtgggg atttcacagc gacaacgaaa cacagatggc caagctgtac    660
ggcgatagca agcctcagaa gtttaccagc tctgccaatg cgtgaccac acactatgtg    720
tctcagatcg gcggcttccc taatcagaca gaagatggcg gactgcctca gtctggaaga    780
atcgtggtgg attacatggt gcagaagtct ggcaagaccg gcaccatcac atatcagaga    840
ggaatcctgc tgccccagaa agtgtggtgc gcttctggaa gatccaaagt gatcaagggc    900
agcctgcctc tgattggaga agccgattgt ctgcacgaga atacggcgg cctgaacaag    960
agcaagcctt actatacagg cgagcacgcc aaggccatcg gcaattgtcc tatttgggtc   1020
aagaccctc tgaagctggc caatggcaca agtatagac ctccagccaa gctgctgaaa   1080
gagagaggct ttttggagc tatcgccggc tttctggaag cggatggga gggaatgatt   1140
gctggatggc atggctacac atctcatggc gcacatggcg tggcagtggc tgctgatctg   1200
aaatctacac aggaagccat caacaagatc accaagaacc tgaacagcct gagcgagctg   1260
gaagtgaaga atctgcagag actgtctggc gccatggacg aactgcacaa tgagatcctg   1320
gaactggacg agaaggtgga cgatctgaga gccgatacaa tcagcagcca gattgaactg   1380
gctgtgctgc tgtctaacga gggcatcatc aatagcgagg acgaacatct gctggccctg   1440
gaaagaaagc tgaagaagat gctgggacct agcgccgtgg aaatcggcaa tggatgcttt   1500
gagacaaagc acaagtgcaa ccagacctgc ctggataaa ttgccgccgg aacatttgat   1560
gccggcgagt tttctctgcc caccttcgat agcctgaata tcacatccgg aggcgacatc   1620
atcaagctgc tgaacgagca ggtgaacaag gagatgcaga gcagcaacct gtacatgagc   1680
atgagcagct ggtgctacac ccacagcctg gacggcgccg gcctgttcct gttcgaccac   1740
gccgccgagg agtacgagca cgccaagaag ctgatcatct tcctgaacga gaacaacgtg   1800
cccgtgcagc tgaccagcat cagcgcccccc gagcacaagt cgagggcct gacccagatc   1860
ttccagaagg cctacgagca cgagcagcac atcagcgaga gcatcaacaa catcgtggac   1920
cacgccatca gagcaagga ccacgccacc ttcaacttcc tgcagtggta cgtggccgag   1980
cagcacgagg aggaggtgct gttcaaggac atcctggaca agatcgagct gatcggcaac   2040
gagaaccacg gcctgtacct ggccgaccag tacgtgaagg catcgccaa gagcaggaag   2100
agcggatcct ag                                                       2112
```

<210> SEQ ID NO 68
<211> LENGTH: 703
<212> TYPE: PRT
<213> ORGANISM: Artificial Sequence
<220> FEATURE:
<223> OTHER INFORMATION: Synthetic

<400> SEQUENCE: 68

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys

-continued

```
            20                  25                  30
Thr Ala Thr Gln Gly Glu Val Asn Val Thr Gly Val Ile Pro Leu Thr
            35                  40                  45
Thr Thr Pro Thr Lys Ser His Phe Ala Asn Leu Lys Gly Thr Glu Thr
    50                  55                  60
Arg Gly Lys Leu Cys Pro Lys Cys Leu Asn Cys Thr Asp Leu Asp Val
65                  70                  75                  80
Ala Leu Gly Arg Pro Lys Cys Thr Gly Lys Ile Pro Ser Ala Arg Val
                85                  90                  95
Ser Ile Leu His Glu Val Arg Pro Val Thr Ser Gly Cys Phe Pro Ile
            100                 105                 110
Met His Asp Arg Thr Lys Ile Arg Gln Leu Pro Asn Leu Leu Arg Gly
            115                 120                 125
Tyr Glu His Ile Arg Leu Ser Thr His Asn Val Ile Asn Ala Glu Asn
            130                 135                 140
Ala Pro Gly Gly Pro Tyr Lys Ile Gly Thr Ser Gly Ser Cys Pro Asn
145                 150                 155                 160
Ile Thr Asn Gly Asn Gly Phe Phe Ala Thr Met Ala Trp Ala Val Pro
                165                 170                 175
Lys Asn Asp Lys Asn Lys Thr Ala Thr Asn Pro Leu Thr Ile Glu Val
                180                 185                 190
Pro Tyr Ile Cys Thr Glu Gly Glu Asp Gln Ile Thr Val Trp Gly Phe
            195                 200                 205
His Ser Asp Asn Glu Thr Gln Met Ala Lys Leu Tyr Gly Asp Ser Lys
            210                 215                 220
Pro Gln Lys Phe Thr Ser Ser Ala Asn Gly Val Thr Thr His Tyr Val
225                 230                 235                 240
Ser Gln Ile Gly Gly Phe Pro Asn Gln Thr Glu Asp Gly Gly Leu Pro
                245                 250                 255
Gln Ser Gly Arg Ile Val Val Asp Tyr Met Val Gln Lys Ser Gly Lys
                260                 265                 270
Thr Gly Thr Ile Thr Tyr Gln Arg Gly Ile Leu Leu Pro Gln Lys Val
            275                 280                 285
Trp Cys Ala Ser Gly Arg Ser Lys Val Ile Lys Gly Ser Leu Pro Leu
            290                 295                 300
Ile Gly Glu Ala Asp Cys Leu His Glu Lys Tyr Gly Gly Leu Asn Lys
305                 310                 315                 320
Ser Lys Pro Tyr Tyr Thr Gly Glu His Ala Lys Ala Ile Gly Asn Cys
                325                 330                 335
Pro Ile Trp Val Lys Thr Pro Leu Lys Leu Ala Asn Gly Thr Lys Tyr
                340                 345                 350
Arg Pro Pro Ala Lys Leu Leu Lys Glu Arg Gly Phe Phe Gly Ala Ile
            355                 360                 365
Ala Gly Phe Leu Glu Gly Gly Trp Glu Gly Met Ile Ala Gly Trp His
            370                 375                 380
Gly Tyr Thr Ser His Gly Ala His Gly Val Ala Val Ala Ala Asp Leu
385                 390                 395                 400
Lys Ser Thr Gln Glu Ala Ile Asn Lys Ile Thr Lys Asn Leu Asn Ser
                405                 410                 415
Leu Ser Glu Leu Glu Val Lys Asn Leu Gln Arg Leu Ser Gly Ala Met
                420                 425                 430
Asp Glu Leu His Asn Glu Ile Leu Glu Leu Asp Glu Lys Val Asp Asp
            435                 440                 445
```

Leu Arg Ala Asp Thr Ile Ser Ser Gln Ile Glu Leu Ala Val Leu Leu
            450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ser Gly Gly Asp Ile Ile Lys Leu Leu
    530                 535                 540

Asn Glu Gln Val Asn Lys Glu Met Gln Ser Ser Asn Leu Tyr Met Ser
545                 550                 555                 560

Met Ser Ser Trp Cys Tyr Thr His Ser Leu Asp Gly Ala Gly Leu Phe
                565                 570                 575

Leu Phe Asp His Ala Ala Glu Glu Tyr Glu His Ala Lys Lys Leu Ile
            580                 585                 590

Ile Phe Leu Asn Glu Asn Asn Val Pro Val Gln Leu Thr Ser Ile Ser
        595                 600                 605

Ala Pro Glu His Lys Phe Glu Gly Leu Thr Gln Ile Phe Gln Lys Ala
    610                 615                 620

Tyr Glu His Glu Gln His Ile Ser Glu Ser Ile Asn Asn Ile Val Asp
625                 630                 635                 640

His Ala Ile Lys Ser Lys Asp His Ala Thr Phe Asn Phe Leu Gln Trp
                645                 650                 655

Tyr Val Ala Glu Gln His Glu Glu Val Leu Phe Lys Asp Ile Leu
            660                 665                 670

Asp Lys Ile Glu Leu Ile Gly Asn Glu Asn His Gly Leu Tyr Leu Ala
        675                 680                 685

Asp Gln Tyr Val Lys Gly Ile Ala Lys Ser Arg Lys Ser Gly Ser
    690                 695                 700

<210> SEQ ID NO 69
<211> LENGTH: 2112
<212> TYPE: DNA
<213> ORGANISM: Artificial Sequence
<220> FEATURE:
<223> OTHER INFORMATION: Synthetic

<400> SEQUENCE: 69
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggcgc tgatgctggt   300 cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttg atgatgtcgc ctccggatgt gatattcagg ctatcgaagg tgggcagaga   540
aaactcgccg gcatcaaatg ttccggcggc aattctatcc aggcaggtct ggttgcactt   600

```
gtgctttgtc tcaaagcatc cattgccgat ttccacggcg ctaggtccca gcatcttctt    660
cagctttctt tccagggcca gcagatgttc gtcctcgcta ttgatgatgc cctcgttaga    720
cagcagcaca gccagttcaa tctggctgct gattgtatcg gctctcagat cgtccacctt    780
ctcgtccagt tccaggatct cattgtgcag ttcgtccatg cgccagaca gtctctgcag     840 attcttcact tccagctcgc tcaggctgtt caggttcttg gtgatcttgt tgatggcttc    900
ctgtgtagat ttcagatcag cagccactgc cacgccatgt gcgccatgag atgtgtagcc    960
atgccatcca gcaatcattc cctcccatcc gccttccaga aagccggcga tagctccaaa    1020
aaagcctctc tctttcagca gcttggctgg aggtctatac tttgtgccat ggccagctt    1080 cagaggggtc ttgacccaaa taggacaatt gccgatggcc ttggcgtgct cgcctgtata    1140
gtaaggcttg ctcttgttca ggccgccgta tttctcgtgc agacaatcgg cttctccaat    1200
cagaggcagg ctgcccttga tcactttgga tcttccagaa gcgcaccaca ctttctgggg    1260
cagcaggatt cctctctgat atgtgatggt gccggtcttg ccagacttct gcaccatgta    1320
atccaccacg attcttccag actgaggcag tccgccatct tctgtctgat tagggaagcc    1380
gccgatctga gacacatagt gtgtggtcac gccattggca gagctggtaa acttctgagg    1440
cttgctatcg ccgtacagct tggccatctg tgtttcgttg tcgctgtgaa atccccacac    1500
ggtgatctga tcctcgccct ctgtacagat atatggcacc tcgattgtca ggggggttggt    1560 ggcggtcttg ttcttatcgt tcttaggcac ggcccaagcc atggtggcaa agaagccatt    1620
gccatttgta atgttggggc agctgccaga tgtgccgatc ttataagggc gccaggagc     1680 attttcggcg ttgatcacat tgtgggtgct cagtctgatg tgctcgtagc ctctcagcag    1740
attaggcagc tgtctgatct tggtccggtc gtgcataata ggaaaacagc cgctggtcac    1800
aggtcgcact tcatgcagaa tggacactct ggcgctaggg attttgcctg tacacttagg    1860
tctgcccaga gccacatcca gatctgtgca attcaggcac ttgggacaca gcttgcctct    1920
tgtctctgtg cccttcagat tggcgaagtg gctctttgta ggtgttgtgg tcagagggat    1980
cacgccggtc acattcactt cgccctgtgt agctgttttc acgacgtgag ggctattgct    2040
gctggtgatg ccggtacaga ttctatcggc gttgcttgtg accaccatca gcagcacgat    2100
gatggccttc at                                                        2112

<210> SEQ ID NO 70
<211> LENGTH: 837
<212> TYPE: DNA
<213> ORGANISM: Influenza virus

<400> SEQUENCE: 70
atgaaggcca agctgctggt gctgctgtgc acctttaccg ccacctacgc cgacaccatc     60
tgcattggct accgccaa caacagcacc gacaccgtgg ataccgtgct ggaaaagaac     120
gtgaccgtga cccacagcgt gaacctggga tccggactga aatggtcac cggcctgaga    180 aacatcccca gcatccagag cagaggcctg tttggagcca ttgccggctt tattgagggc    240
ggatggaccg gaatggtgga tgggtggtac ggctaccacc accagaatga gcagggctct    300
ggctatgccg ccgatcagaa gtctacccag aacgccatca cggcatcac caacaaagtg    360 aacagcgtga tcgagaagat gggcggcgat cctgaatggg acagagagat caacaactac    420
accagcatca tctacagcct gatcgaggaa agccagaacc agcaggaaaa cggcacaggc    480
ggcggatctg aattgtgca gcagcagaac aacctgctga gagccattga gcccagcag    540 catctgctgc agctgacagt gtgggcatc aagcagctgc agacctacaa tgccgagctg    600
```

```
ctggtcctcc tggaaaacga gagaaccctg gacttccacg acagcaacgt gaagaacctg    660
tacgagaaag tgaagtccca gctgaagaac aacgccaaag atcggcaa cggctgcttc     720 gagttctacc acaagtgcaa caacgagtgc atggaaagcg tgaagaacgg cacctacgac    780 tacccccaagt acagcgagga aagcaagctg aacagagaga gatcgactc cggaggc      837
```

<210> SEQ ID NO 71
<211> LENGTH: 279
<212> TYPE: PRT
<213> ORGANISM: Influenza virus

<400> SEQUENCE: 71

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Gly Asp Pro Glu Trp Asp Arg Glu Ile Asn Asn Tyr Thr Ser Ile Ile
    130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Phe His Asp Ser Asn Val Lys Asn Leu Tyr Glu Lys Val
    210                 215                 220

Lys Ser Gln Leu Lys Asn Asn Ala Lys Glu Ile Gly Asn Gly Cys Phe
225                 230                 235                 240

Glu Phe Tyr His Lys Cys Asn Asn Glu Cys Met Glu Ser Val Lys Asn
                245                 250                 255

Gly Thr Tyr Asp Tyr Pro Lys Tyr Ser Glu Glu Ser Lys Leu Asn Arg
            260                 265                 270

Glu Lys Ile Asp Ser Gly Gly
        275
```

<210> SEQ ID NO 72
<211> LENGTH: 837
<212> TYPE: DNA
<213> ORGANISM: Influenza virus

<400> SEQUENCE: 72

```
gcctccggag tcgatcttct ctctgttcag cttgctttcc tcgctgtact tggggtagtc    60
gtaggtgccg ttcttcacgc tttccatgca ctcgttgttg cacttgtggt agaactcgaa   120
gcagccgttg ccgatctctt tggcgttgtt cttcagctgg acttcacttt tctcgtacag   180
gttcttcacg ttgctgtcgt ggaagtccag ggttctctcg ttttccagga ggaccagcag   240
ctcggcattg taggtctgca gctgcttgat gccccacact gtcagctgca gcagatgctg   300
ctgggcctca atggctctca gcaggttgtt ctgctgctgc acaattccag atccgccgcc   360
tgtgccgttt tcctgctggt tctggctttc ctcgatcagg ctgtagatga tgctggtgta   420
gttgttgatc tctctgtccc attcaggatc gccgcccatc ttctcgatca cgctgttcac   480
tttgttggtg atgccgttga tggcgttctg ggtagacttc tgatcggcgg catagccaga   540
gccctgctca ttctggtggt ggtagccgta ccacccatcc accattccgg tccatccgcc   600
ctcaataaag ccggcaatgg ctccaaacag gcctctgctc tggatgctgg ggatgtttct   660
caggccggtg accattctca gtccggatcc caggttcacg ctgtgggtca cggtcacgtt   720
cttttccagc acggtatcca cggtgtcggt gctgttgttg gcgtggtagc caatgcagat   780
ggtgtcggcg taggtggcgg taaaggtgca cagcagcacc agcagcttgg ccttcat     837

<210> SEQ ID NO 73
<211> LENGTH: 828
<212> TYPE: DNA
<213> ORGANISM: Influenza virus

<400> SEQUENCE: 73
atgaaggcta tcctggtggt gctgctgtac acctttgcca ccgccaatgc cgacaccctg    60
tgtattggct accacgccaa caacagcacc gacaccgtgg ataccgtgct ggaaaagaac   120
gtgaccgtga cccacagcgt gaacctgggc tccggcctga ctggccac cggcctgaga   180 aacatcccca gcattcagag cagaggcctg tttggagcca ttgccggctt tattgagggc   240
ggatggaccg aatggtgga tggtggtac ggctaccacc accagaatga gcagggctct   300
ggctatgccg ccgacctgaa gtctacccag aacgccatcg acgagatcac caacaaagtg   360
aacagcgtga tcgagaagat gggcggctgg gacccatggg acagagagat caacaactac   420
accagcatca tctacagcct gatcgaggaa agccagaacc agcaggaaaa cggcacaggc   480
ggcggatctg gaattgtgca gcagcagaac aacctgctga gagccattga ggcccagcag   540
catctgctgc agctgacagt gtggggcatc aagcagctgc agacctacaa cgccgagctg   600
ctggtgctgc tcgagaatga gagaacccct gactaccacg acagcaacgt gaagaacctg   660
tacgagaaag tgcggagcca gctgaagaac aacgccaaag atcggcaa cggctgcttc   720 gagttctacc acaagtgcga caatacctgc atggaaagcg tgaagaacgg cacctacgac   780 tacccccaagt acagcgagga agccaagctg aaccgggaag agatcgat           828

<210> SEQ ID NO 74
<211> LENGTH: 276
<212> TYPE: PRT
<213> ORGANISM: Influenza virus

<400> SEQUENCE: 74

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
```

|   | 35 |   |   |   | 40 |   |   |   | 45 |   |   |
|---|---|---|---|---|---|---|---|---|---|---|---|

Leu Gly Ser Gly Leu Arg Leu Ala Thr Gly Leu Arg Asn Ile Pro Ser
 50                  55                  60

Ile Gln Ser Arg Gly Leu Phe Gly Ala Ile Ala Gly Phe Ile Glu Gly
 65                  70                  75                  80

Gly Trp Thr Gly Met Val Asp Gly Trp Tyr Gly Tyr His His Gln Asn
                 85                  90                  95

Glu Gln Gly Ser Gly Tyr Ala Ala Asp Leu Lys Ser Thr Gln Asn Ala
                100                 105                 110

Ile Asp Glu Ile Thr Asn Lys Val Asn Ser Val Ile Glu Lys Met Gly
            115                 120                 125

Gly Trp Asp Pro Trp Asp Arg Glu Ile Asn Asn Tyr Thr Ser Ile Ile
130                 135                 140

Tyr Ser Leu Ile Glu Glu Ser Gln Asn Gln Glu Asn Gly Thr Gly Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
                180                 185                 190

Leu Gln Thr Tyr Asn Ala Glu Leu Leu Val Leu Leu Glu Asn Glu Arg
            195                 200                 205

Thr Leu Asp Tyr His Asp Ser Asn Val Lys Asn Leu Tyr Glu Lys Val
210                 215                 220

Arg Ser Gln Leu Lys Asn Asn Ala Lys Glu Ile Gly Asn Gly Cys Phe
225                 230                 235                 240

Glu Phe Tyr His Lys Cys Asp Asn Thr Cys Met Glu Ser Val Lys Asn
                245                 250                 255

Gly Thr Tyr Asp Tyr Pro Lys Tyr Ser Glu Glu Ala Lys Leu Asn Arg
                260                 265                 270

Glu Glu Ile Asp
            275

<210> SEQ ID NO 75
<211> LENGTH: 828
<212> TYPE: DNA
<213> ORGANISM: Influenza virus

<400> SEQUENCE: 75

| atcgatctct | tcccggttca | gcttggcttc | ctcgctgtac | ttggggtagt | cgtaggtgcc | 60 |
| gttcttcacg | ctttccatgc | aggtattgtc | gcacttgtgg | tagaactcga | agcagccgtt | 120 |
| gccgatctct | ttggcgttgt | tcttcagctg | gctccgcact | ttctcgtaca | ggttcttcac | 180 |
| gttgctgtcg | tggtagtcca | gggttctctc | attctcgagc | agcaccagca | gctcggcgtt | 240 |
| gtaggtctgc | agctgcttga | tgccccacac | tgtcagctgc | agcagatgct | gctgggcctc | 300 |
| aatggctctc | agcaggttgt | tctgctgctg | cacaattcca | gatccgccgc | ctgtgccgtt | 360 |
| ttcctgctgg | ttctggcttt | cctcgatcag | gctgtagatg | atgctggtgt | agttgttgat | 420 |
| ctctctgtcc | catgggtccc | agccgcccat | cttctcgatc | acgctgttca | ctttgttggt | 480 |
| gatctcgtcg | atggcgttct | gggtagactt | caggtcggcg | gcatagccag | agccctgctc | 540 |
| attctggtgg | tggtagccgt | accacccatc | caccattccg | gtccatccgc | cctcaataaa | 600 |
| gccggcaatg | ctccaaaaca | ggcctctgct | ctgaatgctg | ggatgtttc | tcaggccggt | 660 |
| ggccagtctc | aggccggagc | ccaggttcac | gctgtgggtc | acggtcacgt | tcttttccag | 720 |

```
cacggtatcc acggtgtcgg tgctgttgtt ggcgtggtag ccaatacaca gggtgtcggc    780
attggcggtg gcaaaggtgt acagcagcac caccaggata gccttcat              828
```

<210> SEQ ID NO 76
<211> LENGTH: 822
<212> TYPE: DNA
<213> ORGANISM: Influenza virus

<400> SEQUENCE: 76

```
atggccatca tctacctgat tctgctgttt acagccgtca gaggcgatca gatctgtatt    60
ggctaccacg ccaacaatag caccgagaaa gtggatacca tcctggaaag aaatgtgaca   120
gtgacacacg ccaaggatat tggatcagga ctggtgctgg ctacaggact gagaaatgtg   180
cctcagattg agagcagagg cctgtttgga gccattgctg gctttattga aggcggatgg   240
cagggaatga ttgatgggtg gtacggctac caccactcta atgatcaggg atctggatat   300
gccgccgaca agaatctac acagaaagcc ttcgacggca tcaccaacaa agtgaatagc   360
gtgatcgaga agatgggcgg agatcccgaa tgggacagag agatcaacaa ctacaccagc   420
atcatctaca gcctgatcga ggaaagccaa atcagcagg aaaatggaac aggcggagga   480
tctggaattg tgcagcagca gaacaatctg ctgagagcta ttgaagctca gcagcatctg   540
ctgaatctga cagtgtgggg aatcaaacag ctgcagacat acaatgctga gctgctggtg   600
ctgatggaaa atgagagaac cctggacttc cacgacagca tgtgaagaa cctgtacgac   660 aaagtgcgga tgcagctgag agacaatgtg aagaactgg gcaatggctg cttcgagttc   720
taccacaagt gcgacgatga gtgtatgaac agcgtgaaga acggcaccta cgactaccct   780
aagtacgagg aagagagcaa gctgaacaga atgagatca ag                      822
```

<210> SEQ ID NO 77
<211> LENGTH: 274
<212> TYPE: PRT
<213> ORGANISM: Influenza virus

<400> SEQUENCE: 77

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Gly
        35                  40                  45

Ser Gly Leu Val Leu Ala Thr Gly Leu Arg Asn Val Pro Gln Ile Glu
    50                  55                  60

Ser Arg Gly Leu Phe Gly Ala Ile Ala Gly Phe Ile Glu Gly Gly Trp
65                  70                  75                  80

Gln Gly Met Ile Asp Gly Trp Tyr Gly Tyr His His Ser Asn Asp Gln
                85                  90                  95

Gly Ser Gly Tyr Ala Ala Asp Lys Glu Ser Thr Gln Lys Ala Phe Asp
            100                 105                 110

Gly Ile Thr Asn Lys Val Asn Ser Val Ile Glu Lys Met Gly Gly Asp
        115                 120                 125

Pro Glu Trp Asp Arg Glu Ile Asn Asn Tyr Thr Ser Ile Ile Tyr Ser
    130                 135                 140

Leu Ile Glu Glu Ser Gln Asn Gln Gln Glu Asn Gly Thr Gly Gly Gly
145                 150                 155                 160

Ser Gly Ile Val Gln Gln Gln Asn Asn Leu Leu Arg Ala Ile Glu Ala
```

```
                    165                 170                 175
Gln Gln His Leu Leu Asn Leu Thr Val Trp Gly Ile Lys Gln Leu Gln
            180                 185                 190

Thr Tyr Asn Ala Glu Leu Leu Val Leu Met Glu Asn Glu Arg Thr Leu
            195                 200                 205

Asp Phe His Asp Ser Asn Val Lys Asn Leu Tyr Asp Lys Val Arg Met
        210                 215                 220

Gln Leu Arg Asp Asn Val Lys Glu Leu Gly Asn Gly Cys Phe Glu Phe
225                 230                 235                 240

Tyr His Lys Cys Asp Asp Glu Cys Met Asn Ser Val Lys Asn Gly Thr
                    245                 250                 255

Tyr Asp Tyr Pro Lys Tyr Glu Glu Glu Ser Lys Leu Asn Arg Asn Glu
            260                 265                 270

Ile Lys

<210> SEQ ID NO 78
<211> LENGTH: 822
<212> TYPE: DNA
<213> ORGANISM: Influenza virus

<400> SEQUENCE: 78
cttgatctca tttctgttca gcttgctctc ttcctcgtac ttagggtagt cgtaggtgcc    60
gttcttcacg ctgttcatac actcatcgtc gcacttgtgg tagaactcga agcagccatt   120
gcccagttct ttcacattgt ctctcagctg catccgcact tgtcgtaca ggttcttcac    180
attgctgtcg tggaagtcca gggttctctc attttccatc agcaccagca gctcagcatt   240
gtatgtctgc agctgtttga ttccccacac tgtcagattc agcagatgct gctgagcttc   300
aatagctctc agcagattgt tctgctgctg cacaattcca gatcctccgc ctgttccatt   360
ttcctgctga ttctggcttt cctcgatcag gctgtagatg atgctggtgt agttgttgat   420
ctctctgtcc cattcgggat ctccgcccat ctttctcgatc acgctattca ctttgttggt   480
gatgccgtcg aaggctttct gtgtagattc tttgtcggcg gcatatccag atccctgatc   540
attagagtgg tggtagccgt accacccatc aatcattccc tgccatccgc cttcaataaa   600
gccagcaatg gctccaaaca ggcctctgct ctcaatctga ggcacatttc tcagtcctgt   660
agccagcacc agtcctgatc caatatcctt ggcgtgtgtc actgtcacat ttctttccag   720
gatggtatcc actttctcgg tgctattgtt ggcgtggtag ccaatacaga tctgatcgcc   780
tctgacggct gtaaacagca gaatcaggta gatgatggcc at                      822

<210> SEQ ID NO 79
<211> LENGTH: 858
<212> TYPE: DNA
<213> ORGANISM: Influenza virus

<400> SEQUENCE: 79
atgaagacca tcatcgccct gagctacatc ttctgcctgg ccctgggcca ggacctgccc    60
ggcaacgaca acagcaccgc caccctgtgc ctgggccacc acgccgtgcc caacggcacc   120
ctggtgaaga ccatcaccga cgaccagatc gaggtgacca acgccaccga gctgggctcc   180
ggcctgaagc tggccaccgg catgcggaac gtgcccgaga gcagacccg ggcctgttc    240
ggcgccatcg ccggcttcat cgagaacggc tgggagggca tgatcgacgg ctggtacggc   300
ttccggcacc agaacagcga gggcaccggc caggccgccg acctgaagag cacccaggcc   360
gccatcgacc agatcaacgg caagctgaac cgggtgatcg agaagaccgg cggcgatccc   420
```

```
gagtgggacc gggagatcaa caactacacc agcatcatct acagcctgat cgaggagagc    480
cagaaccaga aggagaacgg caccggcggc ggcagcggca tcgtgcagca gcagaacaac    540
ctgctgcggg ccatcgaggc ccagcagcac ctgctgcagc tgaccgtgtg gggcatcaag    600
cagctgcaga gctacaacgc cgagctgctg gtggccctgg agaaccagca caccatcgac    660
ctgaccgaca gcgagatgaa caagctgttc gagaagaccc ggcggcagct gcgggagaac    720
gccgaggaca tgggcaacgg ctgcttcaag atctaccaca gtgcgacaa cgcctgcatc    780 gagagcatcc ggaacggcac ctacgaccac gacgtgtacc gggacgaggc cctgaacaac    840
cggttccaga tcaagggc                                                  858
```

<210> SEQ ID NO 80
<211> LENGTH: 286
<212> TYPE: PRT
<213> ORGANISM: Influenza virus

<400> SEQUENCE: 80

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Leu Phe
65                  70                  75                  80

Gly Ala Ile Ala Gly Phe Ile Glu Asn Gly Trp Glu Gly Met Ile Asp
                85                  90                  95

Gly Trp Tyr Gly Phe Arg His Gln Asn Ser Glu Gly Thr Gly Gln Ala
            100                 105                 110

Ala Asp Leu Lys Ser Thr Gln Ala Ala Ile Asp Gln Ile Asn Gly Lys
        115                 120                 125

Leu Asn Arg Val Ile Glu Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
    210                 215                 220

Glu Met Asn Lys Leu Phe Glu Lys Thr Arg Arg Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Glu Ser Ile Arg Asn Gly Thr Tyr Asp His Asp Val
            260                 265                 270

Tyr Arg Asp Glu Ala Leu Asn Asn Arg Phe Gln Ile Lys Gly
        275                 280                 285
```

<210> SEQ ID NO 81
<211> LENGTH: 858
<212> TYPE: DNA
<213> ORGANISM: Influenza virus

<400> SEQUENCE: 81
gcccttgatc tggaaccggt tgttcagggc ctcgtcccgg tacacgtcgt ggtcgtaggt 60
gccgttccgg atgctctcga tgcaggcgtt gtcgcacttg tggtagatct tgaagcagcc 120
gttgcccatg tcctcggcgt tctcccgcag ctgccgccgg gtcttctcga acagcttgtt 180
catctcgctg tcggtcaggt cgatggtgtg ctggttctcc agggccacca gcagctcggc 240
gttgtagctc tgcagctgct tgatgcccca cacggtcagc tgcagcaggt gctgctgggc 300
ctcgatggcc cgcagcaggt tgttctgctg ctgcacgatg ccgctgccgc cgccggtgcc 360
gttctcctgc tggttctggc tctcctcgat caggctgtag atgatgctgg tgtagttgtt 420
gatctcccgg tcccactcgg gatcgccgcc ggtcttctcg atcacccggt tcagcttgcc 480
gttgatctgg tcgatggcgg cctgggtgct cttcaggtcg gcggcctggc cggtgccctc 540
gctgttctgg tgccggaagc cgtaccagcc gtcgatcatg ccctcccagc cgttctcgat 600
gaagccggcg atggcgccga acaggccccg ggtctgcttc tcgggcacgt tccgcatgcc 660
ggtggccagc ttcaggccgg agcccagctc ggtggcgttg gtcacctcga tctggtcgtc 720
ggtgatggtc ttcaccaggg tgccgttggg cacggcgtgg tggcccaggc acagggtggc 780
ggtgctgttg tcgttgccgg gcaggtcctg gcccagggcc aggcagaaga tgtagctcag 840
ggcgatgatg gtcttcat 858

<210> SEQ ID NO 82
<211> LENGTH: 867
<212> TYPE: DNA
<213> ORGANISM: Influenza virus

<400> SEQUENCE: 82
atgaaaacca tcattgccct gagctacatc ctgtgcctgg tgttcacaca gaagctgccc 60
ggcaacgata atagcaccgc cacactgtgt ctgggacacc acgccgtgcc taatggcacc 120
atcgtgaaaa caatcaccaa cgaccagatc gaagtgacca atgccacaga gctgggctcc 180
ggcctgaagc tggccaccgg catgagaaat gtgcccgaga agcagaccag aggcatcttt 240
ggcgccattg ccggctttat cgagaatggc tgggagggaa tggtggatgg gtggtacggc 300
ttcagacacc agaatagcga gggaattgga caggccgccg atctgaaatc tacccaggcc 360
gccatcgacc agatcaacgg caagctgaac aggctgatcg gcaagaccgg cggcgatccc 420
gagtgggacc gggagatcaa caactacacc agcatcatct acagcctgat cgaggagagc 480
cagaaccagc aggagaacgg caccggcggc ggcagcggca tcgtgcagca gcagaacaac 540
ctgctgcggg ccatcgaggc ccagcagcac ctgctgcagc tgaccgtgtg gggcatcaag 600
cagctgcaga gctacaatgc cgaactgctg gtcgccctgg aaaaccagca cacaattgat 660
ctgacagaca gtgagatgaa taagctgttc gagaaaacca agaagcagct gagagaaaac 720
gccgaggaca tgggcaacgg ctgcttcaag atctaccaca agtgcgacaa cgcctgcatc 780
ggcagcatca gaaacggcac ctacgaccac gacgtgtaca gagatgaggc cctgaacaac 840
cggtttcaga tcaagggctc cggaggc 867

<210> SEQ ID NO 83
<211> LENGTH: 289

<212> TYPE: PRT
<213> ORGANISM: Influenza virus

<400> SEQUENCE: 83

```
Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Ile Phe
65                  70                  75                  80

Gly Ala Ile Ala Gly Phe Ile Glu Asn Gly Trp Glu Gly Met Val Asp
                85                  90                  95

Gly Trp Tyr Gly Phe Arg His Gln Asn Ser Glu Gly Ile Gly Gln Ala
            100                 105                 110

Ala Asp Leu Lys Ser Thr Gln Ala Ala Ile Asp Gln Ile Asn Gly Lys
        115                 120                 125

Leu Asn Arg Leu Ile Gly Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
        180                 185                 190

Gln Leu Thr Val Trp Gly Ile Lys Gln Leu Gln Ser Tyr Asn Ala Glu
    195                 200                 205

Leu Leu Val Ala Leu Glu Asn Gln His Thr Ile Asp Leu Thr Asp Ser
210                 215                 220

Glu Met Asn Lys Leu Phe Glu Lys Thr Lys Lys Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Gly Ser Ile Arg Asn Gly Thr Tyr Asp His Asp Val
            260                 265                 270

Tyr Arg Asp Glu Ala Leu Asn Asn Arg Phe Gln Ile Lys Gly Ser Gly
        275                 280                 285

Gly
```

<210> SEQ ID NO 84
<211> LENGTH: 867
<212> TYPE: DNA
<213> ORGANISM: Influenza virus

<400> SEQUENCE: 84

```
gcctccggag cccttgatct gaaaccggtt gttcagggcc tcatctctgt acacgtcgtg     60
gtcgtaggtg ccgtttctga tgctgccgat gcaggcgttg tcgcacttgt ggtagatctt    120
gaagcagccg ttgcccatgt cctcggcgtt ttctctcagc tgcttcttgg ttttctcgaa    180
cagcttattc atctcactgt ctgtcagatc aattgtgtgc tggttttcca gggcgaccag    240
cagttcggca ttgtagctct gcagctgctt gatgccccac acggtcagct gcagcaggtg    300
```

```
ctgctgggcc tcgatggccc gcagcaggtt gttctgctgc tgcacgatgc cgctgccgcc        360
gccggtgccg ttctcctgct ggttctggct ctcctcgatc aggctgtaga tgatgctggt        420
gtagttgttg atctcccggt cccactcggg atcgccgccg tcttgccga tcagcctgtt         480 cagcttgccg ttgatctggt cgatggcggc ctgggtagat ttcagatcgg cggcctgtcc        540
aattccctcg ctattctggt gtctgaagcc gtaccaccca tccaccattc cctcccagcc        600
attctcgata aagccggcaa tggcgccaaa gatgcctctg gtctgcttct cgggcacatt        660
tctcatgccg gtggccagct tcaggccgga gcccagctct gtggcattgg tcacttcgat        720
ctggtcgttg gtgattgttt tcacgatggt gccattaggc acggcgtggt gtcccagaca        780
cagtgtggcg gtgctattat cgttgccggg cagcttctgt gtgaacacca ggcacaggat        840
gtagctcagg gcaatgatgg ttttcat                                            867

<210> SEQ ID NO 85
<211> LENGTH: 837
<212> TYPE: DNA
<213> ORGANISM: Influenza virus

<400> SEQUENCE: 85
atggagaaga tcgtgctgct gctggccatc gtgagcctgg tgaagagcga ccagatctgc         60
atcggctacc acgccaacaa cagcaccgag caggtggaca ccatcatgga gaagaacgtg        120
accgtgaccc acgcccagga catcggctcc ggcctggtgc tggccaccgg cctgcggaac        180
agcccccagc gggagagccg gcggaagaag cggggcctgt tcggcgccat cgccggcttc        240
atcgagggcg gctggcaggg catggtggac ggctggtacg gctaccacca cagcaacgag        300
cagggcagcg gctacgccgc cgacaaggag agcacccaga aggccatcga cggcgtgacc        360
aacaaggtga acagcatcat cgacaagatg ggcggcgatc ccgagtggga ccggagagatc        420 aacaactaca ccagcatcat ctacagcctg atcgaggaga gccagaacca gcaggagaac        480
ggcaccggcg gcggcagcgg catcgtgcag cagcagaaca cctgctgcg ggccatcgag         540 gcccagcagc acctgctgca gctgaccgtg tgggcatca gcagctgca gacctacaac          600 gccgagctgc tggtgctgat ggagaacgag cggacccctgg acttccacga cagcaacgtg       660
aagaacctgt acgacaaggt gcggctgcag ctgcgggaca cgccaagga gctgggcaac         720 ggctgcttcg agttctacca caagtgcgac aacgagtgca tggagagcat ccggaacggc        780
acctacaact accccagta cagcgaggag gcccggctga gcgggagga gatcagc             837

<210> SEQ ID NO 86
<211> LENGTH: 279
<212> TYPE: PRT
<213> ORGANISM: Influenza virus

<400> SEQUENCE: 86

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Gly Ser Gly Leu Val Leu Ala Thr Gly Leu Arg Asn Ser Pro Gln Arg
    50                  55                  60

Glu Ser Arg Arg Lys Lys Arg Gly Leu Phe Gly Ala Ile Ala Gly Phe
65                  70                  75                  80
```

Ile Glu Gly Gly Trp Gln Gly Met Val Asp Gly Trp Tyr Gly Tyr His
            85                  90                  95

His Ser Asn Glu Gln Gly Ser Gly Tyr Ala Ala Asp Lys Glu Ser Thr
        100                 105                 110

Gln Lys Ala Ile Asp Gly Val Thr Asn Lys Val Asn Ser Ile Ile Asp
        115                 120                 125

Lys Met Gly Gly Asp Pro Glu Trp Asp Arg Glu Ile Asn Asn Tyr Thr
130                 135                 140

Ser Ile Ile Tyr Ser Leu Ile Glu Glu Ser Gln Asn Gln Gln Glu Asn
145                 150                 155                 160

Gly Thr Gly Gly Ser Gly Ile Val Gln Gln Gln Asn Asn Leu Leu
            165                 170                 175

Arg Ala Ile Glu Ala Gln Gln His Leu Leu Gln Leu Thr Val Trp Gly
        180                 185                 190

Ile Lys Gln Leu Gln Thr Tyr Asn Ala Glu Leu Leu Val Leu Met Glu
        195                 200                 205

Asn Glu Arg Thr Leu Asp Phe His Asp Ser Asn Val Lys Asn Leu Tyr
    210                 215                 220

Asp Lys Val Arg Leu Gln Leu Arg Asp Asn Ala Lys Glu Leu Gly Asn
225                 230                 235                 240

Gly Cys Phe Glu Phe Tyr His Lys Cys Asp Asn Glu Cys Met Glu Ser
            245                 250                 255

Ile Arg Asn Gly Thr Tyr Asn Tyr Pro Gln Tyr Ser Glu Glu Ala Arg
            260                 265                 270

Leu Lys Arg Glu Glu Ile Ser
        275

<210> SEQ ID NO 87
<211> LENGTH: 837
<212> TYPE: DNA
<213> ORGANISM: Influenza virus

<400> SEQUENCE: 87
gctgatctcc tcccgcttca gccgggcctc ctcgctgtac tgggggtagt tgtaggtgcc     60
gttccggatg ctctccatgc actcgttgtc gcacttgtgg tagaactcga agcagccgtt    120
gcccagctcc ttggcgttgt cccgcagctg cagccgcacc ttgtcgtaca ggttcttcac    180
gttgctgtcg tggaagtcca gggtccgctc gttctccatc agcaccagca gctcggcgtt    240
gtaggtctgc agctgcttga tgccccacac ggtcagctgc agcaggtgct gctgggcctc    300
gatggcccgc agcaggttgt tctgctgctg cacgatgccg ctgccgccgc cggtgccgtt    360
ctcctgctgg ttctggctct cctcgatcag gctgtagatg atgctggtgt agttgttgat    420
ctcccggtcc cactcgggat cgccgcccat cttgtcgatg atgctgttca ccttgttggt    480
cacgccgtcg atggccttct gggtgctctc cttgtcggcg gcgtagccgc tgccctgctc    540
gttgctgtgg tggtagccgt accagccgtc caccatgccc tgccagccgc cctcgatgaa    600
gccggcgatg gcgccgaaca ggccccgctt cttccgccgg ctctcccgct gggggctgtt    660
ccgcaggccg gtggccagca ccaggccgga gccgatgtcc tgggcgtggg tcacggtcac    720
gttcttctcc atgatggtgt ccacctgctc ggtgctgttg ttggcgtggt agccgatgca    780
gatctggtcg ctcttcacca ggctcacgat ggccagcagc agcacgatct ctccat       837

<210> SEQ ID NO 88
<211> LENGTH: 837
<212> TYPE: DNA

<213> ORGANISM: Influenza virus

<400> SEQUENCE: 88

```
atgaaggcca tcatcgtgct gctgatggtg gtgaccagca acgccgatag aatctgcacc    60
ggcatcacca gcagcaatag cccccatgtg gtgaaaacag ccacccaggg cgaagtgaat   120
gtgacaggcg tgatccctct gggatcagga ctgaagctgg ccaatggcac caagtacaga   180
cctcccgcca agctgctgaa agagagaggc ttctttggcg ccattgccgg atttctggaa   240
ggcggctggg agggaatgat tgccggctgg cacggctata catctcatgg ggcccatggc   300
gtggctgtgg ccgccgatct gaagtctacc caggaagcca tcaacaagat caccaagaac   360
ctgaacagcc tgagcgagct ggaaggaggc gaccccgagt gggatcgcga aatcaacaac   420
tacacatcta tcatctacag tctgattgag gaaagccaga accagcagga gaatgggact   480
gggggaggct ccggaatcgt gcagcagcag aacaatctgc tgcgagccat tgaagctcag   540
cagcacctgc tgcagctgac agtgtgggga tcaagcagc tgcaggggtc ccagattgaa   600
ctggccgtgc tgctgtccaa cgagggcatc atcaacagcg aggatgaaca cctgctggcc   660
ctggaacgga agctgaagaa gatgctgggc ccttctgccg tggagatcgg caacggctgc   720
ttcgagacaa agcacaagtg caaccagacc tgcctggata aatcgccgc tggcaccttc   780
aatgccggcg agttcagcct gcctaccttc gacagcctga atatcacctc cggaggc      837
```

<210> SEQ ID NO 89
<211> LENGTH: 279
<212> TYPE: PRT
<213> ORGANISM: Influenza virus

<400> SEQUENCE: 89

```
Met Lys Ala Ile Ile Val Leu Leu Met Val Val Thr Ser Asn Ala Asp
  1               5                  10                  15

Arg Ile Cys Thr Gly Ile Thr Ser Ser Asn Ser Pro His Val Val Lys
             20                  25                  30

Thr Ala Thr Gln Gly Glu Val Asn Val Thr Gly Val Ile Pro Leu Gly
         35                  40                  45

Ser Gly Leu Lys Leu Ala Asn Gly Thr Lys Tyr Arg Pro Pro Ala Lys
     50                  55                  60

Leu Leu Lys Glu Arg Gly Phe Phe Gly Ala Ile Ala Gly Phe Leu Glu
 65                  70                  75                  80

Gly Gly Trp Glu Gly Met Ile Ala Gly Trp His Gly Tyr Thr Ser His
                 85                  90                  95

Gly Ala His Gly Val Ala Val Ala Ala Asp Leu Lys Ser Thr Gln Glu
            100                 105                 110

Ala Ile Asn Lys Ile Thr Lys Asn Leu Asn Ser Leu Ser Glu Leu Glu
        115                 120                 125

Gly Gly Asp Pro Glu Trp Asp Arg Glu Ile Asn Asn Tyr Thr Ser Ile
    130                 135                 140

Ile Tyr Ser Leu Ile Glu Glu Ser Gln Asn Gln Gln Glu Asn Gly Thr
145                 150                 155                 160

Gly Gly Gly Ser Gly Ile Val Gln Gln Gln Asn Asn Leu Leu Arg Ala
                165                 170                 175

Ile Glu Ala Gln Gln His Leu Leu Gln Leu Thr Val Trp Gly Ile Lys
            180                 185                 190

Gln Leu Gln Gly Ser Gln Ile Glu Leu Ala Val Leu Leu Ser Asn Glu
        195                 200                 205
```

```
Gly Ile Ile Asn Ser Glu Asp Glu His Leu Leu Ala Leu Glu Arg Lys
            210                 215                 220

Leu Lys Lys Met Leu Gly Pro Ser Ala Val Glu Ile Gly Asn Gly Cys
225                 230                 235                 240

Phe Glu Thr Lys His Lys Cys Asn Gln Thr Cys Leu Asp Arg Ile Ala
                245                 250                 255

Ala Gly Thr Phe Asn Ala Gly Glu Phe Ser Leu Pro Thr Phe Asp Ser
            260                 265                 270

Leu Asn Ile Thr Ser Gly Gly
            275

<210> SEQ ID NO 90
<211> LENGTH: 837
<212> TYPE: DNA
<213> ORGANISM: Influenza virus

<400> SEQUENCE: 90
gcctccggag gtgatattca ggctgtcgaa ggtaggcagg ctgaactcgc cggcattgaa      60
ggtgccagcg gcgattctat ccaggcaggt ctggttgcac ttgtgctttg tctcgaagca     120
gccgttgccg atctccacgg cagaagggcc cagcatcttc ttcagcttcc gttccagggc     180
cagcaggtgt tcatcctcgc tgttgatgat gccctcgttg acagcagca cggccagttc      240 aatctgggac ccctgcagct gcttgatgcc ccacactgtc agctgcagca ggtgctgctg     300
agcttcaatg gctcgcagca gattgttctg ctgctgcacg attccggagc tccccccagt     360
cccattctcc tgctggttct ggctttcctc aatcagactg tagatgatag atgtgtagtt     420
gttgatttcg cgatcccact cggggtcgcc tccttccagc tcgctcaggc tgttcaggtt     480
cttggtgatc ttgttgatgg cttcctgggt agacttcaga tcggcggcca cagccacgcc     540
atgggcccca tgagatgtat agccgtgcca gccggcaatc attccctccc agccgccttc     600
cagaaatccg gcaatggcgc caaagaagcc tctctctttc agcagcttgg cgggaggtct     660
gtacttggtg ccattggcca gcttcagtcc tgatcccaga gggatcacgc tgtcacatt     720 cacttcgccc tgggtggctg ttttcaccac atgggggcta ttgctgctgg tgatgccggt     780
gcagattcta tcggcgttgc tggtcaccac catcagcagc acgatgatgg ccttcat       837

<210> SEQ ID NO 91
<211> LENGTH: 867
<212> TYPE: DNA
<213> ORGANISM: Influenza virus

<400> SEQUENCE: 91
atgaaaacca taattgcgct gtcctacata ctgtgtctgg tgtttgccca gaaactgccg      60
ggcaatgaca actcaacagc cacgctctgc ttggggcacc atgccgtccc taacgggacc     120
attgtgaaaa ccattactaa cgatcagata gaggtgacta atgccaccga gctgggctcc     180
ggcttgaaac tggcgaccgg tatgcgcaat gtccccgaaa acagacccgc gggatatttt     240
ggggctatcg caggctttat cgagaatggc tgggaaggga tggtggatgg ttggtatggt     300
tttagacatc aaaactccga aggcagaggc caggctgccg atctcaagag cacgcaggcc     360
gctatagatc agatcaatgg aaagctcaac agactgatcg gaaaaccgg cggcgatccc     420 gagtgggacc gggagatcaa caactacacc agcatcatct acagcctgat cgaggagagc     480
cagaaccagc aggagaacgg caccggcgg ggcagcggca tcgtgcagca gcagaacaac     540
ctgctgcggg ccatcgaggc ccagcagcac ctgctgcagc tgaccgtgtg gggcatcaag     600
```

```
cagctgcagt cctacaatgc cgagctgctg gtggctctgg agaatcagca cactattgac      660
ctgaccgatt cagagatgaa caaactttt gagaagacga agaagcagct tagagaaaat      720
gcagaggaca tggggaacgg atgctttaaa atatatcata agtgtgataa tgcctgcatc      780
ggatcaatta gaaatggtac ctatgatcac gatgtttaca gggacgaagc gctgaataac      840
aggttccaga taaaaggctc cggaggc                                          867
```

<210> SEQ ID NO 92
<211> LENGTH: 289
<212> TYPE: PRT
<213> ORGANISM: Influenza virus

<400> SEQUENCE: 92

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Ile Phe
65                  70                  75                  80

Gly Ala Ile Ala Gly Phe Ile Glu Asn Gly Trp Glu Gly Met Val Asp
                85                  90                  95

Gly Trp Tyr Gly Phe Arg His Gln Asn Ser Glu Gly Arg Gly Gln Ala
            100                 105                 110

Ala Asp Leu Lys Ser Thr Gln Ala Ala Ile Asp Gln Ile Asn Gly Lys
        115                 120                 125

Leu Asn Arg Leu Ile Gly Lys Thr Gly Gly Asp Pro Glu Trp Asp Arg
130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
    210                 215                 220

Glu Met Asn Lys Leu Phe Glu Lys Thr Lys Lys Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Gly Ser Ile Arg Asn Gly Thr Tyr Asp His Asp Val
            260                 265                 270

Tyr Arg Asp Glu Ala Leu Asn Asn Arg Phe Gln Ile Lys Gly Ser Gly
        275                 280                 285

Gly

<210> SEQ ID NO 93
<211> LENGTH: 867
<212> TYPE: DNA
<213> ORGANISM: Influenza virus

<400> SEQUENCE: 93

```
gcctccggag ccttttatct ggaacctgtt attcagcgct tcgtccctgt aaacatcgtg      60
atcataggta ccatttctaa ttgatccgat gcaggcatta tcacacttat gatatatttt     120
aaagcatccg ttccccatgt cctctgcatt ttctctaagc tgcttcttcg tcttctcaaa     180
aagtttgttc atctctgaat cggtcaggtc aatagtgtgc tgattctcca gagccaccag     240
cagctcggca ttgtaggact gcagctgctt gatgccccac acggtcagct gcagcaggtg     300
ctgctgggcc tcgatggccc gcagcaggtt gttctgctgc tgcacgatgc cgctgccgcc     360
gccggtgccg ttctcctgct ggttctggct ctcctcgatc aggctgtaga tgatgctggt     420
gtagttgttg atctcccggt cccactcggg atcgccgccg ttttcccga tcagtctgtt      480
gagctttcca ttgatctgat ctatagcggc ctgcgtgctc ttgagatcgg cagcctggcc     540
tctgccttcg gagttttgat gtctaaaacc ataccaacca tccaccatcc cttcccagcc     600
attctcgata aagcctgcga tagccccaaa tatcccgcgg gtctgttttt cggggacatt     660
gcgcataccg gtcgccagtt tcaagccgga gcccagctcg gtggcattag tcacctctat     720
ctgatcgtta gtaatggttt tcacaatggt cccgttaggg acggcatggt gccccaagca     780
gagcgtggct gttgagttgt cattgcccgg cagtttctgg gcaaacacca gacacagtat     840
gtaggacagc gcaattatgg ttttcat                                         867
```

<210> SEQ ID NO 94
<211> LENGTH: 837
<212> TYPE: DNA
<213> ORGANISM: Influenza virus

<400> SEQUENCE: 94

```
atgaaagtga agctgctggt gctgctgtgt acctttaccg ccacctacgc cgataccatc      60
tgtatcggct accacgccaa caatagcacc gacaccgtgg ataccgtgct ggaaaagaac     120
gtgaccgtga cccacagcgt gaacctggga tcaggactga gatggtgac cggcctgagg      180
aatatcccca gcatccagag cagaggcctg tttggcgcca ttgccggctt tatcgagggc     240
ggatggacag gcatggtgga tgggtggtac ggctaccacc accagaatga gcagggatct     300
ggctatgccg ccgatcagaa gagcacccag aacgccatca acggcatcac caacaaagtg     360
aacagcgtga tcgagaagat gggcggcgat cctgaatggg acagagagat caacaactac     420
accagcatca tctacagcct gatcgaggaa agccagaacc agcaggaaaa cggcacaggc     480
ggcggatctg gaattgtgca gcagcagaac aacctgctga gagccattga ggcccagcag     540
catctgctgc agctgacagt gtgggggcatc aagcagctgc agacctacaa cgccgaactc     600
ctggtcctcc tggaaaatga gaggaccctg gacttccacg acagcaacgt gaagaacctg     660
tacgagaaag tgaagagcca gctgaagaac aacgccaaag atcggcaa cggctgcttc      720
gagttctacc acaagtgcaa cgacgagtgc atggaaagcg tgaagaacgg cacctacgac     780
tacccccaagt acagcgagga aagcaagctg aaccgggaga gatcgattc cggaggc        837
```

<210> SEQ ID NO 95
<211> LENGTH: 276
<212> TYPE: PRT
<213> ORGANISM: Influenza virus

<400> SEQUENCE: 95

```
Met Lys Val Lys Leu Leu Val Leu Leu Cys Thr Phe Thr Ala Thr Tyr
1               5                   10                  15
```

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Gly Asp Pro Glu Trp Asp Arg Glu Ile Asn Asn Tyr Thr Ser Ile Ile
    130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Phe His Asp Ser Asn Val Lys Asn Leu Tyr Glu Lys Val
    210                 215                 220

Lys Ser Gln Leu Lys Asn Asn Ala Lys Glu Ile Gly Asn Gly Cys Phe
225                 230                 235                 240

Glu Phe Tyr His Lys Cys Asn Asp Glu Cys Met Glu Ser Val Lys Asn
                245                 250                 255

Gly Thr Tyr Asp Tyr Pro Lys Tyr Ser Glu Glu Ser Lys Leu Asn Arg
            260                 265                 270

Glu Lys Ile Asp
        275

<210> SEQ ID NO 96
<211> LENGTH: 837
<212> TYPE: DNA
<213> ORGANISM: Influenza virus

<400> SEQUENCE: 96
gcctccggaa tcgatcttct cccggttcag cttgctttcc tcgctgtact tggggtagtc    60
gtaggtgccg ttcttcacgc tttccatgca ctcgtcgttg cacttgtggt agaactcgaa   120
gcagccgttg ccgatctctt tggcgttgtt cttcagctgg ctcttcactt tctcgtacag   180
gttcttcacg ttgctgtcgt ggaagtccag ggtcctctca ttttccagga ggaccaggag   240
ttcggcgttg taggtctgca gctgcttgat gccccacact gtcagctgca gagatgctg    300 ctgggcctca atggctctca gcaggttgtt ctgctgctgc acaattccag atccgccgcc   360
tgtgccgttt tcctgctggt tctggctttc ctcgatcagg ctgtagatga tgctggtgta   420
gttgttgatc tctctgtccc attcaggatc gccgcccatc ttctcgatca cgctgttcac   480
tttgttggtg atgccgttga tggcgttctg ggtgctcttc tgatcggcgg catagccaga   540
tccctgctca ttctggtggt ggtagccgta ccacccatcc accatgcctg tccatccgcc   600
```

```
ctcgataaag ccggcaatgg cgccaaacag gcctctgctc tggatgctgg ggatattcct    660
caggccggtc accattctca gtcctgatcc caggttcacg ctgtgggtca cggtcacgtt    720
cttttccagc acggtatcca cggtgtcggt gctattgttg gcgtggtagc cgatacagat    780
ggtatcggcg taggtggcgg taaaggtaca cagcagcacc agcagcttca ctttcat      837

<210> SEQ ID NO 97
<211> LENGTH: 837
<212> TYPE: DNA
<213> ORGANISM: Influenza virus

<400> SEQUENCE: 97
atgaaggcca tcatcgtgct gctgatggtg gtcacaagca acgccgatag aatctgtacc     60
ggcatcacca gcagcaatag ccctcacgtc gtgaaaacag ctacacaggg cgaagtgaat    120
gtgaccggcg tgatccctct gggatcagga ctgaagctgg ccaatggcac aaagtataga    180
cctccagcca agctgctgaa agagagaggc ttttttggag ctatcgccgg ctttctggaa    240
ggcggatggg agggaatgat tgctggatgg catggctaca catctcatgg cgcacatggc    300
gtggcagtgg ctgctgatct gaaatctaca caggaagcca tcaacaagat caccaagaac    360
ctgaacagcc tgagcgagct ggaaggaggc gaccccgagt gggatcgcga aatcaacaac    420
tacacatcta tcatctacag tctgattgag aaagccaga accagcagga gaatgggact    480
gggggaggct ccggaatcgt gcagcagcag aacaatctgc tgcgagccat tgaagctcag    540
cagcacctgc tgcagctgac agtgtggggc atcaagcagc tgcaggggag ccagattgaa    600
ctggctgtgc tgctgtctaa cgagggcatc atcaatagcg aggacgaaca tctgctggcc    660
ctggaaagaa agctgaagaa gatgctggga cctagcgccg tggaaatcgg caatggatgc    720
tttgagacaa agcacaagtg caaccagacc tgcctggata gaattgccgc cggaacattt    780
gatgccggcg agttttctct gcccaccttc gatagcctga atatcacatc cggaggc     837

<210> SEQ ID NO 98
<211> LENGTH: 279
<212> TYPE: PRT
<213> ORGANISM: Influenza virus

<400> SEQUENCE: 98

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Gly
        35                  40                  45

Ser Gly Leu Lys Leu Ala Asn Gly Thr Lys Tyr Arg Pro Pro Ala Lys
    50                  55                  60

Leu Leu Lys Glu Arg Gly Phe Phe Gly Ala Ile Ala Gly Phe Leu Glu
65                  70                  75                  80

Gly Gly Trp Glu Gly Met Ile Ala Gly Trp His Gly Tyr Thr Ser His
                85                  90                  95

Gly Ala His Gly Val Ala Val Ala Ala Asp Leu Lys Ser Thr Gln Glu
            100                 105                 110

Ala Ile Asn Lys Ile Thr Lys Asn Leu Asn Ser Leu Ser Glu Leu Glu
        115                 120                 125

Gly Gly Asp Pro Glu Trp Asp Arg Glu Ile Asn Asn Tyr Thr Ser Ile
    130                 135                 140
```

```
Ile Tyr Ser Leu Ile Glu Glu Ser Gln Asn Gln Glu Asn Gly Thr
145                 150                 155                 160

Gly Gly Gly Ser Gly Ile Val Gln Gln Gln Asn Asn Leu Leu Arg Ala
            165                 170                 175

Ile Glu Ala Gln Gln His Leu Leu Gln Leu Thr Val Trp Gly Ile Lys
        180                 185                 190

Gln Leu Gln Gly Ser Gln Ile Glu Leu Ala Val Leu Leu Ser Asn Glu
    195                 200                 205

Gly Ile Ile Asn Ser Glu Asp Glu His Leu Leu Ala Leu Glu Arg Lys
210                 215                 220

Leu Lys Lys Met Leu Gly Pro Ser Ala Val Glu Ile Gly Asn Gly Cys
225                 230                 235                 240

Phe Glu Thr Lys His Lys Cys Asn Gln Thr Cys Leu Asp Arg Ile Ala
                245                 250                 255

Ala Gly Thr Phe Asp Ala Gly Glu Phe Ser Leu Pro Thr Phe Asp Ser
            260                 265                 270

Leu Asn Ile Thr Ser Gly Gly
        275

<210> SEQ ID NO 99
<211> LENGTH: 837
<212> TYPE: DNA
<213> ORGANISM: Influenza virus

<400> SEQUENCE: 99
gcctccggat gtgatattca ggctatcgaa ggtgggcaga gaaaactcgc cggcatcaaa      60
tgttccggcg gcaattctat ccaggcaggt ctggttgcac ttgtgctttg tctcaaagca     120
tccattgccg atttccacgg cgctaggtcc cagcatcttc ttcagctttc tttccagggc     180
cagcagatgt tcgtcctcgc tattgatgat gccctcgtta gacagcagca gccagttc       240
aatctggctc ccctgcagct gcttgatgcc ccacactgtc agctgcagca ggtgctgctg     300
agcttcaatg gctcgcagca gattgttctg ctgctgcacg attccggagc tccccccagt     360
cccattctcc tgctggttct ggcttttcctc aatcagactg tagatgatag atgtgtagtt    420
gttgatttcg cgatcccact cggggtcgcc tccttccagc tcgctcaggc tgttcaggtt     480
cttggtgatc ttgttgatgg cttcctgtgt agatttcaga tcagcagcca ctgccacgcc     540
atgtgcgcca tgagatgtgt agccatgcca tccagcaatc attccctccc atccgccttc    600
cagaaagccg gcgatagctc caaaaaagcc tctctctttc agcagcttgg ctggaggtct    660
atactttgtg ccattggcca gcttcagtcc tgatcccaga gggatcacgc cggtcacatt    720
cacttcgccc tgtgtagctg ttttcacgac gtgagggcta ttgctgctgg tgatgccggt    780
acagattcta tcggcgttgc ttgtgaccac catcagcagc acgatgatgg ccttcat       837

<210> SEQ ID NO 100
<211> LENGTH: 1332
<212> TYPE: DNA
<213> ORGANISM: Artificial Sequence
<220> FEATURE:
<223> OTHER INFORMATION: Synthetic

<400> SEQUENCE: 100
atgaaggcca agctgctggt gctgctgtgc acctttaccg ccacctacgc cgacaccatc      60
tgcattggct accgccaaca acagcaccc gacaccgtgg ataccgtgct ggaaaagaac     120
gtgaccgtga cccacagcgt gaacctggga tccggactga atggtcac cggcctgaga      180
```

-continued

```
aacatcccca gcatccagag cagaggcctg tttggagcca ttgccggctt tattgagggc    240
ggatggaccg gaatggtgga tgggtggtac ggctaccacc accagaatga gcagggctct    300
ggctatgccg ccgatcagaa gtctacccag aacgccatca acggcatcac caacaaagtg    360
aacagcgtga tcgagaagat gggcggcgat cctgaatggg acagagagat caacaactac    420
accagcatca tctacagcct gatcgaggaa agccagaacc agcaggaaaa cggcacaggc    480
ggcggatctg gaattgtgca gcagcagaac aacctgctga gagccattga ggcccagcag    540
catctgctgc agctgacagt gtggggcatc aagcagctgc agacctacaa tgccgagctg    600
ctggtcctcc tggaaaacga gagaaccctg gacttccacg cagcaacgt gaagaacctg    660 tacgagaaag tgaagtccca gctgaagaac aacgccaaag atcggcaa cggctgcttc    720 gagttctacc acaagtgcaa caacgagtgc atggaaagcg tgaagaacgg cacctacgac    780
taccccaagt acagcgagga agcaagctg aacagagaga gatcgactc cggaggcgac    840 atcatcaagc tgctgaacga gcaggtgaac aaggagatgc agagcagcaa cctgtacatg    900
agcatgagca gctggtgcta cacccacagc ctggacggcg ccggcctgtt cctgttcgac    960
cacgccgccg aggagtacga gcacgccaag aagctgatca tcttcctgaa cgagaacaac   1020
gtgcccgtgc agctgaccag catcagcgcc cccgagcaca gttcgaggg cctgacccag   1080 atcttccaga aggcctacga gcacgagcag cacatcagcg agagcatcaa caacatcgtg   1140
gaccacgcca tcaagagcaa ggaccacgcc accttcaact tcctgcagtg gtacgtggcc   1200
gagcagcacg aggaggaggt gctgttcaag gacatcctgg acaagatcga gctgatcggc   1260
aacgagaacc acggcctgta cctggccgac cagtacgtga agggcatcgc caagagcagg   1320
aagagcggat cc                                                        1332
```

<210> SEQ ID NO 101
<211> LENGTH: 444
<212> TYPE: PRT
<213> ORGANISM: Artificial Sequence
<220> FEATURE:
<223> OTHER INFORMATION: Synthetic

<400> SEQUENCE: 101

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Gly Asp Pro Glu Trp Asp Arg Glu Ile Asn Asn Tyr Thr Ser Ile Ile
    130                 135                 140

Tyr Ser Leu Ile Glu Glu Ser Gln Asn Gln Gln Glu Asn Gly Thr Gly
```

```
                145                 150                 155                 160
Gly Gly Ser Gly Ile Val Gln Gln Asn Asn Leu Leu Arg Ala Ile
                165                 170                 175
Glu Ala Gln Gln His Leu Leu Gln Leu Thr Val Trp Gly Ile Lys Gln
                180                 185                 190
Leu Gln Thr Tyr Asn Ala Glu Leu Leu Val Leu Glu Asn Glu Arg
                195                 200                 205
Thr Leu Asp Phe His Asp Ser Asn Val Lys Asn Leu Tyr Glu Lys Val
210                 215                 220
Lys Ser Gln Leu Lys Asn Asn Ala Lys Glu Ile Gly Asn Gly Cys Phe
225                 230                 235                 240
Glu Phe Tyr His Lys Cys Asn Asn Glu Cys Met Glu Ser Val Lys Asn
                245                 250                 255
Gly Thr Tyr Asp Tyr Pro Lys Tyr Ser Glu Glu Ser Lys Leu Asn Arg
                260                 265                 270
Glu Lys Ile Asp Ser Gly Gly Asp Ile Ile Lys Leu Leu Asn Glu Gln
                275                 280                 285
Val Asn Lys Glu Met Gln Ser Ser Asn Leu Tyr Met Ser Met Ser Ser
                290                 295                 300
Trp Cys Tyr Thr His Ser Leu Asp Gly Ala Gly Leu Phe Leu Phe Asp
305                 310                 315                 320
His Ala Glu Glu Tyr Glu His Ala Lys Lys Leu Ile Ile Phe Leu
                325                 330                 335
Asn Glu Asn Asn Val Pro Val Gln Leu Thr Ser Ile Ser Ala Pro Glu
                340                 345                 350
His Lys Phe Glu Gly Leu Thr Gln Ile Phe Gln Lys Ala Tyr Glu His
                355                 360                 365
Glu Gln His Ile Ser Glu Ser Ile Asn Asn Ile Val Asp His Ala Ile
                370                 375                 380
Lys Ser Lys Asp His Ala Thr Phe Asn Phe Leu Gln Trp Tyr Val Ala
385                 390                 395                 400
Glu Gln His Glu Glu Val Leu Phe Lys Asp Ile Leu Asp Lys Ile
                405                 410                 415
Glu Leu Ile Gly Asn Glu Asn His Gly Leu Tyr Leu Ala Asp Gln Tyr
                420                 425                 430
Val Lys Gly Ile Ala Lys Ser Arg Lys Ser Gly Ser
                435                 440

<210> SEQ ID NO 102
<211> LENGTH: 1332
<212> TYPE: DNA
<213> ORGANISM: Artificial Sequence
<220> FEATURE:
<223> OTHER INFORMATION: Synthetic

<400> SEQUENCE: 102
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg gggcgctga tgctggtcag     300 ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
```

```
gctgctcatg ctcatgtaca ggttgctgct ctgcatctcc ttgttcacct gctcgttcag    480
cagcttgatg atgtcgcctc cggagtcgat cttctctctg ttcagcttgc tttcctcgct    540
gtacttgggg tagtcgtagg tgccgttctt cacgctttcc atgcactcgt tgttgcactt    600
gtggtagaac tcgaagcagc cgttgccgat ctctttggcg ttgttcttca gctgggactt    660
cactttctcg tacaggttct tcacgttgct gtcgtggaag tccagggttc tctcgttttc    720
caggaggacc agcagctcgg cattgtaggt ctgcagctgc ttgatgcccc acactgtcag    780
ctgcagcaga tgctgctggg cctcaatggc tctcagcagg ttgttctgct gctgcacaat    840
tccagatccg ccgcctgtgc cgttttcctg ctggttctgg ctttcctcga tcaggctgta    900
gatgatgctg gtgtagttgt tgatctctct gtcccattca ggatcgccgc ccatcttctc    960
gatcacgctg ttcactttgt tggtgatgcc gttgatggcg ttctgggtag acttctgatc   1020
ggcggcatag ccagagccct gctcattctg gtggtggtag ccgtaccacc catccaccat   1080
tccggtccat ccgccctcaa taagccggca aatggctcca aacaggcctc tgctctggat   1140
gctggggatg tttctcaggc cggtgaccat tctcagtccg gatcccaggt tcacgctgtg   1200
ggtcacggtc acgttctttt ccagcacggt atccacggtg tcggtgctgt tgttggcgtg   1260
gtagccaatg cagatggtgt cggcgtaggt ggcggtaaag gtgcacagca gcaccagcag   1320
cttggccttc at                                                       1332

<210> SEQ ID NO 103
<211> LENGTH: 1332
<212> TYPE: DNA
<213> ORGANISM: Artificial Sequence
<220> FEATURE:
<223> OTHER INFORMATION: Synthetic

<400> SEQUENCE: 103
atgaaggcta tcctggtggt gctgctgtac acctttgcca ccgccaatgc cgacaccctg     60
tgtattggct accacgccaa caacagcacc gacaccgtgg ataccgtgct ggaaaagaac    120
gtgaccgtga cccacagcgt gaacctgggc tccggcctga actggccac cggcctgaga    180 aacatcccca gcattcagag cagaggcctg tttggagcca ttgccggctt tattgagggc    240
ggatggaccg gaatggtgga tgggtggtac ggctaccacc accagaatga gcagggctct    300
ggctatgccc ccgacctgaa gtctacccag aacgccatcg acgagatcac caacaaagtg    360
aacagcgtga tcgagaagat gggcggctgg gacccatggg acagagagat caacaactac    420
accagcatca tctacagcct gatcgaggaa agccagaacc agcaggaaaa cggcacaggc    480
ggcggatctg aattgtgca gcagcagaac aacctgctga gagccattga ggcccagcag    540
catctgctgc agctgacagt gtggggcatc aagcagctgc agacctacaa cgccgagctg    600
ctggtgctgc tcgagaatga gaaccctg gactaccacg acagcaacgt gaagaacctg    660
tacgagaaag tgcggagcca gctgaagaac aacgccaaag atcggcaa cggctgcttc    720 gagttctacc acaagtgcga caatacctgc atggaaagcg tgaagaacgg cacctacgac    780 tacccccaagt acagcgagga agccaagctg aaccgggaag atcgattc cggaggcgac    840 atcatcaagc tgctgaacga gcaggtgaac aaggagatgc agagcagcaa cctgtacatg    900
agcatgagca gctggtgcta cacccacagc ctggacggcg ccggcctgtt cctgttcgac    960
cacgccgccg aggagtacga gcacgccaag aagctgatca tcttcctgaa cgagaacaac   1020
gtgcccgtgc agctgaccag catcagcgcc ccgagcaca agttcgaggg cctgacccag   1080
```

-continued

```
atcttccaga aggcctacga gcacgagcag cacatcagcg agagcatcaa caacatcgtg    1140
gaccacgcca tcaagagcaa ggaccacgcc accttcaact tcctgcagtg gtacgtggcc    1200
gagcagcacg aggaggaggt gctgttcaag gacatcctgg acaagatcga gctgatcggc    1260
aacgagaacc acggcctgta cctggccgac cagtacgtga agggcatcgc caagagcagg    1320
aagagcggat cc                                                        1332
```

<210> SEQ ID NO 104
<211> LENGTH: 444
<212> TYPE: PRT
<213> ORGANISM: Artificial Sequence
<220> FEATURE:
<223> OTHER INFORMATION: Synthetic

<400> SEQUENCE: 104

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Leu Ala Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Leu Lys Ser Thr Gln Asn Ala
            100                 105                 110

Ile Asp Glu Ile Thr Asn Lys Val Asn Ser Val Ile Glu Lys Met Gly
        115                 120                 125

Trp Asp Pro Trp Asp Arg Glu Ile Asn Asn Tyr Thr Ser Ile Ile
    130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Tyr His Asp Ser Asn Val Lys Asn Leu Tyr Glu Lys Val
    210                 215                 220

Arg Ser Gln Leu Lys Asn Asn Ala Lys Glu Ile Gly Asn Gly Cys Phe
225                 230                 235                 240

Glu Phe Tyr His Lys Cys Asp Asn Thr Cys Met Glu Ser Val Lys Asn
                245                 250                 255

Gly Thr Tyr Asp Tyr Pro Lys Tyr Ser Glu Glu Ala Lys Leu Asn Arg
            260                 265                 270

Glu Glu Ile Asp Ser Gly Gly Asp Ile Ile Lys Leu Leu Asn Glu Gln
        275                 280                 285

Val Asn Lys Glu Met Gln Ser Ser Asn Leu Tyr Met Ser Met Ser Ser
    290                 295                 300

Trp Cys Tyr Thr His Ser Leu Asp Gly Ala Gly Leu Phe Leu Phe Asp
305                 310                 315                 320
```

```
His Ala Ala Glu Glu Tyr Glu His Ala Lys Lys Leu Ile Ile Phe Leu
                325                 330                 335
Asn Glu Asn Asn Val Pro Val Gln Leu Thr Ser Ile Ser Ala Pro Glu
            340                 345                 350
His Lys Phe Glu Gly Leu Thr Gln Ile Phe Gln Lys Ala Tyr Glu His
        355                 360                 365
Glu Gln His Ile Ser Glu Ser Ile Asn Asn Ile Val Asp His Ala Ile
    370                 375                 380
Lys Ser Lys Asp His Ala Thr Phe Asn Phe Leu Gln Trp Tyr Val Ala
385                 390                 395                 400
Glu Gln His Glu Glu Val Leu Phe Lys Asp Ile Leu Asp Lys Ile
                405                 410                 415
Glu Leu Ile Gly Asn Glu Asn His Gly Leu Tyr Leu Ala Asp Gln Tyr
            420                 425                 430
Val Lys Gly Ile Ala Lys Ser Arg Lys Ser Gly Ser
        435                 440

<210> SEQ ID NO 105
<211> LENGTH: 1332
<212> TYPE: DNA
<213> ORGANISM: Artificial Sequence
<220> FEATURE:
<223> OTHER INFORMATION: Synthetic

<400> SEQUENCE: 105
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg ggggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggaatcgat ctcttcccgg ttcagcttgg cttcctcgct     540
gtacttgggg tagtcgtagg tgccgttctt cacgctttcc atgcaggtat tgtcgcactt     600
gtggtagaac tcgaagcagc cgttgccgat ctctttggcg ttgttcttca gctggctccg     660
cactttctcg tacaggttct tcacgttgct gtcgtggtag tccagggttc tctcattctc     720
gagcagcacc agcagctcgg cgttgtaggt ctgcagctgc ttgatgcccc acactgtcag     780
ctgcagcaga tgctgctggg cctcaatggc tctcagcagg ttgttctgct gctgcacaat     840
tccagatccg ccgcctgtgc cgttttcctg ctggttctgg ctttcctcga tcaggctgta     900
gatgatgctg gtgtagttgt tgatctctct gtcccatggg tcccagccgc ccatcttctc     960
gatcacgctg ttcactttgt tggtgatctc gtcgatggcg ttctgggtag acttcaggtc    1020
ggcggcatag ccagagccct gctcattctg tggtggtag ccgtaccacc catccaccat    1080
tccggtccat ccgccctcaa taaagccggc aatggctcca acaggcctc tgctctgaat     1140
gctggggatg tttctcaggc cggtggccag tctcaggccg agcccaggt tcacgctgtg      1200
ggtcacggtc acgttctttt ccagcacggt atccacggtg tcggtgctgt tgttggcgtg    1260
gtagccaata cacagggtgt cggcattggc ggtggcaaag gtgtacagca gcaccaccag    1320
```

<210> SEQ ID NO 106
<211> LENGTH: 1326
<212> TYPE: DNA
<213> ORGANISM: Artificial Sequence
<220> FEATURE:
<223> OTHER INFORMATION: Synthetic

<400> SEQUENCE: 106

```
atggccatca tctacctgat tctgctgttt acagccgtca gaggcgatca gatctgtatt      60
ggctaccacg ccaacaatag caccgagaaa gtggatacca tcctggaaag aaatgtgaca     120
gtgacacacg ccaaggatat tggatcagga ctggtgctgg ctacaggact gagaaatgtg     180
cctcagattg agagcagagg cctgtttgga gccattgctg gctttattga aggcggatgg     240
cagggaatga ttgatgggtg gtacggctac caccactcta atgatcaggg atctggatat     300
gccgccgaca agaatctac acagaaagcc ttcgacggca tcaccaacaa agtgaatagc     360
gtgatcgaga gatgggcgg agatcccgaa tgggacagag atcaacaa ctacaccagc       420
atcatctaca gcctgatcga ggaaagccaa atcagcagg aaaatggaac aggcggagga     480
tctggaattg tgcagcagca gaacaatctg ctgagagcta ttgaagctca gcagcatctg     540
ctgaatctga cagtgtgggg aatcaaacag ctgcagacat acaatgctga gctgctggtg     600
ctgatgaaa atgagagaac cctggacttc acgacagca atgtgaagaa cctgtacgac      660
aaagtgcgga tgcagctgag agacaatgtg aagaactgg gcaatggctg cttcgagttc     720
taccacaagt gcgacgatga gtgtatgaac agcgtgaaga acggcaccta cgactaccct     780
aagtacgagg aagagagcaa gctgaacaga aatgagatca gtccggagg cgacatcatc     840
aagctgctga cgagcaggt gaacaaggag atgcagagca gcaacctgta catgagcatg     900
agcagctggt gctacaccca gcctggac ggcgccggcc tgttcctgtt cgaccacgcc       960
gccgaggagt acgagcacgc caagaagctg atcatcttcc tgaacgagaa caacgtgccc    1020
gtgcagctga ccagcatcag cgcccccgag cacaagttcg agggcctgac ccagatcttc    1080
cagaaggcct acgagcacga gcagcacatc agcgagagca tcaacaacat cgtggaccac    1140
gccatcaaga gcaaggacca cgccaccttc aacttcctgc agtggtacgt ggccgagcag    1200
cacgaggagg aggtgctgtt caaggacatc ctggacaaga tcgagctgat cggcaacgag    1260
aaccacggcc tgtacctggc cgaccagtac gtgaagggca tcgccaagag caggaagagc    1320
ggatcc                                                                1326
```

<210> SEQ ID NO 107
<211> LENGTH: 442
<212> TYPE: PRT
<213> ORGANISM: Artificial Sequence
<220> FEATURE:
<223> OTHER INFORMATION: Synthetic

<400> SEQUENCE: 107

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Gly
        35                  40                  45

Ser Gly Leu Val Leu Ala Thr Gly Leu Arg Asn Val Pro Gln Ile Glu
    50                  55                  60
```

Ser Arg Gly Leu Phe Gly Ala Ile Ala Gly Phe Ile Glu Gly Gly Trp
 65                  70                  75                  80

Gln Gly Met Ile Asp Gly Trp Tyr Gly Tyr His His Ser Asn Asp Gln
                 85                  90                  95

Gly Ser Gly Tyr Ala Ala Asp Lys Glu Ser Thr Gln Lys Ala Phe Asp
            100                 105                 110

Gly Ile Thr Asn Lys Val Asn Ser Val Ile Glu Lys Met Gly Gly Asp
        115                 120                 125

Pro Glu Trp Asp Arg Glu Ile Asn Asn Tyr Thr Ser Ile Ile Tyr Ser
130                 135                 140

Leu Ile Glu Glu Ser Gln Asn Gln Gln Glu Asn Gly Thr Gly Gly Gly
145                 150                 155                 160

Ser Gly Ile Val Gln Gln Gln Asn Asn Leu Leu Arg Ala Ile Glu Ala
            165                 170                 175

Gln Gln His Leu Leu Asn Leu Thr Val Trp Gly Ile Lys Gln Leu Gln
        180                 185                 190

Thr Tyr Asn Ala Glu Leu Leu Val Leu Met Glu Asn Glu Arg Thr Leu
    195                 200                 205

Asp Phe His Asp Ser Asn Val Lys Asn Leu Tyr Asp Lys Val Arg Met
210                 215                 220

Gln Leu Arg Asp Asn Val Lys Glu Leu Gly Asn Gly Cys Phe Glu Phe
225                 230                 235                 240

Tyr His Lys Cys Asp Asp Glu Cys Met Asn Ser Val Lys Asn Gly Thr
            245                 250                 255

Tyr Asp Tyr Pro Lys Tyr Glu Glu Glu Ser Lys Leu Asn Arg Asn Glu
        260                 265                 270

Ile Lys Ser Gly Gly Asp Ile Ile Lys Leu Leu Asn Glu Gln Val Asn
    275                 280                 285

Lys Glu Met Gln Ser Ser Asn Leu Tyr Met Ser Met Ser Ser Trp Cys
290                 295                 300

Tyr Thr His Ser Leu Asp Gly Ala Gly Leu Phe Leu Phe Asp His Ala
305                 310                 315                 320

Ala Glu Glu Tyr Glu His Ala Lys Lys Leu Ile Ile Phe Leu Asn Glu
            325                 330                 335

Asn Asn Val Pro Val Gln Leu Thr Ser Ile Ser Ala Pro Glu His Lys
        340                 345                 350

Phe Glu Gly Leu Thr Gln Ile Phe Gln Lys Ala Tyr Glu His Glu Gln
    355                 360                 365

His Ile Ser Glu Ser Ile Asn Asn Ile Val Asp His Ala Ile Lys Ser
370                 375                 380

Lys Asp His Ala Thr Phe Asn Phe Leu Gln Trp Tyr Val Ala Glu Gln
385                 390                 395                 400

His Glu Glu Glu Val Leu Phe Lys Asp Ile Leu Asp Lys Ile Glu Leu
            405                 410                 415

Ile Gly Asn Glu Asn His Gly Leu Tyr Leu Ala Asp Gln Tyr Val Lys
        420                 425                 430

Gly Ile Ala Lys Ser Arg Lys Ser Gly Ser
    435                 440

<210> SEQ ID NO 108
<211> LENGTH: 1326
<212> TYPE: DNA
<213> ORGANISM: Artificial Sequence
<220> FEATURE:

<223> OTHER INFORMATION: Synthetic

<400> SEQUENCE: 108

| | |
|---|---|
| ggatccgctc ttcctgctct tggcgatgcc cttcacgtac tggtcggcca ggtacaggcc | 60 |
| gtggttctcg ttgccgatca gctcgatctt gtccaggatg tccttgaaca gcacctcctc | 120 |
| ctcgtgctgc tcggccacgt accactgcag gaagttgaag gtggcgtggt ccttgctctt | 180 |
| gatggcgtgg tccacgatgt tgttgatgct ctcgctgatg tgctgctcgt gctcgtaggc | 240 |
| cttctggaag atctgggtca ggccctcgaa cttgtgctcg ggggcgctga tgctggtcag | 300 |
| ctgcacgggc acgttgttct cgttcaggaa gatgatcagc ttcttggcgt gctcgtactc | 360 |
| ctcggcggcg tggtcgaaca ggaacaggcc ggcgccgtcc aggctgtggg tgtagcacca | 420 |
| gctgctcatg ctcatgtaca ggttgctgct ctgcatctcc ttgttcacct gctcgttcag | 480 |
| cagcttgatg atgtcgcctc cggacttgat ctcatttctg ttcagcttgc tctcttcctc | 540 |
| gtacttaggg tagtcgtagg tgccgttctt cacgctgttc atacactcat cgtcgcactt | 600 |
| gtggtagaac tcgaagcagc cattgcccag ttctttcaca ttgtctctca gctgcatccg | 660 |
| cactttgtcg tacaggttct tcacattgct gtcgtggaag tccagggttc tctcattttc | 720 |
| catcagcacc agcagctcag cattgtatgt ctgcagctgt ttgattcccc acactgtcag | 780 |
| attcagcaga tgctgctgag cttcaatagc tctcagcaga ttgttctgct gctgcacaat | 840 |
| tccagatcct ccgcctgttc cattttcctg ctgattctgg cttcctcga tcaggctgta | 900 |
| gatgatgctg gtgtagttgt tgatctctct gtcccattcg ggatctccgc ccatcttctc | 960 |
| gatcacgcta ttcactttgt tggtgatgcc gtcgaaggct ttctgtgtag attctttgtc | 1020 |
| ggcggcatat ccagatccct gatcattaga gtggtggtag ccgtaccacc catcaatcat | 1080 |
| tccctgccat ccgccttcaa taaagccagc aatggctcca aacaggcctc tgctctcaat | 1140 |
| ctgaggcaca tttctcagtc ctgtagccag caccagtcct gatccaatat ccttggcgtg | 1200 |
| tgtcactgtc acatttcttt ccaggatggt atccactttc tcggtgctat tgttggcgtg | 1260 |
| gtagccaata cagatctgat cgcctctgac ggctgtaaac agcagaatca ggtagatgat | 1320 |
| ggccat | 1326 |

<210> SEQ ID NO 109
<211> LENGTH: 1362
<212> TYPE: DNA
<213> ORGANISM: Artificial Sequence
<220> FEATURE:
<223> OTHER INFORMATION: Synthetic

<400> SEQUENCE: 109

| | |
|---|---|
| atgaagacca tcatcgccct gagctacatc ttctgcctgg ccctgggcca ggacctgccc | 60 |
| ggcaacgaca acagcaccgc caccctgtgc ctgggccacc acgccgtgcc caacggcacc | 120 |
| ctggtgaaga ccatcaccga cgaccagatc gaggtgacca cgccaccga gctgggctcc | 180 |
| ggcctgaagc tggccaccgg catgcggaac gtgcccgaga gcagacccg ggcctgttc | 240 |
| ggcgccatcg ccggcttcat cgagaacggc tgggagggca tgatcgacgg ctggtacggc | 300 |
| ttccggcacc agaacagcga gggcaccggc caggccgccg acctgaagag cacccaggcc | 360 |
| gccatcgacc agatcaacgg caagctgaac cgggtgatcg agaagaccgg cggcgatccc | 420 |
| gagtgggacc gggagatcaa caactacacc agcatcatct acagcctgat cgaggagagc | 480 |
| cagaaccagc aggagaacgg caccggcggc ggcagcggca tcgtgcagca gcagaacaac | 540 |
| ctgctgcggg ccatcgaggc ccagcagcac ctgctgcagc tgaccgtgtg gggcatcaag | 600 |

-continued

```
cagctgcaga gctacaacgc cgagctgctg gtggccctgg agaaccagca caccatcgac      660
ctgaccgaca cgagatgaa caagctgttc gagaagaccc ggcggcagct gcggagaac       720 gccgaggaca tgggcaacgg ctgcttcaag atctaccaca agtgcgacaa cgcctgcatc      780
gagagcatcc ggaacggcac ctacgaccac gacgtgtacc gggacgaggc cctgaacaac     840
cggttccaga tcaagggctc cggaggcgac atcatcaagc tgctgaacga gcaggtgaac     900
aaggagatgc agagcagcaa cctgtacatg agcatgagca gctggtgcta cacccacagc     960
ctggacggcg ccggcctgtt cctgttcgac cacgccgccg aggagtacga gcacgccaag    1020
aagctgatca tcttcctgaa cgagaacaac gtgcccgtgc agctgaccag catcagcgcc    1080
cccgagcaca agttcgaggg cctgacccag atcttccaga aggcctacga gcacgagcag    1140
cacatcagcg agagcatcaa caacatcgtg gaccacgcca tcaagagcaa ggaccacgcc    1200
accttcaact tcctgcagtg gtacgtggcc gagcagcacg aggaggaggt gctgttcaag    1260
gacatcctgg acaagatcga gctgatcggc aacgagaacc acggcctgta cctggccgac    1320
cagtacgtga agggcatcgc caagagcagg aagagcggat cc                        1362
```

<210> SEQ ID NO 110
<211> LENGTH: 454
<212> TYPE: PRT
<213> ORGANISM: Artificial Sequence
<220> FEATURE:
<223> OTHER INFORMATION: Synthetic

<400> SEQUENCE: 110

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Leu Phe
65                  70                  75                  80

Gly Ala Ile Ala Gly Phe Ile Glu Asn Gly Trp Glu Gly Met Ile Asp
                85                  90                  95

Gly Trp Tyr Gly Phe Arg His Gln Asn Ser Glu Gly Thr Gly Gln Ala
            100                 105                 110

Ala Asp Leu Lys Ser Thr Gln Ala Ala Ile Asp Gln Ile Asn Gly Lys
        115                 120                 125

Leu Asn Arg Val Ile Glu Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
    210                 215                 220
```

Glu Met Asn Lys Leu Phe Glu Lys Thr Arg Arg Gln Leu Arg Glu Asn
225                 230                 235                 240

Ala Glu Asp Met Gly Asn Gly Cys Phe Lys Ile Tyr His Lys Cys Asp
            245                 250                 255

Asn Ala Cys Ile Glu Ser Ile Arg Asn Gly Thr Tyr Asp His Asp Val
        260                 265                 270

Tyr Arg Asp Glu Ala Leu Asn Asn Arg Phe Gln Ile Lys Gly Ser Gly
    275                 280                 285

Gly Asp Ile Ile Lys Leu Leu Asn Glu Gln Val Asn Lys Glu Met Gln
290                 295                 300

Ser Ser Asn Leu Tyr Met Ser Met Ser Ser Trp Cys Tyr Thr His Ser
305                 310                 315                 320

Leu Asp Gly Ala Gly Leu Phe Leu Phe Asp His Ala Ala Glu Glu Tyr
            325                 330                 335

Glu His Ala Lys Lys Leu Ile Ile Phe Leu Asn Glu Asn Asn Val Pro
        340                 345                 350

Val Gln Leu Thr Ser Ile Ser Ala Pro Glu His Lys Phe Glu Gly Leu
    355                 360                 365

Thr Gln Ile Phe Gln Lys Ala Tyr Glu His Glu Gln His Ile Ser Glu
370                 375                 380

Ser Ile Asn Asn Ile Val Asp His Ala Ile Lys Ser Lys Asp His Ala
385                 390                 395                 400

Thr Phe Asn Phe Leu Gln Trp Tyr Val Ala Glu Gln His Glu Glu Glu
            405                 410                 415

Val Leu Phe Lys Asp Ile Leu Asp Lys Ile Glu Leu Ile Gly Asn Glu
        420                 425                 430

Asn His Gly Leu Tyr Leu Ala Asp Gln Tyr Val Lys Gly Ile Ala Lys
    435                 440                 445

Ser Arg Lys Ser Gly Ser
450

<210> SEQ ID NO 111
<211> LENGTH: 1362
<212> TYPE: DNA
<213> ORGANISM: Artificial Sequence
<220> FEATURE:
<223> OTHER INFORMATION: Synthetic

<400> SEQUENCE: 111
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg gggcgctga tgctggtcag     300 ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggagccctt gatctggaac cggttgttca gggcctcgtc     540
ccggtacacg tcgtggtcgt aggtgccgtt ccggatgctc tcgatgcagg cgttgtcgca     600
cttgtggtag atcttgaagc agccgttgcc catgtcctcg gcgttctccc gcagctgccg     660
ccgggtcttc tcgaacagct tgttcatctc gctgtcggtc aggtcgatgg tgtgctggtt     720

```
ctccagggcc accagcagct cggcgttgta gctctgcagc tgcttgatgc cccacacggt    780
cagctgcagc aggtgctgct gggcctcgat ggcccgcagc aggttgttct gctgctgcac    840
gatgccgctg ccgccgccgg tgccgttctc ctgctggttc tggctctcct cgatcaggct    900
gtagatgatg ctggtgtagt tgttgatctc ccggtccac tcgggatcgc cgccggtctt     960
ctcgatcacc cggttcagct tgccgttgat ctggtcgatg gcggcctggg tgctcttcag   1020
gtcggcggcc tggccggtgc cctcgctgtt ctggtgccgg aagccgtacc agccgtcgat   1080
catgccctcc cagccgttct cgatgaagcc ggcgatggcg ccgaacaggc cccgggtctg   1140
cttctcgggc acgttccgca tgccggtggc cagcttcagg ccggagccca gctcggtggc   1200
gttggtcacc tcgatctggt cgtcggtgat ggtcttcacc agggtgccgt tgggcacggc   1260
gtggtggccc aggcacaggg tggcggtgct gttgtcgttg ccgggcaggt cctggcccag   1320
ggccaggcag aagatgtagc tcagggcgat gatggtcttc at                      1362
```

<210> SEQ ID NO 112
<211> LENGTH: 1341
<212> TYPE: DNA
<213> ORGANISM: Artificial Sequence
<220> FEATURE:
<223> OTHER INFORMATION: Synthetic

<400> SEQUENCE: 112

```
atggagaaga tcgtgctgct gctggccatc gtgagcctgg tgaagagcga ccagatctgc     60
atcggctacc acgccaacaa cagcaccgag caggtggaca ccatcatgga agaacgtg     120 accgtgaccc acgcccagga catcggctcc ggcctggtgc tggccaccgg cctgcggaac   180
agcccccagc gggagagccg gcggaagaag cggggcctgt tcggcgccat cgccggcttc   240
atcgagggcg gctggcaggg catggtggac ggctggtacg gctaccacca cagcaacgag   300
cagggcagcg gctacgccgc cgacaaggag agcacccaga aggccatcga cggcgtgacc   360
aacaaggtga acagcatcat cgacaagatg gcggcgatc ccgagtggga ccgggagatc   420
aacaactaca ccagcatcat ctacagcctg atcgaggaga ccagaaccca gcaggagaac   480
ggcaccggcg gcgcagcgg catcgtgcag cagcagaaca acctgctgcg ggccatcgag   540
gcccagcagc acctgctgca gctgaccgtg tggggcatca gcagctgca gacctacaac   600 gccgagctgc tggtgctgat ggagaacgag cggaccctgg acttccacga cagcaacgtg   660
aagaacctgt acgacaaggt gcggctgcag ctgcgggaca cgccaagga gctgggcaac   720 ggctgcttcg agttctacca caagtgcgac aacgagtgca tggagagcat ccggaacggc   780
acctacaact acccccagta cagcgaggag gcccggctga gcgggagga gatcagctcc   840 ggaggcgaca tcatcaagct gctgaacgag caggtgaaca aggagatgca gagcagcaac   900
ctgtacatga gcatgagcag ctggtgctac acccacagcc tggacggcgc cggcctgttc   960
ctgttcgacc acgccgccga ggagtacgag cacgccaaga agctgatcat cttcctgaac  1020
gagaacaacg tgcccgtgca gctgaccagc atcagcgccc ccgagcacaa gttcgagggc  1080
ctgacccaga tcttccagaa ggcctacgag cacgagcagc acatcagcga gcatcaac   1140 aacatcgtgg accacgccat caagagcaag accacgcca ccttcaactt cctgcagtgg  1200
tacgtggccg agcagcacga ggaggaggtg ctgttcaagg acatcctgga caagatcgag  1260
ctgatcggca acgagaacca cggcctgtac ctggccgacc agtacgtgaa gggcatcgcc  1320
aagagcagga gagcggatc c                                              1341
```

```
<210> SEQ ID NO 113
<211> LENGTH: 447
<212> TYPE: PRT
<213> ORGANISM: Artificial Sequence
<220> FEATURE:
<223> OTHER INFORMATION: Synthetic

<400> SEQUENCE: 113

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Gly Ser Gly Leu Val Leu Ala Thr Gly Leu Arg Asn Ser Pro Gln Arg
    50                  55                  60

Glu Ser Arg Arg Lys Lys Arg Gly Leu Phe Gly Ala Ile Ala Gly Phe
65              70                  75                  80

Ile Glu Gly Gly Trp Gln Gly Met Val Asp Gly Trp Tyr Gly Tyr His
                85                  90                  95

His Ser Asn Glu Gln Gly Ser Gly Tyr Ala Ala Asp Lys Glu Ser Thr
            100                 105                 110

Gln Lys Ala Ile Asp Gly Val Thr Asn Lys Val Asn Ser Ile Ile Asp
        115                 120                 125

Lys Met Gly Gly Asp Pro Glu Trp Asp Arg Glu Ile Asn Asn Tyr Thr
    130                 135                 140

Ser Ile Ile Tyr Ser Leu Ile Glu Glu Ser Gln Asn Gln Gln Glu Asn
145             150                 155                 160

Gly Thr Gly Gly Gly Ser Gly Ile Val Gln Gln Gln Asn Asn Leu Leu
                165                 170                 175

Arg Ala Ile Glu Ala Gln Gln His Leu Leu Gln Leu Thr Val Trp Gly
            180                 185                 190

Ile Lys Gln Leu Gln Thr Tyr Asn Ala Glu Leu Leu Val Leu Met Glu
        195                 200                 205

Asn Glu Arg Thr Leu Asp Phe His Asp Ser Asn Val Lys Asn Leu Tyr
210                 215                 220

Asp Lys Val Arg Leu Gln Leu Arg Asp Asn Ala Lys Glu Leu Gly Asn
225                 230                 235                 240

Gly Cys Phe Glu Phe Tyr His Lys Cys Asp Asn Glu Cys Met Glu Ser
                245                 250                 255

Ile Arg Asn Gly Thr Tyr Asn Tyr Pro Gln Tyr Ser Glu Glu Ala Arg
            260                 265                 270

Leu Lys Arg Glu Glu Ile Ser Ser Gly Gly Asp Ile Ile Lys Leu Leu
        275                 280                 285

Asn Glu Gln Val Asn Lys Glu Met Gln Ser Ser Asn Leu Tyr Met Ser
    290                 295                 300

Met Ser Ser Trp Cys Tyr Thr His Ser Leu Asp Gly Ala Gly Leu Phe
305                 310                 315                 320

Leu Phe Asp His Ala Ala Glu Glu Tyr Glu His Ala Lys Lys Leu Ile
                325                 330                 335

Ile Phe Leu Asn Glu Asn Asn Val Pro Val Gln Leu Thr Ser Ile Ser
            340                 345                 350

Ala Pro Glu His Lys Phe Glu Gly Leu Thr Gln Ile Phe Gln Lys Ala
        355                 360                 365

Tyr Glu His Glu Gln His Ile Ser Glu Ser Ile Asn Asn Ile Val Asp
```

His Ala Ile Lys Ser Lys Asp His Ala Thr Phe Asn Phe Leu Gln Trp
385                 390                 395                 400

Tyr Val Ala Glu Gln His Glu Glu Val Leu Phe Lys Asp Ile Leu
            405                 410                 415

Asp Lys Ile Glu Leu Ile Gly Asn Glu Asn His Gly Leu Tyr Leu Ala
            420                 425                 430

Asp Gln Tyr Val Lys Gly Ile Ala Lys Ser Arg Lys Ser Gly Ser
            435                 440                 445

<210> SEQ ID NO 114
<211> LENGTH: 1341
<212> TYPE: DNA
<213> ORGANISM: Artificial Sequence
<220> FEATURE:
<223> OTHER INFORMATION: Synthetic

<400> SEQUENCE: 114

```
ggatccgctc ttcctgctct tggcgatgcc cttcacgtac tggtcggcca ggtacaggcc    60
gtggttctcg ttgccgatca gctcgatctt gtccaggatg tccttgaaca gcacctcctc   120
ctcgtgctgc tcggccacgt accactgcag gaagttgaag gtggcgtggt ccttgctctt   180
gatggcgtgg tccacgatgt tgttgatgct ctcgctgatg tgctgctcgt gctcgtaggc   240
cttctggaag atctgggtca ggccctcgaa cttgtgctcg gggcgctga tgctggtcag   300
ctgcacgggc acgttgttct cgttcaggaa gatgatcagc ttcttggcgt gctcgtactc   360
ctcggcggcg tggtcgaaca ggaacaggcc ggcgccgtcc aggctgtggg tgtagcacca   420
gctgctcatg ctcatgtaca ggttgctgct ctgcatctcc ttgttcacct gctcgttcag   480
cagcttgatg atgtcgcctc cggagctgat ctcctcccgc ttcagccggg cctcctcgct   540
gtactggggg tagttgtagg tgccgttccg gatgctctcc atgcactcgt tgtcgcactt   600
gtggtagaac tcgaagcagc cgttgcccag ctccttggcg ttgtcccgca gctgcagccg   660
caccttgtcg tacaggttct tcacgttgct gtcgtggaag tccagggtcc gctcgttctc   720
catcagcacc agcagctcgg cgttgtaggt ctgcagctgc ttgatgcccc acacggtcag   780
ctgcagcagg tgctgctggg cctcgatggc ccgcagcagg ttgttctgct gctgcacgat   840
gccgctgccg ccgccggtgc cgttctcctg ctggttctgg ctctcctcga tcaggctgta   900
gatgatgctg gtgtagttgt tgatctcccg gtcccactcg gatcgccgc ccatcttgtc   960
gatgatgctg ttcaccttgt tggtcacgcc gtcgatggcc ttctgggtgc tctccttgtc  1020
ggcggcgtag ccgctgccct gctcgttgct gtggtggtag ccgtaccagc cgtccaccat  1080
gccctgccag ccgccctcga tgaagccggc gatggcgccg aacaggcccc gcttcttccg  1140
ccggctctcc cgctgggggc tgttccgcag gccggtggcc agcaccaggc cggagccgat  1200
gtcctgggcg tgggtcacgg tcacgttctt ctccatgatg gtgtccacct gctcggtgct  1260
gttgttggcg tggtagccga tgcagatctg gtcgctcttc accaggctca cgatggccag  1320
cagcagcacg atcttctcca t                                           1341
```

<210> SEQ ID NO 115
<211> LENGTH: 1332
<212> TYPE: DNA
<213> ORGANISM: Artificial Sequence
<220> FEATURE:
<223> OTHER INFORMATION: Synthetic

<400> SEQUENCE: 115

```
atgaaagtga agctgctggt gctgctgtgt acctttaccg ccacctacgc cgataccatc        60
tgtatcggct accacgccaa caatagcacc gacaccgtgg ataccgtgct ggaaaagaac       120
gtgaccgtga cccacagcgt gaacctggga tcaggactga aatggtgac cggcctgagg        180
aatatcccca gcatccagag cagaggcctg tttggcgcca ttgccggctt tatcgagggc       240
ggatggacag gcatggtgga tgggtggtac ggctaccacc accagaatga gcagggatct       300
ggctatgccg ccgatcagaa gagcacccag aacgccatca acggcatcac caacaaagtg       360
aacagcgtga tcgagaagat gggcggcgat cctgaatggg acagagagat caacaactac       420
accagcatca tctacagcct gatcgaggaa gccagaacc agcaggaaaa cggcacaggc         480
ggcggatctg aattgtgca gcagcagaac aacctgctga gagccattga ggcccagcag        540
catctgctgc agctgacagt gtggggcatc aagcagctgc agacctacaa cgccgaactc       600
ctggtcctcc tggaaaatga aggaccctg gacttccacg acagcaacgt gaagaacctg        660
tacgagaaag tgaagagcca gctgaagaac aacgccaaag atcggcaa cggctgcttc         720
gagttctacc acaagtgcaa cgacgagtgc atggaaagcg tgaagaacgg cacctacgac       780
taccccaagt acagcgagga aagcaagctg aaccgggaga gatcgattc cggaggcgac        840
atcatcaagc tgctgaacga gcaggtgaac aaggagatgc agagcagcaa cctgtacatg       900
agcatgagca gctggtgcta cacccacagc ctggacggcg ccggcctgtt cctgttcgac       960
cacgccgccg aggagtacga gcacgccaag aagctgatca tcttcctgaa cgagaacaac      1020
gtgcccgtgc agctgaccag catcagcgcc cccgagcaca gttcgaggg cctgacccag       1080
atcttccaga aggcctacga gcacgagcag cacatcagcg agagcatcaa caacatcgtg      1140
gaccacgcca tcaagagcaa ggaccacgcc accttcaact tcctgcagtg gtacgtggcc      1200
gagcagcacg aggaggaggt gctgttcaag gacatcctgg acaagatcga gctgatcggc      1260
aacgagaacc acggcctgta cctggccgac cagtacgtga agggcatcgc caagagcagg      1320
aagagcggat cc                                                          1332
```

<210> SEQ ID NO 116
<211> LENGTH: 444
<212> TYPE: PRT
<213> ORGANISM: Artificial Sequence
<220> FEATURE:
<223> OTHER INFORMATION: Synthetic

<400> SEQUENCE: 116

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Ser
    50                  55                  60

Ile Gln Ser Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
```

```
            115                 120                 125
Gly Asp Pro Glu Trp Asp Arg Glu Ile Asn Asn Tyr Thr Ser Ile Ile
130                 135                 140

Tyr Ser Leu Ile Glu Glu Ser Gln Asn Gln Gln Glu Asn Gly Thr Gly
145                 150                 155                 160

Gly Gly Ser Gly Ile Val Gln Gln Gln Asn Asn Leu Leu Arg Ala Ile
                165                 170                 175

Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Phe His Asp Ser Asn Val Lys Asn Leu Tyr Glu Lys Val
210                 215                 220

Lys Ser Gln Leu Lys Asn Asn Ala Lys Glu Ile Gly Asn Gly Cys Phe
225                 230                 235                 240

Glu Phe Tyr His Lys Cys Asn Asp Glu Cys Met Glu Ser Val Lys Asn
                245                 250                 255

Gly Thr Tyr Asp Tyr Pro Lys Tyr Ser Glu Glu Ser Lys Leu Asn Arg
            260                 265                 270

Glu Lys Ile Asp Ser Gly Gly Asp Ile Ile Lys Leu Leu Asn Glu Gln
        275                 280                 285

Val Asn Lys Glu Met Gln Ser Ser Asn Leu Tyr Met Ser Met Ser Ser
290                 295                 300

Trp Cys Tyr Thr His Ser Leu Asp Gly Ala Gly Leu Phe Leu Phe Asp
305                 310                 315                 320

His Ala Ala Glu Glu Tyr Glu His Ala Lys Lys Leu Ile Ile Phe Leu
                325                 330                 335

Asn Glu Asn Asn Val Pro Val Gln Leu Thr Ser Ile Ser Ala Pro Glu
            340                 345                 350

His Lys Phe Glu Gly Leu Thr Gln Ile Phe Gln Lys Ala Tyr Glu His
        355                 360                 365

Glu Gln His Ile Ser Glu Ser Ile Asn Asn Ile Val Asp His Ala Ile
370                 375                 380

Lys Ser Lys Asp His Ala Thr Phe Asn Phe Leu Gln Trp Tyr Val Ala
385                 390                 395                 400

Glu Gln His Glu Glu Val Leu Phe Lys Asp Ile Leu Asp Lys Ile
                405                 410                 415

Glu Leu Ile Gly Asn Glu Asn His Gly Leu Tyr Leu Ala Asp Gln Tyr
            420                 425                 430

Val Lys Gly Ile Ala Lys Ser Arg Lys Ser Gly Ser
        435                 440

<210> SEQ ID NO 117
<211> LENGTH: 1332
<212> TYPE: DNA
<213> ORGANISM: Artificial Sequence
<220> FEATURE:
<223> OTHER INFORMATION: Synthetic

<400> SEQUENCE: 117
ggatccgctc ttcctgctct tggcgatgcc cttcacgtac tggtcggcca ggtacaggcc    60
gtggttctcg ttgccgatca gctcgatctt gtccaggatg tccttgaaca gcacctcctc   120
ctcgtgctgc tcggccacgt accactgcag gaagttgaag gtggcgtggt ccttgctctt   180
gatggcgtgg tccacgatgt tgttgatgct ctcgctgatg tgctgctcgt gctcgtaggc   240
```

| | |
|---|---|
| cttctggaag atctgggtca ggccctcgaa cttgtgctcg ggggcgctga tgctggtcag | 300 |
| ctgcacgggc acgttgttct cgttcaggaa gatgatcagc ttcttggcgt gctcgtactc | 360 |
| ctcggcggcg tggtcgaaca ggaacaggcc ggcgccgtcc aggctgtggg tgtagcacca | 420 |
| gctgctcatg ctcatgtaca ggttgctgct ctgcatctcc ttgttcacct gctcgttcag | 480 |
| cagcttgatg atgtcgcctc cggaatcgat cttctcccgg ttcagcttgc tttcctcgct | 540 |
| gtacttgggt tagtcgtagg tgccgttctt cacgctttcc atgcactcgt cgttgcactt | 600 |
| gtggtagaac tcgaagcagc cgttgccgat ctctttggcg ttgttcttca gctggctctt | 660 |
| cactttctcg tacaggttct tcacgttgct gtcgtggaag tccagggtcc tctcattttc | 720 |
| caggaggacc aggagttcgg cgttgtaggt ctgcagctgc ttgatgcccc acactgtcag | 780 |
| ctgcagcaga tgctgctggg cctcaatggc tctcagcagg ttgttctgct gctgcacaat | 840 |
| tccagatccg ccgcctgtgc cgttttcctg ctggttctgg ctttcctcga tcaggctgta | 900 |
| gatgatgctg gtgtagttgt tgatctctct gtcccattca ggatcgccgc ccatcttctc | 960 |
| gatcacgctg ttcactttgt tggtgatgcc gttgatggcg ttctgggtgc tcttctgatc | 1020 |
| ggcggcatag ccagatccct gctcattctg gtggtggtag ccgtaccacc catccaccat | 1080 |
| gcctgtccat ccgccctcga taaagccggc aatggcgcca acaggcctc tgctctggat | 1140 |
| gctggggata ttcctcaggc cggtcaccat tctcagtcct gatcccaggt tcacgctgtg | 1200 |
| ggtcacggtc acgttctttt ccagcacggt atccacggtg tcggtgctat tgttggcgtg | 1260 |
| gtagccgata cagatggtat cggcgtaggt ggcggtaaag gtacacagca gcaccagcag | 1320 |
| cttcactttc at | 1332 |

<210> SEQ ID NO 118
<211> LENGTH: 1362
<212> TYPE: DNA
<213> ORGANISM: Artificial Sequence
<220> FEATURE:
<223> OTHER INFORMATION: Synthetic

<400> SEQUENCE: 118

| | |
|---|---|
| atgaaaacca tcattgccct gagctacatc ctgtgcctgg tgttcacaca gaagctgccc | 60 |
| ggcaacgata atagcaccgc cacactgtgt ctgggacacc acgccgtgcc taatggcacc | 120 |
| atcgtgaaaa caatcaccaa cgaccagatc gaagtgacca atgccacaga gctgggctcc | 180 |
| ggcctgaagc tggccaccgg catgagaaat gtgcccgaga agcagaccag aggcatcttt | 240 |
| ggcgccattg ccggctttat cgagaatggc tgggaggaa tggtggatgg gtggtacggc | 300 |
| ttcagacacc agaatagcga gggaattgga caggccgccg atctgaaatc tacccaggcc | 360 |
| gccatcgacc agatcaacgg caagctgaac aggctgatcg caagaccgg cggcgatccc | 420 |
| gagtgggacc gggagatcaa caactacacc agcatcatct acagcctgat cgaggagagc | 480 |
| cagaaccagc aggagaacgg caccggcggc ggcagcggca tcgtgcagca gcagaacaac | 540 |
| ctgctgcggg ccatcgaggc ccagcagcac ctgctgcagc tgaccgtgtg gggcatcaag | 600 |
| cagctgcaga gctacaatgc cgaactgctg gtcgccctgg aaaaccagca cacaattgat | 660 |
| ctgacagaca gtgagatgaa taagctgttc gagaaaacca gaagcagct gagagaaaac | 720 |
| gccgaggaca tgggcaacgg ctgcttcaag atctaccaca gtgcgacaa cgcctgcatc | 780 |
| ggcagcatca gaaacggcac ctacgaccac gacgtgtaca gagatgaggc cctgaacaac | 840 |
| cggtttcaga tcaagggctc cggaggcgac atcatcaagc tgctgaacga gcaggtgaac | 900 |

-continued

```
aaggagatgc agagcagcaa cctgtacatg agcatgagca gctggtgcta cacccacagc    960
ctggacggcg ccggcctgtt cctgttcgac cacgccgccg aggagtacga gcacgccaag   1020
aagctgatca tcttcctgaa cgagaacaac gtgcccgtgc agctgaccag catcagcgcc   1080
cccgagcaca gttcgaggg cctgacccag atcttccaga aggcctacga gcacgagcag    1140
cacatcagcg agagcatcaa caacatcgtg gaccacgcca tcaagagcaa ggaccacgcc   1200
accttcaact tcctgcagtg gtacgtggcc gagcagcacg aggaggaggt gctgttcaag   1260
gacatcctgg acaagatcga gctgatcggc aacgagaacc acggcctgta cctggccgac   1320
cagtacgtga agggcatcgc caagagcagg aagagcggat cc                      1362
```

<210> SEQ ID NO 119
<211> LENGTH: 454
<212> TYPE: PRT
<213> ORGANISM: Artificial Sequence
<220> FEATURE:
<223> OTHER INFORMATION: Synthetic

<400> SEQUENCE: 119

```
Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Gly Ser Gly Leu Lys Leu
    50                  55                  60

Ala Thr Gly Met Arg Asn Val Pro Glu Lys Gln Thr Arg Gly Ile Phe
65                  70                  75                  80

Gly Ala Ile Ala Gly Phe Ile Glu Asn Gly Trp Glu Gly Met Val Asp
                85                  90                  95

Gly Trp Tyr Gly Phe Arg His Gln Asn Ser Glu Gly Ile Gly Gln Ala
            100                 105                 110

Ala Asp Leu Lys Ser Thr Gln Ala Ala Ile Asp Gln Ile Asn Gly Lys
        115                 120                 125

Leu Asn Arg Leu Ile Gly Lys Thr Gly Gly Asp Pro Glu Trp Asp Arg
    130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
    210                 215                 220

Glu Met Asn Lys Leu Phe Glu Lys Thr Lys Lys Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Gly Ser Ile Arg Asn Gly Thr Tyr Asp His Asp Val
            260                 265                 270

Tyr Arg Asp Glu Ala Leu Asn Asn Arg Phe Gln Ile Lys Gly Ser Gly
        275                 280                 285
```

```
Gly Asp Ile Ile Lys Leu Leu Asn Glu Gln Val Asn Lys Glu Met Gln
            290                 295                 300
Ser Ser Asn Leu Tyr Met Ser Met Ser Ser Trp Cys Tyr Thr His Ser
305                 310                 315                 320
Leu Asp Gly Ala Gly Leu Phe Leu Phe Asp His Ala Ala Glu Glu Tyr
                325                 330                 335
Glu His Ala Lys Lys Leu Ile Ile Phe Leu Asn Glu Asn Asn Val Pro
            340                 345                 350
Val Gln Leu Thr Ser Ile Ser Ala Pro Glu His Lys Phe Glu Gly Leu
        355                 360                 365
Thr Gln Ile Phe Gln Lys Ala Tyr Glu His Gln His Ile Ser Glu
    370                 375                 380
Ser Ile Asn Asn Ile Val Asp His Ala Ile Lys Ser Lys Asp His Ala
385                 390                 395                 400
Thr Phe Asn Phe Leu Gln Trp Tyr Val Ala Glu Gln His Glu Glu
                405                 410                 415
Val Leu Phe Lys Asp Ile Leu Asp Lys Ile Glu Leu Ile Gly Asn Glu
            420                 425                 430
Asn His Gly Leu Tyr Leu Ala Asp Gln Tyr Val Lys Gly Ile Ala Lys
        435                 440                 445
Ser Arg Lys Ser Gly Ser
    450
```

<210> SEQ ID NO 120
<211> LENGTH: 1362
<212> TYPE: DNA
<213> ORGANISM: Artificial Sequence
<220> FEATURE:
<223> OTHER INFORMATION: Synthetic

<400> SEQUENCE: 120

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg ggggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggagcccct gatctgaaac cggttgttca gggcctcatc     540
tctgtacacg tcgtggtcgt aggtgccgtt tctgatgctg ccgatgcagg cgttgtcgca     600
cttgtggtag atcttgaagc agccgttgcc catgtcctcg gcgttttctc tcagctgctt     660
cttggtttc tcgaacagct tattcatctc actgtctgtc agatcaattg tgtgctggtt     720
ttccagggcg accagcagtt cggcattgta gctctgcagc tgcttgatgc cccacacggt     780
cagctgcagc aggtgctgct gggcctcgat ggcccgcagc aggttgttct gctgctgcac     840
gatgccgctg ccgccgccgg tgccgttctc ctgctggttc tggctctcct cgatcaggct     900
gtagatgatg ctggtgtagt tgttgatctc ccggtccac tcgggatcgc cgccggtctt     960
gccgatcagc ctgttcagct tgccgttgat ctggtcgatg cggcctggg tagatttcag    1020
atcggcggcc tgtccaattc cctcgctatt ctggtgtctg aagccgtacc acccatccac    1080
```

```
cattccctcc cagccattct cgataaagcc ggcaatggcg ccaaagatgc ctctggtctg    1140
cttctcgggc acatttctca tgccggtggc cagcttcagg ccggagccca gctctgtggc    1200
attggtcact tcgatctggt cgttggtgat tgttttcacg atggtgccat taggcacggc    1260
gtggtgtccc agacacagtg tggcggtgct attatcgttg ccgggcagct tctgtgtgaa    1320
caccaggcac aggatgtagc tcagggcaat gatggttttc at                      1362
```

<210> SEQ ID NO 121
<211> LENGTH: 1362
<212> TYPE: DNA
<213> ORGANISM: Artificial Sequence
<220> FEATURE:
<223> OTHER INFORMATION: Synthetic

<400> SEQUENCE: 121

```
atgaaaacca taattgcgct gtcctacata ctgtgtctgg tgtttgccca gaaactgccg     60
ggcaatgaca actcaacagc cacgctctgc ttggggcacc atgccgtccc taacgggacc    120
attgtgaaaa ccattactaa cgatcagata gaggtgacta atgccaccga gctgggctcc    180
ggcttgaaac tggcgaccgg tatgcgcaat gtccccgaaa acagacccg cgggatattt     240 ggggctatcg caggctttat cgagaatggc tgggaaggga tggtggatgg ttggtatggt    300
tttagacatc aaaactccga aggcagaggc caggctgccg atctcaagag cacgcaggcc    360
gctatagatc agatcaatgg aaagctcaac agactgatcg gaaaaccgg cggcgatccc     420 gagtgggacc gggagatcaa caactacacc agcatcatct acagcctgat cgaggagagc    480
cagaaccagc aggagaacgg caccggcggc ggcagcggca tcgtgcagca gcagaacaac    540
ctgctgcggg ccatcgaggc ccagcagcac ctgctgcagc tgaccgtgtg ggcatcaag    600 cagctgcagt cctacaatgc cgagctgctg gtggctctgg agaatcagca cactattgac    660
ctgaccgatt cagagatgaa caaacttttt gagaagacga agaagcagct tagagaaaat    720
gcagaggaca tgggaacgg atgctttaaa atatatcata agtgtgataa tgcctgcatc     780
ggatcaatta gaaatggtac ctatgatcac gatgtttaca gggacgaagc gctgaataac    840
aggttccaga taaaaggctc cggaggcgac atcatcaagc tgctgaacga gcaggtgaac    900
aaggagatgc agagcagcaa cctgtacatg agcatgagca gctggtgcta cacccacagc    960
ctggacggcg ccggcctgtt cctgttcgac acgccgccg aggagtacga gcacgccaag    1020
aagctgatca tcttcctgaa cgagaacaac gtgcccgtgc agctgaccag catcagcgcc    1080
cccgagcaca agttcgaggg cctgacccag atcttccaga aggcctacga gcacgagcag    1140
cacatcagcg agagcatcaa caacatcgtg gaccacgcca tcaagagcaa ggaccacgcc    1200
accttcaact cctgcagtg gtacgtggcc gagcagcacg aggaggaggt gctgttcaag    1260
gacatcctgg acaagatcga gctgatcggc aacgagaacc acggcctgta cctggccgac    1320
cagtacgtga agggcatcgc caagagcagg aagagcggat cc                       1362
```

<210> SEQ ID NO 122
<211> LENGTH: 454
<212> TYPE: PRT
<213> ORGANISM: Artificial Sequence
<220> FEATURE:
<223> OTHER INFORMATION: Synthetic

<400> SEQUENCE: 122

```
Met Lys Thr Ile Ile Ala Leu Ser Tyr Ile Leu Cys Leu Val Phe Ala
1               5                   10                  15
```

```
Gln Lys Leu Pro Gly Asn Asp Asn Ser Thr Ala Thr Leu Cys Leu Gly
             20                  25                  30

His His Ala Val Pro Asn Gly Thr Ile Val Lys Thr Ile Thr Asn Asp
         35                  40                  45

Gln Ile Glu Val Thr Asn Ala Thr Glu Leu Gly Ser Gly Leu Lys Leu
 50                  55                  60

Ala Thr Gly Met Arg Asn Val Pro Glu Lys Gln Thr Arg Gly Ile Phe
 65                  70                  75                  80

Gly Ala Ile Ala Gly Phe Ile Glu Asn Gly Trp Glu Gly Met Val Asp
                 85                  90                  95

Gly Trp Tyr Gly Phe Arg His Gln Asn Ser Glu Gly Arg Gly Gln Ala
            100                 105                 110

Ala Asp Leu Lys Ser Thr Gln Ala Ala Ile Asp Gln Ile Asn Gly Lys
        115                 120                 125

Leu Asn Arg Leu Ile Gly Lys Thr Gly Gly Asp Pro Glu Trp Asp Arg
130                 135                 140

Glu Ile Asn Asn Tyr Thr Ser Ile Ile Tyr Ser Leu Ile Glu Glu Ser
145                 150                 155                 160

Gln Asn Gln Gln Glu Asn Gly Thr Gly Gly Ser Gly Ile Val Gln
                165                 170                 175

Gln Gln Asn Asn Leu Leu Arg Ala Ile Glu Ala Gln Gln His Leu Leu
            180                 185                 190

Gln Leu Thr Val Trp Gly Ile Lys Gln Leu Gln Ser Tyr Asn Ala Glu
        195                 200                 205

Leu Leu Val Ala Leu Glu Asn Gln His Thr Ile Asp Leu Thr Asp Ser
210                 215                 220

Glu Met Asn Lys Leu Phe Glu Lys Thr Lys Gln Leu Arg Glu Asn
225                 230                 235                 240

Ala Glu Asp Met Gly Asn Gly Cys Phe Lys Ile Tyr His Lys Cys Asp
                245                 250                 255

Asn Ala Cys Ile Gly Ser Ile Arg Asn Gly Thr Tyr Asp His Asp Val
            260                 265                 270

Tyr Arg Asp Glu Ala Leu Asn Asn Arg Phe Gln Ile Lys Gly Ser Gly
        275                 280                 285

Gly Asp Ile Ile Lys Leu Leu Asn Glu Gln Val Asn Lys Glu Met Gln
290                 295                 300

Ser Ser Asn Leu Tyr Met Ser Met Ser Ser Trp Cys Tyr Thr His Ser
305                 310                 315                 320

Leu Asp Gly Ala Gly Leu Phe Leu Phe Asp His Ala Ala Glu Glu Tyr
                325                 330                 335

Glu His Ala Lys Lys Leu Ile Ile Phe Leu Asn Glu Asn Asn Val Pro
            340                 345                 350

Val Gln Leu Thr Ser Ile Ser Ala Pro Glu His Lys Phe Glu Gly Leu
        355                 360                 365

Thr Gln Ile Phe Gln Lys Ala Tyr Glu His Glu Gln His Ile Ser Glu
370                 375                 380

Ser Ile Asn Asn Ile Val Asp His Ala Ile Lys Ser Lys Asp His Ala
385                 390                 395                 400

Thr Phe Asn Phe Leu Gln Trp Tyr Val Ala Glu Gln His Glu Glu Glu
                405                 410                 415

Val Leu Phe Lys Asp Ile Leu Asp Lys Ile Glu Leu Ile Gly Asn Glu
            420                 425                 430
```

Asn His Gly Leu Tyr Leu Ala Asp Gln Tyr Val Lys Gly Ile Ala Lys
    435                 440                 445

Ser Arg Lys Ser Gly Ser
    450

<210> SEQ ID NO 123
<211> LENGTH: 1362
<212> TYPE: DNA
<213> ORGANISM: Artificial Sequence
<220> FEATURE:
<223> OTHER INFORMATION: Synthetic

<400> SEQUENCE: 123

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg gggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggagccttt tatctggaac ctgttattca gcgcttcgtc     540
cctgtaaaca tcgtgatcat aggtaccatt tctaattgat ccgatgcagg cattatcaca     600
cttatgatat attttaaagc atccgttccc catgtcctct gcattttctc taagctgctt     660
cttcgtcttc tcaaaaagtt tgttcatctc tgaatcggtc aggtcaatag tgtgctgatt     720
ctccagagcc accagcagct cggcattgta ggactgcagc tgcttgatgc ccacacggt      780
cagctgcagc aggtgctgct gggcctcgat ggcccgcagc aggttgttct gctgctgcac     840
gatgccgctg ccgccgccgg tgccgttctc tgctggttc tggctctcct cgatcaggct     900
gtagatgatg ctggtgtagt tgttgatctc ccggtccac tcgggatcgc cgccggtttt     960
cccgatcagt ctgttgagct ttccattgat ctgatctata gcggcctgcg tgctcttgag    1020
atcggcagcc tggcctctgc cttcggagtt tgatgtcta aaaccatacc aaccatccac    1080
catcccttcc cagccattct cgataaagcc tgcgatagcc caaatatcc cgcgggtctg    1140
tttttcgggg acattgcgca taccggtcgc cagtttcaag ccggagccca gctcggtggc    1200
attagtcacc tctatctgat cgttagtaat ggttttcaca atggtcccgt tagggacggc    1260
atggtgcccc aagcagagcg tggctgttga gttgtcattg cccggcagtt tctgggcaaa    1320
caccagacac agtatgtagg acagcgcaat tatggttttc at                       1362
```

<210> SEQ ID NO 124
<211> LENGTH: 1332
<212> TYPE: DNA
<213> ORGANISM: Artificial Sequence
<220> FEATURE:
<223> OTHER INFORMATION: Synthetic

<400> SEQUENCE: 124

```
atgaaggcca tcatcgtgct gctgatggtg gtcacaagca cgccgatag aatctgtacc      60
ggcatcacca gcagcaatag ccctcacgtc gtgaaaacag ctacacaggg cgaagtgaat     120
gtgaccggcg tgatccctct gggatcagga ctgaagctgg ccaatggcac aaagtataga     180
cctccagcca agctgctgaa agagagaggc tttttttggag ctatcgccgg ctttctggaa     240
```

```
ggcggatggg agggaatgat tgctggatgg catggctaca catctcatgg cgcacatggc      300
gtggcagtgg ctgctgatct gaaatctaca caggaagcca tcaacaagat caccaagaac      360
ctgaacagcc tgagcgagct ggaaggaggc gaccccgagt gggatcgcga aatcaacaac      420
tacacatcta tcatctacag tctgattgag gaaagccaga accagcagga gaatgggact      480
gggggaggct ccggaatcgt gcagcagcag aacaatctgc tgcgagccat tgaagctcag      540
cagcacctgc tgcagctgac agtgtggggc atcaagcagc tgcaggggag ccagattgaa      600
ctggctgtgc tgctgtctaa cgagggcatc atcaatagcg aggacgaaca tctgctggcc      660
ctggaaagaa agctgaagaa gatgctggga cctagcgccg tggaaatcgg caatggatgc      720
tttgagacaa agcacaagtg caaccagacc tgcctggata aattgccgc cggaacattt       780
gatgccggcg agttttctct gcccaccttc gatagcctga atatcacatc cggaggcgac      840
atcatcaagc tgctgaacga gcaggtgaac aaggagatgc agagcagcaa cctgtacatg      900
agcatgagca gctggtgcta cacccacagc ctggacggcg ccggcctgtt cctgttcgac      960
cacgccgccg aggagtacga gcacgccaag aagctgatca tcttcctgaa cgagaacaac     1020
gtgcccgtgc agctgaccag catcagcgcc cccgagcaca gttcgaggg cctgacccag      1080
atcttccaga aggcctacga gcacgagcag cacatcagcg agagcatcaa caacatcgtg     1140
gaccacgcca tcaagagcaa ggaccacgcc accttcaact tcctgcagtg gtacgtggcc     1200
gagcagcacg aggaggaggt gctgttcaag gacatcctgg acaagatcga gctgatcggc     1260
aacgagaacc acggcctgta cctggccgac cagtacgtga agggcatcgc caagagcagg     1320
aagagcggat cc                                                          1332
```

<210> SEQ ID NO 125
<211> LENGTH: 444
<212> TYPE: PRT
<213> ORGANISM: Artificial Sequence
<220> FEATURE:
<223> OTHER INFORMATION: Synthetic

<400> SEQUENCE: 125

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Gly
        35                  40                  45

Ser Gly Leu Lys Leu Ala Asn Gly Thr Lys Tyr Arg Pro Pro Ala Lys
    50                  55                  60

Leu Leu Lys Glu Arg Gly Phe Phe Gly Ala Ile Ala Gly Phe Leu Glu
65                  70                  75                  80

Gly Gly Trp Glu Gly Met Ile Ala Gly Trp His Gly Tyr Thr Ser His
                85                  90                  95

Gly Ala His Gly Val Ala Val Ala Ala Asp Leu Lys Ser Thr Gln Glu
            100                 105                 110

Ala Ile Asn Lys Ile Thr Lys Asn Leu Asn Ser Leu Ser Glu Leu Glu
        115                 120                 125

Gly Gly Asp Pro Glu Trp Asp Arg Glu Ile Asn Asn Tyr Thr Ser Ile
    130                 135                 140

Ile Tyr Ser Leu Ile Glu Glu Ser Gln Asn Gln Gln Glu Asn Gly Thr
145                 150                 155                 160
```

Gly Gly Gly Ser Gly Ile Val Gln Gln Asn Asn Leu Leu Arg Ala
            165                 170                 175
Ile Glu Ala Gln Gln His Leu Leu Gln Leu Thr Val Trp Gly Ile Lys
        180                 185                 190
Gln Leu Gln Gly Ser Gln Ile Glu Leu Ala Val Leu Leu Ser Asn Glu
        195                 200                 205
Gly Ile Ile Asn Ser Glu Asp Glu His Leu Leu Ala Leu Glu Arg Lys
    210                 215                 220
Leu Lys Lys Met Leu Gly Pro Ser Ala Val Glu Ile Gly Asn Gly Cys
225                 230                 235                 240
Phe Glu Thr Lys His Lys Cys Asn Gln Thr Cys Leu Asp Arg Ile Ala
                245                 250                 255
Ala Gly Thr Phe Asp Ala Gly Glu Phe Ser Leu Pro Thr Phe Asp Ser
            260                 265                 270
Leu Asn Ile Thr Ser Gly Gly Asp Ile Ile Lys Leu Leu Asn Glu Gln
        275                 280                 285
Val Asn Lys Glu Met Gln Ser Ser Asn Leu Tyr Met Ser Met Ser Ser
    290                 295                 300
Trp Cys Tyr Thr His Ser Leu Asp Gly Ala Gly Leu Phe Leu Phe Asp
305                 310                 315                 320
His Ala Ala Glu Glu Tyr Glu His Ala Lys Lys Leu Ile Ile Phe Leu
                325                 330                 335
Asn Glu Asn Asn Val Pro Val Gln Leu Thr Ser Ile Ser Ala Pro Glu
            340                 345                 350
His Lys Phe Glu Gly Leu Thr Gln Ile Phe Gln Lys Ala Tyr Glu His
        355                 360                 365
Glu Gln His Ile Ser Glu Ser Ile Asn Asn Ile Val Asp His Ala Ile
    370                 375                 380
Lys Ser Lys Asp His Ala Thr Phe Asn Phe Leu Gln Trp Tyr Val Ala
385                 390                 395                 400
Glu Gln His Glu Glu Val Leu Phe Lys Asp Ile Leu Asp Lys Ile
                405                 410                 415
Glu Leu Ile Gly Asn Glu Asn His Gly Leu Tyr Leu Ala Asp Gln Tyr
            420                 425                 430
Val Lys Gly Ile Ala Lys Ser Arg Lys Ser Gly Ser
        435                 440

<210> SEQ ID NO 126
<211> LENGTH: 1332
<212> TYPE: DNA
<213> ORGANISM: Artificial Sequence
<220> FEATURE:
<223> OTHER INFORMATION: Synthetic

<400> SEQUENCE: 126
ggatccgctc ttcctgctct tggcgatgcc cttcacgtac tggtcggcca ggtacaggcc     60
gtggttctcg ttgccgatca gctcgatctt gtccaggatg tccttgaaca gcacctcctc    120
ctcgtgctgc tcggccacgt accactgcag gaagttgaag gtggcgtggt ccttgctctt    180
gatggcgtgg tccacgatgt tgttgatgct ctcgctgatg tgctgctcgt gctcgtaggc    240
cttctggaag atctgggtca ggccctcgaa cttgtgctcg ggggcgctga tgctggtcag    300
ctgcacgggc acgttgttct cgttcaggaa gatgatcagc ttcttggcgt gctcgtactc    360
ctcggcggcg tggtcgaaca ggaacaggcc ggcgccgtcc aggctgtggg tgtagcacca    420
gctgctcatg ctcatgtaca ggttgctgct ctgcatctcc ttgttcacct gctcgttcag    480

```
cagcttgatg atgtcgcctc cggatgtgat attcaggcta tcgaaggtgg gcagagaaaa        540
ctcgccggca tcaaatgttc cggcggcaat tctatccagg caggtctggt tgcacttgtg        600
ctttgtctca aagcatccat tgccgatttc cacggcgcta ggtcccagca tcttcttcag        660 cttctttcc  agggccagca gatgttcgtc ctcgctattg atgatgccct cgttagacag        720
cagcacagcc agttcaatct ggctcccctg cagctgcttg atgccccaca ctgtcagctg        780
cagcaggtgt tgctgagctt caatggctcg cagcagattg ttctgctgct gcacgattcc        840
ggagcctccc ccagtcccat tctcctgctg gttctggctt tcctcaatca gactgtagat        900
gatagatgtg tagttgttga tttcgcgatc ccactcgggg tcgcctcctt ccagctcgct        960
caggctgttc aggttcttgg tgatcttgtt gatggcttcc tgtgtagatt tcagatcagc       1020
agccactgcc acgccatgtg cgccatgaga tgtgtagcca tgccatccag caatcattcc       1080
ctcccatccg ccttccagaa agccggcgat agctccaaaa agcctctct  ctttcagcag       1140 cttggctgga ggtctatact ttgtgccatt ggccagcttc agtcctgatc ccagagggat       1200
cacgccggtc acattcactt cgccctgtgt agctgttttc acgacgtgag ggctattgct       1260
gctggtgatg ccggtacaga ttctatcggc gttgcttgtg accaccatca gcagcacgat       1320
gatggccttc at                                                          1332

<210> SEQ ID NO 127
<211> LENGTH: 1332
<212> TYPE: DNA
<213> ORGANISM: Artificial Sequence
<220> FEATURE:
<223> OTHER INFORMATION: Synthetic

<400> SEQUENCE: 127
atgaaggcca tcatcgtgct gctgatggtg gtgaccagca acgccgatag aatctgcacc         60
ggcatcacca gcagcaatag ccccccatgtg gtgaaaacag ccacccaggg cgaagtgaat        120
gtgacaggcg tgatccctct gggatcagga ctgaagctgg ccaatggcac caagtacaga        180
cctcccgcca agctgctgaa agagagaggc ttctttggcg ccattgccgg atttctggaa        240
ggcggctggg agggaatgat tgccggctgg cacggctata catctcatgg ggcccatggc        300
gtggctgtgg ccgccgatct gaagtctacc caggaagcca tcaacaagat caccaagaac        360
ctgaacagcc tgagcgagct ggaaggaggc gaccccgagt gggatcgcga atcaacaac         420 tacacatcta tcatctacag tctgattgag aaagccaga  accagcagga gaatgggact        480 ggggggaggct ccggaatcgt gcagcagcag aacaatctgc tgcgagccat tgaagctcag       540
cagcacctgc tgcagctgac agtgtggggc atcaagcagc tgcagggggtc ccagattgaa       600 ctggccgtgc tgctgtccaa cgagggcatc atcaacagcg aggatgaaca cctgctggcc       660
ctggaacgga agctgaagaa gatgctgggc ccttctgccg tggagatcgg caacggctgc       720
ttcgagacaa agcacaagtg caaccagacc tgcctggata gaatcgccgc tggcaccttc       780
aatgccggcg agttcagcct gcctaccttc gacagcctga atatcacctc cggaggcgac       840
atcatcaagc tgctgaacga gcaggtgaac aaggagatgc agagcagcaa cctgtacatg       900
agcatgagca gctggtgcta cacccacagc ctggacggca ccggcctgtt cctgttcgac       960
cacgccgccg aggagtacga gcacgccaag aagctgatca tcttcctgaa cgagaacaac      1020
gtgcccgtgc agctgaccag catcagcgcc cccgagcaca gttcgagggg cctgacccag      1080
atcttccaga aggcctacga gcacgagcag cacatcagcg agagcatcaa caacatcgtg      1140
```

```
gaccacgcca tcaagagcaa ggaccacgcc accttcaact tcctgcagtg gtacgtggcc   1200
gagcagcacg aggaggaggt gctgttcaag gacatcctgg acaagatcga gctgatcggc   1260
aacgagaacc acggcctgta cctggccgac cagtacgtga agggcatcgc caagagcagg   1320
aagagcggat cc                                                       1332
```

<210> SEQ ID NO 128
<211> LENGTH: 444
<212> TYPE: PRT
<213> ORGANISM: Artificial Sequence
<220> FEATURE:
<223> OTHER INFORMATION: Synthetic

<400> SEQUENCE: 128

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Gly
        35                  40                  45

Ser Gly Leu Lys Leu Ala Asn Gly Thr Lys Tyr Arg Pro Pro Ala Lys
50                  55                  60

Leu Leu Lys Glu Arg Gly Phe Phe Gly Ala Ile Ala Gly Phe Leu Glu
65                  70                  75                  80

Gly Gly Trp Glu Gly Met Ile Ala Gly Trp His Gly Tyr Thr Ser His
                85                  90                  95

Gly Ala His Gly Val Ala Val Ala Ala Asp Leu Lys Ser Thr Gln Glu
            100                 105                 110

Ala Ile Asn Lys Ile Thr Lys Asn Leu Asn Ser Leu Ser Glu Leu Glu
        115                 120                 125

Gly Gly Asp Pro Glu Trp Asp Arg Glu Ile Asn Asn Tyr Thr Ser Ile
130                 135                 140

Ile Tyr Ser Leu Ile Glu Glu Ser Gln Asn Gln Gln Glu Asn Gly Thr
145                 150                 155                 160

Gly Gly Gly Ser Gly Ile Val Gln Gln Gln Asn Asn Leu Leu Arg Ala
                165                 170                 175

Ile Glu Ala Gln Gln His Leu Leu Gln Leu Thr Val Trp Gly Ile Lys
            180                 185                 190

Gln Leu Gln Gly Ser Gln Ile Glu Leu Ala Val Leu Leu Ser Asn Glu
        195                 200                 205

Gly Ile Ile Asn Ser Glu Asp Glu His Leu Leu Ala Leu Glu Arg Lys
210                 215                 220

Leu Lys Lys Met Leu Gly Pro Ser Ala Val Glu Ile Gly Asn Gly Cys
225                 230                 235                 240

Phe Glu Thr Lys His Lys Cys Asn Gln Thr Cys Leu Asp Arg Ile Ala
                245                 250                 255

Ala Gly Thr Phe Asn Ala Gly Glu Phe Ser Leu Pro Thr Phe Asp Ser
            260                 265                 270

Leu Asn Ile Thr Ser Gly Gly Asp Ile Ile Lys Leu Leu Asn Glu Gln
        275                 280                 285

Val Asn Lys Glu Met Gln Ser Ser Asn Leu Tyr Met Ser Met Ser Ser
290                 295                 300

Trp Cys Tyr Thr His Ser Leu Asp Gly Ala Gly Leu Phe Leu Phe Asp
305                 310                 315                 320

His Ala Ala Glu Glu Tyr Glu His Ala Lys Lys Leu Ile Ile Phe Leu
```

```
                        325                 330                 335
Asn Glu Asn Asn Val Pro Val Gln Leu Thr Ser Ile Ser Ala Pro Glu
                340                 345                 350

His Lys Phe Glu Gly Leu Thr Gln Ile Phe Gln Lys Ala Tyr Glu His
            355                 360                 365

Glu Gln His Ile Ser Glu Ser Ile Asn Asn Ile Val Asp His Ala Ile
        370                 375                 380

Lys Ser Lys Asp His Ala Thr Phe Asn Phe Leu Gln Trp Tyr Val Ala
385                 390                 395                 400

Glu Gln His Glu Glu Val Leu Phe Lys Asp Ile Leu Asp Lys Ile
                405                 410                 415

Glu Leu Ile Gly Asn Glu Asn His Gly Leu Tyr Leu Ala Asp Gln Tyr
                420                 425                 430

Val Lys Gly Ile Ala Lys Ser Arg Lys Ser Gly Ser
                435                 440
```

<210> SEQ ID NO 129
<211> LENGTH: 1332
<212> TYPE: DNA
<213> ORGANISM: Artificial Sequence
<220> FEATURE:
<223> OTHER INFORMATION: Synthetic

<400> SEQUENCE: 129

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
gatggcgtgg tccacgatgt tgttgatgct ctcgctgatg tgctgctcgt gctcgtaggc     240
cttctggaag atctgggtca ggccctcgaa cttgtgctcg gggcgctga tgctggtcag     300
ctgcacgggc acgttgttct cgttcaggaa gatgatcagc ttcttggcgt gctcgtactc     360
ctcggcggcg tggtcgaaca ggaacaggcc ggcgccgtcc aggctgtggg tgtagcacca     420
gctgctcatg ctcatgtaca ggttgctgct ctgcatctcc ttgttcacct gctcgttcag     480
cagcttgatg atgtcgcctc cggaggtgat attcaggctg tcgaaggtag caggctgaa      540
ctcgccggca ttgaaggtgc cagcggcgat tctatccagg caggtctggt tgcacttgtg     600
ctttgtctcg aagcagccgt tgccgatctc cacggcagaa gggcccagca tcttcttcag     660
cttccgttcc agggccagca ggtgttcatc ctcgctgttg atgatgccct cgttggacag     720
cagcacggcc agttcaatct gggacccctg cagctgcttg atgccccaca ctgtcagctg     780
cagcaggtgc tgctgagctt caatggctcg cagcagattg ttctgctgct gcacgattcc     840
ggagcctccc ccagtcccat tctcctgctg gttctggctt tcctcaatca gactgtagat     900
gatagatgtg tagttgttga tttcgcgatc ccactcgggg tcgcctcctt ccagctcgct     960
caggctgttc aggttcttgg tgatcttgtt gatggcttcc tgggtagact tcagatcggc    1020
ggccacagcc acgccatggg ccccatgaga tgtatagccg tgccagccgg caatcattcc    1080
ctcccagccg cctccagaa atccggcaat ggcgccaaag aagcctctct ctttcagcag    1140
cttggcggga ggtctgtact tggtgccatt ggccagcttc agtcctgatc ccagagggat    1200
cacgcctgtc acattcactt cgccctgggt ggctgtttttc accacatggg ggctattgct    1260
gctggtgatg ccggtgcaga ttctatcggc gttgctggtc accaccatca gcagcacgat    1320
gatggccttc at                                                         1332
```

What is claimed is:

1. A nanoparticle comprising a fusion protein, wherein the fusion protein comprises a monomeric ferritin subunit protein joined to an influenza hemagglutinin (HA) protein, such that the nanoparticle comprises influenza virus HA protein trimers on its surface.

2. The nanoparticle of claim 1, wherein the monomeric ferritin subunit protein is a monomeric subunit of a *Helicobacter pylori* ferritin protein.

3. The nanoparticle of claim 1, wherein the hemagglutinin protein is from an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and B/Brisbane/60/2008 (2008 Bris, B).

4. The nanoparticle of claim 1, wherein the hemagglutinin protein comprises a region selected from the group consisting of:
   a) a region corresponding to amino acids 1-519 of SEQ ID NO:8;
   b) a region comprising amino acids 1-519 of SEQ ID NO:8;
   c) a region comprising an amino acid sequence at least about 80% identical to an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98; and,
   d) a region comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

5. The nanoparticle of claim 1, wherein the nanoparticle elicits an immune response to:
   a) an influenza virus strain that is heterologous to the strain of influenza virus from which the hemagglutinin protein was obtained; or,
   b) a protein comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

6. The nanoparticle of claim 1, wherein the fusion protein comprises an amino acid sequence selected from the group consisting of
SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

7. A method to produce a vaccine against influenza virus, the method comprising a) expressing a fusion protein comprising a monomeric ferritin protein joined to an influenza hemagglutinin protein under conditions such that the fusion proteins form a nanoparticle displaying hemagglutinin trimers on its surface, and b) recovering the nanoparticle.

8. A method to vaccinate an individual against influenza, the method comprising administering a vaccine produced according to the method of claim 7 to an individual such that the nanoparticle elicits an immune response against influenza virus.

9. The method of claim 8, wherein the nanoparticle elicits an immune response to an influenza virus strain that is heterologous to the sub-type of influenza virus from which the hemagglutinin protein was obtained.

10. The method of claim 8, wherein the nanoparticle elicits an immune response to an influenza virus strain that is heterologous to the strain of influenza virus from which the hemagglutinin protein was obtained.

11. The method of claim 8, wherein the nanoparticle elicits an immune response to an influenza virus that is antigenically divergent from the influenza virus from which the hemagglutinin protein was obtained.

12. The method of claim 8, wherein administering comprises administering to the individual a first vaccine composition and then at a later time, administering a second vaccine composition comprising a nanoparticle that comprises an HA-SS-ferritin fusion protein.

13. The method of claim 12, wherein the HA portion of the HA SS-ferritin fusion protein comprises a region selected from the group consisting of:
   a) a region corresponding to amino acids 1-519 of SEQ ID NO:8;
   b) a region comprising amino acids 1-519 of SEQ ID NO:8
   c) a region comprising an amino acid sequence at least about 80% identical to an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98, wherein the HA SS-ferritin fusion protein elicits an immune response to an influenza virus; and,
   d) a region comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

14. The method of claim 12, wherein the HA SS-ferritin fusion protein comprises an amino acid sequence selected from the group consisting of:
SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

15. The method of claim 12, wherein the first vaccine composition comprises a nanoparticle comprising a hemagglutinin protein from an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and B/Brisbane/60/2008 (2008 Bris, B).

16. The method of claim 15, wherein the hemagglutinin protein comprises a region selected from the group consisting of:
   a) a region comprising an amino acid sequence at least about 80% identical to an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98;
   b) a region comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98
   c) a region corresponding to amino acids 1-519 of SEQ ID NO:8; and,
   d) a region comprising amino acids 1-519 of SEQ ID NO:8.

17. The method of claim 12, wherein the first vaccine composition comprises an HA-ferritin fusion protein comprising an amino acid sequence selected from the group consisting of
SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

18. A fusion protein comprising a monomeric ferritin subunit protein joined to an influenza hemagglutinin protein, wherein the monomeric ferritin subunit protein comprises a domain that allows the fusion protein to self-assemble into nanoparticles.

19. The fusion protein of claim 18, wherein the monomeric subunit is a monomeric subunit of a *Helicobacter pylori* ferritin protein.

20. The fusion protein of claim 18, wherein the hemagglutinin protein comprises a region selected from the group consisting of:
   a) a region comprising an amino acid sequence comprising at least 25 amino acids from a second hemagglutinin protein from an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and B/Brisbane/60/2008 (2008 Bris, B);
   b) a region corresponding to amino acids 1-519 of SEQ ID NO:8;
   c) a region comprising amino acids 1-519 of SEQ ID NO:8;
   d) a region comprising an amino acid sequence at least about 80% identical to an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98; and,
   e) a region comprising an amino acid sequence selected from the group consisting of SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:71, SEQ ID NO:74, SEQ ID NO:77, SEQ ID NO:80, SEQ ID NO:83, SEQ ID NO:86, SEQ ID NO:89, SEQ ID NO:92, SEQ ID NO:95 and SEQ ID NO:98.

21. The fusion protein of claim 18, wherein the fusion protein comprises an amino acid sequence selected from the group consisting of
SEQ ID NO:41, SEQ ID NO:44, SEQ ID NO:47, SEQ ID NO:50, SEQ ID NO:53, SEQ ID NO:56, SEQ ID NO:59, SEQ ID NO:62, SEQ ID NO:65, SEQ ID NO:68, SEQ ID NO:101, SEQ ID NO:104 SEQ ID NO:107 SEQ ID NO:110 SEQ ID NO:113 SEQ ID NO:116 SEQ ID NO:119 SEQ ID NO:122 SEQ ID NO:125 and SEQ ID NO:128.

* * * * *

UNITED STATES PATENT AND TRADEMARK OFFICE
CERTIFICATE OF CORRECTION

PATENT NO. : 9,441,019 B2
APPLICATION NO. : 14/346849
DATED : September 13, 2016
INVENTOR(S) : Gary J. Nabel et al.

It is certified that error appears in the above-identified patent and that said Letters Patent is hereby corrected as shown below:

Column 13, Line 59, replace (SEQ ID NO:152) with --(SEQ ID NO:153)--
    Column 13, Line 61, replace (SEQ ID NO:152) with --(SEQ ID NO:154)--
    Column 13, Line 63, replace (SEQ ID NO:152) with --(SEQ ID NO:155)--
    Column 13, Line 65, replace (SEQ ID NO:152) with --(SEQ ID NO:156)--
    Column 13, Line 67, replace (SEQ ID NO:152) with --(SEQ ID NO:157)--
    Column 14, Line 2, replace (SEQ ID NO:152) with --(SEQ ID NO:158)--
    Column 14, Line 4, replace (SEQ ID NO:152) with --(SEQ ID NO:159)--
    Column 14, Line 6, replace (SEQ ID NO:152) with --(SEQ ID NO:160)--
    Replace the SEQUENCE LISTING, that begins under Column 65 (starting with SEQ ID NO:1) and ends under Column 296 (ending with SEQ ID NO:129) with the attached SEQUENCE LISTING for SEQ ID NO:1 through SEQ ID NO:160

Signed and Sealed this
Fourth Day of September, 2018

Andrei Iancu
*Director of the United States Patent and Trademark Office*

SEQUENCE LISTING

```
<110>  The United States of America, as represented by the
       Secretary, Department of Health and Human Services
       Nabel, Gary J.
       Kanekiyo, Masaru
       Wei, Chih-Jen
       McTamney, Patrick M.
       Yassine, Hadi M.
       Boyington, Jeffrey C.

<120>  NOVEL INFLUENZA HEMAGGLUTININ PROTEIN-BASED VACCINES

<130>  6137NIAID-26-C1-PUS

<140>  US 14/346,849
<141>  2014-03-24

<150>  61/538,663
<151>  2011-09-23

<150>  61/661,209
<151>  2012-06-18

<150>  PCT/US12/56822
<151>  2012-09-24

<160>  160

<170>  PatentIn version 3.5

<210>  1
<211>  504
<212>  DNA
<213>  Helicobacter pylori

<400>  1
atgttatcaa aagacatcat taagttgcta acgaacaag tgaataagga aatgaactct        60
tccaacttgt atatgagcat gagttcatgg tgctataccc atagcttaga tggcgcgggg      120
cttttcttgt tgaccatgc ggctgaagaa tacgagcatg ctaaaaagct tattatcttc      180
```

```
ttgaatgaaa acaatgtgcc tgtgcaattg accagcatca gcgcgcctga gcataagttt       240
gaaggtttga ctcaaatttt ccaaaaagcc tatgaacatg agcaacacat cagcgagtct       300
attaacaata tcgtagatca cgccataaaa agcaaagatc atgcgacttt caatttcttg       360
caatggtatg tggctgaaca gcatgaagaa gaagtgcttt tcaaggatat tttggataaa       420
attgagttga ttggtaatga aaaccatggc ttgtatttag ccgatcagta tgtcaaaggg       480
atcgctaaaa gcaggaaatc ttaa                                              504

<210>  2
<211>  167
<212>  PRT
<213>  Helicobacter pylori

<400>  2
```

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

```
Glu Gly Leu Thr Gln Ile Phe Gln Lys Ala Tyr Glu His Glu Gln His
            85                  90                  95

Ile Ser Glu Ser Ile Asn Asn Ile Val Asp His Ala Ile Lys Ser Lys
            100                 105                 110

Asp His Ala Thr Phe Asn Phe Leu Gln Trp Tyr Val Ala Glu Gln His
            115                 120                 125

Glu Glu Glu Val Leu Phe Lys Asp Ile Leu Asp Lys Ile Glu Leu Ile
            130                 135                 140

Gly Asn Glu Asn His Gly Leu Tyr Leu Ala Asp Gln Tyr Val Lys Gly
145                 150                 155                 160

Ile Ala Lys Ser Arg Lys Ser
                165

<210> 3
<211> 504
<212> DNA
<213> Helicobacter pylori

<400> 3
ttaagatttc ctgcttttag cgatcccttt gacatactga tcggctaaat acaagccatg      60 gtttcatta ccaatcaact caattttatc caaaatatcc ttgaaaagca cttcttcttc     120
atgctgttca gccacatacc attgcaagaa attgaaagtc gcatgatctt tgcttttat     180 ggcgtgatct acgatattgt taatagactc gctgatgtgt tgctcatgtt cataggcttt     240
```

```
ttggaaaatt tgagtcaaac cttcaaactt atgctcaggc gcgctgatgc tggtcaattg      300
cacaggcaca ttgttttcat tcaagaagat aataagcttt ttagcatgct cgtattcttc      360
agccgcatgg tcaaacaaga aaagccccgc gccatctaag ctatgggtat agcaccatga      420
actcatgctc atatacaagt tggaagagtt catttcctta ttcacttgtt cgtttagcaa      480
cttaatgatg tcttttgata acat                                             504

<210>  4
<211>  489
<212>  DNA
<213>  Helicobacter pylori

<400>  4
gacatcatca agctgctgaa cgagcaggtg aacaaggaga tgcagagcag caacctgtac       60
atgagcatga gcagctggtg ctacacccac agcctggacg gcgccggcct gttcctgttc      120
gaccacgccg ccgaggagta cgagcacgcc aagaagctga tcatcttcct gaacgagaac      180
aacgtgcccg tgcagctgac cagcatcagc gccccgagc acaagttcga gggcctgacc      240
cagatcttcc agaaggccta cgagcacgag cagcacatca gcgagagcat caacaacatc      300
gtggaccacg ccatcaagag caaggaccac gccaccttca acttcctgca gtggtacgtg      360
gccgagcagc acgaggagga ggtgctgttc aaggacatcc tggacaagat cgagctgatc      420
ggcaacgaga accacggcct gtacctggcc gaccagtacg tgaagggcat cgccaagagc      480
aggaagagc                                                             489

<210>  5
<211>  163
<212>  PRT
<213>  Helicobacter pylori
```

<400> 5

Asp Ile Ile Lys Leu Leu Asn Glu Gln Val Asn Lys Glu Met Gln Ser
1               5                   10                  15

Ser Asn Leu Tyr Met Ser Met Ser Ser Trp Cys Tyr Thr His Ser Leu
            20                  25                  30

Asp Gly Ala Gly Leu Phe Leu Phe Asp His Ala Ala Glu Glu Tyr Glu
        35                  40                  45

His Ala Lys Lys Leu Ile Ile Phe Leu Asn Glu Asn Asn Val Pro Val
    50                  55                  60

Gln Leu Thr Ser Ile Ser Ala Pro Glu His Lys Phe Glu Gly Leu Thr
65                  70                  75                  80

Gln Ile Phe Gln Lys Ala Tyr Glu His Glu Gln His Ile Ser Glu Ser
                85                  90                  95

Ile Asn Asn Ile Val Asp His Ala Ile Lys Ser Lys Asp His Ala Thr
            100                 105                 110

Phe Asn Phe Leu Gln Trp Tyr Val Ala Glu Gln His Glu Glu Glu Val
        115                 120                 125

Leu Phe Lys Asp Ile Leu Asp Lys Ile Glu Leu Ile Gly Asn Glu Asn
    130                 135                 140

His Gly Leu Tyr Leu Ala Asp Gln Tyr Val Lys Gly Ile Ala Lys Ser
145                 150                 155                 160

Arg Lys Ser

<210> 6
<211> 489
<212> DNA
<213> Helicobacter pylori

<400> 6

```
gctcttcctg ctcttggcga tgcccttcac gtactggtcg gccaggtaca ggccgtggtt       60
ctcgttgccg atcagctcga tcttgtccag gatgtccttg aacagcacct cctcctcgtg      120
ctgctcggcc acgtaccact gcaggaagtt gaaggtggcg tggtccttgc tcttgatggc      180
gtggtccacg atgttgttga tgctctcgct gatgtgctgc tcgtgctcgt aggccttctg      240
gaagatctgg gtcaggccct cgaacttgtg ctcgggggcg ctgatgctgg tcagctgcac      300
gggcacgttg ttctcgttca ggaagatgat cagcttcttg gcgtgctcgt actcctcggc      360
ggcgtggtcg aacaggaaca ggccggcgcc gtccaggctg tgggtgtagc accagctgct      420
catgctcatg tacaggttgc tgctctgcat ctccttgttc acctgctcgt tcagcagctt      480
gatgatgtc                                                              489
```

<210> 7
<211> 1695
<212> DNA
<213> Influenza virus

<400> 7

```
atgaaggcca aactgctggt gctgctgtgt acctttaccg ccacctacgc cgacacaatc       60
tgtatcggct accacgccaa caatagcacc gacaccgtgg atacagtgct ggagaagaac      120
gtgaccgtga cccactctgt gaacctgctg gaggacagcc acaatggcaa gctgtgtctg      180
ctgaaaggca ttgcccctct gcagctgggc aattgttctg tggccggatg gattctgggc      240
aaccccgagt gtgagctgct gatttctaag gagagctgga gctacatcgt ggagaccccc      300
```

```
aatcctgaga atggcacctg ctaccctggc tacttcgccg attacgagga gctgcgcgag      360
cagctgtcta gcgtgtccag cttcgagaga ttcgagatct tccccaagga gtccagctgg      420
cctaatcaca cagtgacagg cgtgtctgcc agctgtagcc acaacggcaa agcagcttc       480 taccggaacc tgctgtggct gacaggcaag aatggcctgt accccaacct gagcaagagc      540
tacgtgaaca acaaggaaaa ggaagtgctg gtgctgtggg gagtgcacca ccctcccaac      600
atcggaaatc agcgggccct gtaccacaca gagaacgcct atgtgagcgt ggtgtccagc      660
cactacagca gaagattcac ccccgagatc gccaagagac caaagtgag agaccaggag      720 ggccggatca attactactg gaccctgctg gagcctggcg ataccatcat cttcgaggcc      780
aacggcaatc tgatcgcccc ttggtatgcc tttgccctga gcagaggctt tggcagcggc      840
atcatcacaa gcaacgcccc catggatgag tgtgatgcca agtgccagac acctcagggc      900
gccatcaata gcagcctgcc cttccagaat gtgcaccctg tgaccatcgg cgagtgcccc      960
aagtatgtga aagcgccaa gctgagaatg gtgaccggcc tgagaaacat ccctagcatc      1020
cagagcagag gactgtttgg agccatcgcc ggattcatcg agggaggatg gacaggcatg      1080
gtggatggct ggtacggcta ccaccaccag aatgagcagg gctctggata tgccgccgat      1140
cagaagtcta cccagaacgc catcaacggc atcaccaaca aggtgaacag cgtgatcgag      1200
aagatgaaca cccagtttac cgctgtgggc aaggagttca acaagctgga gcggaggatg      1260
gagaacctga acaagaaggt ggacgacggc tttctggaca tctggaccta caatgccgaa      1320
ctcctggtcc tcctcgagaa tgagaggacc ctggacttcc acgacagcaa cgtgaagaac      1380
ctgtatgaga aggtgaagag ccagctgaag aacaacgcca aggagatcgg caacggctgc      1440
ttcgagttct accacaagtg taacaacgag tgtatggaga gcgtgaagaa cggcacctac      1500 gactaccta agtacagcga ggagagcaag ctgaaccggg agaagatcga tggcgtgaag      1560
```

```
ctggagagca tgggcgtgta tcagatcctg gccatctaca gcacagtggc ctcttctctg        1620
gtgctgctgg tgtctctggg cgccatctcc ttttggatgt gctccaacgg cagcctgcag        1680
tgcaggatct gtatc                                                          1695

<210>  8
<211>  565
<212>  PRT
<213>  Influenza virus

<400>  8

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
                100                 105                 110
```

```
Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285
```

```
Asp Glu Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445
```

```
        Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
        465                 470                 475                 480

Phe Glu Phe Tyr His Lys Cys Asn Asn Glu Cys Met Glu Ser Val Lys
                            485                 490                 495

Asn Gly Thr Tyr Asp Tyr Pro Lys Tyr Ser Glu Glu Ser Lys Leu Asn
                        500                 505                 510

Arg Glu Lys Ile Asp Gly Val Lys Leu Glu Ser Met Gly Val Tyr Gln
                    515                 520                 525

Ile Leu Ala Ile Tyr Ser Thr Val Ala Ser Ser Leu Val Leu Leu Val
                530                 535                 540

Ser Leu Gly Ala Ile Ser Phe Trp Met Cys Ser Asn Gly Ser Leu Gln
        545                 550                 555                 560

Cys Arg Ile Cys Ile
                        565

<210>  9
<211>  1695
<212>  DNA
<213>  Influenza virus

<400>  9
gatacagatc ctgcactgca ggctgccgtt ggagcacatc caaaaggaga tggcgcccag      60
```

```
agacaccagc agcaccagag aagaggccac tgtgctgtag atggccagga tctgatacac      120
gcccatgctc tccagcttca cgccatcgat cttctcccgg ttcagcttgc tctcctcgct      180
gtacttaggg tagtcgtagg tgccgttctt cacgctctcc atacactcgt tgttacactt      240
gtggtagaac tcgaagcagc cgttgccgat ctccttggcg ttgttcttca gctggctctt      300
caccttctca tacaggttct tcacgttgct gtcgtggaag tccagggtcc tctcattctc      360
gaggaggacc aggagttcgg cattgtaggt ccagatgtcc agaaagccgt cgtccacctt      420
cttgttcagg ttctccatcc tccgctccag cttgttgaac tccttgccca cagcggtaaa      480
ctgggtgttc atcttctcga tcacgctgtt caccttgttg gtgatgccgt tgatggcgtt      540
ctgggtagac ttctgatcgg cggcatatcc agagccctgc tcattctggt ggtggtagcc      600
gtaccagcca tccaccatgc ctgtccatcc tccctcgatg aatccggcga tggctccaaa      660
cagtcctctg ctctggatgc tagggatgtt tctcaggccg gtcaccattc tcagcttggc      720
gcttctcaca tacttggggc actcgccgat ggtcacaggg tgcacattct ggaagggcag      780
gctgctattg atggcgccct gaggtgtctg gcacttggca tcacactcat ccatggggc       840 gttgcttgtg atgatgccgc tgccaaagcc tctgctcagg gcaaaggcat accaagggc       900 gatcagattg ccgttggcct cgaagatgat ggtatcgcca ggctccagca gggtccagta      960
gtaattgatc cggccctcct ggtctctcac tttgggtctc ttggcgatct cggggtgaa      1020 tcttctgctg tagtggctgg acaccacgct cacataggcg ttctctgtgt ggtacagggc     1080
ccgctgattt ccgatgttgg gagggtggtg cactccccac agcaccagca cttcctttc     1140 cttgttgttc acgtagctct tgctcaggtt ggggtacagg ccattcttgc ctgtcagcca     1200
cagcaggttc cggtagaagc tgcttttgcc gttgtggcta cagctggcag acacgcctgt     1260
```

```
cactgtgtga ttaggccagc tggactcctt ggggaagatc tcgaatctct cgaagctgga    1320
cacgctagac agctgctcgc gcagctcctc gtaatcggcg aagtagccag ggtagcaggt    1380
gccattctca ggattggggg tctccacgat gtagctccag ctctccttag aaatcagcag    1440
ctcacactcg gggttgccca gaatccatcc ggccacagaa caattgccca gctgcagagg    1500
ggcaatgcct ttcagcagac acagcttgcc attgtggctg tcctccagca ggttcacaga    1560
gtgggtcacg gtcacgttct tctccagcac tgtatccacg gtgtcggtgc tattgttggc    1620
gtggtagccg atacagattg tgtcggcgta ggtggcggta aggtacaca gcagcaccag     1680 cagtttggcc ttcat                                                     1695
```

```
<210>  10
<211>  1551
<212>  DNA
<213>  Influenza virus

<400>  10
atgaaggcca aactgctggt gctgctgtgt acctttaccg ccacctacgc cgacacaatc      60
tgtatcggct accacgccaa caatagcacc gacaccgtgg atacagtgct ggagaagaac     120
gtgaccgtga cccactctgt gaacctgctg gaggacagcc acaatggcaa gctgtgtctg     180
ctgaaaggca ttgcccctct gcagctgggc aattgttctg tggccggatg gattctgggc     240
aaccccgagt gtgagctgct gatttctaag gagagctgga gctacatcgt ggagaccccc     300
aatcctgaga atggcacctg ctaccctggc tacttcgccg attacgagga gctgcgcgag     360
cagctgtcta gcgtgtccag cttcgagaga ttcgagatct cccccaagga gtccagctgg     420
cctaatcaca cagtgacagg cgtgtctgcc agctgtagcc acaacggcaa aagcagcttc     480
taccggaacc tgctgtggct gacaggcaag aatggcctgt accccaacct gagcaagagc     540
```

```
tacgtgaaca acaaggaaaa ggaagtgctg gtgctgtggg gagtgcacca ccctcccaac     600
atcggaaatc agcgggccct gtaccacaca gagaacgcct atgtgagcgt ggtgtccagc     660
cactacagca gaagattcac ccccgagatc gccaagagac caaagtgag agaccaggag      720 ggccggatca attactactg gaccctgctg gagcctggcg ataccatcat cttcgaggcc     780
aacggcaatc tgatcgcccc ttggtatgcc tttgccctga gcagaggctt tggcagcggc    840
atcatcacaa gcaacgcccc catggatgag tgtgatgcca agtgccagac acctcagggc    900
gccatcaata gcagcctgcc cttccagaat gtgcaccctg tgaccatcgg cgagtgcccc    960
aagtatgtga aagcgccaa gctgagaatg gtgaccggcc tgagaaacat ccctagcatc    1020
cagagcagag gactgtttgg agccatcgcc ggattcatcg agggaggatg gacaggcatg   1080
gtggatggct ggtacggcta ccaccaccag aatgagcagg gctctggata tgccgccgat   1140
cagaagtcta cccagaacgc catcaacggc atcaccaaca aggtgaacag cgtgatcgag   1200
aagatgaaca cccagtttac cgctgtgggc aaggagttca acaagctgga gcggaggatg   1260
gagaacctga acaagaaggt ggacgacggc tttctggaca tctggaccta caatgccgaa
```